United States Patent
Loew et al.

(10) Patent No.: US 9,512,199 B2
(45) Date of Patent: Dec. 6, 2016

(54) FIBRONECTIN CRADLE MOLECULES AND LIBRARIES THEREOF

(75) Inventors: Andreas Loew, Somerville, MA (US); Brian Edward Vash, Cambridge, MA (US); Shohei Koide, Chicago, IL (US); John Bernard Wojcik, Chicago, IL (US); Akiko Koide, Chicago, IL (US); Ryan Nicholas Gilbreth, Chicago, IL (US)

(73) Assignees: NOVARTIS AG, Basel (CH); UNIVERSITY OF CHICAGO, Chicago, IL (US)

( * ) Notice: Subject to any disclaimer, the term of this patent is extended or adjusted under 35 U.S.C. 154(b) by 751 days.

(21) Appl. No.: 13/813,409

(22) PCT Filed: Aug. 1, 2011

(86) PCT No.: PCT/US2011/046160
§ 371 (c)(1),
(2), (4) Date: Nov. 7, 2013

(87) PCT Pub. No.: WO2012/016245
PCT Pub. Date: Feb. 2, 2012

(65) Prior Publication Data
US 2014/0057807 A1   Feb. 27, 2014

Related U.S. Application Data

(60) Provisional application No. 61/369,160, filed on Jul. 30, 2010, provisional application No. 61/369,203, filed on Jul. 30, 2010, provisional application No. 61/369,222, filed on Jul. 30, 2010, provisional application No. 61/474,632, filed on Apr. 12, 2011, provisional application No. 61/474,648, filed on Apr. 12, 2011.

(51) Int. Cl.
C07K 14/78  (2006.01)
C07K 16/18  (2006.01)
(Continued)

(52) U.S. Cl.
CPC ............... *C07K 14/78* (2013.01); *C07K 16/18* (2013.01); *C07K 16/40* (2013.01); *C07K 16/42* (2013.01); *C07K 2317/34* (2013.01); *C07K 2318/20* (2013.01)

(58) Field of Classification Search
CPC ...... C07K 14/78; C07K 16/18; C07K 16/40; C07K 16/42; C07K 2317/34; C07K 2318/20
See application file for complete search history.

(56) References Cited

U.S. PATENT DOCUMENTS 6,703,199 B1 * 3/2004 Koide ................... C07K 14/78
435/69.1
9,139,825 B2 * 9/2015 Loew ................ C12N 15/1044
(Continued)

FOREIGN PATENT DOCUMENTS

WO    WO-02/32925    4/2002
WO    WO-03/104418   12/2003
(Continued)

OTHER PUBLICATIONS

International Search Report and Written Opinion for PCT/US2011/046160, mailed Mar. 28, 2013, 21 pages.
(Continued)

*Primary Examiner* — James H Alstrum Acevedo
*Assistant Examiner* — Randall L Beane
(74) *Attorney, Agent, or Firm* — John T. Prince

(57) ABSTRACT

The here described invention discloses a combination of a top and bottom loop binder library using the CD and the FG loops of a number of FnIII domains (FnIII) (e.g., FnIII[7], FnIII[10] and FnIII[14]) together with the surface exposed residues of the beta-sheet. The invention also pertains to a method of forming a library of FnIII domain polypeptides useful in screening for the presence of one or more polypeptides having a selected binding or enzymatic activity.

5 Claims, 66 Drawing Sheets

(51) Int. Cl.
*C07K 16/40* (2006.01)
*C07K 16/42* (2006.01)

(56) References Cited

U.S. PATENT DOCUMENTS

| | | | |
|---|---|---|---|
| 2003/0027319 A1* | 2/2003 | Koide | C07K 14/78 435/226 |
| 2003/0186385 A1 | 10/2003 | Koide | |
| 2010/0278801 A1 | 11/2010 | Shepard et al. | |
| 2011/0038866 A1* | 2/2011 | Hastewell | C07K 14/78 424/134.1 |
| 2011/0229406 A1 | 9/2011 | Hettmann et al. | |
| 2012/0208704 A1* | 8/2012 | Loew | C12N 15/1044 506/1 |

FOREIGN PATENT DOCUMENTS

| | | |
|---|---|---|
| WO | WO-2007/077028 | 7/2007 |
| WO | WO-2007/146959 | 12/2007 |
| WO | WO-2009/023184 | 2/2009 |
| WO | WO-2009/023266 | 2/2009 |
| WO | WO-2010/060095 | 5/2010 |
| WO | WO-2011/051333 | 5/2011 |

OTHER PUBLICATIONS

Chen et al., "Inhibition of Heregulin Signaling by an Aptamer that Preferentially Binds to the Oligomeric Form of Human Epidermal Growth Factor Receptor-3," PNAS (2003) 100(16):9226-9231.

Cho and Leahy, "Structure of the Extracellular Region of HER3 Reveals an Interdomain Tether," Science (2002) 297:1330-1333.

Garrett et al., "Crystal Structure of a Truncated Epidermal Growth Factor Receptor Extracellular Domain Bound to Transforming Growth Factor α," Cell (2002) 110:763-773.

Kani et al., "Oligomers of ERBB3 Have Two Distinct Interfaces that Differ in Their Sensitivity to Disruption by Heregulin," The Journal of Biological Chemistry (2005) 280(9):8238-8247.

Ogiso et al., "Crystal Structure of the Complex of Human Epidermal Growth Factor and Receptor Extracellular Domains," Cell (2002) 110:775-787.

\* cited by examiner

| Length | %    |
|--------|------|
| 6      | 0.6  |
| 7      | 0.4  |
| 8      | 2.1  |
| 9      | 70.7 |
| 10     | 15.2 |
| 11     | 6.2  |
| 12     | 2.2  |
| 13     | 0.5  |
| 14     | 2.1  |

| Length | %    |
|--------|------|
| 1      | 0.2  |
| 2      | 0.1  |
| 3      | 7.4  |
| 4      | 24.8 |
| 5      | 31.6 |
| 6      | 24.8 |
| 7      | 4.5  |
| 8      | 3.1  |
| 9      | 1.8  |
| 10     | 0.4  |
| 11     | 1.5  |

| Length | % |
|---|---|
| 8 | 0.4 |
| 9 | 1.8 |
| 10 | 94.9 |
| 11 | 2.1 |
| 12 | 0.6 |
| 13 | 0.3 |

| Length | % |
|---|---|
| 2 | 0.1 |
| 3 | 0.1 |
| 4 | 0.3 |
| 5 | 32.6 |
| 6 | 62.1 |
| 7 | 3.4 |
| 8 | 1.0 |
| 10 | 0.4 |

FnIII[10] Cradle

FnIII[10] Cradle Surface = 2457 Å$^2$

FnIII[10] Top Side

FnIII[10] Top Side Surface = 1834 Å$^2$

FnIII¹⁰ Bottom Side

FnIII¹⁰ Bottom Side Surface = 1140 Å²

FnIII[10] Cradle β-Sheets
Sheet C: Positions 1 - 9
Sheet F: Positions 10 - 19
Gray = Varied in Cradle

| Position | SF | CP | H | C | Varied |
|---|---|---|---|---|---|
| 1 | 50.9 | 41.5 | 7.1 | 0.6 | Yes |
| 2 | 0.2 | 1.2 | 98.0 | 0.6 | No |
| 3 | 15.1 | 35.4 | 49.4 | 0.2 | Yes |
| 4 | 0.7 | 0.5 | 98.8 | 0.1 | No |
| 5 | 17.3 | 69.0 | 13.7 | 0.2 | Yes |
| 6 | 4.8 | 18.9 | 73.4 | 3.7 | No |
| 7 | 19.5 | 63.6 | 14.7 | 2.3 | Yes |
| 8 | 38.4 | 54.3 | 6.9 | 0.3 | Yes |
| 9 | 43.4 | 34.1 | 22.5 | 0.0 | Yes |
| 10 | 24.1 | 60.1 | 15.4 | 0.8 | Yes |
| 11 | 0.0 | 0.1 | 99.7 | 0.1 | No |
| 12 | 19.2 | 54.6 | 25.9 | 0.4 | Yes |
| 13 | 3.6 | 0.1 | 94.4 | 1.0 | No |
| 14 | 23.5 | 64.4 | 11.0 | 1.3 | Yes |
| 15 | 2.1 | 0.0 | 98.0 | 0.0 | No |
| 16 | 24.2 | 29.1 | 44.6 | 2.3 | Yes |
| 17 | 91.5 | 0.8 | 5.2 | 2.7 | No |
| 18 | 10.4 | 31.1 | 56.2 | 2.4 | No |
| 19 | 25.4 | 63.6 | 10.6 | 0.4 | Yes |

Sheet C: Positions 1 - 9
Sheet F: Positions 10 - 19
SF: Small/Flexible amino acids - A, G, P, S, T
CP: Charged/Polar amino acids - D, E, H, K, N, Q, R
H: Hydrophobic amino acids - F, I, L, M, V, W, Y
C: Cysteine

Figure 7B

| Amino Acid | Sheet Distribution X (%) | Loop Distribution Y (%) |
| --- | --- | --- |
| Alanine/Ala/A | 6 | 6 |
| Cysteine/Cys/C | 0 | 0 |
| Aspartic Acid/Asp/D | 7 | 7 |
| Glutamic Acid/Glu/E | 4 | 4 |
| Phenylalanine/Phe/F | 2 | 2 |
| Glycine/Gly/G | 17 | 17 |
| Histidine/His/H | 2 | 2 |
| Isoleucine/Ile/I | 2 | 2 |
| Lysine/Lys/K | 2 | 2 |
| Leucine/Leu/L | 4 | 4 |
| Methionine/Met/M | 1 | 1 |
| Asparagine/Asn/N | 4 | 4 |
| Proline/Pro/P | 0 | 2 |
| Glutamine/Gln/Q | 2 | 2 |
| Arginine/Arg/R | 5 | 5 |
| Serine/Ser/S | 12 | 10 |
| Threonine/Thr/T | 4 | 4 |
| Valine/Val/V | 4 | 4 |
| Tryptophan/Trp/W | 3 | 3 |
| Tyrosine/Tyr/Y | 19 | 19 |

```
              A         AB    B         BC         C            CD
FnIII⁰⁷  PLSPPTNLHLEANPDTGVLTVSWERSTTPDITXYYXIXTXXX  [Y₄₋₉]
FnIII¹⁰  VSDVPRDLEVVAATPT-SLLISWD-APAVTVRXYYXIXYXXX  [Y₄₋₉]
FnIII¹⁴  NVSPPRRARVTDATET-TITISWR-TKTETITXFXVXAXPX  [Y₄₋₉]

D     DE    E         EF         F          FG        G
FnIII⁰⁷  LEEVVHADQSSCTFDNLSPGLXYYXVXXTVX  [Y₅₋₆] PISDTIIP
FnIII¹⁰  QEFTVPGSKSTATISGLKPGVXYYXIXVXAVX  [Y₅₋₆] PISINYRT
FnIII¹⁴  IQRTIKPDVRSYTITGLQPGTXYYXIXLXTLX  [Y₅₋₆] PVVIDAST
```

Figure 9E

|  | | A | AB | B | BC | C | CD | |
|---|---|---|---|---|---|---|---|---|
| FnIII⁰⁷ | 01 | PLSPPTNLHLEANP | DTGVLTVS | WERSTTPDIT | GYRITTPTNGQQGNS | | | 48 |
| FnIII¹⁰ | 01 | VSDVPRDLEVVAA | TPT-SLLIS | WD-APAVTVR | YYRITYGETGGN-SPV | | | 45 |
| FnIII¹⁴ | 01 | NVSPPRRARVTDATET- | TITISWR- | TKTETITGFQVDAVPANGQ--TP | | | | 44 |

|  | | D | DE | E | EF | F | FG | G | |
|---|---|---|---|---|---|---|---|---|---|
| FnIII⁰⁷ | 49 | LEEVVHADQSSCTFDNLSPGL | EYNVSVYTVKDDKES----VPISDTIIP | | | | | | 93 |
| FnIII¹⁰ | 46 | QEFTVPGSKSTATISGLKPGV | DYTITVYAVTGRGDSPASSKPISINYRT | | | | | | 94 |
| FnIII¹⁴ | 45 | IQRTIKPDVRSYTITGLQPGT | DYKIYLYTLNDNARS----SPVVIDAST | | | | | | 89 |

Figure 9F

FnIII structural element residue ranges

| FnIII | A | AB | B | BC | C | CD | D | DE | E | EF | F | FG | G |
|---|---|---|---|---|---|---|---|---|---|---|---|---|---|
| 07 | 8-13 | 14-17 | 18-22 | 23-32 | 33-41 | 42-48 | 49-54 | 55-58 | 59-63 | 64-69 | 70-79 | 80-85 | 86-93 |
| 10 | 8-13 | 14-16 | 17-21 | 22-30 | 31-39 | 40-45 | 46-51 | 52-55 | 56-60 | 61-66 | 67-76 | 77-86 | 87-94 |
| 14 | 8-13 | 14-16 | 17-12 | 22-30 | 31-39 | 40-44 | 45-50 | 51-54 | 55-59 | 60-65 | 66-75 | 76-81 | 82-89 |

FnIII Cradle residues ranges

| FnIII | Sheet C | Loop CD | Sheet F | Loop FG |
|---|---|---|---|---|
| 07 | 33,35,37,39-41 | 42-48 | 70,72,74,76,79 | 80-85 |
| 10 | 31,33,35,37-39 | 40-45 | 67,69,71,73,76 | 77-86 |
| 14 | 31,33,35,37,39 | 40-44 | 66,68,70,72,75 | 76-81 |

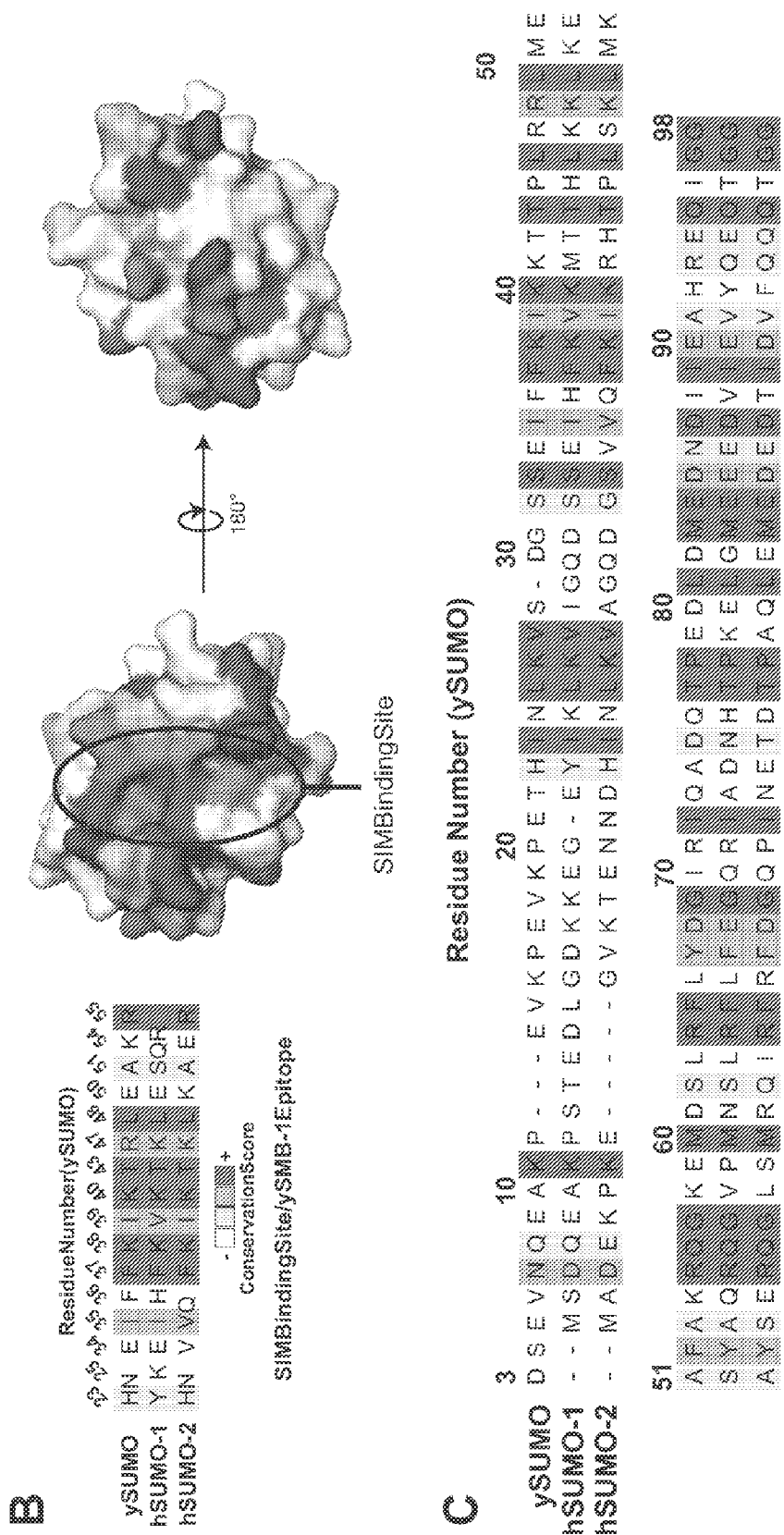
Figure 10B-C

C

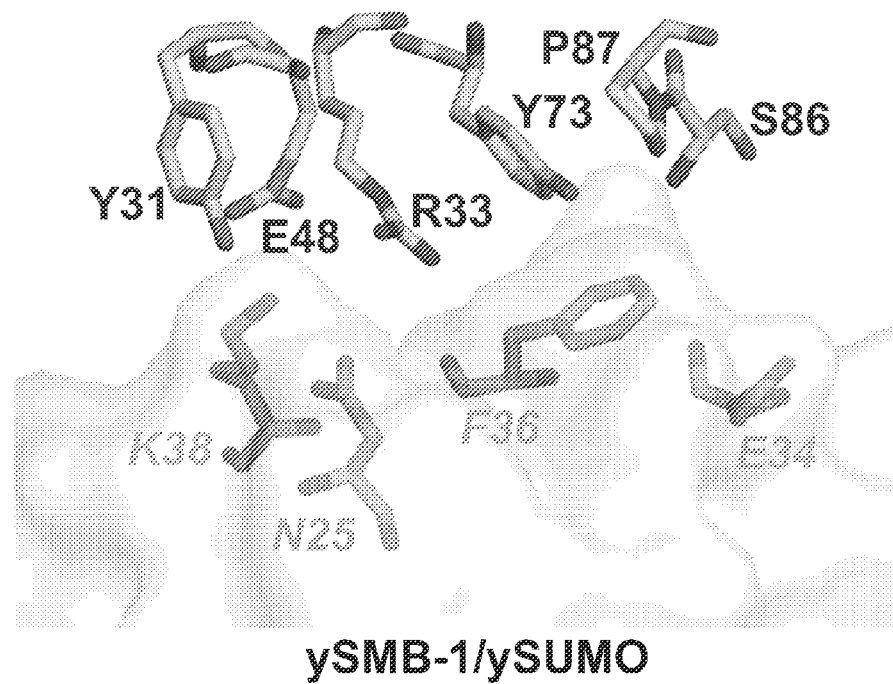
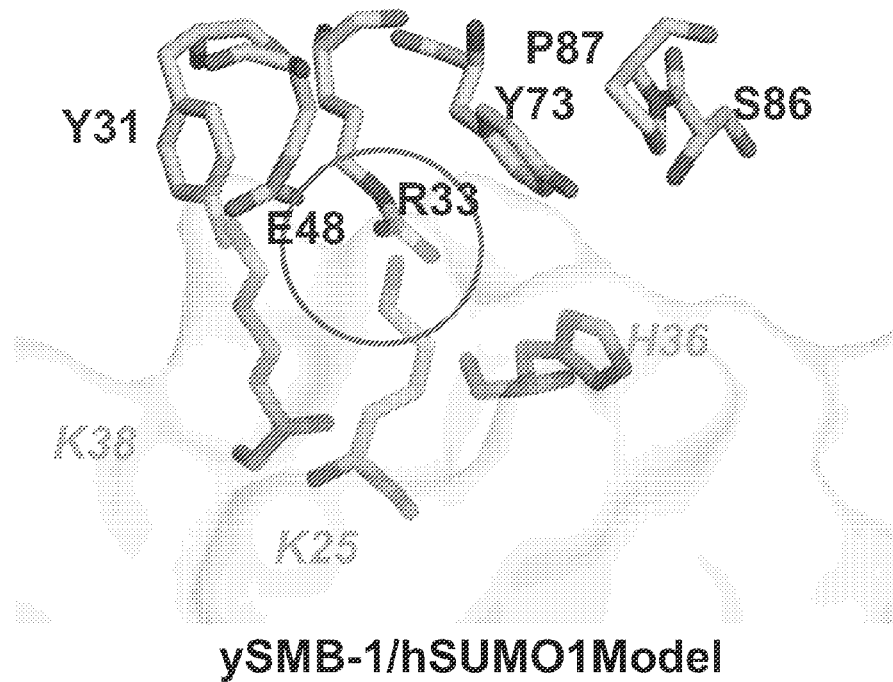
Figure 13

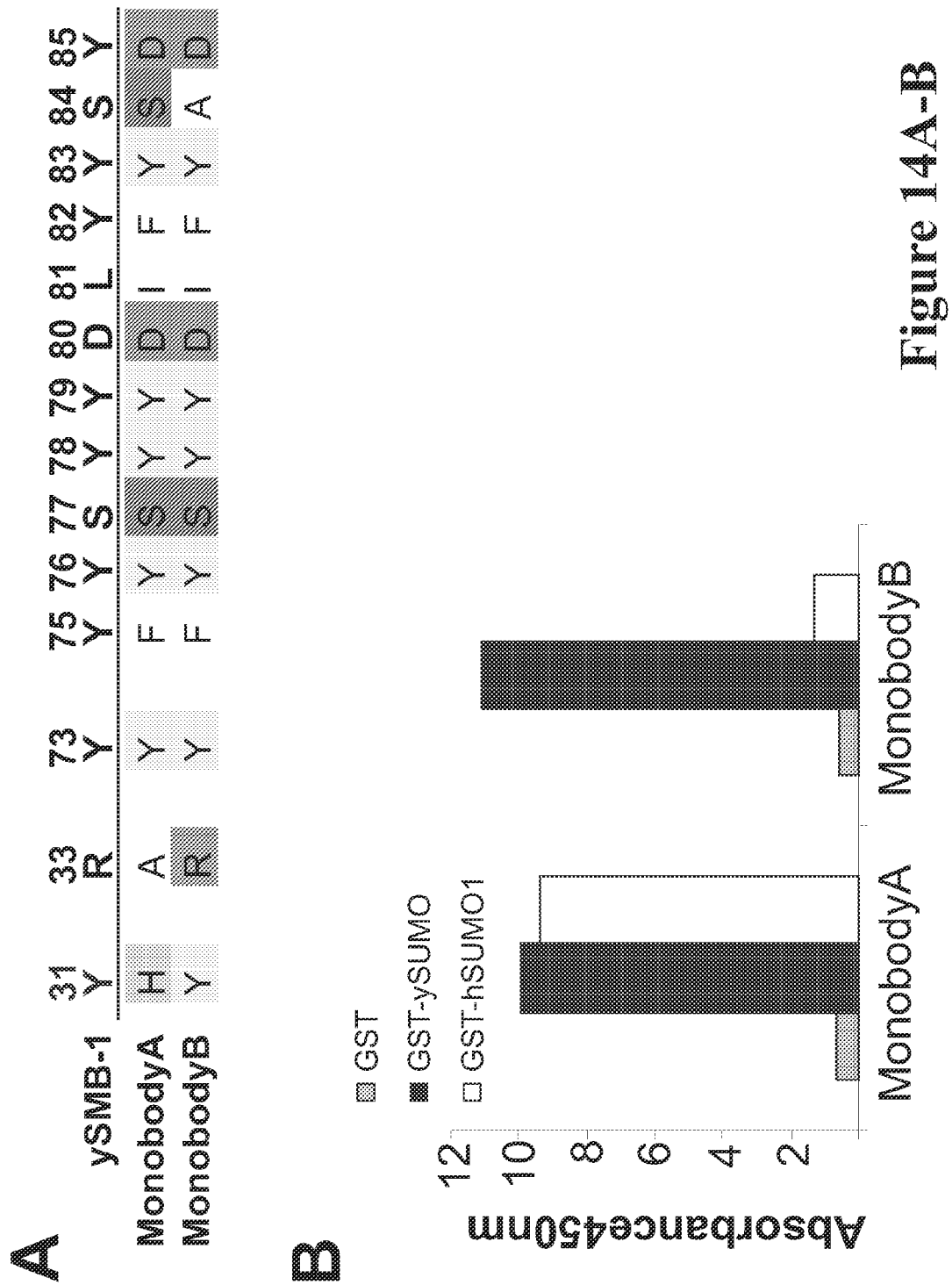
Figure 14A-B

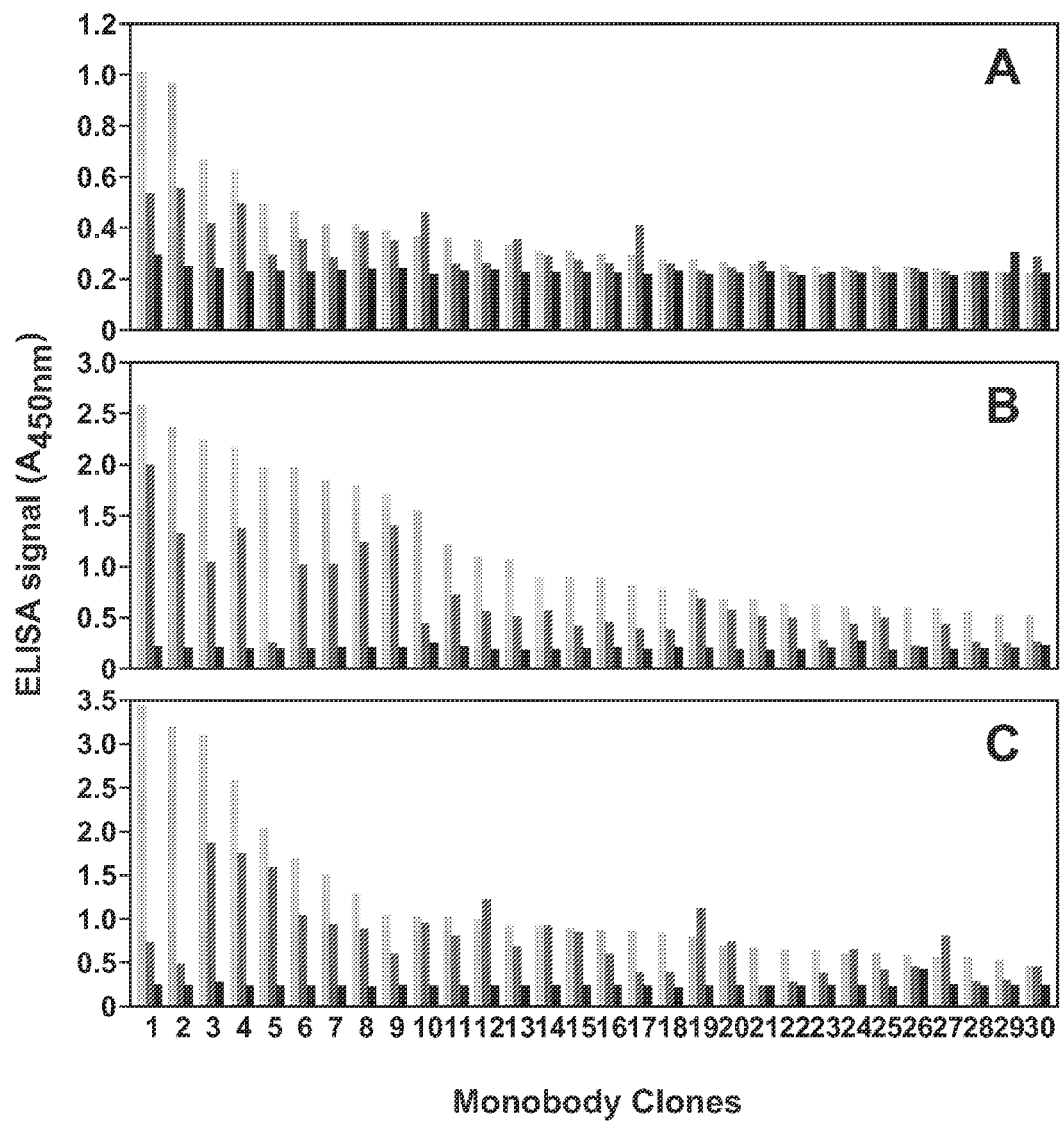
Figure 15A-C

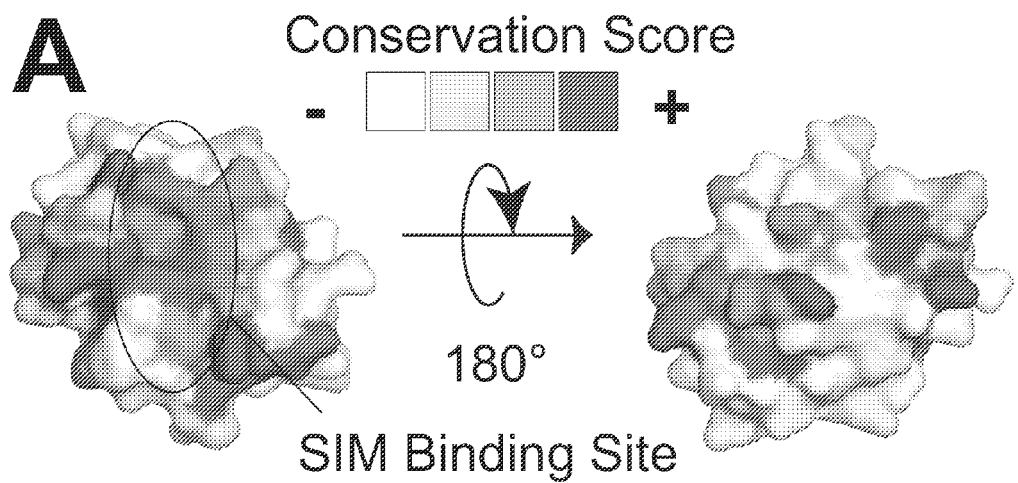
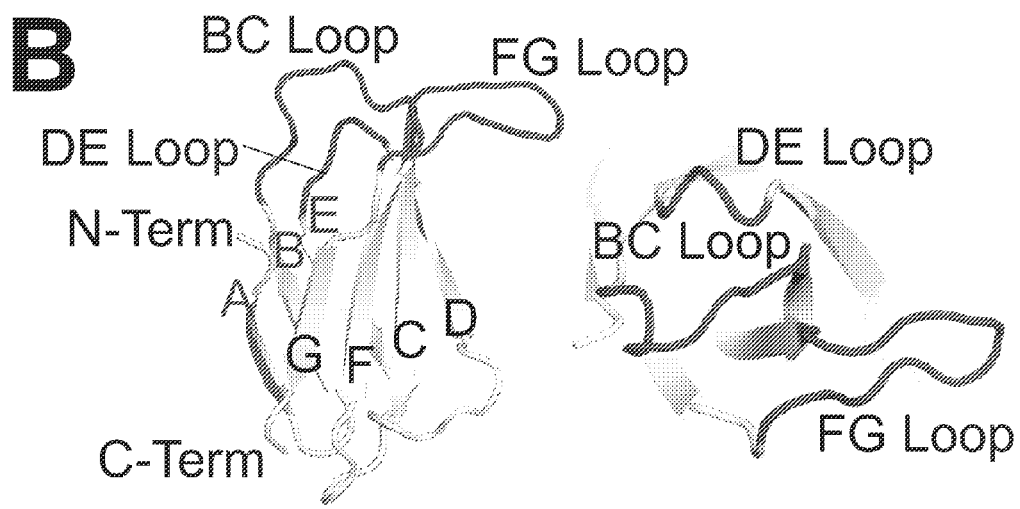
Figure 16A-B

| Clone | BC Loop | DE Loop | FG Loop | $K_d$ (nM) |
|---|---|---|---|---|
| ySMB-1 | S S S S V S | G S S S | Y Y S Y Y D L Y Y S Y | 82 |
| ySMB-2 | S S S S V S | G S S S | Y W T Y E W G Y M Y D | 45 |
| ySMB-3 | Y S V W D V A | G Y S S | Y Y P Y Y G L Y Y S Q | 210 |
| ySMB-4 | P W A Y S Q S V A | G S S S | Y Y G T P W G E G W Y S W | 100 |
| ySMB-5 | P A N S V S | G S S S | Y E W Y G W G W T Y | 166 |
| ySMB-6 | S S S S V S | S Y S S | Y W E F Y G Y W S Y | 800 |
| ySMB-7 | S S S S V S | G S S S | Y Q E W S Y G W S S E | 350 |
| ySMB-8 | Y V G Y G S S V A | G S S S | Y Y Y E G D D L Y S S M | 8000 |
| ySMB-9 | G Y W F I D | G Y S S | Y Y D N Y G W | |

Figure 16C

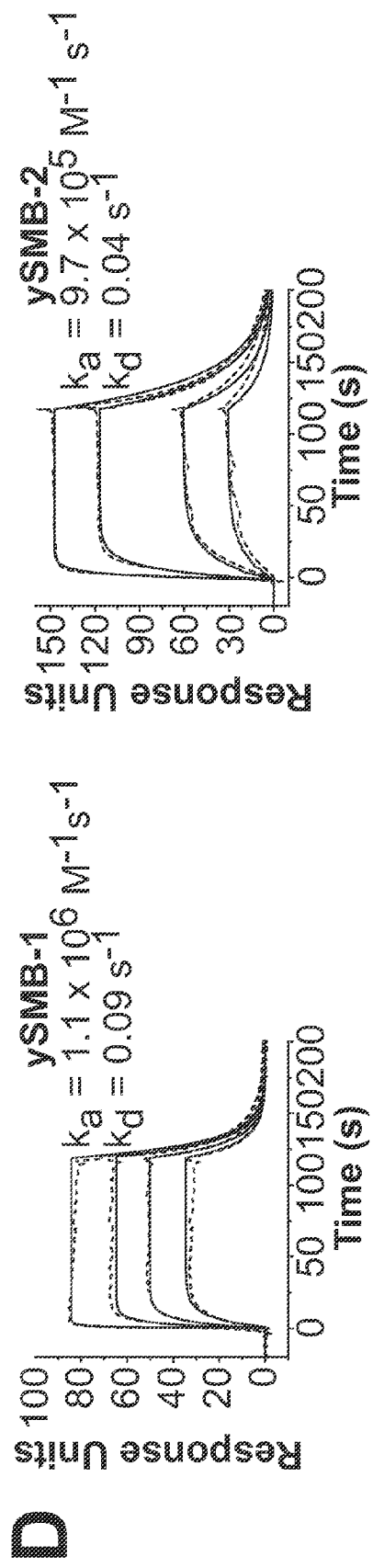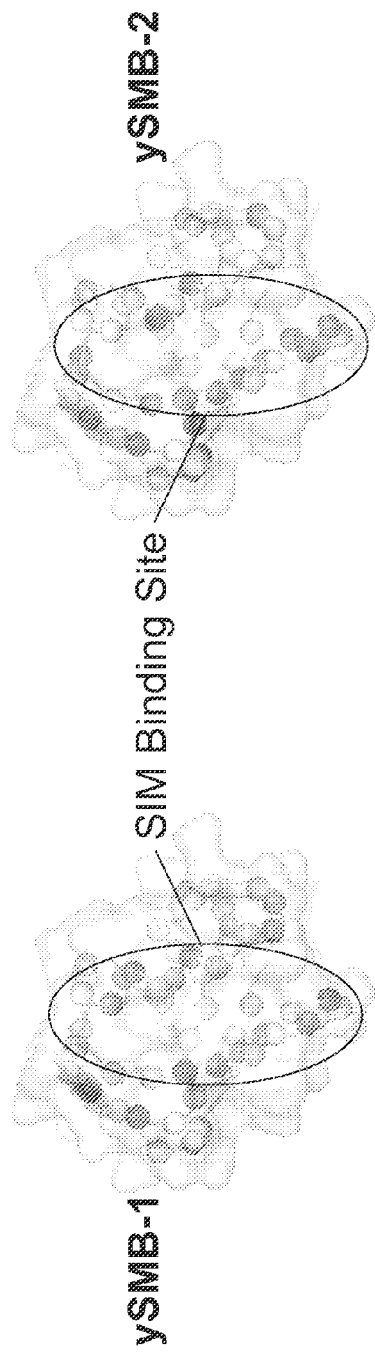
Figure 16D-E

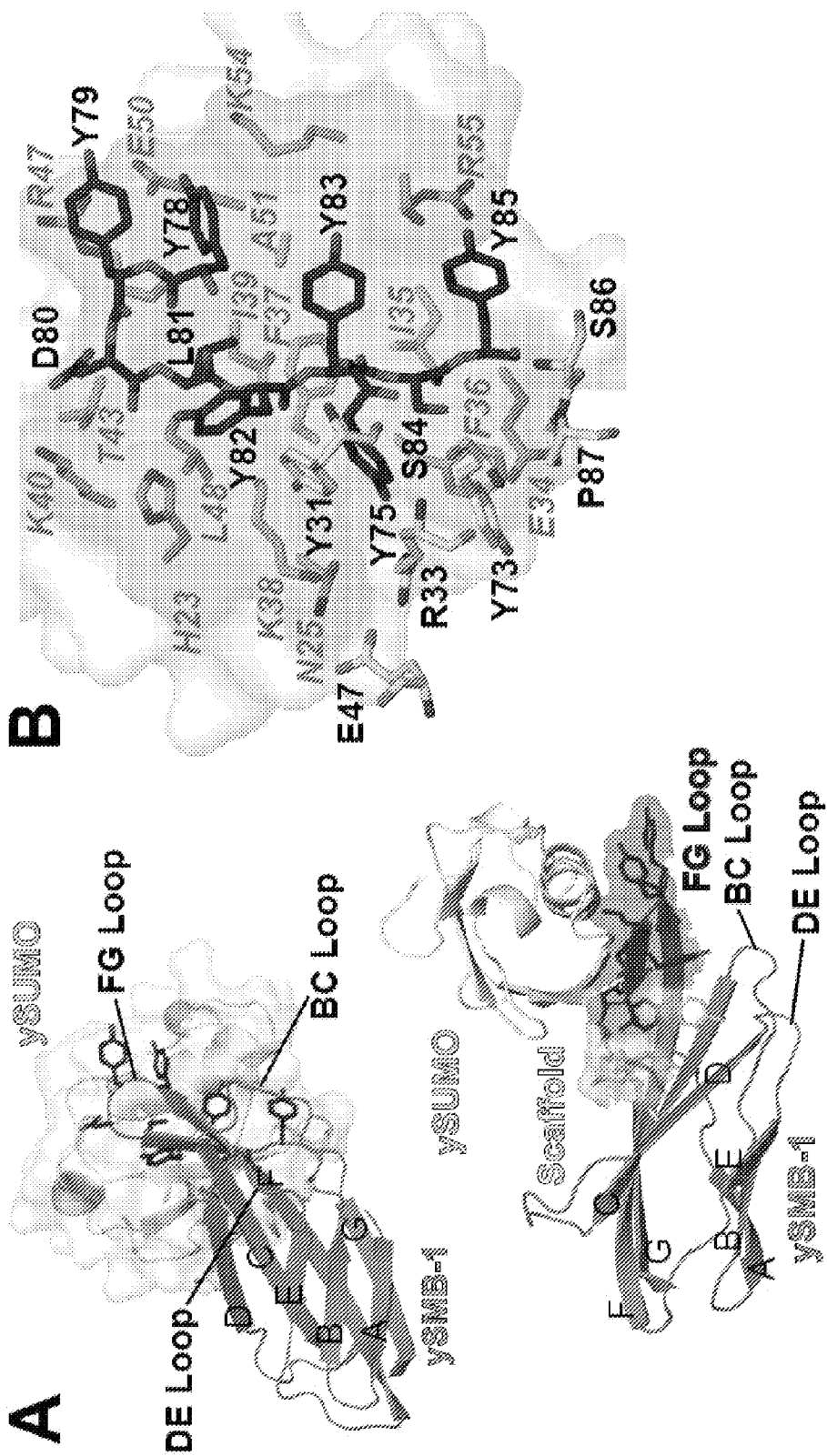
Figure 20A-B

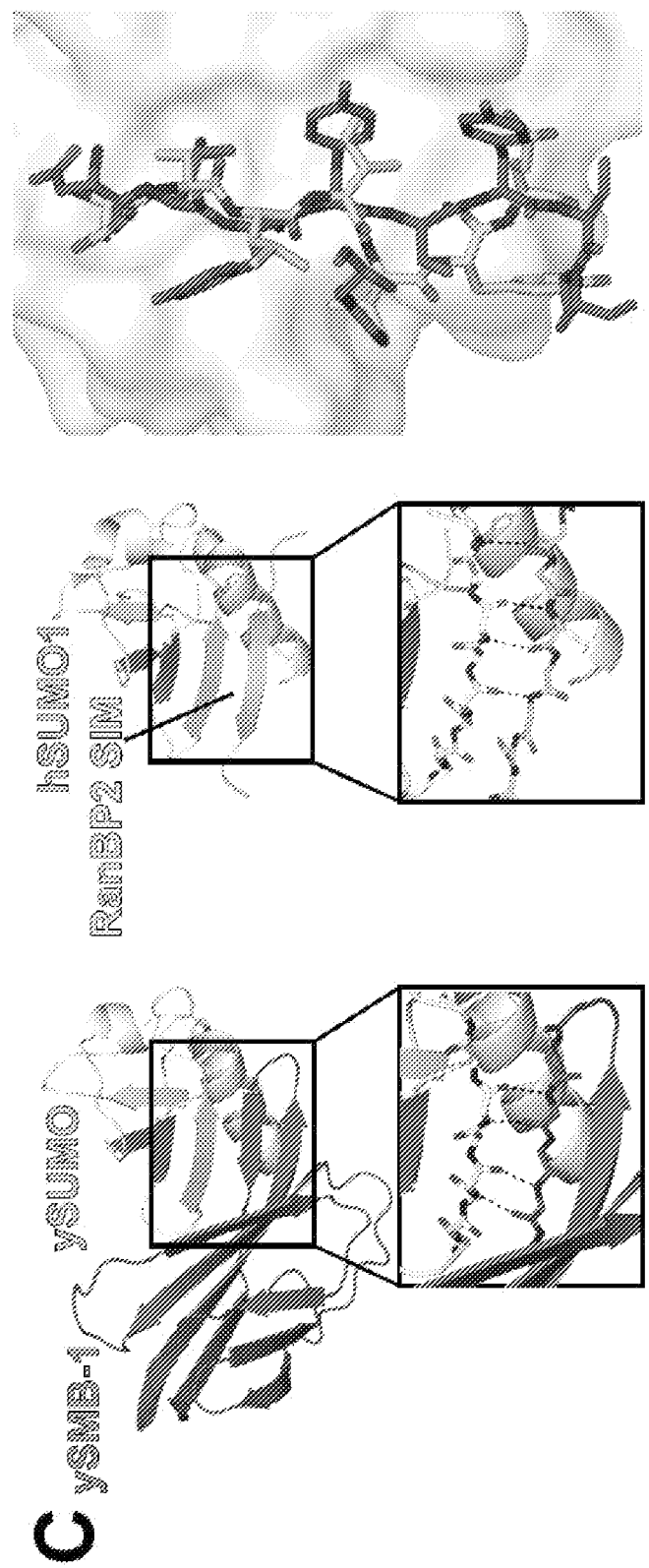

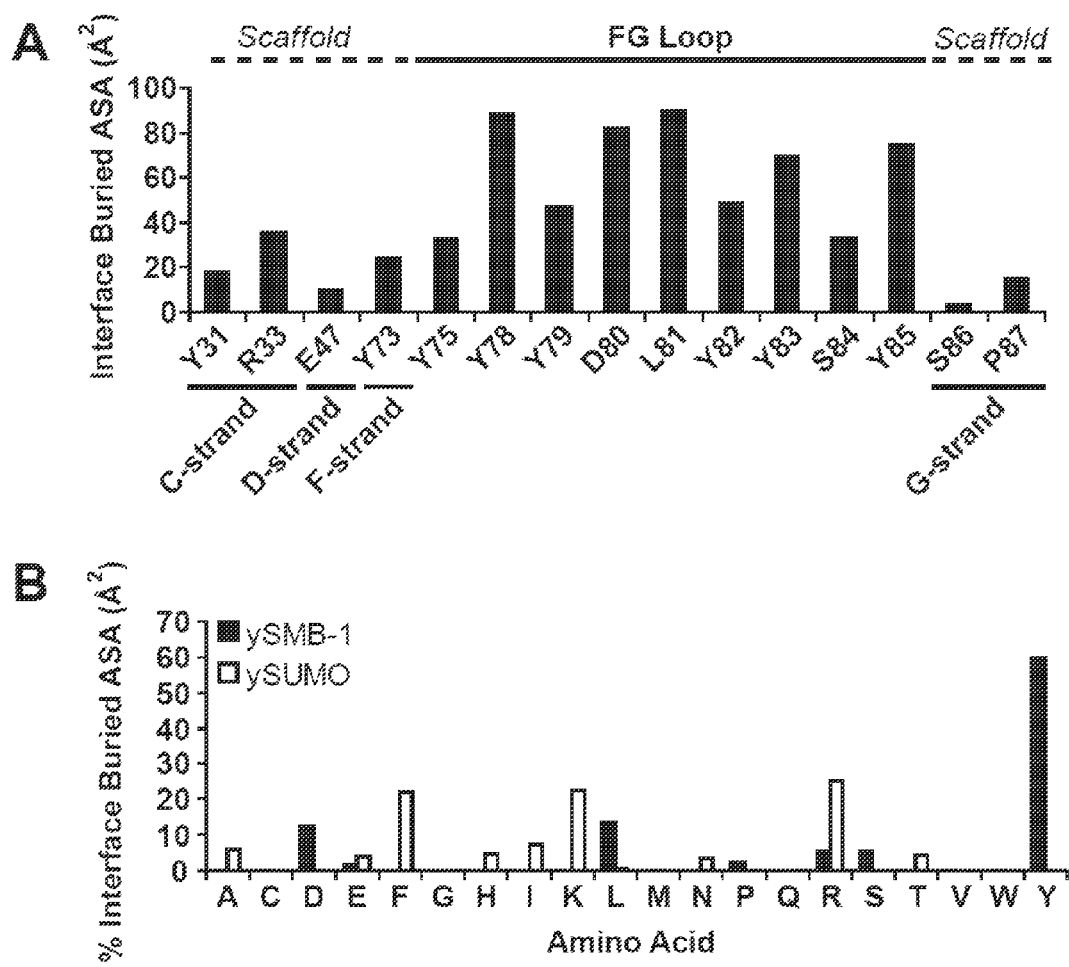
Figure 21A-B

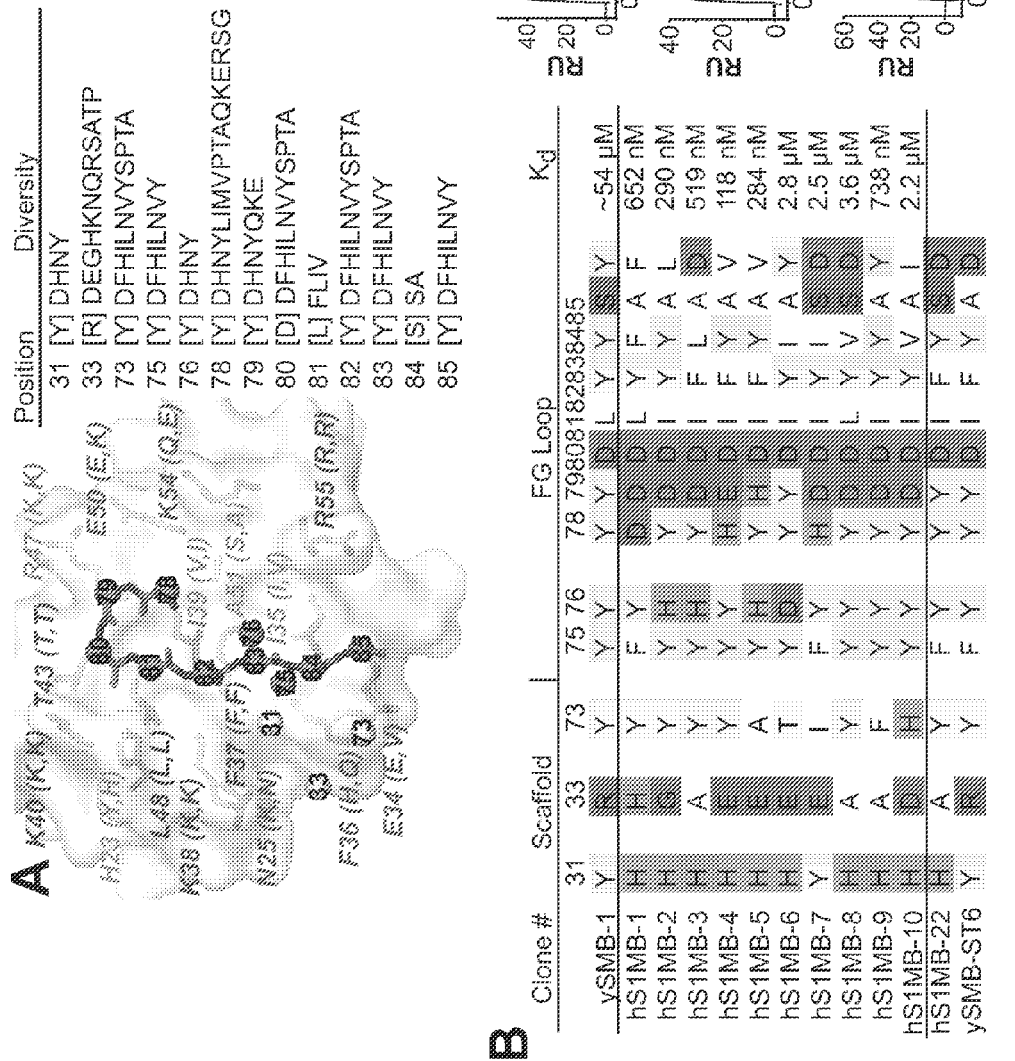
Figure 22A-B

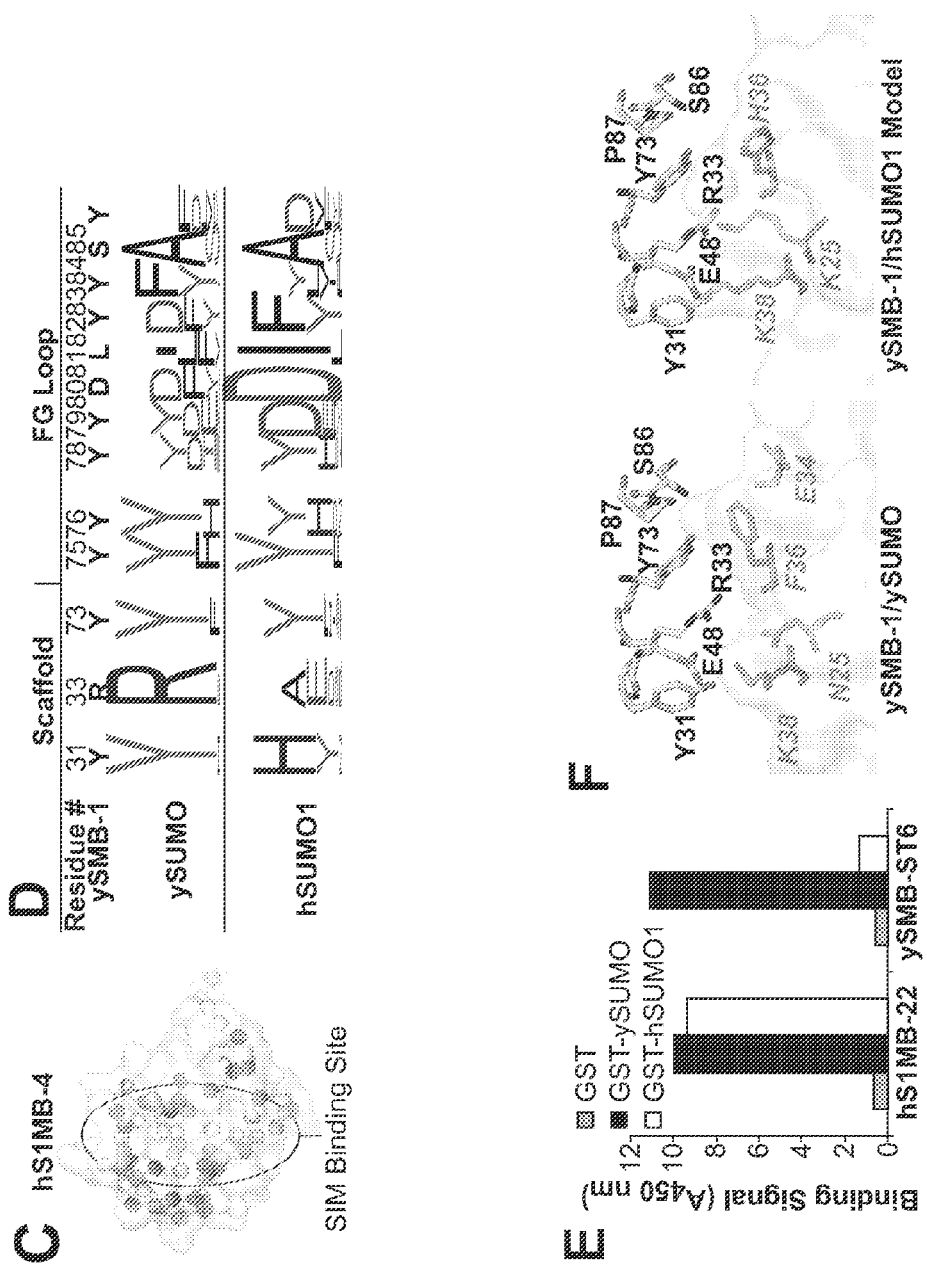
Figure 22C-F

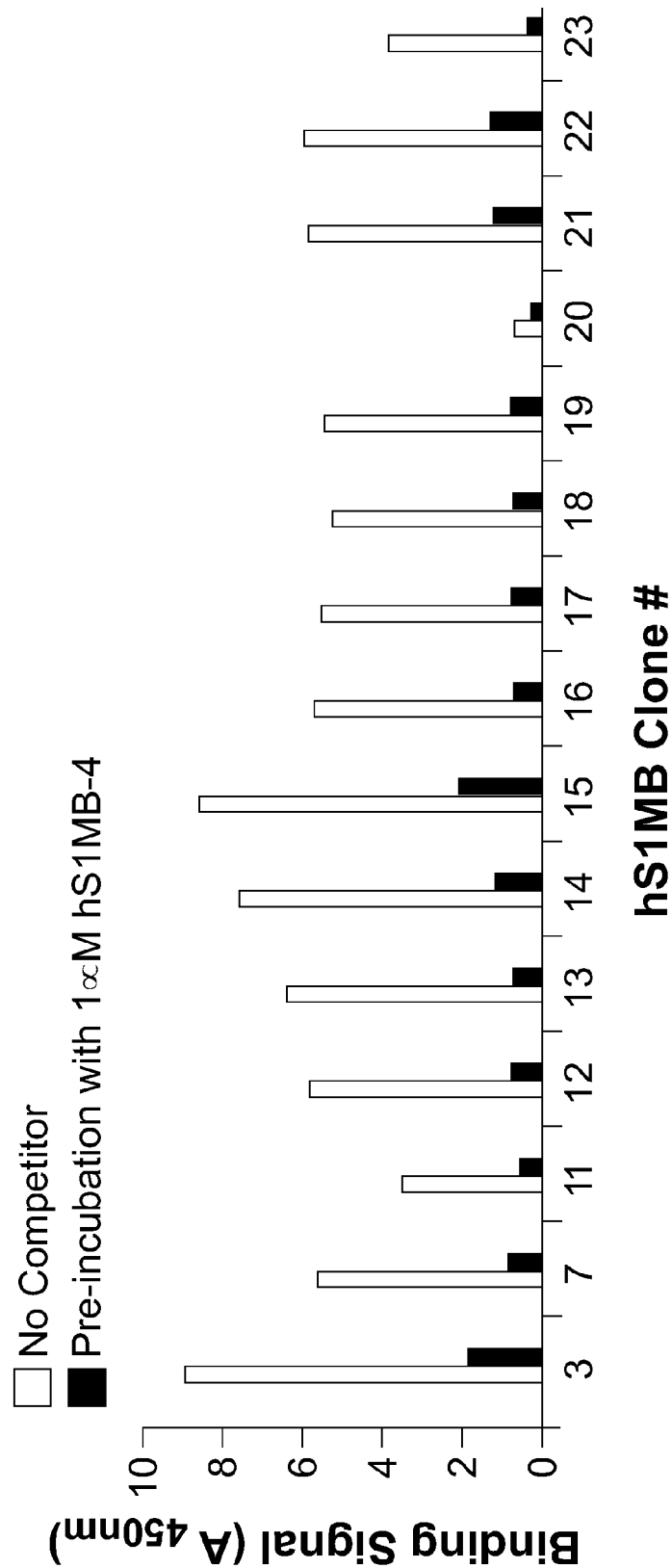

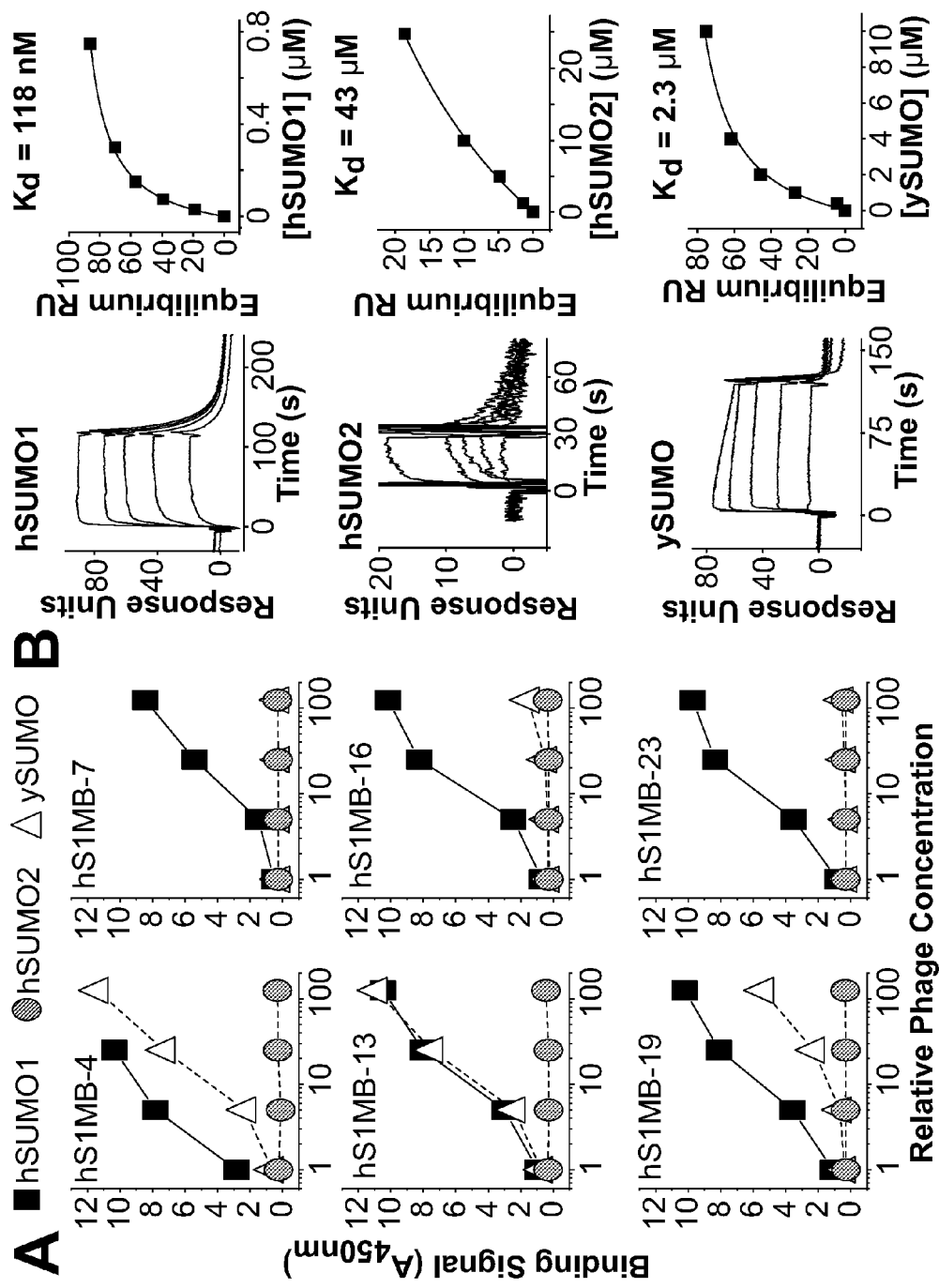
Figure 25A-B

B

| Clone | Scaffold | | | | FG Loop | | | | | | | | | Specificity Factor | |
|---|---|---|---|---|---|---|---|---|---|---|---|---|---|---|---|
| | 31 | 33 | 73 | 75 | 76 | 78 | 79 | 80 | 81 | 82 | 83 | 84 | 85 | | |
| hS1MB-22 | H | A | Y | F | Y | – | Y | D | I | F | Y | S | D | 0.6 | Low Specificity (0-10) |
| hS1MB-21 | H | G | Y | Y | Y | – | Y | Y | – | F | Y | A | L | 0.7 | |
| hS1MB-13 | Y | A | Y | Y | H | – | Y | D | – | Y | F | A | F | 1.4 | |
| hS1MB-14 | H | H | Y | Y | Y | – | Y | N | – | F | F | A | D | 2.6 | |
| hS1MB-15 | Y | D | Y | Y | Y | – | D | D | – | Y | Y | A | D | 2.9 | |
| hS1MB-12 | Y | E | F | Y | H | – | Y | D | – | Y | Y | A | F | 4.4 | |
| hS1MB-19 | H | G | Y | Y | Y | L | Y | D | – | F | Y | A | V | 8.0 | |
| hS1MB-4 | H | E | Y | Y | Y | – | H | E | – | F | F | Y | A | 10.5 | Moderate Specificity (10-100) |
| hS1MB-3 | H | A | Y | Y | H | – | Y | D | – | F | F | L | D | 12.3 | |
| hS1MB-11 | N | A | Y | Y | Y | – | Y | D | – | F | F | V | D | 13.1 | |
| hS1MB-23 | H | E | Y | Y | H | – | H | D | – | F | Y | A | F | 52.5 | |
| hS1MB-7 | Y | E | – | F | D | – | H | D | – | Y | Y | S | D | >100 | High Specificity (>100) |
| hS1MB-16 | H | D | Y | Y | N | – | Y | D | – | F | F | A | Y | >100 | |
| hS1MB-17 | Y | E | S | Y | N | – | Y | D | – | Y | Y | A | V | >100 | |
| hS1MB-18 | Y | E | F | Y | D | – | V | E | – | Y | V | S | Y | >100 | |
| hS1MB-20 | H | S | Y | Y | D | – | – | D | – | Y | I | A | D | >100 | |

Figure 26B

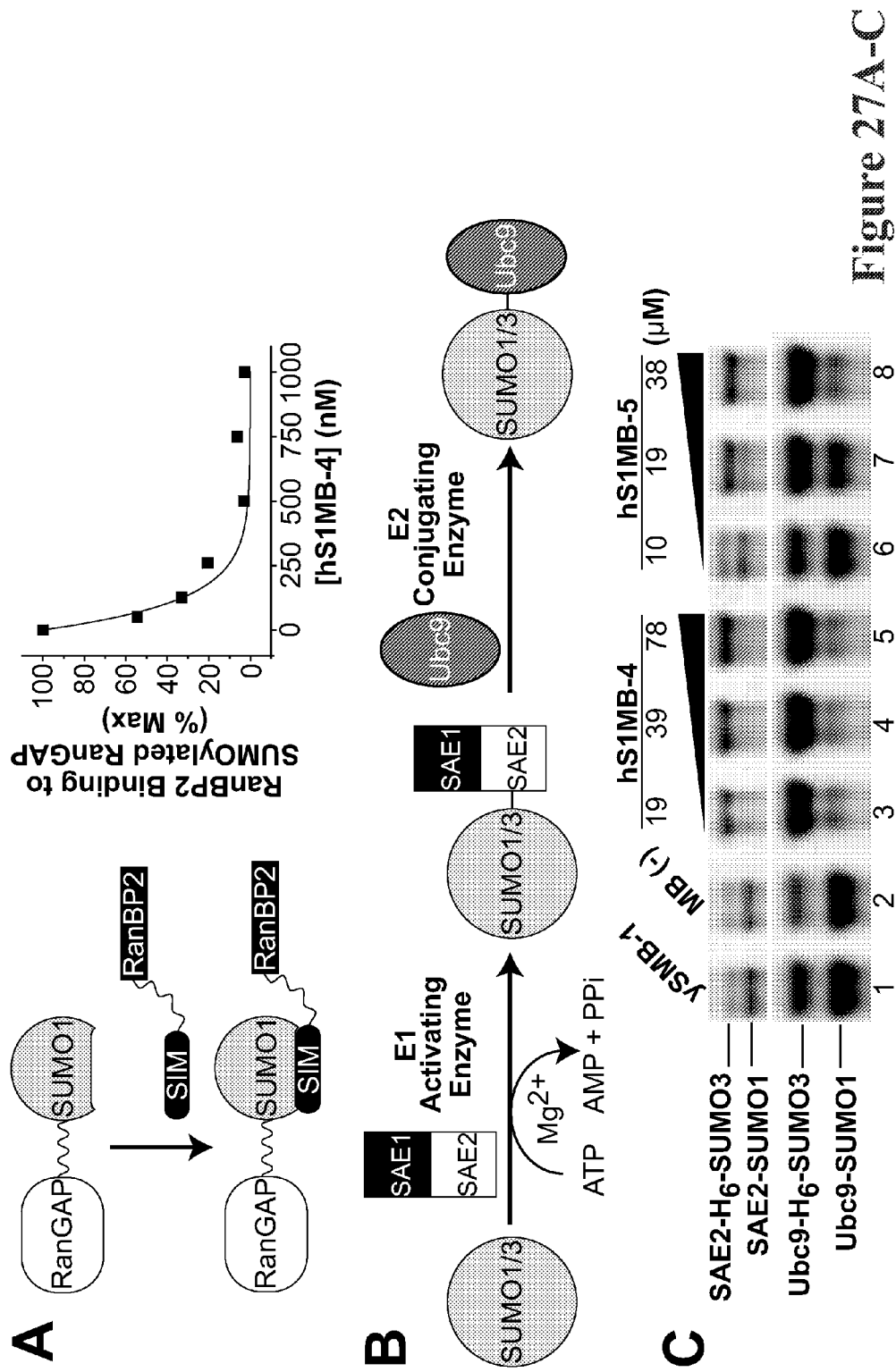
Figure 27A-C

A
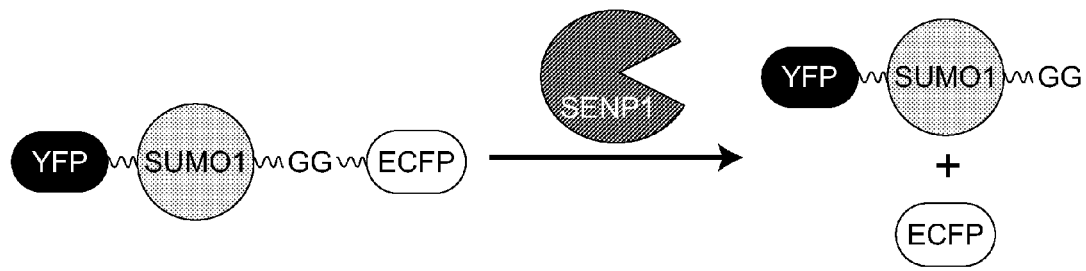
B
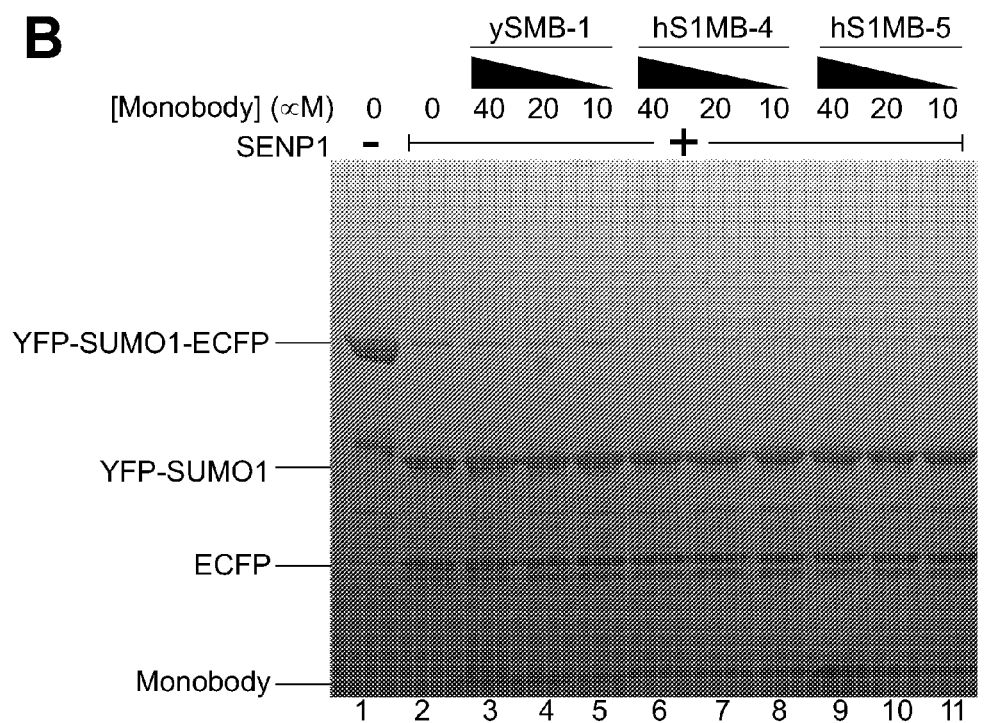
Figure 29A-B

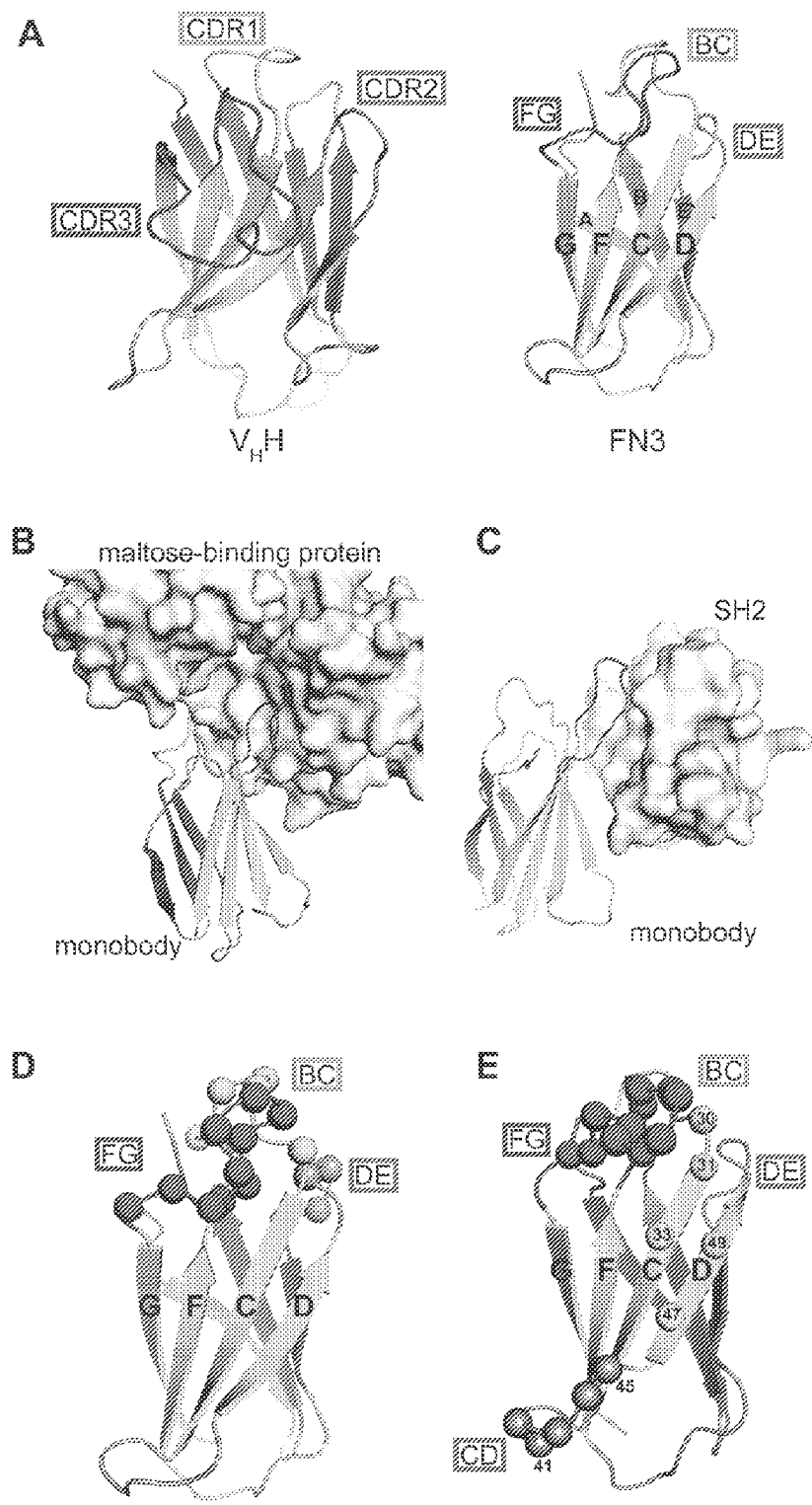
Figure 30A-E

Figure 31A-B

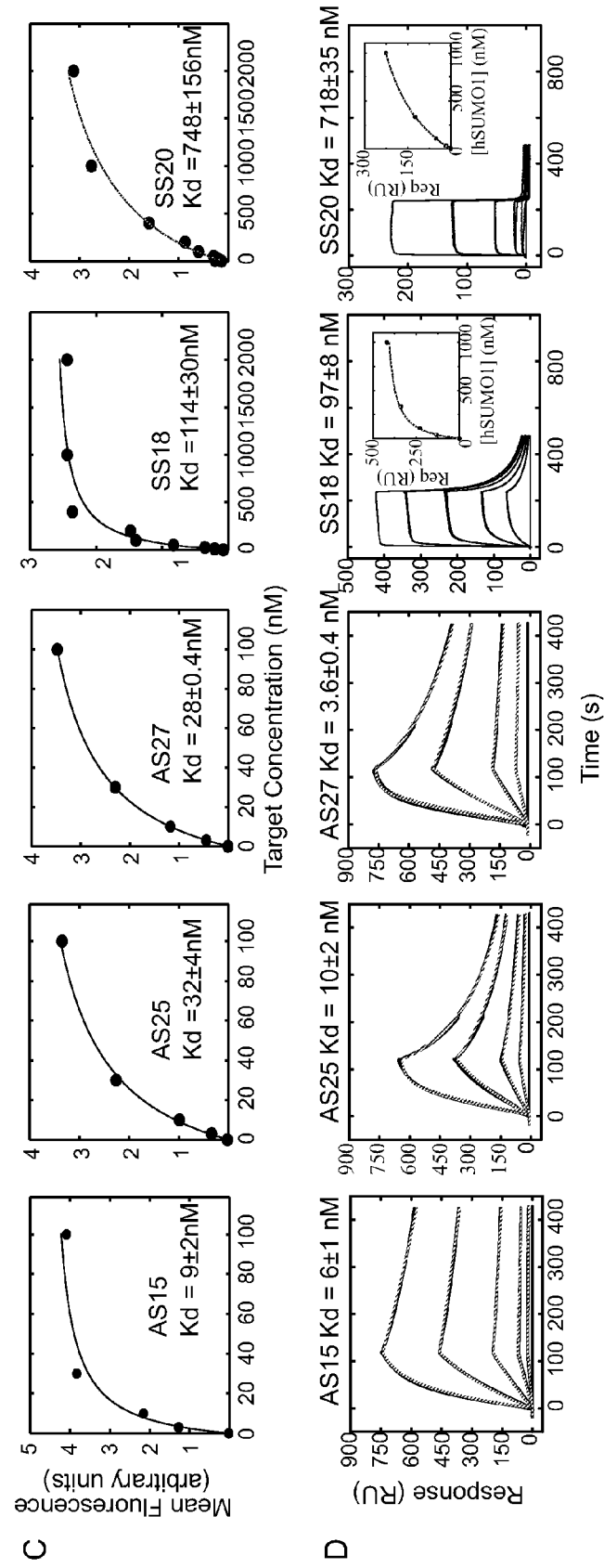
Figure 31C-D

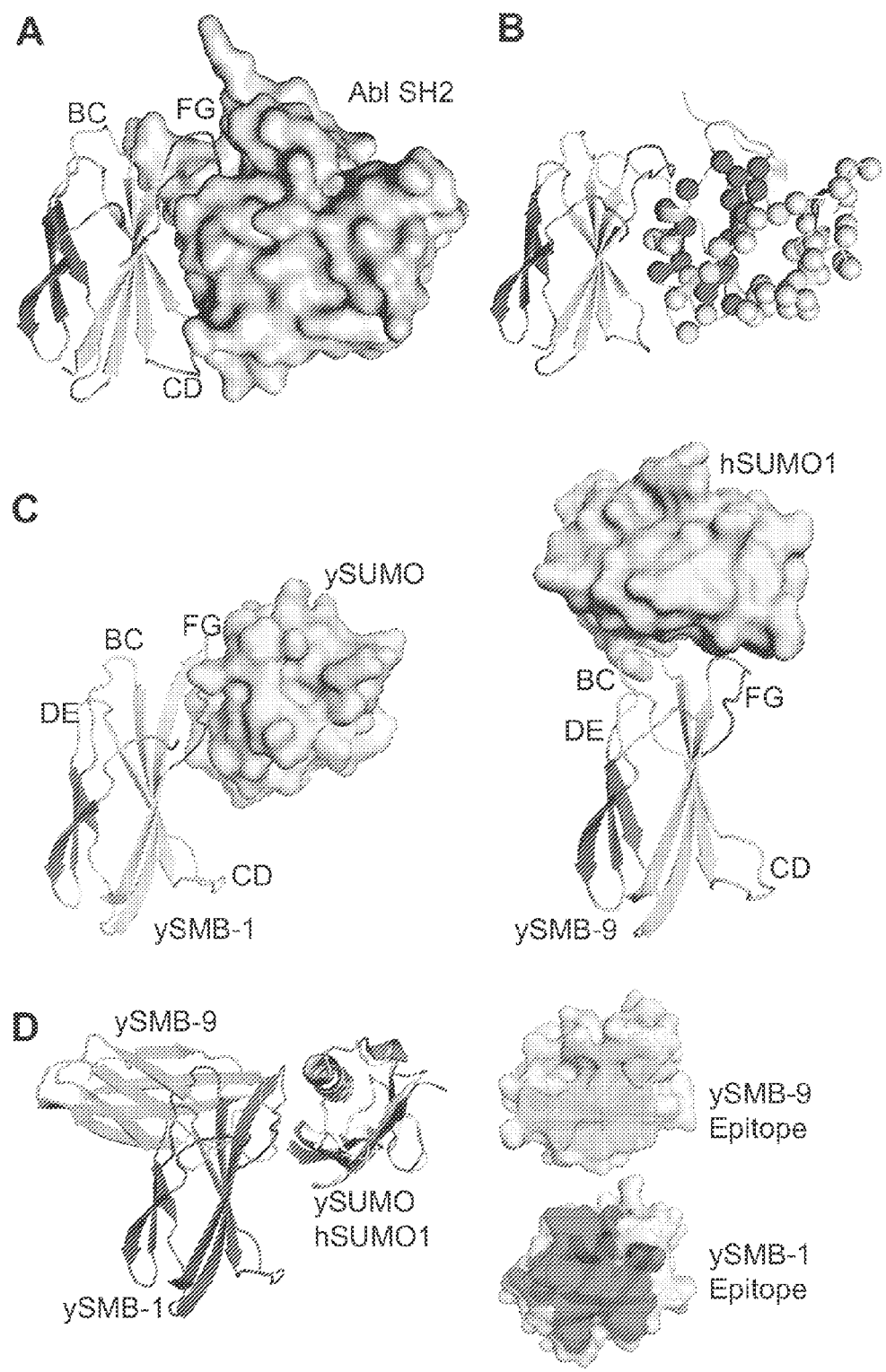
Figure 32A-D

FIBRONECTIN CRADLE MOLECULES AND LIBRARIES THEREOF

STATEMENT OF RIGHTS TO INVENTIONS MADE UNDER FEDERALLY SPONSORED RESEARCH

Part of this invention was made with government support under contract R01-GM72688 and U54 GM74946 awarded by the National Institutes of Health to the University of Chicago. The government has certain rights in part of the invention.

CROSS-REFERENCE TO RELATED APPLICATIONS

This application is the national phase of PCT Application PCT/US2011/046160 having an international filing date of Aug. 1, 2011, entitled "Fibronectin Cradle Molecules And Libraries Thereof," which is related to U.S. Provisional Patent Application No. 61/369,160 filed on Jul. 30, 2010, U.S. Provisional Patent Application No. 61/369,203 filed on Jul. 30, 2010, U.S. Provisional Patent Application No. 61/369,222 filed on Jul. 30, 2010, U.S. Provisional Patent Application No. 61/474,632 filed on Apr. 12, 2011, and U.S. Provisional Patent Application No. 61/474,648 filed on Apr. 12, 2011. Each of the foregoing applications is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 636092109300SeqList.txt, date recorded: Jun. 20, 2013, size: 335,659 bytes).

TECHNICAL FIELD

The present application relates to novel Fibronectin Type III domain (FnIII) polypeptides and the methods of making and using such FnIII polypeptides. More specifically, the present invention relates to a library of FnIII polypeptides using the CD and the FG loops of a number of FnIII domains (e.g., FnIII$^{07}$, FnIII$^{10}$ and FnIII$^{14}$) together with the surface exposed residues of the beta-sheet.

BACKGROUND ART

Scaffold based binding proteins are becoming legitimate alternatives to antibodies in their ability to bind specific ligand targets. These scaffold binding proteins share the quality of having a stable framework core that can tolerate multiple substitutions in the ligand binding regions. Some scaffold frameworks have immunoglobulin like protein domain architecture with loops extending from a beta sandwich core. A scaffold framework core can be synthetically engineered and used to form a library comprising different sequence variants. The sequence diversity of such libraries is typically concentrated in the exterior surfaces of the proteins such as loop structures or other exterior surfaces that can serve as ligand binding regions.

The fibronectin type III domain (FnIII) has been established as an effective non-antibody "alternative" scaffold for the generation of novel binding proteins. A member of the immunoglobulin superfamily, FnIII has three surface exposed loops at one end of the molecule which are analogous to antibody complementarity determining regions (CDRs). Engineering strategies using this scaffold are based on combinatorial libraries created by diversifying both the length and amino acid sequence of these surface loops. From such libraries, FnIII variants capable of binding to a target of interest can be isolated using various selection methods. The FnIII scaffold offers many advantages compared to conventional antibodies or fragments thereof because it lacks disulfide bonds, can be readily and highly expressed in bacterial systems, and is relatively small. However, a need exists for improved FnIII based polypeptides and methods of producing libraries of such polypeptides.

SUMMARY OF THE INVENTION

The present invention is based on the unexpected discovery that modifications to a beta sheet of a FnIII polypeptide in addition to modifications to at least one loop region of the FnIII based polypeptide result in an FnIII based binding molecule with improved binding ability for a target molecule. The improved binding is a result of increased surface area available for binding to a target molecule by using amino acid residues in the beta sheet to form part of the binding surface and to bind to a target molecule. Modifications to the beta sheets can also be used to distinguish targets. The invention pertains to modifications in the beta strand and loop of all FnIII molecules, e.g., FnIII$^{07}$, FnIII$^{10}$ and FnIII$^{14}$. In particular, the invention pertains to modifications in F and/or C beta strands and modifications in the FG loop and the CD loop of FnIII molecules, e.g., FnIII$^{07}$, FnII$^{10}$ and FnIII$^{14}$ Accordingly, in one aspect, the invention pertains to an FnIII domain-based cradle polypeptide comprising one or more amino acid substitutions in at least a loop region and at least a non-loop region.

In some embodiments, the cradle polypeptide may comprise amino acid substitutions in both the beta strands in conjunction with substitutions in the AB loop, the BC loop, the CD loop, the DE loop, and/or the FG loop of FnIII. In some embodiments the cradle polypeptide may comprise amino acid substitution in beta strand C, beta strand D, beta strand F and/or beta strand G. In some embodiments the cradle polypeptide may comprise one or more amino acid substitutions in two loop regions and/or two non-loop regions, wherein the non-loop regions may be the beta strands C and F, and the loop regions may be the CD and FG loops. In some embodiments the one or more amino acid substitutions may be introduced to the cradle residues in the beta strands. In some embodiments the cradle polypeptide may further comprise an insertion and/or deletion of at least one amino acid in at least one loop and/or non-loop region. In some embodiments the cradle polypeptide may further comprise an insertion and/or deletion of at least one amino acid in two loop regions and/or two non-loop regions, wherein the non-loop regions may be the beta strands C and F, and the loop regions may be the CD and FG loops. In some embodiments the FnIII domain may be the 1$^{st}$, 2$^{nd}$, 3$^{rd}$, 4$^{th}$, 5$^{th}$, 6$^{th}$, 7$^{th}$, 8$^{th}$, 9$^{th}$, 10$^{th}$, 11$^{th}$, 12$^{th}$, 13$^{th}$, 14$^{th}$, 15$^{th}$ or 16$^{th}$ FnIII domain of human fibronectin. In some embodiments, the one or more amino acid substitutions in the non-loop region may not change the structure of the FnIII domain scaffold and/or the shape of the loop regions. In some embodiments, the one or more amino acid substitutions in the non-loop region may exclude the non-cradle residues.

In some embodiments, loop CD may be about 3-11, about 4-9, or 5 residues in length, wherein loop FG may be about 1-10, 5 or 6 residues in length. Position 1 of the FG loop may be a Gly residue, position 2 may be a Leu, Val, or Ile residue, position 3 may be a charged or polar residue, position 4 may be a Pro residue, position 5 may be a Gly residue, and position 6 may be a polar residue. In some embodiments, positions 3 and/or 5 of the loop may be a Gly residue.

In some embodiments, the beta strand lengths may be about 6-14, about 8-11, or 9 residues for beta strand C and for beta strand F about 8-13, about 9-11, or 10 residues. In some embodiments, the residue at positions 2, 4, and 6 of the C beta strand may be a hydrophobic residue, and positions 1, 3, 5, and 7-9 of the C beta strand may be altered relative to the wild type sequence, wherein the residue at position 1 of the C beta strand may be selected from the group consisting of Ala, Gly, Pro, Ser, Thr, Asp, Glu, Asn, Gln, His, Lys, and Arg. The residue at position 3 of the C beta strand may be a hydrophobic residue, or may be selected from the group consisting of Ile, Val, Arg, Leu, Thr, Glu, Lys, Ser, Gln, and His. Position 5, 7, 8, and 9 of the C beta strand may be selected from the group consisting of Ala, Gly, Pro, Ser, Thr, Asp, Glu, Asn, Gln, His, Lys, and Arg.

In some embodiments, the residue at positions 1, 3, 5, and 10 of the F beta strand may be altered relative to the wild type sequence, wherein the residues at positions 1, 3, 5, and 10 of the F beta strand may be individually selected from the group consisting of Ala, Gly, Pro, Ser, Thr, Asp, Glu, Asn, Gln, His, Lys, and Arg. The residue at positions 2, 4, and 6 of the F beta strand may be a hydrophobic residue. The residue at position 7 of the F beta strand may be a hydrophobic residue, or may be selected from the group consisting of Arg, Tyr, Ala, Thr, and Val. The residue at position 8 of the F beta strand may be selected from the group consisting of Ala, Gly, Ser, Val, and Pro. The residue at position 9 of the F beta strand may be selected from the group consisting of Val, Leu, Glu, Arg, and Ile.

In some embodiments the cradle polypeptide may comprise a substitution that corresponds to a substitution in one or more of the amino acids at positions 30, 31, 33, 35, 37-39, 40-45, 47, 49, 67, 69, 71, 73, 75, 76, 77, 78, 79, 80, 81, 82, 83, 84, 85, and/or 86 of SEQ ID NO:1. In some embodiments the cradle polypeptide may comprise amino acid substitution in one or more of the amino acids at positions 33, 35, 37, 39, 40, 41, 42, 43, 44, 45, 46, 47, 48, 70, 72, 74, 76, 79, 80, 81, 82, 83, 84 and/or 85 of SEQ ID NO:97. In some embodiments the cradle polypeptide may comprise amino acid substitution in one or more of the amino acids at positions 31, 33, 35, 37, 39, 40, 41, 42, 43, 44, 66, 68, 70, 72, 75, 76, 77, 78, 79, 80 and/or 81 of SEQ ID NO:129. In some embodiments the cradle polypeptide may comprise an amino acid sequence set forth in SEQ ID NOs: 468, 469 and 470. In some embodiments the cradle polypeptide may be modified by inserting or deleting 1, 2, 3, 4, 5, 6, 7, 8, 9, 10, 20 or more amino acids, or any range derivable therein, in an FnIII loop. In some embodiments, substitutions in loops AB, CD, and EF may be specifically excluded, either individually or in various combinations. In some embodiments modifications in the bottom loop(s) may be limited to 1, 2, 3, 4, or 5 or fewer substitutions, insertions, and/or deletions. In some embodiments the amino acid substitutions may contribute to the binding specificity of the cradle polypeptide.

Also provided herein is a chimeric cradle polypeptide comprising one or more amino acid substitutions in at least a loop region and at least a non-loop region, wherein part of the cradle polypeptide is replaced by a non-FnIII domain polypeptide that enhances the binding affinity of the cradle polypeptide for a target molecule. In some embodiments the chimeric cradle polypeptide may comprise all or part of a complementarity determining region (CDR) of an antibody or a T-cell receptor, wherein the CDR may be a CDR1, CDR2 or CDR3 of a single domain antibody. In some embodiments the single domain antibody may be a nanobody. In some embodiments the CDR may replace part or all of the AB, BC, CD, DE, EF or FG loop.

Further provided herein is a multispecific cradle polypeptide comprising multiple copies of one or more monomer cradle polypeptides disclosed herein, wherein the monomer cradle polypeptides may be linked by a linker sequence. In some embodiments the linker sequence may be selected from the group consisting of GGGGSGGGGS (SEQ ID NO: 471), GSGSGSGSGS (SEQ ID NO: 472), PSTSTST (SEQ ID NO: 473) and EIDKPSQ (SEQ ID NO: 474).

In another aspect, the present invention provides a cradle library comprising a plurality of cradle polypeptides having amino acid substitutions in both the beta strands in conjunction with substitutions in the AB loop, the BC loop, the CD loop, the DE loop, and/or the FG loop of FnIII. In some embodiments the cradle polypeptides may comprise one or more amino acid substitutions corresponding to amino acid positions 30, 41, 42, 43, 44, 45, 76, 77, 78, 79, 80, 81, 82, 83, 84 and/or 85 of SEQ ID NO:1. In some embodiments the cradle polypeptides may further comprise one or more amino acid substitutions corresponding to amino acid positions 15, 16, 17, 18, 19, 20, 21, 22, 23, 24, 25, 26, 27, 28, 29, 32, 34, 35, 36, 37, 38, 39, 40, 46, 48, 50, 51, 52, 53, 54, 55, 56, 57, 58, 59, 60, 61, 62, 63, 64, 65, 66, 67, 68, 69, 70, 72, 74, 75, 86, 87, 88, 89, 90, 91, 92, 93 and/or 94 of SEQ ID NO:1. In some embodiments the cradle polypeptides may be at least 50%, 60%, 70%, 80%, or 90% identical to SEQ ID NO:1. In some embodiments the cradle polypeptides may further comprise an insertion of at least 1, 2, or about 2-25 amino acids in at least one loop region. In some embodiments the cradle polypeptides may comprise a deletion of at least 1, 2 or about 2-10 amino acids in at least one loop region. In some embodiments the cradle polypeptides may comprise a deletion of at least 2 amino acids in two loop regions. In some embodiments the cradle polypeptides may comprise at least 1 amino acid insertion and 1 amino acid deletion in at least one loop region. In some embodiments the cradle polypeptides may comprise an insertion and deletion of at least 1 amino acid in the same loop region. In some embodiments the cradle library may be pre-selected to bind a target molecule. In some embodiments the cradle polypeptides may comprise an amino acid sequence selected from the group consisting of SEQ ID NOs: 3, 79, 86 and 468-470. In some embodiments the cradle library may contain 10, 100, 1000, $10^4$, $10^5$, $10^6$, $10^7$, $10^8$, $10^9$, $10^{10}$, $10^{11}$, $10^{12}$, $10^{13}$, $10^{14}$, $10^{15}$ or more different polypeptide variants, including all values and ranges there between. In some embodiments, the amino acid sequence of the FnIII domain from which the library is generated is derived from the wild type amino acid sequences of the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or $16^{th}$ FnIII domain of human fibronectin. In some embodiments, the cradle polypeptide sequences may be a a loop FG comprising 5 or 6 residues, a loop CD comprising 3 to 11 residues, a beta strand C comprising 6 to 14 residues, a beta F comprising 8 to 13 residues, or a combination of the loops and strands.

Further provided herein are polynucleotides encoding one or more cradle polypeptide described herein. In some embodiments the polynucleotide may be an expression cassette or an expression construct. In some embodiments the expression construct may be capable of expressing the encoded polypeptide in a host cell, such as a prokaryotic or eukaryotic cell line or strain. In some embodiments the expression construct may be functional in one or more polypeptide expression systems known in the art. In some embodiments the expression construct may be functional in bacteria, yeast, insect cells, mammalian cells or the like.

Further provided herein is a method of producing a cradle polypeptide by: a) expressing a polynucleotide encoding a cradle polypeptide disclosed herein in a host cell; and b) isolating and/or purifying the expressed cradle polypeptide. In some embodiments the method may include the engineering of various amino acids substitutions, deletions, and/or insertions described herein.

In a further aspect, provided herein is a method of forming a cradle library of FnIII domain polypeptides useful in screening for the presence of one or more polypeptides having a selected binding or enzymatic activity, which comprises: (i) aligning loops FG and CD, and preferably beta strands C and F amino acid sequences in a collection of native FnIII domain polypeptides, (ii) segregating the aligned loop and beta strand sequences according to length, (iii) for a selected loop, beta strand, and length from step (ii), performing positional amino acid frequency analysis to determine the frequencies of amino acids at each position, (iv) for each loop, beta strand, and length analyzed in step (iii), identifying at each position a conserved or selected semi-conserved consensus amino acid and other natural-variant amino acids, (v) for at least one selected loop, beta strand, and length, forming: (1) a library of mutagenesis sequences expressed by a library of coding sequences that encode, at each loop position, the consensus amino acid, and if the consensus amino acid has a occurrence frequency equal to or less than a selected threshold frequency of at least 50%, a single common target amino acid and any co-produced amino acids, or (2) a library of natural-variant combinatorial sequences expressed by a library of coding sequences that encode at each position, a consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents, (vi) incorporating the library of coding sequences into framework FnIII coding sequences to form an FnIII expression library, and (vi) expressing the FnIII polypeptides of the expression library.

In some embodiments, the cradle library may include cradle polypeptides which may comprise: (a) regions A, AB, B, C, CD, D, E, EF, F, and G having wildtype amino acid sequences of a selected native FnIII polypeptide, and (b) loop regions FG, CD, and/or beta strands C and F, having selected lengths, wherein at least one selected loop and/or beta strand region of a selected length contains a library of mutagenesis sequences expressed by a library of coding sequences that encode, at each loop position, a conserved or selected semi-conserved consensus amino acid and, if the consensus amino acid has an occurrence frequency equal to or less than a selected threshold frequency of at least 50%, a single common target amino acid and any co-produced amino acids.

In some embodiments, the cradle polypeptides may comprise: (a) regions A, AB, B, C, CD, D, E, EF, F, and G having wildtype amino acid sequences of a selected native FnIII polypeptide, and (b) loop regions FG, CD, and non-loop regions C and F having selected lengths, where at least one selected loop and/or beta strand region of a selected length contains a library of natural-variant combinatorial sequences expressed by a library of coding sequences that encode at each position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

In some embodiments, the cradle library may have a given threshold of 100%, unless the amino acid position contains only one dominant and one variant amino acid, and the dominant and variant amino acids are chemically similar amino acids, in which case the given threshold may be 90%. In some embodiments, the cradle library may contain all natural variants or their chemical equivalents having at least some reasonable occurrence frequency, e.g., 10%, in the in the selected loop, beta strand, and position.

In some embodiments, the cradle library may have at least one or more loops FG and CD and/or beta-strands C and F which comprise beneficial mutations identified by screening a natural-variant combinatorial library containing amino acid variants in the loops, beta strands, or combinations thereof. In some embodiments, one or more members of the library may be then isolated from other members of the library and analyzed. In some embodiments, the cradle library may be pre-selected to bind a target and those preselected members are then further diversified in selected amino acid position to generate a targeted cradle library that is subsequently screened for a particular characteristic or property.

Further provided herein is a method of identifying a cradle polypeptide having a desired binding affinity to a target molecule, comprising: a) reacting a cradle library of FnIII domain polypeptides disclosed herein with the target molecule, and b) screening the cradle library of FnIII domain polypeptides to select those having a desired binding affinity to the target molecule. In some embodiments, after conducting the binding assay(s) one or more cradle polypeptides may be selected that have a particular property, such as binding specificity and/or binding affinity to a target. In some embodiments, the amino acid or nucleic acid sequence of one or more of the selected library members may be determined using conventional methods. The sequence of the selected FnIII polypeptide(s) may then be used to produce a second cradle library that introduces further substitution of the selected sequences. The second cradle library may then be screened for FnIII polypeptides having a particular property. The process can be repeated 1, 2, 3, 4, 5, 6, 7, 8, 9, 10 or more times. Additional iterations may enrich the cradle library as well as potentially include other variants.

In some embodiments, the method may further comprise conducting a first screen of a cradle library having amino acid substitutions in only FnIII loops or only FnIII beta strands and conducting a second screen using substitutions in only FnIII loops or only FnIII beta strands. In some embodiments, the first screen may use only substitutions in the FnIII loops and the second screen may use only substitutions in the FnIII beta-strands. In some embodiments, the second screen may use substitutions in both FnIII loops and beta-strands. In some embodiments, the FnIII amino acid residues varied in the first screen may or may not be varied in the second screen.

Also provided herein is a method of detecting a target molecule which comprises contacting a sample containing the target with an FnIII binding domain that specifically binds the target. Further provided herein is a method of producing an FnIII variant comprising: (a) expressing a polypeptide comprising an amino acid sequence; and (b) isolating and/or purifying the expressed variant FnIII domain from a host cell expressing the variant FnIII.

Further provided herein is a cradle polypeptide selected using the method of identifying a cradle polypeptide having a desired binding affinity to a target molecule disclosed herein. In some embodiments, the cradle polypeptide may comprise an amino acid sequence selected from the group consisting of SEQ ID NOs:4-78, 80-85, 87-96, 98, 99, 101-128, 130-141, 143, 145-147, 149-159, 161-199, 201-238 and 240-277.

In still a further aspect, the present invention provides a kit comprising a plurality of cradle polypeptides as described herein. Also provided herein is a kit comprising a plurality of polynucleotides encoding the FnIII cradle polypeptides as disclosed herein. Further provided herein is a kit comprising a cradle library and/or the polynucleotides encoding the cradle library as disclosed herein.

BRIEF DESCRIPTION OF THE DRAWINGS

FIG. 4A: Sheet C; FIG. 4B: Loop CD; FIG. 4C: Sheet F; FIG. 4D: Loop FG.

FIG. 5A: Sheet C, length 9; FIG. 5B: Sheet C, length 10; FIG. 5C: Loop CD, length 4; FIG. 5D: Loop CD, length 5; FIG. 5E: Loop CD, length 6; FIG. 5F: Sheet F, length 10; FIG. 5G: Loop FG, length 5; FIG. 5H: Loop FG, length 6.

FIG. 6A: Cradle shown in white on a ribbon diagram of FnIII$^{10}$; FIG. 6B: Surface representation of the Cradle; FIG. 6C: Top Side shown in white on a ribbon diagram of FnIII$^{10}$; FIG. 6D: Surface representation of the Top Side; FIG. 6E: Bottom Side shown in white on a ribbon diagram of FnIII$^{10}$; FIG. 6F: Surface representation of the Bottom Side.

FIGS. 7A-B show the conservation of amino acid type in sheets C and F of FnIII$^{10}$ and indicates which residues are varied in the Cradle molecule and which ones were left as wild type. FIG. 7A: Ribbon diagram of FnIII$^{10}$ with the amino acids in sheets C and F numbered 1-19. The C$\alpha$ for each amino acid is shown as a sphere and the C$\beta$ is shown as a stick to indicate the direction of the amino acid R group. Varied amino acids are colored gray and unvaried are colored white. FIG. 7B: Table showing the amino acid type conservation for each position in sheets C and F.

FIGS. 9A-F describe the design of the Cradle library on FnIII$^{07}$, FnIII$^{10}$, and FnIII$^{14}$. FIG. 9A: Length distribution of loop CD; FIG. 9B: Length distribution of loop FG; FIG. 9C: Amino acid distribution in the sheets and loops. FIG. 9D: Alignment of cradle residues for FnIII$^{07}$, FnIII$^{10}$ and FnIII$^{14}$ (SEQ ID NOs: 468-470). Beta sheets are shown as white residues on a black background and loops are shown as black text. Cradle residues are shown in bold with X representing the amino acid distribution for the beta sheets and Y representing the amino acid distribution for the loops with the loop length range given as a subscript.

FIG. 9E: Alignment of FnIII$^{07}$, FnIII$^{10}$ and FnIII$^{14}$ (SEQ ID NOs:97, 100, 129) illustrating the cradle residues in beta sheets C and F and loops CD and FG. Beta sheets are shown as white residues on a black background and loops are shown as black text with Cradle residues shown in bold. FIG. 9F: Shown are the FnIII structural element residue ranges and FnIII cradle residues ranges.

FIGS. 10A-C show a shared epitope for a monobody and a SIM peptide and conservation of the SIM binding site in SUMO proteins. FIG. 10A: The structures of the ySMB-1 monobody bound to ySUMO (left) and a SIM peptide bound to hSUMO-1 15 (PDB ID 1Z5S) (right) are shown. Because there are no structures of natural SIM peptides in complex with ySUMO, the structure of a SIM peptide bound to hSUMO-1 is shown for comparison. FIG. 10B: An alignment of SIM binding site/ySMB-1 epitope residues in ySUMO, and two human homologs, hSUMO-1 and hSUMO-2 are shown (top left) (SEQ ID NOs:297-299). Residues are ranked according to their conservation score: residues identical in all 3 SUMO proteins (i), similar with a conservation score of 9 (ii), and similar with a conservation score of 8 (iii). Conservation scores were calculated using methods outlined by Livingstone and Barton, *Comput. Appl. Biosci.* (1993) 9:745-756 using the Jalview program (Clamp, et al., Bioinformatics (2004) 20:426-427). These scores reflect conservation of chemical and structural properties of side chains. The structure of ySUMO is shown (top right). FIG. 10C: A full sequence alignment of ySUMO, hSUMO-1 and hSUMO-2 is shown (SEQ ID NOs:300-302).

FIG. 11A: Shown is the structure of the ySMB-1/ySUMO interface. The ySUMO structure is shown as a surface with epitope residues shown as sticks. FIG. 11B: Shown is a sequence alignment (top) of ySMB-1 epitope residues in ySUMO and equivalent residues in hSUMO-1 and hSUMO-2 (SEQ ID NOs:297-299). Below, the residues of ySMB-1 varied in the SUMO-targeted library are listed. Interactions between ySMB-1 residues and ySUMO residues in the ySMB-1/ySUMO structure are indicated by lines. Below each ySMB-1 residue, the amino acids allowed at that position in the SUMO-targeted library are listed along with the degenerate codon used to introduce them in parentheses. FIG. 11C: Shown is a cartoon of the ySMB-1 structure with the positions varied in the SUMO-targeted library indicated.

FIG. 12A:

ySUMO (left) and hSUMO-1 (right) are shown with the ySMB-1 paratope structure modeled as if binding to each target. Monobody residue positions are shown as spheres corresponding to Cα atoms of indicated residue numbers. FG loop residues (75, 76, 78, 79, 80, 81, 82, 83, 84, and 85) and scaffold residues (31, 33, and 73) are indicated. In the center, a table is shown listing the amino acid diversities introduced at monobody positions in the SUMO-targeted library. Wildtype residues at each position are indicated in brackets. FIG. 12B: Shown are the amino acid sequences of monobodies recovered against ySUMO and hSUMO-1 as well as representative SPR binding traces (SEQ ID NOs: 303-318). Estimated dissociation constants from SPR are given for all clones. FIG. 12C: Shown are the sequence logo representations of 40 ySUMO monobodies and 44 hSUMO-1 monobodies. The wild-type sequence of ySMB-1 is shown above (SEQ ID NO:303). In this depiction, the relative height of individual letters reflects how frequently that amino acid is recovered at that position, the letters stacked at a given position are ordered from more frequently occurring to less frequently occurring, and the overall height of an individual stack reflects the overall level of sequence conservation at that position. Figures generated using WebLogo (Crooks, et al., *Genome Res.* (2004) 14:1188-1190; Schneider and Stephens, *Nucleic Acids Res.* (1990) 18:6097-6100).

FIG. 13 shows the rationale for scaffold residue preferences in ySUMO and hSUMO-1 monobodies. Contacts made by scaffold residues in the ySMB-1/ySUMO complex (left) and in a modeled ySMB-1/hSUMO-1 complex (right) are shown. A potential steric and electrostatic clash between R33 of the monobody scaffold and K25 of hSUMO-1 is circled.

FIGS. 14A-D show the specificity in ySUMO and hSUMO-1 binding monobodies. FIG. 14A: Amino Acid Sequences of Two Nearly Identical ySUMO and hSUMO-1 Monobodies are shown (SEQ ID NOs:303, 319-320). Monobody A was recovered as a hSUMO1 binder, and monobody B as a ySUMO binder. FIG. 14B: Phage ELISA data is shown for binding of Monobody A and B to ySUMO and hSUMO-1. Both ySUMO and hSUMO-1 were produced as GST fusion proteins. Binding to GST is shown as a negative control. FIG. 14C: Phage ELISA data for the binding of 32 hSUMO-1 monobodies to ySUMO, hSUMO-1, and hSUMO-2 is shown. All SUMO proteins were produced as GST fusions. Binding to GST is shown as a negative control. FIG. 14D: Sequence alignments of monobodies specific for hSUMO-1 and cross-reacting with ySUMO are shown in sequence logo format (see FIG. 13 legend for explanation of sequence logos). The wild-type ySMB-1 sequence is shown above. Clone numbers 1, 3, 4, 5, 6, 8, 9, 12, 13, 17, 18, 20, 21, 23, 31 and 32 in FIG. 25C were classified as cross-reactive. The remaining 16 clones were classified as specific.

FIGS. 15A-C show the representative binding data for monobodies generated from the cradle libraries. Phage ELISA signals of selected clones are shown. FIGS. 15 A, B and C show clones selected from the BL1 library with hSUMO1, human ubiquitin and Abl SH2 as a target, respectively. ELISA wells were coated with the cognate target. The left bars show data in the absence of a soluble target (which serves as a competitor), and the middle bars show data in the presence of a soluble competitor (100 nM for hSUMO1 and 200 nM for the others). The right bars show binding to wells containing no target (negative control).

FIGS. 16A-E show the sequences and properties of ySUMO-binding monobodies.

FIG. 16A: yeast SUMO (ySUMO) structure shaded by conservation score among ySUMO and hSUMO isoforms (Livingstone and Barton, supra, 1993). FIG. 16B: Schematic of the FnIII scaffold with beta strands A-G labeled and surface loops (BC loop, DE loop, and FG loop) diversified in monobody libraries. FIG. 16C: Amino acid sequences of variable loops of ySUMO-binding monobodies with $K_d$ values from SPR (SEQ ID NOs:321-329). FIG. 16D: SPR traces for ySMB-1 and ySMB-2 binding to ySUMO with kinetic parameters calculated from a bet fit (solid line) of the raw data (dashed line) to a 1:1 binding model. FIG. 16E: Epitopes of ySMB-1 and ySMB-2 mapped from NMR chemical shift perturbation shown on the ySUMO structure.

FIG. 19A: Binding of eight ySUMO-binding monobodies to ySUMO, hSUMO1 and hSUMO2 assayed using phage ELISA. Clone numbers are of the format ySMB-X in FIGS. 27C and 28. FIG. 19B: Equilibrium SPR measurements of ySMB-1 (left column) and ySMB-9 (right column) binding to ySUMO, hSUMO1 and hSUMO2. Equilibrium responses at multiple concentrations left panels) were fit with a simple 1:1 binding model (right panels).

FIGS. 20A-C show the crystal structure of the monobody ySMB-1/ySUMO complex. FIG. 20A: Top: ySUMO and ySMB-1 are shown with monobody paratope residues shown as sticks; FG loop residues and scaffold residues are indicated. ySUMO is shown in the same orientation as in FIG. 16E. Bottom: An alternative view with the monobody paratope depicted as a surface. FIG. 20B: Close-up of the ySMB-1/ySUMO interface. ySUMO (surface/sticks) is shown with residues comprising the hydrophobic center of the epitope and the charged/polar rim. Monobody paratope residues are shown as in (A). FIG. 20C: Left and Middle: comparison of the binding modes of ySMB-1 to ySUMO and the SIM of RanBP2 to hSUMO1. Both form intermolecular beta sheets with their SUMO targets (expanded box). Right: Overlay of the RanBP2 SIM and SIM mimicking monobody residues with the ySUMO surface shown.

FIGS. 21A-B show the ySMB-1/ySUMO interface analysis. FIG. 21A: Buried surface area contributed by each residue in the ySMB-1 paratope. FIG. 21B: Percent of total ySMB-1 and ySUMO buried surface area contributed by each amino acid type.

FIGS. 22A-F show the hSUMO1-binding monobodies from the SUMO-targeted library. FIG. 22A: Design of the SUMO-targeted cradle library. Left: ySMB-1 paratope residues (backbone sticks/spheres) are shown with FG loop and scaffold residues indicated. ySUMO (surface) is shown with ySMB-1 epitope residues as sticks. ySUMO residues F37, K38, K40, T43, L48, and R55 are completely conserved, H23, I35, I39, R47 and A51 are conservative substitution and N25, E34, F36, E50, and K54 are non-conservative substitution, according to conservation between ySUMO and hSUMOs. The residue types at each position in hSUMO1 and hSUMO2/3 are shown in parentheses. Right: Amino acid diversity used in the SUMO-targeted library. The wild-type ySMB-1 residue is in brackets. FIG. 22B: Amino acid sequences of hSUMO1-binding monobodies from the SUMO-targeted library. $K_d$ values from SPR are also shown. Representative SPR traces are shown. At bottom, sequences of an additional hSUMO1 binding monobody (hS1MB-22) and a very similar ySUMO binding monobody (ySMB-ST6) recovered from the SUMO targeted library are shown (SEQ ID NOs:303, 416-427). FIG. 22C: Epitope of hS1MB-4 mapped from chemical shift perturbation shown on the hSUMO1 structure. Data are represented using the same scheme as in FIG. 16E. FIG. 22D: (SEQ ID NO:303) Sequence conservation of ySUMO- and hSUMO1-binding monobodies shown as sequence logos (Schneider and Stephens, supra, 1990; Crooks, et al., supra, 2004). The height of individual letters reflects how frequently that amino acid was recovered at that position, the letters stacked at a position are ordered from most to least frequently occurring and the overall height of a stack reflects the overall conservation level at that position. FIG. 22E: Binding of hS1MB-22 and ySMB-ST6 to ySUMO and hSUMO1 measured by phage ELISA. FIG. 22F: Contacts made by scaffold residues in the ySMB-1/ySUMO complex (left) and in a modeled ySMB-1/hSUMO-1 complex (right). Monobody (sticks) and SUMO residues (surface/sticks) are indicated. The ySMB-1/hSUMO1 complex was modeled by superposition of the ySUMO portion of the ySMB-1 complex with the hSUMO1 structure.

FIG. 24 shows the epitope mapping ELISA of hSUMO1-binding monobodies. Binding of sixteen phage-displayed hSUMO1-binding monobodies to hSUMO1 measured by ELISA in the presence or absence of 1 µM hS1MB-4 competitor. Clone numbers correspond to those of the format hS1MB-X in FIGS. 22B and 26.

FIGS. 25A-B shows the specificity of hSUMO-1-binding monobodies. FIG. 25A: Binding curves derived from phage ELISA of six hSUMO1-binding monobodies binding to ySUMO, hSUMO1 and hSUMO2. Data for additional monobodies are shown in FIG. 26A. Serial dilutions of phage containing culture supernatant (titer ~$10^8$) were used. Absorbance values were scaled to 1 cm path-length. FIG. 25B: Equilibrium SPR measurements of hS1MB-4 binding to ySUMO, hSUMO1 and hSUMO2. Equilibrium responses at multiple concentrations (left panels) were fit to a simple 1:1 binding model (right panels).

FIGS. 26A-B show the selectivity of hSUMO1-binding monobodies. FIG. 26A: Binding curves derived from phage ELISA of 10 hSUMO-binding monbodies binding to ySUMO, hSUMO1 and hSUMO2. Data for six additional monobodies are shown. FIG. 26B: The amino acid sequences of 16 hSUMO1-binding monobodies are shown (SEQ ID NOs:433-448) and grouped according to their specificity factor for hSUMO1 over ySUMO. The specificity factor is the ratio of apparent affinity measured for hSUMO1 to that for ySUMO in the titration phage ELISA experiment shown in FIG. 25A and FIG. 26A.

FIGS. 27A-C show the effects of hSUMO1-specific monobodies on SUMO/SIM interactions and SUMOylation. FIG. 27A: Left: Schematic of SIM-containing RanBP2's interaction with SUMOylated RanGAP (modified with hSUMO1). Right: Binding of RanBP2 to SUMO1-RanGAP in the presence of monobody hS1MB-4 in ELISA. FIG. 27B: Schematic of the E1- and E2-dependent steps in the SUMOylation cascade. Covalently linked intermediates are formed sequentially between SUMO and E1 (SAE1/2) and E2 (Ubc9). FIG. 27C: SDS-PAGE of SUMOylation reactions carried out in the presence of hS1MB-4 (lanes 3-5) and hS1MB-5 (lanes 6-8). Lanes 1 and 2 are negative controls with ySMB-1 and without a monobody, respectively. All reactions contained SAE1/2, Ubc9 and both hSUMO1 and hSUMO3 as substrates. Bands corresponding to the SAE2-SUMO and Ubc9-SUMO covalent intermediates for each isoform are indicated. $His_6$-tagged SUMO3 (H6-SUMO3) was used to distinguish hSUMO1 from hSUMO3 on the gel.

FIGS. 29A-B show the monobody effects on deSUMOylation. FIG. 29A: Schematic of the deSUMOylation assay in which a YFP-hSUMO1-ECFP fusion protein is cleaved by SENP1 at the hSUMO1 C-terminal di-glycine sequence. FIG. 29B: SDS-PAGE analysis of deSUMOylation reactions carried out in the presence of hSMB-4 (lanes 6-8) or hS1MB-5 (lanes 9-11). Controls are also shown without SENP1 or a monobody (lane 1) or with SENP1 cleavage carried out in the presence of the ySUMO specific ySMB-1 (lanes 2-5). Bands corresponding to the YFP-hSUMO1-ECFP fusion and the YFP-hSUMO1 and ECFP cleavage products are indicated as well as the band corresponding to the monobodies.

FIGS. 30A-E shows monobody library design. FIG. 30A: A comparison of the VHH scaffold (left) and the FnIII scaffold (right). The two beta sheet regions are colored in dark grey and light grey, respectively. The CDR regions of the VHH and the corresponding loops in FnIII are colored in greyscale and labeled. The beta strands of FnIII are labeled with A-G. FIG. 30B: The structure of a monobody bound to its target, maltose-binding protein (Gilbreth, R. N., et al., *J Mol Biol* (2008) 381:407-418). The monobody is depicted in the same manner as in A. Only a portion of maltose-binding protein is shown as a surface model. FIG. 30C: The structure of a monobody bound to the Abl SH2 domain depicted as in B (Wojcik, et al., supra, 2010). FIG. 30D: The locations of diversified residues in the cradle library shown as spheres on the FnIII structure. FIG. 30E: The locations of diversified residues in the cradle library.

FIGS. 31A-D show monobody library designs and generated clones Amino acid sequences of monobodies generated from the new cradle library (FIG. 31A) (SEQ ID NOs:449-457) and the "loop only" library (FIG. 31B) (SEQ ID NOs:458-467). "X" denotes a mixture of 30% Tyr, 15% Ser, 10% Gly, 5% Phe, 5% Trp and 2.5% each of all the other amino acids except for Cys; "B", a mixture of Gly, Ser and Tyr; "J", a mixture of Ser and Tyr; "O", a mixture of Asn, Asp, His, Ile, Leu, Phe, Tyr and Val; "U", a mixture of His, Leu, Phe and Tyr; "Z", a mixture of Ala, Glu, Lys and Thr. FIG. 31C: Binding measurements by yeast surface display of representative monobodies. The mean fluorescence intensities of yeast cells displaying a monobody are plotted as a function of the concentration of the target as indicated in panel A. FIG. 31D: SPR sensorgrams for target binding of representative monobodies. The thin lines show the best global fit of the 1:1 binding model. The insets show dose-dependence analysis of the sensorgrams and the best fit of the 1:1 binding model.

FIGS. 32A-D show the crystal structures of monobodies originating from the two libraries. The structures are shown with the monobodies in similar orientations. FIG. 32A: The structure of the SH13 monobody bound to the Abl SH2 domain depicted as in FIG. 30C. FIG. 32B: NMR-based epitope mapping of the SH13/Abl SH2 complex. The spheres show residues of Abl SH2 whose amide resonances were strongly affected (shift of >1.5 peak width), weakly affected (shift of 0.5-1.5 peak width) and minimally affected (shift of <0.5 peak width) by monobody binding, respectively. FIG. 32C: The crystal structures of the ySMB-1/ySUMO complex (left) and ySMB-9/hSUMO1 complex (right). FIG. 32D: The two monobodies bound to equivalent epitopes on the targets using distinct modes. The left panel shows a comparison of the two crystal structures shown in C with ySUMO and hSUMO1 superimposed. The right panel shows ySUMO and hSUMO1 in equivalent orientations with the epitopes for the indicated monobodies.

DETAILED DESCRIPTION OF THE INVENTION

I. Definitions

Figure 1:
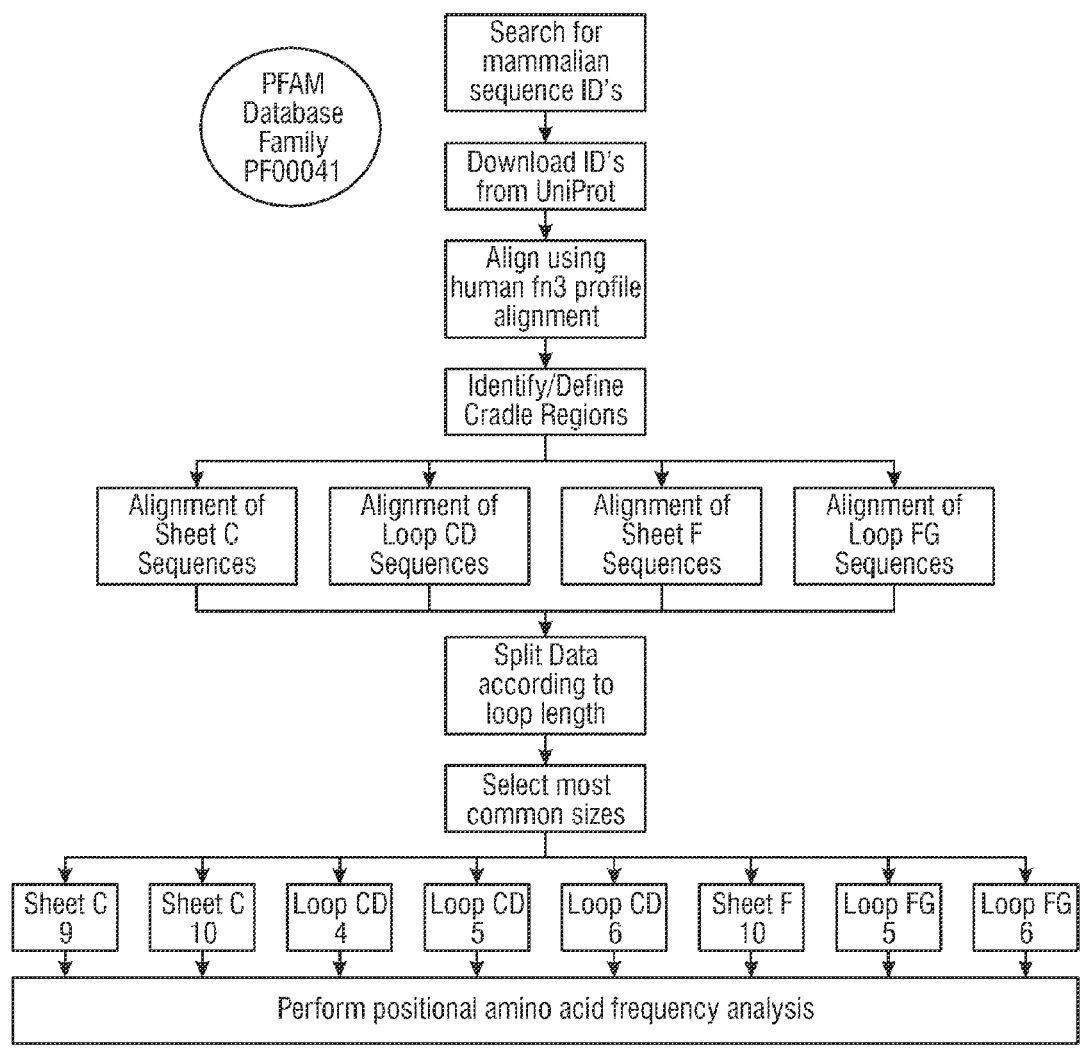
FIG. 1 is a schematic diagram illustrating the method for constructing FnIII cradle libraries using computer assisted genetic database biomining and delineation of beta-scaffold and loop structures.

The terms below have the following meanings unless indicated otherwise in the specification:

The term "fibronectin type III domain" or "FnIII domain" refers to a domain (region) from a wild-type fibronectin from any organism. In one specific embodiment, the FnIII domain is selected from the group consisting of $FnIII^{01}$, $FnIII^{02}$, $FnIII^{03}$, $FnIII^{04}$, $FnIII^{05}$, $FnIII^{06}$, $FnIII^{07}$, $FnIII^{08}$, $FnIII^{09}$, $FnIII^{10}$, $FnIII^{11}$, $FnIII^{12}$, $FnIII^{13}$, $FnIII^{14}$, $FnIII^{15}$, and $FnIII^{16}$ and the like. In another embodiment, the FnIII domain is selected from the group consisting of $FnIII^{07}$, $FnIII^{10}$, and $FnIII^{14}$. In another embodiment, the FnIII domain is $FnIII^{07}$. In another embodiment, the FnIII domain is $FnIII^{10}$. In another embodiment, the FnIII domain is $FnIII^{14}$.

The term "FnIII domain variant" or "variant FnIII domain" refers to a polypeptide region in which modifications have been made to the wildtype FnIII domain. Modifications include one or more amino acid substitutions, deletions, and/or insertions are present as compared to the amino acid sequence of a wildtype FnIII domain. In one embodiment, the FnIII variant or FnIII variant domain has an alteration with respect to specifically the human tenth domain of the FnIII domain sequence (SEQ ID NO:1). In one embodiment, the FnIII variant or FnIII variant domain has an alteration with respect to specifically the human seventh domain of the FnIII domain sequence (SEQ ID NO:97). In one embodiment, the FnIII variant or FnIII variant domain has an alteration with respect to specifically the human fourteenth domain of the FnIII domain sequence (SEQ ID NO:129). The term "substitutional variant" includes the replacement of one or more amino acids in a peptide sequence with a conservative or non-conservative amino acid(s). In some embodiments, the FnIII domain variant has increased binding properties compared to the wildtype FnIII domain relative to a particular target. In some embodiments, the FnIII domain variant has an increased surface area available for binding to a target moelcule compared with the wild type FnIII domain.

The term "FnIII domain polypeptide" refers to a polypeptide that includes at least one FnIII domain. A "variant FnIII domain polypeptide" or "FnIII domain-based polypeptide" refers to a polypeptide that includes at least one FnIII domain variant. It is contemplated that such polypeptides are capable of specifically binding a target polypeptide or protein. "FnIII domain-based molecule" refers to a molecule having an amino acid sequence of an FnIII domain or FnIII variant domain.

A "β sheet" or "beta sheet" is a form of regular secondary structure in proteins. Beta sheets consist of beta strands connected laterally by at least two or three backbone hydrogen bonds, forming a generally twisted, pleated sheet. A "beta strand" or "β strand" is a stretch of polypeptide chain typically 3 to 10 amino acids long with backbone in an almost fully extended conformation. The term beta strand A, also referred to as sheet A, refers to the amino acids preceding the AB loop. The term beta strand B, also referred to as sheet B, refers to the amino acids connecting the AB and BC loops. The term beta strand C, also referred to as sheet C or β1, refers to the amino acids connecting the BC and CD loops, e.g., amino acid position 31-39 of SEQ ID NO:1. The term beta strand D, also referred to as sheet D or β2, refers to the amino acids connecting the CD and DE loops, e.g., amino acid position 44-51 of SEQ ID NO:1. The term beta strand E, also referred to as sheet E, refers to the amino acids connecting the DE and EF loops. The term beta strand F, also referred to as sheet F or β3, refers to the amino acids connecting the EF and FG loops, e.g., amino acid position 67-75 of SEQ ID NO:1. The term beta strand G, also referred to as sheet G or β4, refers to the amino acids after the FG loop, e.g., amino acid position 85-94 of SEQ ID NO:1.

A loop is a less ordered, flexible stretch of amino acids (as compared to alpha helices and beta sheets) that typically connect other structural elements of a protein. In the context of FnIII, the loops are designated by the beta-strands they connect, for example the loop connecting beta-strand A and beta-strand B is the AB loop. The term BC loop refers to the amino acids corresponding to amino acids 22 to 30 of SEQ ID NO:1. The term CD loop refers to the amino acids corresponding to amino acids 39 to 45 of SEQ ID NO:1. The term DE loop refers to the amino acids corresponding to amino acids 51 to 55 of SEQ ID NO:1. The term FG loop refers to the amino acids corresponding to amino acids 76 to 87 of SEQ ID NO:1. The term "non-loop region" refers to parts of the polypeptide sequence that do not form a loop, which include, but are not limited to, the beta sheets and beta strands. In the context of FnIII, the non-loop regions include beta strands A, B, C, D, E, F and G.

The term "library" refers to a collection (e.g., to a plurality) of polypeptides having different amino acid sequences and different protein binding properties. In some embodiments there is a variant FnIII domain library comprising polypeptides having different variations of the FnIII domain. Unless otherwise noted, the library is an actual physical library of polypeptides or nucleic acids encoding the polypeptides. In further embodiments, there is a database that comprises information about a library that has been generated or a theoretical library that can be generated. This information may be a compound database comprising descriptions or structures of a plurality of potential variant FnIII domains.

The term "specifically binds" or "specific binding" refers to the measurable and reproducible ability of an FnIII domain variant to bind another molecule (such as a target), that is determinative of the presence of the target molecule in the presence of a heterogeneous population of molecules including biological molecules. For example, an FnIII domain variant that specifically or preferentially binds to a target is a polypeptide that binds this target with greater affinity, avidity, more readily, and/or with greater duration than it binds to most or all other molecules. "Specific binding" does not necessarily require (although it can include) exclusive binding.

An polypeptide that specifically binds to a target with an affinity of at least $1 \times 10^{-6}$ M at room temperature under physiological salt and pH conditions, as measured by surface plasmon resonance. An example of such a measurement is provided in the Example section.

The term "target" refers to a peptide, antigen or epitope that specifically binds to an FnIII-based binding molecule or monobody described herein. Targets include, but are not limited to, epitopes present on proteins, peptides, carbohydrates, and/or lipids.

The term "non-natural amino acid residue" refers to an amino acid residue that is not present in the naturally occurring FnIII domain in a mammal, such as a human.

The terms "tag", "epitope tag" or "affinity tag" are used interchangeably herein, and usually refer to a molecule or domain of a molecule that is specifically recognized by an antibody or other binding partner. The term also refers to the binding partner complex as well. Thus, for example, biotin and a biotin/avidin complex are both regarded as an affinity tag. In addition to epitopes recognized in epitope/antibody interactions, affinity tags also comprise "epitopes" recognized by other binding molecules (e.g., ligands bound by receptors), ligands bound by other ligands to form heterodimers or homodimers, His6 bound by Ni-NTA, biotin bound by avidin, streptavidin, or anti-biotin antibodies, and the like.

The term "conjugate" in the context of an FnIII domain variant refers to a chemical linkage between the FnIII domain variant and a non-FnIII domain variant. It is specifically contemplated that this excludes a regular peptide bond found between amino acid residues under physiologic conditions in some embodiments of the invention.

The terms "inhibiting," "reducing," or "preventing," or any variation of these terms, when used in the claims and/or the specification includes any measurable decrease or complete inhibition to achieve a desired result.

As used herein the term "cradle molecule" or "FnIII-based cradle molecule" refers to an FnIII domain that has been altered to contain one or more modifications in at least one beta strand and at least one loop region, wherein the loop region is a top loop region selected from the group consisting of BC, DE, and FG. In one embodiment, the cradle molecule refers to an FnIII domain that has been altered to contain one or more modifications in at least one beta strand and at least one loop region, wherein the loop region is a bottom loop region selected from the group consisting of AB, CD, and EF. In one embodiment, the cradle molecule refers to an FnIII domain that has been altered to contain one or more modifications in at least one beta strand and at least one top loop region selected from the group consisting of BC, DE, and FG and at least one bottom loop region selected from the group consisting of AB, CD, and EF. It is understood that not all three loops from the top or bottom region need to be used for binding the target molecule. In one embodiment, the cradle molecule refers to an FnIII domain that has been altered to contain one or more modifications in at least one beta strand and the top FG loop region and the bottom CD loop region.

In one embodiment, the cradle molecule refers to an FnIII domain that has been altered to contain one or more modifications in at least one beta strand selected from the group consisting of sheet A, sheet B, sheet C, sheet D, sheet E, sheet F and sheet G and at least one loop region, wherein the loop region is a top loop region selected from the group consisting of BC, DE, and FG. In one embodiment, the cradle molecule refers to an FnIII domain that has been altered to contain one or more modifications in at least one beta strand selected from the group consisting of sheet A, sheet B, sheet C, sheet D, sheet E, sheet F and sheet G and at least one loop region, wherein the loop region is a bottom loop region selected from the group consisting of AB, CD, and EF. In one embodiment, the cradle molecule refers to an FnIII domain that has been altered to contain one or more modifications in at least one beta strand selected from the group consisting of sheet A, sheet B, sheet C, sheet D, sheet E, sheet F and sheet G and at least one loop region, wherein the loop region is a bottom loop region selected from the group consisting of AB, CD, and EF. In one embodiment, the cradle molecule refers to an FnIII domain that has been altered to contain one or more modifications in at least one beta strand selected from the group consisting of sheet A, sheet B, sheet C, sheet D, sheet E, sheet F and sheet G and at least one top loop region selected from the group consisting of BC, DE, and FG and at least one bottom loop region selected from the group consisting of AB, CD, and EF. In one embodiment, the cradle molecule refers to an FnIII domain that has been altered to contain one or more modifications in beta strand C and the top FG loop region and the bottom CD loop region. In one embodiment, the cradle molecule refers to an FnIII domain that has been altered to contain one or more modifications in beta strand F and the top FG loop region and the bottom CD loop region.

In a further embodiment, two or more cradle molecules are linked together. Such molecules are referred to herein as "multispecific cradle molecules".

The cradle molecules can be linked together (e.g., in a pearl-like fashion) to form a multispecific cradle molecules that comprises, for example, at least two cradle molecules that are linked together. In some embodiments, this multispecific cradle molecule binds to different target regions of a same target molecule (e.g., Target A). For example, one cradle molecule of the multispecific cradle molecule can bind to a first target region of Target A and another cradle molecule of the multispecific cradle molecule can bind to a second target region of Target A. This can be used to increase avidity of the multispecific cradle molecule for the target molecule. In another embodiment, the multispecific cradle molecule binds to multiple target molecules. For example, one cradle molecule of the multispecific cradle molecule can bind to Target A and another cradle molecule of the multispecific cradle molecule can bind to Target B (e.g., a half life extender). In yet another embodiment, the multispecific cradle molecule comprises at least two cradle molecules that bind to different target regions of Target A and at least two cradle molecules that bind to different target regions of Target B. The skilled artisan will appreciate that any number of cradle molecules can be linked in this fashion to create a multispecific cradle molecule that are able to bind to different target regions of the same target molecule or different target molecules. In one embodiment, the C-terminal region of one cradle molecule is linked to the N-terminal region of another cradle molecule.

The term "complementarity determining region (CDR)" refers to a hypervariable loop from an antibody variable domain or from a T-cell receptor. The position of CDRs within a antibody variable region have been defined (see, e.g., Kabat, E. A., et al. Sequences of Proteins of Immunological Interest, Fifth Edition, U.S. Department of Health and Human Services, NIH Publication No. 91-3242, 1991; MacCallum et al., J. Mol. Biol. 262, 732-745, 1996; Al-Lazikani et al., J. Mol. Biol. 273, 927-948, 1997, Lefranc et al., Dev. Comp. Immunol. 27(1):55-77, 2003; Honegger and Plückthun, J. Mol. Biol. 309(3):657-70, 2001; and Chothia, C. et al., J. Mol. Biol. 196:901-917, 1987, which are incorporated herein by reference).

The term "non-FnIII moiety" refers to a biological or chemical entity that imparts additional functionality to a molecule to which it is attached. In a particular embodiment, the non-FnIII moiety is a polypeptide, e.g., human serum albumin (HSA), or a chemical entity, e.g., polyethylene gycol (PEG) which increases the half-life of the FnIII-based binding molecule in vivo.

The term "cradle library" refers to an FnIII polypeptide library in which amino acid diversity in at least one beta strand and at least one top loop selected from the group consisting of BC, DE, and FG and/or at least one bottom loop selected from the group consisting of AB, CD, and EF loop regions is determined by or reflects the amino acid variants present in a collection of known FnIII sequences.

The term "universal N+− binding library" or "N+/− libraries" refers to a more sophisticated or fine tuned library in which the most frequent amino acids surrounding an fixed amino acid are determined in the library design. These N+/− libraries are contructed with variations in beta strands, (e.g., sheet A, sheet B, sheet C, sheet D, sheet E, sheet F and sheet G, in particular sheet C and F), bottom loops, AB, CD, and EF, the top loops, BC, DE, FG, or any combination of the beta strands (e.g., sheet A, sheet B, sheet C, sheet D, sheet E, sheet F and sheet G, in particular sheet C and F) and top and bottom loops. For "N+/− libraries," N is the most predominant amino acid at a particular position and amino acids upstream or downstream are designated +N or −N, respectively. For example, N+3 is an amino acid 3 positions upstream of N, while N−3 is an amino acid 3 positions downstream of N in a 3D structure of FnIII Likewise, N+2 and N+1 are amino acids at positions 2 and 1 upstream of N, respectively, while N−2 and N−1 are amino acids at positions 2 and 1 downstream of N, respectively. By altering N from the most predominantly abundant amino acid to a less abundant amino acid, the effect of that modification can be assessed on the abundance of amino acids at 1, 2, or 3 positions away from N. In designing such a library, the frequency and abundance of amino acids surrounding the fixed N position are determined. These differences can be used to generate universal fibronectin bottom-side binding domain libraries, top-side binding domain libraries, or a combination of both bottom-side and top-side binding domain libraries.

The term "conserved amino acid residue" or "fixed amino acid" refers to an amino acid residue determined to occur with a frequency that is high, typically at least 50% or more (e.g., at about 60%, 70%, 80%, 90%, 95%, or 100%), for a given residue position. When a given residue is determined to occur at such a high frequency, i.e., above a threshold of about 50%, it may be determined to be conserved and thus represented in the libraries of the invention as a "fixed" or "constant" residue, at least for that amino acid residue position in the loop region being analyzed.

The term "semi-conserved amino acid residue" refers to amino acid residues determined to occur with a frequency that is high, for 2 to 3 residues for a given residue position. When 2-3 residues, preferably 2 residues, that together, are represented at a frequency of about 40% of the time or higher (e.g., 50%, 60%, 70%, 80%, 90% or higher), the residues are determined to be semi-conserved and thus represented in the libraries of the invention as a "semi-fixed" at least for that amino acid residue position in the loop region being analyzed. Typically, an appropriate level of nucleic acid mutagenesis/variability is introduced for a semi-conserved amino acid (codon) position such that the 2 to 3 residues are properly represented. Thus, each of the 2 to 3 residues can be said to be "semi-fixed" for this position. A "selected semi-conserved amino acid residue" is a selected one of the 2 or more semi-conserved amino acid residues, typically, but not necessarily, the residue having the highest occurrence frequency at that position.

The term "variable amino acid residue" refers to amino acid residues determined to occur with a lower frequency (less than 20%) for a given residue position. When many residues appear at a given position, the residue position is determined to be variable and thus represented in the libraries of the invention as variable at least for that amino acid residue position in the loop region being analyzed. Typically, an appropriate level of nucleic acid mutagenesis/variability is introduced for a variable amino acid (codon) position such that an accurate spectrum of residues is properly represented. Of course, it is understood that, if desired, the consequences or variability of any amino acid residue position, i.e., conserved, semi-conserved, or variable, can be represented, explored or altered using, as appropriate, any of the mutagenesis methods disclosed herein. A lower threshold frequency of occurrence of variable amino acids may be, for example, 5-10% or lower. Below this threshold, variable amino acids may be omitted from the natural-variant amino acids at that position.

The term "natural-variant amino acids" includes conserved, semi-conserved, and variable amino acid residues observed, in accordance with their occurrence frequencies, at a given position in a selected loop of a selected length. The natural-variant amino acids may be substituted by chemically equivalent amino acids, and may exclude variable amino acid residues below a selected occurrence frequency, e.g., 5-10%, or amino acid residues that are chemically equivalent to other natural-variant amino acids.

The term "library of mutagenesis sequences" refers to a library of sequences within a selected FnIII loop and loop length which is expressed by a library of coding sequences that encode, at each loop position, a conserved or selected semi-conserved consensus amino acid and, if the consensus amino acid has an occurrence frequency equal to or less than a selected threshold frequency of at least 50%, a single common target amino acid and any co-produced amino acids. Thus, for each of target amino acid, the library of sequences within a given loop will contain the target amino acid at all combinations of one to all positions within the loop at which the consensus amino acid has an occurrence frequency equal to or less than the given threshold frequency. If this threshold frequency is set at 100%, each position in the loop will be contain the target amino acid in at least one library member. The "library mutagenesis sequences" can be generated from the Tables and Figures disclosed herein using commercial vendors such as Geneart, or DNA2.0.

The term "library of natural-variant combinatorial sequences" refers to a library of sequences within a selected FnIII beta strand and FnIII loop which is expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents. Thus, for each amino acid position in a selected beta strand or loop, the library of natural variant combinatorial sequences will contain the consensus amino acid at that position plus other amino acid variants identified as having at least some minimum frequency at that position, e.g., at least 5-10% frequency, or chemically equivalent amino acids. In addition, natural variants may be substituted or dropped if the coding sequence for that amino acid produces a significant number of co-produced amino acids, via codon degeneracy.

The term "variability profile" or "VP" refers to the cataloguing of amino acids and their respective frequency rates of occurrence present at a particular beta strand or loop position. The beta strand and loop positions are derived from an aligned fibronectin dataset.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

II. FnIII Polypeptides

Fibronectin Type III (FnIII) polypeptides refer to a group of proteins composed of momomeric subunits having FnIII structure or motif made up of seven beta strands with six connecting loops (three at the top and three at the bottom). Beta strands A, B, and E form one half beta sandwich and beta strands C, D, F, and G form the other half, and having molecular weights of about 94 amino acids and molecular weights of about 10 Kda. The overall fold of the FnIII domain is closely related to that of the immunoglobulin domains, and the three loops near the N-terminus of FnIII, named BC, DE, and FG can be considered structurally analogous to the antibody variable heavy (VH) domain complementarity-determining regions, CDR1, CDR2, and CDR3, respectively. The top and bottom loops of FnIII have typically been thought to confer structural stability rather than being used for binding targets. However, the methods of the invention demonstrate that the top and bottom loops, as well as the beta sheets, can indeed be used for binding targets. Libraries of FnIII binding molecules can also be generated that use the top loops, the bottom loops or any combination of the top and bottom loops and the surface exposed residues of the beta-sheets for binding.

In one embodiment, the FnIII polypeptide is FnIII[10] with the following amino acid sequence:

(SEQ ID NO: 1)
Val Ser Asp Val Pro Arg Asp Leu Glu Val Val Ala
Ala Thr Pro Thr Ser Leu Leu Ile Ser Trp Asp Ala
Pro Ala Val Thr Val Arg Tyr Tyr Arg Ile Thr Tyr
Gly Glu Thr Gly Gly Asn Ser Pro Val Gln Glu Phe
Thr Val Pro Gly Ser Lys Ser Thr Ala Thr Ile Ser
Gly Leu Lys Pro Gly Val Asp Tyr Thr Ile Thr Val
Tyr Ala Val Thr Gly Arg Gly Asp Ser Pro Ala Ser
Ser Lys Pro Ile Ser Ile Asn Tyr Arg Thr.

In another embodiment, the FnIII polypeptide is FnIII[07] with the following amino acid sequence:

(SEQ ID NO: 97)
Pro Leu Ser Pro Pro Thr Asn Leu His Leu Glu Ala
Asn Pro Asp Thr Gly Val Leu Thr Val Ser Trp Glu
Arg Ser Thr Thr Pro Asp Ile Thr Gly Tyr Arg Ile
Thr Thr Thr Pro Thr Asn Gly Gln Gln Gly Asn Ser
Leu Glu Glu Val Val His Ala Asp Gln Ser Ser Cys
Thr Phe Asp Asn Leu Ser Pro Gly Leu Glu Tyr Asn
Val Ser Val Tyr Thr Val Lys Asp Asp Lys Glu Ser
Val Pro Ile Ser Asp Thr Ile Ile Pro

In another embodiment, the FnIII polypeptide or scaffold is FnIII[14] with the following amino acid sequence:

(SEQ ID NO: 129)
Asn Val Ser Pro Pro Arg Arg Ala Arg Val Thr Asp
Ala Thr Glu Thr Thr Ile Thr Ile Ser Trp Arg Thr
Lys Thr Glu Thr Ile Thr Gly Phe Gln Val Asp Ala
Val Pro Ala Asn Gly Gln Thr Pro Ile Gln Arg Thr
Ile Lys Pro Asp Val Arg Ser Tyr Thr Ile Thr Gly
Leu Gln Pro Gly Thr Asp Tyr Lys Ile Tyr Leu Tyr
Thr Leu Asn Asp Asn Ala Arg Ser Ser Pro Val Val
Ile Asp Ala Ser Thr

III. FnIII Cradle Molecules

The present invention pertains to methods and compositions for generating FnIII cradle molecules and libraries containing the same.

The cradle molecules included in the methods set forth herein are variants in that they comprise a wild type FnIII domain that has been altered by substitution, insertion and/or deletion of one or more amino acid. The cradle molecules set forth herein may demonstrate a selective and/or specific binding affinity for particular target molecules or portions thereof.

In some embodiments, the cradle molecule is a fusion polypeptide that includes a variant FnIII domain linked at the N- or C-terminus to a second peptide or polypeptide. In other embodiments, the cradle molecule comprises a linker interposed between the variant FnIII domain and the second peptide or polypeptide sequence. Linkers are discussed in greater detail in the specification below.

Furthermore, the cradle molecules set forth herein may comprise a sequence of any number of additional amino acid residues at either the N-terminus or C-terminus of the amino acid sequence that includes the variant FnIII domain. For example, there may be an amino acid sequence of about 3 to about 1,000 or more amino acid residues at either the N-terminus, the C-terminus, or both the N-terminus and C-terminus of the amino acid sequence that includes the variant FnIII domain.

The cradle molecule may include the addition of an antibody epitope or other tag, to facilitate identification, targeting, and/or purification of the polypeptide. The use of 6×His and GST (glutathione S transferase) as tags is well known. Inclusion of a cleavage site at or near the fusion junction will facilitate removal of the extraneous cradle molecule after purification. Other amino acid sequences that may be included in the cradle molecule include functional domains, such as active sites from enzymes such as a hydrolase, glycosylation domains, cellular targeting signals or transmembrane regions. The cradle molecule may further include one or more additional tissue-targeting moieties.

Cradle molecules may possess deletions and/or substitutions of amino acids relative to the native sequence. Sequences with amino acid substitutions are contemplated, as are sequences with a deletion, and sequences with a deletion and a substitution. In some embodiments, these cradle molecules may further include insertions or added amino acids.

Substitutional or replacement variants typically contain the exchange of one amino acid for another at one or more sites within the protein and may be designed to modulate one or more properties of the cradle molecule, particularly to increase its efficacy or specificity. Substitutions of this kind may or may not be conservative substitutions. Conservative substitution is when one amino acid is replaced with one of similar shape and charge. Being that the libraries of variant FnIII domains serves to provide a diversity of amino acid sequences and binding selectivity conservative substitutions are not required. However, if used, conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Changes other than those discussed above are generally considered not to be conservative substitutions. It is specifically contemplated that one or more of the conservative substitutions above may be included as embodiments. In other embodiments, such substitutions are specifically excluded. Furthermore, in additional embodiments, substitutions that are not conservative are employed in the variants.

In addition to a deletion or substitution, the cradle molecules may possess an insertion of one or more residues.

The variant FnIII domain may be structurally equivalent to the native counterparts. For example, the variant FnIII domain forms the appropriate structure and conformation for binding targets, proteins, or peptide segments.

The following is a discussion based upon changing of the amino acids of a cradle molecule to create a library of cradle molecules or a second-generation cradle molecule. For example, certain amino acids may be substituted for other amino acids in a cradle molecule without appreciable loss of function, such as ability to interact with a target peptide sequence. Since it is the interactive capacity and nature of a cradle molecule that defines that cradle molecule's functional activity, certain amino acid substitutions can be made in a cradle molecule sequence and nevertheless produce a cradle molecule with like properties.

In making such changes, the hydropathic index of amino acids may be considered. The importance of the hydropathic amino acid index in conferring interactive function on a protein is generally understood in the art (Kyte and Doolittle, $J\ Mol.\ Biol.$ (1982) 157(1):105-32). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. However, in some aspects a non-conservative substitution is contemplated. In some embodiments a random substitution is also contemplated. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

FnIII polypeptides can be modified by inserting or deleting 1, 2, 3, 4, 5, 6, 7, 8, 9, 10, 20 or more amino acids, or any range derivable therein, in an FnIII loop or beta strand. Variants of the loop region are discussed in U.S. Pat. No. 6,673,901 and U.S. Patent Publication No. 20110038866, which are hereby incorporated by reference.

In some embodiments the one or more amino acid substitution in beta strand C may be one or more amino acid substitution corresponding to position 30, 31, 32, 33, 34, 35, 36, 37, 38 and/or 39 of SEQ ID NO:1. In some embodiments, the amino acid substitution in beta strand C may correspond to position 31, 33, 35, 37, 38 and/or 39 of SEQ ID NO:1. In some embodiments, the amino acid substitution in beta strand C may correspond to position 31 and/or 33 of SEQ ID NO:1.

In some embodiments the one or more amino acid substitution in CD loop may be one or more amino acid substitution corresponding to position 40, 41, 42, 43, 44 and/or 45 of SEQ ID NO:1.

In some embodiments, the one or more amino acid substitution in beta strand D may be one or more amino acid substitution corresponding to position 44, 45, 46, 47, 48, 49, 50 or 51 of SEQ ID NO:1. In some embodiments, the amino acid substitution in beta strand D may correspond to position 44, 45, 47, or 49 of SEQ ID NO:1.

In still a further aspect, the one or more amino acid substitution in beta strand F may be one or more amino acid substitution corresponding to position 67, 68, 69, 70, 71, 72, 73, 74, 75 and/or 76 of SEQ ID NO:1. In some embodiments, the amino acid substitution in beta strand F may correspond to position 67, 69, 71, 73 and/or 76 of SEQ ID NO:1. In some embodiments, the amino acid substitution in beta strand F may correspond to position 71, 73, 75 and/or 76 of SEQ ID NO:1.

In some embodiments the one or more amino acid substitution in FG loop may be one or more amino acid substitution corresponding to position 76, 77, 78, 79, 80, 81, 82, 83, 84, 85 and/or 86 of SEQ ID NO:1.

In some embodiments, the one or more amino acid substitution in beta strand G may be one or more amino acid substitution corresponding to position 85, 86, 87, 88, 89, 90, 91, 92, 93, or 94 of SEQ ID NO:1. In some embodiments, the amino acid substitution in beta strand G may correspond to position 84 or 85 of SEQ ID NO:1.

The cradle molecules can include amino acid substitutions correspond to one or more amino acid substitutions at position 31, 33, 47, 49, 73, and/or 75 of SEQ ID NO:1. In some embodiments, the cradle molecule may further comprise an amino acid substitution corresponding to amino acid position 30 of SEQ ID NO:1. In some embodiments, the cradle molecule may comprise one or more amino acid substitution corresponding to amino acid position 41, 42, 43, 44, or 45 of SEQ ID NO:1. The cradle molecule can further comprise one or more amino acid substitution corresponding to amino acid position 76, 77, 78, 79, 80, 81, 82, 83, 84, or 85 of SEQ ID NO:1. In one embodiment, the substitution may be in at least one beta strand.

In some embodiments, the cradle molecule can comprise 1, 2, 3, 4 or more insertions and/or deletions of amino acids corresponding to amino acids of SEQ ID NO:1. Insertions can include, but are not limited to stretches of poly-serine, poly-alanine, poly-valine, poly-threonine, or polymers of any other of the 20 amino acids, that is subsequently mutagenized or diversified for generating a combinatorial cradle molecule library. Diversification of these inserted residues can include alteration to 1, 2, 3, 4, 5, 6, 7, 8, 9, 10, 11, 12, 13, 14, 15, 16, 17, 18, or 19 of the other natural amino acids. In some embodiments 1, 2, 3, 4, 5, 6, 7, 8, 9, 10, 11, 12, 13, 14, 15, 16, 17, 18, 19, 20, 21, 22, 23, 24, 25 or more contiguous amino acids are inserted into one or more of the beta strands (e.g., C and/or F) or AB, BC, CD, DE, EF, FG loops of an FnIII domain cradle molecule. In some embodiments, the cradle molecule can comprise an insertion, a deletion, or both an insertion and a deletion. The insertion and deletion need not be located at the same position and may be located at sites distal or proximal to each other. The insertion and/or deletion can be in a loop or beta strands of the FnIII domain polypeptide. In some embodiments, at least one loop region of FnIII may comprise an insertion of at least 2 amino acids. In some embodiments, at least one region of FnIII may comprise an insertion of 2 to 25 amino acids in at least one loop region. In some embodiments at least 2, 3, or more loop regions comprise an insertion. In some embodiments, the cradle molecule has at least one loop region of FnIII may comprise a deletion of at least 1, 2, 3, 4, 5, 6, 7, 8, 9, or 10 amino acids, including all values and ranges there between. In some embodiments, at least 2, 3, or 4 loop or beta strands, portions, or regions comprise a deletion of at least 1 amino acid. In some embodiments, the cradle molecule may comprise at least one insertion and one deletion in at least one loop and at least one beta strand. In some embodiments, the cradle molecule may comprise an insertion and a deletion in the same loop or beta strand region. In some embodiments, the cradle molecule may comprise at least one insertion or deletion in at least one beta strand. In some embodiments, the cradle molecule may comprise at least one insertion or deletion in at least one beta strand and at least one loop region.

In some embodiments, variants in any one or more of positions that correspond with amino acid position 15, 16, 17, 21, 22, 23, 24, 25, 26, 27, 28, 29, 30, 38, 39, 40, 41, 42, 43, 44, 45, 51, 52, 53, 54, 55, 56, 60, 61, 62, 63, 64, 65, 66, 76, 77, 78, 79, 80, 81, 82, 83, 84, 85, 86, 87, 88, 93, 95, and/or 96, including all ranges there between, can be specifically included in the claimed embodiments. In other embodiments, variants in any one or more of positions that correspond with amino acid position 15, 16, 17, 21, 22, 23, 24, 25, 26, 27, 28, 29, 30, 38, 39, 40, 41, 42, 43, 44, 45, 51, 52, 53, 54, 55, 56, 60, 61, 62, 63, 64, 65, 66, 76, 77, 78, 79, 80, 81, 82, 83, 84, 85, 86, 87, 88, 93, 95, and/or 96, including all ranges there between, can be specifically excluded. In other embodiments, variants in any one or more of positions that correspond with amino acid position 32, 34, 36, 68, 70, 72, 74, and/or 75, including all ranges there between, can be specifically excluded. It will be understood that these recited positions are based on the sequence of the tenth domain in human FnIII (SEQ ID NO:1). In some embodiments, the FnIII domain may be the $1^{st}$, $2^{nd}$, $3^{rd}$, $4^{th}$, $5^{th}$, $6^{th}$, $7^{th}$, $8^{th}$, $9^{th}$, $10^{th}$, $11^{th}$, $12^{th}$, $13^{th}$, $14^{th}$, $15^{th}$ or $16^{th}$ FnIII domain of human fibronectin. In some embodiments, the FnIII domain may be the $7^{th}$, $10^{th}$ or $14^{th}$ FnIII domain of human fibronectin. In some embodiments, the FnIII variants in other organisms are also contemplated based on their alignment with human FnIII.

In some embodiments the one or more amino acid substitution in beta strand C may be one or more amino acid substitution corresponding to position 33, 35, 37, 39, 40 and/or 41 of SEQ ID NO:97. In some embodiments the one or more amino acid substitution in CD loop may be one or more amino acid substitution corresponding to position 42, 43, 44, 45, 46, 47 and/or 48 of SEQ ID NO:97. In some embodiments, the amino acid substitution in beta strand F may correspond to position 70, 72, 74, 76 and/or 79 of SEQ ID NO:97. In some embodiments the one or more amino acid substitution in FG loop may be one or more amino acid substitution corresponding to position 80, 81, 82, 83, 84 and/or 85 of SEQ ID NO:97.

In some embodiments the one or more amino acid substitution in beta strand C may be one or more amino acid substitution corresponding to position 31, 33, 35, 37 and/or 39 of SEQ ID NO:129. In some embodiments the one or more amino acid substitution in CD loop may be one or more amino acid substitution corresponding to position 40, 41, 42, 43 and/or 44 of SEQ ID NO:129. In some embodiments, the amino acid substitution in beta strand F may correspond to position 66, 68, 70, 72 and/or 75 of SEQ ID NO:129. In some embodiments the one or more amino acid substitution in FG loop may be one or more amino acid substitution corresponding to position 76, 77, 78, 79, 80 and/or 81 of SEQ ID NO:129.

In other embodiments, variants in any one or more of positions that correspond with amino acid position 34, 36, 38, 71, 73, 75, 77 and/or 78 of SEQ ID NO:97, including all ranges there between, can be specifically excluded. In other embodiments, variants in any one or more of positions that correspond with amino acid position 332, 34, 36, 38, 67, 69, 71, 73 and/or 74 of SEQ ID NO:129, including all ranges there between, can be specifically excluded.

In some embodiments one or more of the altered or variant amino acids may correspond to position 30, 31, 33, 49, 47, 75, 76, 84, and/or 85 of SEQ ID NO:1. In some embodiments, the variant FnIII domains may comprise an insertion or deletion of at least 1, 2, 3, 4, 5, 6, 7, 8, 9, 10, 15, 20, 25 amino acids in at least one beta strand and at least one loop region of FnIII. In some embodiments, the variant FnIII domains may comprise an amino acid insertion in loop CD, FG and/or a combination of CD and FG loops and at least one beta strand with a substitution, deletion or addition. In some embodiments, the variant FnIII domains may comprise an amino acid insertion in loop BC, FG and/or a combination of BC and FG loops and at least one beta strand with a substitution, deletion, or addition. In some embodiments, the polypeptide may be at least 50%, 60%, 70%, 80%, or 90%, including all values and ranges there between, identical to SEQ ID NOs: 1, 97 and 129.

In some embodiments, FnIII cradle molecules may have at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions that may include, but are not limited to the following FnIII residue substitutions (corresponding to SEQ ID NO:1): R30A, R30N, R30D, R30C, R30Q, R30E, R30G, R30H, R30L, R30L, R30K, R30M, R30F, R30P, R30S, R30T, R30W, R30Y, R30V, Y31A, Y31R, Y31N, Y31D, Y31C, Y31Q, Y31E, Y31G, Y31H, Y31I, Y31L, Y31K, Y31M, Y31F, Y31P, Y31S, Y31T, Y31W, Y31V, R33A, R33N, R33D, R33C, R33Q, R33E, R33G, R33H, R33I, R33L, R33K, R33M, R33F, R33P, R33S, R33T, R33W, R33Y, R33V, T35A, T35R, T35N, T35D, T35C, T35Q, T35E, T35G, T35H, T35I, T35L, T35K, T35M, T35F, T35P, T35S, T35W, T35Y, T35V, G37A, G37N, G37R, G37D, G37C, G37Q, G37E, G37H, G37I, G37L, G37K, G37M, G37F, G37P, G37S, G37T, G37W, G37Y, G37V, E38A, E38N, E38R, E38D, E38C, E38Q, E38G, E38H, E38I, E38L, E38K, E38M, E38F, E38P, E38S, E38T, E38W, E38Y, E38V, T39A, T39N, T39R, T39D, T39C, T39Q, T39E, T39G, T39H, T39I, T39L, T39K, T39M, T39F, T39P, T39S, T39W, T39Y, T39V, G40A, G40N, G40R, G40D, G40C, G40Q, G40E, G40H, G40I, G40L, G40K, G40M, G40F, G40P, G40S, G40T, G40W, G40Y, G40V, G41A, G41R, G41N, G41D, G41C, G41Q, G41E, G41H, G41I, G41L, G41K, G41M, G41F, G41P, G41S, G41T, G41W, G41Y, G41V, N42A, N42R, N42D, N42C, N42Q, N42E, N42G, N42H, N42I, N42L, N42K, N42M, N42F, N42P, N42S, N42T, N42W, N42Y, N42V, S43A, S43R, S43N, S43D, S43C, S43Q, S43E, S43G, S43H, S43I, S43L, S43K, S43M, S43F, S43P, S43T, S43W, S43Y, S43V, P44A, P44R, P44N, P44D, P44C, P44Q, P44E, P44G, P44H, P44I, P44L, P44K, P44M, P44F, P44S, P44T, P44W, P44Y, P44V, V45A, V45R, V45N, V45D, V45C, V45Q, V45E, V45G, V45H, V45I, V45L, V45K, V45M, V45F, V45P, V45S, V45T, V45W, V45Y, E47A, E47R, E47N, E47D, E47C, E47Q, E47G, E47H, E47I, E47L, E47K, E47M, E47F, E47P, E47S, E47T, E47W, E47Y, E47V, T49A, T49R, T49N, T49D, T49C, T49Q, T49E, T49G, T49H, T49I, T49L, T49K, T49M, T49F, T49P, T49S, T49W, T49Y, T49V, V50A, V50R, V50N, V50D, V50C, V50Q, V50E, V50G, V50H, V50I, V50L, V50K, V50M, V50F, V50P, V50S, V50T, V50W, V50Y, D67A, D67R, D67N, D67C, D67Q, D67E, D67G, D67H, D67I, D67L, D67K, D67M, D67F, D67P, D67S, D67T, D67W, D67Y, D67V, T69A, T69R, T69N, T69D, T69C, T69Q, T69E, T69G, T69H, T69I, T69L, T69K, T69M, T69F, T69P, T69S, T69W, T69Y, T69V, T71A, T71R, T71N, T71D, T71C, T71Q, T71E, T71G, T71H, T71I, T71L, T71K, T71M, T71F, T71P, T71S, T71W, T71Y, T71V, Y73A, Y73R, Y73N, Y73D, Y73C, Y73Q, Y73E, Y73G, Y73H, Y73I, Y73L, Y73K, Y73M, Y73F, Y73P, Y73S, Y73T, Y73W, Y73V, V75A, V75R, V75N, V75D, V75C, V75Q, V75E, V75G, V75H, V75I, V75L, V75K, V75M, V75F, V75P, V75S, V75T, V75W, V75Y, T76A, T76R, T76N, T76D, T76C, T76Q, T76E, T76G, T76H, T76I, T76L, T76K, T76M, T76F, T76P, T76S, T76W, T76Y, T76V, G77A, G77R, G77N, G77D, G77C, G77Q, G77E, G77H, G77I, G77L, G77K, G77M, G77F, G77P, G77S, G77T, G77W, G77Y, G77V, R78A, R78N, R78D, R78C, R78Q, R78E, R78G, R78H, R78I, R78L, R78K, R78M, R78F, R78P, R78S, R78T, R78W, R78Y, R78V, G79A, G79R, G79N, G79D, G79C, G79Q, G79E, G79H, G79I, G79L, G79K, G79M, G79F, G79P, G79S, G79T, G79W, G79Y, G79V, D80A, D80R, D80N, D80C, D80Q, D80E, D80O, D80H, D80I, D80L, D80K, D80M, D80F, D80P, D80S, D80T, D80W, D80Y, D80V, S81A, S81R, S81N, S81D, S81C, S81Q, S81E, S81G, S81H, S81I, S81L, S81K, S81M, S81F, S81P, S81T, S81W, S81Y, S81V, P82A, P82R, P82N, P82D, P82C, P82Q, P82E, P82G, P82H, P82I, P82L, P82K, P82M, P82F, P82S, P82T, P82W, P82Y, P82V, A83R, A83N, A83D, A83C, A83Q, A83E, A83G, A83H, A83I, A83L, A83K, A83M, A83F, A83P, A83S, A83T, A83W, A83Y, A83V, S84A, S84R, S84N, S84D, S84C, S84Q, S84E, S84G, S84H, S84I, S84L, S84K, S84M, S84F, S84P, S84T, S84W, S84Y, S84V, S85A, S85R, S85N, S85D, S85C, S85Q, S85E, S85G, S85H, S85I, S85L, S85K, S85M, S85F, S85P, S85T, S85W, S85Y, S85V, K86A, K86R, K86N, K86D, K86C, K86Q, K86E, K86G, K86H, K86I, K86L, K86M, K86F, K86P, K86S, K86T, K86W, K86Y, and K86V.

In still further embodiments other amino acid substitutions can be introduced before, during, or after introduction of those amino acid substitutions listed above. The other substitutions (corresponding to SEQ ID NO:1) may include, but is not limited to 1, 2, 3, 4, 5, 6, 7, 8, 9, 10, 11, or 12 of W22A, W22R, W22N, W22D, W22C, W22Q, W22E, W22G, W22H, W22I, W22L, W22K, W22M, W22F, W22P, W22S, W22T, W22Y, W22V, D23A, D23R, D23N, D23C, D23Q, D23E, D23G, D23H, D23I, D23L, D23K, D23M, D23F, D23P, D23S, D23T, D23W, D23Y, D23V, A24R, A24N, A24D, A24C, A24Q, A24E, A24G, A24H, A24I, A24L, A24K, A24M, A24F, A24P, A24S, A24T, A24W, A24Y, A24V, P25A, P25R, P25N, P25D, P25C, P25Q, P25E, P25G, P25H, P25I, P25L, P25K, P25M, P25F, P25S, P25T, P25W, P25Y, P25V, A26R, A26N, A26D, A26C, A26Q, A26E, A26G, A26H, A26I, A26L, A26K, A26M, A26F, A26P, A26S, A26T, A26W, A26Y, A26V, V27A, V27R, V27N, V27D, V27C, V27Q, V27E, V27G, V27H, V27I, V27L, V27K, V27M, V27F, V27P, V27S, V27T, V27W, V27Y, T28A, T28R, T28N, T28D, T28C, T28Q, T28E, T28G, T28H, T28I, T28L, T28K, T28M, T28F, T28P, T28S, T28W, T28Y, T28V, V29A, V29R, V29N, V29D, V29C, V29Q, V29E, V29G, V29H, V29I, V29L, V29K, V29M, V29F, V29P, V29S, V29T, V29W, V29Y, G52A, G52N, G52R, G52D, G52C, G52Q, G52E, G52H, G52I, G52L, G52K, G52M, G52F, G52P, G52S, G52T, G52W, G52Y, G52V, S53A, S53R, S53N, S53D, S53C, S53Q, S53E, S53G, S53H, S53I, S53L, S53K, S53M, S53F, S53P, S53T, S53W, S53Y, S53V, K54A, K54R, K54N, K54D, K54C, K54Q, K54E, K54G, K54H, K54I, K54L, K54M, K54F, K54P, K54S, K54T, K54W, K54Y, K54V, S55A, S55R, S55N, S55D, S55C, S55Q, S55E, S55G, S55H, S55I, S55L, S55K, S55M, S55F, S55P, S55T, S55W, S55Y, or S55V.

In some embodiments, FnIII cradle molecules may have at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions that may include, but are not limited to the following FnIII residue substitutions (corresponding to SEQ ID NO:97): G33A, G33N, G33R, G33D, G33C, G33Q, G33E, G33H, G33I, G33L, G33K, G33M, G33F, G33P, G33S, G33T, G33W, G33Y, G33V, R35A, R35N, R35D, R35C, R35Q, R35E, R35G, R35H, R35I, R35L, R35K, R35M, R35F, R35P, R35S, R35T, R35W, R35Y, R35V, T37A, T37R, T37N, T37D, T37C, T37Q, T37E, T37G, T37H, T37I, T37L, T37K, T37M, T37F, T37P, T37S, T37W, T37Y, T37V, T39A, T39N, T39R, T39D, T39C, T39Q, T39E, T39G, T39H, T39I, T39L, T39K, T39M, T39F, T39P, T39S, T39W, T39Y, T39V, P40A, P40R, P40N, P40D, P40C, P40Q, P40E, P40G, P40H, P40I, P40L, P40K, P40M, P40F, P40S, P40T, P40W, P40Y, P40V, T41A, T41R, T41N, T41D, T41C, T41Q, T41E, T41G, T41H, T41I, T41L, T41K, T41M, T41F, T41P, T41S, T41W, T41Y, T41V, N42A, N42R, N42D, N42C, N42Q, N42E, N42G, N42H, N42I, N42L, N42K, N42M, N42F, N42P, N42S, N42T, N42W, N42Y, N42V, G43A, G43N, G43R, G43D, G43C, G43Q, G43E, G43H, G43I, G43L, G43K, G43M, G43F, G43P, G43S, G43T, G43W, G43Y, G43V, Q44A, Q44R, Q44N, Q44D, Q44C, Q44E, Q44G, Q44H, Q44I, Q44L, Q44K, Q44M, Q44F, Q44P, Q44S, Q44T, Q44W, Q44Y, Q44V, Q45A, Q45R, Q45N, Q45D, Q45C, Q45E, Q45G, Q45H, Q45I, Q45L, Q45K, Q45M, Q45F, Q45P, Q45S, Q45T, Q45W, Q45Y, Q45V, G46A, G46R, G46N, G46D, G46C, G46Q, G46E, G46H, G46I, G46L, G46K, G46M, G46F, G46P, G46S, G46T, G46W, G46Y, G46V, N47A, N47R, N47D, N47C, N47Q, N47E, N47G, N47H, N47I, N47L, N47K, N47M, N47F, N47P, N47S, N47T, N47W, N47Y, N47V, S48A, S48R, S48N, S48D, S48C, S48Q, S48E, S48G, S48H, S48I, S48L, S48K, S48M, S48F, S48P, S48T, S48W, S48Y, S48V, E70A, E70R, E70N, E70D, E70C, E70Q, E70G, E70H, E70I, E70L, E70K, E70M, E70F, E70P, E70S, E70T, E70W, E70Y, E70V, N72A, N72R, N72D, N72C, N72Q, N72E, N72G, N72H, N72I, N72L, N72K, N72M, N72F, N72P, N72S, N72T, N72W, N72Y, N72V, S74A, S74R, S74N, S74D, S74C, S74Q, S74E, S74G, S74H, S74I, S74L, S74K, S74M, S74F, S74P, S74T, S74W, S74Y, S74V, Y76A, Y76R, Y76N, Y76D, Y76C, Y76Q, Y76E, Y76G, Y76H, Y76I, Y76L, Y76K, Y76M, Y76F, Y76P, Y76S, Y76T, Y76W, Y76V, K79A, K79R, K79N, K79D, K79C, K79Q, K79E, K79G, K79H, K79I, K79L, K79M, K79F, K79P, K79S, K79T, K79W, K79Y, K79V, D80A, D80R, D80N, D80C, D80Q, D80E, D80G, D80H, D80I, D80L, D80K, D80M, D80F, D80P, D80S, D80T, D80W, D80Y, D80V, D81A, D81R, D81N, D81C, D81Q, D81E, D81G, D81H, D81I, D81L, D81K, D81M, D81F, D81P, D81S, D81T, D81W, D81Y, D81V, K82A, K82R, K82N, K82D, K82C, K82Q, K82E, K82G, K82H, K82I, K82L, K82M, K82F, K82P, K82S, K82T, K82W, K82Y, K82V, E83A, E83R, E83N, E83D, E83C, E83Q, E83G, E83H, E83I, E83L, E83K, E83M, E83F, E83P, E83S, E83T, E83W, E83Y, E83V, S84A, S84R, S84N, S84D, S84C, S84Q, S84E, S84G, S84H, S84I, S84L, S84K, S84M, S84F, S84P, S84T, S84W, S84Y, S84V, V85A, V85R, V85N, V85D, V85C, V85Q, V85E, V85G, V85H, V85I, V85L, V85K, V85M, V85F, V85P, V85S, V85T, V85W, and V85Y.

In some embodiments, FnIII cradle molecules may have at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more amino acid substitutions that may include, but are not limited to the following FnIII residue substitutions (corresponding to SEQ ID NO:129): G31A, G31N, G31R, G31D, G31C, G31Q, G31E, G31H, G31I, G31L, G31K, G31M, G31F, G31P, G31S, G31T, G31W, G31Y, G31V, Q33A, Q33R, Q33N, Q33D, Q33C, Q33E, Q33G, Q33H, Q33I, Q33L, Q33K, Q33M, Q33F, Q33P, Q33S, Q33T, Q33W, Q33Y, Q33V, D35A, D35R, D35N, D35C, D35Q, D35E, D35G, D35H, D35I, D35L, D35K, D35M, D35F, D35P, D35S, D35T, D35W, D35Y, D35V, V37A, V37R, V37N, V37D, V37C, V37Q, V37E, V37G, V37H, V37I, V37L, V37K, V37M, V37F, V37P, V37S, V37T, V37W, V37Y, A39N, A39R, A39D, A39C, A39Q, A39E, A39G, A39H, A39I, A39L, A39K, A39M, A39F, A39P, A39S, A39T, A39W, A39Y, A39V, N40A, N40R, N40D, N40C, N40Q, N40E, N40G, N40H, N40I, N40L, N40K, N40M, N40F, N40P, N40S, N40T, N40W, N40Y, N40V, G41A, G41R, G41N, G41D, G41C, G41Q, G41E, G41H, G41I, G41L, G41K, G41M, G41F, G41P, G41S, G41T, G41W, G41Y, G41V, Q42A, Q42R, Q42N, Q42D, Q42C, Q42E, Q42G, Q42H, Q42I, Q42L, Q42K, Q42M, Q42F, Q42P, Q42S, Q42T, Q42W, Q42Y, Q42V, T43A, T43R, T43N, T43D, T43C, T43Q, T43E, T43G, T43H, T43I, T43L, T43K, T43M, T43F, T43P, T43S, T43W, T43Y, T43V, P44A, P44R, P44N, P44D, P44C, P44Q, P44E, P44G, P44H, P44I, P44L, P44K, P44M, P44F, P44S, P44T, P44W, P44Y, P44V, D66A, D66R, D66N, D66C, D66Q, D66E, D66G, D66H, D66I, D66L, D66K, D66M, D66F, D66P, D66S, D66T, D66W, D66Y, D66V, K68A, K68R, K68N, K68D, K68C, K68Q, K68E, K68G, K68H, K68I, K68L, K68M, K68F, K68P, K68S, K68T, K68W, K68Y, K68V, Y70A, Y70R, Y70N, Y70D, Y70C, Y70Q, Y70E, Y70G, Y70H, Y70I, Y70L, Y70K, Y70M, Y70F, Y70P, Y70S, Y70T, Y70W, Y70V, Y72A, Y72R, Y72N, Y72D, Y72C, Y72Q, Y72E, Y72G, Y72H, Y72I, Y72L, Y72K, Y72M, Y72F, Y72P, Y72S, Y72T, Y72W, Y72V, N75A, N75R, N75D, N75C, N75Q, N75G, N75H, N75I, N75L, N75K, N75M, N75F, N75P, N75S, N75T, N75W, N75Y, N75V, D76A, D76R, D76N, D76C, D76Q, D76E, D76G, D76H, D76I, D76L, D76K, D76M, D76F, D76P, D76S, D76T, D76W, D76Y, D76V, N77A, N77R, N77D, N77C, N77Q, N77E, N77G, N77H, N77I, N77L, N77K, N77M, N77F, N77P, N77S, N77T, N77W, N77Y, N77V, A78R, A78N, A78D, A78C, A78Q, A78E, A78G, A78H, A78I, A78L, A78K, A78M, A78F, A78P, A78S, A78T, A78W, A78Y, A78V, R79A, R79N, R79D, R79C, R79Q, R79E, R79G, R79H, R79I, R79L, R79K, R79M, R79F, R79P, R79S, R79T, R79W, R79Y, R79V, S80A, S80R, S80N, S80D, S80C, S80Q, S80E, S80G, S80H, S80I, S80L, S80K, S80M, S80F, S80P, S80T, S80W, S80Y, S80V, S81A, S81R, S81N, S81D, S81C, S81Q, S81E, S81G, S81H, S81I, S81L, S81K, S81M, S81F, S81P, S81T, S81W, S81Y, and S81V.

The cradle molecule can further comprise a second FnIII domain that may or may not have been selected for affinity to a particular target. The second FnIII domain may or may not contain additional amino acid variations or diversification. In other aspects, the cradle molecule can further comprise a non-FnIII polypeptide that enhances the FnIII polypeptide binding affinity for a target molecule. The non-FnIII polypeptide may include additional variations or diversification that enhances or increases the cradle molecule binding affinity for another target molecule such as a half-life extender, e.g., HSA. The non-FnIII polypeptide can include, but is not limited to domains involved in phospho-tyrosine binding (e.g., SH2, PTB), phospho-serine binding (e.g., UIM, GAT, CUE, BTB/POZ, VHS, UBA, RING, HECT, WW, 14-3-3, Polo-box), phospho-threonine binding (e.g., FHA, WW, Polo-box), proline-rich region binding (e.g., EVH1, SH3, GYF), acetylated lysine binding (e.g., Bromo), methylated lysine binding (e.g., Chromo, PHD), apoptosis (e.g., BIR, TRAF, DED, Death, CARD, BH), cytoskeleton modulation (e.g., ADF, GEL, DH, CH, FH2), or other cellular functions (e.g., EH, CC, VHL, TUDOR, PUF Repeat, PAS, MH1, LRR1IQ, HEAT, GRIP, TUBBY, SNARE, TPR, TIR, START, SOCS Box, SAM, RGS, PDZ, PB1, LIM, F-BOX, ENTH, EF-Hand, SHADOW, ARM, ANK).

Multispecific FnIII Domain Cradle Molecules

In another aspect, the invention provides multispecific cradle molecules which comprise two or more individual cradle molecules linked together (e.g., genetically or chemically). The multispecific cradle molecules comprise at least one cradle molecule that uses at least one beta strand to bind to a target.

In one embodiment, the multispecific cradle molecule comprises two or more individual cradle molecules linked, in pearl-like fashion, wherein each individual cradle molecule binds to a specific target. Such targets can be present on the same molecule or on different molecules, such that the different molecules become juxtaposed by the binding of the multispecific cradle molecule. The targets can also be identical, such that the multispecific cradle molecule is able to cluster target molecules, in a similar way to an antibody. Avidity is also increased by binding to the same target molecule with two binding sites on the multispecific cradle molecule capable of independently binding to different regions of the target molecule.

A number of individual cradle molecules can be incorporated into the multispecific cradle molecules, for example, at least 2, 3, 4, 5, 6, 7, 8, 9, 10, or more individual cradle molecules.

Multispecific cradle molecules can be produced using art recognized methods. For example, cradle molecules may be linked genetically, such that multispecific cradle molecules are expressed as a single polypeptide. This linkage may be direct or conferred by an additional amino acid "linker" sequence. Suitable non-limiting methods and linkers are described, for example, in U.S. Patent Publication No. 20060286603 and Patent Cooperation Treaty Publication No. WO04041862A2. Exemplary polypeptide linkers include, but are not limited to, GS linkers, such as GGGGSGGGGS (SEQ ID NO: 471), GSGSGSGSGS (SEQ ID NO: 472), PSTSTST (SEQ ID NO: 473), and EIDKPSQ (SEQ ID NO: 474), and multimers thereof.

The multispecific cradle molecules generated using linker sequences have an improved steric hinderance for binding to target molecules, thus enabling shorter linker sequences to be used to link two or more individual cradle molecules together. Shorter linker sequences cause less immunogenic responses and are less likely to get cleaved.

Alternatively, multispecific cradle molecules can be prepared by chemically conjugating the individual cradle molecules using methods known in the art. A variety of coupling or cross-linking agents can be used for covalent conjugation. Examples of cross-linking agents include, e.g., protein A, carbodiimide, N-succinimidyl-5-acetyl-thioacetate (SATA), 5,5'-dithiobis(2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-1-carboxylate (sulfo-SMCC) (see e.g., Karpovsky et al. (1984) *J. Exp. Med.* 160:1686; Liu, M A et al. (1985) *Proc. Natl. Acad. Sci. U.S.A* 82:8648). Other methods include those described in Paulus (1985) *Behring Ins. Mitt. No.* 78:118-132; Brennan et al. (1985) *Science* 229:81-83, and Glennie et al. (1987) *J. Immunol.* 139: 2367-2375. Preferred conjugating agents are SATA and sulfo-SMCC, both available from Pierce Chemical Co. (Rockford, Ill.). Cysteine residues can be introduced into the FnIII domain variants at specific positions and then crosslink with reagents to sulfhydryl such as DPDPB or DTME (available from Pierce) to link two individual cradle molecules together to form a multispecific cradle molecule.

Methods for Grafting CDRs onto FnIII Cradle Molecules

In one aspect, the present invention features an FnIII cradle molecule altered compared to the wild-type FnIII domain to contain all or a portion of a complementarity determining region (CDR) of an antibody or a T-cell receptor.

The CDR regions of any antibody or T-cell receptor variable region, or antigen binding fragments thereof, are suitable for grafting. The CDRs can be obtained from the antibody or T-cell receptor repertoire of any animal including, but not limited to, rodents, primates, camelids or sharks. In a one embodiment, the CDRs are obtained from CDR1, CDR2 and CDR3 of a single domain antibody, for example a nanobody. In a more specific embodiment, CDR1, 2 or 3 of a single domain antibody, such as a nanobody, are grafted into any of the AB, BC, CD, DE, EF or FG loops of an FnIII domain, thereby providing target binding specificity of the original nanobody to the cradle molecule. In one embodiment, the CDR is heavy chain CDR3. In one embodiment, the CDR is grafted into the FG loop. Engineered libraries of camelid antibodies and antibody fragments are commercially available, for example, from Ablynx, Ghent, Belgium. The antibody repertoire can be from animals challenged with one or more antigens or from naïve animals that have not been challenged with antigen. Additionally or alternatively, CDRs can be obtained from antibodies, or antigen binding fragments thereof, produced by in vitro or in vivo library screening methods, including, but not limited to, in vitro polysome or ribosome display, phage display or yeast display techniques. This includes antibodies not originally generated by in vitro or in vivo library screening methods but which have subsequently undergone mutagenesis or one or more affinity maturation steps using in vitro or in vivo screening methods. Example of such in vitro or in vivo library screening methods or affinity maturation methods are described, for example, in U.S. Pat. Nos. 7,195,880; 6,951, 725; 7,078,197; 7,022,479; 5,922,545; 5,830,721; 5,605, 793, 5,830,650; 6,194,550; 6,699,658; 7,063,943; 5866344 and Patent Cooperation Treaty Publication No. WO06023144.

Methods to identify antibody CDRs are well known in the art (see Kabat et al., U.S. Dept. of Health and Human Services, "Sequences of Proteins of Immunological Interest" (1983); Chothia et al., (1987) *J. Mol. Biol.* 196:901-917; MacCallum et al., (1996) *J. Mol. Biol.* 262:732-745). The nucleic acid encoding a particular antibody can be isolated and sequenced, and the CDR sequences deduced by inspection of the encoded protein with regard to the established antibody sequence nomenclature. Methods for grafting hypervariable regions or CDRs into FnIII include, for example, genetic engineering, de novo nucleic acid synthesis or PCR-based gene assembly (see, e.g., U.S. Pat. No. 5,225,539).

The above techniques allow for the identification of a suitable loop for selection and presentation of a hypervariable region or CDR, e.g., the FG loop. However, additional metrics can be invoked to further improve the fit and presentation of the hypervariable region based on structural modeling of the FnIII domain and the donor antibody.

In one aspect, specific amino acid residues in any of the beta-strands of an FnIII domain are mutated to allow the CDR loops to adopt a conformation that retains or improves binding to antigen. This procedure can be performed in an analogous way to that CDR grafting into a heterologous antibody framework, using a combination of structural modeling and sequence comparison. In one embodiment, the FnIII domain residues adjacent to a CDR are mutated in a similar manner to that performed by Queen et al. (see U.S. Pat. Nos. 6,180,370; 5,693,762; 5,693,761; 5,585,089; 7,022,500). In another embodiment, FnIII domain residues within one Van der Waals radius of CDR residues are mutated in a similar manner to that performed by Winter et al. (see U.S. Pat. Nos. 6,548,640; 6,982,321). In another embodiment, FnIII domain residues that are non-adjacent to CDR residues but are predicted, based upon structural modeling of the FnIII domain and the donor antibody, to modify the conformation of CDR residues are mutated in a similar manner to that performed by Carter et al. or Adair et al (see U.S. Pat. Nos. 6,407,213; 6,639,055; 5,859,205; 6,632,927).

IV. FnIII Cradle Libraries

The ability to generate novel binding proteins capable of interacting with other proteins with high-affinity and specificity is important in biotechnology, medicine and molecular biology. Such designed binding proteins can be used in numerous applications. They can be used to bind a target protein, label a protein of interest for detection and visualization, to purify a target protein from a complex mixture or to functionally perturb a target by blocking a functional site.

Combinatorial methods are effective platforms for the production of novel binding proteins. In these methods, large libraries of protein variants are created by introducing a large amount of sequence diversity and sometimes structural diversity into a contiguous surface in a protein scaffold. The central idea in combinatorial approaches is to create a sufficiently diverse repertoire of candidate binding surfaces that vary in shape and chemical character. Variants capable of binding a target of interest can then be isolated using various selection methods.

Though powerful, a significant limitation of combinatorial systems is their limited sampling capacity. For instance, phage display libraries are generally limited to approximately $10^{10}$ members. Considering a small binding surface consisting of 15 positions in a protein scaffold, if all 15 positions are varied to all 20 amino acids, this gives $20^{15}$ or $3 \times 10^{19}$ theoretical sequence combinations. Thus, only a very small percentage of the possible binding site configurations would actually be sampled in the library. Since discovery of a binding surface suitable for a given target is already likely to be a rare event, the sampling limitations of combinatorial methods make isolation of functional binding proteins a difficult and unlikely task.

Several strategies have been explored for combating the sampling problem in combinatorial libraries. The most widely used approach is to couple simple library selection with so-called affinity maturation strategies. Usually, these strategies involve introduction of additional sequence diversity into the protein population at various stages during the selection process to effectively increase sampling capacity. The idea in such approaches is to first recover hits from an under-sampled library, then introduce point mutations to gradually optimize these clones for increased affinity. These approaches have been used successfully in a variety of systems. However, in most cases, the introduced mutations are random in terms of their positions and amino acid types. Thus, while this strategy has proven effective, the likelihood of accumulating productive mutations is very low. As a result, such methods often require several rounds of additional selection for affinity maturation after initial hits are recovered and effective binders are not always produced.

Another type of strategy for combating the sampling problem in combinatorial methods involves focusing the sequence and structural properties of the binding site library toward those likely to be useful for binding to a target-type of interest. These strategies are based on structural information (both primary and tertiary) of existing binding molecules. This approach has been explored in synthetic antibodies with the creation of peptide-targeted and small molecule hapten targeted libraries (Cobaugh, et al., *J. Mol. Biol.* (2008) 378:622-633; Persson, et al., *J. Mol. Biol.* (2006) 357:607-620). In each of these examples, antibody complementarity determining region (CDR) lengths were chosen that are frequently observed in peptide- or small molecule-binding antibodies. These structural features are pre-encoded in the antibody binding site, and then sequence diversity is introduced in this context using amino acid types frequently observed in antibodies recognizing the target-type of interest. In this way, a proven useful architecture is simply "reprogrammed" to recognize another molecule with similar characteristics.

In embodiments discussed herein, an FnIII domain is used as a basis for generating a combinatorial library of protein binding domains.

Artificial antibody scaffolds that bind specific ligands are becoming legitimate alternatives to antibodies generated using traditional techniques, in part because antibodies can be difficult and expensive to produce. The limitations of antibodies have spurred the development of alternative binding proteins based on immunoglobulin like folds or other protein topologies. These non-antibody scaffold share the general quality of having a structurally stable framework core that is tolerant to multiple substitutions in other parts of the protein.

The present invention provides a library of FnIII cradle molecules that use the CD and the FG loops of FnIII domains together with the surface exposed residues of the beta-strands. The proposed library, referred to as the "cradle library" herein, will increase the surface area available for binding over the traditional previously disclosed top and bottom side libraries. Furthermore, loops FG and CD are highly variable in natural occurring fibronectins and can be randomized without restrictions both in composition and loop length. This will enable a highly diverse library without generating instable molecules which should overcome some of the restrictions in the traditional libraries previously disclosed. Additionally, surface exposed beta sheet residues will also be randomized to generate a large cradle-like surface to be available for binding to target proteins.

By creating artificial diversity, the library size can be controlled so that they can be readily screened using, for example, high throughput methods to obtain new therapeutics. The FnIII cradle library with bottom and top side loop regions and the surface exposed residues of the beta-sheets can be screened using positive physical clone selection by FACS, phage panning or selective ligand retention. These in vitro screens bypass the standard and tedious methodology inherent in generating an antibody hybridoma library and supernatant screening.

Furthermore, the FnIII cradle library with the bottom and top loop regions (CD and FG, respectively) and the surface exposed residues of the beta-sheets has the potential to recognize any target as the constituent amino acids in the target binding loop are created by in vitro diversity techniques. This produces the significant advantages of the library controlling diversity size and the capacity to recognize self antigens. Still further, the FnIII cradle library with the bottom and top side loop regions (CD and FG) and the surface exposed residues of the beta-sheets can be propagated and re-screened to discover additional fibronectin binding domains against other desired targets.

A combinatorial library is a collection of diverse compounds generated by either chemical synthesis or biological synthesis by combining a number of chemical "building blocks." For example, a linear combinatorial chemical library such as a polypeptide (e.g., mutein or variant) library is formed by combining a set of chemical building blocks called amino acids in every possible way for a given compound length. Millions of compounds can be synthesized through such combinatorial mixing of chemical building blocks. For example, one commentator has observed that the systematic, combinatorial mixing of 100 interchangeable chemical building blocks results in the theoretical synthesis of 100 million tetrameric compounds or 10 billion pentameric compounds (Gallop, et al., *J. Med. Chem.* (1994) 37:1233-1250).

Embodiments of the invention are directed to a combinatorial library of FnIII domains. In some embodiments, polypeptides of the library include variations of amino acid sequence in one or more of the beta strands of the FnIII domains. In some embodiments, the library includes variations of amino acid sequences in one or more loops of the FnIII domains. In some embodiments, the library includes variation in both loops and beta strands of the FnIII domain. Libraries can be generated using (i) a directed approach; and (ii) a random approach, both of which are illustrated in the Examples.

Universal Mutagenesis Cradle Libraries

The present invention pertains to a mutagenesis cradle library of FnIII domain polypeptides useful in screening for the presence of one or more polypeptides having a selected binding or enzymatic activity. The library polypeptides include (a) regions A, AB, B, BC, C, CD, D, E, EF, F, FG, and G having wildtype amino acid sequences of a selected native FnIII domain polypeptide or polypeptides, (b) beta-strands C and F and loop regions CD and FG having one or more selected lengths. At least one selected beta-strand or loop region of a selected length contains a library of sequences encoded by a library of coding sequences that encode, at each beta-strand or loop position, a conserved or selected semi-conserved consensus amino acid and, if the consensus amino acid has a occurrence frequency equal to or less than a selected threshold frequency of at least 50%, a single common target amino acid and any co-produced amino acids (amino acids produced by the coding sequences at a given position as a result of codon degeneracy).

In constructing a library within a given loop/strand of a given loop/strand length, the variability profile is used to define a sequence of fixed and "variable" positions, i.e., positions at which a target amino acid can be introduced. The number of fixed positions will depend on the selected threshold frequency for the consensus amino acid at each position.

Once the beta-strand and loop sequences are selected, a library of coding-sequence oligonucleotides encoding all of the identified sequences is constructed, making codon substitutions as shown that are effective to preserve the existing consensus amino acid, but also encode the selected target amino acid, and any other co-product amino acids encoded by degenerate codons.

The library of coding sequences for the beta strands and loops is added to the framework sequences, to construct the library of coding sequences for the polypeptide libraries.

The library of polypeptides may be encoded by an expression library format that includes a ribosome display library, a polysome display library, a phage display library, a bacterial expression library, or a yeast display library.

The libraries may be used in a method of identifying a polypeptide having a desired binding affinity, in which the natural-variant combinatorial library are screened to select for an FnIII domain having a desired binding affinity. The same methodology can be used to generate FnIII libraries using any combination of beta sheets and top and bottom loop regions.

Natural-Variant Combinatorial Cradle Library

Further provided is a natural-variant combinatorial cradle library of FnIII polypeptides useful in screening for the presence of one or more polypeptides having a selected binding or enzymatic activity. The cradle library polypeptides include (a) regions A, AB, B, BC, C, CD, D, DE, E, EF, F, FG and G having wildtype amino acid sequences of a selected native FnIII polypeptide or polypeptides, and (b) beta-strands C and F and loop regions CD and FG having selected lengths. At least one selected beta strand or loop region of a selected length contains a library of natural-variant combinatorial sequences expressed by a library of coding sequences that encode at each loop position, a conserved or selected semi-conserved consensus amino acid and, if the consensus amino acid has a frequency of occurrence equal to or less than a selected threshold frequency of at least 50%, other natural variant amino acids, including semi-conserved amino acids and variable amino acids whose occurrence rate is above a selected minimum threshold occurrence at that position, or their chemical equivalents.

In constructing a natural-variant combinatorial cradle library for a given loop/sheet and loop/sheet length, the variability profile is used to define a sequence of fixed and "variable" positions, i.e., positions at which amino acid variations can be introduced. In the cradle libraries, the number of fixed positions will depend on the selected threshold frequency for the consensus amino acid at each position. If, for example, the selected frequency threshold was set at about 60%, the conserved or semi-conserved residues and natural-variant substitutions would not be made at these positions. Conversely, if the threshold frequency is set at 100%, all positions would be considered open to variation, recognizing that a single amino acid with a frequency of 100% at a loop position would not be substituted, and a position that had one very dominant amino acid, e.g., with a frequency of 90%, might be substituted only if the low-frequency variant(s) were chemically dissimilar to the dominant amino acid.

From the amino acid profile for a given loop/sheet and loop/sheet length, and knowing which of the positions will be held fixed and which will be admit variations, the amino acid substitutions at each variable position can be selected. In general, the number of variations that are selected (including co-produced amino acids) will depend on the number of variable substitution positions in the loop/sheet and the average number of variations per substituted loop/sheet position. Of course, if natural-variant substitutions are introduced into a single loop only, many more variations per position can be accommodated.

The particular natural variant amino acids that are selected for each position will generally include the amino acids having the highest frequencies, while limited the number of co-produced amino acids, and secondarily, preserving chemical diversity at each site. Once the natural-variant loop/sheet sequences are selected, a library of coding-sequence oligonucleotides encoding all of the identified natural-variant sequences is constructed, making codon substitutions that are effective to preserve the existing consensus amino acid, and encode the selected variant amino acids, including variants encoded by degenerate codons.

The library of coding sequences for the natural-variants loops/sheets is added to the framework sequences, to construct the library of coding sequences for the natural-variant polypeptide libraries. In some embodiments, the coding library includes coding sequences for a pair of AB/CD, AB/EF, CD/EF or CD/FG loops, where each loop in the pair has one selected length. In another embodiment, the coding library includes coding sequences for any combination of all five loops, AB, BC, CD, EF and FG. In yet another embodiment, the coding library includes coding sequences for the C and F sheets. In still another embodiment, the coding library includes coding sequences for any combination of all beta sheets.

N+/− Libraries

In addition, the methods of the invention also provide other libraries referred to as the "N+/− libraries." These N+/− libraries are constructed with variations in bottom loops, AB, CD, and EF, the top loops, BC, DE, FG, or any combination of top and bottom loops, and any combination of the beta strands (e.g., C and/or F). For "N+/− libraries," N is the most predominant amino acid at a particular position and amino acids upstream or downstream are designated +N or −N, respectively. For example, N+3 is an amino acid 3 positions upstream of N, while N−3 is an amino acid 3 positions downstream of N in a 3D structure of FnIII. Likewise, N+2 and N+1 are amino acids at positions 2 and 1 upstream of N, respectively, while N−2 and N−1 are amino acids at positions 2 and 1 downstream of N, respectively. By altering, N from the most predominantly abundant amino acid to a less abundant amino acid, the effect of that modification can be assessed on the abundance of amino acids at 1, 2, or 3 positions away from N. In designing such a library, the frequency and abundance of amino acids surrounding the fixed N position are determined. These differences can be used to generate FnIII cradle libraries.

For illustrative purposes only, the consensus sequence in the CD/5 loop is SGGEW (SEQ ID NO:278) at loop positions 1, 2, 3, 4, and 5, with G being the predominant amino acid. Using the N+/− theory, if G in loop position 3 is fixed as it is the predominant amino acid (N), then the structural and microenvironmental effect of G on loop position 1 (N−2), loop position 2 (N−1), loop position 4 (N+1), and loop position 5 (N+2) is determined. The amino acid frequency of each position N−2, N−1, N+1, N+2 in the context of a fixed G at position N is calculated. Then, if G at loop position 3 is changed to S, the effect of S on positions N−2, N−1, N+1, N+2 (i.e., loop positions 1, 2, and 4, 5,) is determined, and so forth. After all possible combinations are calculated the information yielded is an amino acid distribution (N−2, N−1, N, N+1, N+2) of a given position N within a predetermined loop region in the context of a specific amino acid at this position N. This information can then be used to generate a library.

In another illustration, the consensus sequence of sheet C is GYIVEYREK (SEQ ID NO:279) at sheet positions 1, 2, 3, 4, 5, 6, 7, 8 and 9, respectively of the sheet C. Using the N+/− theory, if Y in position 2 is kept fixed as it is the predominant amino acid (N), then the structural and local microenvironmental effect on G at position 1 (N−1), I at position 3 (N+1), V at position 4 (N+2), E at position 5 (N+3), Y at position 6 (N+4), R at position 7 (N+5), E at position 8 (N+6) and K at position 9 (N+7) is determined. Moreover, if Y at position 2 is changed to V, then the effect of this change on positions N−1, N+1, N+2, N+3, N+4, N+5, N+6 and N+7 (i.e., sheet positions 1, 3, 4, 5, 6, 7, 8 and 9) is determined.

The FnIII cradle molecules in a cradle library may be represented by a sequence set forth in SEQ ID NOs: 468-470. Cradle residues are shown in bold with X representing the amino acid substitution for the beta strands and Y representing the amino acid substitution for the loops with the loop length range given as a subscript. Any substitutions, including natural or engineered amino acids, or other molecules are contemplated. In some embodiments, any of the 19 amino acids other than the native residue can be substituted for the cradle residues. Substitutions may include, but are not limited to conservative substitutions that have little or no effect on the overall net charge, polarity, or hydrophobicity of the protein. Substitutions may also include an insertion and a deletion of one or more amino acids. FnIII cradle molecules can include alanine substitutions at one or more of amino acid positions.

In some embodiments, the FG loop may be about 1-10 residues in length. In some embodiments, the FG loop may be about 5 or 6 residues in length. In some embodiments, the FG loop may be five residues in length. In some embodiments, positions 3 and/or 5 of the FG loop are a Gly residue. In some embodiments, position 1 of the FG loop is an Ala, Gly, Ser, Asn or Asp residue, position 2 of the FG loop is an Ala, Lys, Gly, Val or Gln residue, position 3 of the FG loop is a Gly, Leu, Val, Arg or Tyr residue, position 4 of the FG loop is an Glu, Leu, Asp, Tyr or Pro residue, and position 5 of the FG loop is a Gly, Ser, Thr, Asn or His residue. In some embodiments, the FG loop may be six amino acids in length. In some embodiments, position 1 of the FG loop is a Gly residue, position 2 of the FG loop is a Leu, Val or Ile residue, position 3 of the FG loop is a charged or polar residue, position 4 of the FG loop is a Pro residue, position 5 of the FG loop is a Gly residue, and position 6 of the FG loop is a polar residue. In some embodiments, position 1 of the FG loop is a Gly, Glu, Asp, Ser or Ala residue, position 2 of the FG loop is an Ala, Gly, Tyr, Val or Asn residue, position 3 of the FG loop is a Gly, Gln, Lys, Arg or Glu residue, position 4 of the FG loop is an Arg, Glu, Val, Ile or Leu residue, position 5 of the FG loop is a Ser, Gly, Val, Thr or Leu residue, and position 6 of the FG loop is a Glu, Gly, Lys, Ser or Pro residue.

In some embodiments, the CD loop may be about 3-11 residues in length. In some embodiments, the CD loop may be about 4-9 residues in length. In some embodiments, the CD loop may be four residues in length. In some embodiments, position 1 of the CD loop is a Asp, Gly, Glu, Ser or Asn residue, position 2 of the CD loop is a Gly, Ala, Asp, Asn or Glu residue, position 3 of the CD loop is a Gln, Glu, Arg, Gly or Thr residue, position 4 of the CD loop is a Pro, Thr, Glu, Ser or Gln residue. In some embodiments, the CD loop may be five amino acids in length. In some embodiments, position 1 of the CD loop is a Ser, Asp, Gly, Glu or Thr residue, position 2 of the CD loop is a Gly, Ser, Arg, Glu or Thr residue, position 3 of the CD loop is a Gly, Glu, Arg, Lys or Thr residue, position 4 of the CD loop is a Glu, Trp, Ala, Ser or Thr residue, position 5 of the CD loop is a Trp, Pro, Leu, Val or Thr residue. In some embodiments, the CD loop may be six amino acids in length. In some embodiments, position 1 of the CD loop is a Gly, Asn, Asp, Glu or Lys/Ser residue, position 2 of the CD loop is a Gly, Ser, Lys, Thr or Ala residue, position 3 of the CD loop is a Glu, Pro, Asp, Thr or Asn residue, position 4 of the CD loop is a Gly, Glu, Leu, Arg or Ser residue, position 5 of the CD loop is a Trp, Glu, Asp, Pro or Arg residue, and position 6 of the CD loop is a Glu, Val, Thr, Pro or Ala residue.

In some embodiments, the beta strand C may be about 6-14 residues in length. In some embodiments, the beta strand C may be about 8-11 residues in length. In some embodiments, the beta strand C may be 9 residues in length. In some embodiments, positions 2, 4 and 6 of the beta strand C are a hydrophobic residue. In some embodiments, positions 1, 3, 5 and 7-9 of the beta strand C are altered relative to the wild type sequence. In some embodiments, position 1 of the beta strand C is selected from the group consisting of Ala, Gly, Pro, Ser, Thr, Asp, Glu, Asn, Gln, His, Lys and Arg. In some embodiments, position 3 of the beta strand C is a hydrophobic residue. In some embodiments, position 3 of the beta strand C is selected from the group consisting of Ile, Val, Arg, Leu, Thr, Glu, Lys, Ser, Gln and His. In some embodiments, positions 5 and 7-9 of the beta strand C are selected from the group consisting of Ala, Gly, Pro, Ser, Thr, Asp, Glu, Asn, Gln, His, Lys and Arg.

In some embodiments, the beta strand F may be about 8-13 residues in length. In some embodiments, the beta strand F may be about 9-11 residues in length. In some embodiments, the beta strand F may be 10 residues in length. In some embodiments, positions 1, 3, 5 and 10 of the beta strand F are altered relative to the wild type sequence. In some embodiments, positions 1, 3, 5 and 10 of the beta strand F are selected from the group consisting of Ala, Gly, Pro, Ser, Thr, Asp, Glu, Asn, Gln, His, Lys and Arg. In some embodiments, positions 2, 4 and 6 of the beta strand F are a hydrophobic residue. In some embodiments, position 7 of the beta strand F is a hydrophobic residue. In some embodiments, position 7 of the beta strand F is selected from the group consisting of Arg, Tyr, Ala, Thr and Val. In some embodiments, position 8 of the beta strand F is selected from the group consisting of Ala, Gly, Ser, Val and Pro. In some embodiments, position 9 of the beta strand F is selected from the group consisting of Val, Leu, Glu, Arg and Ile.

In some embodiments, the cradle library comprises a variation in an amino acid corresponding to amino acid 30 of SEQ ID NO:1 in combination with one or more residue corresponding to amino acid 31, 33, 35, 37, 38, 39, 40, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 31 of SEQ ID NO:1 in combination with one or more residue corresponding to amino acid 30, 33, 35, 37, 38, 39, 40, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 33 of SEQ ID NO:1 in combination with one or more residue corresponding to amino acid 30, 31, 35, 37, 38, 39, 40, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 35 of SEQ ID NO:1 in combination with one or more residue corresponding to amino acid 30, 31, 33, 37, 38, 39, 40, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 37 of SEQ ID NO:1 in combination with one or more residue corresponding to amino acid 30, 31, 33, 35, 38, 39, 40, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 38 of SEQ ID NO:1 in combination with one or more residue corresponding to amino acid 30, 31, 33, 35, 37, 39, 40, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 39 of SEQ ID NO:1 in combination with one or more residue corresponding to amino acid 30, 31, 33, 35, 37, 38, 40, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 40 of SEQ ID NO:1 in combination with one or more residue corresponding to amino acid 30, 31, 33, 35, 37, 38, 39, 41, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 41 of SEQ ID NO:1 in combination with one or more residue corresponding to amino acid 30, 31, 33, 35, 37, 38, 39, 40, 42, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 42 of SEQ ID NO:1 in combination with one or more residue corresponding to amino acid 30, 31, 33, 35, 37, 38, 39, 40, 41, 43, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 43 of SEQ ID NO:1 in combination with one or more residue corresponding to amino acid 30, 31, 33, 35, 37, 38, 39, 40, 41, 42, 44, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 44 of SEQ ID NO:1 in combination with one or more residue corresponding to amino acid 30, 31, 33, 35, 37, 38, 39, 40, 41, 42, 43, 45, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 45 of SEQ ID NO:1 in combination with one or more residue corresponding to amino acid 30, 31, 33, 35, 37, 38, 39, 40, 41, 42, 43, 44, 47, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 47 of SEQ ID NO:1 in combination with one or more residue corresponding to amino acid 30, 31, 33, 35, 37, 38, 39, 40, 41, 42, 43, 44, 45, 49, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 49 of SEQ ID NO:1 in combination with one or more residue corresponding to amino acid 30, 31, 33, 35, 37, 38, 39, 40, 41, 42, 43, 44, 45, 47, 50, 67, 69, 71, 73, 75, 76, 77, 78, 79, 80, 81, 82, 83, 84, 85 and/or 86.

In some embodiments, the cradle library comprises a variation in an amino acid corresponding to amino acid 50 of SEQ ID NO:1 in combination with one or more residue corresponding to amino acid 30, 31, 33, 35, 37, 38, 39, 40, 41, 42, 43, 44, 45, 47, 49, 67, 69, 71, 73, 75, 76, 77, 78, 79, 80, 81, 82, 83, 84, 85 and/or 86.

In some embodiments, the cradle library comprises a variation in an amino acid corresponding to amino acid 67 of SEQ ID NO:1 in combination with one or more residue corresponding to amino acid 30, 31, 33, 35, 37, 38, 39, 40, 41, 42, 43, 44, 45, 47, 49, 50, 69, 71, 73, 75, 76, 77, 78, 79, 80, 81, 82, 83, 84, 85 and/or 86.

In some embodiments, the cradle library comprises a variation in an amino acid corresponding to amino acid 69 of SEQ ID NO:1 in combination with one or more residue corresponding to amino acid 30, 31, 33, 35, 37, 38, 39, 40, 41, 42, 43, 44, 45, 47, 49, 50, 67, 71, 73, 75, 76, 77, 78, 79, 80, 81, 82, 83, 84, 85 and/or 86.

In some embodiments, the cradle library comprises a variation in an amino acid corresponding to amino acid 71 of SEQ ID NO:1 in combination with one or more residue corresponding to amino acid 30, 31, 33, 35, 37, 38, 39, 40, 41, 42, 43, 44, 45, 47, 49, 50, 67, 69, 73, 75, 76, 77, 78, 79, 80, 81, 82, 83, 84, 85 and/or 86.

In some embodiments, the cradle library comprises a variation in an amino acid corresponding to amino acid 73 of SEQ ID NO:1 in combination with one or more residue corresponding to amino acid 30, 31, 33, 35, 37, 38, 39, 40, 41, 42, 43, 44, 45, 47, 49, 50, 67, 69, 71, 75, 76, 77, 78, 79, 80, 81, 82, 83, 84, 85 and/or 86.

In some embodiments, the cradle library comprises a variation in an amino acid corresponding to amino acid 75 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 76, 77, 78, 79, 80, 81, 82, 83, 84, 85 and/or 86.

In some embodiments, the cradle library comprises a variation in an amino acid corresponding to amino acid 76 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 77, 78, 79, 80, 81, 82, 83, 84, 85 and/or 86.

In some embodiments, the cradle library comprises a variation in an amino acid corresponding to amino acid 77 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 78, 79, 80, 81, 82, 83, 84, 85 and/or 86.

In some embodiments, the cradle library comprises a variation in an amino acid corresponding to amino acid 78 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 79, 80, 81, 82, 83, 84, 85 and/or 86.

In some embodiments, the cradle library comprises a variation in an amino acid corresponding to amino acid 79 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 80, 81, 82, 83, 84, 85 and/or 86.

In some embodiments, the cradle library comprises a variation in an amino acid corresponding to amino acid 80 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 79, 81, 82, 83, 84, 85 and/or 86.

In some embodiments, the cradle library comprises a variation in an amino acid corresponding to amino acid 81 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 79, 80, 82, 83, 84, 85 and/or 86.

In some embodiments, the cradle library comprises a variation in an amino acid corresponding to amino acid 82 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 79, 81, 82, 83, 84, 85 and/or 86.

In some embodiments, the cradle library comprises a variation in an amino acid corresponding to amino acid 83 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 79, 80, 81, 82, 84, 85 and/or 86.

In some embodiments, the cradle library comprises a variation in an amino acid corresponding to amino acid 84 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 79, 80, 81, 82, 83, 85 and/or 86.

In some embodiments, the cradle library comprises a variation in an amino acid corresponding to amino acid 85 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 79, 80, 81, 82, 83, 84 and/or 86.

In some embodiments, the cradle library comprises a variation in an amino acid corresponding to amino acid 86 of SEQ ID NO:1 in combination with one or more residue corresponding to amino acid 30, 31, 33, 35, 37, 38, 39, 40, 41, 42, 43, 44, 45, 47, 49, 50, 67, 69, 71, 73, 75, 76, 77, 78, 79, 80, 81, 82, 83, 84 and/or 85.

In some embodiments, the cradle library comprises a variation in an amino acid corresponding to amino acid 33 of SEQ ID NO:97 in combination with one or more residue corresponding to amino acid 35, 37, 39, 40, 41, 42, 43, 44, 45, 46, 47, 48, 70, 72, 74, 76, 79, 80, 81, 82, 83, 84 and/or 85.

In some embodiments, the cradle library comprises a variation in an amino acid corresponding to amino acid 35 of SEQ ID NO:97 in combination with one or more residue corresponding to amino acid 33, 37, 39, 40, 41, 42, 43, 44, 45, 46, 47, 48, 70, 72, 74, 76, 79, 80, 81, 82, 83, 84 and/or 85.

In some embodiments, the cradle library comprises a variation in an amino acid corresponding to amino acid 37 of SEQ ID NO:97 in combination with one or more residue corresponding to amino acid 33, 35, 39, 40, 41, 42, 43, 44, 45, 46, 47, 48, 70, 72, 74, 76, 79, 80, 81, 82, 83, 84 and/or 85.

In some embodiments, the cradle library comprises a variation in an amino acid corresponding to amino acid 39 of SEQ ID NO:97 in combination with one or more residue corresponding to amino acid 33, 35, 37, 40, 41, 42, 43, 44, 45, 46, 47, 48, 70, 72, 74, 76, 79, 80, 81, 82, 83, 84 and/or 85.

In some embodiments, the cradle library may comprise a variation in an amino acid corresponding to amino acid 40 of SEQ ID NO:97 in combination with one or more residue corresponding to amino acid 33, 35, 37, 39, 41, 42, 43, 44, 45, 46, 47, 48, 70, 72, 74, 76, 79, 80, 81, 82, 83, 84 and/or 85.

In some embodiments, the cradle library may comprise a variation in an amino acid corresponding to amino acid 41 of SEQ ID NO:97 in combination with one or more residue corresponding to amino acid 33, 35, 37, 39, 40, 42, 43, 44, 45, 46, 47, 48, 70, 72, 74, 76, 79, 80, 81, 82, 83, 84 and/or 85.

In some embodiments, the cradle library may comprise a variation in an amino acid corresponding to amino acid 42 of SEQ ID NO:97 in combination with one or more residue corresponding to amino acid 33, 35, 37, 39, 40, 41, 43, 44, 45, 46, 47, 48, 70, 72, 74, 76, 79, 80, 81, 82, 83, 84 and/or 85.

In some embodiments, the cradle library may comprise a variation in an amino acid corresponding to amino acid 43 of SEQ ID NO:97 in combination with one or more residue corresponding to amino acid 33, 35, 37, 39, 40, 41, 42, 44, 45, 46, 47, 48, 70, 72, 74, 76, 79, 80, 81, 82, 83, 84 and/or 85.

In some embodiments, the cradle library may comprise a variation in an amino acid corresponding to amino acid 44 of SEQ ID NO:97 in combination with one or more residue corresponding to amino acid 33, 35, 37, 39, 40, 41, 42, 43, 45, 46, 47, 48, 70, 72, 74, 76, 79, 80, 81, 82, 83, 84 and/or 85.

In some embodiments, the cradle library may comprise a variation in an amino acid corresponding to amino acid 45 of SEQ ID NO:97 in combination with one or more residue corresponding to amino acid 33, 35, 37, 39, 40, 41, 42, 43, 44, 46, 47, 48, 70, 72, 74, 76, 79, 80, 81, 82, 83, 84 and/or 85.

In some embodiments, the cradle library may comprise a variation in an amino acid corresponding to amino acid 46 of SEQ ID NO:97 in combination with one or more residue corresponding to amino acid 33, 35, 37, 39, 40, 41, 42, 43, 44, 45, 47, 48, 70, 72, 74, 76, 79, 80, 81, 82, 83, 84 and/or 85.

In some embodiments, the cradle library may comprise a variation in an amino acid corresponding to amino acid 47 of SEQ ID NO:97 in combination with one or more residue corresponding to amino acid 33, 35, 37, 39, 40, 41, 42, 43, 44, 45, 46, 48, 70, 72, 74, 76, 79, 80, 81, 82, 83, 84 and/or 85.

In some embodiments, the cradle library may comprise a variation in an amino acid corresponding to amino acid 48 of SEQ ID NO:97 in combination with one or more residue corresponding to amino acid 33, 35, 37, 39, 40, 41, 42, 43, 44, 45, 46, 47, 70, 72, 74, 76, 79, 80, 81, 82, 83, 84 and/or 85.

In some embodiments, the cradle library may comprise a variation in an amino acid corresponding to amino acid 70 of SEQ ID NO:97 in combination with one or more residue corresponding to amino acid 33, 35, 37, 39, 40, 41, 42, 43, 44, 45, 46, 47, 48, 72, 74, 76, 79, 80, 81, 82, 83, 84 and/or 85.

In some embodiments, the cradle library may comprise a variation in an amino acid corresponding to amino acid 72 of SEQ ID NO:97 in combination with one or more residue corresponding to amino acid 33, 35, 37, 39, 40, 41, 42, 43, 44, 45, 46, 47, 48, 70, 74, 76, 79, 80, 81, 82, 83, 84 and/or 85.

In some embodiments, the cradle library may comprise a variation in an amino acid corresponding to amino acid 74 of SEQ ID NO:97 in combination with one or more residue corresponding to amino acid 33, 35, 37, 39, 40, 41, 42, 43, 44, 45, 46, 47, 48, 70, 72, 76, 79, 80, 81, 82, 83, 84 and/or 85.

In some embodiments, the cradle library may comprise a variation in an amino acid corresponding to amino acid 76 of SEQ ID NO:97 in combination with one or more residue corresponding to amino acid 33, 35, 37, 39, 40, 41, 42, 43, 44, 45, 46, 47, 48, 70, 72, 74, 79, 80, 81, 82, 83, 84 and/or 85.

In some embodiments, the cradle library may comprise a variation in an amino acid corresponding to amino acid 79 of SEQ ID NO:97 in combination with one or more residue corresponding to amino acid 33, 35, 37, 39, 40, 41, 42, 43, 44, 45, 46, 47, 48, 70, 72, 74, 76, 80, 81, 82, 83, 84 and/or 85.

In some embodiments, the cradle library may comprise a variation in an amino acid corresponding to amino acid 80 of SEQ ID NO:97 in combination with one or more residue corresponding to amino acid 33, 35, 37, 39, 40, 41, 42, 43, 44, 45, 46, 47, 48, 70, 72, 74, 76, 79, 81, 82, 83, 84 and/or 85.

In some embodiments, the cradle library may comprise a variation in an amino acid corresponding to amino acid 81 of SEQ ID NO:97 in combination with one or more residue corresponding to amino acid 33, 35, 37, 39, 40, 41, 42, 43, 44, 45, 46, 47, 48, 70, 72, 74, 76, 79, 80, 82, 83, 84 and/or 85.

In some embodiments, the cradle library may comprise a variation in an amino acid corresponding to amino acid 82 of SEQ ID NO:97 in combination with one or more residue corresponding to amino acid 33, 35, 37, 39, 40, 41, 42, 43, 44, 45, 46, 47, 48, 70, 72, 74, 76, 79, 80, 81, 83, 84 and/or 85.

In some embodiments, the cradle library may comprise a variation in an amino acid corresponding to amino acid 83 of SEQ ID NO:97 in combination with one or more residue corresponding to amino acid 33, 35, 37, 39, 40, 41, 42, 43, 44, 45, 46, 47, 48, 70, 72, 74, 76, 79, 80, 81, 82, 84 and/or 85.

In some embodiments, the cradle library may comprise a variation in an amino acid corresponding to amino acid 84 of SEQ ID NO:97 in combination with one or more residue corresponding to amino acid 33, 35, 37, 39, 40, 41, 42, 43, 44, 45, 46, 47, 48, 70, 72, 74, 76, 79, 80, 81, 82, 83 and/or 85.

In some embodiments, the cradle library may comprise a variation in an amino acid corresponding to amino acid 85 of SEQ ID NO:97 in combination with one or more residue corresponding to amino acid 33, 35, 37, 39, 40, 41, 42, 43, 44, 45, 46, 47, 48, 70, 72, 74, 76, 79, 80, 81, 82, 83 and/or 84.

In some embodiments, the cradle library comprises a variation in an amino acid corresponding to amino acid 31 of SEQ ID NO:129 in combination with one or more residue corresponding to amino acid 33, 35, 37, 39, 40, 41, 42, 43, 44, 66, 68, 70, 72, 75, 76, 77, 78, 79, 80 and/or 81.

In some embodiments, the cradle library comprises a variation in an amino acid corresponding to amino acid 31 of SEQ ID NO:129 in combination with one or more residue corresponding to amino acid 33, 35, 37, 39, 40, 41, 42, 43, 44, 66, 68, 70, 72, 75, 76, 77, 78, 79, 80 and/or 81.

In some embodiments, the cradle library comprises a variation in an amino acid corresponding to amino acid 33 of SEQ ID NO:129 in combination with one or more residue corresponding to amino acid 31, 35, 37, 39, 40, 41, 42, 43, 44, 66, 68, 70, 72, 75, 76, 77, 78, 79, 80 and/or 81.

In some embodiments, the cradle library comprises a variation in an amino acid corresponding to amino acid 35 of SEQ ID NO:129 in combination with one or more residue corresponding to amino acid 31, 33, 37, 39, 40, 41, 42, 43, 44, 66, 68, 70, 72, 75, 76, 77, 78, 79, 80 and/or 81.

In some embodiments, the cradle library comprises a variation in an amino acid corresponding to amino acid 37 of SEQ ID NO:129 in combination with one or more residue corresponding to amino acid 31, 33, 35, 39, 40, 41, 42, 43, 44, 66, 68, 70, 72, 75, 76, 77, 78, 79, 80 and/or 81.

In some embodiments, the cradle library comprises a variation in an amino acid corresponding to amino acid 39 of SEQ ID NO:129 in combination with one or more residue corresponding to amino acid 31, 33, 35, 37, 40, 41, 42, 43, 44, 66, 68, 70, 72, 75, 76, 77, 78, 79, 80 and/or 81.

In some embodiments, the cradle library comprises a variation in an amino acid corresponding to amino acid 40 of SEQ ID NO:129 in combination with one or more residue corresponding to amino acid 31, 33, 35, 37, 39, 41, 42, 43, 44, 66, 68, 70, 72, 75, 76, 77, 78, 79, 80 and/or 81.

In some embodiments, the cradle library comprises a variation in an amino acid corresponding to amino acid 41 of SEQ ID NO:129 in combination with one or more residue corresponding to amino acid 31, 33, 35, 37, 39, 40, 42, 43, 44, 66, 68, 70, 72, 75, 76, 77, 78, 79, 80 and/or 81.

In some embodiments, the cradle library comprises a variation in an amino acid corresponding to amino acid 42 of SEQ ID NO:129 in combination with one or more residue corresponding to amino acid 31, 33, 35, 37, 39, 40, 41, 43, 44, 66, 68, 70, 72, 75, 76, 77, 78, 79, 80 and/or 81.

In some embodiments, the cradle library comprises a variation in an amino acid corresponding to amino acid 43 of SEQ ID NO:129 in combination with one or more residue corresponding to amino acid 31, 33, 35, 37, 39, 40, 41, 42, 44, 66, 68, 70, 72, 75, 76, 77, 78, 79, 80 and/or 81.

In some embodiments, the cradle library comprises a variation in an amino acid corresponding to amino acid 44 of SEQ ID NO:129 in combination with one or more residue corresponding to amino acid 31, 33, 35, 37, 39, 40, 41, 42, 43, 66, 68, 70, 72, 75, 76, 77, 78, 79, 80 and/or 81.

In some embodiments, the cradle library comprises a variation in an amino acid corresponding to amino acid 66 of SEQ ID NO:129 in combination with one or more residue corresponding to amino acid 31, 33, 35, 37, 39, 40, 41, 42, 43, 44, 68, 70, 72, 75, 76, 77, 78, 79, 80 and/or 81.

In some embodiments, the cradle library comprises a variation in an amino acid corresponding to amino acid 68 of SEQ ID NO:129 in combination with one or more residue corresponding to amino acid 31, 33, 35, 37, 39, 40, 41, 42, 43, 44, 66, 70, 72, 75, 76, 77, 78, 79, 80 and/or 81.

In some embodiments, the cradle library comprises a variation in an amino acid corresponding to amino acid 70 of SEQ ID NO:129 in combination with one or more residue corresponding to amino acid 31, 33, 35, 37, 39, 40, 41, 42, 43, 44, 66, 68, 72, 75, 76, 77, 78, 79, 80 and/or 81.

In some embodiments, the cradle library comprises a variation in an amino acid corresponding to amino acid 72 of SEQ ID NO:129 in combination with one or more residue corresponding to amino acid 31, 33, 35, 37, 39, 40, 41, 42, 43, 44, 66, 68, 70, 75, 76, 77, 78, 79, 80 and/or 81.

In some embodiments, the cradle library comprises a variation in an amino acid corresponding to amino acid 75 of SEQ ID NO:129 in combination with one or more residue corresponding to amino acid 31, 33, 35, 37, 39, 40, 41, 42, 43, 44, 66, 68, 70, 72, 76, 77, 78, 79, 80 and/or 81.

In some embodiments, the cradle library comprises a variation in an amino acid corresponding to amino acid 76 of SEQ ID NO:129 in combination with one or more residue corresponding to amino acid 31, 33, 35, 37, 39, 40, 41, 42, 43, 44, 66, 68, 70, 72, 75, 77, 78, 79, 80 and/or 81.

In some embodiments, the cradle library comprises a variation in an amino acid corresponding to amino acid 77 of SEQ ID NO:129 in combination with one or more residue corresponding to amino acid 31, 33, 35, 37, 39, 40, 41, 42, 43, 44, 66, 68, 70, 72, 75, 76, 78, 79, 80 and/or 81.

In some embodiments, the cradle library comprises a variation in an amino acid corresponding to amino acid 78 of SEQ ID NO:129 in combination with one or more residue corresponding to amino acid 31, 33, 35, 37, 39, 40, 41, 42, 43, 44, 66, 68, 70, 72, 75, 76, 77, 79, 80 and/or 81.

In some embodiments, the cradle library comprises a variation in an amino acid corresponding to amino acid 79 of SEQ ID NO:129 in combination with one or more residue corresponding to amino acid 31, 33, 35, 37, 39, 40, 41, 42, 43, 44, 66, 68, 70, 72, 75, 76, 77, 78, 80 and/or 81.

In some embodiments, the cradle library comprises a variation in an amino acid corresponding to amino acid 80 of SEQ ID NO:129 in combination with one or more residue corresponding to amino acid 31, 33, 35, 37, 39, 40, 41, 42, 43, 44, 66, 68, 70, 72, 75, 76, 77, 78, 79 and/or 81.

In some embodiments, the cradle library comprises a variation in an amino acid corresponding to amino acid 81 of SEQ ID NO:129 in combination with one or more residue corresponding to amino acid 31, 33, 35, 37, 39, 40, 41, 42, 43, 44, 66, 68, 70, 72, 75, 76, 77, 78, 79 and/or 80.

V. Computer-Assisted FnIII Cradle Library Construction

Further provided herein are methods of making a cradle library of FnIII domain variants based on sequence information obtained through, e.g., bioinformatics and/or structural analysis. The first step in building a fibronectin library of the invention is selecting sequences that meet certain predetermined criteria. PFAM, ProSite and similar databases were searched for sequences containing FnIII domains (FIG. 1). These electronic databases contain catalogued expressed fibronectin and fibronectin-like protein sequences and can be queried for those FnIII domains and similar sequences (e.g., using the BLAST search algorithm). The FnIII domain sequences can then be grouped to predefined criteria such as domain subclasses, sequence similarity or originating organism(s).

The choice of FnIII domains based on the criteria of the invention dictates both the loop sizes and the initial amino acid sequence diversity to be introduced. By bioinformatics led design, the loop regions are flexible for insertion into multiple FnIII domains. By specific targeted loop substitutions, overall scaffold stability is maximized while concurrently, non-immunogenic substitutions are minimized. Additionally, the library can be size tailored so that the overall diversity can be readily screened in different systems. Furthermore, the representative diversity of the designed loops is still capable of binding a number of pre-defined targets. Moreover, the systematic design of loop still allows subsequent affinity maturation of recovered binding clones.

FnIII domain sequences are then delineated whereupon the intervening beta strand and loop regions and constituent amino acids are then identified. This then determines the length of the existing loops and beta strands, the amino acid profiles for each loop length and beta strand length, hence the physical size and amino acid diversity that can be accommodated within these frameworks. Once the loops and beta strands are identified, sequences within each loop and beta strand are aligned, and the aligned sequences are then split into groups according to loop length and beta strand length. The distributions of beta strands lengths for sheets A-G and loop lengths for AB, BC, CD, EF and FG loops were identified (see, e.g., FIG. 4). Using this information, the most common beta strand lengths and loop sizes are selected. In some embodiments, the selected loop lengths are CD/4, CD/5, CD/6, FG/5 and FG/6, and the selected beta strand lengths are 9 residues for beta strand C and 10 residues for beta strand F.

For each beta strand, one can determine the preferred loop acceptor sites based on both comparative structural and sequence analysis. For example, one can use the structural overlay comparison of the overall loop and beta strand scaffolds between the FnIII$^{07}$, FnIII$^{10}$, FnIII$^{14}$ or any of the other known FnIII domains. In identifying precise loop positions, the above step greatly minimizes necessary diversity loop mutations that would not result in functional ligand binding specificity.

Once loop lengths are selected, a positional amino acid frequency analysis is performed at each loop position, to determine the frequency of occurrence, in a set of native FnIII domains. This method may include a frequency analysis and the generation of the corresponding variability profiles (VP) of existing loop sequences (see Example 6). In addition, the outward facing amino acids of sheets C and F were analyzed to determine the frequency of occurrence, in a set of native FnIII domains (FIG. 7B) Amino acids 1, 3, 5, 7-9 in beta strand C and amino acids 1, 3, 5, 7, and 10 in beta strand F are intended for use in the cradle library. High frequency (e.g., >50%) positions are considered conserved or fixed. Moderately high frequency or "semi-conserved" amino acids or (when 2 or 3 are combined account for >40%) are chosen as "wildtype" at other positions. These wildtype amino acids are then systematically altered using, mutagenesis, e.g., walk-through mutagenesis, to generate the cradle library. "Variable" positions are those where typically, no one amino acid accounts for more than 20% of the represented set.

A variability profile analysis of the FnIII domain databases allows identification of loop/beta strand amino acid residue positions that fall within three categories, e.g., 1) positions that should be conserved or "fixed," 2) semi-conserved, and/or 3) variable positions that are suitable for diversity generation. A variability profile analysis is performed and a threshold frequency is used to identify the most favorable sequences to be used in designating the overall loop/sheet diversity.

The conserved or a selected semi-conserved sequence (typically the most frequent amino acid in the semi-conserved residues) is considered the "wild type" or "consensus" residue in the loop sequence. This "consensus" or "frequency" approach identifies those particular amino acids under high selective pressure that occurs most frequently at a particular position.

Accordingly, these residue positions are typically fixed, with diversity being introduced into remaining amino acid positions (taking into account the identified preference for certain amino acids to be present at these positions). The threshold for occurrence frequency at which amino acid variation will be introduced can vary between selected levels as low as 40%, preferably 50% to as high as 100%. At the 100% threshold frequency, mutagenesis of amino acids can be introduced at all positions of the loop, and the only constraints on natural-variant amino acids will be the total number of variants and whether chemical equivalents are available.

When designing the diversity for any of the above-mentioned loops and beta strands, modified amino acid residues, for example, residues outside the traditional 20 amino acids used in most polypeptides, e.g., homocysteine, can be incorporated into the loops as desired. This is carried out using art recognized techniques which typically introduce stop codons into the polynucleotide where the modified amino acid residue is desired. The technique then provides a modified tRNA linked to the modified amino acid to be incorporated (a so-called suppressor tRNA of, e.g., the stop codon amber, opal, or ochre) into the polypeptide (see, e.g., Köhrer, et al., *PNAS* (2001) 98:14310-14315).

The FnIII cradle libraries of the invention and their construction are conducted with the benefit of sequence and structural information such that the potential for generating improved FnIII cradle moleculesis increased. Structural molecular replacement modeling information can also be used to guide the selection of amino acid diversity to be introduced into the defined beta strand and loop regions. Still further, actual results obtained with the FnIII cradle molecules of the invention can guide the selection (or exclusion), e.g., affinity maturation, of subsequent FnIII cradle molecules to be made and screened in an iterative manner.

Further provided herein is a method for selecting a protein binding domain specific for a target comprises (a) detecting target specific binding of one or more members of a cradle library comprising a plurality of FnIII domain polypeptides having amino acid substitutions that correspond to at least amino acid position 31, 33, 47, 49, 71, 73, and/or 75 of SEQ ID NO:1; and (b) selecting the protein binding domain that specifically binds the target. In some embodiments the method may further comprise first preparing the plurality of FnIII domain polypeptide variants described herein, e.g., FnIII domains having amino acid substitutions that correspond to at least amino acid position 31, 33, 47, 49, 71, 73, and/or 75 of SEQ ID NO:1. In some embodiments a polypeptide identified as exhibiting a particular characteristic may be isolated. In some embodiments, the method may further comprise determining the nucleic acid and/or the amino acid of sequence of the selected protein binding domain. In some embodiments, the selected protein binding domain may be synthesized or expressed.

In some embodiments, in silico modeling is used to eliminate the production of any FnIII cradle molecules predicted to have poor or undesired structure and/or function. In this way, the number of FnIII cradle molecules to be produced can be sharply reduced thereby increasing signal-to-noise in subsequent screening assays. In another particular embodiment, the in silico modeling is continually updated with additional modeling information, from any relevant source, e.g., from gene and protein sequence and three-dimensional databases and/or results from previously tested FnIII cradle molecules, so that the in silico database becomes more precise in its predictive ability (FIG. 1).

In yet another embodiment, the in silico database is provided with the assay results, e.g., binding affinity/avidity of previously tested FnIII cradle molecules and categorizes the FnIII cradle molecules, based on the assay criterion or criteria, as responders or nonresponders, e.g., as FnIII cradle molecules that bind well or not so well. In this way, the affinity maturation of the invention can equate a range of functional responses with particular sequence and structural information and use such information to guide the production of future FnIII cradle molecules to be tested. The method is especially suitable for screening FnIII cradle molecules for a particular binding affinity to a target ligand using, e.g., a Biacore™ assay.

Accordingly, mutagenesis of noncontiguous residues within a loop region or a beta-strand can be desirable if it is known, e.g., through in silico modeling, that certain residues in the region will not participate in the desired function. The coordinate structure and spatial interrelationship between the defined regions, e.g., the functional amino acid residues in the defined regions of the FnIII cradle molecules, e.g., the diversity that has been introduced, can be considered and modeled. Such modeling criteria include, e.g., amino acid residue side group chemistry, atom distances, crystallography data, etc. Accordingly, the number of FnIII cradle molecules to be produced can be intelligently minimized.

In some embodiments, one or more of the above steps are computer-assisted. In a particular embodiment, the computer assisted step comprises, e.g., mining the NCBI, Genbank, PFAM, and ProSite databases and, optionally, cross-referencing the results against PDB structural database, whereby certain criteria of the invention are determined and used to design the desired loop diversity (FIG. 1). The method is also amenable to being carried out, in part or in whole, by a device, e.g., a computer driven device. For example, database mining fibronectin domain sequence selection, diversity design, oligonucleotide synthesis, PCR-mediated assembly of the foregoing, and expression and selection of candidate FnIII cradle molecules that bind a given target, can be carried out in part or entirely, by interlaced devices. In addition, instructions for carrying out the method, in part or in whole, can be conferred to a medium suitable for use in an electronic device for carrying out the instructions. In sum, the methods of the invention are amendable to a high throughput approach comprising software (e.g., computer-readable instructions) and hardware (e.g., computers, robotics, and chips).

Further details regarding fibronectin and FnIII sequence classification, identification, and analysis may be found, e.g., PFAM. A program to screen aligned nucleotide and amino acid sequences, Johnson, G., *Methods Mol. Biol.* (1995) 51:1-15; and Wu, et al., "Clustering of highly homologous sequences to reduce the size of large protein databases." *Bioinformatics* (2001) 17:282-283; Databases and search and analysis programs include the PFAM database at the Sanger Institute (pfam.sanger.ac.uk); the ExPASy PROSITE database (expasv.ch/prosite/); SBASE web (hydra.icgeb.trieste.it/sbase/); BLAST (located on the World Wide Web at ncbi.nlm nih gov/BLAST/); CD-HIT (bioinformatics.ljcrf.edu/cd-hi/); EMBOSS (hqmp.mrc.ac.uk/Software/EMBOSS/); PHYLIP (evolution.genetics.washington.edu/phylip.html); and FASTA (fasta.bioch.virginia.edu).

The bioinformatic analysis focuses on FnIII domains genes for descriptive purposes, but it will be understood that genes for other Fn domains and other scaffold protein are similarly evaluated.

VI. Synthesizing FnIII Cradle Libraries

The cradle library of polypeptides may be encoded by an expression library that has the format of a ribosome display library, a polysome display library, a phage display library, a bacterial expression library, or a yeast display library.

In some embodiments, the FnIII cradle libraries of the invention are generated for screening by synthesizing individual oligonucleotides that encode the defined region of the polypeptide and have no more than one codon for the predetermined amino acid. This is accomplished by incorporating, at each codon position within the oligonucleotide either the codon required for synthesis of the wild-type polypeptide or a codon for the predetermined amino acid and is referred to as look-through mutagenesis (LTM) (see, e.g., U.S. Patent Publication No. 20050136428).

In some embodiments, when diversity at multiple amino acid positions is required, walk-through mutagenesis (WTM) can be used (see, e.g., U.S. Pat. Nos. 6,649,340; 5,830,650; and 5,798,208; and U.S. Patent Publication No. 20050136428). In another embodiment, diversity can be created using the methods available from commercial vendors such as DNA2.0 and Geneart by providing information about the loop lengths of the AB, BC, CD, EF and FG loops, the positional distribution of amino acids at each position of the loop, and the top 7 amino acid abundance at each position of the loop.

The mixture of oligonucleotides for generation of the library can be synthesized readily by known methods for DNA synthesis. The preferred method involves use of solid phase beta-cyanoethyl phosphoramidite chemistry (see, e.g., U.S. Pat. No. 4,725,677). For convenience, an instrument for automated DNA synthesis can be used containing specified reagent vessels of nucleotides. The polynucleotides may also be synthesized to contain restriction sites or primer hybridization sites to facilitate the introduction or assembly of the polynucleotides representing, e.g., a defined region, into a larger gene context.

The synthesized polynucleotides can be inserted into a larger gene context, e.g., a single scaffold domain using standard genetic engineering techniques. For example, the polynucleotides can be made to contain flanking recognition sites for restriction enzymes (see, e.g., U.S. Pat. No. 4,888, 286). The recognition sites can be designed to correspond to recognition sites that either exist naturally or are introduced in the gene proximate to the DNA encoding the region. After conversion into double stranded form, the polynucleotides are ligated into the gene or gene vector by standard techniques. By means of an appropriate vector (including, e.g., phage vectors, plasmids) the genes can be introduced into a cell-free extract, phage, prokaryotic cell, or eukaryotic cell suitable for expression of the fibronectin binding domain molecules.

When partially overlapping polynucleotides are used in the gene assembly, a set of degenerate nucleotides can also be directly incorporated in place of one of the polynucleotides. The appropriate complementary strand is synthesized during the extension reaction from a partially complementary polynucleotide from the other strand by enzymatic extension with a polymerase. Incorporation of the degenerate polynucleotides at the stage of synthesis also simplifies cloning where more than one domain or defined region of a gene is mutagenized or engineered to have diversity.

In another approach, the fibronectin binding domain is present on a single stranded plasmid. For example, the gene can be cloned into a phage vector or a vector with a filamentous phage origin of replication that allows propagation of single-stranded molecules with the use of a helper phage. The single-stranded template can be annealed with a set of degenerate polynucleotides representing the desired mutations and elongated and ligated, thus incorporating each analog strand into a population of molecules that can be introduced into an appropriate host (see, e.g., Sayers, J. R., et al., *Nucleic Acids Res*. (1988) 16:791-802). This approach can circumvent multiple cloning steps where multiple domains are selected for mutagenesis.

Polymerase chain reaction (PCR) methodology can also be used to incorporate polynucleotides into a gene, for example, loop diversity into beta strand framework regions. For example, the polynucleotides themselves can be used as primers for extension. In this approach, polynucleotides encoding the mutagenic cassettes corresponding to the defined region (or portion thereof) are complementary to each other, at least in part, and can be extended to form a large gene cassette (e.g., a fibronectin binding domain) using a polymerase, e.g., using PCR amplification.

The size of the library will vary depending upon the loop/sheet length and the amount of sequence diversity which needs to be represented using mutagenesis methods. For example, the library is designed to contain less than $10^{15}$, $10^{14}$, $10^{13}$, $10^{12}$, $10^{11}$, $10^{10}$, $10^9$, $10^8$, $10^7$, and $10^6$ fibronectin binding domain.

The description above has centered on representing fibronectin binding domain diversity by altering the polynucleotide that encodes the corresponding polypeptide. It is understood, however, that the scope of the invention also encompasses methods of representing the fibronectin binding domain diversity disclosed herein by direct synthesis of the desired polypeptide regions using protein chemistry. In carrying out this approach, the resultant polypeptides still incorporate the features of the invention except that the use of a polynucleotide intermediate can be eliminated.

For the libraries described above, whether in the form of polynucleotides and/or corresponding polypeptides, it is understood that the libraries may be also attached to a solid support, such as a microchip, and preferably arrayed, using art recognized techniques.

The method of this invention is especially useful for modifying candidate fibronectin binding domain molecules by way of affinity maturation. Alterations can be introduced into the loops and/or into the beta strand framework (constant) region of a fibronectin binding domain. Modification of the beta sheets and loop regions can produce fibronectin binding domains with better ligand binding properties, and, if desired, catalytic properties. Modification of the beta strand framework region can also lead to the improvement of chemo-physical properties, such as solubility or stability, which are especially useful, for example, in commercial production, bioavailability, and affinity for the ligand. Typically, the mutagenesis will target the loop region(s) of the fibronectin binding domain, i.e., the structure responsible for ligand-binding activity which can be made up of the three loop regions. In a preferred embodiment, an identified candidate binding molecule is subjected to affinity maturation to increase the affinity/avidity of the binding molecule to a target ligand. In one embodiment, modifications to at least one loop and at least one beta sheet produces an FnIII cradle molecule with an increased surface area available for binding to a target molecule. In one embodiment, modifications to at least one top loop, at least one bottom loop, and at least one beta sheet produces an FnIII cradle molecule with an increased surface area available for binding to a target molecule. In one embodiment, modifications to the FG and CD loops and the C and/or F beta sheet produces an FnIII cradle molecule with an increased surface area available for binding to a target molecule. In one embodiment, modifications to at least one loop and at least one beta sheet produces an FnIII cradle molecule that can bind to different target molecules.

In general, the practice of the present invention employs, unless otherwise indicated, conventional techniques of chemistry, molecular biology, recombinant DNA technology, PCR technology, immunology (especially, e.g., antibody technology), expression systems (e.g., cell-free expression, phage display, ribosome display, and Profusion™), and any necessary cell culture that are within the skill of the art and are explained in the literature. See, e.g., Sambrook, Fritsch and Maniatis, *Molecular Cloning*: Cold Spring Harbor Laboratory Press (1989); DNA Cloning, Vols. 1 and 2, (D. N. Glover, Ed. 1985); *Oligonucleotide Synthesis* (M. J. Gait, Ed. 1984); *PCR Handbook Current Protocols in Nucleic Acid Chemistry*, Beaucage, Ed. John Wiley & Sons (1999) (Editor); *Oxford Handbook of Nucleic Acid Structure*, Neidle, Ed., Oxford Univ Press (1999); *PCR Protocols: A Guide to Methods and Applications*, Innis, et al., Academic Press (1990); *PCR Essential Techniques: Essential Techniques*, Burke, Ed., John Wiley & Son Ltd (1996); *The PCR Technique: RT-PCR*, Siebert, Ed., Eaton Pub. Co. (1998); *Current Protocols in Molecular Biology*, eds. Ausubel, et al., John Wiley & Sons (1992); *Large-Scale Mammalian Cell Culture Technology*, Lubiniecki, A., Ed., Marcel Dekker, Pub., (1990). *Phage Display: A Laboratory Manual*, C. Barbas (Ed.), CSHL Press, (2001); *Antibody Phage Display*, P. O'Brien (Ed.), Humana Press (2001); Border, et al., "Yeast surface display for screening combinatorial polypeptide libraries," *Nature Biotechnology* (1997) 15:553-557; Border, et al., "Yeast surface display for directed evolution of protein expression, affinity, and stability," *Methods Enzymol.* (2000) 328:430-444; ribosome display as described by Pluckthun, et al., in U.S. Pat. No. 6,348,315, and Profusion™ as described by Szostak, et al., in U.S. Pat. Nos. 6,258,558; 6,261,804; and 6,214,553, and bacterial periplasmic expression as described in U.S. Patent Publication No. 20040058403A1.

VII. Expression and Screening Systems

Libraries of polynucleotides generated by any of the above techniques or other suitable techniques can be expressed and screened to identify FnIII cradle molecules having desired structure and/or activity. Expression of the FnIII cradle molecules can be carried out using cell-free extracts (e.g., ribosome display), phage display, prokaryotic cells, or eukaryotic cells (e.g., yeast display).

In some embodiments, the polynucleotides are engineered to serve as templates that can be expressed in a cell free extract. Vectors and extracts as described, for example in U.S. Pat. Nos. 5,324,637; 5,492,817; 5,665,563, can be used and many are commercially available. Ribosome display and other cell-free techniques for linking a polynucleotide (i.e., a genotype) to a polypeptide (i.e., a phenotype) can be used, e.g., Profusion™ (see, e.g., U.S. Pat. Nos. 6,348,315; 6,261,804; 6,258,558; and 6,214,553).

Alternatively, the polynucleotides of the invention can be expressed in a convenient *E. coli* expression system, such as that described by Pluckthun, *Meth. Enzymol.* (1989) 178: 476-515; and Skerra, et al. *Biotechnology* (1991) 9:273-278. The mutant proteins can be expressed for secretion in the medium and/or in the cytoplasm of the bacteria, as described by Better and Horwitz *Meth. Enzymol.* (1989) 178:476. In some embodiments, the FnIII cradle molecules are attached to the 3' end of a sequence encoding a signal sequence, such as the ompA, phoA or pelB signal sequence (Lei, et al., *J. Bacteriol.* (1987) 169:4379). These gene fusions are assembled in a dicistronic construct, so that they can be expressed from a single vector, and secreted into the periplasmic space of *E. coli* where they will refold and can be recovered in active form (Skerra, et al., *Biotechnology* (1991) 9:273-278).

In some embodiments, the FnIII cradle molecule sequences are expressed on the membrane surface of a prokaryote, e.g., *E. coli*, using a secretion signal and lipidation moiety as described, e.g., in U.S. Patent Publication Nos. 20040072740A1; 20030100023A1; and 20030036092A1.

In some embodiments, the polynucleotides can be expressed in eukaryotic cells such as yeast using, for example, yeast display as described, e.g., in U.S. Pat. Nos. 6,423,538; 6,331,391; and 6,300,065. In this approach, the FnIII cradle molecules of the library are fused to a polypeptide that is expressed and displayed on the surface of the yeast.

Higher eukaryotic cells for expression of the FnIII cradle molecules of the invention can also be used, such as mammalian cells, for example myeloma cells (e.g., NS/0 cells), hybridoma cells, or Chinese hamster ovary (CHO) cells. Typically, the FnIII cradle molecules when expressed in mammalian cells are designed to be expressed into the culture medium, or expressed on the surface of such a cell. The FnIII cradle molecules can be produced, for example, as single individual domain or as multimeric chains comprising dimers, trimers, that can be composed of the same domain or of different FnIII variant domain types (FnIII$^{03}$-FnIII$^{10}$: homodimer; FnIII$^{10}$-FnIII$^{08}$: heterodimer; FnIII$^{10}$-FnIII$^{10}_n$, where n is an integer from 1-20 or wild type or variant FnIII domains; FnIII$^{07}$-FnIII$^{07}_n$, where n is an integer from 1-20 or wild type or variant FnIII domains; FnIII$^{14}$-FnIII$^{14}_n$, where n is an integer from 1-20 or wild type or variant FnIII domains; FnIII$^{07}$-FnIII$^{10}_n$, where n is an integer from 1-20 or wild type or variant FnIII domains; FnIII$^{10}$-FnIII$^{14}_n$, where n is an integer from 1-20 or wild type or variant FnIII domains; FnIII$^{07}$-FnIII$^{14}_n$, where n is an integer from 1-20 or wild type or variant FnIII domains; FnIII$^{07}$-FnIII$^{10}$-FnIII$^{14}_n$, where n is an integer from 1-20 or wild type or variant FnIII domains; FnIII$^{08}$-FnIII$^{09}$-FnIII$^{10}_n$, where n is an integer from 1-20 or wild type or variant FnIII domains; and the like).

The screening of the expressed FnIII cradle molecules (or FnIII cradle molecules produced by direct synthesis) can be done by any appropriate means. For example, binding activity can be evaluated by standard immunoassay and/or affinity chromatography. Screening of the FnIII cradle molecules of the invention for catalytic function, e.g., proteolytic function can be accomplished using a standard hemoglobin plaque assay as described, for example, in U.S. Pat. No. 5,798,208. Determining the ability of candidate FnIII cradle molecules to bind therapeutic targets can be assayed in vitro using, e.g., a Biacore™ instrument, which measures binding rates of a FnIII cradle molecule to a given target or ligand, or using the methods disclosed herein. In vivo assays can be conducted using any of a number of animal models and then subsequently tested, as appropriate, in humans.

The FnIII cradle library is transfected into the recipient bacterial/yeast hosts using standard techniques as described in the Examples. Yeast can readily accommodate library sizes up to 107, with 103-105 copies of each FnIII fusion protein being displayed on each cell surface. Yeast cells are easily screened and separated using flow cytometry and fluorescence-activated cell sorting (FACS) or magnetic beads. The yeast eukaryotic secretion system and glycosylation pathways of yeast also allow FnIII type molecules to be displayed with N and O linked sugars on the cell surface. Details of yeast display are outlined in the Examples section.

In another embodiment, the yeast display system utilizes the a-agglutinin yeast adhesion receptor to display proteins on the cell surface. The proteins of interest, in this case, FnIII libraries, are expressed as fusion partners with the Aga2 protein.

These fusion proteins are secreted from the cell and become disulfide linked to the Aga1 protein, which is attached to the yeast cell wall (see Invitrogen, pYD1 *Yeast Display* product literature). The plasmid, e.g., pYD1, prepared from an *E. coli* host by plasmid purification (Qiagen), is digested with the restriction enzymes, Bam HI and Not I, terminally dephosphorylated with calf intestinal alkaline phosphatase. Ligation of the pYD1 and CR products libraries, *E. coli* (DH5α) transformation and selection on LB-ampicillin (50 mg/ml) plates were performed using standard molecular biology protocols to amplify the libraries before electroporation into yeast cell hosts.

Methods for selecting expressed FnIII library variants having substantially higher affinities for target ligands (e.g., TNF, VEGF, VEGF-R etc), relative to the reference wild type FnIII domain, can be accomplished as follows.

Candidate test ligands (e.g., TNF, VEGF, VEGF-R etc), are fluorescently labeled (either directly or indirectly via a biotin-streptavidin linkage as described above). Those library clones that efficiently bind the labeled antigens are then enriched for by using FACS. This population of yeast cells is then re-grown and subjected to subsequent rounds of selection using increased levels of stringency to isolate a smaller subset of clones that recognize the target with higher specificity and affinity. The libraries are readily amenable to high-throughput formats, using, e.g., FITC labeled anti-Myc-tag FnIII binding domain molecules and FACS analysis for quick identification and confirmation. In addition, there are carboxyl terminal tags included which can be utilized to monitor expression levels and/or normalize binding affinity measurements.

To check for the display of the Aga2-FnIII fusion protein, an aliquot of yeast cells ($8 \times 10^5$ cells in 40 µl) from the culture medium is centrifuged for 5 minutes at 2300 rpm. The supernatant is aspirated and the cell pellet is washed with 200 µl of ice cold PBS/BSA buffer (PBS/BSA 0.5% w/v). The cells are re-pelleted and supernatant removed before re-suspending in 100 µl of buffer containing the biotinylated TNFα (200 nM). The cells were left to bind the TNFα at 20° C. for 45 minutes after which they were washed twice with PBS/BSA buffer before the addition and incubation with streptavidin-FITC (2 mg/L) for 30 minutes on ice. Another round of washing in buffer was performed before final re-suspension volume of 400 µl in PBS/BSA. The cells were then analyzed on FACScan™ (Becton Dickinson) using CellQuest software as per manufacturer's directions.

To generate a library against TNFα, kinetic selections of the yeast displayed TNF-α fibronectin binding domain libraries involve initial labeling of cells with biotinylated TNF-α ligand followed by time dependent chase in the presence of large excess of un-biotinylated TNF-α ligand. Clones with slower dissociation kinetics can be identified by streptavidin-PE labeling after the chase period and sorted using a high speed FACS sorter. After Aga2-FnIII induction, the cells are incubated with biotinylated TNFα at saturating concentrations (400 nM) for 3 hours at 25° C. under shaking. After washing the cells, a 40 hour cold chase using unlabelled TNFα (1 µM) at 25° C. The cells are then be washed twice with PBS/BSA buffer, labeled with Streptavidin PE (2 mg/ml) anti-HIS-FITC (25 nM) for 30 minutes on ice, washed and re-suspended and then analyzed on FACS ARIA sorter.

Library screening can be conducted in order to select FnIII variants that bind to specific ligands or targets. Combinatorial screening can easily produce and screen a large number of variants, which is not feasible with specific mutagenesis ("rational design") approaches Amino acid variant at various amino acid positions in FnIII can be generated using a degenerate nucleotide sequence. FnIII variants with desired binding capabilities can be selected in vitro, recovered and amplified. The amino acid sequence of a selected clone can be identified readily by sequencing the nucleic acid encoding the selected FnIII.

In some embodiments, a particular FnIII cradle molecule has an affinity for a target that is at least 2-fold greater than the affinity of the polypeptide prior to substitutions discussed herein. In some embodiments, the affinity is, is at least, or is at most about 2-, 3-, 4-, 5-, 6-, 7-, 8-, 9-, 10-, 15-, 20-, 25-, 30-, 35-, 40-, 45-, 50-, 60-, 70-, 80-, 90-, 100-fold increased compared to another FnIII cradle molecule.

Further provided herein is a cradle polypeptide selected using the method of identifying a cradle polypeptide having a desired binding affinity to a target molecule disclosed herein. In some embodiments, the cradle polypeptide may comprise an amino acid sequence selected from the group consisting of SEQ ID NOs:4-78, 80-85, 87-96, 98, 99, 101-128, 130-141, 143, 145-147, 149-159, 161-199, 201-238 and 240-277.

Analysis and Screening of FnIII Libraries for Function

FnIII libraries can also be used to screen for FnIII proteins that possess functional activity. The study of proteins has revealed that certain amino acids play a crucial role in their structure and function. For example, it appears that only a discrete number of amino acids participate in the functional event of an enzyme. Protein libraries generated by any of the above techniques or other suitable techniques can be screened to identify variants of desired structure or activity.

By comparing the properties of a wild-type protein and the variants generated, it is possible to identify individual amino acids or domains of amino acids that confer binding and/or functional activity. Usually, the region studied will be a functional domain of the protein such as a binding domain. For example, the region can be the AB, BC, CD, DE, EF and FG loop binding regions or the beta sheets of FnIII domain. The screening can be done by any appropriate means. For example, activity can be ascertained by suitable assays for substrate conversion and binding activity can be evaluated by standard immunoassay and/or affinity chromatography.

From the chemical properties of the side chains, it appears that only a selected number of natural amino acids preferentially participate in a catalytic event. These amino acids belong to the group of polar and neutral amino acids such as Ser, Thr, Asn, Gln, Tyr, and Cys, the group of charged amino acids, Asp and Glu, Lys and Arg, and especially the amino acid His. Typical polar and neutral side chains are those of Cys, Ser, Thr, Asn, Gln and Tyr. Gly is also considered to be a borderline member of this group. Ser and Thr play an important role in forming hydrogen-bonds. Thr has an additional asymmetry at the beta carbon, therefore only one of the stereoisomers is used. The acid amide Gln and Asn can also form hydrogen bonds, the amido groups functioning as hydrogen donors and the carbonyl groups functioning as acceptors. Gln has one more CH2 group than Asn which renders the polar group more flexible and reduces its interaction with the main chain. Tyr has a very polar hydroxyl group (phenolic OH) that can dissociate at high pH values. Tyr behaves somewhat like a charged side chain; its hydrogen bonds are rather strong.

Histidine (His) has a heterocyclic aromatic side chain with a pK value of 6.0. In the physiological pH range, its imidazole ring can be either uncharged or charged, after taking up a hydrogen ion from the solution. Since these two states are readily available, His is quite suitable for catalyzing chemical reactions. It is found in most of the active centers of enzymes.

Asp and Glu are negatively charged at physiological pH. Because of their short side chain, the carboxyl group of Asp is rather rigid with respect to the main chain. This may be the reason why the carboxyl group in many catalytic sites is provided by Asp and not by Glu. Charged acids are generally found at the surface of a protein.

Therefore, several different regions or loops of an FnIII protein domain can be mutagenized simultaneously. This enables the evaluation of amino acid substitutions in conformationally related regions such as the regions which, upon folding of the protein, are associated to make up a functional site or the binding site. This method provides a way to create modified or completely new binding sites. The two loop regions and two beta sheets of FnIII, which can be engineered to confer target ligand binding, can be mutagenized simultaneously, or separately within the CD and FG loops or C and F sheets to assay for contributing binding functions at this binding site. Therefore, the introduction of additional "functionally important" amino acids into a ligand binding region of a protein may result in de novo improved binding activity toward the same target ligand.

Hence, new FnIII cradle molecules can be built on the natural "scaffold" of an existing FnIII polypeptide by mutating only relevant regions by the method of this invention. The method of this invention is suited to the design of de novo improved binding proteins as compared to the isolation of naturally occurring FnIIIs.

VII. Kits

Kits are also contemplated as being made or used in some embodiments of the present invention. For instance, a polypeptide or nucleic acid of the present invention can be included in a kit or in a library provided in a kit. A kit can be included in a sealed container. Non-limiting examples of containers include a microtiter plate, a bottle, a metal tube, a laminate tube, a plastic tube, a dispenser, a pressurized container, a barrier container, a package, a compartment, or other types of containers such as injection or blow-molded plastic containers into which the dispersions or compositions or desired bottles, dispensers, or packages are retained. Other examples of containers include glass or plastic vials or bottles. The kit and/or container can include indicia on its surface. The indicia, for example, can be a word, a phrase, an abbreviation, a picture, or a symbol.

The containers can dispense or contain a pre-determined amount of a composition of the present invention. The composition can be dispensed as a liquid, a fluid, or a semi-solid. A kit can also include instructions for using the kit and/or compositions. Instructions can include an explanation of how to use and maintain the compositions.

VIII. Examples

The following examples are offered to illustrate but not to limit the invention.

EXAMPLE 1

Phage Display Library and Selection

An FnIII$^{10}$ gene template was constructed (Koide, A., et al., *J Mol Biol* (1998) 284:1141-1151). A library can be created using a "shaved" template containing polyserine sequence at locations to be diversified (Koide, et al., supra, 2007 and Wojcik, et al., supra, 2010). A synthetic DNA fragment that encodes signal sequence of DsbA (Steiner, et al., *Nat. Biotechnol.* (2006) 24:823-831) was fused to the gene for the template, and the fusion gene was cloned into the phage display vector pAS38 (Koide, A., et al., supra, 1998). A phage-display combinatorial library was constructed by introducing codons for amino acid variation into the FnIII$^{10}$ gene. Library construction procedures have previously been described (Koide, A., and Koide, S., *Methods Mol. Biol.* (2007) 352:95-109).

Phagemid particles can be prepared by growing XL1-Blue cells transfected with the phagemid library in the presence of 0.2 mM IPTG and helper phage (Lo Conte, et al., *J. Mol. Biol.* (1999) 285:2177-2198; Fellouse, et al., *J. Mol. Biol.*

(2005) 348:1153-1162). Phagemid library selection can be performed as follows. In the first round, 0.5 μM of a target protein modified with EZ-Link Sulfo-NHS-SS-Biotin (Sulfosuccinimidyl 2(biotinamido)-ethyl-1,3-dithiopropionate; Pierce) is mixed with a sufficient amount of streptavidin-conjugated magnetic beads (Streptavidin MagneSphere® Pramagnetic Particles; Promega, Z5481/2) in TBS (50 mM Tris HCl buffer pH 7.5 150 mM NaCl) containing 0.5% Tween20 (TBST). To this target solution, $10^{12-13}$ phagemids suspended in 1 ml TBST plus 0.5% BSA is added, and the solution is mixed and incubated for 15 min at room temperature. After washing the beads twice with TBST, the beads suspension containing bound phagemids is added to fresh E. coli culture. Phagemids were amplified as described before (Fellouse, et al., supra, 2005). In a second round, phagemids are incubated with 0.1 μM target in TBST plus 0.5% BSA, and then captured by streptavidin-conjugated magnetic beads. Phagemids bound to the target protein are eluted from the beads by cleaving the linker within the biotinylation reagent with 100 mM DTT in TBST. The phagemids are washed and recovered as described above. After amplification, the third round of selection is performed using 0.02 μM target. Phage display is an established technique for generating binding members and has been described in detail in many publications such as Kontermann & Dubel (ed.), In: *Antibody Engineering: Miniantibodies*, 637-647, Springer-Verlag, (2001) and WO92/01047, each of which is incorporated herein by reference in its entirety.

EXAMPLE 2

Yeast Surface Display

Yeast surface experiments are performed according to Boder, E. T., and Wittrup, K. D., *Methods Enzymol.* (2000) 328:430-444 with minor modifications. The Express-tag in the yeast display vector, pYD1, (Invitrogen) was removed because it cross-reacts with anti-FLAG antibodies (Sigma). The genes for cradle molecules in the phagemid library after three rounds of selection are amplified using PCR and mixed with the modified pYD 1 cut with EcoRI and XhoI, and yeast EBY100 cells are transformed with this mixture. The transformed yeast cells are grown in the SD-CAA media at 30° C. for two days, and then monobody expression is induced by growing the cells in the SG-CAA media at 30° C. for 24 h.

Sorting of monobody-displaying yeast cells is performed as follows. The yeast cells are incubated with a biotinylated target (50 nM) and mouse anti-V5 antibody (Sigma), then after washing incubated with anti-mouse antibody-FITC conjugate (Sigma) and NeutrAvidin®-PE conjugate (Invitrogen). The stained cells are sorted based on the FITC and PE intensities. Typically, cells exhibiting the top ~1% PE intensity and top 10% FITC intensity are recovered.

After FACS sorting, individual clones are analyzed. Approximate Kd values are determined from a titration curve by FACS analysis (Boder and Wittrup, supra, 2000) Amino acid sequences are deduced from DNA sequencing.

Effects of E. coli lysate on monobody-target interaction are tested by comparing binding in the presence and absence of E. coli lysate prepared from cell suspension with $OD_{600}$ of 50.

EXAMPLE 3

Protein Expression and Purification

The nucleic acid encoding any targets are cloned in the appropriate expression vector. In one example, genes for monobodies are cloned in the expression vector, pHFT2, which is a derivative of pHFT1 (Huang, et al., supra, 2006) in which the His-6 tag had been replaced with a His-10 tag. Protein expression and purification can be performed as described previously (Huang, et al., supra, 2006).

An expression vector comprising cDNA encoding an FnIII polypeptide or a target molecule is introduced into *Escherichia coli*, yeast, an insect cell, an animal cell or the like for expression to obtain the polypeptide. Polypeptides used in the present invention can be produced, for example, by expressing a DNA encoding it in a host cell using a method described in *Molecular Cloning, A Laboratory Manual*, Second Edition, Cold Spring Harbor Laboratory Press (1989), *Current Protocols in Molecular Biology*, John Wiley & Sons (1987-1997) or the like. A recombinant vector is produced by inserting a cDNA downstream of a promoter in an appropriate expression vector. The vector is then introduced into a host cell suitable for the expression vector. The host cell can be any cell so long as it can express the gene of interest, and includes bacteria (e.g., *E. coli*), an animal cell and the like. Expression vector can replicate autonomously in the host cell to be used or vectors which can be integrated into a chromosome comprising an appropriate promoter at such a position that the DNA encoding the polypeptide can be transcribed.

EXAMPLE 4

Ribosome Display

Ribosome display utilizes cell free in vitro coupled transcription/translation machinery to produce protein libraries. The FnIII library genes are inserted upstream to kappa light immunoglobulin gene that does not have a termination stop codon causing the ribosome to stall, but not release, when it reaches the end of the mRNA. Additionally, the kappa domain spacer serves to physically distance the FnIII protein from the ribosome complex so that FnIII binding domain has better accessibility to recognize its cognate ligand. The mRNA library is introduced into either S30 *E. coli* ribosome extract preparations (Roche) or rabbit reticulate lysate (Promega). In either case, the 5' end of the nascent mRNA can bind to ribosomes and undergo translation. During translation, the ligand-binding protein remains non-covalently attached to the ribosome along with its mRNA progenitor in a macromolecular complex.

The functional FnIII proteins can then bind to a specific ligand that is either attached to magnetic beads or microtiter well surface. During the enrichment process, non-specific variants are washed away before the specific FnIII binders are eluted. The bound mRNA is detected by RT-PCR using primers specific to the 5' FnIII and 3' portion of the kappa gene respectively. The amplified double stranded cDNA is then cloned into an expression vector for sequence analysis and protein production.

For prokaryotic translation reactions, the reaction mix can contain 0.2 M potassium glutamate, 6.9 mM magnesium acetate, 90 mg/ml protein disulfide isomerase (Fluka), 50 mM Tris acetate (pH 7.5), 0.35 mM each amino acid, 2 mM ATP, 0.5 mM GTP, 1 mM cAMP, 30 mM acetyl phosphate, 0.5 mg/ml *E. coli* tRNA, 20 mg/ml folinic acid, 1.5% PEG 8000, 40 ml S30 *E. coli* extract and 10 mg mRNA in a total volume of 110 ml. Translation can be performed at 37° C. for 7 min, after which ribosome complexes can be stabilized by 5-fold dilution in ice-cold selection buffer (50 mM Tris acetate (pH 7.5), 150 mM NaCl, 50 mM magnesium acetate, 0.1% Tween 20, 2.5 mg/ml heparin).

Affinity Selection for Target Ligands

Stabilized ribosome complexes can be incubated with biotinylated hapten (50 nM fluorescein-biotin (Sigma)) or antigen (100 nM IL-13 (Peprotech) biotinylated) as appropriate at 4° C. for 1-2 h, followed by capture on streptavidin-coated M280 magnetic beads (Dynal). Beads were then washed to remove non-specifically bound ribosome complexes. For prokaryotic selections, five washes in ice-cold selection buffer can be performed. For eukaryotic selections, three washes in PBS containing 0.1% BSA and 5 mM magnesium acetate were performed, followed by a single wash in PBS alone. Eukaryotic complexes can then be incubated with 10 U DNAse I in 40 mM Tris-HCl, 6 mM $MgCl_2$, 10 mMNaCl, 10 mM $CaCl_2$ for 25 min at 37° C., followed by three further washes with PBS, 5 mM magnesium acetate, 1% Tween 20.

Recovery of mRNA from Selected Ribosome Complexes

For analysis of mRNA recovery without a specific disruption step, ribosome complexes bound to magnetic beads can directly be processed into the reverse transcription reaction. For recovery of mRNA from prokaryotic selections by ribosome complex disruption, selected complexes can be incubated in EB20 [50 mM Tris acetate (pH 7.5), 150 mM NaCl, 20 mM EDTA, 10 mg/ml *Saccharomyces cerevisae* RNA] for 10 min at 4° C. To evaluate the efficiency of the 20 mM EDTA for recovery of mRNA from eukaryotic selections, ribosome complexes can be incubated in PBS20 (PBS, 20 mM EDTA, 10 mg/ml *S. cerevisae* RNA) for 10 min at 4° C. mRNA can be purified using a commercial kit (High Pure RNA Isolation Kit, Roche). For prokaryotic samples, the DNAse I digestion option of the kit was performed; however, this step is not required for eukaryotic samples, as DNAse I digestion was performed during post-selection washes. Reverse transcription can be performed on either 4 ml of purified RNA or 4 ml of immobilized, selected ribosome complexes (i.e., a bead suspension).

For prokaryotic samples, reactions contained 50 mM Tris-HCl (pH 8.3), 75 mM KCl, 3 mMMgCl$_2$, 10 mMDTT, 1.25 primer, 0.5 mM PCR nucleotide mix (Amersham Pharmacia), 1 URNAsin (Promega) and 5 U SuperScript II (Invitrogen) and were performed by incubation at 50° C. for 30 min. For eukaryotic samples, reactions contained 50 mM Tris-HCl (pH 8.3), 50 mM KCl, 10 mM $MgCl_2$, 0.5 mM spermine, 10 mM DTT, 1.25 mM RT primers, 0.5 mM PCR nucleotide mix, 1 U RNasin and 5 U AMV reverse transcriptase (Promega) and can be performed by incubation at 48° C. for 45 min.

PCR of Selection Outputs

End-point PCR can be performed to visualize amplification of the full-length construct. A 5 ml sample of each reverse transcription reaction can be amplified with 2.5 UTaq polymerase (Roche) in 20 mM Tris-HCl (pH 8.4), 50 mM KCl, 1 mM $MgCl_2$, 5% DMSO, containing 0.25 mM PCR nucleotide mix, 0.25 mM forward primer (T7B or T7KOZ for prokaryotic and or eukaryotic experiments, respectively) and 0.25 mM RT primer. Thermal cycling comprised 94° C. for 3 min, then 94° C. for 30 s, 50° C. for 30 s and 72° C. for 1.5 min for 30 cycles, with a final step at 72° C. for 5 min PCR products were visualized by electrophoresis on an ethidium bromide stained agarose gels. The isolated PCR products can then be sub-cloned into a bacterial pBAD expression vector for soluble protein production.

Bacterial Expression and Production

Competent *E. coli* host cells are prepared as per manufacturer's instructions (Invitrogen PBAD expression system). Briefly, 40 μl LMG 194 competent cells and 0.5 μl pBAD FnIII constructs (approximately 1 μg DNA) can be incubated together on ice for 15 minutes after which, a one minute 42° C. heat shock was applied. The cells are then allowed to recover for 10 minutes at 37° C. in SOC media before plating onto LB-Amp plates and 37° C. growth overnight. Single colonies are picked the next day for small scale liquid cultures to initially determine optimal L-arabinose induction concentrations for FnIII production. Replicates of each clone after reaching an OD600=0.5 can be tested induced with serial (1:10) titrations of L-arabinose (0.2% to 0.00002% final concentration) after overnight growth at room temperature. Test cultures (1 ml) can be collected, pelleted and 100 μl 1×BBS buffer (10 mM, 160 mM NaCl, 200 mM Boric acid, pH=8.0) added to resuspend the cells before the addition of 50 μl of lysozyme solution for 1 hour (37° C.). Cell supernatants from the lysozyme digestions can be collected after centrifugation, and MgSO4 can be added to final concentration 40 mM. This solution can be applied to PBS pre-equilibrated Ni-NTA columns His-tagged bound FnIII samples are washed twice with PBS buffer upon which elution can be accomplished with the addition of 250 mM imidazole. Purity of the soluble FnIII expression can be examined by SDS-PAGE.

EXAMPLE 5

Design of a Cradle library Based on the FnIII Domain Exemplified with the FnIII$^{07}$, FnIII$^{10}$ and FnIII$^{14}$ Domains In this example, universal CD and FG loop sequences along with 3 beta strands between the loops which face outward for fibronectin binding domain library sequences are identified and selected using bioinformatics and the criteria of the invention. A generalized schematic of this process is presented in FIG. 1.

```
Sequences
7th FnIII domain (FnIII07)-FINC_HUMAN(1173-1265):
                                         (SEQ ID NO: 97)
PLSPPTNLHLEANPDTGVLTVSWERSTTPDITGYRITTTPTNGQQGNSLE
EVVHADQSSCTFDNLSPGLEYNVSVYTVKDDKESVPISDTIIP 10th FnIII domain (FnIII10)-FINC_HUMAN(1447-1542):
                                        (SEQ ID NO: 280)
VSDVPRDLEVVAATPTSLLISWDAPAVTVRYYRITYGETGGNSPVQEFT
VPGSKSTATISGLKPGVDYTITVYAVTGRGDSPASSKPISINYRTEI 14th FnIII domain (FnIII14)-FINC_HUMAN(1813-1901):
                                        (SEQ ID NO: 129)
NVSPPRRARVTDATETTITISWRTKTETITGFQVDAVPANGQTPIQRTIK
PDVRSYTITGLQPGTDYKIYLYTLNDNARSSPVVIDAST
```

Alignment

Below is the sequence alignment of FnIII repeats 7, 10, and 14 (SEQ ID NOs: 97, 280, 129 respectively). The structurally conserved hydrophobic core residues are shown in bold.

```
            |-AB--|          |---BC---|
FnIII07 PLSPPTNLHL-EA|NPDTG|VLTVSWE|RSTTPDIT|GYRITTTPT
FnIII10 VSDVPRDLEVVAA|T--PT|SLLISWD|APAV-TVR|YYRITYGET
FNIII14 NVSPPRRARVTDA|T--ET|TITISWR|TKTE-TIT|GFQVDAVPA
                     |-----|       |--------|

|---CD--|       |DE-|    |--EF--|
FnIII07 |NGQQGNS|LEEVVH|ADQ|SSCTFD|NLSPGL|EYNVSVYTVK
FnIII10 |-GGNSPV|QEFTVP|GSK|STATIS|GLKPGV|DYTITVYAVT
FnIII14 |-NGQT-P|IQRTIK|PDV|RSYTIT|GLQPGT|DYKIYLYTLN
        |-------|      |---|      |------|

|----FG-----|
FnIII07 |D--DKE--SVP|ISDTIIP--
FnIII10 |GRGDSPASSKP|ISINYRTEI
FNIII14 |D-NA---RSSP|VVIDAST--
        |-----------|
```

Definition of the Cradle

Figure 2A:
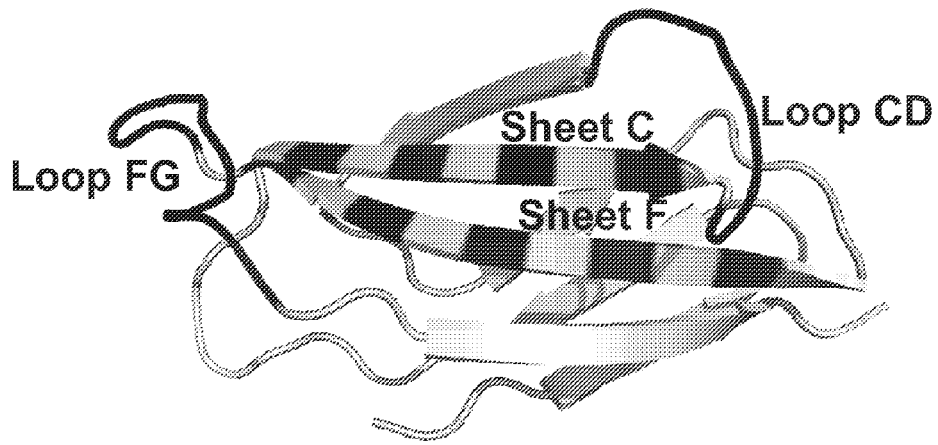
FIG. 2A shows the structure and sequence of the wild type FnIII$^{10}$ (SEQ ID NO:1). Loops CD and FG along with the specific residues of beta strands C and F are shown in black in the structure and boldface black in the sequence.
Figure 2B:
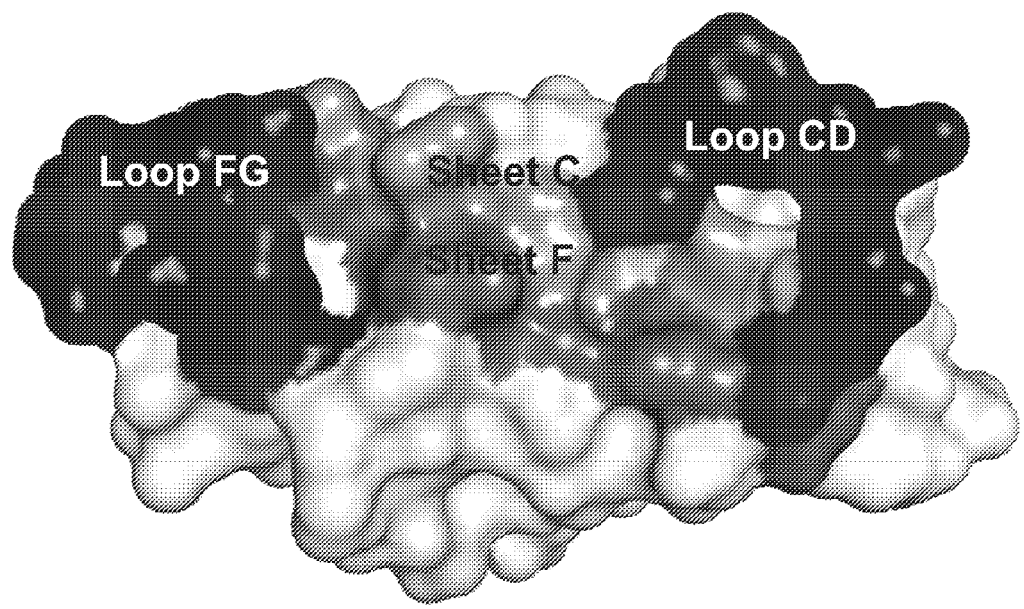
FIG. 2B shows the binding surface formed by the Cradle. Loops CD and FG are black, sheet C is light gray, and sheet F is dark gray.
Figure 3A:
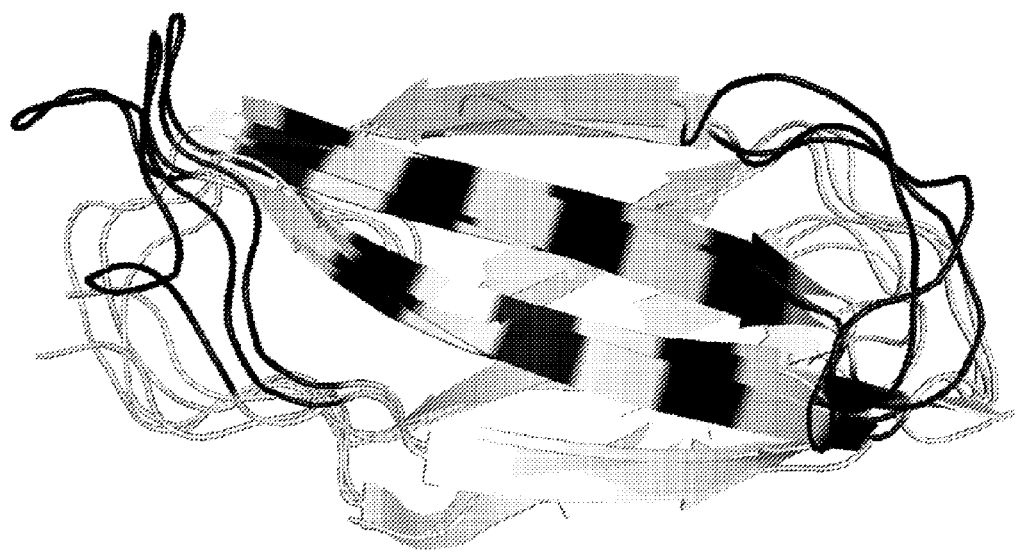
FIG. 3A shows the placement of the cradle residues on the ribbon diagrams of the FnIII domains. The structure for the FnIII$^{07}$ domain is from RCSB code 1FNF, the structure for the FnIII$^{10}$ domain is from 1FNA, and the structure for the FnIII$^{14}$ domain is from 1FNH.
Figure 3B:
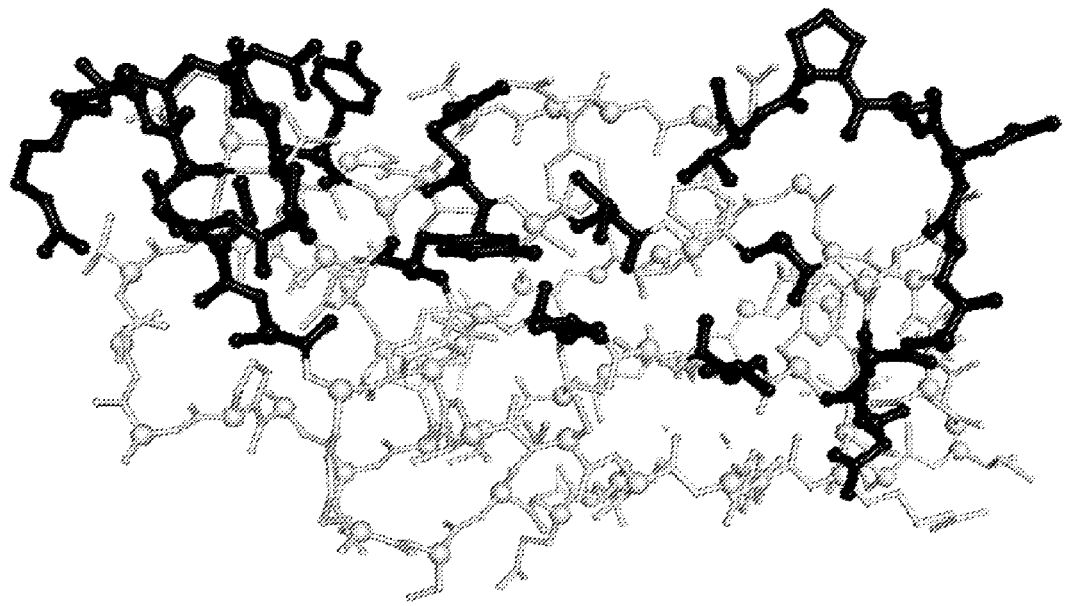
FIG. 3B is a ball and stick representation of the location of the cradle on the FnIII$^{10}$ molecule, where cradle residues are black and other residues are white.

The portion of the fibronectin deemed the cradle are loops CD and FG along with amino acids in 3 beta strands between the loops which face outward (FIGS. 2 and 3). Cradle residues are highlighted in bold in the alignment shown below (SEQ ID NOs:97, 280, 129 respectively).

```
FnIII07 PLSPPTNLHL-EANPDTGVLTVSWERSTTPDITGYRITTTPT
FnIII10 VSDVPRDLEVVAAT--PTSLLISWDAPAV-TVRYYRITYGET
FNIII14 NVSPPRRARVTDAT--ETTITISWRTKTE-TITGFQVDAVPA

|---CD--|
FnIII07 |NGQQGNS|LEEVVHADQSSCTFDNLSPGLEYNVSVYTVK
FnIII10 |-GGNSPV|QEFTVPGSKSTATISGLKPGVDYTITVYAVT
FnIII14 |-NGQT-P|IQRTIKPDVRSYTITGLQPGTDYKIYLYTLN

|----FG-----|
FnIII07 |D--DKE--SVP|ISDTIIP--
FnIII10 |GRGDSPASSKP|ISINYRTEI
FnIII14 |D-NA---RSSP|VVIDAST--
```

Distribution of the Cradle Loops

The fibronectin family alignment, PF00041.full, was downloaded from PFAM in Stockholm (1.0 format located on the World Wide Web at pfam.sanger.ac.uk/family/PF00041#tabview=2). The FG loop was truncated in PF00041.full and the data from US20090176654(A1) was used instead. The FG loop was defined to include the sequence TGRGDSPASSKPI and the terminal T and I are not defined as part of the FG loop in the cradle. As a result, the distribution data for the FG loop from U.S. Patent Publication No. 2009017654(A1) will be amended by subtracting 2 from each loop length in the distribution.

The BC loop was calculated for PF00041.full based on the definition in U.S. Patent Publication No. 2009017654(A1) of the DE loop to be the sequence 1 amino acid before the conserved W and up to, but not including, the conserved Y. The BC loop corresponded to columns 125-248 in PF00041.full. The BC loops were extracted and the gaps were removed. The length of each loop was determined and range of loop lengths was found to be 1-26. The distribution of loop length was determined.

Figure 4A:
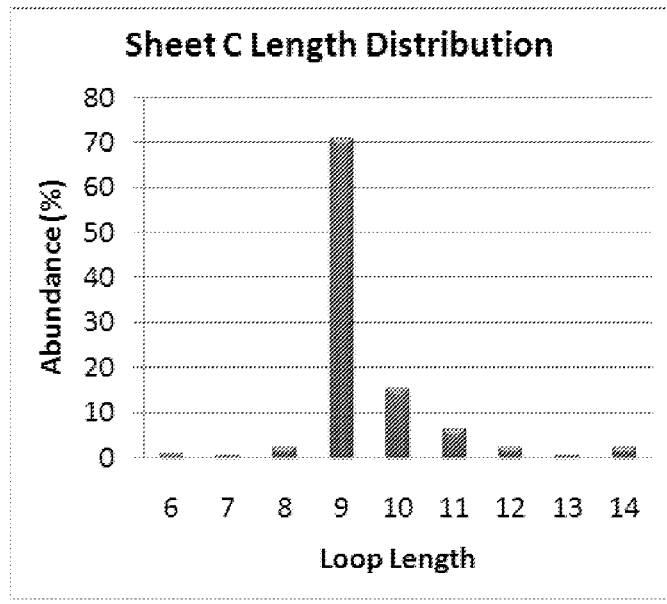
FIGS. 4A-D show the length distribution calculated from mammalian FnIII domains found in the PFAM family PF00041.

The output is captured as BC_Loop.txt and formatted in Excel® to generate the table and graph which were saved as BC_Loop.xlsx and shown in FIG. 4A. Following is the sequence of FnIII$^{10}$ (SEQ ID NO:280) with the cradle loops/sheets in bold.

```
                                         β1
VSDVPRDLEVVAATPTSLLISWDAPAVTVRYYRITYGET

CD      β2                        β3
|GGNSPV|QEFTVPGSKSTATISGLKPGVDYTITVYAVT

FG
|GRGDSPASSKP|ISINYRTEI
```

The sheet before the CD loop was designated β1 (also referred to as sheet C) and included the sequence YYRITY-GET (residues 31-39 of SEQ ID NO:280). The CD loop was the sequence GGNSPV (residues 40-45 of SEQ ID NO:280). The sheet directly following the CD loop was β2 (also referred to as sheet D) and included the sequence QEFTV (residues 46-50 of SEQ ID NO:280). The sheet before the FG loop was β3 (also referred to as sheet F) and included the sequence DYTITVYAVT (residues 67-76 of SEQ ID NO:280). The FG loop was the sequence GRGDSPASSKP (residues 77-87 of SEQ ID NO:280). β1 corresponded to columns 236-271. The CD loop was columns 271-317. β2 was columns 318-323. β3 was columns 400-415.

Figure 4B:
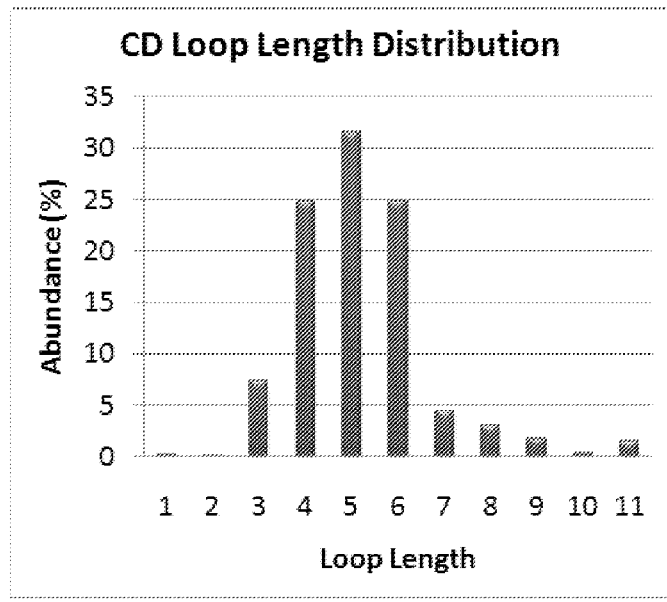
Figure 4C:
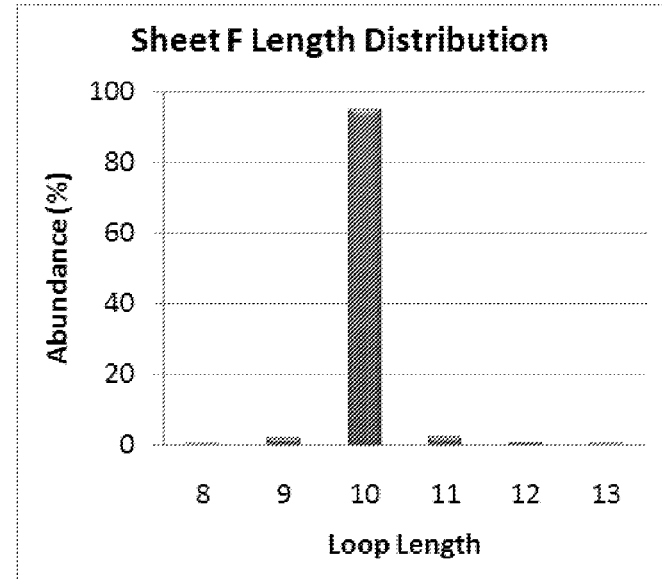
Figure 4D:
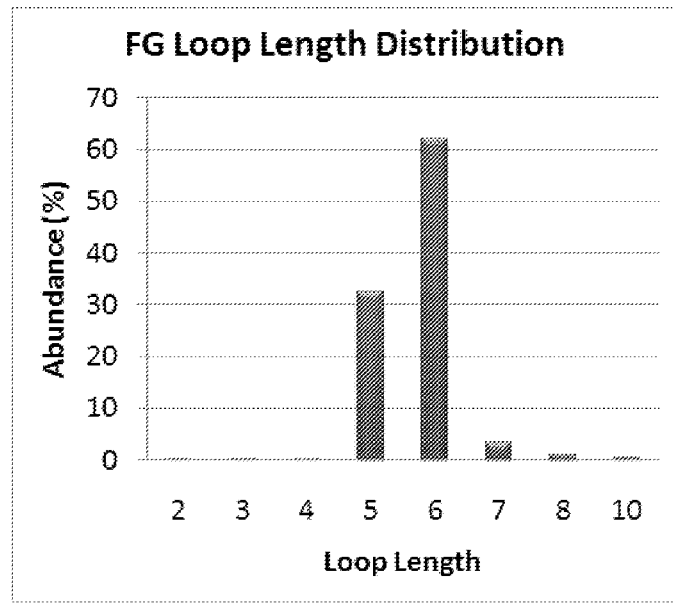

The distribution for each sheet or loop was calculated with same Python code as the BC loop using the appropriate columns. The length distribution showed that the sheets, β1-β3, have a high amount of length conservation which correlates well with the structural duties of the sheets within the fibronectin molecule (FIGS. 4A and 4C). The CD and FG loops of the cradle show acceptance of a wide array of loop lengths (FIGS. 4B and 4D).

Sequence Conservation of the Beta Sheets in the Cradle

Amino acid sequences on β1 length 9, β2 length 4, and β3 length 10 were analyzed for sequence conservation.

Figure 5A:
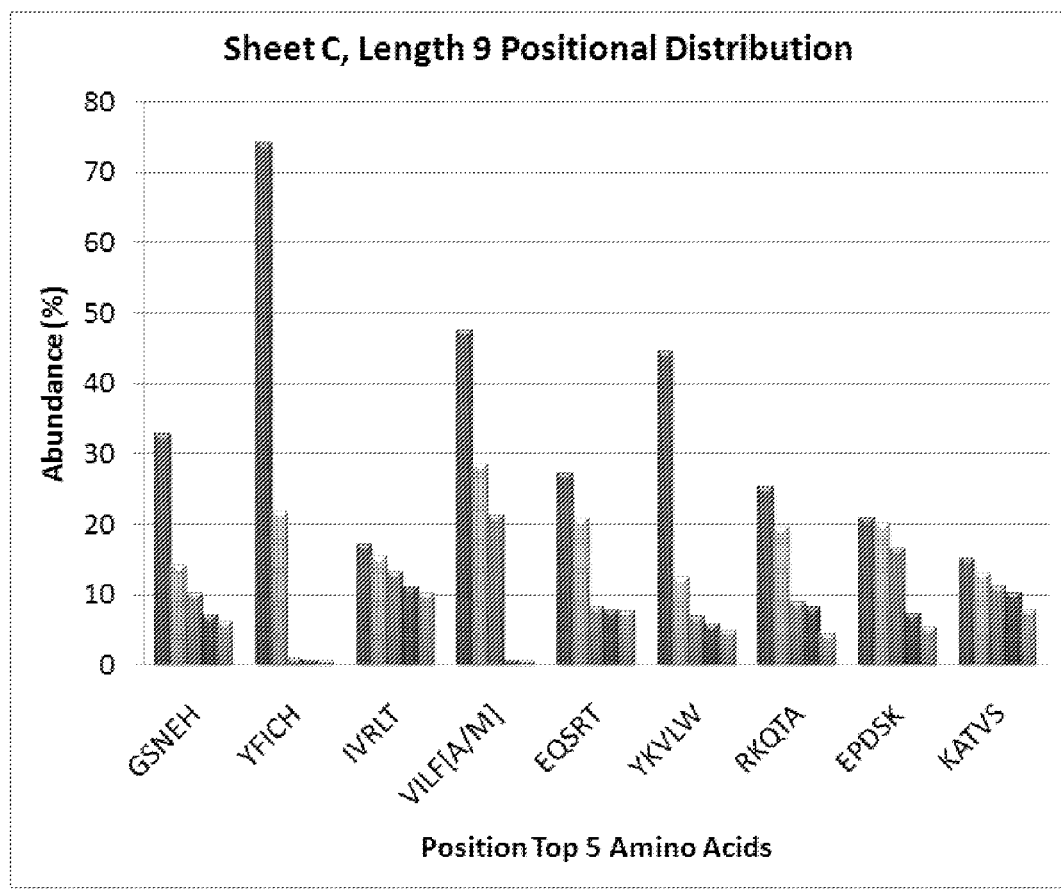
FIGS. 5A-H show the positional amino acid distribution found in the structural elements of the Cradle. The conservation of the top 5 amino acids for each position in each Cradle is shown.
Figure 5B:
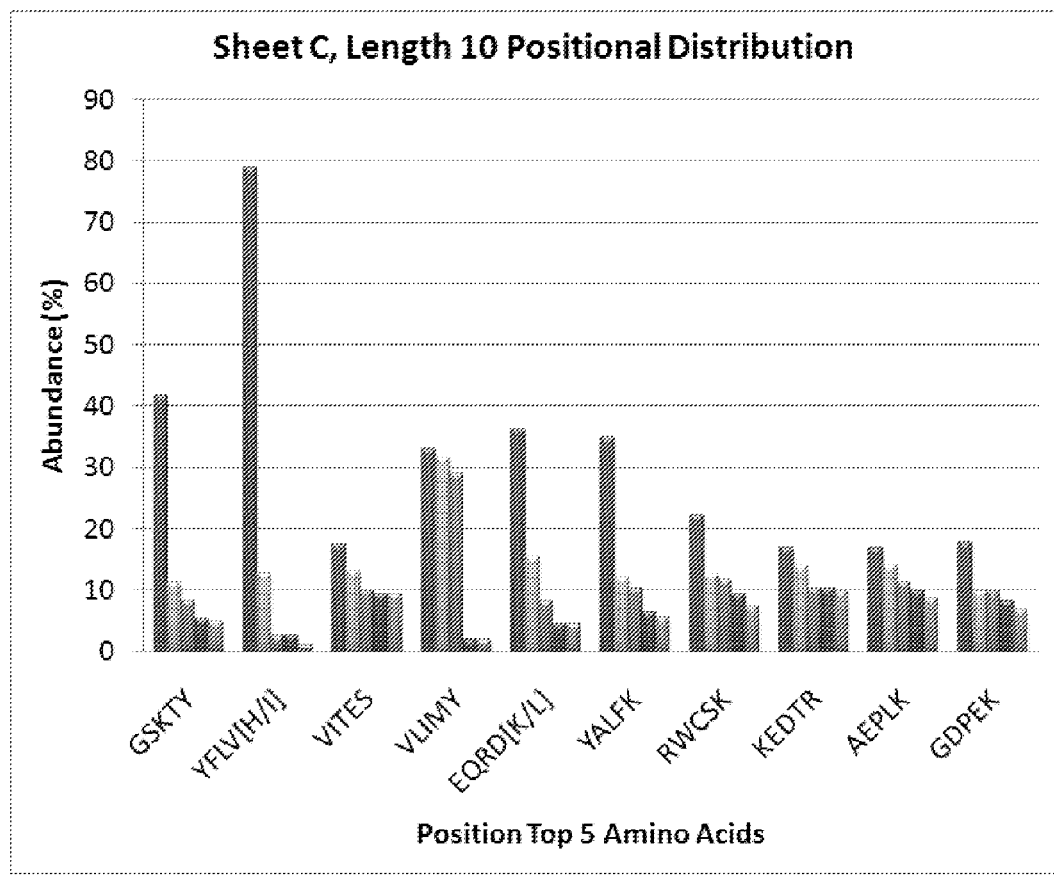
Figure 5C:
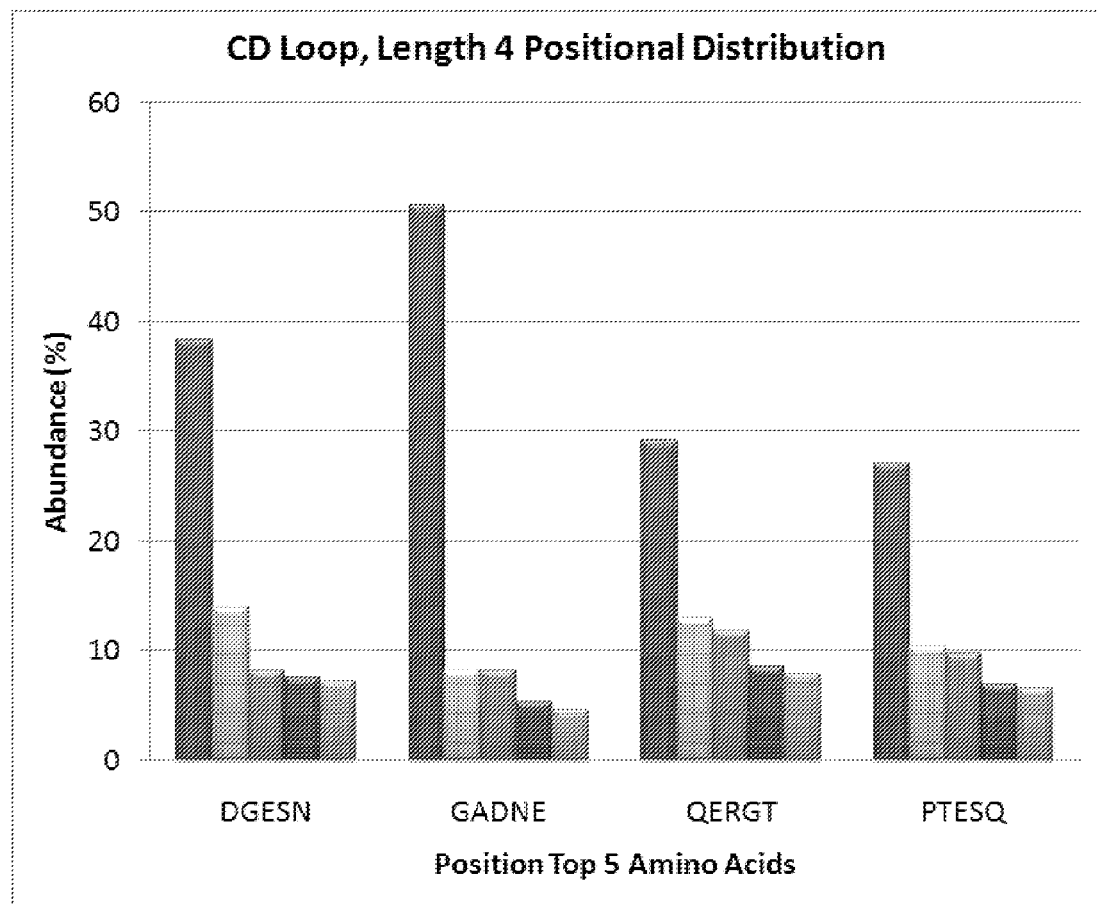
Figure 5D:
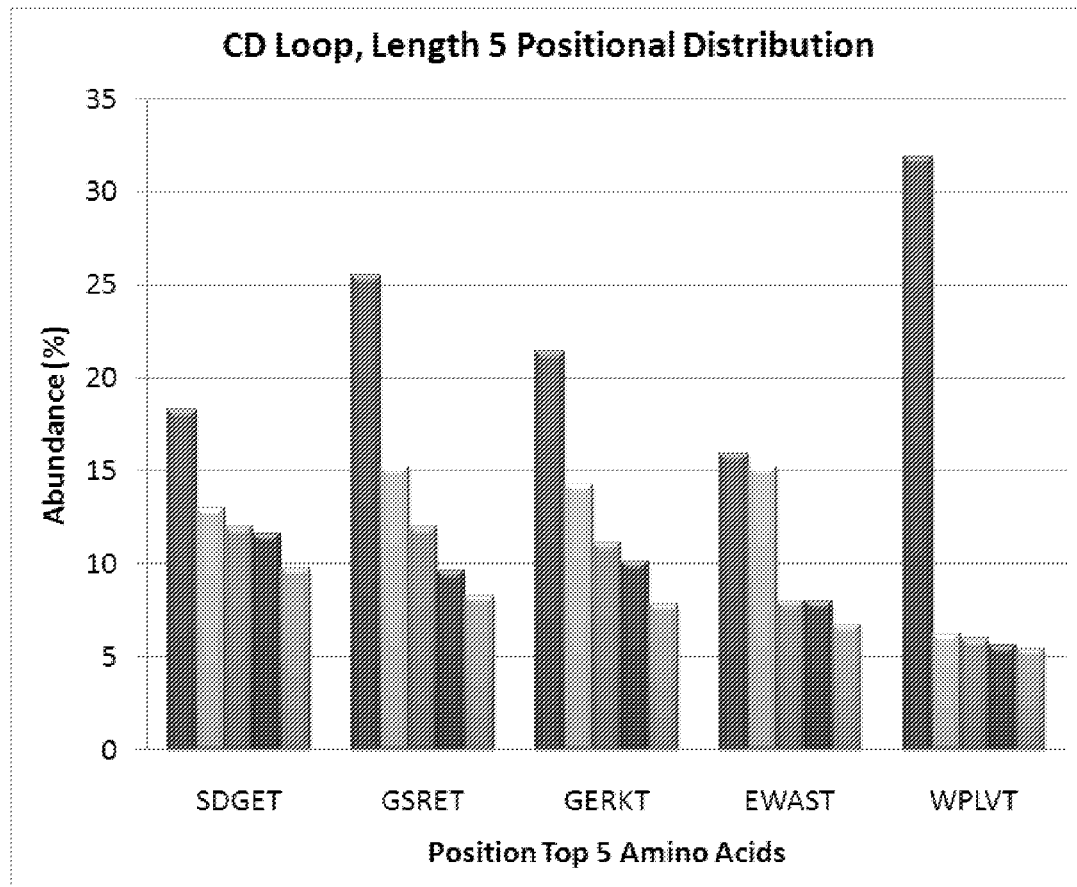
Figure 5E:
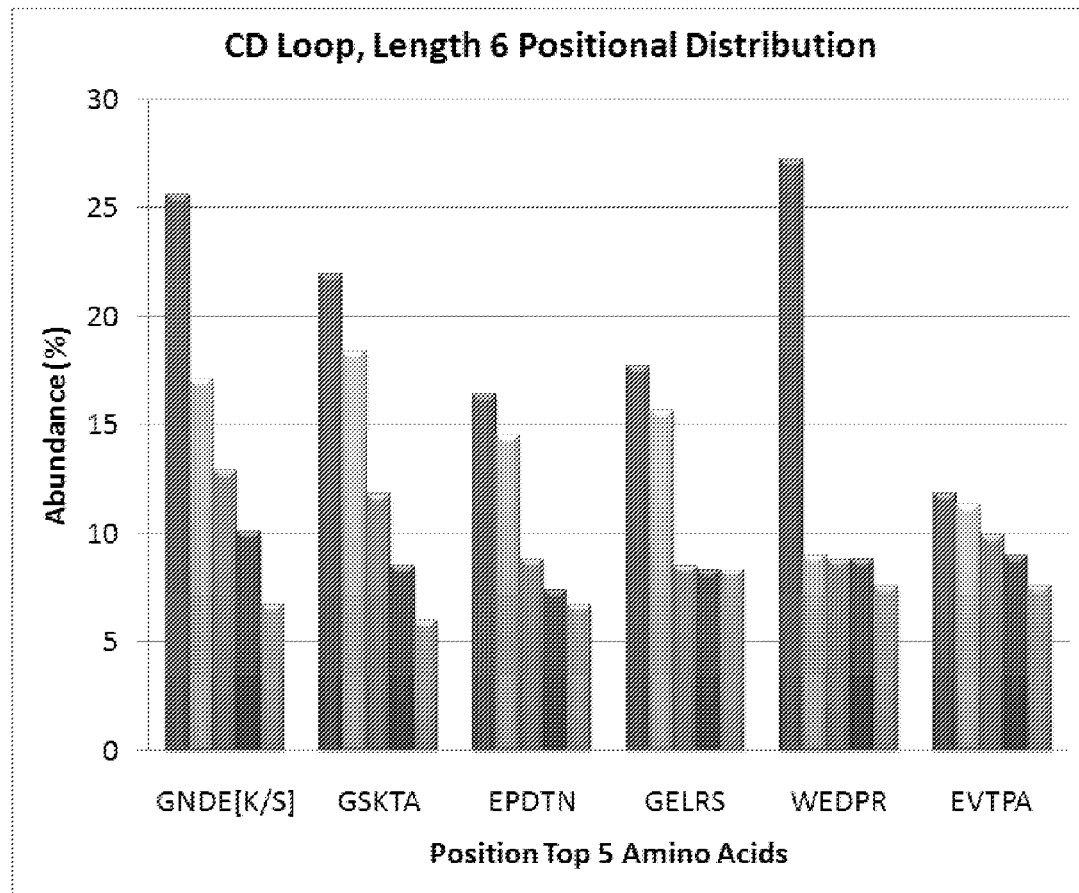
Figure 5F:
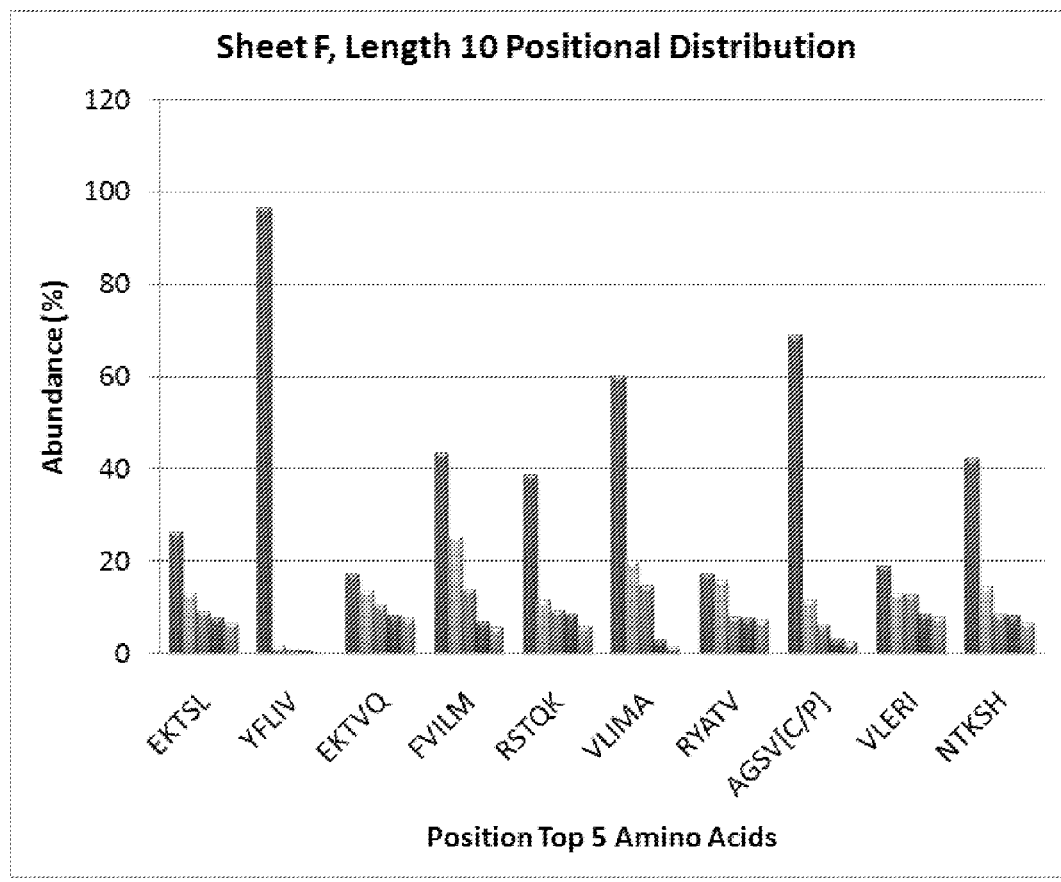
Figure 5G:
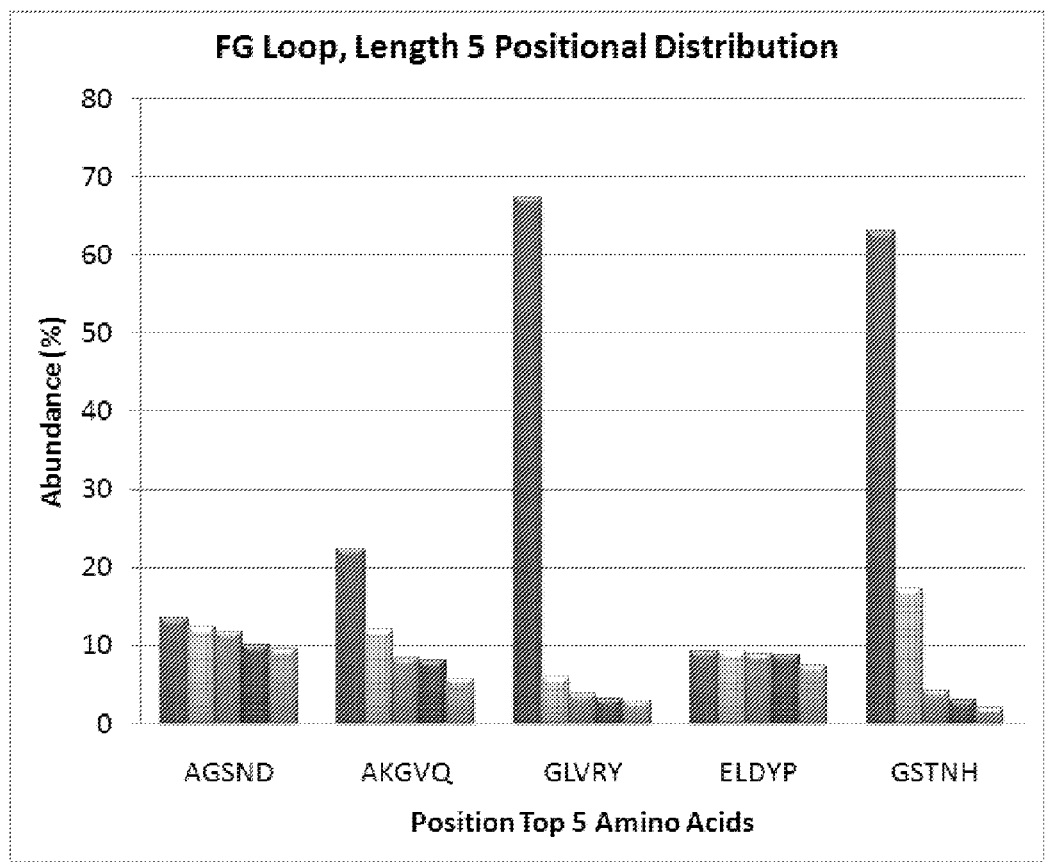
Figure 5H:
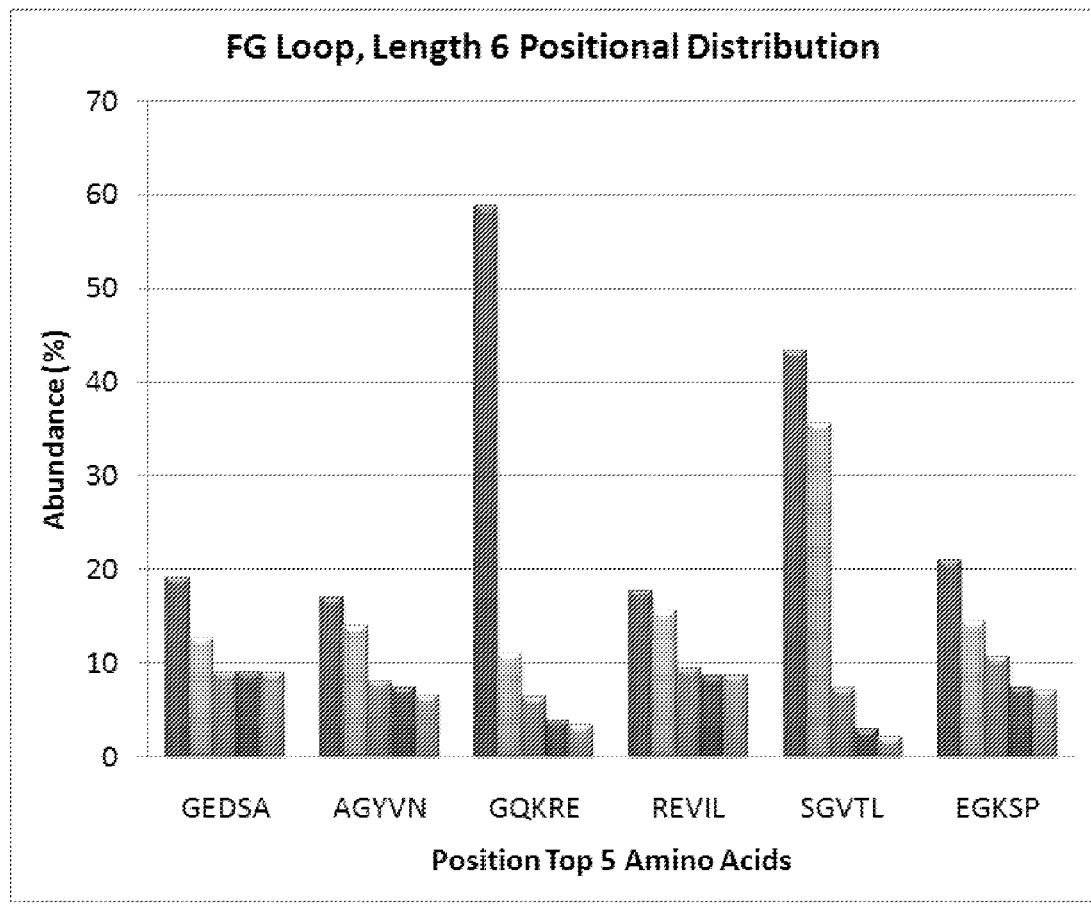
Figure 6A:
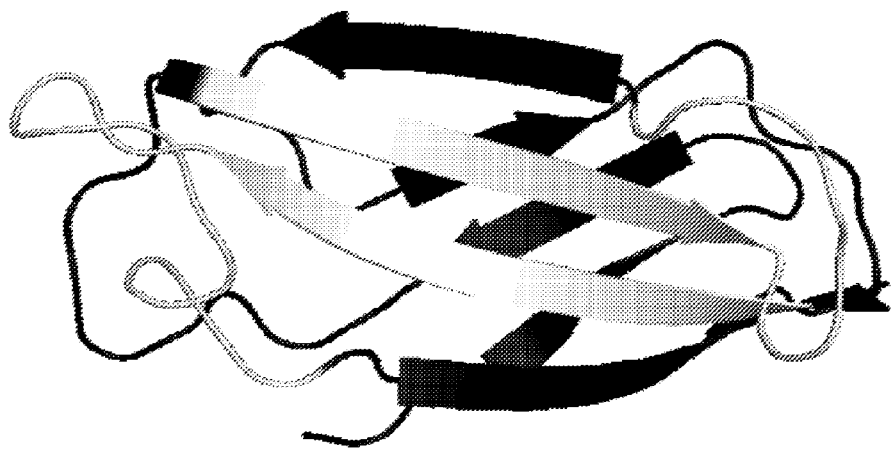
FIGS. 6A-F show the binding surface comparison of the FnIII$^{10}$ Cradle, the FnIII$^{10}$ Top Side and the FnIII$^{10}$ Bottom Side binding sites.
Figure 6B:
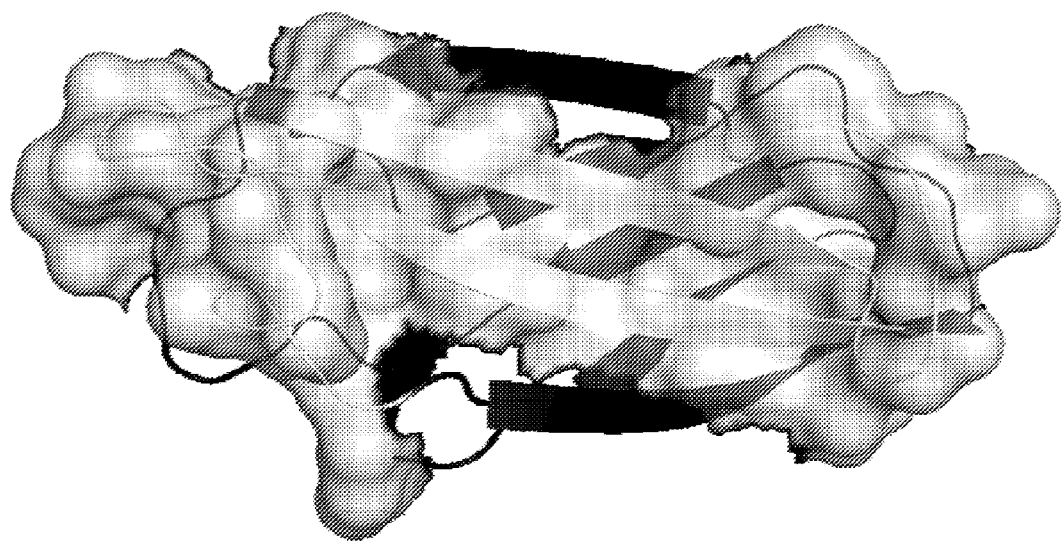
Figure 6C:
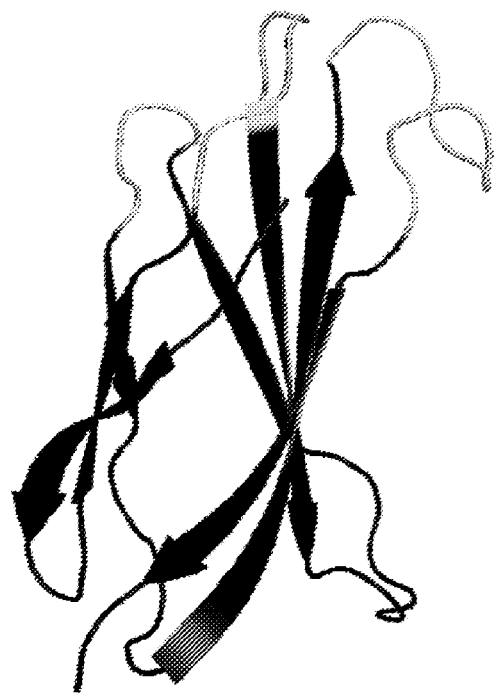
Figure 6D:
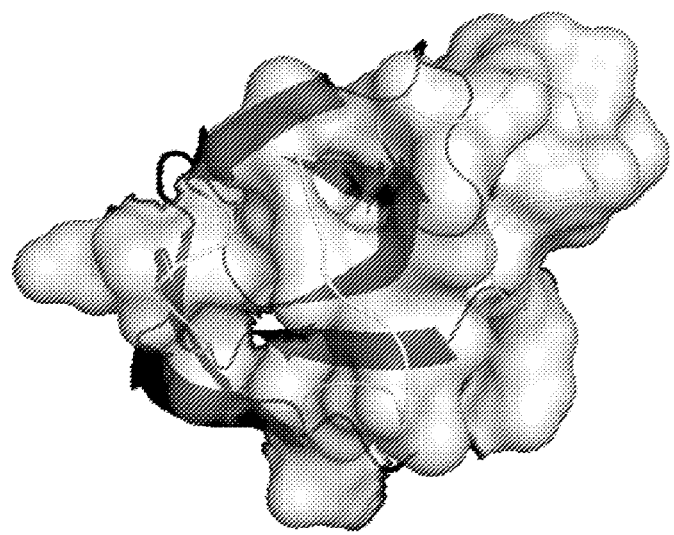
Figure 6E:
Figure 6F:
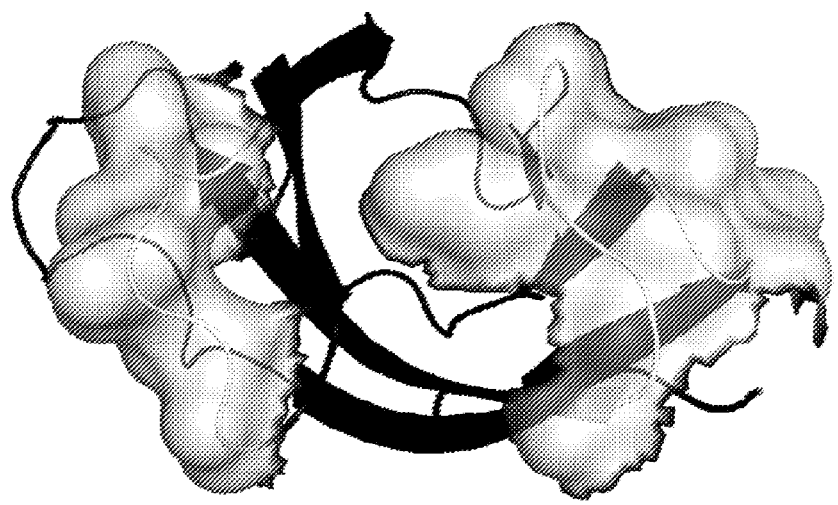

The same code was used to calculate the distributions of β2 and β3. Position 1, 3, 5, 7, and 9 are of interest for design of the cradle library and showed moderately low sequence conservation as shown in FIG. 5A. Position 2 is known to be a highly conserved Tyrosine which has an important packing role with a Tryptophan from the opposite sheet of the beta sandwich (FIG. 5A). Positions 4 and 6 also have beta sandwich packing roles in the structure and show high sequence conservation (FIG. 5A). Positions 2 and 4 of are interest in the cradle library and showed low conservation (FIG. 5C). Overall β2 is not as highly conserved as β1 or β3 (FIG. 5B). Like in β1, the odd positions of β3 are intended to be used in library and show low to moderate conservation and even positions, which have structural support functions, show high sequence conservation.

The conservation was mapped onto FnIII$^{07}$, FnIII$^{10}$, and FnIII$^{14}$ where the cartoon and balls/sticks on β1-β3 are shown in FIG. 6, colored according to conservation (White=high conservation, gray=moderate conservation, and black=low conservation).

Area of Binding Surface

A distinct advantage that the cradle library provides over a top or bottom side library is an increase in surface area of the binding surface on the fibronectin as shown in FIG. 6. The top side binding fibronectin library consists of the BC, DE, and FG loops. The bottom side library is the AB, CD, and EF loops. The cradle is the CD and FG loops along with three beta strands.

The following alignment (SEQ ID NOs:97, 280, 129 respectively) shows top-side residues in bold.

```
FnIII07  PLSPPTNLHL-EANPDTGVLTVSWERSTTPDITGYRITTTPT

FnIII10  VSDVPRDLEVVAAT--PTSLLISWDAPAV-TVRYYRITYGET

FNIII14  NVSPPRRARVTDAT--ETTITISWRTKTE-TITGFQVDAVPA

FnIII07  NGQQGNSLEEVVHADQSSCTFDNLSPGLEYNVSVYTVK

FnIII10  -GGNSPVQEFTVPGSKSTATISGLKPGVDYTITVYAVT

FnIII14  -NGQT-PIQRTIKPDVRSYTITGLQPGTDYKIYLYTLN

FnIII07  D--DKE--SVPISDTIIP--

FnIII10  GRGDSPASSKPISINYRTEI

FnIII14  D-NA---RSSPVVIDAST-
```

The following alignment (SEQ ID NOs: 97, 280, 129 respectively) shows bottom-side residues in bold.

```
FnIII07  PLSPPTNLHL-EANPDTGVLTVSWERSTTPDITGYRITTTPT

FnIII10  VSDVPRDLEVVAAT--PTSLLISWDAPAV-TVRYYRITYGET

FNIII14  NVSPPRRARVTDAT--ETTITISWRTKTE-TITGFQVDAVPA

FnIII07  NGQQGNSLEEVVHADQSSCTFDNLSPGLEYNVSVYTVK

FnIII10  -GGNSPVQEFTVPGSKSTATISGLKPGVDYTITVYAVT

FnIII14  -NGQT-PIQRTIKPDVRSYTITGLQPGTDYKIYLYTLN

FnIII07  D--DKE--SVPISDTIIP--

FnIII10  GRGDSPASSKPISINYRTEI

FnIII14  D-NA---RSSPVVIDAST--
```

The following alignment (SEQ ID NOs: 97, 280, 129 respectively) shows cradle residues in bold.

```
FnIII07  PLSPPTNLHL-EANPDTGVLTVSWERSTTPDITGYRITTTPT

FnIII10  VSDVPRDLEVVAAT--PTSLLISWDAPAV-TVRYYRITYGET

FNIII14  NVSPPRRARVTDAT--ETTITISWRTKTE-TITGFQVDAVPA

FnIII07  NGQQGNSLEEVVHADQSSCTFDNLSPGLEYNVSVYTVK

FnIII10  -GGNSPVQEFTVPGSKSTATISGLKPGVDYTITVYAVT

FnIII14  -NGQT-PIQRTIKPDVRSYTITGLQPGTDYKIYLYTLN

FnIII07  D--DKE--SVPISDTIIP--

FnIII10  GRGDSPASSKPISINYRTEI

FnIII14  D-NA---RSSPVVIDAST--
```

Analysis Summary

The following Table 1 (and FIG. 2B) shows that the cradle offers approximately two times the binding surface of the top or bottom side loops and has less conservation of the residues intended for library design than the top or bottom side libraries.

TABLE 1

| | Surface Area of the loops | | | |
|---|---|---|---|---|
| Protein | Total Area | Top Side Loops | Bottom Side Loops | Cradle |
| FnIII07 | 9178 Å$^2$ | 2116 Å$^2$ | 1600 Å$^2$ | 3705 Å$^2$ |
| FnIII10 | 8804 Å$^2$ | 2001 Å$^2$ | 1453 Å$^2$ | 3932 Å$^2$ |
| FnIII14 | 8716 Å$^2$ | 1962 Å$^2$ | 1194 Å$^2$ | 3469 Å$^2$ |

Additionally, of the loops in the fibronectin molecule only the CD and FG loops have a large variation in allowed loop length. The length variation may indicate that these loops will tolerate more variation than the top or bottom side loops such as the EF loop which has a >90% conservation of loop length 6 as, defined with FnIII$^{10}$ sequence GLKPGV (residues 61-66 of SEQ ID NO:280), along with a >95% sequence conservation of the leucine in position 2. Although the cradle contains 3 beta strands of the largest beta sheet, it offers more amino acid residues to modify than the top or bottom loops. The alignment below shows sequences for FnIII$^{07}$, FnIII$^{10}$, and FnIII$^{14}$ (SEQ ID NOs:97, 280, 129 respectively) where the top loops are italics, the bottom side loops are underlined, and cradle residues are bold. Only residues that are amenable to library design are marked.

```
FnIII07  PLSPPTNLHL-EANPDTGVLTVSWER*STTPDIT*GYRITTTPT

FnIII10  VSDVPRDLEVVAAT--PTSLLISWDAPAV-TVRYYRITYGET

FNIII14  NVSPPRRARVTDAT--ETTITISWRTKTE-TITGFQVDAVPA

FnIII07  NGQQGNSLEEVVHADQSSCTFDNLSPGLEYNVSVYTVK

FnIII10  -GGNSPVQEFTVPGSKSTATISGLKPGVDYTITVYAVT

FnIII14  -NGQT-PIQRTIKPDVRSYTITGLQPGTDYKIYLYTLN

FnIII07  D--DKE--SV PISDTIIP--

FnIII10  GRGDSPASSK PISINYRTEI

FnIII14  D-NA---RSS PVVIDAST-
```

The top side, bottom side, cradle contain 19-23, 12-14, and 19-24 residues respectively that can be used when loop length variation is not applied. The top and bottom side contain only one loop whose length can be aggressively changed, whereas the cradle contains both of them.

EXAMPLE 6

Creating a Diverse Mammalian FnIII Domain Alignment

A profile was created using the FnIII domains found in the human fibronectin protein, uniprot FINC_HUMAN or P02751.

The list below shows the profile members.
FnIII$^{01}$: FINC_HUMAN(607-699)
FnIII$^{02}$: FINC_HUMAN(720-808)
FnIII$^{03}$: FINC_HUMAN(811-898)
FnIII$^{04}$: FINC_HUMAN(908-995)
FnIII$^{05}$: FINC_HUMAN(996-1083)

FnIII⁰⁶: FINC_HUMAN(1087-1172)
FnIII⁰⁷: FINC_HUMAN(1173-1265)
FnIII⁰⁸: FINC_HUMAN(1266-1356)
FnIII⁰⁹: FINC_HUMAN(1357-1445)
FnIII¹⁰: FINC_HUMAN(1447-1540)
FnIII¹¹: FINC_HUMAN(1541-1630)
FnIII¹²: FINC_HUMAN(1631-1720)
FnIII¹³: FINC_HUMAN(1723-1810)
FnIII¹⁴: FINC_HUMAN(1813-1901)
FnIII¹⁵: FINC_HUMAN(1902-1991)

The fasta sequence for each profile member was derived from the Uniprot entry. The sequences were aligned with Clustal X 2.0.11. The crystal structure of the FnIII¹⁰, RCSB entry 1fna, was used to highlight secondary structure and define regions on the alignment for later analysis. The sheets on the fibronectin were designated A-G and named from N-terminal to C-terminal in the protein.

The loops were labeled according to which sheets they were between. Example: Loop CD was between sheet C and sheet D.

Alignment Profile

The following alignment (FnIII_template.aln) (SEQ ID NOs:100, 97, 129, 281-292 respectively) was loaded into Clustal X as Profile 1.

```
CLUSTAL 2.0.11 multiple sequence alignment
1fna SS    *******AAB  B***B C****C**C DDDE
FnIII10    VSDVPRDLEVVAATPT--SLLISWDAP-AVTVRYYRITYGETGGN-SPVQEFTVPGSKST FnIII07    PLSPPTNLHLEANPDTG-VLTVSWERSTTPDITGYRITTTPTNGQQGNSLEEVVHADQSS FnIII14    NVSPPRRARVTDATET--TITISWRTKTET-ITGFQVDAVPANGQ--TPIQRTIKPDVRS FnIII08    AVPPPTDLRFTNIGPD--TMRVTWAPPPSIDLTNFLVRYSPVKNE-EDVAELSISPSDNA FnIII13    --PAPTDLKFTQVTPT--SLSAQWTPP-NVQLTGYRVRVTPKEKT-GPMKEINLAPDSSS FnIII04    --PSPRDLQFVEVTDV--KVTIMWTPP-ESAVTGYRVDVIPVNLP-GEHGQRLPISRNTF FnIII05    KLDAPTNLQFVNETDS--TVLVRWTPP-RAQITGYRLTVGLTR-R-GQPRQYNVGPSVSK FnIII09    GLDSPTGIDFSDITAN--SFTVHWIAP-RATITGYRIRHHPEHFS-GRPREDRVPHSRNS FnIII15    AIDAPSNLRFLATTPN--SLLVSWQPP-RARITGYIIKYEKPGSP-PREVVPRPRPGVTE FnIII12    NIDRPKGLAFTDVDVD--SIKIAWESP-QGQVSRYRVTYSSPEDG-IHELFPAPDGEEDT FnIII02    -PLVATSESVTEITAS--SFVVSWVSA-SDTVSGFRVEYELSEEG-DEPQYLDLPSTATS FnIII03    -PDAPPDPTVDQVDDT--SIVVRWSRP-QAPITGYRIVYSPSVEG-S-STELNLPETANS FnIII11    EIDKPSQMQVTDVQDN--SISVKWLPSSSP-VTGYRVTTTPKNGP-GPTKTKTAGPDQTE FnIII06    -PGSSIPPYNTEVTET--TIVITWTPA---PRIGFKLGVRPSQGG--- EAPREVTSDSGS FnIII01    SSSGPVEVFITETPSQPNSHPIQWNAPQPSHISKYILRWRPKNSV-GRWKEATIPGHLNS
                            .                 *             :  :

1fna SS           *E**   EF******F**********FG*******G***
FnIII10           ATISGLKPGVDYTITVYAVTGRGDSPASSKPISINYRT FnIII07           CTFDNLSPGLEYNVSVYTVKDDKES----VPISDTIIP FnIII14           YTITGLQPGTDYKIYLYTLNDNARS----SPVVIDAST FnIII08           VVLTNLLPGTEYVVSVSSVYEQHES----TPLRGRQKT FnIII13           VVVSGLMVATKYEVSVYALKDTLTS----RPAQGVVTT FnIII04           AEVTGLSPGVTYYFKVFAVSHGRES----KPLTAQQTT FnIII05           YPLRNLQPASEYTVSLVAIKGNQES-----PKATGVFT FnIII09           ITLTNLTPGTEYVVSIVALNGREES-----PLLIGQQS FnIII15           ATITGLEPGTEYTIYVIALKNNQKS----EPLIGRKKT FnIII12           AELQGLRPGSEYTVSVVALHDDMES----QPLIGTQST FnIII02           VNIPDLLPGRKYIVNVYQISEDGEQ----SLILSTSQT FnIII03           VTLSDLQPGVQYNITIYAVEENQES----TPVVIQQET FnIII11           MTIEGLQPTVEYVVSVYAQNPSGES----QPLVQTAVT FnIII06           IVVSGLTPGVEYVYVTIQVLRDGQER---DAPIVNKVVT FnIII01           YTIKGLKPGVVYEGQLISIQQYGHQ----EVTRFDFTT
                     . .*     *    :              .
```

Mammalian Fibronectin Sequences

The FnIII domain alignment was obtained from PFAM and saved as PF00041.full. The alignment from PFAM was truncated at the C-terminal portion of the FG loop and the entire Sheet G. The alignment was in Stockholm 1.0 format.

The file fn3.in contained 1985 unique mammalian sequences and was loaded into Clustal X as Profile 2. All the sequences in Profile 2 were aligned to Profile 1. Outliers were removed and all the sequences in Profile 2 were aligned to Profile 1. The final alignment for Profile 2 was fn3_final.aln which contained 1750 sequences.

The file fn3_final.aln was reformatted so that each protein had 1 line, all amino acids past the C-terminus of FnIII[10] were trimmed, and a header was added to the top. The file was saved as fibronectins.aln and was the base alignment for further analysis.

Amino Acid Distribution

The SWISS_PROT release current for Jul. 15, 2010 was downloaded in fasta format. The release contained 518,415 non redundant sequences for a total 182,829,264 amino acids. The amino acid distribution in the SWISS_PROT release was calculated as a random occurrence reference.

TABLE 2

Table of amino acid distribution

| | Random | FnIII | A | B | C | D | E | F | G | AB | BC | CD | DE | EF | FG |
|---|---|---|---|---|---|---|---|---|---|---|---|---|---|---|---|
| A | 8.3 | 5.8 | 6.4 | 5.6 | 3.6 | 5.1 | 4.9 | 8.6 | 7.4 | 4.1 | 5.1 | 4.5 | 5.8 | 2.3 | 7.0 |
| C | 1.4 | 0.8 | 0.7 | 1.0 | 1.2 | 1.1 | 1.6 | 1.2 | 0.7 | 0.7 | 0.4 | 0.4 | 1.4 | 0.1 | 0.8 |
| D | 5.5 | 4.5 | 4.8 | 0.7 | 3.2 | 3.5 | 1.7 | 1.9 | 2.5 | 10.3 | 7.4 | 8.4 | 6.7 | 5.5 | 4.7 |
| E | 6.8 | 6.6 | 6.2 | 3.0 | 8.1 | 7.1 | 5.1 | 5.3 | 7.2 | 6.1 | 5.9 | 10.2 | 7.4 | 8.8 | 8.0 |
| F | 3.9 | 2.6 | 2.4 | 1.8 | 3.8 | 2.6 | 5.0 | 5.7 | 3.4 | 0.3 | 2.0 | 0.8 | 0.4 | 0.9 | 1.5 |
| G | 7.1 | 7.4 | 2.3 | 1.5 | 5.7 | 2.3 | 1.5 | 5.2 | 3.6 | 6.0 | 9.3 | 14.3 | 9.3 | 10.0 | 25.5 |
| H | 2.3 | 1.8 | 2.1 | 1.7 | 1.8 | 2.1 | 2.6 | 2.0 | 1.0 | 2.0 | 1.7 | 2.2 | 2.4 | 1.4 | 1.5 |
| I | 6.0 | 4.8 | 7.4 | 7.7 | 6.2 | 5.0 | 8.4 | 4.5 | 5.3 | 0.3 | 5.9 | 2.0 | 2.7 | 1.8 | 3.0 |
| K | 5.9 | 4.7 | 4.3 | 2.3 | 7.3 | 6.4 | 3.8 | 4.5 | 3.5 | 5.2 | 3.8 | 5.0 | 5.1 | 6.2 | 5.3 |
| L | 9.7 | 7.4 | 13.1 | 18.2 | 6.4 | 6.5 | 11.4 | 5.6 | 5.0 | 1.1 | 4.7 | 3.8 | 4.1 | 20.8 | 3.7 |
| M | 2.4 | 1.2 | 1.3 | 2.1 | 1.2 | 1.7 | 1.6 | 1.6 | 1.0 | 0.5 | 0.7 | 1.1 | 0.6 | 0.9 | 0.9 |
| N | 4.1 | 3.9 | 3.2 | 2.0 | 2.4 | 4.9 | 1.8 | 5.6 | 1.7 | 7.3 | 3.8 | 4.7 | 5.3 | 4.0 | 3.2 |
| P | 4.7 | 7.3 | 3.7 | 0.1 | 2.7 | 6.7 | 1.0 | 0.7 | 12.4 | 6.2 | 14.0 | 6.4 | 6.2 | 13.1 | 3.1 |
| Q | 3.9 | 3.8 | 2.9 | 2.8 | 4.4 | 5.3 | 3.1 | 3.2 | 3.2 | 2.5 | 4.0 | 5.6 | 4.8 | 3.5 | 4.3 |
| R | 5.5 | 5.2 | 4.3 | 3.3 | 7.0 | 6.2 | 4.0 | 7.5 | 3.3 | 4.8 | 3.4 | 5.7 | 6.1 | 4.0 | 5.7 |
| S | 6.5 | 8.8 | 6.5 | 21.2 | 5.5 | 6.2 | 8.3 | 5.6 | 13.6 | 18.3 | 6.7 | 8.6 | 9.3 | 6.0 | 10.8 |
| T | 5.3 | 8.4 | 9.2 | 10.5 | 4.7 | 9.1 | 13.3 | 7.9 | 12.1 | 21.4 | 6.0 | 6.4 | 15.4 | 7.3 | 3.2 |
| V | 6.9 | 8.9 | 18.1 | 13.2 | 9.3 | 15.2 | 15.1 | 11.5 | 10.6 | 1.1 | 5.2 | 3.5 | 5.9 | 2.4 | 4.9 |
| W | 1.1 | 2.1 | 0.5 | 0.4 | 1.6 | 1.2 | 0.8 | 0.7 | 1.1 | 0.9 | 8.8 | 5.7 | 0.2 | 0.4 | 0.8 |
| Y | 2.9 | 4.0 | 0.7 | 0.9 | 13.9 | 1.9 | 5.1 | 11.1 | 1.6 | 0.9 | 1.1 | 0.8 | 0.9 | 0.6 | 2.3 |

Mammalian FnIII Domain Motif

Below shows the mammalian FnIII domain motif. Key: H=hydrophilic, P=polar, B=Basic, A=Acid, C=Charged, X=no preference, sheets are in bold, specific amino acids are underlined, subscripts indicate length variations without % and percent occurrence with %.

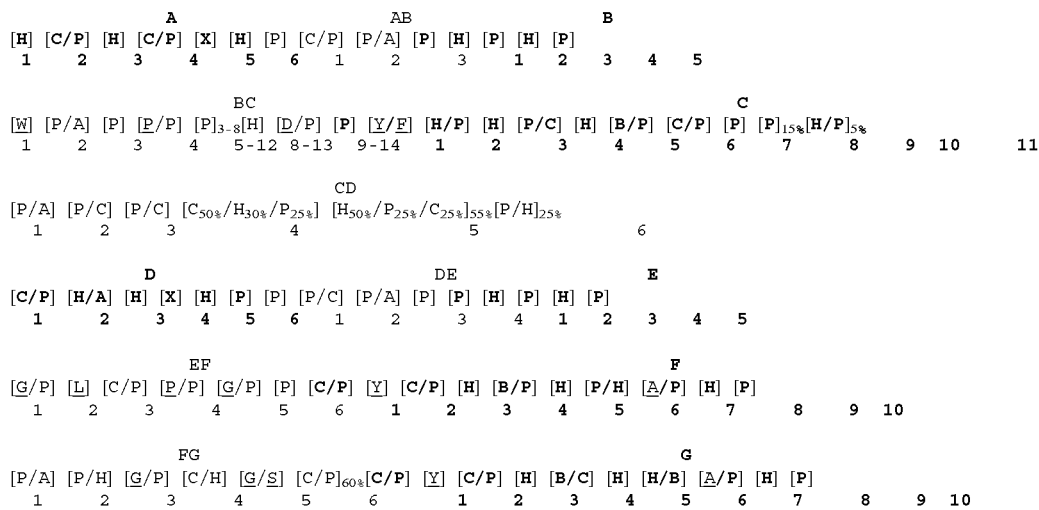

Cradle Library Description

The cradle library was originally defined as sheets C, D, and F with loops CD and FG. Sheet D is on the outside of the fibronectin molecule and unlikely to significantly contribute to binding residues. The definition of the cradle library is refined to be sheets C and F with loops CD and FG, and various combinations thereof.

Cradle library mapped onto the human fibronectin sequences (SEQ ID NOs:292, 288, 289, 283, 284, 291, 97, 281, 285, 100, 290, 287, 282, 129, and 286, respectively) is shown below. Cradle residues are shown in bold.

for a large variation of loop length with no individual length conserved more than 28.8%. However, the BC loop does contain a critical Tryptophan residue at position 1 which is conserved at >92% in all BC lengths and is necessary for proper folding of the fibronectin. Additionally, position 4 in the BC loop is a Proline with >33% conservation and the N−1 position is a hydrophobic residue.

The CD loop has a Poisson distribution of length centered at 5 amino acids. The most abundant amino acid in the CD loop is Glycine in position 2 and N-2, and when there is a

```
1fna SS    *******AAB  B***B C****C  *C DDDE
FnIII01    SSSGPVEVFITETPSQPNSHPIQWNAPQPSHISKYILRWRPKNSV-GRWKEATIPGHLNS FnIII02    -PLVATSESVTEITAS--SFVVSWVSA-SDTVSGFRVEYELSEEG-DEPQYLDLPSTATS FnIII03    -PDAPPDPTVDQVDDT--SIVVRWSRP-QAPITGYRIVYSPSVEG-S-STELNLPETANS FnIII04    --PSPRDLQFVEVTDV--KVTIMWTPP-ESAVTGYRVDVIPVNLP-GEHGQRLPISRNTF FnIII05    KLDAPTNLQFVNETDS--TVLVRWTPP-RAQITGYRLTVGLTR-R-GQPRQYNVGPSVSK FnIII06    -PGSSIPPYNTEVTET--TIVITWTPA---PRIGFKLGVRPSQGG---EAPREVTSDSGS FnIII07    PLSPPTNLHLEANPDTG-VLTVSWERSTTPDITGYRITTTPTNGQQGNSLEEVVHADQSS FnIII08    AVPPPTDLRFTNIGPD--TMRVTWAPPPSIDLTNFLVRYSPVKNE-EDVAELSISPSDNA FnIII09    GLDSPTGIDFSDITAN--SFTVHWIAP-RATITGYRIRHHPEHFS-GRPREDRVPHSRNS FnIII10    VSDVPRDLEVVAATPT--SLLISWDAP-AVTVRYYRITYGETGGN-SPVQEFTVPGSKST FnIII11    EIDKPSQMQVTDVQDN--SISVKWLPSSSP-VTGYRVTTTPKNGP-GPTKTKTAGPDQTE FnIII12    NIDRPKGLAFTDVDVD--SIKIAWESP-QGQVSRYRVTYSSPEDG-IHELFPAPDGEEDT FnIII13    --PAPTDLKFTQVTPT--SLSAQWTPP-NVQLTGYRVRVTPKEKT-GPMKEINLAPDSSS FnIII14    NVSPPRRARVTDATET--TITISWRTKTET-ITGFQVDAVPANGQ--TPIQRTIKPDVRS FnIII15    AIDAPSNLRFLATTPN--SLLVSWQPP-RARITGYIIKYEKPGSP-PREVVPRPRPGVTE 1fna SS         *E  EF**F******FG***G*
FnIII01         YTIKGLKPGVVYEGQLISIQQYGHQ----EVTRFDFTT FnIII02         VNIPDLLPGRKYIVNVYQISEDGEQ----SLILSTSQT FnIII03         VTLSDLQPGVQYNITIYAVEENQES----TPVVIQQET FnIII04         AEVTGLSPGVTYYFKVFAVSHGRES----KPLTAQQTT FnIII05         YPLRNLQPASEYTVSLVAIKGNQES-----PKATGVFT FnIII06         IVVSGLTPGVEYVYTIQVLRDGQER---DAPIVNKVVT FnIII07         CTFDNLSPGLEYNVSVYTVKDDKES----VPISDTIIP FnIII08         VVLTNLLPGTEYVVSVSSVYEQHES----TPLRGRQKT FnIII09         ITLTNLTPGTEYVVSIVALNGREES-----PLLIGQQS FnIII10         ATISGLKPGVDYTITVYAVTGRGDSPASSKPISINYRT FnIII11         MTIEGLQPTVEYVVSVYAQNPSGES----QPLVQTAVT FnIII12         AELQGLRPGSEYTVSVVALHDDMES----QPLIGTQST FnIII13         VVVSGLMVATKYEVSVYALKDTLTS----RPAQGVVTT FnIII14         YTITGLQPGTDYKIYLYTLNDNARS----SPVVIDAST FnIII15         ATITGLEPGTEYTIYVIALKNNQKS----EPLIGRKKT
```

The top side library is loops BC, DE, and FG and the bottom library is loops AB, CD, and EF. The AB loop has a length constraint of 3 amino acids with position 1 being Threonine or Serine 67.4% of the time. The BC loop allows position 5, it a Tryptophan 30% of the time. The DE loop has a length constraint of 4 amino acids. The EF loop has a length constraint of 6 amino acids with a high amount of sequence conservation.

Position 1: Glycine conserved at 44.2%
Position 2: Leucine, Valine, or Isoleucine conserved at 97.8%
Position 3: Charged or polar amino acid
Position 4: Proline conserved at 57.5%
Position 5: Glycine conserved at 44.4%
Position 6: Tends to be a polar amino acid The FG loop length is either 5 (32.6%) or 6 (62.1%) with positions 3 and 5 having a Glycine >43% of the time. The remaining positions have conservation of <22% for any given amino acid.

The top side library is limited due to length constraint of the DE loop and conserved amino acids in the BC loop. The bottom side library is limited by the 3 amino acid length constraint on the AB loop and the high amount of conservation throughout the EF loop.

The amino acid most participating in hydrophobic packing of the fibronectin are BC loop position 1 (W), sheet C position 2 (Y/F), EF loop position 2 (L), and sheet F position 2 (Y). Both the top and bottom side libraries contain loops which have important packing residues which may hinder effective variation. The cradle library loops do not contain structurally necessary amino acids. In addition, the cradle library utilizes the outward facing amino acids of sheets C and F to expand the binding surface.

Figure 7A:
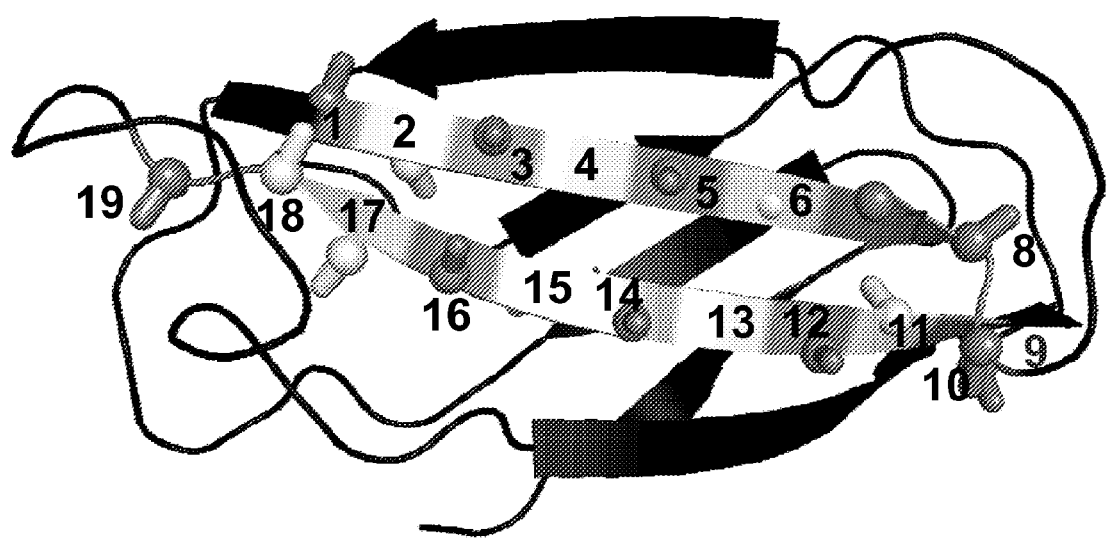

The cradle library beta strands C and F are the two longest in the fibronectin molecule and interact extensively to form an anti-parallel beta sheet which may stabilize the protein when changes to the outward facing amino acids are made. Amino acids 1, 3, 5, 7-9 in sheet C and amino acids 1, 3, 5, 7, and 10 in sheet F are intended for use in the cradle library (FIG. 7A).

The residue in sheets C and F were analyzed using a simplified amino acid type scheme where A/G/P/S/T are considered small and flexible, D/E/N/Q/H/K/R are considered polar/charged, F/Y/W/I/L/V/M are considered hydrophobic, and C is disulfide making.

FIG. 7B shows the simplified positional distribution for sheet C length 9 (SF=amino acids A/G/P/S/T; CP=D/E/N/Q/H/K/R; H=F/Y/W/I/L/V/M; C=C). Positions 2, 4, and 6 showed a clear preference for hydrophobic amino acid and are pointing inwards towards the core of the fibronectin. Position 3 had a preference for hydrophobic amino acids, but not as strongly, and is pointing outward toward solvent. The top 10 amino acids by conservation in sheet C, length 9, position 3 were:

| | |
|---|---|
| I, | 17.2% |
| V, | 15.4% |
| R, | 13.2% |
| L, | 10.9% |
| T, | 10.2% |
| E, | 8.5% |
| K, | 5.6% |
| S, | 3.9% |
| Q, | 3.2% |
| H, | 3.0% |

Position 1, 5, 7, 8, and 9 showed a clear preference for small flexible or charged/polar amino acid and were pointing outwards towards solvent.

FIG. 7B shows the simplified positional distribution for sheet F length 10. Position 2, 4, and 6 showed a clear preference for hydrophobic amino acid and were pointing inwards towards the core of the fibronectin. Position 7 had a preference for hydrophobic amino acids, but not as strongly, and is pointing outward toward solvent. The top 5 amino acids by conservation in sheet F, length 10, position 7 were:

| | |
|---|---|
| R | 17.1% |
| Y | 15.6% |
| A | 7.8% |
| T | 7.4% |
| V | 7.1% |

Position 1, 3, 5, and 10 showed a clear preference for small flexible or charged/polar amino acid and were pointing outwards towards solvent. Position 9 had a preference for hydro-phobic amino acids. The top 5 amino acids by conservation in sheet F, length 10, position 9 were:

| | |
|---|---|
| V | 18.7% |
| L | 13.0% |
| E | 12.7% |
| R | 8.3% |
| I | 7.8% |

Position 8 contained a highly conserved Alanine residue with Alanine or Glycine at 80% conservation. The top 5 amino acids by conservation in sheet F, length 10, position 8 were:

| | |
|---|---|
| A | 68.7% |
| G | 11.5% |
| S | 6.1% |
| V | 2.9% |
| P | 2.5% |

Binding Surface Comparison

Shown below is the cradle library for FnIII[07], FnIII[10], and FnIII[14] (SEQ ID NOs:97, 100, 129, respectively).

```
1fna    SS      *******AAB  B***B C****C *C DDDE

FnIII07         PLSPPTNLHLEANPDTG-VLTVSWERSTTPDITGYRITTTPTNGQQGNSLEEVVHADQSS

FnIII10         VSDVPRDLEVVAATPT--SLLISWDAP-AVTVRYYRITYGETGGN-SPVQEFTVPGSKST

FnIII14         NVSPPRRARVTDATET--TITISWRTKTET-ITGFQVDAVPANGQ--TPIQRTIKPDVRS
```

```
                  -continued
1fna SS          *E**  EF******F**********FG*******G***

FnIII07          CTFDNLSPGLEYNVSVYTVKDDKES----VPISDTIIP

FnIII10          ATISGLKPGVDYTITVYAVTGRGDSPASSKPISINYRT

FnIII14          YTITGLQPGTDYKIYLYTLNDNARS----SPVVIDAST
```

Shown below is the top side library for FnIII[07], FnIII[10], and FnIII[14] (SEQ ID NOs:97, 100, 129, respectively).

```
1fna SS  *******AAB  B***B C****C *C DDDE

FnIII07  PLSPPTNLHLEANPDTG-VLTVSWERSTTPDITGYRITTTPTNGQQGNSLEEWHADQSS

FnIII10  VSDVPRDLEVVAATPT--SLLISWDAP-AVTVRYYRITYGETGGN-SPVQEFTVPGSKST

FnIII14  NVSPPRRARVTDATET--TITISWRTKTET-ITGFQVDAVPANGQ--TPIQRTIKPDVRS

1fna SS          *E**  EF******F**********FG*******G***

FnIII07          CTFDNLSPGLEYNVSVYTVKDDKES----VPISDTIIP

FnIII10          ATISGLKPGVDYTITVYAVTGRGDSPASSKPISINYRT

FnIII14          YTITGLQPGTDYKIYLYTLNDNARS----SPVVIDAST
```

Shown below is the bottom side library for FnIII[07], FnIII[10], and FnIII[14] (SEQ ID NOs:97, 100, 129, respectively).

```
1fna SS  *******AAB  B***B C****C *C DDDE

FnIII07  PLSPPTNLHLEANPDTG-VLTVSWERSTTPDITGYRITTTPTNGQQGNSLEEVVHADQSS

FnIII10  VSDVPRDLEVVAATPT--SLLISWDAP-AVTVRYYRITYGETGGN-SPVQEFTVPGSKST

FnIII14  NVSPPRRARVTDATET--TITISWRTKTET-ITGFQVDAVPANGQ--TPIQRTIKPDVRS

1fna SS          *E**  EF******F**********FG*******G***

FnIII07          CTFDNLSPGLEYNVSVYTVKDDKES----VPISDTIIP

FnIII10          ATISGLKPGVDYTITVYAVTGRGDSPASSKPISINYRT

FnIII14          YTITGLQPGTDYKIYLYTLNDNARS----SPVVIDAST
```

TABLE 3

Binding Surface of each library

| Domain | Top Side Library | Bottom Side Library | Cradle Library |
|---|---|---|---|
| FnIII[07] | 1769 Å² | 1382 Å² | 2345 Å² |
| FnIII[10] | 1834 Å² | 1140 Å² | 2457 Å² |
| FnIII[14] | 1700 Å² | 1088 Å² | 1949 Å² |

TABLE 4

Binding Surface of each library relative to the Top Side library.

| Domain | Top Side Library | Bottom Side Library | Cradle Library |
|---|---|---|---|
| FnIII[07] | 100% | 78% | 133% |
| FnIII[10] | 100% | 62% | 216% |
| FnIII[14] | 100% | 64% | 115% |

Cradle Library Summary

The cradle library consisting of beta strand C, beta strand F, loop CD, and loop FG of the FnIII domain offers better stability and available binding surface than the directional loop based Top and Bottom Side libraries.

Figure 8:
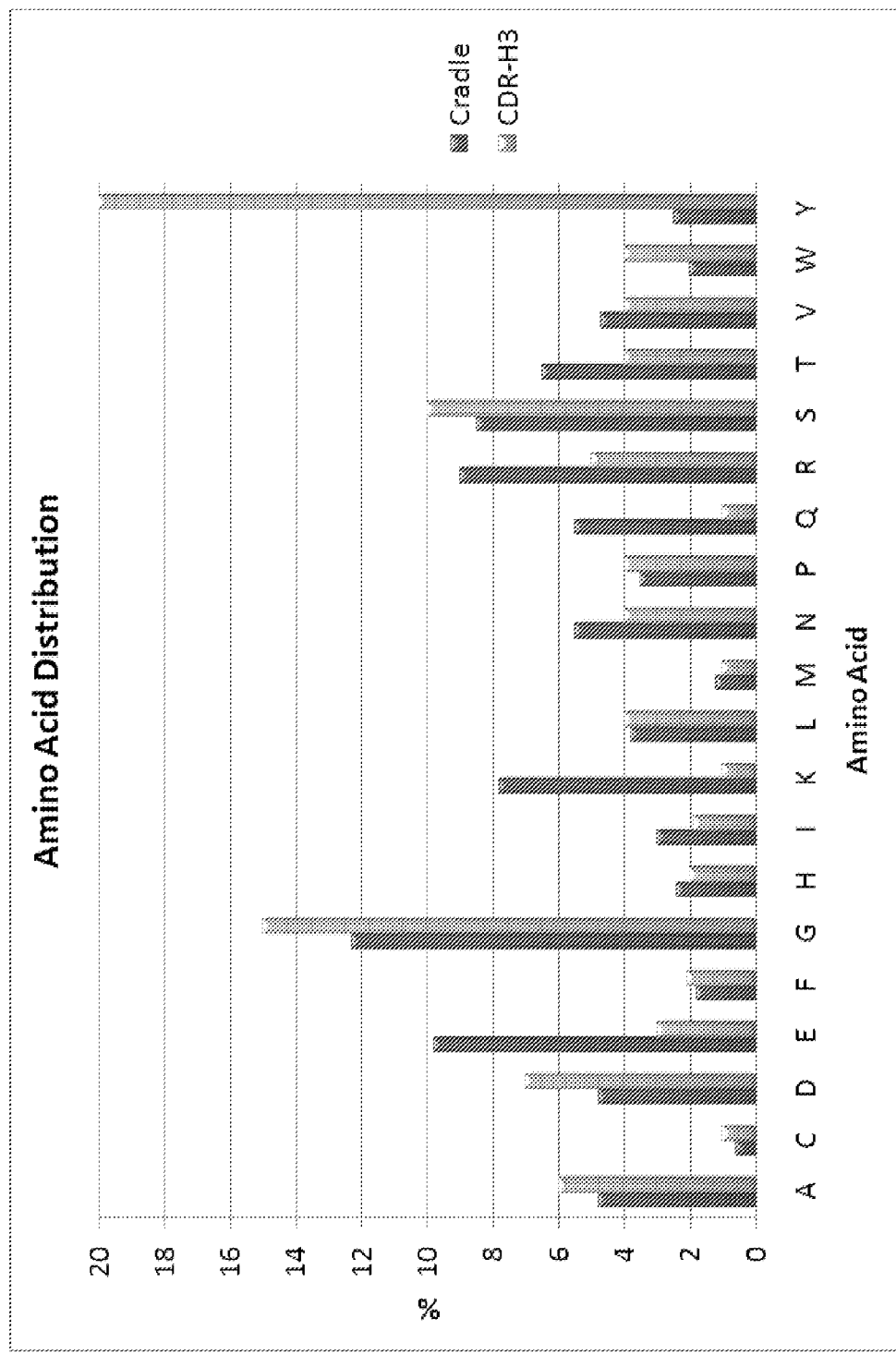
FIG. 8 is the amino acid distribution in the varied residues of the Cradle and CDR-H3 domains known to bind antigens.
Figure 9A:
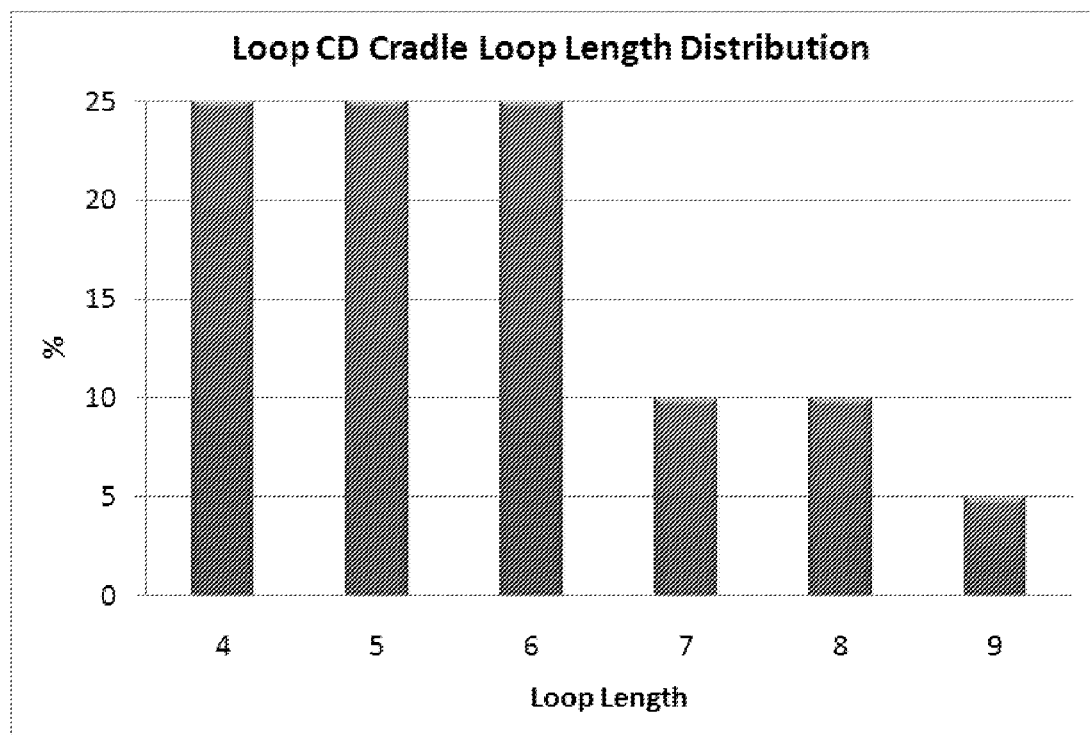
Figure 9B:
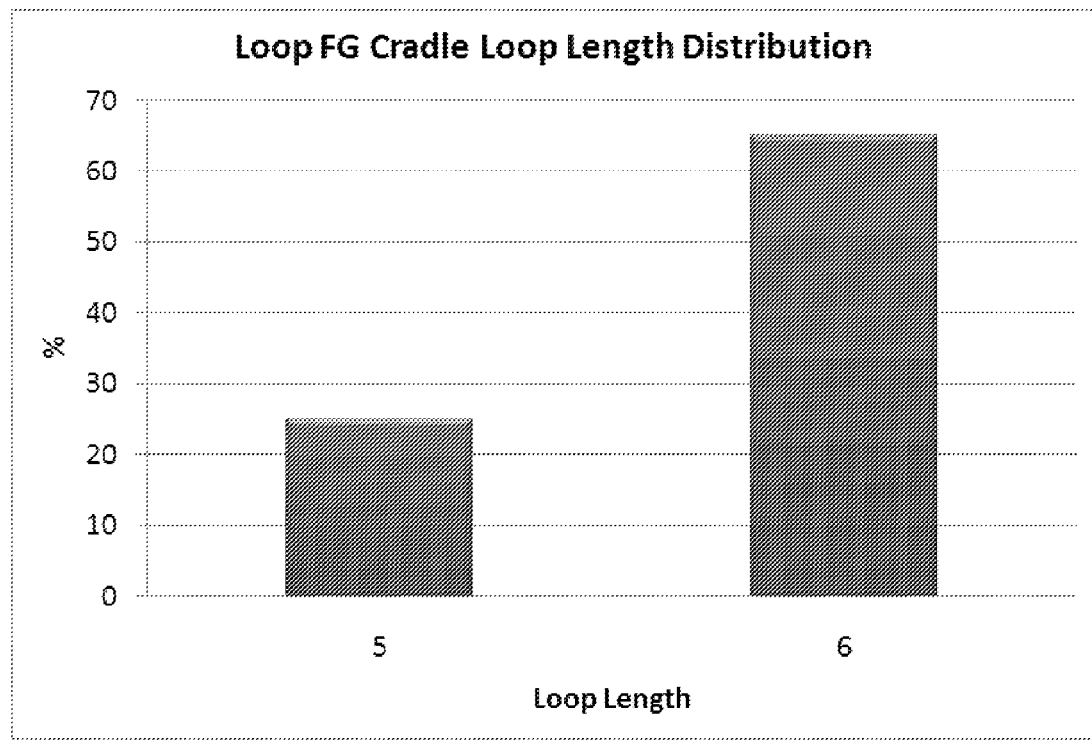

FIG. 8 shows the amino acid distribution of the residues and amino acid variation compared with the distribution on CDR-H3 domains known to bind antigens. FIG. 9C shows the biased amino acid distribution desired for the Cradle residues marked X and Y.

FIGS. 9D-9F show the mapping of the cradle library definition on the sequences of FnIII[07], FnIII[10], and FnIII[14]. FIG. 9D: Alignment of cradle residues for FnIII[07], FnIII[10] and FnIII[14]. Beta sheets are shown as white residues on a black background and loops are shown as black text. Cradle residues are shown in bold with X representing the amino acid distribution for the beta sheets and Y representing the amino acid distribution for the loops with the loop length range given as a subscript. FIG. 9E: Alignment of FnIII[07], FnIII[10] and FnIII[14] illustrating the cradle residues in beta sheets C and F and loops CD and FG. Beta sheets are shown as white residues on a black background and loops are shown as black text with Cradle residues shown in bold. FIG. 9F: Shown are the FnIII structural element residue ranges and FnIII cradle residues ranges.

EXAMPLE 7

Cradle Molecules Binding to Lysozyme, Fc, and Human Serum Albumin (HSA)

The Example demonstrates the proof of principle for generating cradle molecules that bind to target molecules using calculated design libraries. Using the approaches described above, cradle binders were created against three targets (lysozyme, human Fc, and HSA) with FnIII07, FnIII10, and FnIII14.

```
FnIII07 hits for lysozyme (SEQ ID NOs: 97-99, respectively):
***<A>AB<B*>*BC*<*C>*CD*<*D*>**DE*<E>*EF*<**F*>FG*<*G*>**
PLSPPTNLHLEANPDTGVLTVSWERSTTPDITGYRITTTPTNGQQGNSLEEVVHADQSSCTFDNLSPGLEYNVSVYTVKDDKES-VPISDTIIP PLSPPTNLHLEANPDTGVLTVSWERSTTPDITAYYIYTYKSDKTRY--LEEVVHADQSSCTFDNLSPGLYYGVGAVATVRPHPTAGPISDTIIP PLSPPTNLHLEANPDTGVLTVSWERSTTPDITHYLIYTYG-HHSAG--LEEVVHADQSSCTFDNLSPGLGYSVYVNTVAYK--TMGPISDTIIP FnIII10 hits for lysozyme (SEQ ID NOs: 100-128, respectively):
*******<*A**>*AB<*B*>**BC<*C*>CD**<*D**>*DE*<*E*>*EF<*F>FG<G***>
VSDVPRDLEVVAATPTSLLISWDAPAVTVR-YYRITYGETGGNSPV----QEFTVPGSKSTATISGLKPG-VDYTITVYAVTGRGDSPASSKPISINYRT VSDVPRDLEVVAATPTSLLISWDAPAVTVR-TYYIMYSLWQHYVTNAL--QEFTVPGSKSTATISGLKPG-VFYGILVYAVSWWS-R-W---PISINYRT VSDVPRDLEVVAATPTSLLISWDAPAVTVR-SYYIKYSTCSHYVRSGVG-QEFTVPGSKSTATISGLKPG-VDYMIDVNAVLSEG-RGD---PISINYRT VSDVPRDLEVVAATPTSLLISWDAPAVTVR-GYTT-YS-----YRDS---QEFTVPGSKSTATISGLKPGVIYNILVSAVSEWW-K-Y---PISINYRT VSDVPRDLEVVAATPTSLLISWDAPAVTVR-YYEIWYESYFY-----VLWQEFTVPGSKSTATISGLKPG-VSYEITVSAVYWH-YAY----PISINYRT VSDVPRDLEVVAATPTSLLISWDAPAVTVR-LYAIMYTAYEYRVMDAKLYQEFTVPGSKSTATISGLKPG-VSYYINVAAVYLHR-YFY---PISINYRT VSDVPRDLEVVAATPTSLLIPWDAPAVTVR-GYKIDYVVQTW-----AYYQEFTVPGSKSTATISGLKPG-VSYAITVLAVYRW-YYS----PISINYRT VSDVPRDLEVVAATPTSLLISWDAPAVTVR-GYGIDYGQRDYQQ---GSQQEFTVPGSKSTATISGLKPG-VQYDIYVGAVETYV-YAR---PISINYRT VSDVPRDLEVVAATPTSLLIS-DAPAVTVR-SYYIYY--YDYDG---GSVQEFTVPGSKSTATISGLKPG-VSYVISVAAVWYAA-YRY---PISINYRT VSDVPRDLEVVAATPTSLLISWDAPAVTVR-NYLIDYGYKNYSI---AG-QEFTVPGSKSIATISGLKPG-VFYAILVAAVRYFW-YF----PISINYRT ISDVPRDLEVVAATPTSLLISWDAPAVTVR-GYSIHYYY--YSF---TG-QEFTVPGSKSTATISGLKPG-VSYWIRVWAVRFWE-YLP---PISINYRT VSDVPRDLEVVAATPTSLLISWDAPAVTVR-GYDIAYGVNYYYY---SY-QEFTVPGSKSTATISGLKPG-VVYGIYVAAVRYWH-YLF---PISINYRT VSDVPRDLEVVAATPTSLLISWDAPAVTVR-IYSIGS-------------QEFTVPGSKSTATISGLKPG-VWYWIYVAAVRAWS-YWH---PISINYRT VSDVPRDLEVVAATPTSLLISWDAPAVTVR-EYYIYYGSSQE-----TEGQEFTVPGSKSTATISGLKPG-VNYSIGVAAVQNIY-TYY---PISINYRT VSDVPRDLEVVAATPTSLLISWDAPAVTVR-SYEIGYEYIYLQY-----SQEFTVPGSKSTATISGLKPG-VMYSIVVYAVNKVY-SYF---PISINYRT VSDVPRDLEVVAATPTSLLISWDAPAVTVR-TYSISY--FDYLHL---YSQEFTVQGSKSTATISGLKPG-VYYAIYVWAVG-WW-LAD---PISINYRT VSDVPRDLGVVAATPTSLLISWDAPAVTVR-KYMISYTLMGHLHYG--ASQEFTVPGSKSTATISGLKPGVVYYGIYVLAVSEYQ-VAS---PISINYRT VSDVPRDLEVVAATPTSLLISWDAPAVTVR-SYNISYSKYHYSPA----YQEFTVPGSKSTATISGLKPG-VQYYISVSAVHAHN-VAG---PISINYRT VSDVPRDLEVVAATPTSLLISWDAPAVTVRGGYGIGYAKAGSVDA----YQEFTVPGSKSTTTISGLKPG-VXYYIYVRAVFAH-PAY----PISINYRT VSDVPRDLEVVAATPTSLLISWDAPAVTVR-KYQISYG--YYSNT----DQEFTVPGSKSTATISGLKPG-VDYWIYVSAVAWQA-DQG---PISINYRT VSDVPRDLEVVAATPTSLLISWDAPAVTVR-TYSISYR--YGKWS----GQEFTVPGSKSTATISGLKPG-VYYDIGVTAVTSVV-SG----PISINYRT VSDVPRDLEVVAATPTSLLISWDAPAVTVRQVYVIAYR--YYVRSW---GQEFTVPGSKSTATISGLKPG-VYYSINVLAVYYRT-WR----PISINYRT VSDVPRDLEVVAATPTSLLISWDAPAVTVR-SYDISYNGMAYTKTL---VQEFTVPGSKSTATISGLKPG-VNYLIDVIAVSFRR-WWS---PISINYRT VSDVPRDLEVVAATPTSLLISWDAPAVTVR-NYAISYQ---DDSPY---VQEFTVPGSKSTATISGLKPG-VNYDISVTAVGWWR-SGM---PISINYRT VSDVPRDLEVVAATPTSLLISWDAPAVTVR-TYDIGYSSFNSSTLY---VQEFTVPGSKSTATISGLKPG-VNYDISVTAVRLQE-SQR---PISINYRT VSDVPRDLEVVAATPTSLLISWDAPAVTVR-EYDIYYVDSYYYFEGQYPHQEFTVPGSKSTATISDLKPG-VTYDIGVKAVYNGSRIVE---PISINYRT VSDVPRDLEVVAATPTSLLISWDAPAVTVR-VYEISYYSSESYL----PGQEFTVPGSKSTATISGLKPG-VTYDIHVSAVAYRG-AS----PISINYRT VSDVPRDLEVVAATPTSLLISWDAPAVTVR-EYLIGYAV-----TEYGDRQEFTVPGSKSTATISGLKPG-VLYDIRVLAVYARW-PK----PISINYRT VSDVPRDLEVVAATPTSLPISWDAPAVTVR-YYSIWYYHY------YPYAQEFTVPGSKSTATISSLKQG-VRYFIDVLAVAWVR-WAY---PISINYRT FnIII14 hits for lysozyme (SEQ ID NOs: 129-141, respectively):
*******<*A**>*AB<*B*>*BC<C*>CD<*D**>*DE*<*E*>EF<*F>*FG<*G**>
NVSPPRRARVTDATETTITISWRTKTETITGF-QVDAVPANGQ-TPIQRTIKPDVRSYTITGLQPGTDYKIYLYTLNDNARS-SPVVIDAST NVSPPRRARVTDATETTITISWRTKTETITSF-WVVAKPYSYYWGSIQRTIKPDVRSYTITGLQPGTWYAINLYTLT-YRFWGDPVVIDAST NVSPPRRARVTDATETTITISWRTKTETITYFGDVSAGPSSTYIESIQRTIKPDVRSYTITGLQPGTWYNIVLQTLYSWSYW--PVVIDAST NVSPPRRARVTDATETTITISWSTKTETITSF-VVGARP--YYYPYIQRTIKPDVRSYTITGLQPGTVYGIWLQTLR-YYYGYTPVVIDAST
```

```
NVSPPRRARVTDATETTITISWRTKTETITAF-EVVAHP--NYDYYIQRTIKPDVRSYTITGLQPGTSYWIYLYTL--YSRRYLPVVIDAST

NVSPPRRARVTDATETTITISWRTKTETITSF-SVIAFPLRERAATIQRTIKPDVRSYTITGLQPGTLYSIILNTL--WRYYPIPVVIDAST

NVSPPHRARVTDATETTITISWRTKTETITNF-LVYAYP--TEHVRIQRTIKPDVRSYTITGLQPGTKYWIYLYTLIYNMYY--PVVIDAST

NVSPPRRARVTDATETTITISWRTKTETITGF-SVWAQP--GYLEEIQRTIKPDVRSYTITGLQPGTSYDSIALSTLGRYRWSDPVVIDAST

NVSPPRRARVTDATETTITISWRTKTETITQF-HVTAGP--HWVGRIQRTIKPDVRSYTITGLQPGTAYLIYALSTLRSYRYQWPVVIDAST

NVSPPRRARVTDATETTITISWRTKTETITYF-HVSALP-LVYGSYIQRTIKPDVRSYTITGLQPGTTYDIYLSTLN-SHWLTAPVVIDAST

NVSPPRRARVTDATETTITISWRTKTETITRF-YVEATPSAAANTSIQRTIKPDVRSYTITGLQPGTMYQIWLATLS-YYASHYPVVIDAST

NVSPPRRARVTDATETTITISWRTKTETITSF-GVTAKP-VWSWGSIQRTIKPDVRSYTITGLQPGTGYAISLYTLLRYWYRYYPVVIDAST

NVSPPRRARVTDATETTITISWRTKTETITAF-YVQAYP--YSDHSIQRTIKPDVRSYTITGLQPGTYYDITLSTLR--SYYYRPVVIDAST

FnIII07 hit for human Fc (SEQ ID NOs: 142-143, respectively):
***<A>AB<B*>*BC*<*C>*CD*<*D*>**DE*<*E*>*EF*<**F*>FG*<*G*>**
PLSPPTNLHLEANPDTGVLTVSWERSTTPDITGYRITTTPTNGQQGNSLEEVVHADQSSCTFDNLSPGLEYNVSVYTVKDDKES-V**PISDTIIP PLSPPTNLHLEANPDTGVLTVSWERSTTPDITGYTIVAVSYSFYYY-LEEVVHADQSSCTFDNLSPGLSYDEVYVVTVAYKSHGVPISDTAPS FnIII10 hits for human Fc (SEQ ID NOs: 144-147, respectively):
*******<*A**>*AB*<*B*>*BC<*C*>CD**<*D*>DE*<*E*>*EF<*F**>FG*<*G*>
VSDVPRDLEVVAATPTSLLISWDAPAVTVRYYRITYGETGGNSPVQEFTVPGSKSTATISGLKPGVDYTITVYAVTGRGDSPASSKPISINYRT VSDVPRDLEVVAATPTSLLISWDAPAVTVRTYQIGYG-YNRGTS-QEFTVPGSKSTATISGLKPGVSYGIYVYAVYE---WSYS--PISINYRT VSDVPRDLEVVAATPTSLLISWDAPAVTVRYYSITYTYYQAFG-TQEFTVPGSKSTATISGLKPGVGYYIQVYAVGDRVS---NGGPISINYRT VSDVPRDLEVVAATPTSLLISWDAPAVTVRYYGIYYS-MSSYG-RQEFTVPGSKSTATISGLKPGVTYQIYMSAVDN---WGVG-YPISINYRT FnIII14 hits for human Fc (SEQ ID NOs: 148-159, respectively):
*******<*A**>*AB*<*B*>*BC<*C*>*CD****<*D*>*DE*<*E*>EF*<*F*>*FG*<*G>
NVSPPRRARVTDATETTITISWRTKTETITGFQVDAVPANGQ-----TPIQRTIKPDVRSYTITGLQPGTDYKIYLYTLNDNARS--SPVVIDAST NVSPPRRARVTDATETTITISWRTKTETITSFTVWASP---RSYTH--IQRTIKPDVRSYTITGLQPGTYYR-IYLYTLY-NTYFS-PVVIDAST NVSPPRHARVTDATETTITISWRTKTETITSFRVWAAP---TMYQYLYIQRTIKPDVRSYTITGLQPGTYYQAIILGTLS-TSNTPSPVVIDAST NVSPPRRARVTDATETTITISWRTKTETITSFFVQAYP-----YGELYIQRTIKPDVRSYTITGLQPGTSYG-IRLSTLI-DSDSYGPVVIDAST NVSPPRRARVTDATETTITISWRTKTETITRFTVVAHP-----GYPGYIQRTIKPDVRSYTITGLQPGTYYS-IDLRTLA-YAQGYSPVVIDAST NVSPPRRARVTDATETTITISWRTKTETITRFTVTADP-----WYWYGIQRTIKPDVRSYTITGLQPGTYYSGIVLDTLS-WVSGGYPVVIDAST NVSPPRRARVTDATETTITISWRTKTETITNFSVQAGPSI---YYGYYIQRTIKPDVRSYTITGLQPGTQYS-ISLRTLWRWYGTYWPVVIDAST NVSPPRRARVTDATETTITISWRTKTETITGFLVNAWP-----HWANVIQRTIKPDVRSYTITGLQPGTFYV-IYLATLQ-YSSVYSPVVIDAST NVSPPRRARVTDATETTITISWRTKTETITSFAVHAQP-----VYANWIQRTIKPDVRSYTITGLQPGTYYG-INLATL--YGPNYWPVVIDAST NVSPPRRARVTDATETTITISWRTKTETITYFSVFAYPES-GAYN---IQRTIKPDVRSYTITGLQPGTAYD-IKLDTLL-SSYWYHPVVIDAST NVSPPRRARVTDATETTITISWRTKTETITTFGVYAMHPEEGGYYY--IQRTIKPDVRSYTITGLQPGTWYG-IGLDTLY-SVHDERPVVIDAST NVSPPRRARVTDATETTITISWRTKTETITRFYVTDALPG-DAYRYHRIQRTIKPDVRSYTITGLQPGTLYG-ISLTTLY-YAS-AIPVVIDAST FnIII07 hits for HSA (SEQ ID NOs: 160-199, respectively):
***<A>AB<B*>*BC*<*C>**CD**<*D*>*DE*<*E*>*EF<*F>FG***<*G*>**
PLSPPTNLHLEANPDTGVLTVSWERSTTPDITGYRITTTPTNGQQG--NSLEEVVHADQSSCTFDNLSPGLE-YNV-SVYTVKDDKESVPISDTIIP PLSPPTNLHLEANPDTGVLTVSWERSTTRDITTYGIETEYDHSV-----GLEEVVHADQSSCTFDNLSPGLN-YDV-EVVTGWGVYQRPISDTIIP PLSPPTNLHLEANPDTGVLTVSWERSTTPDITTYVISTVTSHTGP----RLEEVVHADQSSCTFDNLSPGLX-YDV-YVYTVTDTAYTTPISDTIIP SLSPPTNLHLEANPDTGVLTVSWGERSTTPGITSYSIDTAKDDVPY-----LEEVVHADQSSCTFDNLSPGLN-YTV-VVATVGWS-VDGPISDTIIP PLSPPTNLHLEANPDTGVLTVSWERSTTPDITYYEINTTGYYGFYPG--GLEEVVHADQSSCTFDNLSPGLY-YQV-TVQTVVYSMWYHPISDTIIP PLSPPTNLHLEANPDTGVLTVSWERSTTPDITYYGIWTLTWLQYYSYRWGLEEAVHADQSSCTFDNLSPGLV-YLV-YVGTVRSP-MARPISDTIIP PLSPPTNLHLEANPDTGVLTVSWERSTTPDITWYWIGTWY--SGYMV--GLEEVVHADQSSCTFDNLSPGLT-YWV-LVGTVRSPSRRPISDTIIP PLSPPTNLHLEANPDTGVLTVSWERSTTPDVTTYSIYTYGYWDSHYM--SLEEVVHADQSSRCTFDNLSPGLY-YSV-EVYTVYYGLYVVPISDTIIP PLSPPTNLHLEANPDTGVLTVSWERSTTPDITTYGIETQTVEWVY----YLEEVVHADQSSCTFDNLSPGLY-YNV-TVGTVMLD-AAYPISDTIIP PLSPPTNLHLEANPDTGVLTVSWERSTTPDITDYYIITRS---RW-G--YLEEVVHADQSSCTFDNLSPGLR-YHV-YVWTVGH-Y-RDPISDTIIP
```

```
PLSPPTNLHLEANPDTGVLTVSWERSTTPDITNYLIQTDYFAFIK-G--VLEEVVHADQSSCTFDNLSPGLY-YYV-GVDTVSVPSH-GPISDTIIP
PLSPPTNLHLEANPDTGVLTVSWERSTTPDITYYTIATADYTYSY-A--HLEEVVHADQSSCTFDNLSPGLN-YEV-GVGTVSVYSYIGPISDTIIP
PLSPPTNLHLEANPDTGVLTVSWERSTTPDITYYSIDTWT-FGQW----GLEEVVHADQSSCTFDNLSPGLY-YYV-EVVTVYEWAYSYPISDTIIP
PLSPPTNLHLEANPDTGVLTVSWERSTTPDITMYAITTYEYSRAW-Q--YLEEVVHADQSSCTFDNLSPGLT-YYV-EVYTVRYT-WSDPISDTIIP
PLSPPTNLHLEANPDTGVLTVSWERSTTPDITDYNISTWLYTSVSVYT-ELEEVVHAGQSSCTFDNLSPGLA-YVVYVWSTVWEHFYPSPISDTIIP
PLSPPTNLHLEANPDTGVLTVSWERSTTPDITWYWINTSLANVRM----SLEEVVHADQSGCTFDNLSPGLY-YDV-QVRTVSAA-EGYPISDTIIP
PLSPPTNLHLEANPDTGVLTVSWERSTTPDITKYII--YTGYGAS-Y--DLEEVVHADQSSCTFDNLSPGLK-YTV-TVWTVSYA-SQVPISDTIIP
PLSPPTNLHLEANPDTGVLTVSWERSTTPDITMYSIYTYDYTRNY----VLEEAVHADQSSCTFDNLSPGLYGYYV-GVGTVTGA-GWHPISDTIIP
PLSPPTNLHLEVNPDTGVLTVSWERSTTPGITQYDIATLSYGGRS-G--GLEEVVHADQSSCTFDNLSPGLS-YVV-SVSTVTSNEYSAPISDTIIP
PLSPPTNLHLEANPDTGVLTVSWERSTTPDITMYDIKTIYYKAYY-Y--GLEEVVHADQSSCTFDNLSPGLY-YFV-GVVTVERP-RYYPISDTIIP
PLSPPTNLHLEANPDTGVLTVSWERSTTPDITYYYIDTNG-G-YW-S--YLEEVVHADQSSCTFDNLSPGLG-YPVGYVRTVYAGWLKGPISDTIIP
PLSPPTNLHLEANPDTGVLTVSWERSTTPDITYYYIGTYQ-GTTY-E--HLEEVVHADQSSCTFDNLSPGLI-YLV-YVSTVYWDSMSSPISDTIIP
PLSPPANLRLEANPDTGVLTVSWERSTTPDITRYVIATGYGGSWY----HLEEVVHADQSRCTFDNLSPGLA-YYV-DVYTVTPGEKHSPISDTIIP
PLSPPTNLHLEANPDTGVLTVSWERSTTPDITKYIISTYVDYGGY-----LEEVVHADQSSCTFDNLSPGLG-YSV-TVSTVSAG-WDSPISDTIIP
PLSPPTNLHLEANPDTGVLTVSWERSTTPDITSYRISTEWRWRYT----GLEEVVHADQSSCTFDNLSPGLI-YGV-GVSTVWKHNSQAPISDTIIP
PLSPPTNLHLEANPDTGVLTVSWERSTTPDITMYYISTGGSSYKPD---RLEEVVHADQSSCTFDNLSPGLD-YMV-YVRTVMY-YNRSPISDTIIP
PLSPPTNLHLEANPDTGVLTVSWERSTTPDITGYSIATYLTYSNLV---GLEEVVHADQSSCTFDNLSPGLS-YKV-SVYTVYGY-SYGPISDTIIP
PLSPPTNLHLEANPDTGVLTVSWERSTTSDITKYYIATWFGDYGY----SLEEVVHADQSSCTFDNLSPGLQ-YGV-SVATVKGGQAHYPISDTIIP
PLSPPTNLHLEANPDTGVLTVSWERSTTPDITKYYILTSG--YWG-G--GLEEVVHADQSSCTFDNLSPGLT-YLV-SVWTVTH-YAGYPISDTIIP
PLSPPTNLHLEANPDTGVLTVSWERSTTPDITYYSITTSF-Y--Y-S--ELEEVVHADQSSCTFDNLSPGLK-YMV-SVSTVSYS-VGSPISDTIIP
PLSPPTNLHLEANPDTGVLTVSWERSTTPDITTYYISTQGQDERG-Y--VLEEVVHADQSSCTFDKLSPGLI-YXV-IVWTVDDN-RYDPISDTIIP
PLSPPTNLHLEANPDTGVLTVSWERSTTPDITRYYIRTSYVRHGR-----LEEVVHADQSSCTFDNLSPGLY-YNV-SVSTVGYY-YMLPISDTIIP
PLSPPTNLHLEANPDTGVLTVSRERSTTPDITTYSIYTHS-----GALYVLEEVVHADQSSCTFDNPSPGLN-YNV-SVSTVHSRWRYGPISDTIIP
PLSPPTNLHLEANPDTGVLTVSWERSTTPDITMYGIVTIY--TRYY---SLEEVVHADQSSCTFDNLSPGLI-YWV-YVLTVYY-SWYRPISDTIIP
PLSPPTNLHLEANPDTGVLTVSWERSTTPDITTYVIDTGA--AVNY---VLEEVVHADQSSCTFDNLSPGLQ-YSV-DVVVTVWYSWYMPISDTIIP
PLSPPTNPHLEANPDTGVLTVSWERSTTPDITTYWIGTYY-----SADERLEEVVHADQSSCTFDNLSPGLY-YAV-VVGTVGVWYRVAPISDTIIP
PLSPPTNLHLEANPDTGVLTVSWERSTTPDITYYYIHTYY-WKHWQ---SLEEVVHADQSSCTFDNLSPGLK-YGV-WVSTVYRV-VYYPISDTIIP
PLSPPTNLHLEASPDTGVLTVSWERSTTPDITTYLILTYLGYSR-----VLEEVVHADQSSCTFDNLSPGLW-YMV-YVDTVGRVPYIGPISDTIIP
PLSPPTNLHLEANPDTGVLTVSWERSTTPDITVYYIYTYT-YNADL---ILEEVVHADQSSCTFDNLSPGLI-YSV-YVGTVAS-DDGRPISDTIIP
PLSPPTNLHLEANPDTGVLTVSWERSTTPDITAYVI----YTYSESDGRVLEEVVHADQSSCTFDNLSPGLR-YSV-KVSTVY-YSYAYPISDTIIP
```

FnIII[10] hits for HSA (SEQ ID NOs: 200-238, respectively):

```
*******<*A**>*AB<*B*>*BC<*C*>*CD****<*D*>*DE*<*E*>EF<*F*>FG<G***>
VSDVPRDLEVVAATPTSLLISWDAPAVTVRYYRITYGETGGN---SPVQEFTVPGSKSTATISGLKPGVDY-TITVYAVTGRGDSPASSKPISINYRT
VSDVPRDLEVVAATPTSLLISWDAPAVTVRGYYISYYHSTRD----SQEFTVPGSKSTATISGLKPGVSY-YVGVGAV-WKKDYYF---PISINYRT
VSDVPRDLEVVAATPTSLLISWDAPAVTVRYYYILYGDYNAYMD-YAGQEFTVPGSKSTATISGLKPGVGYVEIDVYAV-RTSEEQ----PISINYRT
VSDVPRDLEVVAATPTSLLISWDAPAVTVRAYQIRYAY-YSVG----RQEFTVPGSKSTATISGLRPGVKY-HISVYAV-NGGMVTD---PISINYRT
VSDVPRDLEVVAATPTSLLISWDAPAVTVRYYWIIYWEAWEYVQ---AQEFTVPGSKSTATISGLKPGVHY-GIMVSAV-SGEQPWY---PISINYRT
VSDVPRDLEVVAATPTSLLISWDAPAVTVRIYSIYYYSYVMRGYY--FQEFTVLGSKSTATISGLKPGVNY-DINVQAV-YHRGWRY---PISINYRT
VSDVPRDLEVVAATPTSLLISWDAPAVAVRAYSIDYY-HDNGDG---TQEFTVPGSKSTATISGLKPGVTY-GILVYAV-VS-NMGI---PISINYRT
VSDVPRDLEVVAATPTSLLISWDAPAVTVRSYYIGYSAYDEYGG---RQEFTVPGSKSTATISGLKPGVSY-SINVFAV-YTMTGRA---PISINYRT
VSDVPRDLEVVAATPTSLLISWDAPAVTVRKYSIYYFSSYSGI----AQEFTVPGSKSTATISGLKPGVYY-GIYVEAV-YH-HYSP---PISINYRT
```

```
VSDVPRDLEVVAATPTSLLISWDAPAVTVRNYYIQYM-VNYND----TQEFTVPGSKSTATISGLKPGVYY-DIKVAAV-YV-AEDR---PISINYRT
VSDVPRDLEVVAATPTSLLISWDAPAVTVRKYYITYYRGRSG-----NQEFTVPGSKSTATISGLKPGVKY-HILVSAV-KYPFRRL---PISINYRT
VSDVPRDLEVVAATPTSLLISWDAPAVTVRTYWIVY-YRSVYSN---GQEFTVPGSKSTATISGLKPGVIY-SIRVIAV-SYYYYG----PISINYRT
VSDVPRDLEVVAATPTSLLISWDAPAVTVRTYSISYSFGLDYEY---DQEFTVPGSKSTATISGLKPGVQY-YIVVDAV-AGWQYY----PISINYRT
VSDVPRDLEVVAATPTSLLISWDAPAVTVRGYSIKYG-ST-ISA---DQEFTVPGSKSTATISGLKPGVFY-VIMVWAV-YYAYANY---PISINYRT
VSDVPRDLEVVAATPTSLLISWDAPAVTVRSYHIYDYYNVHSYY---GQEFTVPGSKSTATISGLKPGVSY-AIYVGAV-NE-KQLG---PISINYRT
VSDVPRDLEVVAATPTSLLISWDAPAVTVRTYVISYMSYDAQGG-Q-NQEFTVPGSKSTATISGLKPGVAY-NIIVSAV-GGGQQAV---PISINYRT
VSDVPRDLEVVAATPTSLLISWDAPAVTVREYSIYHSWTLVYR----RQEFTVPGSKSTATISGLKPGVNY-YIYVGAV-DNGYGPD---PISINYRT
VSDVPRDLEVVAATPTSLLISWDAPAVTLRYYEIKYSGSSLY-----VQXFTVPGSKSTATIXGLKPGVSY-NIGVSXV-WQAFWPV---PISINYRT
VSDVPRDLGVVAATPTSLRISWDAPAVTVRSYDIYYWYTTGG-----SQEFTVPGSKSTATISGLKPGVMY-NIYVTAV-DA-DVGG---PISINYRT
VSDVPRDLEVVAATPTSLLISWDAPAVTVRRYYIGYNWQSPAW----NQEFTVPGSKSTATISGLKPGVYY-QIYVAAVLRYGDY-A---PISINYRT
VSDVPRDLEVVAATPTSLLISWDAPAVTVRSYSIGYF-GAYRNW---VQEFTVPGSKSTATISGLKPGVTY-YIEVYAV-YS-NPVY---PISINYRT
VSDVPRDLEVVAATPTSLLISWDAPAVTVRKYQIYYYYSAYVKE---SQEFTVPGSKSTATISGLKPGVSY-NIAVYAV-SKSRYQP---PISINYRT
VSDVPRDLEVVAATPTSLLTSWDAPAVTVRNYAIYYYDD--DTG---RQEFTVPGSKSTATISGLKPGVDY-YIGVEAV-WY-WVSS---PISINYRT
VSDVPRDLEVVAATPTSLLISWDAPAVTVRTYTIWYV---QRYAY--SQEFTVPGSKSTATISGLKPGVSY-SISVRAV-STDRYY----PISINYRT
VSDVPRDLEVVAATPTSLLISWDAPAVTVRYYSIAYW---QLYLP--VQEFTVPGSKSTATISGLKPGVSY-GITVEAV-MSGYSIY---PISINYRT
VSDVPRDLEVVAAAPTSLLISWDAPAVTVRKYYIWYGYSY-FVAYSSYQEFTVPGSKSTATISGLKPGVRY-YIGVLAV-KYPGDYY---PISINYRT
VSDVPRDLEVVAATPTSLLISWDAPAVTVRYHSIGYNY------YGMYQEFTVPGSKSTATISGLKPGVYY-YIYVRAV-TGREAA----PISINYRT
VSDVPRDLEVVAATPTSLLISWDAPAVTVRTYQIEYV----SSYYRWTQEFTVPGSKSTATISGLKPGVVY-FIYVAAV-RDGPN-D---PISINYRT
VSDVPRDLEVVAATPTSLLISWDAPAVTVRSYKISYYGY-----HWVYQEFTVPGSKSTATISGLKPGVSY-LISVSAV-DY-YGVL---PISINYRT
VSDVPRDLEVVAATPTSLLISWDAPAVTVRTYYIGYGMYT------YGQEFTVPGSKSTTTISGLKPGVVY-DIYVWAV-GFGRYVD---PISINYRT
VSDVPRDLEVVAATPTSLLISWDAPAVTVRNYYIGYRY---TVANWCYQEFTVPGSKSTATISGLKPGVSY-WITAKAV-VF-EGDH---PISINYRT
VSDVPRDLEVVAATPTSLLISWDAPAVTVRKYYIGYKL----QVMEPDQEFTVPGSKSTATISGLKPGVEY-WIGVDAV-SYYWGFD---PISINYRT
VSDVPRDLEVVAATPTSLLISWDAPAVTVRGYGIYYGDT------GDTQEFTVPGSKSTATISGLKPGVMY-SIVVFAV-EW-YMWQ---PISINYRT
VSDVPRDLEVVAATPTSLLISWDAPAVTVRYYWIQYYI----YYSRGTQEFTVPGSKSTATISGLKPGVNY-SIGVQAV-QAYFGE----PISINYRT
VSDVPRDLEVVAATPTSLLISWDAPAVTVRSYRIMYS--GYYAWEYSRQEFTVPGSKSTATISGLKPGVIY-AIHVSAV-VT-NWEG---PISINYRT
VSDVPRDLEVVAATPTSLLISWDAPAVTVRDYWIYYRYS----WPYGSQEFTVPGSKSTATISGLKPGVTY-DIQVEAV-YG-SESG---PISINYRT
VSDVPRDLEVVAATPTSLLISWDAPAVTVRYYGIYYAGKAGGDYFITQEFTVPGSKSTATISGLKPGVEY-RIYVAAV-GY-HYTP---PISINYRT
VSDVPRDLEVVAATPTSLLISWDAPAVTVRNYSIKYK----YIPYVSHQEFTVPGSKSTATISGLKPGVTY-SIRVQAV-YYLIERY---PISINYRT
VSDVPRDLEVVAATPTSLLISWDAPAVTVRIYYIAYGY-YPGWGRAGSQEFTVPGSKSTATISGLKPGVTY-GISVSAV-EE-RRKV---PISINYRT

FnIII¹⁴ hits for HSA (SEQ ID NOs: 239-277, respectively):
*******<*A**>*AB<*B*>*BC<*C*>CD***<*D**>*DE*<*E*>EF<*F>*FG*<*G**>
NVSPPRRARVTDATETTITISWRTKTETITGFQVDAVPANGQ------TPIQRTIKPDVRSYTITGLQPGTDYKIYLYTLNDNARS--S**PVVIDAST
NVSPPRRARVTDATETTITISWRTKTETITDFEVAALPMVST-------GIQRTIKPDVRSYTITGLQPGTTYYISLYTLDDDGPG--TPVVIDAST
NVSPPRRARVTDATETTITISWRTKTETITSFNVVAYPS-SQDG------IQRTIKPDVRSYTITGLQPGTGYQIHLTTLG-HLSF--SPVVIDAST
NVSPPRRARVTDATETTITISWRTKTETITYFTVDAAPSLVVD------NIQRTIKPDVRSYTITGLQPGTYYIILLYTLYNYDA---LPVVIDAST
NVSPPRRARVTDATETTITISWRTKTETITLFEVYADPQVSNGT-----YIQRTIKPDVRSYTITGLQPGTYYRIGLYTLSDYEKS--TPVVIDAST
NVSPPRRARVTDATETTITISWRTKTETITRFFVSAVPF----ETG---TIQRTIKPDVRSYTITGLQPGTAYDIALYTLF-GYYY--YPVVIDAST
NVSPPRRARVTDATETTITISWRTKTETITDFGVVASPY----LGQ---GIQRTIKPDVRSYTITGLQPGTAYSIKLHTLH-VHDY--YPVVIDAST
NVSPPRRARVTDATETTITISWRTKTETITYFYVAADPTEDG-------KIQRTIKPDVRSYTITGLQPGTYYTIHLRTLYYLVA---VPVVIDAST
```

```
NVSPPRRARVTDATETTITISWRTKTETITYFDVAANPSYLG-------AIQRTIKPDVRSYTITGLQPGTAYDIALGTL---EXYVSGPVVIDAST
NVSPPRRARVTDATETTITISWRTKTETITYFGVGADPA-MYIEYP---YIQRTIKPDVRSYTITGLQPGTQYGIYLTTLS-QASD--YPVVIDAST
NVSPPRRARVTDATETTITISWRTKTETITYFGVRAYPTYRS-------SIQRTIKPDVRSYTITGLQPGTLYRISLYTLDSAG-Y--NPVVIDAST
NVSPPRRARVTDATETTITISWRTKTETITQFSVYAYPARSKYH------IQRTIKPDVRSYTITGLQPGTGYRIYLQTLG-GYSD--EPVVIDAST
NVSPPRRARVTDATETTITISWRTKTETITEFDVGADPG----KGH---AIQRTIKPDVRSYTITGLQPGTSYLIGLRTLN-RVLH--YPVVIDAST
NVSPPRRARVTDATETTITISWRTKTETITSFRVDAGPGVAG-------SIQRTIKPDVRSYTITGLQPGTYYQIQLAALAYGY----YPVVIDAST
NVSPPRRARVTDATETTITISWRTKTETITRFYVSAQPRFYYYN------IQRTIKPDVRSYTITGLQPGTDYTIGLYTLG-VYMH--YPVVIDAST
NVSPPRRARVTDATETTITISWRTKTETITYFSVEAYPRWYAL-------IQRTIKPDVRSYTITGLQPGTSYYIYLWTLMMDTS---SPVVIDAST
NVSPPRRARVTDATETTITISWRTKTETITEFFVMAEP--YYGEGY---YIQRTIKPDVRSYTITGLQPGTSYSINLYTLK-RPYL--YPVVIDAST
NVSPPRRARVTDATETTITISWRTKTETITSFYVMAQPTNYYGQST---YIQRTIKPDVRSYTITGLQPGTYYGIQLYTLMYRAS---APVVIDAST
NVSPPRRARVTDATETTITISWRTKTETITTFDVYAYPG-YGGSYW---SIQRTIKPDVRSYTITGLQPGTSYEIELETLH-YSHA--YPVVIDAST
NVSPPRRARVTDATETTITISWRTKTETITYFSVLAHPL--EVSSY---SIQRTIKPDVRSYTITGLQPGTGYRIFLSTLR-WYYG--MPVVIDAST
NVSPPRRARVTDATETTITISWRTKTETITYFSVYANPMYPFY-------IQRTIKPDVRSYTITGLQPGTYYEIYLGTLYYFAT---YPVVIDAST
NVSPPRRARVTDATETTITISWRTKTETITYFYVSAYPYYVAY------DIQRTIKPDVRSYTITGLQPGTYYDINLSTLSYSDN---SPVVIDAST
NVSPPRRARVTDATETTITISWRTKTETITYFKVRAYPA-YNYGGW---SIQRTIKPDVRSYTITGLQPGTYYSIYLDTLYLGAYW--YPVVIDAST
NVSPPRSARVTDATETTITISWRTKTETITYFVVGAFPAYSAHV-----DIQRTIKPDVRSYTITGLQPGTGYIINLETLINATG---YPVVIDAST
NVSPPRRARVTDATETTITISWRTKTETITQFWVLAGPSVWTGRM----SIQRTIKPDVRSYTITGLQPGTTYYIGLYTLQYYEY---SPVVIDAST
NVSPPRRARVTDATETTITISWRTKTETITTFRVWARPYLYYW-------IQRTIKPDVRSYTITGLQPGTHYDIGLSTLS-STWY--YPVVIDAST
NVSPPRRARVTDATETTITISWRTKTETITYFHVNAQPSSPP-------WIQRTIKPDVRSYTITGLQPGTYYGISLYTLSWRGEY--HPVVIDAST
NVSPPRRARVTDATETTITISWRTKTETITRFSVLAYPS-KRTTYT---PIQRTIKPDVRSYTITGLQPGTGYTIRLYTLSPYYWV--YPVVIDAST
NVSPPRRARVTDATETTITISWRTKTETITWFYVSAFPL-LVDG------IQRTIKPDVRSYTITGLQPGTYYGINLYTLS----S--YPVVIDAST
NVSPPRRARVTDATETTITISWRTKTETITYFYVYAKPRYIN-------SIQRTIKPDVRSYTITGLQPGTDYSIYLDTLYWGGEY--GPVVIDAST
NVSPPRRARVTDATETTITISWRTKTETITAFNVYASPEYWRYGYFR--FIQRTIKPDVRSYTITGLQPGTGYYIYLYTLYHKYGY--YPVVIDAST
NVSPPRRARVTDATETTITISWRTKTETITAFYVHAVPMLWVVNG-----IQRTIKPDVRSYTITGLQPGTSYTINLETLRMSSHY--YPVVIDAST
NVSPPRRARVTDATETTITISWRTKTETITSFYVRALPVSAW-------PIQRTIKPDVRSYTITGLQPGTGYNIGLVTLYYGASY--VPVVIDAST
NVSPPRRARVTDATETTITISWRTKTETITAFYVGAHPWYNL-------EIQRTIKPDVRSYTITGLQPGTGYVISLYTLWHHNE---APVVIDAST
NVSPPRRARVTDATETTITISWRTKTETITSFWVHAYPSGASGG------IQRTIKPDVRSYTITGLQPGTNYGIALATLTHYYTY--SPVVIDAST
NVSPPRRARVTDATETTITISWRTKTETITGFHVFASPWYSGSQ-----SIQRTIKPDVRSYTITGLQPGTTYYIGLNTLYIPGHE--PPVVIDAST
NVSPPRRARVTDATETTITISWRTKTETITSFYVDAGP---WYRPDAYEYIQRTIKPDVRSYTITGLQPGTGYSIQLYTLYAYAYL--YPVVIDAST
NVSPPRRARVTDATETTITISWRTKTETITLFYVYAYPR-YYPG-----IQRTIKPDVRSYTITGLQPGTSYSIYLSTLW-DTKG--YPVVIDAST
NVSPPRRARVTDATETTITISWRTKTETITTFMVVAYPM-FQYR------IQRTIKPDVRSYTITGLQPGTSYTIYLQTLG-YASW--YPVVIDAST
```

EXAMPLE 8

Proof of Principle with Small Ubiquitin-Like Modifier (SUMO) Using Structure-Guided Design The inventors used SUMO as a non-limiting model for demonstration of the methods described herein. The following description is given for the purpose of illustrating various embodiments of the invention and is not meant to limit the present invention in any fashion. One skilled in the art will appreciate that the present invention is well adapted to carry out the objects mentioned, as well as those objects, ends and advantages inherent herein. SUMO is used to represent the general embodiments for the purpose of proof of principle and is not intended to limit the scope of the invention. The described methods and compositions can be used with respect to a plethora of target molecules and are not limited solely to SUMO. Changes therein and other uses which are encompassed within the spirit of the invention as defined by the scope of the claims will occur to those skilled in the art.

SUMOs are structurally similar to ubiquitin and are post-translationally conjugated to other proteins resulting in a variety of functional modulations. In humans, there are four SUMO isoforms (SUMO1-4) (Gareau and Lima, Nature Rev. (2010) 11:861-871). SUMO1 and SUMO2 share 41% sequence identity (72% similarity) but are functionally distinct (FIG. 10B, bottom) (Saitoh and Hinchey, *J. Biolog. Chem.* (2000) 275:6252-6258; Vertegaal, et al., *Mol. Cell. Proteomics* (2006) 5:2298-2310). SUMO2 and SUMO3, collectively referred to as SUMO2/3, share 97% sequence identity and are assumed to be functionally identical (Gareau and Lima, supra, 2010; Johnson, *Annual Rev. Biochem.* (2004) 73:355-382). SUMO4's relevance as a post-translational modification is not clear (Bohren, et al., *Protein Express. Purif.* (2007) 54:289-294; Owerbach, et al., *Biochemical Biophysical Res. Comm.* (2005) 337:517-520). Thus, most studies in SUMO biology have focused on SUMO1 and SUMO2/3. SUMOylation play important roles in regulating diverse cellular processes including DNA repair, transcription, nuclear transport and chromosome dynamics (Gareau and Lima, supra, 2010; Johnson, supra, 2004). The dominant mechanism by which SUMOylation alters protein function appears to be through SUMO-mediated interactions with other proteins containing a short peptide motif known as a SUMO-interacting motif (SIM) (Johnson, supra, 2004; Kerscher, *EMBO Repts.* (2007) 8:550-555; Song, et al., *Proc. Natl. Acad. Sci. USA* (2004) 101:14373-14378).

The existence of few inhibitors of SUMO/SIM interactions limits the ability to finely dissect SUMO biology and provides for an ideal model system to demonstrate the effectiveness of the methods and compositions described herein. In the only reported example of such an inhibitor, a SIM-containing linear peptide was used to inhibit SUMO/SIM interactions, establishing their importance in coordinating DNA repair by non-homologous end joining (NHEJ) (Li, et al., *Oncogene* (2010) 29:3509-3518). This peptide sensitized cancer cells to radiation and chemotherapeutic-induced DNA damage, illustrating a therapeutic potential for SUMO/SIM inhibitors. These findings clearly establish the utility of SUMO/SIM inhibitors, but the peptide inhibitor suffers from two significant shortcomings. First, the peptide binds equally well to SUMO1 and SUMO2/3, making it impossible to differentiate the roles of each isoform. Second, the peptide has low affinity for SUMO ($K_d$~5 µM) (Song, et al., supra, 2004). As a result, high concentrations of the peptide are required for inhibition. Most natural SIM peptides exhibit similarly low affinities and discriminate individual SUMO isoforms by ~10-fold or less (Kerscher, supra, 2007; Chang, et al., *J. Biological Chem.* (2010) 285:5266-5273; Hecker, et al., *J. Biol. Chem.* (2006) 281:16117-16127; Sekiyama, et al., *J. Biological Chem.* (2008) 283: 35966-35975; Zhu, et al., *J. Biological Chem.* (2008) 283: 29405-29415). Higher affinity reagents capable of selectively inhibiting the SIM interactions of individual SUMO isoforms could be powerful tools for better defining the functions of each isoform and potentially as more potent therapeutics. However, the development of such highly selective inhibitors presents a formidable challenge as the SIM binding site is highly conserved among SUMO isoforms (FIGS. 16A, and 10B, bottom) (Chupreta, et al., *Molec. Cell. Biol.* (2005) 25:4272-4282). The development of a SUMO/SIM inhibitor or affinity agent that distinguishes between certain isoforms of SUMO can be used as a model system to demonstrate the ability to design and produce such affinity agents using the methods and compositions described herein.

FnIII Cradle Library

Libraries have been designed and constructed in which positions in the beta-strand regions of the FnIII scaffold, in addition to loop positions, are diversified. Two different libraries are described herein that differ in that positions in the CD loop (residues 41-45) were diversified in Library BL1 but not the other, library BL2. The libraries were constructed in the phage display format following procedures that have been published (Wojcik, et al., supra, 2010) and described herein. The BL1 and BL2 libraries were estimated to contain $6 \times 10^{10}$ and $1 \times 10^{10}$ unique sequences, respectively.

Selection of cradle molecules from the libraries was performed as described previously (Koide, A., et al., 2009). The following targets in the form of poly-histidine tagged proteins were used: human SUMO1, human ubiquitin, human Abl SH2 domain, human SFMBT2 domain, human SCMH1 domain, and green fluorescent protein. Multiple clones were identified for most of targets. Representative binding data are shown in FIG. 15. The amino acid sequences of monobody clones are given in Table 6.

TABLE 5

Amino acid diversity used for the cradle libraries.

| Position | Diversity |
|---|---|
| BL1 library | |
| 30 (R) | D, F, H, I, L, N, V, or Y |
| 31 (Y) | F, H, L, or Y |
| 33 (R) | D, F, H, I, L, N, V, or Y |
| 41-45 | 5 and 6 residues of [Y(30%), S(15%), G(10%), F(5%), W(5%), all others except for C (2.5% each)] |
| 47 (E) | A, E, K, or T |
| 49 (T) | A, E, K, or T |
| 75-85 | 7-13 residues of [Y(30%), S(15%), G(10%), F(5%), W(5%), all others except for C (2.5% each)] |
| BL2 library | |
| 30 (R) | D, F, H, I, L, N, V, or Y |
| 31 (Y) | F, H, L, or Y |
| 33 (R) | D, F, H, I, L, N, V, or Y |
| 47 (E) | A, E, K, or T |
| 49 (T) | A, E, K, or T |
| 75-85 | 7-13 residues of [Y(30%), S(15%), G(10%), F(5%), W(5%), all others except for C (2.5% each)] |
| ST1 library | |
| 31 (Y) | D, H, N, or Y |
| 33 (R) | A, D, E, G, H, K, N, P, Q, R, S, or T |
| 73 (Y) | A, D, F, H, I, L, N, P, S, T, V, or Y |
| 75 (V) | D, F, H, I, L, N, V, or Y |
| 76 (T) | D, H, N, or Y |
| 77 (G) | S |
| 78 (R) | A, D, E, G, H, I, K, L, M, N, P, Q, R, S, T, V, or Y |
| 79 (G) | D, E, H, K, N, Q, or Y |
| 80 (D) | A, D, F, H, I, L, N, P, S, T, V, or Y |
| 81 (S) | F, I, L, or V |
| 82 (P) | A, D, F, H, I, L, N, P, S, T, V, or Y |
| 83 (A) | D, F, H, I, L, N, V, or Y |
| 84 (S) | A or S |
| 85 (S) | D, F, H, I, L, N, V, or Y |
| 88 (I) | S |

Wild-type residues are shown in parenthesis.

TABLE 6

Amino acid sequences of cradle molecules generated from cradle libraries.
Sequences are grouped according to their binding target.
"x" designates a diversified position in the libraries. Because the lengths of the CD and FG
loops were varied in the BL1 and BL2 libraries, the numbers of "x"s shown for these libraries are
for guidance only and they do not accurately reflect the actual numbers of residues.

```
BL1 Library (SEQ ID NO: 3)
Library
VSSVPTKLEVVAATPTSLLISWDAPAVTVxxYxITYGETG-xxxxxxQxFxVPGSKSTATISGLSPGVDYTITVYAxxxxxxxxxxxxxxxSPISINYRT
         .         .         . ------           .         .         . ---------------  .
        10        20        30        40 CD loop 50        60        70        FG loop 90 human SUMO1 (SEQ ID NOS: 4-11, respectively)
VSSVPTKLEVVAATPTSLLISWDAPAVTVDHYVITYGETG-SYSSYGQEFAVPGSKSTATISGLSPGVDYTITVYAY---EFQFEMYMSYSPISINYRT VSSVPTKLEVVAATPTSLLISWDAPAVTVDYYVITYGETG-G-VYGPQEFEVPGSKSTATISGLSPGVDYTITVYAW-F-YQQAYEHYVSSPISINYRT VSSVPTKLEVVAATPTSLLISWDAPAVTVLFYHITYGETG-GN-SPVQEFTVPGSKSTATISGLSPGVDYTITVYAYYS-DYTY------SPISINYRT VSSVPTKLEVVAATPTSLLISWDAPAVTVDHYVITYGETG-GN-SPVQEFTVPGSKSTATISGLSPGVDYTITVYAWD--YSWG-YYGYSPISINYRT VSSVPTKLEVVAATPTSLLISWDAPAVTVDFYVITYGETG-GN-SPVQEFEVPGSKSTATISGLSPGVDYTITVYAW---IYS-DSVYSASPISINYRT VSSVPTKLEVVAATPTSLLISWDAPAVTVDHYVITYGETGGYAYSASQEFEVPGSKSTATISGLSPGVDYTITVYAY---ESYYWGFAGYSPISINYRT VSSVPTKLEVVAATPTSLLISWDAPAVTVDYYVITYGETG-VFGAGPQEFEVPGSKSTATISGLSPGVDYTITVYAY-E-EWSESMYMSYSPISINYRT VSSVPTKLEVVAATPTSLLISWDAPAVTVDHYHITYGETG-GN-SPVQEFTVPGSKSTATISGLSPGVDYTITVYAYWE-AFSGDLYYSSSPISINYRT human ubiquitin (SEQ ID NOS: 12-27, respectively)
VSSVPTKLEVVAATPTSLLISWDAPAVTVDHYNITYGETG-AFWHYVQAFTVPGSKSTATISGLSPGVDYTITVYAEW--DQYVVG----SPISINYRT VSSVPTKLEVVAATPTSLLISWDAPAVTVDYYVITYGETG-GGYYSFQAFEVPGSKSTATISGLSPGVDYTITVYAFWP-DDYYYGGSEYSPISINYRT VSSVPTKLEVVAATPTSLLISWDAPAVTVDHYHITYGETG-GSWSGYQEFTVPGSKSTATISGLSPGVDYTITVYANS-------SWYWYNPISINYRT VSSVPTKLEVVAATPTSLLISWDAPAVTVDHYVITYGETG-AHYYYFQEFEVPGSKSTATISGLSPGVDYTITVYAVSH-GTDGNKLYFFSPISINYRT VSSVPTKLEVVAATPTSLLISWDAPAVTVDFYVITYGETG-GWWYGVQAFTVPGSKSTATISGLSPGVDYTITVYAEDS-----GGRHSISPISXNYRT VSSVPTKLEVVAATPTSLLISWDAPAVTVDYYVITYGETG-WY-SPPQEFTVPGSKSTATISGLSPGVDYTITVYAWNW--SAG----LQSPISINYRT VSSVPTKLEVVAATPTSLLISWDAPAVTVDYYVITYGETG-GN-SPVQEFTVPGSKSTATISGLSPGVDYTITVYAWS-----WKYWYHGSPISINYRT VSSVPTKLEVVAATPTSLLISWDAPAVTVDFYIITYGETG-GGYYSYQTFTVPGSKSTATISGLSPGVDYTITVYAN---EFGKSYPYTMNPISINYRT VSSVPTKLEVVAATPTSLLISWDAPAVTVLYYVITYGETG-GN-SPVQEFTVPGSKSTATISGLSPGVDYTITVYATDY-GPGYPY---ESPISINYRT VSSVPTKLEVVAATPTSLLISWDAPAVTVDLYHITYGETG-GVWSGYQEFTVPGSKSTATISGLSPGVDYTITVYAVQH---QEIWPYYYSPISINYRT VSSVPTKLEVVAATPTSLLISWDAPAVTVDHYFITYGETG-GSWSYYQEFAVPGSKSTATISGLSPGVDYTITVYAYSY-----EPYYYYNPISINYRT VSSVPTKLEVVAATPTSLLISWDAPAVTVDFYVITYGETG-SF-SPPQEFTVPGSKSTATISGLSPGVDYTITVYAMMW--GWEYYDYNISPISINYRT VSSVPTKLEVVAATPTSLLISWDAPAVTVDLYIITYGETG-SYHGW-QTFTVPGSKSTATISGLSPGVDYTITVYADSS---TWPYWYYSSPISINYRT VSSVPTKLEVVAATPTSLLISWDAPAVTVDFYVITYGETG-SF-SPPQEFTVPGSKSTATISGLSPGVDYTITVYAMMW--GWEYYDYNISPISINYRT VSSVPTKLEVVAATPTSLLISWDAPAVTVDHYVITYGETG-GVWYGYQEFTVPGSKSTATISGLSPGVDYTITVYAMTS-----YFQEYWSPISINYRT VSSVPTKLEVVAATPTSLLISWDAPAVTVDFYVITYGETG-SF-SPPQEFTVPGSKSTATISGLSPGVDYTITVYAMMW--GWEYYDYNISPISINYRT human Abl SH2 domain (SEQ ID NOS: 28-44, respectively)
VSSVPTKLEVVAATPTSLLISWDAPAVTVDHYVITYGETG-GYPSPVQTFTVPGSKSTATISGLSPGVDYTITVYAWD---YDW--YAIGSPISINYRT VSSVPTKLEVVAATPTSLLISWDAPAVTVVYYVITYGETG-GN-SPVQEFTVPGSKSTATISGLSPGVDYTITVYAWYTFQYDYYVTQS-SPISINYRT VSSVPTKLEVVAATPTSLLISWDAPAVTVDFYFITYGETG-GN-SPVQEFTVPGSKSTATISGLSPGVDYTITVYAWDNWD-DYYY----SPISINYRT VSSVPTKLEVVAATPTSLLISWDAPAVTVVFYVITYGETG-SYSGW-QEFEVPGSKSTATISGLSPGVDYTITVYAY---YYQNPE-SYYSPISINYRT VSSVPTKLEVVAATPTSLLISWDAPAVTVDLYFITYGETG-GN-SPVQEFTVPGSKSTATISGLSPGVDYTITVYAWY---YGYYGPQYTSPISINYRT VSSVPTKLEVVAATPTSLLISWDAPAVTVDYYYITYGETG-GN-SPVQEFTVPGSKSTATISGLSPGVDYTITVYAWYQHDFDYHVWGS-SPISINYRT VSSVPTKLEVVAATPTSLLISWDAPAVTVHYYVITYGETG-WW-GPVQEFTVPGSKSTATISGLSPGVDYTITVYAY------WKYSYKYSPISINYRT VSSVPTKLEVVAATPTSLLISWDAPAVTVDYYVITYGETG-AFGSG-QEFEVPGSKSTATISGLSPGVDYTITVYA----KWMYS-YMYN-PISINYRT VSSVPTKLEVVAATPTSLLISWDAPAVTVVYYFITYGETG-GN-SPVQEFTVPGSKSTATISGLSPGVDYTITVYAWSYELTGDYLQQF-SPISINYRT
```

TABLE 6-continued

Amino acid sequences of cradle molecules generated from cradle libraries.
Sequences are grouped according to their binding target.
"x" designates a diversified position in the libraries. Because the lengths of the CD and FG
loops were varied in the BL1 and BL2 libraries, the numbers of "x"s shown for these libraries are
for guidance only and they do not accurately reflect the actual numbers of residues.

```
VSSVPTKLEVVAATPTSLLISWDAPAVTVVYYNITYGETG-GN-SPVQEFTVPGSKSTATISGLSPGVDYTITVYAWY--EYGGYMEID-SPISINYRT

VSSVPTKLEVVAATPTSLLISWDAPAVTVDYYVITYGETG-VPYYGWQEFEVPGSKSTATISGLSPGVDYTITVYAY-P-GSNWFYDWW-SPISINYRT

VSSVPTKLEVVAATPTSLLISWDAPAVTVDFYVITYGETG-SYGSYPQAFEVPGSKSTATISGLSPGVDYTITVY----TESEGYISS--SPISINYRT

VSSVPTKLEVVAATPTSLLISWDAPAVYHVYYLITYGETG-GN-SPVQEFTVPGSKSTATISGLSPGVDYTITVYA----KWKYSYQY--SPISINYRT

VSSVPTKLEVVAATPTSLLISWDAPAVTVDYYYITYGETG-GN-SPVQEFTVPGSKSTATISGLSPGVDYTITVYA-WYWNDYYMSSM--SPISINYRT

VSSVPTKLEVVAATPTSLLISWDAPAVTVDYYVITYGETG-GN-SPVQEFEVPGSKSTATISGLSPGVDYTITVYA--TYGDAYWHYYY-SPISINYRT

VSSVPTKLEVVAATPTSLLISWDAPAVTVVHYHITYGETG-GN-SPVQEFTVPGSKSTATISGLSPGVDYTITVYA----DWQYSYMY--SPISINYRT

VSSVPTKLEVVAATPTSLLISWDAPAVDFYVYLITYGETG-GN-SPVQEFTVPGSKSTATISGLSPGVDYTITVY----GYSDSWNWPY-SPISINYRT
("SH13")

SFMBT2 (SEQ ID NO: 45)
VSSVPTKLEVVAATPTSLLISWDAPAVTVDYYVITYGETG-FSFGSSQTFKVPGSKSTATISGLSPGVDYTITVYA-----FYWSKYY--SPISINYRT

SCMH1 (SEQ ID NO: 46-47, respectively)
VSSVPTKLEVVAATPTSLLISWDAPAVDLYVYLITYGETG-VASWGYQEFTVPGSKSTATISGLSPGVDYTITVYA-----YGGNYWY--SPISINYRT VSSVPTKLEVVAATPTSLLISWDAPAVHYVYLITYGETG-YYSYG-QEFEVPGSKSTATISGLSPGVDYTITVYA----YNGSGWMVQ-SPISINYRT Green fluorescent protein (SEQ ID NO: 48-78, respectively)
VSSVPTKLEVVAATPTSLLISWDAPAVTVDHYYITYGETG--AYWYSQAFTVPGSKSTATISGLSPGVDYTITVYA-----STKENQY--SPISINYRT VSSVPTKLEVVAATPTSLLISWDAPAVTVDYYHITYGETG--HYWYYQAFAVPGSKSTATISGLSPGVDYTITVYA-----SSIDYMY--SPISINYRT VSSVPTKLEVVAATPTSLLISWDAPAVTVDYYYITYGETG-GY-WFPSTFTVPGSKSTATISGLSPGVDYTITVYA-----SMSPSGYFYSPISINYRT VSSVPTKLEVVAATPTSLLISWDAPAVTVDFYFITYGETG-GN-SPVQEFTVPGSKSTATISGLSPGVDYTITVYA----YGEWDWWSW-SPISINYRT VSSVPTKLEVVAATPTSLLISWDAPAVTVDYYFITYGETG-GN-SPVQEFTVPGSKSTATISGLSPGVDYTITVYA-YHVSFPSDEEGM-SPISINYRT VSSVPTKLEVVAATPTSLLISWDAPAVTVDLYYITYGETG-GN-SPVQEFTVPGSKSTATISGLSPGVDYTITIYA---FGSYHYWEH--SPISINYRT VSSVPTKLEVVAATPTSLLISWDAPAVTVDFYVITYGETG-GN-SPVQEFTVPGSKSTATISGLSPGVDYTITVYA---YGEYKWWSY--SPISINYRT VSSVPTKLEVVAATPTSLLISWDAPAVTVDLYVITYGETG-GN-SPVQEFTVPGSKSTATISGLSPGVDYTITVYA---YGGYEYWYY--SPISINYRT VSSVPTKLEVVAATPTSLLISWDAPAVTVDFYVITYGETG-GN-SPVQEFTVPGSKSTATISGLSPGVDYTITVYA---RGYFKWWEY--SPISINYRT VSSVPTKLEVVAATPTSLLISWDAPAVTVDYYFITYGETG-GN-SPVQEFTVPGSKSTATISGLSPGVDYTITVYA--GMVYYGWERES-SPISINYRT VSSVPTKLEVVAATPTSLLISWDAPAVTVVHYVITYGETG-GN-SPVQEFTVPGSKSTATISGLSPGVDYTITVYALYEGGQHFGYSFS-SPISINYRT VSSVPTKLEVVAATPTSLLISWDAPAVTVDFYVITYGETG-GN-SPVQEFTVPGSKSTATISGLSPGVDYTITVYA---YGSYSYWMY--SPISINYRT VSSVPTKLEVVAATPTSLLISWDAPAVTVDYYVITYGETG-GN-SPVQEFTVPGSKSTATISGLSPGVDYTITVYAGYVEWQSAKNVH--SPISINYRT VSSVPTKLEVVAATPTSLLISWDAPAVTVDHYNITYGETG-GSWYAYQTFEVPGSKSTATISGLSPGVDYTITVYA--SFSGDMYYYY--SPISINYRT VSSVPTKLEVVAATPTSLLISWDAPAVTVDYYVITYGETG-GN-SPVQEFTVPGSKSTATISGLSPGVDYTITVYAGYVAFDYYWRGGY-SPISINYRT VSSVPTKLEVVAATPTSLLISWDAPAVTVHYYYITYGETG-GN-SPVQEFTVPGSKSTATISGLSPGVDYTITVYA---SLWDWYSS---SPISINYRT VSSVPTKLEVVAATPTSLLISWDAPAVTVDYYFITYGETG-GYFSSWQEFTVPGSKSTATISGLSPGVDYTITVYA-GYAGSFPSYE---SPISINYRT VSSVPTKLEVVAATPTSLLISWDAPAVTVDLYVITYGETG-GN-SPVQEFTVPGSKSTATISGLSPGVDYTITVYA---YGDYYYWLY--SPISINYRT VSSVPTKLEVVAATPTSLLISWDAPAVTVDFYVITYGETG-GN-SPVQEFTVPGSKSTATISGLSPGVDYTITVYA---YGEFGWWRY--SPISINYRT VSSVPTKLEVVAATPTSLLISWDAPAVTVDLYHITYGETG-GPWWGYQTFAVPGSKSTATISGLSPGVDYTITVYT----SSHHPGWW--SPISINYRT VSSVPTKLEVVAATPTSLLISWDAPAVTVDHYVITYGETG-YYAYSYQTFTVPGSKSTATISGLSPGVDYTITVYA---WSYFDGPVY--SPISINYRT VSSVPTKLEVVAATPTSLLISWDAPAVTVDLYHITYGETG-GPWWGYQTFAVPGSKSTATISGLSPGVDYTITVYT---SSHHPGWWS--SPISINYRT VSSVPTKLEVVAATPTSLLISWDAPAVTVDYYHITYGETG-SYWHY-QAFEVPGSKSTATISGLSPGVDYTITVYA----QTRNRYME--SPISINYRT VSSVPTKLEVVAATPTSLLISWDAPAVTVDLYVITYGETG-GN-SPVQEFTVPGSKSTATISGLSPGVDYTITVYA---YGDFMYWKY--SPISINYRT
```

TABLE 6-continued

Amino acid sequences of cradle molecules generated from cradle libraries.
Sequences are grouped according to their binding target.
"x" designates a diversified position in the libraries. Because the lengths of the CD and FG
loops were varied in the BL1 and BL2 libraries, the numbers of "x"s shown for these libraries are
for guidance only and they do not accurately reflect the actual numbers of residues.

```
VSSVPTKLEVVAATPTSLLISWDAPAVTVDFYVITYGETG-GN-SPVQEFTVPGSKSTATISGLSPGVDYTITVYA---YGGYSYWLH--SPISINYRT

VSSVPTKLEVVAATPTSLLISWDAPAVTVDHYHITYGETG-SHYWSYQKFTVPGSKSTATISGLSPGVDYTITVYA-SPEGRGSYYGW--SPISINYRT

VSSVPTKLEVVAATPTSLLISWDAPAVTVDYYNITYGETG-VWFPY-QTFTVPGSKSTATISGLSPGVDYTITVYA---SMVDYEYWW--SPISINYRT

VSSVPTKLEVVAATPTSLLISWDAPAVTVVHYLITYGETG-GAGSSYQTFAVPGSKSTATISGLSPGVDYTITVYA----YMSNYYSY--SPISINYRT

VSSVPTKLEVVAATPTSLLISWDAPAVTVDLYHITYGETG-GSGWGYQAFAVPGSKSTATISGLSPGVDYTITVYA----SSDYLKYY--SPISINYRT

VSSVPTKLEVVAATPTSLLISWDAPAVTVDFYVITYGETG-GN-SPVQEFTVPGSKSTATISGLSPGVDYTITVYA-YDIGWFPAHYG--SPISINYRT

VSSVPTKLEVVAATPTSLLISWDAPAVTVVFYLITYGETG-GN-SPVQEFTVPGSKSTATISGLSPGVDYTITVYA-YSTGGSYKSQ---SPISINYRT

BL2 Library (SEQ ID NO: 79)
Library
VSSVPTKLEVVAATPTSLLISWDAPAVTVxxYxITYGETG-GN-SPVQxFxVPGSKSTATISGLSPGVDYTITVYAxxxxxxxxxxxxxxxSPISINYRT
         .         .         .         .         .         .         .   ---------------  .
        10        20        30        40        50        60        70       FG loop       90 human Abl SH2 domain (SEQ ID NO: 80-85, respectively)
VSSVPTKLEVVAATPTSLLISWDAPAVTVVHYVITYGETG-GN-SPVQEFTVPGSKSTATISGLSPGVDYTITVYA---LLSSSHWVYE-SPISINYRT
("GG3")

VSSVPTKLEVVAATPTSLLISWDAPAVTVDLYLITYGETG-GN-SPVQEFKVPGSKSTATISGLSPGVDYTITVYAGSDYYYYYQGAYW-SPISINYRT

VSSVPTKLEVVAATPTSLLISWDAPAVTVDFYVITYGETG-GN-SPVQEFTVPGSKSTATISGLSPGVDYTITVYA-----NWAYSYRY-SPISINYRT

VSSVPTKLEVVAATPTSLLISWDAPAVTVFYYVITYGETG-GN-SPVQEFEVPGSKSTATISGLSPGVDYTITVYA-----NYPYSYMY-SPISINYRT

VSSVPTKLEVVAATPTSLLISWDAPAVTVDYYLITYGETG-GN-SPVQEFTVPGSKSTATISGLSPGVDYTITVYA-----WDPYWDVM-SPISINYRT

VSSVPTKLEVVAATPTSLLISWDAPAVTVDLYVITYGETG-GN-SPVQEFTVPGSKSTATISGLSPGVDYTITVYAGWGNWELGYSWS--SPISINYRT

ST1 Library (SEQ ID NO: 86)
Library
VSSVPTKLEVVAATPTSLLISWDASSSSVSxYxITYGETGGNSPVQEFTVPGSSSTATISGLSPGVDYTITVxAxxSxxxxxxxxxSPSSINYRT
         .         .         .         .         .         .         .         .
        10        20        30        40        50        60        70        90 human SUMO1 (SEQ ID NO: 87-96, respectively)
VSSVPTKLEVVAATPTSLLISWDASSSSVSHYHITYGETGGNSPVQEFTVPGSSSTATISGLSPGVDYTITVYAFYSDDDLYFAFSPSSINYRT VSSVPTKLEVVAATPTSLLISWDASSSSVSHYGITYGETGGNSPVQEFTVPGSSSTATISGLSPGVDYTITVYAYHSYDDIYYALSPSSINYRT VSSVPTKLEVVAATPTSLLISWDASSSSVSHYAITYGETGGNSPVQEFTVPGSSSTATISGLSPGVDYTITVYAYHSYDDIFLADSPSSINYRT VSSVPTKLEVVAATPTSLLISWDASSSSVSHYEITYGETGGNSPVQEFTVPGSSSTATISGLSPGVDYTITVYAYYSHEDIFYAVSPSSINYRT VSSVPTKLEVVAATPTSLLISWDASSSSVSHYEITYGETGGNSPVQEFTVPGSSSTATISGLSPGVDYTITVAAYHSYHDIFYAVSPSSINYRT VSSVPTKLEVVAATPTSLLISWDASSSSVSHYEITYGETGGNSPVQEFTVPGSSSTATISGLSPGVDYTITVTAYDSYYDIYIAYSPSSINYRT VSSVPTKLEVVAATPTSLLISWDASSSSVSYYEITYGETGGNSPVQEFTVPGSSSTATISGLSPGVDYTITVIAFYSHDDIYISDSPSSINYRT VSSVPTKLEVVAATPTSLLISWDASSSSVSHYAITYGETGGNSPVQEFTVPGSSSTATISGLSPGVDYTITVYAYYSYDDLYVSDSPSSINYRT VSSVPTKLEVVAATPTSLLISWDASSSSVSHYAITYGETGGNSPVQEFTVPGSSSTATISGLSPGVDYTITVFAYYSYDDIYYAYSPSSINYRT VSSVPTKLEVVAATPTSLLISWDASSSSVSHYDITYGETGGNSPVQEFTVPGSSSTATISGLSPGVDYTITVHAYYSYDDIYVAISPSSINYRT
```

Structure-Guided Library Design

Many proteins are members of large structurally conserved families Binding proteins that can specifically target functional sites on individual members of highly related protein families are valuable tools for studying the unique functions of these molecules. Proteins in such families often exhibit high levels of sequence similarity in addition to conserved structural features making it difficult to generate binding proteins that effectively discriminate individual family members. This problem is more pronounced when targeting a functional site that is particularly highly conserved among family members. Taken together, these factors make the production of such reagents a challenge.

Figure 10A:
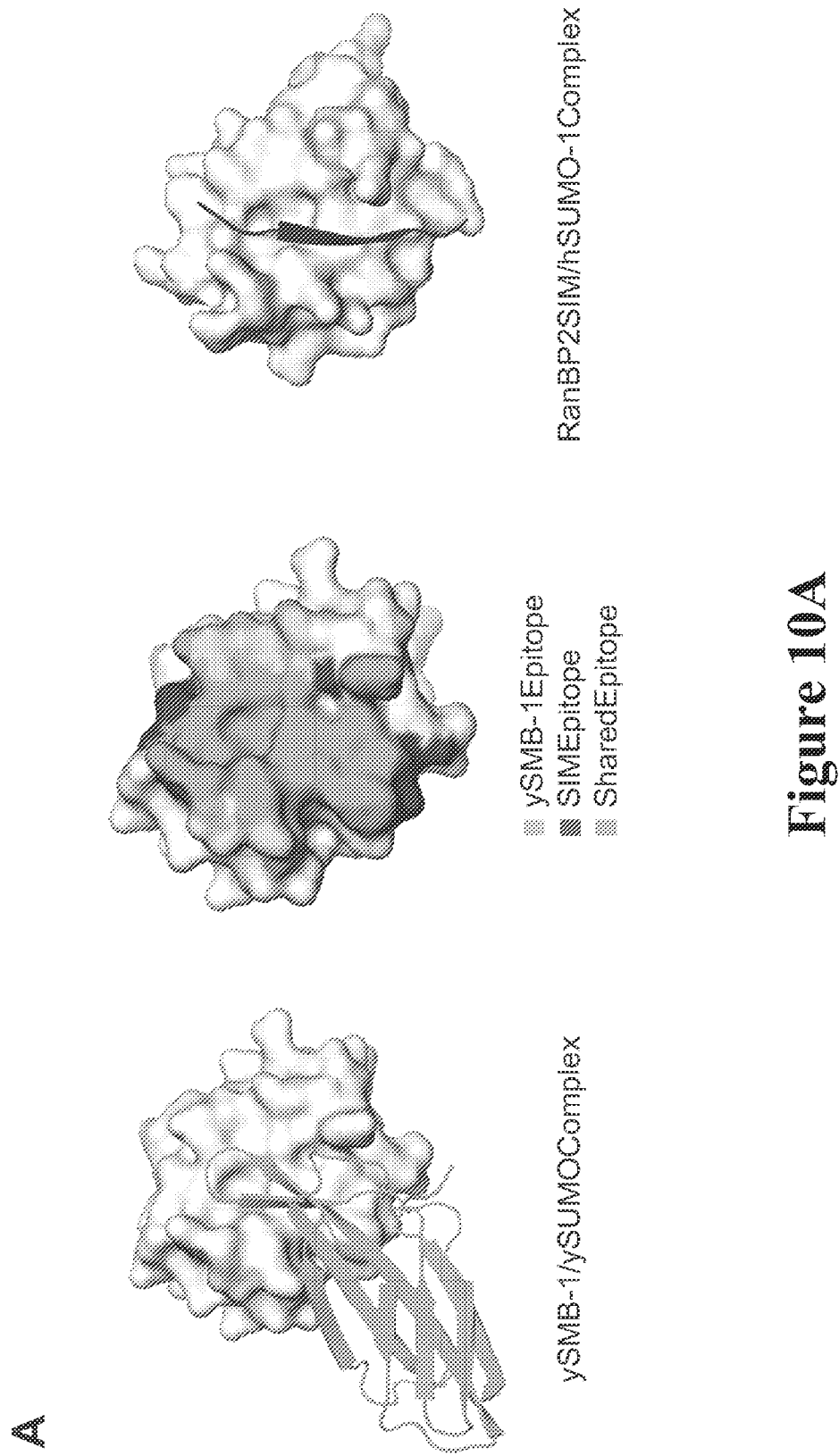

In recent studies, the structure of an FnIII domain variant (ySMB-1) bound to yeast small ubiquitin-like modifier protein (ySUMO) has been determined. ySMB-1 bound to ySUMO at a functional site normally used to interact with short peptide motifs known as SUMO interacting motifs (SIMs) (FIG. 10A). The SIM binding site constitutes the most conserved surface among SUMO family proteins (FIG. 10B) (Hecker, et al., *J. Biol. Chem.* (2006) 281:16117-16127). Despite this high level of conservation, ySMB-1 was shown to effectively discriminate ySUMO from two closely related human homologs, hSUMO-1 and hSUMO-2.

Specific, high-affinity cradle molecules binding to the SIM binding sites of SUMO family proteins could potentially be used as inhibitors of SUMO/SIM interactions. Since the roles of these interactions in different SUMO proteins are not well understood, such cradle molecules could be valuable tools in studying SUMO biology. However, FnIII domain variants to hSUMO-1 and hSUMO-2 have not been identified in combinatorial libraries in which loops of the FnIII domain are diversified, with the exception of a single hSUMO-1 binding clone which crossreacts with ySUMO and hSUMO-2. These difficulties suggest that an alternative approach is required to obtain FnIII domain variants to these targets. Cradle molecules were generated that bind to the SIM binding site of hSUMO-1 by making a structure-guided library based on the architecture of the ySUMO-binding FnIII domain variant ySMB-1. The idea behind this strategy was to maintain the useful binding mode of ySMB-1 and recognition of the SIM binding site, but allow for sufficient alteration in the cradle molecule binding surface to accommodate sequence differences in the predicted epitopes on other SUMO proteins.

Cradle molecules were isolated that specifically target individual human SUMO isoforms as well as the yeast homolog of SUMO (ySUMO), which has about 45% sequence identity (about 67% similarity) with human SUMOs (hSUMOs) (FIGS. 10B, bottom, and 16A). Numerous cradle molecules to ySUMO with mid-nM $K_d$ values were successfully isolated (FIGS. 16C, D and 19).

To further improve the design of a cradle library, the crystal structure of a ySUMO-binding FnIII domain variant bound to ySUMO was determined which revealed the structural basis for targeting ySUMO. Guided by this structural information, a "SUMO-targeted" cradle library that produced isoform-specific cradle molecules to hSUMO1 was developed. Cradle molecules that bound to the SIM-binding site of human SUMO1 with $k_d$ values of ~100 nM but bound to SUMO2 400 times more weakly were obtained from this library. Functional studies also demonstrated that these cradle molecules are highly selective inhibitors of hSUMO1/SIM interactions and also of hSUMO1 conjugation.

Structure-Guided Design of a SUMO-Targeted Phage Display Library

Figure 11A:
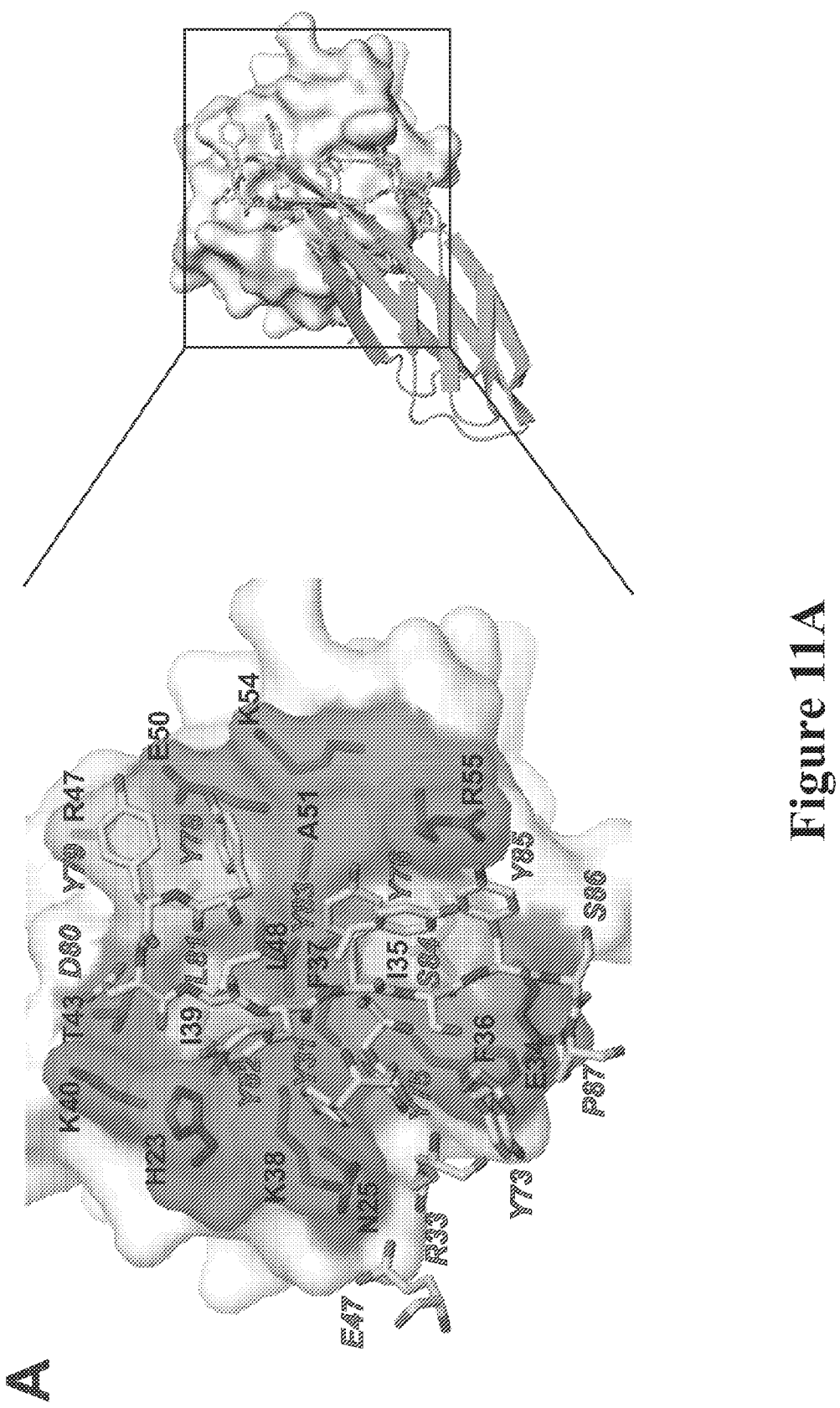
FIGS. 11A-C illustrate the design of a SUMO-targeted cradle library.
Figure 11B:
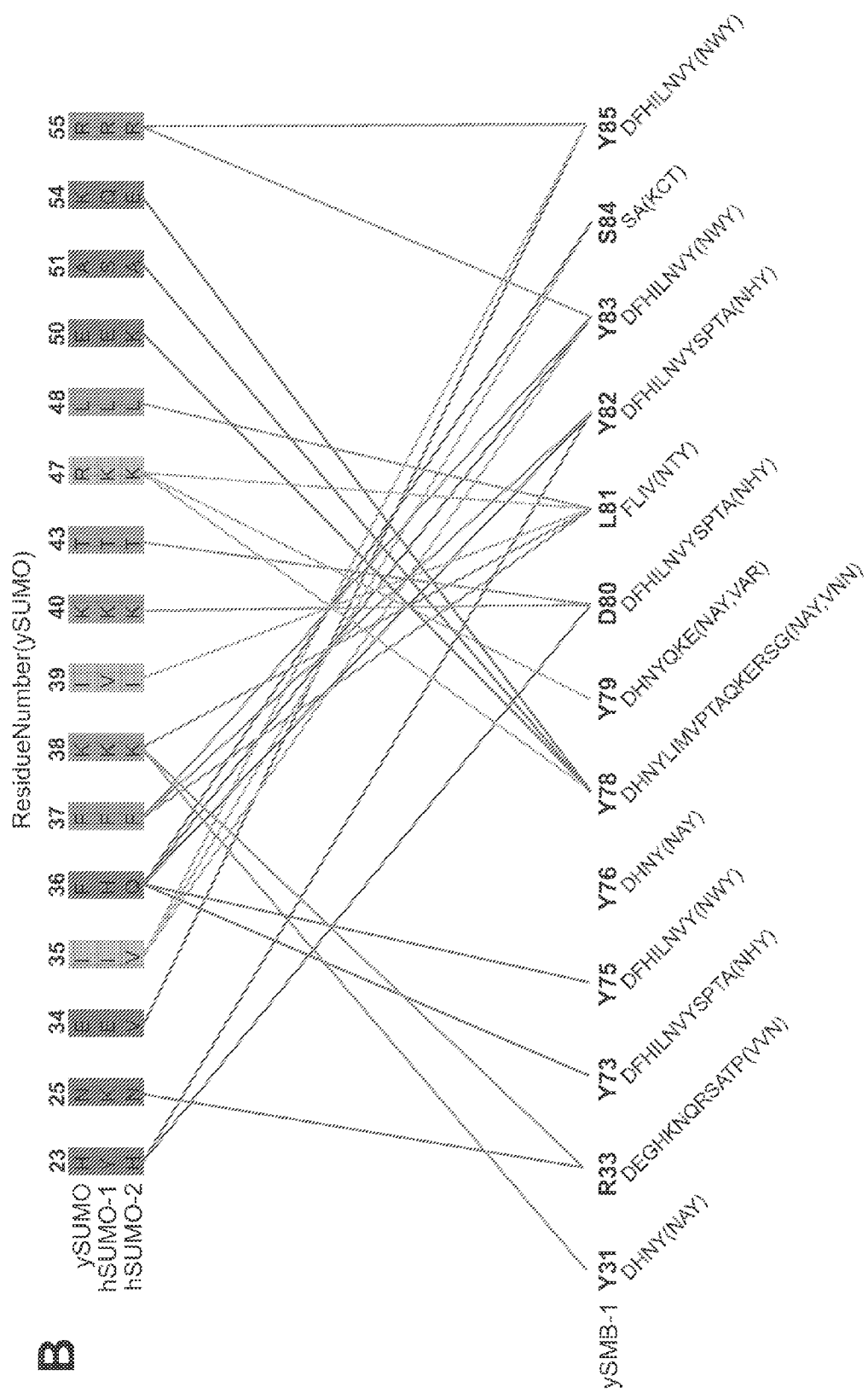
Figure 11C:
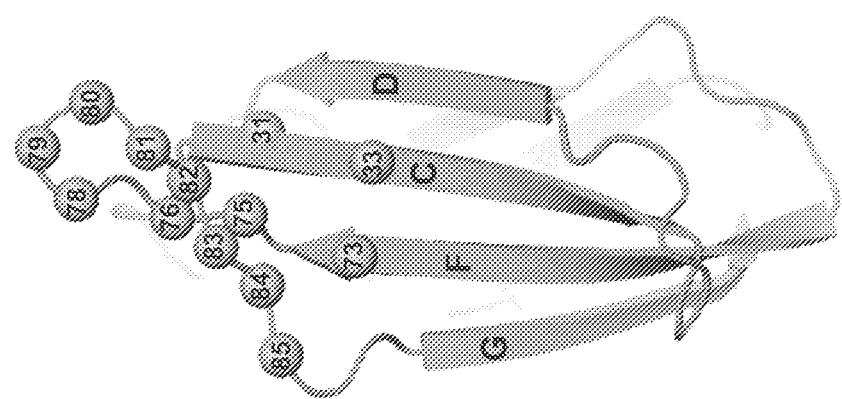

To guide the library design, the residues in the ySMB-1 epitope on ySUMO was compared with the equivalent residues in hSUMO-1 and hSUMO-2. The ySMB-1 paratope residues that contacted or were near each of these epitope positions were then identified (FIGS. 11A, 11B). In the ySMB-1/ySUMO structure, ySMB-1 forms a binding surface using an engineered FG loop and a portion of the undiversified FnIII scaffold. In the SUMO-targeted library both of these surfaces are diversified (FIG. 11C). A SUMO-targeted library was designed by introducing amino acid diversity at each ySMB-1 paratope position that included the wild-type ySMB-1 residue and other amino acid types that might allow effective complementation of any of the three SUMO targets (FIG. 11B). For example, polar amino acids and amino acids with complementary charge were included at positions expected to contact a charged residue in one or more SUMO isoforms, hydrophobic amino acids were included at positions expected to contact hydrophobic surface and small amino acid residues were included at positions that may have steric clashes with larger side chains in some of the SUMO proteins and so on.

All residues of the FG loop were varied except one, S77 that did not contact ySUMO in the ySMB-1/ySUMO crystal structure and did not appear to be capable of direct participation in any similar interface. Y76 was varied to D, H, N and Y, because, although it did not directly contact ySUMO in the ySMB-1 interface, it was suspected that this position may be capable of interacting with the conserved R55 in all SUMOs (FIG. 11A). Leucine 81 of ySMB-1 is buried in a pocket in the ySUMO surface that is conserved across all SUMO isoforms, and an equivalent "anchor" leucine or valine is conserved in all SIM/SUMO complexes for which there are structures. As a result, amino acid diversity was restricted at this position to F, L, I and V. E47 and S86 of the FnIII scaffold made very minimal contact in the ySMB-1 interface and were not varied. Though P87 of the scaffold did make significant contact in the ySMB-1 interface, it was held constant to avoid perturbation of the turn structure it introduces which would likely change the overall positioning of the FG loop. The total number of encoded sequences in the SUMO-targeted library was $1.6 \times 10^{11}$ and the actual size of the phage library produced was $2.0 \times 10^9$.

Selection of Reprogrammed SUMO-Binding Cradle Molecules

Using the SUMO-targeted library described above, four rounds of selection against hSUMO-1, hSUMO-2 and ySUMO were conducted. The enrichment ratio is defined as the number of phage recovered in the presence of target divided by the number recovered in the absence of target and generally reflects the number and affinity level of functional binders in the sorted phage population. After four rounds of selection good enrichment ratios were observed for both ySUMO and hSUMO-1 (~20 and 50 respectively). Thirty-two random clones for each target were assayed for binding activity using phage ELISA and 100% of clones tested positive for binding in the cases of ySUMO and hSUMO-1.

Five random ySUMO clones and 10 random hSUMO-1 clones were expressed as soluble proteins and assessed for binding activity via surface plasmon resonance (SPR). Consistent with phage ELISA results, all clones produced binding signals. For ySUMO $K_d$ estimates ranged from 39 nM to 3.3 µM. Similarly, for hSUMO-1, $K_d$ estimates ranged from 145 nM to 3.6 µM (FIG. 12B). Thus, the SUMO-targeted library succeeded in producing functional cradle molecules to both ySUMO and hSUMO-1 and the library performed similarly against both of these targets.

Sequence Profiles of ySUMO and hSUMO-1 Binding Cradle Molecules

Sequencing revealed that all 10 SPR tested hSUMO-1 cradle molecules contained mutations away from wild-type residues at position 33 in the FnIII scaffold and all but one clone contained mutations at position 31. At position 73, the wild-type tyrosine was recovered ~50% of the time. FG loop sequences in hSUMO-1 monobodies all bore clear resemblance to ySMB-1 suggesting that the ySMB-1 binding mode was maintained in these monobodies as intended.

Figure 12A:
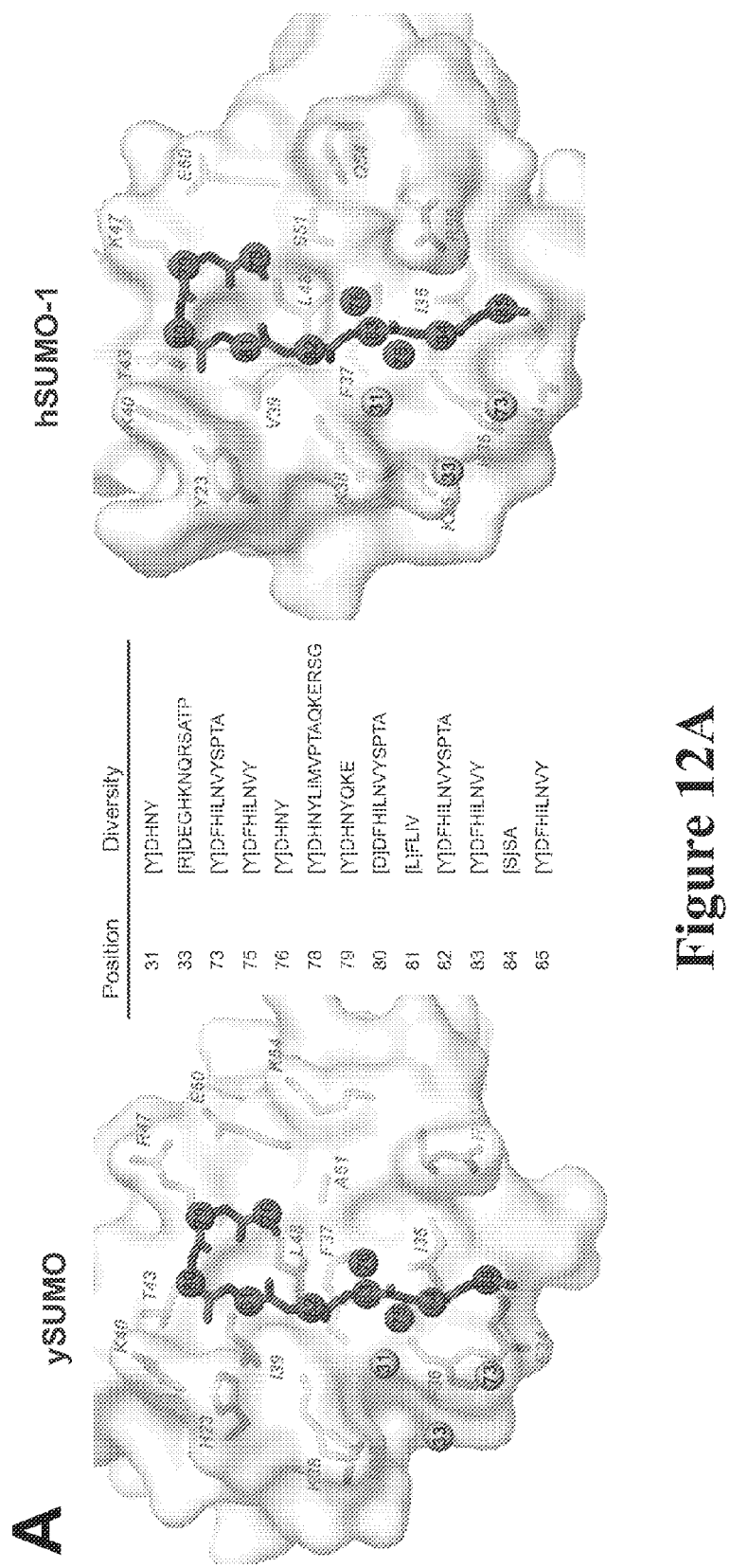
FIGS. 12A-C illustrate the selection and characterization of monobodies from the SUMO-targeted library.
Figure 12B:
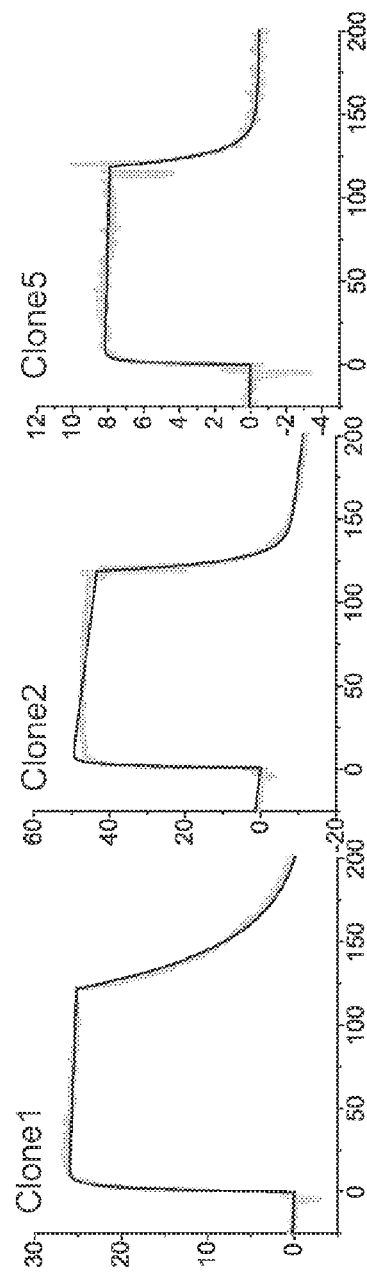
Figure 12B:
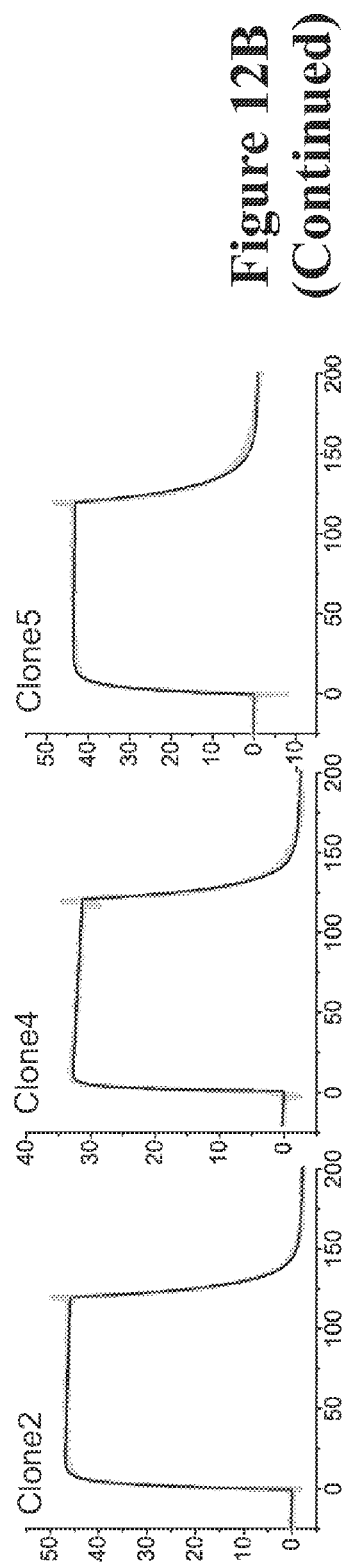

Interestingly, the wild-type scaffold residues were recovered in all SPR tested ySUMO clones except for one which contained a Y to F mutation at position 73 (FIGS. 12A, 12B). FG loop sequences of ySUMO cradle molecules also bore resemblance to ySMB-1 though they were somewhat more divergent than those of hSUMO-1 monobodies.

Figure 12C:
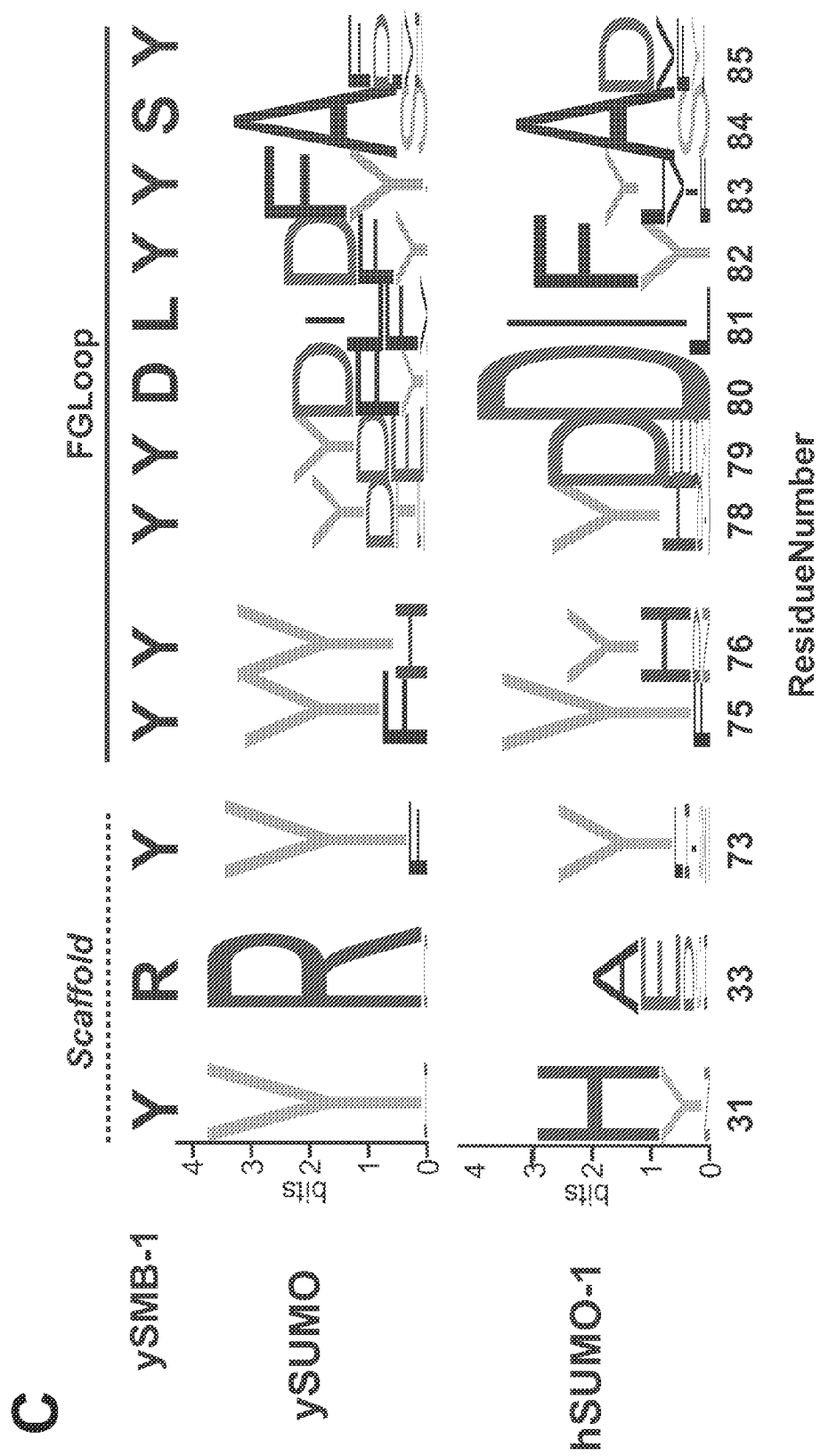

To further examine the sequence properties of ySUMO and hSUMO-1 binding cradle molecules an additional 34 clones for hSUMO-1 and an additional 35 clones for ySUMO were sequenced. All of these clones tested positive for target binding by phage ELISA. Overall sequence profiles for both ySUMO and hSUMO-1 cradle molecules showed close relation to the ySMB-1 sequence and to each other suggesting that, as designed, the cradle molecules from this library maintain a ySMB-1 like binding mode to both targets (FIGS. 12A, 12C). However, a sharp difference was observed between ySUMO and hSUMO-1 binding cradle molecules at beta strand residues. Out of 40 ySUMO binding clones, 39 contained wild-type residues at positions 31 and 33. Out of 44 hSUMO-1 binding clones, none contained the wild-type arginine at position 33 and most did not contain the wild-type tyrosine at position 31. Cradle molecules to both targets show a tendency toward tyrosine at position 73. The strong departure from wild-type beta strand residues in hSUMO-1 cradle molecules suggests that mutations in the FnIII beta strand are necessary to bind hSUMO-1 using a ySMB-1-like binding mode. Thus, modification in the beta strand residues can enhance the selectivity and/or affinity of a cradle molecules or cradle library for a target.

The dominant amino acids at position 33 in hSUMO-1 cradle molecules were alanine and glutamic acid, representing a truncation and inversion of charge compared to the wild-type arginine (FIG. 12C). In a modeled ySMB-1/hSUMO-1 structure, the wild-type arginine residue of the FnIII scaffold exhibits a potential steric and electrostatic clash with K23 of hSUMO-1 (FIG. 13). This clash could be resolved by the observed mutations in the hSUMO-1-binding cradle molecules. An explanation for the strong preference for histidine over the wild-type tyrosine at position 31 in the FnIII beta strand is not clear from the modeled structure.

In contrast to the beta strand residues, the FG loop sequences of cradle molecules recovered against ySUMO and hSUMO-1 exhibit similar amino acid preferences at most positions (75, 76, 78, 80, 81 and 84). This similarity is consistent with FG loop residues contacting predominantly those positions that are conserved between ySUMO and hSUMO-1 (FIG. 11A). Interestingly, at positions 80 and 81, hSUMO-1 cradle molecules show more pronounced preference than ySUMO cradle molecules suggesting stronger selective pressure at these positions in the hSUMO-1 interface. Also, at position 79, cradle molecules to hSUMO-1 have a significant preference for aspartate (FIG. 12C).

Based on the modeled structure of the ySMB-1/hSUMO-1 complex, positions 79 and 80 in hSUMO-1 cradle molecules would be close to two lysine residues of hSUMO-1, one of which is an arginine instead in ySUMO (FIG. 12A). In ySMB-1, Y79 forms a stacking interaction with R47 of ySUMO (FIG. 11A). The lysine residue at position 47 in hSUMO-1 may be better accommodated by aspartate. The basic residues in this region of hSUMO-1 normally interact with a conserved acidic stretch in SIMs and the "DD" motif in hSUMO-1 cradle molecules marks a shift toward a more SIM-like sequence. Interestingly, these two acidic residues are not strongly conserved in ySUMO cradle molecules, suggesting that reliance on these contacts for binding may not be as strong. hSUMO-1 cradle molecules exhibit a significant preference for isoleucine over leucine at the "anchor" position in the SIM interface. In hSUMO-1 the identity of a core residue in the SIM binding surface, I39 (ySUMO) is truncated to Valine (FIG. 12A). This mutation results in a deeper pocket at the "anchor" position (Chupreta, et al., supra. (2005)) which may explain a strong preference for a bulkier side chain in hSUMO-1 cradle molecules.

Despite some differences, overall, FG loop sequence preferences are similar in cradle molecules to ySUMO and hSUMO-1 suggesting that similar FG loop sequences can effectively mediate binding to both targets. In one extreme example of this similarity, one pair of cradle molecules (one to ySUMO and one to hSUMO-1) have FG loop sequences that differ by only one amino acid at position 84. The ySUMO cradle molecule contained alanine at this position while the hSUMO-1 cradle molecule contained serine (FIG. 14A). Since alanine occurs at this position in most hSUMO-1 binders (FIG. 12C), it is highly unlikely that the alanine mutation in the ySUMO cradle molecule would significantly alter binding activity to hSUMO-1. Interestingly, beta strand residues in these two cradle molecules are different suggesting that in this instance beta strand residues alone may dictate which target these cradle molecules bind.

Binding of these two clones to ySUMO and hSUMO-1 was assessed by phage ELISA. The hSUMO-1 cradle molecule bound to both hSUMO-1 and ySUMO. But, as expected, the ySUMO cradle molecule which contained wild-type FnIII scaffold residues bound only to ySUMO (FIG. 14B). These results show that an effectively identical FG loop can be used to recognize both ySUMO and hSUMO-1 but mutations in the FnIII scaffold are necessary to bind hSUMO-1. These results also provide clear evidence supporting the beta strand-based mechanism for specificity in cradle molecules.

Specificity of Selected Cradle Molecules

Figure 14C:
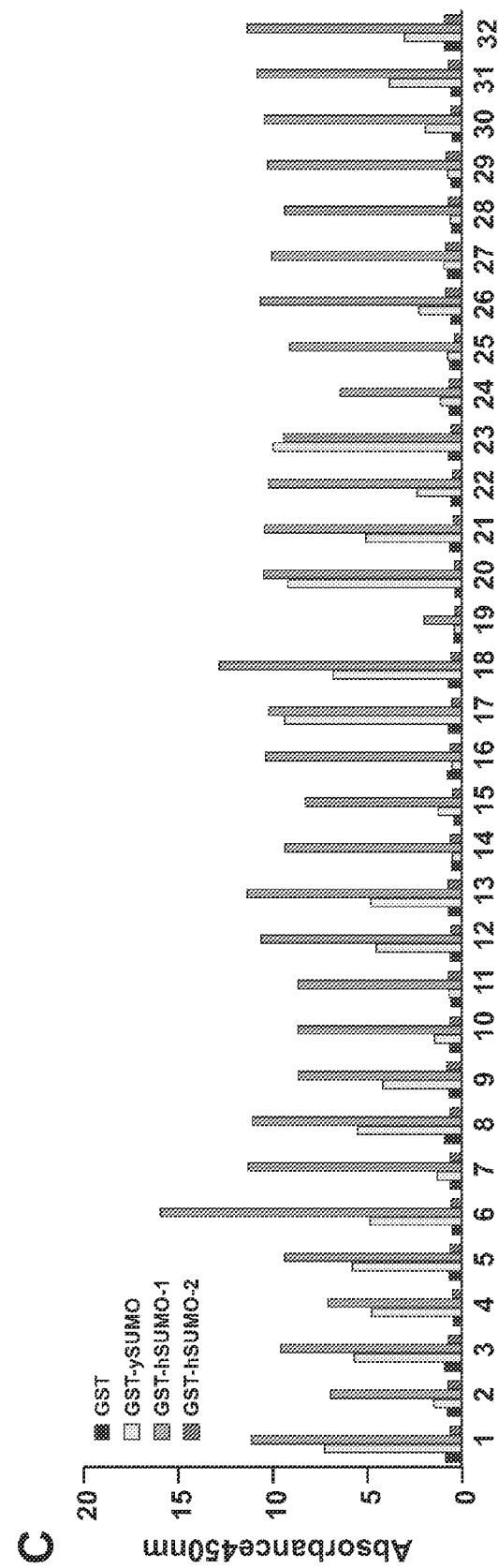
Figure 14D:
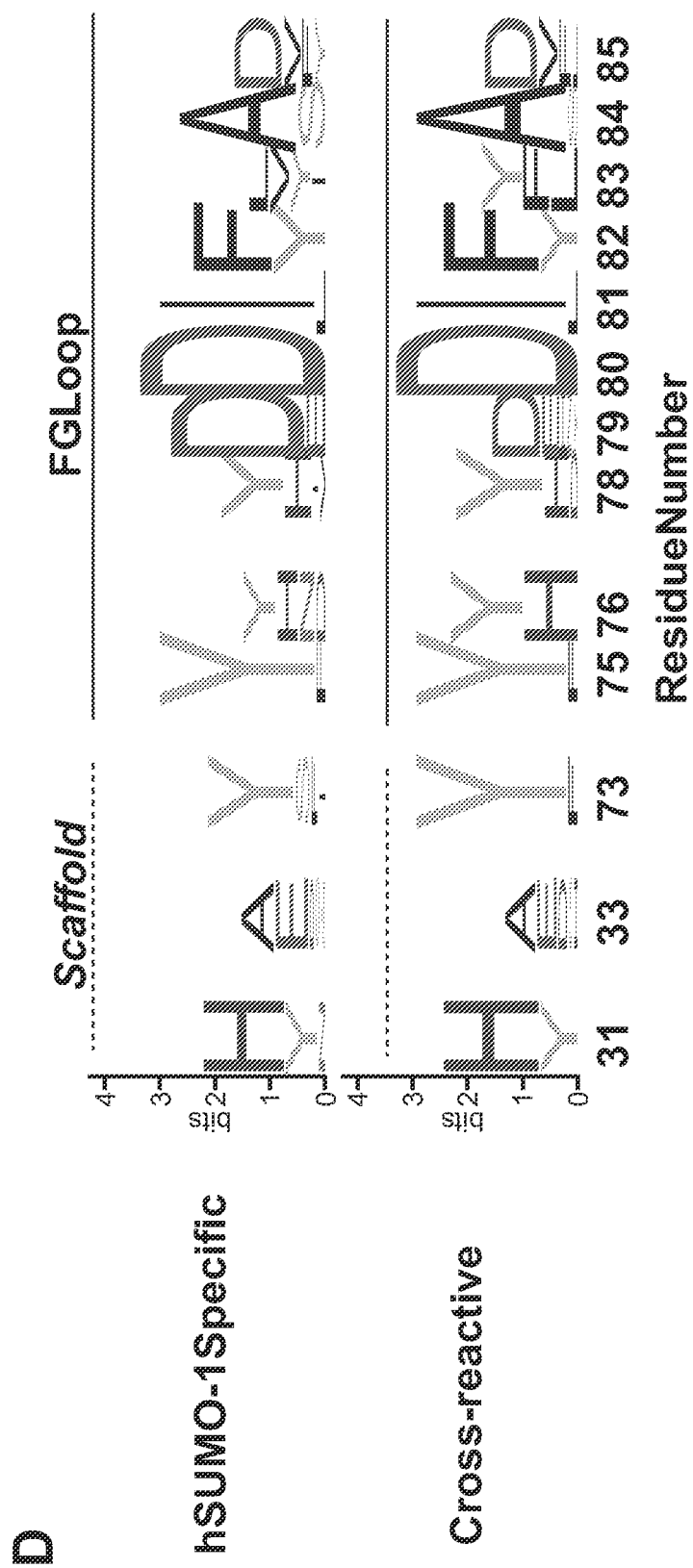

Because the SUMO-targeted library was designed based on the binding mode of a cradle molecule to ySUMO, it is quite possible that ySUMO binding activity may be maintained in the recovered hSUMO-1 cradle molecules. To examine this, the binding of hSUMO-1 cradle molecules to ySUMO using phage ELISA was assessed, cross-reactivity with hSUMO-2 was also tested. No hSUMO-1 cradle molecules showed binding to hSUMO-2, however approximately 50% of hSUMO-1 cradle molecules showed significant binding to ySUMO (FIG. 14C). Interestingly, sequence analysis revealed no obvious differences in amino acid preferences for hSUMO-1 specific and cross-reactive cradle molecules (FIG. 14D). These results suggest different origins of specificity in different cradle molecules and that specific binding to hSUMO-1 likely requires multiple and varying mutations which exploit subtle differences in the amino acid preferences of ySUMO and hSUMO-1 in the binding interface.

An alternative explanation for similar sequences of specific and non-specific cradle molecules is that phage ELISA using GST-fusions of target proteins can produce strong binding signals even for weak interactions. The low resolution of affinity in this assay may produce false positives for cross-reactivity. If many of the hSUMO-1 binding cradle molecules classified as crossreactive are actually specific, this could explain the similarity in sequence profiles between these two groups. Notably, the phage ELISA data are unlikely to produce false negatives for crossreactivity since even weak binding produces a significant signal. Thus, classification of hSUMO-1 cradle molecules as specific is likely to be accurate. However, $K_d$ measurements for these cradle molecules are necessary to thoroughly and quantitatively assess cross-reactivity.

Figure 17:
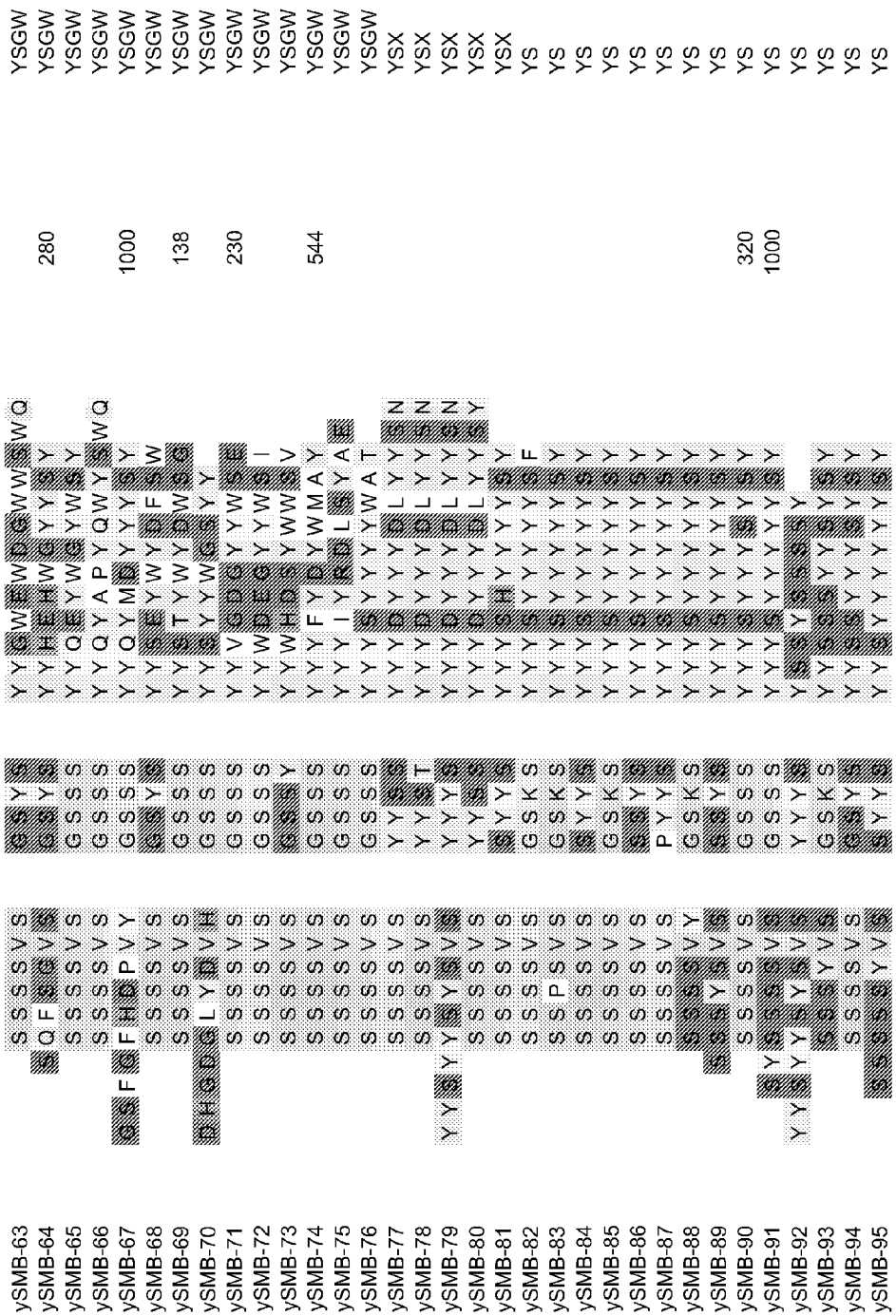
FIG. 17 shows the sequences and affinities of ySUMO-binding monobodies (SEQ ID NOs:321-415) Amino acid sequences of the variable loops of all ySUMO-binding monobodies recovered in our laboratory. If available, $K_d$ values from SPR are given. Monobodies originated from one of three libraries: a binary Tyr/Ser library in which loop lengths and sequences were varied using a combination of 50% Y and 50% S (Koide, A., et al., *Proc. Natl. Acad. Sci. USA* (2007) 104:6632-6637), a "YSX" library which used a combination of 40% Y, 20% S, 10% G, and 5% each of R, L, H, D, N, A (Olsen, et al., *Nature* (2010) 463:906-912), or a "YSGW" library which used a combination of 30% Y, 15% S, 10% G, 5% each of W, F and R, and 2.5% each of all other amino acids except cysteine in the BC and FG loops and 50% Gly, 25% Tyr and 25% Ser at position 52, and a 50/50 mixture of Tyr and Ser at positions 53-55 in the DE loop (Wojcik, et al., supra, 2010).
Figure 18:
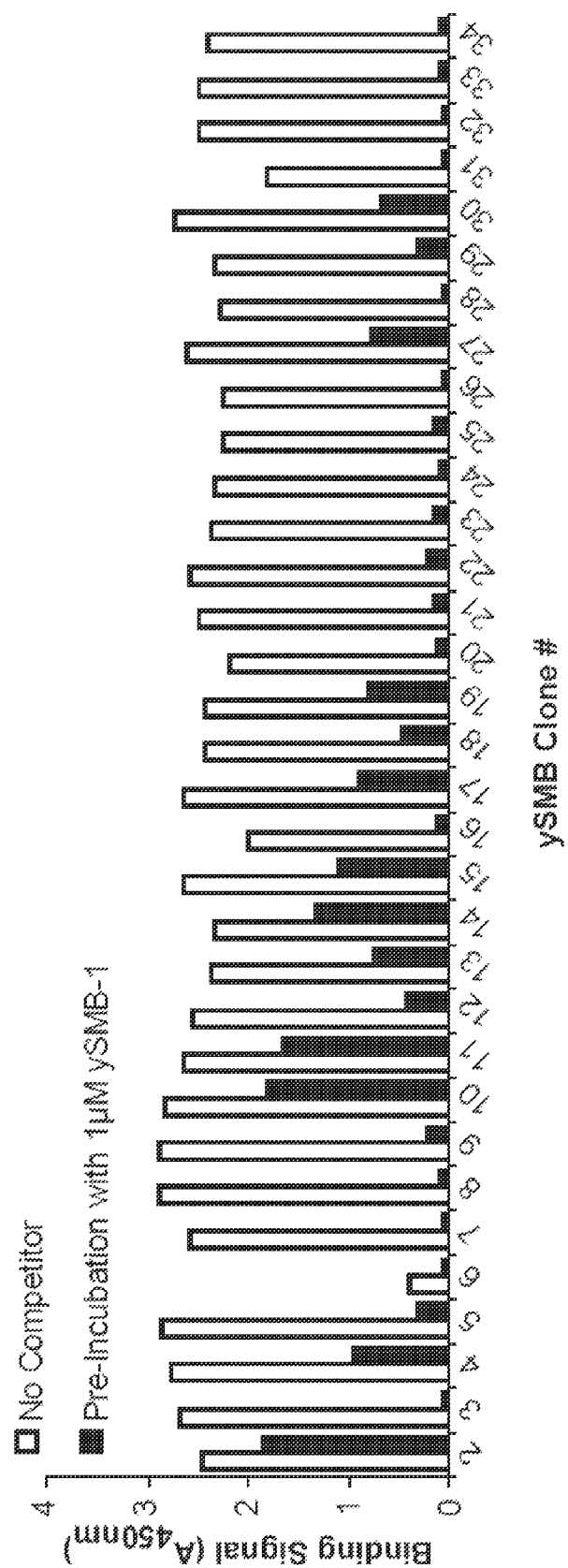
FIG. 18 shows the epitope mapping ELISA of ySUMO-binding monobodies. Binding of 34 phage-displayed ySUMO-binding monobodies measured by ELISA in the presence and absence of 1 μM ySMB-1 competitor. Clone numbers correspond to those of the format ySMB-X in FIG. 28.

Diverse FnIII Domain Variants Recognize the SIM-Binding Site of ySUMO and Discriminate ySUMO from hSUMOs To understand how FnIII domain variants recognize ySUMO, the epitopes of two of the highest affinity ySUMO-binding FnIII domain variants, ySMB-1 and ySMB-2 (FIGS. 16C, D and 17), were mapped using NMR chemical shift perturbation. Despite distinct amino acid sequences in their variable loops (FIG. 16C), both FnIII domain variants bound to similar epitopes centered on the SIM binding site (FIG. 16E). Binding of 33 other ySUMO FnIII domain variants was inhibited by ySMB-1, indicating that they too bound to the SIM-binding site (FIG. 18). Like ySMB-1, most ySUMO-binding FnIII domain variants have polyserine sequences in the BC and DE loops that originate from incomplete mutagenesis of the template vector in library construction, suggesting that these loops do not contribute to binding (FIGS. 16C and 17). Furthermore, many of these FnIII domain variants have an 11-residue FG loop with a centrally located acidic residue and flanking aromatic and hydrophobic residues (FIGS. 16C and 17). Together, these results suggest that essentially all the ySUMO-binding FnIII domain variants recognize the SIM-binding site using a similar mode of interaction.

Figure 19A:
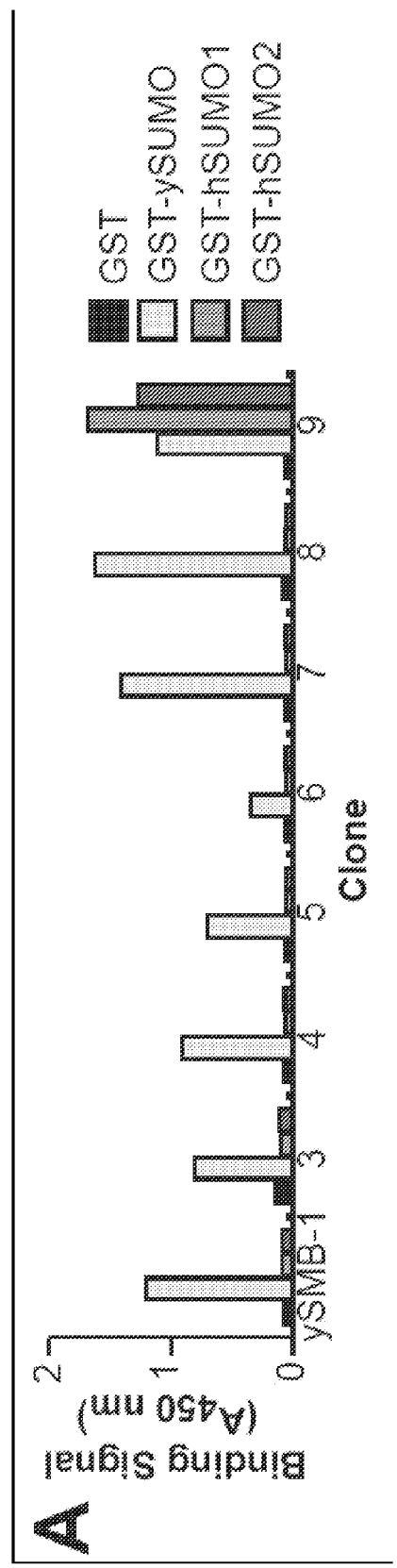
FIGS. 19A-B show the specificity of ySUMO-binding monobodies.
Figure 19B:
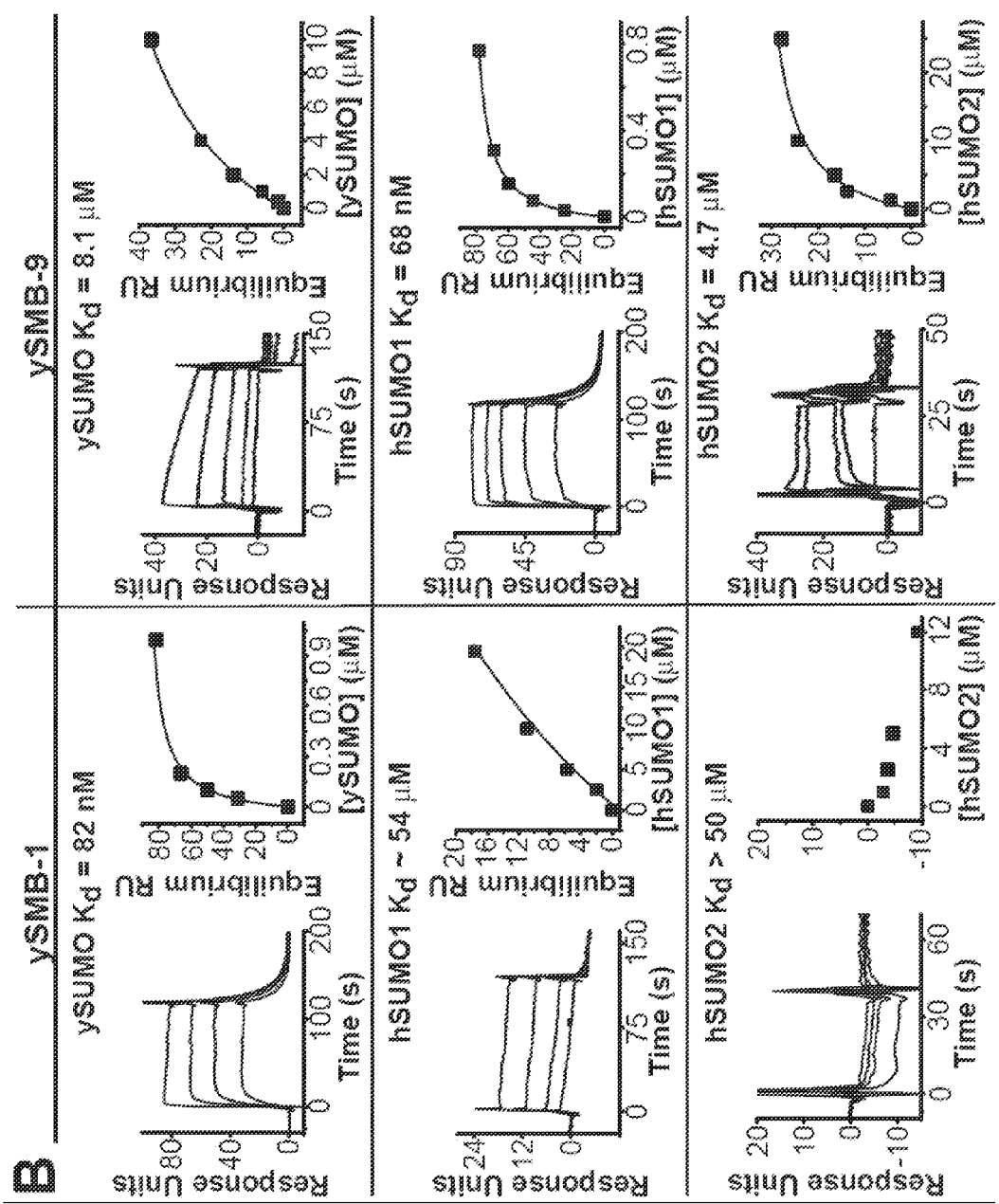

Most ySUMO-binding FnIII domain variants exhibited negligible levels of binding to hSUMO1 or hSUMO2 in phage ELISA assays (FIG. 19A). Such high selectivity was unexpected, because the SIM-binding site is the most highly conserved surface between ySUMO and hSUMO proteins (FIG. 16A). SPR measurements showed that ySMB-1 (selective for ySUMO in ELISA) bound to ySUMO with a 82 nM $K_d$ and to hSUMO1 with a ~54 μM $K_d$ and exhibited no detectable binding to hSUMO2 (FIG. 21B), discriminating ySUMO from hSUMOs by more than 600-fold in affinity. ySMB-9 (non-selective in ELISA) bound to all three SUMO proteins. Although ySMB-9 bound to hSUMO1 with higher affinity (68 nM $K_d$) than either ySUMO or hSUMO2 (FIG. 19B), it discriminated hSUMO2 by only ~70-fold, that is 10-fold less selective than ySMB-1. Notably, ySMB-9 does not have polyserine BC and DE loops like most other ySUMO-binding FnIII domain variants, and it also has a significantly shorter FG loop (FIGS. 16B and 17). Although competition data suggested that ySMB-9 binds to the SIM-binding site (FIG. 17), its distinct sequence features suggest that it employs a different mode of interaction than most ySUMO-binding FnIII domain variants, leading to its lower specificity. Together, these findings demonstrate that the binding mode of most ySUMO-binding FnIII domain variants is particularly effective in discriminating ySUMO and hSUMOs despite binding to the highly conserved SIM-binding site. Thus, it was expected that generating FnIII domain variants that bind to hSUMOs in a mode similar to the ySUMO-binding FnIII domain variants would yield clones with higher isoform selectivity toward hSUMOs.

Crystal Structure of the ySMB-1/ySUMO Complex.

To understand the structural basis for the isoform-selective recognition of the SIM-binding site, the crystal structure of ySMB-1 in complex with ySUMO at 2.4 Å resolution (structural statistics in Table 8) was determined. Consistent with the NMR epitope mapping data, ySMB-1 bound to the SIM binding site (FIGS. 20A and 16E). The FnIII domain variant formed the binding surface using a single variable loop (FG loop) and residues from the invariant FnIII beta strands (FIG. 20A). As inferred from their polyserine sequences, the BC and DE loops of ySMB-1 were not involved in direct contacts with ySUMO.

Residues 78-85 of the ySMB-1 FG loop form a beta hairpin that provides 84% of the FnIII domain variant binding surface with non-loop residues contributing the remainder (FIGS. 20B and 21A). The edge of this hairpin docks along the hydrophobic center of the SIM-binding site forming an intermolecular beta sheet with ySUMO and closely mimicking the interaction mode of SIMs (FIGS. 20B, C) (Kerscher, supra, 2007; Reverter, D., and Lima, C. D., *Nature* (2005) 435:687-692; Song, et al., *J. Biological Chem.* (2005) 280:40122-40129). SIMs generally contain a stretch of hydrophobic residues flanked by a stretch of acidic residues, e.g., DVLIVY (SEQ ID NO:296) in RanBP2 and TLDIVD (SEQ ID NO:294) in PIASx (Song, et al., supra, 2004; Li, et al., supra, 2010; Minty, et al., *J. Biological Chem.* (2000) 275, 36316-36323). In ySMB-1, this motif is mimicked by the FG loop sequence DLYYSY (SEQ ID NO:295) (residues 80-85) (FIGS. 16C, and 20B, C). D80 of the FnIII domain variant aligns with the "top" basic portion of the SIM binding site in a similar orientation as a conserved acidic stretch in SIMs (Kerscher, supra, 2007; Song, et al., supra, 2005) and Tyr residues line the hydrophobic tract where aliphatic residues are usually found in SIMs.

The cystal structure suggests a structural basis for isoform selectivity of ySUMO-binding FnIII domain variants and for difficulties in generating FnIII domain variants to hSUMOs. Only five of the sixteen residues in the ySMB-1 epitope are poorly conserved between ySUMO and hSUMOs (positions 25, 34, 36, 50 and 54) (FIG. 10B, bottom). Three of these residues (N25, E34 and F36) form a cluster at one side of the interface that is highly buried, comprising 23% (147 Å$^2$) of total ySUMO surface buried by the FnIII domain variant (FIGS. 20B and 22A). hSUMO1 contains N25K and F36H. hSUMO2 contains E34V and F36Q. Thus, any FnIII domain variant that forms an interface similar to ySMB-1 is not likely to tightly bind to hSUMO1 or hSUMO2/3. Notably, this cluster is contacted in large part by scaffold residues in ySMB-1 (Y31, R33 and Y73) (FIGS. 20C and 22A). Because these beta strand residues were not varied in the library and are anchored in a conformationally rigid beta sheet, non-conservative substitutions in the cluster in hSUMOs could not have been accommodated, making the generation of ySMB-1-like FnIII domain variants for hSUMOs impossible. These structural restraints would eliminate a potentially very large number of ySMB-1-like FnIII domain variants that have an FG loop otherwise capable of binding to hSUMOs. Thus, these observations strongly suggest that residues within the FnIII beta strands serve as both positive design elements favoring ySUMO binding and negative design elements disfavoring binding to hSUMOs.

TABLE 7

Crystallographic Information And Refinement Statistics For The Structure Of The ySMB-1/ySUMO Complex (PDB ID: 3QHT)

| Data Collection* | |
|---|---|
| Beamline | APS 21-ID-F |
| Space Group | P2$_1$2$_1$2 |
| Cell Parameters | a = 59.64 Å, b = 175.46 Å, c = 52.83 Å |
| | α = β = γ = 90° |
| Wavelength | 0.97872 Å |
| Resolution | 50.00-2.40 Å (2.49-2.40 Å) |
| Unique Reflections | 22,586 |
| R$_{Merge}$† | 0.085 (0.643) |
| Completeness | 100.0% (99.5%) |
| Redundancy | 7.1 (6.6) |
| I/σ(I) | 18.9 (2.2) |
| Refinement Statistics | |
| Resolution Range* | 20.00-2.40 Å (2.46-2.40 Å) |
| Unique Reflections | |
| Working Set | 21,341 |
| Free Set | 1,151 |
| R‡ | 0.223 |
| R$_{Free}$§ | 0.272 |
| Overall Mean B Values | 49.82 Å$^2$ |
| Number of Amino Acid Residues | 338 |
| Number of Water Molecules | 85 |
| Matthews Coefficient | 3.20 (Water Content 61.6%) |
| RMSD From Ideal Values | |

TABLE 7-continued

Crystallographic Information And Refinement Statistics For The Structure Of The ySMB-1/ySUMO Complex (PDB ID: 3QHT)

| | |
|---|---|
| Bonds/Angle | 0.02 Å/1.9° |
| Estimated Overall Coordinate Error Based on Maximum Likelihood | 0.2 Å |
| Estimated Overall Error for B Values Based on Maximum Likelihood | 14.4 Å |
| Ramachandran Plot Statistics | |
| Residues in Most Favored Regions | 87.8% (258) |
| Residues in Additionally Allowed Regions | 9.2% (27) |
| Residues in Generously Allowed Regions | 1.7% (5) |
| Residues in Disallowed Regions | 1.4% (4) |

*Values for highest resolution shell shown in parentheses
[†]$R_{merge} = \Sigma_{HKL}\Sigma_i|I(HKL)_i - <I(hkl)>|/\Sigma_{hkl}\Sigma_i<I(hkl)_i>$ over i observations of a reflection hkl.
[‡]$R = \Sigma||F(obs)| - |F(calc)||/\Sigma|F(obs)|$.
[§]$R_{free}$ is R with 5% of reflections sequestered before refinement.

TABLE 8

Interface Statistics For FnIII Domain Variant ySMB-1 And SIM Peptides

| | ySMB-1 | Average SIM Peptide* |
|---|---|---|
| Buried Surface | 670 Å² | 635 ± 80 Å² |
| SC Value | 0.72 | 0.77 ± 0.02 |
| % Neutral and Non-Polar Atoms in Interface | 64 | 64 ± 12 |

*Values reported are the average for 5 SUMO/SIM complexes (PDB IDS 1WYW, 1Z5S, 2ASQ, 2KQS and 2RPQ). The standard deviations in these values across all five complexes are given. Buried surface and % composition values calculated using the PROTORP server (Reynolds, et al., Bioinformatics (Oxford, England) (2009) 25: 413-414). SC values calculated using the sc program in the CCP4 suite (The CCP4 Suite, Acta Cryst (1994) D50: 760-763; Lawrence and Colman, J. Molec. Biol. (1993) 234: 946-950).

Structure-Guided Design of a SUMO-Targeted Cradle Library.

Based on the theory that the binding mode of ySMB-1 could be used as a template for designing isoform-specific cradle inhibitors of hSUMO/SIM interactions, a library was designed that was aimed at "reprogramming" ySMB-1 for binding to hSUMO proteins. Amino acid diversity at each ySMB-1 paratope position that included the wide-type amino acid and other amino acid types that might allow effective complementation of any of the three SUMO proteins was introduced (FIG. 22A) (SI Methods). Notably, this library included diversity at previously invariant beta strand positions that participated in ySUMO binding. The number of independent clones in the constructed phage-display library was 2.0×10⁹ giving reasonable coverage of the theoretical size of the design (1.6×10¹¹).

Selection of Cradle Molecules from the SUMO-Targeted Cradle Library.

Figure 23:
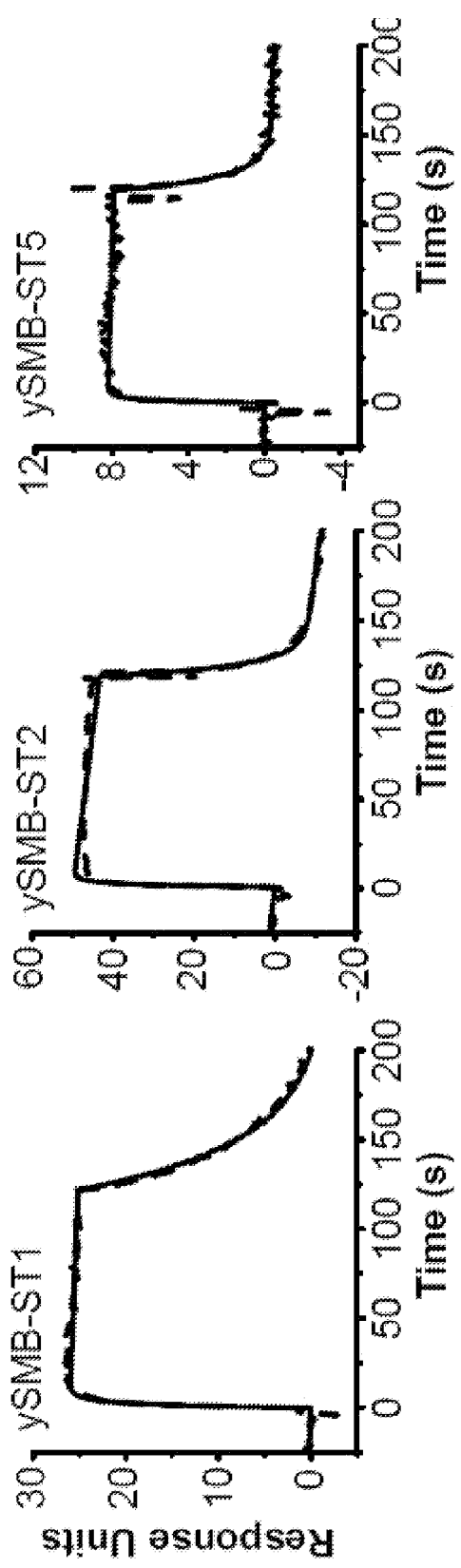
FIG. 23 shows the ySUMO-binding monobodies isolated from the SUMO-targeted library. Shown are the amino acid sequences of monobodies recovered against ySUMO from the SUMO-targeted library with $K_d$ values from SPR (SEQ ID NOs:303, 428-432) and representative SPR traces.

After four rounds of library sorting against hSUMO1, hSUMO2, and ySUMO, 32 randomly chosen clones for each target were assayed for binding activity using phage ELISA. All clones tested positive for binding in the cases of ySUMO and hSUMO1 but none bound to hSUMO2. Five ySUMO-binding and 10 hSUMO1-binding cradle molecules were expressed as soluble proteins and assessed using SPR, all of which produced binding signals (FIG. 22B), consistent with phage ELISA results. For ySUMO, the cradle molecules exhibited $K_d$ values similar to those of FnIII domain variants from the previous naïve library (39 nM to 3.3 μM) (FIGS. 17, 23 and 16C). For hSUMO1, $K_d$ estimates ranged from 118 nM to 3.6 μM (FIG. 22B). Thus, unlike the original library, the SUMO-targeted library readily produced cradle molecules with good affinity to both ySUMO and hSUMO1.

NMR chemical shift perturbation assays validated that a newly generated hSUMO1-binding cradle molecule, hS1MB-4, targeted the SIM-binding site (FIG. 22C). Binding of 15 other hSUMO1-binding cradle molecules was inhibited by hS1MB-4 as tested in ELISA, strongly suggesting that all these hSUMO1-binding cradle molecules targeted the SIM binding site as intended (FIG. 24).

The amino acid sequences of 44 hSUMO1-binding clones and 40 ySUMO-binding clones revealed that cradle molecules to both targets contained FG loop sequences highly similar to ySMB-1 (FIG. 22D), suggesting that a ySMB-1-like binding mode was maintained in these cradle molecules and that ySMB-1-like FG loop sequences are effective for binding to both ySUMO and hSUMO1. In contrast, beta strand residues were sharply different in cradle molecules to the two targets (FIG. 22D). The wild-type ySMB-1 beta strand residues were highly conserved among ySUMO-binding cradle molecules, but in hSUMO1-binding cradle molecules the wild-type amino acid was never recovered at position 33 and only infrequently recovered at position 31. These results strongly support the inventor's position that isoform selectivity in ySUMO-binding cradle molecules arises from contacts made by the non-loop regions of the cradle scaffold. Consistent with this mechanism, in a pair of cradle molecules with nearly identical FG loop sequences, hS1MB-22 and ySMB-ST6, it was observed that ySMB-ST6 containing the wild-type scaffold residues bound only to ySUM, while hS1MB-22 containing altered scaffold residues bound to both ySUMO and hSUMO1 (FIGS. 22A and 22E). Taken together these results illustrate the importance of altering non-loop residues in the FnIII domain in order to facilitate binding to hSUMO1.

Figure 26A:
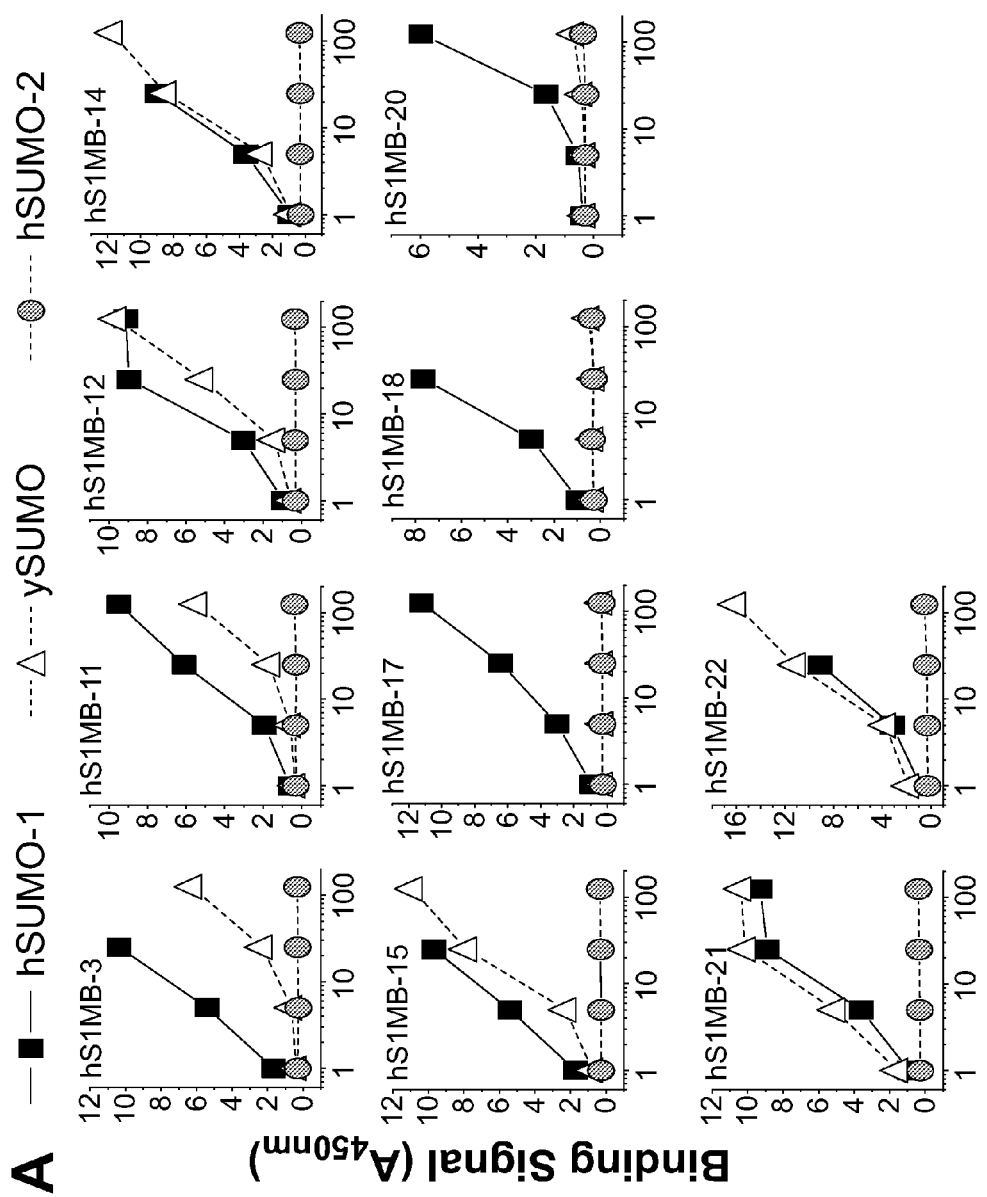

Modeling a ySMB-1 interface with hSUMO1 provides a clear rationale for the observed mutations at non-loop residues in the hSUMO1-binding cradle molecules. N25K and F36H substitutions in hSUMO1 with respect to ySUMO result in a likely electrostatic and steric clash between R33 of the FnIII domain and K25 of hSUMO1 as well as a loss of a close, edge-plane aromatic interaction between Y73 of the FnIII domain and F36 in ySUMO (FIG. 22F). Notably, the most favored amino acid types at position 33 in hSUMO1-binding cradle molecules were Ala and Glu, either of which should resolve a clash with K25, supporting this molecular mechanism for binding specificity.

hSUMO1-Binding Cradle Molecules Are Isoform Specific.

hSUMO1-binding cradle molecules had varied ability to discriminate hSUMO1 and ySUMO as assessed by phage ELISA (FIGS. 25A and 26A). There were several clones (e.g., hS1MB-7, 16 and 23) that showed no detectable binding to ySUMO, representing at least 100-fold weaker binding to ySUMO than to hSUMO1 (FIGS. 25A and 26A). The difference in the affinity of hS1MB-4 to ySUMO and hSUMO1, as measured by SPR, was ~20-fold, validating the phage ELISA experiment that gave a ~10-fold difference (FIGS. 25B and 26B). No distinct features were evident between the sequences of clones that did and did not discriminate ySUMO (FIG. 26B), suggesting that the mechanism of ySUMO/hSUMO1 discrimination is complex, likely involving several positions, and varied across different clones. As expected from the failure of our library to generate cradle molecules to hSUMO2, the hSUMO1-binding cradle molecules showed no measurable binding to hSUMO2 in phage ELISA (FIGS. 25A and 26A), and the affinity of hS1MB-4 to hSUMO2 determined by SPR was very weak ($K_d$=43 µM; FIG. 25B), corresponding to 360 fold discrimination between hSUMO1 and hSUMO2. Taken together, these data demonstrate that the SUMO-targeted cradle library has the capacity of generating diverse cradle molecules that have high affinity and high specificity to hSUMO1.

New Cradle Molecules Inhibit the SUMO1/SIM Interaction and SUMO1 Conjugation.

To investigate the potential utility of hSUMO1-specific cradle molecules as tools for studying SUMO biology, their effects on three major processes: SUMO/SIM interactions, SUMOylation, and deSUMOylation were examined. hS1MB-4 completely inhibited the SIM-mediated interaction between SUMO1-RanGAP and RanBP2 (Johnson, supra, 2004; Mahajan, et al., Cell (1997) 88:97-107; Matunis, et al., J. Cell Biol. (1996) 135:1457-1470) in a dose-dependent manner (FIG. 27A), further validating that these cradle molecules bind to the SIM-binding site as intended and demonstrating their efficacy as inhibitors of SUMO/SIM interactions.

The effects of cradle molecules on SUMOylation were then examined by monitoring the in vitro formation of covalent complexes between SUMOs and the SUMO E1-activating (SAE1/SAE2) and E2-conjugating (Ubc9) enzymes of the SUMO conjugation cascade (FIG. 27B). In this assay, both hSUMO1 and hSUMO3 were present as substrates, enabling the direct assessment of the isoform specificity of the cradle molecules. In the absence of a cradle molecule or in the presence of the ySUMO-specific ySMB-1 cradle molecule, E1 and E2 were conjugated with both hSUMO1 and hSUMO3 (FIG. 27B, lanes 1 and 2). In contrast, in the presence of either hS1MB-4 or hS1MB-5, conjugation of hSUMO1 was inhibited at the E1-dependent step, while hSUMO3 conjugation was enhanced (FIG. 27B, lanes 3-8). Because hSUMO1 and hSUMO3 compete for the same E1-activating enzyme, the enhancement of hSUMO3 conjugation is most likely because hSUMO1 was effectively eliminated as a competitor and thus the E1 enzyme was more available to hSUMO3. The potent inhibition of hSUMO1 conjugation by the cradle molecules was remarkable, because a SIM-based peptide inhibitor did not inhibit this process (Li, et al., supra, 2010).

Figure 28:
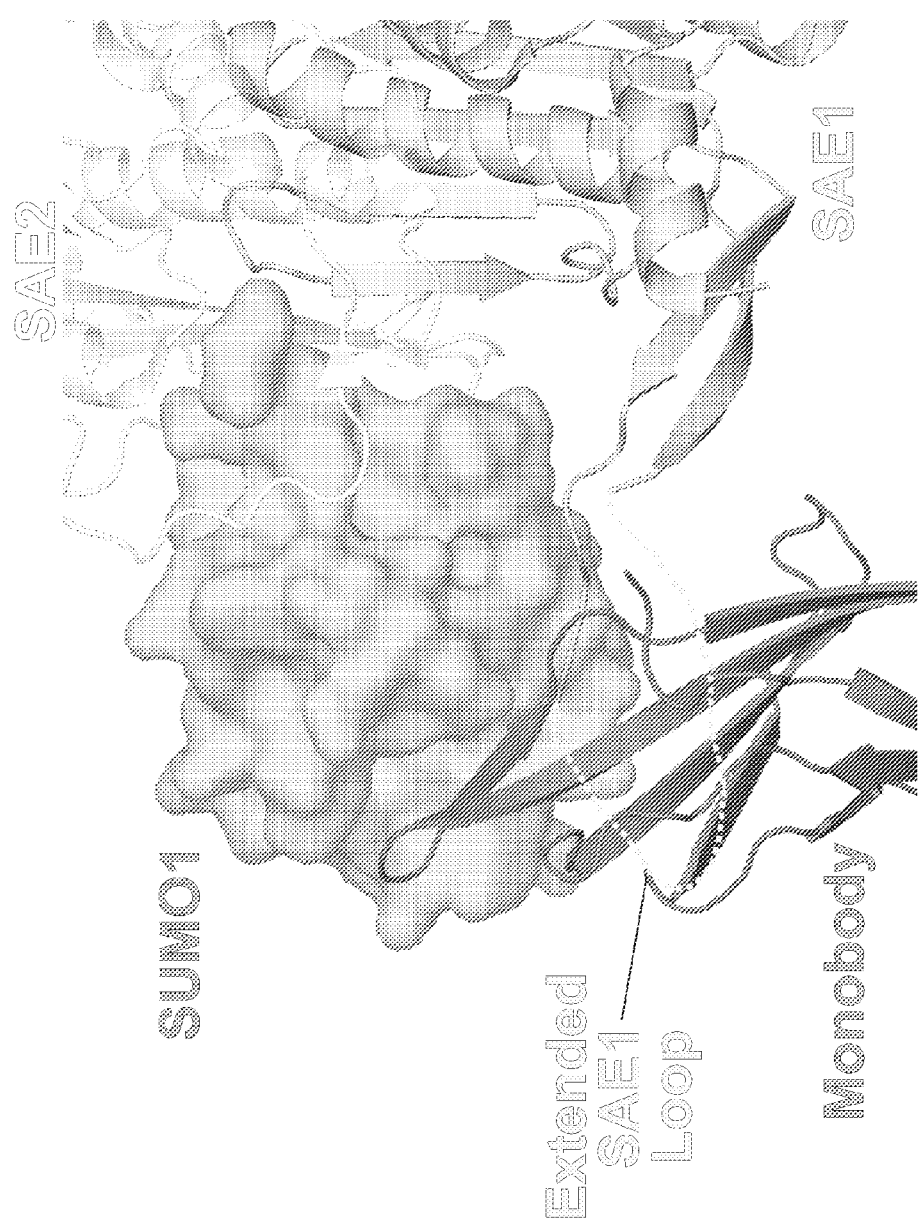
FIG. 28 shows the proposed mechanism for monobody inhibition of hSUMO1 conjugation. A modeled structure of a ySMB-1-like monobody bound to an E1-hSUMO1 complex (PDB ID 3KYD (Olsen, et al., supra, 2010). The trajectory of a long loop of SAE1 that is disordered in the crystal structure is illustrated by a dashed line.

Superposition of the ySMB-1/ySUMO complex structure with the crystal structure of the E1/hSUMO1 complex (Olsen, et al., supra, 2010) suggests that a cradle molecule binding to hSUMO1 in a manner similar to ySMB-1 would not cause steric clashes with the structurally well-defined regions of E1. Rather, the cradle molecule would be positioned in the trajectory of a long disordered loop in the SAE1 subunit (residues ~175-205) (FIG. 28). As a result, it is contemplated that steric clashes between the cradle molecule and the SAE1 loop prevent binding of a cradle molecule/hSUMO1 complex to E1, thus inhibiting SUMOylation at the E1 dependent step. The previously reported inhibitor based on a SIM peptide is much smaller and would not likely cause such a steric hindrance, explaining why it did not inhibit SUMOylation (Li, et al., supra, 2010). hS1MB-4 was significantly more effective than hS1MB-5 in inhibiting SUMOylation (FIG. 27B), although their $K_d$ values for hSUMO1 only differ by ~2-fold and their sizes are essentially identical (FIG. 22B). This difference in inhibition efficacy could be explained by subtle variations in the spatial arrangement of the two cradle molecules when bound to hSUMO1, consistent with the proposed mechanism.

Neither hS1MB-4 nor hS1MB-5 affected deSUMOylation as assayed in vitro by monitoring SENP1 cleavage (Tatham and Hay, Methods Mol. Biol. (2009) 497:253-268) at the hSUMO1 C-terminal di-glycine sequence (FIG. 29). Superposition of the ySMB-1/ySUMO structure with the structure of hSUMO1 bound to SENP1 (Shen, et al., Nat. Struct. Mol. Biol. (2006) 13:1069-1077) suggests no apparent clashes between the cradle molecule and protease and that a cradle molecule binding similarly to ySMB-1 would not inhibit the SENP1/hSUMO1 interaction.

Materials and Methods

Phage Display Library Construction. The SUMO-targeted phage display library was prepared as previously described (Koide, A., et al., supra, 2007) incorporating recent optimizations (Wojcik, et al., supra, 2010). The library was created using a "shaved" template containing polyserine sequences in the BC, DE, and FG loops Amino acid diversity was introduced at FG loop and scaffold positions using degenerate codons as indicated in FIG. 11B and high-efficiency Kunkel mutagenesis.

Phage Display Selection. For use in selection, ySUMO, hSUMO-1 and hSUMO-2 were expressed as a C-terminal fusion to an engineered GST (glutathione-S-transferase) variant devoid of cysteine residues (C to S mutations) except for a single cysteine near the N-terminus. This was accomplished by cloning the genes into a previously reported vector (Wojcik, et al., supra, 2010). In the case of hSUMO-1 a C52A mutant was used and in the case of hSUMO-2 a C47S mutant was used. The GST fusion targets were modified with a redox cleavable biotin moiety using EZ-link Biotin HPDP (Pierce). For phage amplification, XL1-Blue E. Coli cells transformed with the LacI containing plasmid pMCSG21 (termed XL21 cell) were used to maintain transcription silence until IPTG addition. Cradle molecules displaying phage were prepared by growing XL21 cells transfected with the phagemid library in the presence of 0.2 mM IPTG and helper phage K07 (Koide, A., and Koide, S., supra, 2007; Sidhu, S. S., et al., Methods Enzymol. (2000) 328:333-363). In the first round of library selection, 50 nM biotinylated GST-target was mixed with a sufficient amount of streptavidin-conjugated magnetic beads (Streptavidin MagneSphere® Paramagnetic Particles; Promega, Z5481/2) in TBS (50 mM Tris HCl buffer pH 7.5 150 mM NaCl) containing 0.05% Tween 20 (TBST). Beads were blocked with a 5 µM solution of biotin in TBST. To this target solution, $10^{11-12}$ phage suspended in 0.5 ml TBST+0.5% BSA were added, and the solution was mixed and incubated for 15 min. at room temperature. After washing the beads twice with TBST, the beads suspension containing bound phage were added to a fresh XL21 culture. Phages were amplified as described before (Sidhu, et al., supra, 2000). In the second round, phage were preincubated in TBST+0.5% BSA with 500 nM unbiotinylated GST competitor to remove GST binders from the population. Target binding phages were then captured by streptavidin conjugated magnetic beads loaded with 10 nM GST-target. Phages bound to the target protein were eluted from the beads by cleaving the linker within the biotinylation reagent with 100 mM DTT in 50 mM Tris pH=8.0. The phagemids were washed and recovered as described above. After amplification, the third and fourth rounds of selection were performed using 1 nM and 0.1 nM target respectively.

Protein Expression and Purification. GST-fusion proteins were produced by cloning genes into a previously described vector (Wojcik, et al., supra, 2010). All other proteins were expressed by cloning genes into the pHFT2 vector. pHFT2 is a pHFT1 derivative containing a 10-His tag instead of 6-His. Unless otherwise noted, all proteins were expressed by growing BL21(DE3) cells harboring the appropriate pHFT2 vector in ZYP-5052 autoinduction media according to the methods of Studier, et al., *Protein Express. Purif.* (2005) 41:207-234. Proteins were purified using Ni-Sepharose columns (GE Healthcare), or His-Mag magnetic particles (Novagen) in conjunction with a Kingfisher instrument (Thermo).

Surface Plasmon Resonance. Cradle molecules purified as described above were immobilized via His-tag to an NTA surface using a Biacore™ 2000 instrument so that the theoretical maximum response ($R_{max}$) from target binding was 100-200 RU. Target protein at varying concentrations was then flowed over the surface at a flow rate of 30 μL/min and the binding signal recorded. Fitting of kinetic traces was carried out using the BIAevaluation software. For equilibrium experiments, the equilibrium binding response was recorded for multiple target concentrations and fit to a simple 1:1 saturation binding curve.

Phage ELISA. For phage amplification, *E. coli* XL1-Blue cells transformed with the LacI containing plasmid pMCSG21 (Stols, et al., *Protein Express. Purif.* (2007) 53:396-403) (termed "XL21" hereafter) were used. Cradle molecule displaying phage were prepared by growing XL21 cells transfected with phagemid of individual clones in the presence of 0.2 mM IPTG and helper phage K07 (Koide, A., and Koide, S., supra, 2007; Sidhu, et al., supra, 2000). Cultures were then centrifuged and phage containing supernatant used for ELISA assays. All incubations were at room temperature. In all instances except for the phage titration experiment used to test hSUMO1-binding cradle molecule specificity (FIG. 26), wells of a 96-well Microlon© (Greiner) ELISA plate were treated with a 2 μg/mL solution of a GST-fusion of the appropriate target protein, or GST alone in 50 mM Tris Cl buffer containing 150 mM NaCl, pH 7.5 (TBS) and incubated for 1 hour followed by blocking with 0.5% BSA in TBS for 1 hour. In the hSUMO1 binder specificity experiment, 2 μg/mL NeutrAvidin® in TBS was coated, followed by blocking with 0.5% BSA and an addition of a 50 nM solution of his-tagged ySUMO, hSUMO1 or hSUMO2 in complex with the BT-Tris NTA compound, which non-covalently links a biotin moiety to a his-tag (Koide, A., et al., supra, 2007; Reichel, et al., *Analytical Chem.* (2007) 79:8590-8600), and incubated for 30 minutes. In epitope mapping competition experiments, wells coated with GST-target were then incubated with either 1 μM ySMB-1, or 1 μM hS1MB-4 in TBS or TBS only for one hour. In other experiments this step was not performed. After washing the wells with TBS+0.1% Tween 20 (TBST), 50 μl of a 30% solution of phage supernatant in TBS+0.5% BSA was added to the wells and incubated for 30 minutes. In the phage titration experiment, serial 5-fold dilutions of this 30% solution were also tested. In competition experiments, 1 μM ySMB-1, or 1 μM hS1MB-4 was included in the binding mixture. Bound phages were then detected using an anti-M13 antibody conjugated to horseradish peroxidase (GE Healthcare) in conjunction with the Ultra TMBELISA colorimetric substrate (Pierce). Reactions were quenched after 5 minutes by addition of $H_2SO_4$ and phage binding quantified by absorbance measured at 450 nm.

NMR Epitope Mapping. NMR epitope mapping was performed by comparing chemical shifts in the $^1H$-$^{15}N$—HSQC spectra of labeled ySUMO and hSUMO1 in the presence and absence of excess unlabeled cradle molecule. Uniformly $^{15}N$-labeled ySUMO and hSUMO1 were produced by culturing BL21(DE3) cells harboring a pHFT2 derivative containing the ySUMO or hSUMO1 gene in M9 media with $^{15}NH_4Cl$ as the sole nitrogen source. pHFT2 is a pHFT1 (Huang, et al., supra, 2006) derivative containing a 10-His tag instead of 6-His. A hSUMO1 mutant was used containing the C52A mutation. Protein expression was induced by the addition of 1 mM IPTG. Proteins were purified using a Ni-Sepharose column (GE Healthcare). After cleaving the N-terminal tag sequence with TEV protease, the proteins were concentrated and dissolved in 50 mM phosphate, 100 mM NaCl, pH=6.5. $^1H$, $^{15}N$—HSQC spectra were collected on a Varian (Palo Alto, Calif.) INOVA 600 NMR spectrometer using pulse sequences provided by the manufacturer. All ySUMO spectra were recorded at 20° C. All hSUMO1 spectra were recorded at 17° C. ySUMO resonances were assigned using previously reported assignments by Sheng, et al. (Sheng and Liao, *Protein Sci.* (2002) 11:1482-1491). hSUMO1 resonances were assigned using previously reported assignments by Macauley, et al. *J. Biological Chem.* (2004) 279:49131-49137. Spectra were collected for the free [$^{15}N$]-ySUMO (380 μM), free [$^{15}N$]-hSUMO1 (228 μM), [$^{15}N$]-ySUMO (100 μM) in complex with unlabeled cradle molecule (200 μM) and [$^{15}N$]-hSUMO1 (242 μM) in complex with unlabeled cradle molecule (484 μM) in the above buffer. Residues affected by cradle molecule binding were identified by comparing the free and cradle molecule bound spectra. Amide cross-peaks were classified into five categories: strongly affected (a shift of greater than two peak widths), moderately affected (a shift of between one and two peak widths), weakly affected (a shift of approximately 1 peak width), unaffected (a shift of less than one peak width), and excluded (resonances that could not be unambiguously assigned) (Farmer, et al., *Nature Struct. Biol.* (1996) 3:995-997; Huang, et al., *J. Molec. Biol.* (1998) 281:61-67).

X-ray Crystallography. ySMB-1 and ySUMO proteins were expressed and purified as described above. After removal of the tag sequence with TEV protease, the two proteins were mixed in a 1:1 molar ratio, concentrated to a total protein concentration of 4.9 mg/mL and dissolved in 10 mM Tris, 50 mM NaCl, pH=8.0. The formation and monodispersity of the complex was asserted by gel filtration. The ySMB-1/ySUMO complex was crystallized in 14% PEG 8000, 16% glycerol at 19° C. using the hanging drop vapor diffusion method. Crystals were frozen in a mixture of 80% mother liquor and 20% glycerol as a cryoprotectant. Diffraction data were collected at APS beamline 21-ID-F (Advanced Photon Source, Argonne National Laboratory). Crystal and data collection information are reported in Table 4. X-ray diffraction data were processed and scaled with HKL2000 (Otwinowski, Z., and Minor, W., *Methods in Enz.* (1997) 276:307-326). The structure was determined by molecular replacement using sequential search with two different models with the program MOLREP in CCP4 ((1994) The CCP4 suite). The ySUMO structure (residues 1013-1098 of chain C PDB ID code 2EKE) was used as a search model, along with the FnIII structure with the variable loop regions deleted (PDB ID code 1FNA) (Dickinson, C., D., et al., *J. Mol. Biol.* (1994) 236:1079-1092; Duda, et al., *J. Molec. Biol.* (2007) 369:619-630). Rigid body refinement was carried out with REFMAC5 (Murshudov, G. N., et al., *Acta Crystallogr D Biol Crystallogr* (1997) 53:240-255). Model building and the search for water molecules was carried out using the Coot program (Emsley, P., and Cowtan, K., *Acta Crystallogr D Biol Crystallogr* (2004) 60:2126-2132). Simulated annealing was performed in CNS1.1

(Brunger, A. T., et al., *Acta Crystallogr D Biol Crystallogr* (1998) 54:905-921). The TLS (Translation/Libration/Screw) and bulk solvent parameters, restrained temperature factor and final positional refinement were completed with REF-MAC5 (Murshudov, et al., supra, 1997). Molecular graphics were generated using PyMOL (located on the World Wide Web at pymol.org).

Design of the SUMO-targeted Cradle Library. Choice of positions and diversity in the SUMO-targeted library carried the following rationale. All residues of the FG loop were varied except one, S77 that did not contact ySUMO in the ySMB-1/ySUMO crystal structure and did not appear to be capable of direct participation in any similar interface. The inventors varied Y76 to D, H, N and Y, because, although it did not directly contact ySUMO in the ySMB-1 interface, it was suspected that this position may be capable of interacting with the conserved R55 in all SUMOs (FIG. 22A). Leucine 81 of ySMB-1 is buried in a pocket in the ySUMO surface that is conserved across all SUMO isoforms, and an equivalent "anchor" leucine or valine is conserved in all SIM/SUMO complexes for which there are structures. As a result, the amino acid diversity at this position was restricted to F, L, I and V. E47 and S86 made very minimal contact in the ySMB-1 interface and were not varied. Though P87 of the FG loop did make significant contact in the ySMB-1 interface, it was held constant to avoid perturbation of the turn structure it introduces which would likely change the overall positioning of the FG loop.

Cradle Molecule Effects on SUMO/SIM Interactions. Wells of a Microlon© (Greiner) ELISA plate were coated with 2 μg/mL GST-RanBP2 for 1 hour at room temperature. This IR1-M-IR2 construct of RanBP2 has been described previously (Tatham, et al., *Nat. Struct. Mol. Biol.* (2005) 12:67-74). A complex was pre-formed between his-tagged SUMOylated RanGAP (modified with SUMO1) and the BT-Tris-NTA reagent which non-covalently attaches a biotin moiety to a His-tag (Koide, A., et al., *Protein Eng. Des. Sel.* (2009) 22:685-690; Reichel, et al., supra, 2007). This complex was incubated with varying concentrations of hS1MB-4 for 1 hour and then the mixture was added to the ELISA plate and incubated for 30 min. Bound SUMO-RanGAP was then detected using a streptavidin-horseradish peroxidase conjugate in conjunction with the Ultra TMB ELISA reagent (Pierce). The reaction was quenched with 2M $H_2SO_4$, and the absorbance at 450 nm was measured.

Cradle Molecule Effects on SUMOylation. A mixture of hSUMO1 and $His_6$-SUMO3 (24 μM ea.) was combined with either cradle molecule hS1MB-4 or hS1MB-5 at varying concentrations and incubated for 1 hour. A mixture of E1 (SAE1/2, 1.7 μM), E2 (Ubc9, 13.7 μM), and ATP (5.5 mM) was then added and the SUMOylation reaction allowed to proceed for 10 min. at 37° C. The reaction was then quenched by an addition of SDS-PAGE loading dye and reaction mixture was analyzed by SDS-PAGE.

Cradle Molecule Effects on DeSUMOylation. YFP-hSUMO1-ECFP fusion protein (63 μg/mL) was mixed with varying concentrations of cradle molecule hS1MB-4, hS1MB-5 or ySMB-1 as a control and incubated at room temperature for 30 mins. SENP1 was then added at a final concentration of 32 nM and the mixture incubated for 15 min at 37° C. The reaction was stopped by putting the reaction containers on ice, adding SDS-PAGE sample buffer and then boiling for 5 mins. The reaction mixture was then analyzed by SDS-PAGE.

EXAMPLE 9

Cradle Molecules Constructed Using Alternative Surfaces of the FnIII Beta Sheets Library Design The FnIII domain has two beta sheets (FIG. 30A), one constituted by beta strands A, B and E, and the other by beta strands C, D, F and G. The crystal structure of a cradle molecule in complex with its target, the Abl SH2 domain, revealed extensive interactions made by residues in the CDFG beta sheet region of the FnIII domain that were not diversified in our library (FIG. 30C) (Wojcik, et al., supra, 2010). Alanine scanning mutagenesis experiments demonstrated the energetic importance of these residues in binding (Wojcik, et al., supra, 2010). Similar use of these beta sheet surfaces was observed in a cradle molecule that bound to yeast small ubiquitin-like modifier (ySUMO) (Gilbreth, R. N., et al., *Proc Natl Acad Sci USA* (2011) 108:7751-7756). These observations suggest that it may be possible to construct a target-binding surface that is distinct from the conventional design relied upon in antibody-mimic engineering, i.e., interactions dominated by loops equivalent to the antibody complementarity-determining regions (CDRs). The surface of the CDFG beta sheet is slightly concave, suggesting it is suitable for producing recognition surface complementary to convex surfaces found in most globular macromolecules.

To explore the efficacy of such alternative FnIII library designs and how their performance compares to conventional loop-focused FnIII engineering strategies, two distinct cradle molecule libraries were constructed. One library, which is called the cradle library, utilizes residues in beta strands C (residues 31 and 33) and D (residues 47 and 49) as well as residues in the FG and CD loops (FIGS. 30E and 31A) to present a concave binding surface as described above. The other library, which is called the loop-only library, constitutes the conventional FnIII library design utilizing positions in the BC, DE and FG loops with no residues diversified in the beta sheet regions (FIGS. 30D and 31B).

In both libraries, highly biased amino acid diversity and various loop lengths for the FG loop were used, as described previously (Wojcik, et al., supra, 2010). In the loop-only library, this diversity was also used for positions in the BC loop that was also varied in length. The DE loop in the loop-only library was fixed in length and diversified only to Tyr or Ser with Gly also included at position 52 (FIG. 31B). In the cradle library, codons that exclude Pro and Gly, amino acids that are likely detrimental to the structural integrity of the FnIII domain, were used for positions in beta strand C, an internal beta strand. For beta strand D, an edge strand, a small subset of amino acids, Ala, Glu, Lys and Thr, was used. Ala and Thr were intended so as to avoid large side chains that might prevent target binding, and Glu and Lys were included as negative design elements to prevent aggregation mediated by the formation of an intermolecular beta sheet (Richardson, J. S., and Richardson, D. C., *Proc Natl Acad Sci USA* (2002) 99:2754-2759). Tyr73 was not diversified with a hope that this Tyr would always contribute to target interaction, as Tyr is highly suitable for making a protein-interaction interface (Koide, S., and Sidhu, S. S., *ACS Chem Biol* (2009) 4:325-334). Both libraries were constructed in the phage display format with estimated numbers of independent sequences of $2.0 \times 10^{10}$ and $1.5 \times 10^{10}$, respectively.

High-Affinity FNIII Cradle Molecules from the Cradle Librarie

The performance of the new cradle library with the conventional "loop only" library (Wojcik, et al., supra, 2010) were compared using three targets, Abl SH2, human small ubiquitin-like modifier 1 (hSUMO1), and green fluorescent protein (GFP). The molecular platform for these libraries was identical, except for the locations of the diversified residues. These libraries contained similar numbers of independent sequences. For each combination of target and library, the following steps to generate cradle molecules were performed. First, cradle molecules from the phage display libraries were enriched. The N-terminal segment and C-terminal segment were then "shuffled" among cradle molecule clones in the enriched population for a given target, with a junction in the E strand to create a second-generation library in the yeast surface display format (Koide, et al., supra, 2007). The gene shuffling step was incorporated to increase the sequence space beyond that sampled in the starting, phage-display library. Finally, the yeast surface display library was sorted using flow cytometry.

Figure 33:
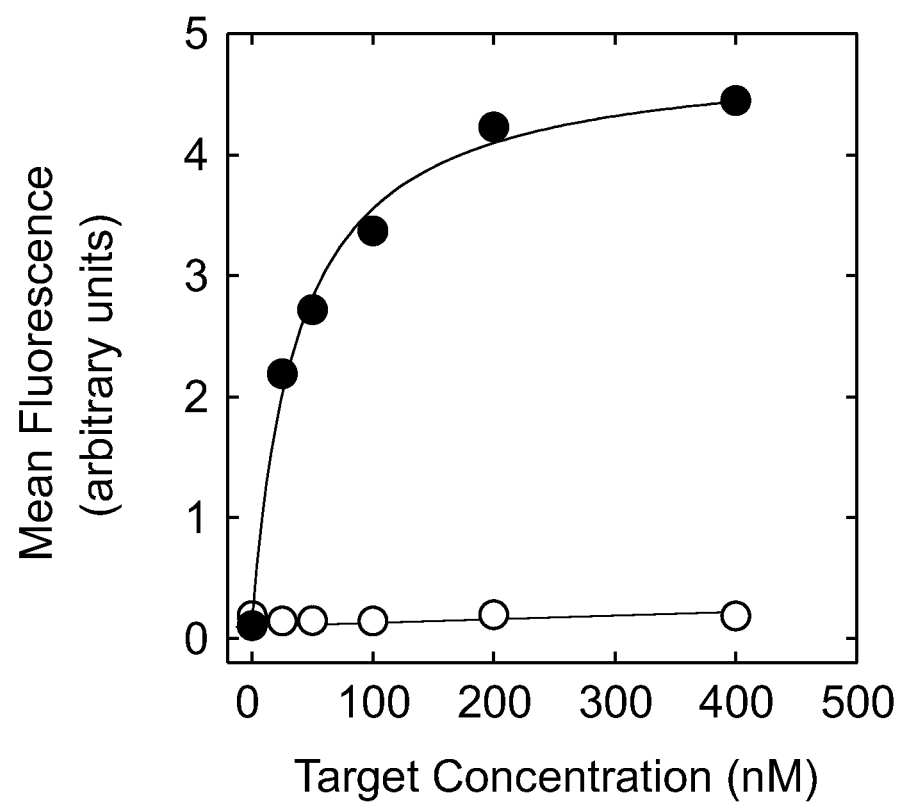
FIG. 33 shows mutations of residues in the C-strand abolished target binding. Residues 30, 31 and 33 of monobody GS5 (see FIG. 31A for its sequence) were mutated back to their respective wild-type amino acids. The mean fluorescence intensities of yeast cells displaying the GS5 monobody (filled circles) and the mutant (open circles) are plotted as a function of the concentration of the target, GFP.

FnIII domain variants to all the targets from both cradle and "loop only" libraries were generated. Many FnIII domain variants exhibited high affinity with $K_d$ values in the low nM range as measured in the yeast display format (FIGS. 31A-31C). These $K_d$ values were in good agreement with those determined using purified FnIII domain variants and surface plasmon resonance (FIG. 31D). As in previously generated FnIII domain variants, residues in the FG loop were mutated in all the FnIII domain variants selected from both libraries, suggesting the central importance of the FG loop residues in target recognition of FnIII domain variants. Some of the cradle molecules originating from the cradle libraries contained the wild-type CD loop and the D strand, suggesting either that these residues are not involved in target recognition in these cradle molecules or that substitutions of the wild-type residues did not confer affinity improvement. In contrast, the diversified positions in the C strand were mutated in all of the selected cradle molecules, and cradle molecules to different targets exhibited different amino acid sequences (FIG. 31A). When the C strand of a GFP-binding cradle molecule, GS#2, was changed back to the wild type sequence, the mutant completely lost binding to GFP (FIG. 33). Together, these results support the importance of the C strand positions in target binding of cradle molecules derived from the cradle libraries.

It appears that the two libraries performed differently against different targets. For GFP, the cradle library clones had higher affinity than the counterparts from the loop-only library, but for hSUMO1 the trend was opposite. High-affinity FnIII domain variants were obtained from both libraries for Abl SH2. These results suggest that, whereas both libraries are capable of generating FnIII domain variants to these diverse targets, the use of two distinct libraries increases the likelihood of generating highly functional FnIII domain variants to a broader range of targets.

This work produced several loop-only FnIII domain variants with good affinity for hSUMO1, whereas in a previous work a FnIII domain variants termed ySMB-9 was the only hSUMO1 binder that was recovered with a sub-μM $K_d$ (Gilbreth, et al., supra, 2011). One notable difference between the two studies is the inclusion of a loop-shuffling step in the present study. As shown below, the ySMB-9/hSUMO1 crystal structure strongly suggests that residues from all three loops are important for binding in ySMB-9 and the same is likely true for the highly homologous cradle molecules isolated from the present work. Thus, consistent with previous studies (Hackel, et al., supra, 2008), loop shuffling expands the sequence space that can be searched and thus increases the probability of generating high-affinity FnIII domain variants.

Crystal Structures of Cradle Molecule-Target Complexes Confirm Library Designs

The crystal structure of a cradle molecule isolated from the cradle library termed SH13 in complex with its target, the SH2 domain of Abl kinase, was determined at a resolution of 1.83 Å (FIGS. 31A and 32A; Table 9). SH13 was among the initial cradle molecule clones generated directly from the phage-display libraries without loop shuffling and yeast display screening. Accordingly, it has low affinity with a $K_d$ value of ~4 μM. The SH13 cradle molecule maintained the FnIII scaffold structure as evidenced by its minimal deviation from a previously determined cradle molecule structure ($C^\alpha$ RMSD<0.7 Å, excluding mutated residues) (Wojcik, et al., supra, 2010; Gilbreth, et al., supra, 2008). The overall structure of the Abl SH2 domain is likewise in good agreement with a previously published crystal structure of the Abl SH2 domain in complex with another cradle molecule ($C^\alpha$ RMSD <0.5 Å) (Wojcik, et al., supra, 2010). The phospho-Tyr binding pocket of the SH2 domain contained electron density consistent with a sulfate ion, which was present in the crystallization solution.

TABLE 9

Data collection and refinement statistics (molecular replacement)

| | SH13/Abl1 SH2 complex (3NKI) | ySMB9/hSUMO1 complex (3RZW) |
|---|---|---|
| Data collection* | | |
| Space group | P2₁2₁2 | C222₁ |
| Cell dimensions | | |
| a, b, c (Å) | 65.55, 49.18, 60.95 | 93.35, 97.83, 96.58 |
| α, β, γ (°) | 90, 90, 90 | 90, 90, 90 |
| Beamline | APS 24 ID-E | APS 21 ID-F |
| Wavelength (Å) | 0.97917 | 0.97872 |
| Resolution (Å) | 1.83 (1.90-1.83) | 2.15 (2.19-2.15) |
| $R_{sym}$ or $R_{merge}$ | 11.5 (52.9) | 8.2 (52.2) |
| I/σI | 24.4 (2.6) | 17.9 (2.1) |
| Completeness (%) | 87.4 (83.0) | 98.2 (96.6) |
| Redundancy | 4.0 (3.1) | 6.7 (6.0) |
| Refinement | | |
| Resolution (Å) | 1.83 | 2.15 |
| No. reflections | 15737 | 22,699 |
| $R_{work}^\ddagger/R_{free}^\S$ | 0.188/0.237 | 0.186/0.237 |
| No. atoms | 1753 | 2,807 |
| Protein | 1614 | 2,657 |
| Ligand/ion | 5 | 12 |
| Water | 134 | 138 |
| B-factors | | |
| Protein | 25.6 | 29.51 |
| Ligand/ion | 37.4 | 64.29 |
| Water | 33.3 | 32.24 |
| R.m.s. deviations | | |
| Bond lengths (Å) | 0.012 | 0.019 |
| Bond angles (°) | 1.337 | 1.828 |
| Ramachandran values | 98.5% favored | 97.2% favored |
| | 1.5% allowed | 2.2% allowed |
| | 0% outliers | 0.6% outliers |

APS, Advanced Photon Source.
*Values for highest resolution shell shown in parentheses
†$R_{merge} = \Sigma_{hkl}\Sigma_i |I(hkl)_i - <I(hkl)>|/\Sigma_{hkl}\Sigma_i <I(hkl)_i>$ over i observations of a reflection hkl.
‡$R = \Sigma ||F(obs)| - |F(calc)||/\Sigma |F(obs)|$.
§$R_{free}$ is R with 5% of reflections sequestered before refinement.

In accordance with the design of the cradle library, the SH13 cradle molecule binds to the target chiefly using the cradle surfaces (FIG. 32A). The mode of interaction observed in the crystal structure is consistent with the epitope mapped using NMR chemical shift perturbation (FIG. 32B). The concave surface presented by the cradle molecule effectively complements a convex surface of the Abl SH2 domain. The total surface area buried at the interaction interface is nearly 2000 Å$^2$, with the SH13 cradle molecule contributing ~1030 Å$^2$ and the Abl SH2 domain 960 Å$^2$. Notably, of the cradle molecule surface area buried in the interface, ~90% is contributed by residues at positions that were diversified in the generation of the library. Similarly, out of 21 cradle molecule residues that are within 5 Å of an SH2 atom, 15 were located at positions that were diversified in the cradle library. All but one of these 15 residues are directly involved in target recognition. The extensive contributions of diversified positions to the interface suggest that the library design is effective in concentrating amino acid diversity at positions that are capable of making direct contacts with a target. These characteristics also provide additional support for the utility of this face of the FnIII beta sheets for constructing protein-interaction interfaces.

The epitope of the Abl SH2 domain recognized by SH13 is distinct from the phosphopeptide-binding interface that a previously reported cradle molecule recognizes (Wojcik, et al., supra, 2010). However, the SH13 epitope is also a known functionally important surface of the SH2 domain. In the context of the full-length Abl kinase, this surface, centered on the αA helix, mediates interactions with the C-lobe of the kinase domain that help to keep the kinase in an inactive conformation. Almost a half (~475 Å$^2$) of the epitope for the SH13 cradle molecule is contributed by a linear segment including the entire αA helix and residues immediately adjacent to this helix (FIG. 32B). The concave paratope of the SH13 cradle molecule seems suitable for recognizing the convex surface presented by this helix. It is unlikely that a cradle molecule with a convex paratope shape, typically observed in cradle molecules with exclusively loop-based binding surfaces, would be able to recognize this surface.

In order to better compare and contrast the structural basis for target recognition in FnIII domain variants isolated from the two distinct types of libraries, the crystal structure of the FnIII domain variant ySMB-9 bound to hSUMO1 was determined at 2.15 Å resolution (FIG. 32C; Table 9). The ySMB-9 FnIII domain variant was recovered from the same "loop only" phage-display library using a slightly different selection scheme (Hogrefe, H. H., et al., *Gene* (1993) 128:119-126) and shows close homology to new hSUMO1 cradle molecules recovered in this study (FIG. 31B). Thus, the structure of the ySMB-9/hSUMO1 complex provides a good example of how "loop only" FnIII variants recognize their targets. The structure showed that ySMB-9 binds to hSUMO1 in a "head-on" fashion using all three loops to form a contiguous binding surface in precisely the manner envisioned in typical loop-based FnIII library designs (FIG. 32C). The BC, DE and FG loops contribute 54%, 6% and 40% of the total FnIII variant buried surface area respectively with no buried surface contributed by the beta sheet regions of the FnIII domain.

The mode of interaction exhibited by the ySMB-9 FnIII variant stands in stark contrast with the "cradle" surface employed by SH13 in binding to Abl SH2 (FIG. 32A) and is also distinct from that previously observed for a yeast SUMO (ySUMO)-binding FnIII variant, ySMB-1 (FIGS. 32C and 32D) (Gilbreth, et al., supra, 2011). The FnIII variant ySMB-1 used the FG loop and the wild-type FnIII scaffold to form a side-and-loop mode of interaction similar to that exhibited by SH13. Interestingly, both ySMB-1 and ySMB-9 bind to structurally equivalent, highly conserved epitopes in hSUMO1 and ySUMO, respectively (FIG. 32D). Thus, this pair of FnIII variants demonstrate that both the "loop only" and "cradle" binding modes can be used to successfully recognize essentially the same target surface and further supports the validity of both library design strategies. Furthermore, the epitope recognized by ySMB-9 is flat in shape, demonstrating that, although loop-only binding surfaces tend to have convex shapes that would seem unsuitable for recognizing flat surfaces, it is possible to effectively produce binders to a flat epitope using a loop-only FnIII variant library.

A new type of FnIII cradle molecule library was developed in which positions for amino acid diversification are distinct from those of conventional FnIII variant libraries. The new cradle library is effective in generating high-affinity cradle molecules, and its performance, compared with that of a conventional "loop only" library, appears different for different target molecules. Furthermore, the crystal structure of a cradle molecule from the new cradle library presents a concave paratope (FIG. 32A), which is distinctly different from flat or convex paratopes often observed in FnIII variants from "loop only" libraries (FIG. 32C). The ability of the new library to produce concave paratopes is likely to be critical in using cradle molecules to inhibit protein-protein interaction interfaces, as the majority of protein surfaces range from flat to convex in shape. The SH13 structure showed that residues in the beta sheet region of the FnIII domain underwent minimal backbone movements upon target binding. Thus, a small entropic penalty incurred by these residues upon binding may favorably contribute to achieving high affinity. Together, these results clearly illustrate that the single FnIII domain can be used to produce diverse types of binding surfaces that collectively are capable of recognizing epitopes with distinct topography. This expands the utility of the FnIII domain for producing synthetic binding interfaces.

In structural comparison of the FnIII and immunoglobulin variable domains, the "DCFG" beta sheet of the FnIII domain used for constructing a new binding site in this work corresponds to the beta sheet of the immunoglobulin variable domain that mediates heterodimerization between the variable domains of the heavy and light chains (Amzel, L. M., and Poljak, R. J., *Annu Rev Biochem* (1979) 48:961-997). Therefore, the immunoglobulin domains utilize this beta sheet surface for specific protein-protein interaction but not for recognizing foreign molecules. In the camelid single-domain antibodies ($V_H$Hs), the equivalent beta sheet contains several mutations, with respect to the conventional variable domain, that prevent heterodimerization (Desmyter, A., et al., *Nat Struct Biol* (1996) 3:803-811; Hamers-Casterman, C., et al., *Nature* (1993) 363:446-448). Although the paratopes of most camelid $V_H$Hs reported to date are made with the three CDR loops and have convex topography (De Genst, et al., *Proc Natl Acad Sci USA* (2006) 103:4586-4591), rare examples of $V_H$H that use a binding mode equivalent to the "side and loop" mode have been identified (Kirchhofer, A., et al., *Nat Struct Mol Biol* (2010) 17:133-138). These examples suggest that the $V_H$H scaffold can also be used in the same manner as the FnIII domain to generate such "side binders". The rarity of such $V_H$H molecules is likely to originate from the manner by which their amino acid diversity is generated in the natural immune system. The gene recombination mechanism underlying the generation of immunoglobulin sequence diversity focuses on the CDRs (Wu, T., T., et al., *Proteins: Struct Funct Genet* (1993)

16:1-7). Consequently, the "side" positions on the beta sheet are not extensively diversified in the natural immune repertoire, limiting the chance of generating "side binder" $V_HH$ molecules.

Whereas the FnIII variants have been viewed as close mimics of antibodies due to their structural similarity, the design of the cradle library represents a departure from this "antibody mimic" mind set. It was emphasized that structural characterization of cradle molecule-target complexes was instrumental in identifying the unanticipated mode of cradle molecule-target interactions and the potential utility of the beta sheet surface for target recognition. Unlike immunoglobulin libraries derived from natural sources, cradle molecule libraries are generated using in vitro mutagenesis, affording full control over the choice of locations for amino acid diversification in a library. This freedom is an obvious but important advantage of synthetic scaffold systems. A similar approach should be effective in identifying distinct surfaces useful for constructing binding interfaces in other scaffolds. This design strategy gives general insights into the design of molecular recognition interfaces.

Materials and Methods

Protein production and modification. Target proteins (Abl SH2, hSUMO1, and GFP) and cradle molecules were produced as His 10-tag proteins using the pHFT2 vector (Koide, et al., supra, 2007), and purified as previously described (Gilbreth, et al., supra, 2011, Koide, A., et al., supra, 2009). The hSUMO1 sample used in this work contained the C52A mutation that prevents dimer formation (Tatham, M. H., et al., *J Biol Chem* (2001) 276:35368-35374). Isotope-enriched samples were prepared as described previously (Pham, T-N, and Koide, S., *J Biomol NMR* (1998) 11:407-414). For SPR experiments, the His-tag segment of the targets was cleaved using the TEV protease. For crystallization the His-tag segment was removed from both the targets and cradle molecules.

Target proteins used for yeast display were biotinylated using EZ-Link NHS-PEG4-Biotin (Thermo Fisher Scientific). Typically 0.3-0.6 mg/ml of a target protein was incubated with 60 µM reagent for 30 min, and quenched the reaction by adding Tris-Cl (pH 8) at a final concentration of 0.1 M. Excess biotinylation reagent was removed by dialysis against 20 mM Tris Cl buffer, pH 8 containing 100 mM NaCl and 1 mM EDTA. The level of biotinylation was determined to be ~1 per molecule using MALDI-TOF mass spectroscopy.

Phage and yeast display, library construction and selection. The "loop only" library has been described (Wojcik, et al., supra, 2010). The cradle library was constructed using the Kunkel mutagenesis method as described previously (Koide, A., and Koide, S., supra, 2007, Sidhu, et al., supra, 2000). Phage display selection was performed according to the methods previously described (Fellouse, F. A., et al. *J Mol Biol* (2007) 373:924-940, Koide, A., et al., supra, 2009). The His-tagged target proteins were incubated with equimolar concentration of BTtrisNTA, a high affinity Ni-NTA compound containing a biotin moiety, for 30 min to form a BTtrisNTA/his-tagged protein complex, and the complex was incubated with cradle molecule phage-display libraries. The target concentrations used for rounds 1, 2 and 3 were 100, 100 and 50 nM for Abl SH2, 100, 50 and 50 nM for GFP, respectively, and 100 nM throughout for hSUMO1. Cradle molecule-displaying phages bound to the BTtrisNTA/target complexes were captured using Streptavidin (SAV)-coated magnetic beads. The captured phages were eluted with 10 mM EDTA solution that disrupts the linkage between the targets and BTtrisNTA. The recovered phages were amplified in the presence of 0.2 mM IPTG to induce the expression of cradle molecule-p3 fusion genes.

After three rounds of the phage-display library selection, the genes of selected cradle molecules was transferred to a yeast-display vector to make yeast libraries, using homologous recombination in yeast (Swers, J. S., et al., *Nucleic Acids Res* (2004) 32:e36). Gene shuffling during the construction of yeast-display libraries was incorporated as follows. A linearized yeast display vector, pGalAgaCamR (Koide, A., et al., *J Mol Biol* (2007) 373:941-953), was prepared using NcoI and XhoI digestion. Cradle molecule gene segments respectively encoding residues 1-74 and those for residues 54-94 separately were amplified using PCR from the enriched pool after the phage selection. Yeast strain EBY100 was then transformed using a mixture of the three DNA fragments. Correctly recombined clones contained the fusion gene for Aga2-cradle molecule-V5 tag. The transformants were selected in tryptophan-deficient media and Aga2-cradle molecule fusion protein was expressed as previously described (Koide, et al., supra, 2007, Boder and Wittrup, supra, 2000).

The yeast display libraries were sorted using 30 nM biotinylated Abl-SH2, 10 nM biotinylated hSUMO1, and 3 nM biotinylated GFP as described previously (Koide, et al., supra, 2007). The surface-displayed cradle molecules were detected with anti-V5 antibody (Sigma). NeutrAvidin® (NAV)-PE (InvitroGen) or SAV-PE (InvitroGen) and Alexa Fluor®-647 chicken anti-rabbit IgG (InvitroGen) were used as the secondary detection reagents for biotinylated protein and anti V5 antibody, respectively. A total of two rounds of library sorting were performed for Abl SH2 and hSUMO1, and one round for GFP.

Affinity measurements using yeast display. Individual clones from sorted libraries were isolated on agar plates and grown in liquid media as described previously (Koide, et al., supra, 2007, Boder and Wittrup, supra, 2000). Fifty thousand yeast cells for each clone were incubated with various concentrations of biotinylated target in the final volume of 20 µl in BSS buffer (50 mM Tris Cl, 150 mM NaCl, pH 8, 1 mg/ml BSA) in the wells of a polypropylene 96-well plate (Greiner 650201) on ice for 30 min with shaking. The wells of a 96-well filter plate (MultiScreenHTS HV, 0.45 µm pore size; Millipore) were washed by adding 100 µl BSS and then removing the liquid by applying a vacuum. The cell suspensions from the binding reactions were transferred to the washed wells of the 96-well filter plate. The binding solution was removed by vacuum filtration. The yeast cells in the wells were washed with 100 µl of BSST (BSS buffer containing 0.1% Tween 20) twice in the same manner. Next, 20 µl of 10 µg/ml NAV-PE (InvitroGen) in BSS was added to each of the wells. After incubation on ice with shaking for 30 min, the cells were washed with BSST once. The cells were suspended in 300 µl BSS and analyzed using a Guava EasyCyte 6/L flow cytometer (Millipore). The Kd values were determined from plots of the mean PE fluorescence intensity versus target concentration by fitting the 1:1 binding model using the KaleidaGraph program (Synergy Software).

Surface plasmon resonance. All SPR measurements were carried out on a Biacore™ 2000 instrument. For kinetic experiments, Abl SH2 was immobilized on a CM5 chip using amine coupling following methods provided by the manufacturer. Cradle molecules at varying concentrations were flowed over the surface at a flow rate of 100 µl/min and the binding signal was recorded. Quintuplicate data sets were processed and fit with a bimolecular model including mass transport using the Scrubber2 program (BioLogic Software, Campbell, Australia). The presence of mass transport was confirmed using varying flow rates. Equilibrium experiments were performed as described previously (Gilbreth, et al., supra, 2011). Duplicate data sets were processed in Scrubber2 and saturation curves were fit with a 1:1 binding model using the Origin software (OriginLab, Northampton, Mass.).

Crystallization and structure determination. The SH13/Abl SH2 domain complex was purified with a Superdex 75 column (GE Lifesciences). The complex was concentrated to ~10 mg/ml and crystallized in 0.2 M Magnesium chloride, 0.1 M Bis-Tris Cl pH 5.5 and 25% PEG 3350 at 19° C. by the hanging-drop vapor-diffusion method. The ySMB-9 and hSUMO1 proteins were mixed in a 1:1 molar ratio, concentrated to a total protein concentration of ~10 mg/mL and dissolved in 10 mM Tris Cl, 50 mM NaCl, pH 8.0. The complex was crystallized in 24% PEG-8000, 0.1 M Imidazole, pH=8.0 at 19° C. using the hanging drop vapor diffusion method. Crystals were frozen in a mixture of 80% mother liquor and 20% glycerol as a cryoprotectant. Crystal and data collection information are reported in Table 1.

X-ray diffraction data were collected at the Advanced Photon Source beamlines (Argonne National Laboratory). Crystal and data collection information are reported in Supplementary Table 1. X-ray diffraction data were processed and scaled with HKL2000 (Otwinowski, Z., supra, 1997). The SH13/Abl SH2 structure was determined by molecular replacement using Phaser in the CCP4 program suite (The CCP4 Suite, supra, 1994; Potterton, E., et al., *Acta Crystallogr D Biol Crystallogr* (2003) 59:1131-1137). A multicopy search was performed with the Abl SH2 domain and the FnIII scaffold, without the loop regions, as the search models (PDB IDs 2ABL and 1FNA, respectively). Simulated annealing, energy-minimization, B-factor refinement and map building were out using CNS (Brunger, A. T., et al., supra, 1998; Brunger, A. T., *Nature protocols* (2007) 2:2728-2733). The ySMB-9/hSUMO1 structure was determined by molecular replacement using sequential search with two different models with the program MOLREP in CCP4 (The CCP4 Suite, supra, 1994). The hSUMO1 structure (residues 20-92 of chain B PDB ID code 1Z5S) was used as a search model, along with the FnIII structure with the variable loop regions deleted (PDB ID code 1FNA) (Dickinson, et al., supra, 1994; Reverter, D., supra, 2005). Model building and the search for water molecules was carried out using the Coot program (Emsley, P., supra, 2004). TLS (Translation/Libration/Screw) and bulk solvent parameters, restrained temperature factor and final positional refinement were completed with REFMAC5 (Murshudov, et al., supra, 1997). Molecular graphics were generated using PyMOL (located on the World Wide Web at pymol.org). Surface area calculations were performed using the PROTORP protein-protein interaction server (Reynolds, et al., supra, 2009).

NMR spectroscopy. The following suite of spectra were taken on a uniformly $^{13}C/^{15}N$ enriched Abl SH2 domain (~200 μM) in 10 mM sodium phosphate buffer, pH 7.4 containing 150 mM NaCl, 50 μM EDTA and 0.005% sodium azide prepared in 90% $H_2O$ and 10% $D_2O$, using a Varian (Palo Alto, Calif.) INOVA 600 NMR spectrometer equipped with a cryogenic probe using pulse sequences provided by the manufacturer: $^1H$, $^{15}N$—HSQC, HNCO, CBCACONH, HNCACB, CCONH, HN(CA)CO. NMR data were processed and analyzed using NMRPipe and NMRView software (Delaglio, F., et al., *J Biomol NMR* (1995) 6:277-293; Johnson, B. A., et al., *J Biomol NMR* (1994) 4:603-614). Resonance assignments were obtained using the PINE server (Bahrami, A., et al., *PLoS Computational Biology* (2009) 5:e1000307) and verified by visual inspection in NMR view. For epitope mapping, the $^1H,^{15}N$—HSQC spectra of the $^{15}N$ enriched Abl SH2 domain (~60 μM) in the absence and presence of 1.25 fold molar excess of unlabeled SH13 cradle molecule were recorded. The $^1H,^{15}N$—HSQC cross peaks were classified according to the degree of migration upon SH13 binding as described previously (Koide, et al., supra, 2007).

We claim:

1. A 10<sup>th</sup> fibronectin type III (FnIII10) domain-based cradle polypeptide capable of binding to a target molecule, wherein the cradle polypeptide comprises the sequence of SEQ ID NO: 44.

2. A molecule comprising two or more cradle polypeptides of claim 1 linked together.

3. A molecule of claim 2, wherein each of the cradle polypeptides binds to the same target molecule.

4. A molecule of claim 2, wherein two or more of the cradle polypeptides bind to different target molecules.

5. A cradle library comprising a plurality of cradle polypeptides of claim 1.

* * * * *

SEQUENCE LISTING

```
<160> NUMBER OF SEQ ID NOS: 474

<210> SEQ ID NO 1
<211> LENGTH: 94
<212> TYPE: PRT
<213> ORGANISM: Homo sapiens
<220> FEATURE:
<223> OTHER INFORMATION: Fibronectin Type III domain polypeptide

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90
```

```
<210> SEQ ID NO 2
<211> LENGTH: 8
<212> TYPE: PRT
<213> ORGANISM: Artificial Sequence
<220> FEATURE:
<223> OTHER INFORMATION: synthetically constructed epitope

<400> SEQUENCE: 2

Asp Tyr Lys Asp Asp Asp Asp Lys
 1               5

<210> SEQ ID NO 3
<211> LENGTH: 98
<212> TYPE: PRT
<213> ORGANISM: Artificial Sequence
<220> FEATURE:
<223> OTHER INFORMATION: synthetically constructed Fibronectin Type III
      domain polypeptide
<220> FEATURE:
<221> NAME/KEY: VARIANT
<222> LOCATION: (30), (33)
<223> OTHER INFORMATION: Xaa = Asp, Phe, His, Ile, Leu, Asn, Val, or Tyr
<220> FEATURE:
<221> NAME/KEY: VARIANT
<222> LOCATION: (31)
<223> OTHER INFORMATION: Xaa = Phe, His, Leu, or Tyr
<220> FEATURE:
<221> NAME/KEY: VARIANT
<222> LOCATION: (41)...(45), (76)...(85)
<223> OTHER INFORMATION: Xaa = any amino acid except Cys
<220> FEATURE:
<221> NAME/KEY: VARIANT
<222> LOCATION: (46), (48), (50), (86)...(89)
<223> OTHER INFORMATION: Xaa = any amino acid

<400> SEQUENCE: 3

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Xaa Xaa Tyr
            20                  25                  30

Xaa Ile Thr Tyr Gly Glu Thr Gly Xaa Xaa Xaa Xaa Xaa Gln Xaa
        35                  40                  45

Phe Xaa Val Pro Gly Ser Lys Ser Thr Ala Thr Ile Ser Gly Leu Ser
 50                  55                  60

Pro Gly Val Asp Tyr Thr Ile Thr Val Tyr Ala Xaa Xaa Xaa Xaa Xaa
65                  70                  75                  80

Xaa Xaa Xaa Xaa Xaa Xaa Xaa Xaa Ser Pro Ile Ser Ile Asn Tyr
                85                  90                  95

Arg Thr

<210> SEQ ID NO 4
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 4

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp His Tyr
            20                  25                  30

Val Ile Thr Tyr Gly Glu Thr Gly Ser Tyr Ser Ser Tyr Gly Gln Glu
        35                  40                  45
```

Phe Ala Val Pro Gly Ser Lys Ser Thr Ala Thr Ile Ser Gly Leu Ser
    50                  55                  60

Pro Gly Val Asp Tyr Thr Ile Thr Val Tyr Ala Tyr Glu Phe Gln Phe
65                  70                  75                  80

Glu Met Tyr Met Ser Tyr Ser Pro Ile Ser Ile Asn Tyr Arg Thr
                85                  90                  95

<210> SEQ ID NO 5
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 5

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Val Ile Thr Tyr Gly Glu Thr Gly Gly Val Tyr Gly Pro Gln Glu Phe
            35                  40                  45

Glu Val Pro Gly Ser Lys Ser Thr Ala Thr Ile Ser Gly Leu Ser Pro
    50                  55                  60

Gly Val Asp Tyr Thr Ile Thr Val Tyr Ala Trp Phe Tyr Gln Gln Ala
65                  70                  75                  80

Tyr Glu His Tyr Val Ser Ser Pro Ile Ser Ile Asn Tyr Arg Thr
                85                  90                  95

<210> SEQ ID NO 6
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 6

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Leu Phe Tyr
                20                  25                  30

His Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Tyr Tyr Ser Asp Tyr Thr
65                  70                  75                  80

Tyr Ser Pro Ile Ser Ile Asn Tyr Arg Thr
                85                  90

<210> SEQ ID NO 7
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 7

Val Ser Ser Val Pro Thr Lys Leu Glu Val Val Ala Ala Thr Pro Thr

```
                 1               5                  10                  15
Ser Leu Leu Ile Ser Trp Asp Ala Pro Ala Val Thr Val Asp His Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
         50                  55                  60

Gly Val Asp Tyr Thr Ile Thr Val Tyr Ala Trp Tyr Asp Tyr Ser Trp
 65                  70                  75                  80

Gly Tyr Tyr Gly Tyr Ser Pro Ile Ser Ile Asn Tyr Arg Thr
                 85                  90
```

<210> SEQ ID NO 8
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 8

```
Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp Phe Tyr
                20                  25                  30

Val Ile Thr Tyr Gly Glu Thr Gly Gly Asn Ser Pro Val Gln Glu Phe
            35                  40                  45

Glu Val Pro Gly Ser Lys Ser Thr Ala Thr Ile Ser Gly Leu Ser Pro
         50                  55                  60

Gly Val Asp Tyr Thr Ile Thr Val Tyr Ala Trp Ile Tyr Ser Asp Ser
 65                  70                  75                  80

Val Tyr Ser Ala Ser Pro Ile Ser Ile Asn Tyr Arg Thr
                 85                  90
```

<210> SEQ ID NO 9
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 9

```
Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp His Tyr
                20                  25                  30

Val Ile Thr Tyr Gly Glu Thr Gly Gly Tyr Ala Tyr Ser Ala Ser Gln
            35                  40                  45

Glu Phe Glu Val Pro Gly Ser Lys Ser Thr Ala Thr Ile Ser Gly Leu
         50                  55                  60

Ser Pro Gly Val Asp Tyr Thr Ile Thr Val Tyr Ala Tyr Glu Ser Tyr
 65                  70                  75                  80

Tyr Trp Gly Phe Ala Gly Tyr Ser Pro Ile Ser Ile Asn Tyr Arg Thr
                 85                  90                  95
```

<210> SEQ ID NO 10
<211> LENGTH: 96
<212> TYPE: PRT

<213> ORGANISM: Artificial Sequence
<220> FEATURE:
<223> OTHER INFORMATION: synthetically constructed Fibronectin Type III
      domain polypeptide

<400> SEQUENCE: 10

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Val Phe Gly Ala Gly Pro Gln Glu
        35                  40                  45

Phe Glu Val Pro Gly Ser Lys Ser Thr Ala Thr Ile Ser Gly Leu Ser
50                  55                  60

Pro Gly Val Asp Tyr Thr Ile Thr Val Tyr Ala Tyr Glu Glu Trp Ser
65                  70                  75                  80

Glu Ser Met Tyr Met Ser Tyr Ser Pro Ile Ser Ile Asn Tyr Arg Thr
                85                  90                  95

<210> SEQ ID NO 11
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 11

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

His Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
50                  55                  60

Gly Val Asp Tyr Thr Ile Thr Val Tyr Ala Tyr Trp Glu Ala Phe Ser
65                  70                  75                  80

Gly Asp Leu Tyr Tyr Ser Ser Ser Pro Ile Ser Ile Asn Tyr Arg Thr
                85                  90                  95

<210> SEQ ID NO 12
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 12

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

Asn Ile Thr Tyr Gly Glu Thr Gly Ala Phe Trp His Tyr Val Gln Ala
        35                  40                  45

Phe Thr Val Pro Gly Ser Lys Ser Thr Ala Thr Ile Ser Gly Leu Ser
50                  55                  60

Pro Gly Val Asp Tyr Thr Ile Thr Val Tyr Ala Glu Trp Asp Gln Tyr
65                  70                  75                  80

```
Val Val Gly Ser Pro Ile Ser Ile Asn Tyr Arg Thr
            85                  90
```

<210> SEQ ID NO 13
<211> LENGTH: 97
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 13

```
Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp Tyr Tyr
            20                  25                  30

Val Ile Thr Tyr Gly Glu Thr Gly Gly Tyr Tyr Ser Phe Gln Ala
            35                  40                  45

Phe Glu Val Pro Gly Ser Lys Ser Thr Ala Thr Ile Ser Gly Leu Ser
 50                  55                  60

Pro Gly Val Asp Tyr Thr Ile Thr Val Tyr Ala Phe Trp Pro Asp Asp
65                  70                  75                  80

Tyr Tyr Tyr Gly Gly Ser Glu Tyr Ser Pro Ile Ser Ile Asn Tyr Arg
                85                  90                  95

Thr
```

<210> SEQ ID NO 14
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 14

```
Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp His Tyr
            20                  25                  30

His Ile Thr Tyr Gly Glu Thr Gly Gly Ser Trp Ser Gly Tyr Gln Glu
            35                  40                  45

Phe Thr Val Pro Gly Ser Lys Ser Thr Ala Thr Ile Ser Gly Leu Ser
 50                  55                  60

Pro Gly Val Asp Tyr Thr Ile Thr Val Tyr Ala Asn Ser Ser Trp Tyr
65                  70                  75                  80

Trp Tyr Asn Pro Ile Ser Ile Asn Tyr Arg Thr
                85                  90
```

<210> SEQ ID NO 15
<211> LENGTH: 97
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 15

```
Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp His Tyr
```

```
                20                  25                  30
Val Ile Thr Tyr Gly Glu Thr Gly Ala His Tyr Tyr Phe Gln Glu
            35                  40                  45

Phe Glu Val Pro Gly Ser Lys Ser Thr Ala Thr Ile Ser Gly Leu Ser
        50                  55                  60

Pro Gly Val Asp Tyr Thr Ile Thr Val Tyr Ala Val Ser His Gly Thr
65                  70                  75                  80

Asp Gly Asn Lys Leu Tyr Phe Phe Ser Pro Ile Ser Ile Asn Tyr Arg
                85                  90                  95

Thr

<210> SEQ ID NO 16
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide
<220> FEATURE:
<221> NAME/KEY: VARIANT
<222> LOCATION: (89)...(89)
<223> OTHER INFORMATION: Xaa = any amino acid

<400> SEQUENCE: 16

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Gly Trp Trp Tyr Gly Val Gln Ala
        35                  40                  45

Phe Thr Val Pro Gly Ser Lys Ser Thr Ala Thr Ile Ser Gly Leu Ser
    50                  55                  60

Pro Gly Val Asp Tyr Thr Ile Thr Val Tyr Ala Glu Asp Ser Gly Gly
65                  70                  75                  80

Arg His Ser Ile Ser Pro Ile Ser Xaa Asn Tyr Arg Thr
                85                  90

<210> SEQ ID NO 17
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 17

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Trp Tyr Ser Pro Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Asn Trp Ser Ala Gly
65                  70                  75                  80

Leu Gln Ser Pro Ile Ser Ile Asn Tyr Arg Thr
                85                  90
```

```
<210> SEQ ID NO 18
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 18

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Ser Trp Lys Tyr Trp
65                  70                  75                  80

Tyr His Gly Ser Pro Ile Ser Ile Asn Tyr Arg Thr
                85                  90

<210> SEQ ID NO 19
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 19

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
                20                  25                  30

Ile Ile Thr Tyr Gly Glu Thr Gly Gly Gly Tyr Ser Tyr Gln Thr
            35                  40                  45

Phe Thr Val Pro Gly Ser Lys Ser Thr Ala Thr Ile Ser Gly Leu Ser
    50                  55                  60

Pro Gly Val Asp Tyr Thr Ile Thr Val Tyr Ala Asn Glu Phe Gly Lys
65                  70                  75                  80

Ser Tyr Pro Tyr Thr Met Asn Pro Ile Ser Ile Asn Tyr Arg Thr
                85                  90                  95

<210> SEQ ID NO 20
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 20

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Leu Tyr Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60
```

Gly Val Asp Tyr Thr Ile Thr Val Tyr Ala Thr Asp Tyr Gly Pro Gly
65                  70                  75                  80

Tyr Pro Tyr Glu Ser Pro Ile Ser Ile Asn Tyr Arg Thr
                85                  90

<210> SEQ ID NO 21
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 21

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
                20                  25                  30

His Ile Thr Tyr Gly Glu Thr Gly Gly Val Trp Ser Gly Tyr Gln Glu
            35                  40                  45

Phe Thr Val Pro Gly Ser Lys Ser Thr Ala Thr Ile Ser Gly Leu Ser
50                  55                  60

Pro Gly Val Asp Tyr Thr Ile Thr Val Tyr Ala Val Gln His Gln Glu
65                  70                  75                  80

Ile Trp Pro Tyr Tyr Tyr Ser Pro Ile Ser Ile Asn Tyr Arg Thr
                85                  90                  95

<210> SEQ ID NO 22
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 22

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
                20                  25                  30

Phe Ile Thr Tyr Gly Glu Thr Gly Gly Ser Trp Ser Tyr Tyr Gln Glu
            35                  40                  45

Phe Ala Val Pro Gly Ser Lys Ser Thr Ala Thr Ile Ser Gly Leu Ser
50                  55                  60

Pro Gly Val Asp Tyr Thr Ile Thr Val Tyr Ala Tyr Ser Tyr Glu Pro
65                  70                  75                  80

Tyr Tyr Tyr Tyr Asn Pro Ile Ser Ile Asn Tyr Arg Thr
                85                  90

<210> SEQ ID NO 23
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 23

Val Ser Ser Val Pro Thr Lys Leu Glu Val Val Ala Ala Thr Pro Thr
1               5                   10                  15

-continued

Ser Leu Leu Ile Ser Trp Asp Ala Pro Ala Val Thr Val Asp Phe Tyr
            20                  25                  30

Val Ile Thr Tyr Gly Glu Thr Gly Ser Phe Ser Pro Pro Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Met Met Trp Gly Trp Glu
65                  70                  75                  80

Tyr Tyr Asp Tyr Asn Ile Ser Pro Ile Ser Ile Asn Tyr Arg Thr
                85                  90                  95

<210> SEQ ID NO 24
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 24

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Ile Ile Thr Tyr Gly Glu Thr Gly Ser Tyr His Gly Trp Gln Thr Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Asp Ser Ser Thr Trp Pro
65                  70                  75                  80

Tyr Trp Tyr Tyr Ser Ser Pro Ile Ser Ile Asn Tyr Arg Thr
                85                  90

<210> SEQ ID NO 25
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 25

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Ser Phe Ser Pro Pro Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Met Met Trp Gly Trp Glu
65                  70                  75                  80

Tyr Tyr Asp Tyr Asn Ile Ser Pro Ile Ser Ile Asn Tyr Arg Thr
                85                  90                  95

<210> SEQ ID NO 26
<211> LENGTH: 93
<212> TYPE: PRT
<213> ORGANISM: Artificial Sequence
<220> FEATURE:

<223> OTHER INFORMATION: synthetically constructed Fibronectin Type III
      domain polypeptide

<400> SEQUENCE: 26

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

Val Ile Thr Tyr Gly Glu Thr Gly Gly Val Trp Tyr Gly Tyr Gln Glu
        35                  40                  45

Phe Thr Val Pro Gly Ser Lys Ser Thr Ala Thr Ile Ser Gly Leu Ser
50                  55                  60

Pro Gly Val Asp Tyr Thr Ile Thr Val Tyr Ala Met Thr Ser Tyr Phe
65                  70                  75                  80

Gln Glu Tyr Trp Ser Pro Ile Ser Ile Asn Tyr Arg Thr
                85                  90

<210> SEQ ID NO 27
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 27

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Ser Phe Ser Pro Pro Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Met Met Trp Gly Trp Glu
65                  70                  75                  80

Tyr Tyr Asp Tyr Asn Ile Ser Pro Ile Ser Ile Asn Tyr Arg Thr
                85                  90                  95

<210> SEQ ID NO 28
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 28

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

Val Ile Thr Tyr Gly Glu Thr Gly Gly Tyr Pro Ser Pro Val Gln Thr
        35                  40                  45

Phe Thr Val Pro Gly Ser Lys Ser Thr Ala Thr Ile Ser Gly Leu Ser
    50                  55                  60

Pro Gly Val Asp Tyr Thr Ile Thr Val Tyr Ala Trp Asp Tyr Asp Trp
65                  70                  75                  80

Tyr Ala Ile Gly Ser Pro Ile Ser Ile Asn Tyr Arg Thr

<210> SEQ ID NO 29
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 29

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Tyr Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Tyr Thr Phe Gln Tyr
65                  70                  75                  80

Asp Tyr Tyr Val Thr Gln Ser Ser Pro Ile Ser Ile Asn Tyr Arg Thr
                85                  90                  95

<210> SEQ ID NO 30
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 30

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Phe Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Asp Asn Trp Asp Asp
65                  70                  75                  80

Tyr Tyr Tyr Ser Pro Ile Ser Ile Asn Tyr Arg Thr
                85                  90

<210> SEQ ID NO 31
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 31

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Phe Tyr
            20                  25                  30

Val Ile Thr Tyr Gly Glu Thr Gly Ser Tyr Ser Gly Trp Gln Glu Phe
        35                  40                  45

```
Glu Val Pro Gly Ser Lys Ser Thr Ala Thr Ile Ser Gly Leu Ser Pro
    50                  55                  60

Gly Val Asp Tyr Thr Ile Thr Val Tyr Ala Tyr Tyr Gln Asn Pro
65                  70                  75                  80

Glu Ser Tyr Tyr Ser Pro Ile Ser Ile Asn Tyr Arg Thr
                85                  90
```

<210> SEQ ID NO 32
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 32

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
                20                  25                  30

Phe Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Tyr Tyr Gly Tyr Tyr
65                  70                  75                  80

Gly Pro Gln Tyr Thr Ser Pro Ile Ser Ile Asn Tyr Arg Thr
                85                  90
```

<210> SEQ ID NO 33
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 33

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Tyr Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Tyr Gln His Asp Phe
65                  70                  75                  80

Asp Tyr His Val Trp Gly Ser Ser Pro Ile Ser Ile Asn Tyr Arg Thr
                85                  90                  95
```

<210> SEQ ID NO 34
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 34

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His Tyr Tyr
            20                  25                  30

Val Ile Thr Tyr Gly Glu Thr Gly Trp Trp Gly Pro Val Gln Glu Phe
            35                  40                  45

Thr Val Pro Gly Ser Lys Ser Thr Ala Thr Ile Ser Gly Leu Ser Pro
50                  55                  60

Gly Val Asp Tyr Thr Ile Thr Val Tyr Ala Tyr Trp Lys Tyr Ser Tyr
65                  70                  75                  80

Lys Tyr Ser Pro Ile Ser Ile Asn Tyr Arg Thr
            85                  90

<210> SEQ ID NO 35
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 35

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Ala Phe Gly Ser Gly Gln Glu Phe
            35                  40                  45

Glu Val Pro Gly Ser Lys Ser Thr Ala Thr Ile Ser Gly Leu Ser Pro
50                  55                  60

Gly Val Asp Tyr Thr Ile Thr Val Tyr Ala Lys Trp Met Tyr Ser Tyr
65                  70                  75                  80

Met Tyr Asn Pro Ile Ser Ile Asn Tyr Arg Thr
            85                  90

<210> SEQ ID NO 36
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 36

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
            20                  25                  30

Phe Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
50                  55                  60

Gly Val Asp Tyr Thr Ile Thr Val Tyr Ala Trp Ser Tyr Glu Leu Thr
65                  70                  75                  80

Gly Asp Tyr Leu Gln Gln Phe Ser Pro Ile Ser Ile Asn Tyr Arg Thr
            85                  90                  95

<210> SEQ ID NO 37
<211> LENGTH: 94

<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 37

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Tyr Tyr
            20                  25                  30

Asn Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
50                  55                  60

Gly Val Asp Tyr Thr Ile Thr Val Tyr Ala Trp Tyr Glu Tyr Gly Gly
65                  70                  75                  80

Tyr Met Glu Ile Asp Ser Pro Ile Ser Ile Asn Tyr Arg Thr
                85                  90

<210> SEQ ID NO 38
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 38

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Val Pro Tyr Tyr Gly Trp Gln Glu
        35                  40                  45

Phe Glu Val Pro Gly Ser Lys Ser Thr Ala Thr Ile Ser Gly Leu Ser
50                  55                  60

Pro Gly Val Asp Tyr Thr Ile Thr Val Tyr Ala Tyr Pro Gly Ser Asn
65                  70                  75                  80

Trp Phe Tyr Asp Trp Trp Ser Pro Ile Ser Ile Asn Tyr Arg Thr
                85                  90                  95

<210> SEQ ID NO 39
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 39

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Ser Tyr Gly Ser Tyr Pro Gln Ala
        35                  40                  45

Phe Glu Val Pro Gly Ser Lys Ser Thr Ala Thr Ile Ser Gly Leu Ser
50                  55                  60

Pro Gly Val Asp Tyr Thr Ile Thr Val Tyr Thr Glu Ser Glu Gly Tyr

```
                65                  70                  75                  80
Ile Ser Ser Ser Pro Ile Ser Ile Asn Tyr Arg Thr
                    85                  90

<210> SEQ ID NO 40
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 40

Val Ser Ser Val Pro Thr Lys Leu Glu Val Val Ala Ala Thr Pro Thr
1               5                   10                  15

Ser Leu Leu Ile Ser Trp Asp Ala Pro Ala Val Tyr His Tyr Val Tyr
                20                  25                  30

Leu Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
        50                  55                  60

Gly Val Asp Tyr Thr Ile Thr Val Tyr Ala Lys Trp Lys Tyr Ser Tyr
65                  70                  75                  80

Gln Tyr Ser Pro Ile Ser Ile Asn Tyr Arg Thr
                85                  90

<210> SEQ ID NO 41
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 41

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Tyr Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
        50                  55                  60

Gly Val Asp Tyr Thr Ile Thr Val Tyr Ala Trp Tyr Trp Asn Asp Tyr
65                  70                  75                  80

Tyr Met Ser Ser Met Ser Pro Ile Ser Ile Asn Tyr Arg Thr
                85                  90

<210> SEQ ID NO 42
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 42

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30
```

```
Val Ile Thr Tyr Gly Glu Thr Gly Asn Ser Pro Val Gln Glu Phe
            35                  40                  45

Glu Val Pro Gly Ser Lys Ser Thr Ala Thr Ile Ser Gly Leu Ser Pro
 50                  55                  60

Gly Val Asp Tyr Thr Ile Thr Val Tyr Ala Thr Tyr Gly Asp Ala Tyr
 65                  70                  75                  80

Trp His Tyr Tyr Ser Pro Ile Ser Ile Asn Tyr Arg Thr
                85                  90

<210> SEQ ID NO 43
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 43

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Val His Tyr
            20                  25                  30

His Ile Thr Tyr Gly Glu Thr Gly Asn Ser Pro Val Gln Glu Phe
            35                  40                  45

Thr Val Pro Gly Ser Lys Ser Thr Ala Thr Ile Ser Gly Leu Ser Pro
 50                  55                  60

Gly Val Asp Tyr Thr Ile Thr Val Tyr Ala Asp Trp Gln Tyr Ser Tyr
 65                  70                  75                  80

Met Tyr Ser Pro Ile Ser Ile Asn Tyr Arg Thr
                85                  90

<210> SEQ ID NO 44
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 44

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Asp Phe Tyr Val Tyr
            20                  25                  30

Leu Ile Thr Tyr Gly Glu Thr Gly Asn Ser Pro Val Gln Glu Phe
            35                  40                  45

Thr Val Pro Gly Ser Lys Ser Thr Ala Thr Ile Ser Gly Leu Ser Pro
 50                  55                  60

Gly Val Asp Tyr Thr Ile Thr Val Tyr Gly Tyr Ser Asp Ser Trp Asn
 65                  70                  75                  80

Trp Pro Tyr Ser Pro Ile Ser Ile Asn Tyr Arg Thr
                85                  90

<210> SEQ ID NO 45
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide
```

<400> SEQUENCE: 45

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Phe Ser Phe Gly Ser Ser Gln Thr
        35                  40                  45

Phe Lys Val Pro Gly Ser Lys Ser Thr Ala Thr Ile Ser Gly Leu Ser
    50                  55                  60

Pro Gly Val Asp Tyr Thr Ile Thr Val Tyr Ala Phe Tyr Trp Ser Lys
65                  70                  75                  80

Tyr Tyr Ser Pro Ile Ser Ile Asn Tyr Arg Thr
                85                  90

<210> SEQ ID NO 46
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 46

Val Ser Ser Val Pro Thr Lys Leu Glu Val Val Ala Ala Thr Pro Thr
1               5                   10                  15

Ser Leu Leu Ile Ser Trp Asp Ala Pro Ala Val Asp Leu Tyr Val Tyr
            20                  25                  30

Leu Ile Thr Tyr Gly Glu Thr Gly Val Ala Ser Trp Gly Tyr Gln Glu
        35                  40                  45

Phe Thr Val Pro Gly Ser Lys Ser Thr Ala Thr Ile Ser Gly Leu Ser
    50                  55                  60

Pro Gly Val Asp Tyr Thr Ile Thr Val Tyr Ala Tyr Gly Gly Asn Tyr
65                  70                  75                  80

Trp Tyr Ser Pro Ile Ser Ile Asn Tyr Arg Thr
                85                  90

<210> SEQ ID NO 47
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 47

Val Ser Ser Val Pro Thr Lys Leu Glu Val Val Ala Ala Thr Pro Thr
1               5                   10                  15

Ser Leu Leu Ile Ser Trp Asp Ala Pro Ala Val His Tyr Tyr Val Tyr
            20                  25                  30

Leu Ile Thr Tyr Gly Glu Thr Gly Tyr Tyr Ser Tyr Gly Gln Glu Phe
        35                  40                  45

Glu Val Pro Gly Ser Lys Ser Thr Ala Thr Ile Ser Gly Leu Ser Pro
    50                  55                  60

Gly Val Asp Tyr Thr Ile Thr Val Tyr Ala Tyr Asn Gly Ser Gly Trp
65                  70                  75                  80

Met Val Gln Ser Pro Ile Ser Ile Asn Tyr Arg Thr
                85                  90

<210> SEQ ID NO 48
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 48

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

Tyr Ile Thr Tyr Gly Glu Thr Gly Ala Tyr Trp Tyr Ser Gln Ala Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Ser Thr Lys Phe Asn Gln
65                  70                  75                  80

Tyr Ser Pro Ile Ser Ile Asn Tyr Arg Thr
                85                  90

<210> SEQ ID NO 49
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 49

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

His Ile Thr Tyr Gly Glu Thr Gly His Tyr Trp Tyr Tyr Gln Ala Phe
        35                  40                  45

Ala Val Pro Gly Ser Lys Ser Thr Ala Thr Ile Ser Gly Leu Ser Pro
    50                  55                  60

Gly Val Asp Tyr Thr Ile Thr Val Tyr Ala Ser Ser Ile Asp Tyr Met
65                  70                  75                  80

Tyr Ser Pro Ile Ser Ile Asn Tyr Arg Thr
                85                  90

<210> SEQ ID NO 50
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 50

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Tyr Ile Thr Tyr Gly Glu Thr Gly Gly Tyr Trp Phe Pro Ser Thr Phe
        35                  40                  45

Thr Val Pro Gly Ser Lys Ser Thr Ala Thr Ile Ser Gly Leu Ser Pro

-continued

```
                    50                  55                  60
Gly Val Asp Tyr Thr Ile Thr Val Tyr Ala Ser Met Ser Pro Ser Gly
 65                  70                  75                  80

Tyr Phe Tyr Ser Pro Ile Ser Ile Asn Tyr Arg Thr
                 85                  90
```

<210> SEQ ID NO 51
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 51

```
Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Asp Phe Tyr
                 20                  25                  30

Phe Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Ser Pro
         50                  55                  60

Gly Val Asp Tyr Thr Ile Thr Val Tyr Ala Tyr Gly Glu Trp Asp Trp
 65                  70                  75                  80

Trp Ser Trp Ser Pro Ile Ser Ile Asn Tyr Arg Thr
                 85                  90
```

<210> SEQ ID NO 52
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 52

```
Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Asp Tyr Tyr
                 20                  25                  30

Phe Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Ser Pro
         50                  55                  60

Gly Val Asp Tyr Thr Ile Thr Val Tyr Ala Tyr His Val Ser Phe Pro
 65                  70                  75                  80

Ser Asp Glu Glu Gly Met Ser Pro Ile Ser Ile Asn Tyr Arg Thr
                 85                  90                  95
```

<210> SEQ ID NO 53
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 53

```
Val Ser Ser Val Pro Thr Lys Leu Glu Val Val Ala Ala Thr Pro Thr
  1               5                  10                  15
```

```
Ser Leu Leu Ile Ser Trp Asp Ala Pro Ala Val Thr Val Asp Leu Tyr
            20                  25                  30

Tyr Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Ile Tyr Ala Phe Gly Ser Tyr His Tyr
65                  70                  75                  80

Trp Glu His Ser Pro Ile Ser Ile Asn Tyr Arg Thr
                85                  90

<210> SEQ ID NO 54
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 54

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Tyr Gly Glu Tyr Lys Trp
65                  70                  75                  80

Trp Ser Tyr Ser Pro Ile Ser Ile Asn Tyr Arg Thr
                85                  90

<210> SEQ ID NO 55
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 55

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Tyr Gly Gly Tyr Glu Tyr
65                  70                  75                  80

Trp Tyr Tyr Ser Pro Ile Ser Ile Asn Tyr Arg Thr
                85                  90

<210> SEQ ID NO 56
<211> LENGTH: 92
<212> TYPE: PRT
<213> ORGANISM: Artificial Sequence
```

```
<220> FEATURE:
<223> OTHER INFORMATION: synthetically constructed Fibronectin Type III
      domain polypeptide

<400> SEQUENCE: 56

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Arg Gly Tyr Phe Lys Trp
65                  70                  75                  80

Trp Glu Tyr Ser Pro Ile Ser Ile Asn Tyr Arg Thr
                85                  90

<210> SEQ ID NO 57
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 57

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Phe Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Gly Met Val Tyr Tyr Gly
65                  70                  75                  80

Trp Glu Arg Glu Ser Ser Pro Ile Ser Ile Asn Tyr Arg Thr
                85                  90

<210> SEQ ID NO 58
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 58

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val His Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Leu Tyr Glu Gly Gly Gln
65                  70                  75                  80
```

His Phe Gly Tyr Ser Phe Ser Pro Ile Ser Ile Asn Tyr Arg Thr
                85                  90                  95

<210> SEQ ID NO 59
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 59

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Tyr Gly Ser Tyr Ser Tyr
65                  70                  75                  80

Trp Met Tyr Ser Pro Ile Ser Ile Asn Tyr Arg Thr
                85                  90

<210> SEQ ID NO 60
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 60

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Gly Tyr Val Glu Trp Gln
65                  70                  75                  80

Ser Ala Lys Asn Val His Ser Pro Ile Ser Ile Asn Tyr Arg Thr
                85                  90                  95

<210> SEQ ID NO 61
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 61

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
                20                  25                  30

Asn Ile Thr Tyr Gly Glu Thr Gly Gly Ser Trp Tyr Ala Tyr Gln Thr

```
                 35                  40                  45
Phe Glu Val Pro Gly Ser Lys Ser Thr Ala Thr Ile Ser Gly Leu Ser
             50                  55                  60
Pro Gly Val Asp Tyr Thr Ile Thr Val Tyr Ala Ser Phe Ser Gly Asp
65                  70                  75                  80
Met Tyr Tyr Tyr Tyr Ser Pro Ile Ser Ile Asn Tyr Arg Thr
                 85                  90

<210> SEQ ID NO 62
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 62

Val Ser Ser Val Pro Thr Lys Leu Glu Val Val Ala Ala Thr Pro Thr
1               5                   10                  15
Ser Leu Leu Ile Ser Trp Asp Ala Pro Ala Val Thr Val Asp Tyr Tyr
                 20                  25                  30
Val Ile Thr Tyr Gly Glu Thr Gly Gly Asn Ser Pro Val Gln Glu Phe
             35                  40                  45
Thr Val Pro Gly Ser Lys Ser Thr Ala Thr Ile Ser Gly Leu Ser Pro
50                  55                  60
Gly Val Asp Tyr Thr Ile Thr Val Tyr Ala Gly Tyr Val Ala Phe Asp
65                  70                  75                  80
Tyr Tyr Trp Arg Gly Gly Tyr Ser Pro Ile Ser Ile Asn Tyr Arg Thr
                 85                  90                  95

<210> SEQ ID NO 63
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 63

Val Ser Ser Val Pro Thr Lys Leu Glu Val Val Ala Ala Thr Pro Thr
1               5                   10                  15
Ser Leu Leu Ile Ser Trp Asp Ala Pro Ala Val Thr Val His Tyr Tyr
                 20                  25                  30
Tyr Ile Thr Tyr Gly Glu Thr Gly Gly Asn Ser Pro Val Gln Glu Phe
             35                  40                  45
Thr Val Pro Gly Ser Lys Ser Thr Ala Thr Ile Ser Gly Leu Ser Pro
50                  55                  60
Gly Val Asp Tyr Thr Ile Thr Val Tyr Ala Ser Leu Trp Asp Trp Tyr
65                  70                  75                  80
Ser Ser Ser Pro Ile Ser Ile Asn Tyr Arg Thr
                 85                  90

<210> SEQ ID NO 64
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 64
```

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Phe Ile Thr Tyr Gly Glu Thr Gly Tyr Phe Ser Ser Trp Gln Glu
            35                  40                  45

Phe Thr Val Pro Gly Ser Lys Ser Thr Ala Thr Ile Ser Gly Leu Ser
50                  55                  60

Pro Gly Val Asp Tyr Thr Ile Thr Val Tyr Ala Gly Tyr Ala Gly Ser
65                  70                  75                  80

Phe Pro Ser Tyr Glu Ser Pro Ile Ser Ile Asn Tyr Arg Thr
            85                  90

<210> SEQ ID NO 65
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 65

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
50                  55                  60

Gly Val Asp Tyr Thr Ile Thr Val Tyr Ala Tyr Gly Asp Tyr Tyr Tyr
65                  70                  75                  80

Trp Leu Tyr Ser Pro Ile Ser Ile Asn Tyr Arg Thr
            85                  90

<210> SEQ ID NO 66
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 66

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
                20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
50                  55                  60

Gly Val Asp Tyr Thr Ile Thr Val Tyr Ala Tyr Gly Glu Phe Gly Trp
65                  70                  75                  80

Trp Arg Tyr Ser Pro Ile Ser Ile Asn Tyr Arg Thr
            85                  90

<210> SEQ ID NO 67

```
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 67

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
                20                  25                  30

His Ile Thr Tyr Gly Glu Thr Gly Gly Pro Trp Trp Gly Tyr Gln Thr
            35                  40                  45

Phe Ala Val Pro Gly Ser Lys Ser Thr Ala Thr Ile Ser Gly Leu Ser
        50                  55                  60

Pro Gly Val Asp Tyr Thr Ile Thr Val Tyr Thr Ser His His Pro
65                  70                  75                  80

Gly Trp Trp Ser Pro Ile Ser Ile Asn Tyr Arg Thr
                85                  90

<210> SEQ ID NO 68
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 68

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
                20                  25                  30

Val Ile Thr Tyr Gly Glu Thr Gly Tyr Tyr Ala Tyr Ser Tyr Gln Thr
            35                  40                  45

Phe Thr Val Pro Gly Ser Lys Ser Thr Ala Thr Ile Ser Gly Leu Ser
        50                  55                  60

Pro Gly Val Asp Tyr Thr Ile Thr Val Tyr Ala Trp Ser Tyr Phe Asp
65                  70                  75                  80

Gly Pro Val Tyr Ser Pro Ile Ser Ile Asn Tyr Arg Thr
                85                  90

<210> SEQ ID NO 69
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 69

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
                20                  25                  30

His Ile Thr Tyr Gly Glu Thr Gly Gly Pro Trp Trp Gly Tyr Gln Thr
            35                  40                  45

Phe Ala Val Pro Gly Ser Lys Ser Thr Ala Thr Ile Ser Gly Leu Ser
        50                  55                  60
```

```
Pro Gly Val Asp Tyr Thr Ile Thr Val Tyr Thr Ser Ser His His Pro
 65                  70                  75                  80

Gly Trp Trp Ser Ser Pro Ile Ser Ile Asn Tyr Arg Thr
                 85                  90

<210> SEQ ID NO 70
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 70

Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Asp Tyr Tyr
                 20                  25                  30

His Ile Thr Tyr Gly Glu Thr Gly Ser Tyr Trp His Tyr Gln Ala Phe
             35                  40                  45

Glu Val Pro Gly Ser Lys Ser Thr Ala Thr Ile Ser Gly Leu Ser Pro
 50                  55                  60

Gly Val Asp Tyr Thr Ile Thr Val Tyr Ala Gln Thr Arg Asn Arg Tyr
 65                  70                  75                  80

Met Glu Ser Pro Ile Ser Ile Asn Tyr Arg Thr
                 85                  90

<210> SEQ ID NO 71
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 71

Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Asp Leu Tyr
                 20                  25                  30

Val Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Ser Pro
 50                  55                  60

Gly Val Asp Tyr Thr Ile Thr Val Tyr Ala Tyr Gly Asp Phe Met Tyr
 65                  70                  75                  80

Trp Lys Tyr Ser Pro Ile Ser Ile Asn Tyr Arg Thr
                 85                  90

<210> SEQ ID NO 72
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 72

Val Ser Ser Val Pro Thr Lys Leu Glu Val Val Ala Ala Thr Pro Thr
  1               5                  10                  15

Ser Leu Leu Ile Ser Trp Asp Ala Pro Ala Val Thr Val Asp Phe Tyr
```

20                  25                  30

Val Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Ser Pro
     50                  55                  60

Gly Val Asp Tyr Thr Ile Thr Val Tyr Ala Tyr Gly Tyr Gly Ser Tyr
65                  70                  75                  80

Trp Leu His Ser Pro Ile Ser Ile Asn Tyr Arg Thr
                85                  90

<210> SEQ ID NO 73
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 73

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
                20                  25                  30

His Ile Thr Tyr Gly Glu Thr Gly Ser His Tyr Trp Ser Tyr Gln Lys
                35                  40                  45

Phe Thr Val Pro Gly Ser Lys Ser Thr Ala Thr Ile Ser Gly Leu Ser
     50                  55                  60

Pro Gly Val Asp Tyr Thr Ile Thr Val Tyr Ala Ser Pro Glu Gly Arg
65                  70                  75                  80

Gly Ser Tyr Tyr Gly Trp Ser Pro Ile Ser Ile Asn Tyr Arg Thr
                85                  90                  95

<210> SEQ ID NO 74
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 74

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Asn Ile Thr Tyr Gly Glu Thr Gly Val Trp Phe Pro Tyr Gln Thr Phe
                35                  40                  45

Thr Val Pro Gly Ser Lys Ser Thr Ala Thr Ile Ser Gly Leu Ser Pro
     50                  55                  60

Gly Val Asp Tyr Thr Ile Thr Val Tyr Ala Ser Met Val Asp Tyr Glu
65                  70                  75                  80

Tyr Trp Trp Ser Pro Ile Ser Ile Asn Tyr Arg Thr
                85                  90

<210> SEQ ID NO 75
<211> LENGTH: 92
<212> TYPE: PRT
<213> ORGANISM: Artificial Sequence
<220> FEATURE:
<223> OTHER INFORMATION: synthetically constructed Fibronectin Type III domain polypeptide

<400> SEQUENCE: 75

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val His Tyr
            20                  25                  30

Leu Ile Thr Tyr Gly Glu Thr Gly Gly Ala Gly Ser Ser Tyr Gln Thr
        35                  40                  45

Phe Ala Val Pro Gly Ser Lys Ser Thr Ala Thr Ile Ser Gly Leu Ser
    50                  55                  60

Pro Gly Val Asp Tyr Thr Ile Thr Val Tyr Ala Tyr Met Ser Asn Tyr
65                  70                  75                  80

Tyr Ser Tyr Ser Pro Ile Ser Ile Asn Tyr Arg Thr
                85                  90

<210> SEQ ID NO 76
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 76

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

His Ile Thr Tyr Gly Glu Thr Gly Gly Ser Gly Trp Gly Tyr Gln Ala
        35                  40                  45

Phe Ala Val Pro Gly Ser Lys Ser Thr Ala Thr Ile Ser Gly Leu Ser
    50                  55                  60

Pro Gly Val Asp Tyr Thr Ile Thr Val Tyr Ala Ser Ser Asp Tyr Leu
65                  70                  75                  80

Lys Tyr Tyr Ser Pro Ile Ser Ile Asn Tyr Arg Thr
                85                  90

<210> SEQ ID NO 77
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 77

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Tyr Asp Ile Gly Trp Phe
65                  70                  75                  80

Pro Ala His Tyr Gly Ser Pro Ile Ser Ile Asn Tyr Arg Thr
                85                  90

<210> SEQ ID NO 78
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 78

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Tyr
            20                  25                  30

Leu Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
        50                  55                  60

Gly Val Asp Tyr Thr Ile Thr Val Tyr Ala Tyr Ser Thr Gly Gly Ser
65                  70                  75                  80

Tyr Lys Ser Gln Ser Pro Ile Ser Ile Asn Tyr Arg Thr
                85                  90

<210> SEQ ID NO 79
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide
<220> FEATURE:
<221> NAME/KEY: VARIANT
<222> LOCATION: (30), (33)
<223> OTHER INFORMATION: Xaa = Asp, Phe, His, Ile, Leu, Asn, Val, or Tyr
<220> FEATURE:
<221> NAME/KEY: VARIANT
<222> LOCATION: (31)...(31)
<223> OTHER INFORMATION: Xaa = Phe, His, Leu, or Tyr
<220> FEATURE:
<221> NAME/KEY: VARIANT
<222> LOCATION: (47), (49)
<223> OTHER INFORMATION: Xaa = Ala, Glu, Lys, or Thr
<220> FEATURE:
<221> NAME/KEY: VARIANT
<222> LOCATION: (75)...(85)
<223> OTHER INFORMATION: Xaa = any amino acid except Cys
<220> FEATURE:
<221> NAME/KEY: VARIANT
<222> LOCATION: (86)...(89)
<223> OTHER INFORMATION: Xaa = any amino acid

<400> SEQUENCE: 79

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Xaa Xaa Tyr
            20                  25                  30

Xaa Ile Thr Tyr Gly Glu Thr Gly Gly Asn Ser Pro Val Gln Xaa Phe
            35                  40                  45

Xaa Val Pro Gly Ser Lys Ser Thr Ala Thr Ile Ser Gly Leu Ser Pro
        50                  55                  60

Gly Val Asp Tyr Thr Ile Thr Val Tyr Ala Xaa Xaa Xaa Xaa Xaa
65                  70                  75                  80

Xaa Xaa Xaa Xaa Xaa Xaa Xaa Xaa Ser Pro Ile Ser Ile Asn Tyr Arg
                85                  90                  95

<210> SEQ ID NO 80
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 80

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val His Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Leu Leu Ser Ser Ser His
65                  70                  75                  80

Trp Val Tyr Glu Ser Pro Ile Ser Ile Asn Tyr Arg Thr
                85                  90

<210> SEQ ID NO 81
<211> LENGTH: 96
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 81

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Leu Ile Thr Tyr Gly Glu Thr Gly Gly Asn Ser Pro Val Gln Glu Phe
        35                  40                  45

Lys Val Pro Gly Ser Lys Ser Thr Ala Thr Ile Ser Gly Leu Ser Pro
    50                  55                  60

Gly Val Asp Tyr Thr Ile Thr Val Tyr Ala Gly Ser Asp Tyr Tyr
65                  70                  75                  80

Tyr Tyr Gln Gly Ala Tyr Trp Ser Pro Ile Ser Ile Asn Tyr Arg Thr
                85                  90                  95

<210> SEQ ID NO 82
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 82

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Ser Pro

Gly Val Asp Tyr Thr Ile Thr Val Tyr Ala Asn Trp Ala Tyr Ser Tyr
65                  70                  75                  80

Arg Tyr Ser Pro Ile Ser Ile Asn Tyr Arg Thr
                85                  90

<210> SEQ ID NO 83
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 83

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Tyr Tyr
                20                  25                  30

Val Ile Thr Tyr Gly Glu Thr Gly Gly Asn Ser Pro Val Gln Glu Phe
            35                  40                  45

Glu Val Pro Gly Ser Lys Ser Thr Ala Thr Ile Ser Gly Leu Ser Pro
    50                  55                  60

Gly Val Asp Tyr Thr Ile Thr Val Tyr Ala Asn Tyr Pro Tyr Ser Tyr
65                  70                  75                  80

Met Tyr Ser Pro Ile Ser Ile Asn Tyr Arg Thr
                85                  90

<210> SEQ ID NO 84
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 84

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
                20                  25                  30

Leu Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Asp Pro Tyr Trp Asp
65                  70                  75                  80

Val Met Ser Pro Ile Ser Ile Asn Tyr Arg Thr
                85                  90

<210> SEQ ID NO 85
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 85

Val Ser Ser Val Pro Thr Lys Leu Glu Val Val Ala Ala Thr Pro Thr
1               5                   10                  15

```
Ser Leu Leu Ile Ser Trp Asp Ala Pro Ala Val Thr Val Asp Leu Tyr
            20                  25                  30

Val Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Ser Pro
50                  55                  60

Gly Val Asp Tyr Thr Ile Thr Val Tyr Ala Gly Trp Gly Asn Trp Glu
65                  70                  75                  80

Leu Gly Tyr Ser Trp Ser Ser Pro Ile Ser Ile Asn Tyr Arg Thr
                85                  90                  95

<210> SEQ ID NO 86
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide
<220> FEATURE:
<221> NAME/KEY: VARIANT
<222> LOCATION: (31), (76)
<223> OTHER INFORMATION: Xaa = Asp, His, Asn, or Tyr
<220> FEATURE:
<221> NAME/KEY: VARIANT
<222> LOCATION: (33)...(33)
<223> OTHER INFORMATION: Xaa = Ala, Asp, Glu, Gly, His, Lys, Asn, Pro,
      Gln, Arg, Ser, or Thr
<220> FEATURE:
<221> NAME/KEY: VARIANT
<222> LOCATION: (73), (80), (82)
<223> OTHER INFORMATION: Xaa = Ala, Asp, Phe, His, Ile, Leu, Asn, Pro,
      Ser, Thr, Val, or Tyr
<220> FEATURE:
<221> NAME/KEY: VARIANT
<222> LOCATION: (75), (83), (85)
<223> OTHER INFORMATION: Xaa = Asp, Phe, His, Ile, Leu, Asn, Val, or Tyr
<220> FEATURE:
<221> NAME/KEY: VARIANT
<222> LOCATION: (78)...(78)
<223> OTHER INFORMATION: Xaa = Ala, Asp, Glu, Gly, His, Ile, Lys, Leu,
      Met, Asn, Pro, Gln, Arg, Ser, Thr, Val or Tyr
<220> FEATURE:
<221> NAME/KEY: VARIANT
<222> LOCATION: (79)...(79)
<223> OTHER INFORMATION: Xaa = Asp, Glu, His, Lys, Asn, Gln, or Tyr
<220> FEATURE:
<221> NAME/KEY: VARIANT
<222> LOCATION: (81)...(81)
<223> OTHER INFORMATION: Xaa = Phe, Ile, Leu, or Val
<220> FEATURE:
<221> NAME/KEY: VARIANT
<222> LOCATION: (84)...(84)
<223> OTHER INFORMATION: Xaa = Ala or Ser

<400> SEQUENCE: 86

Val Ser Ser Val Pro Thr Lys Leu Glu Val Val Ala Ala Thr Pro Thr
 1               5                  10                  15

Ser Leu Leu Ile Ser Trp Asp Ala Ser Ser Ser Val Ser Xaa Tyr
            20                  25                  30

Xaa Ile Thr Tyr Gly Glu Thr Gly Gly Asn Ser Pro Val Gln Glu Phe
            35                  40                  45

Thr Val Pro Gly Ser Ser Ser Thr Ala Thr Ile Ser Gly Leu Ser Pro
50                  55                  60

Gly Val Asp Tyr Thr Ile Thr Val Xaa Ala Xaa Xaa Ser Xaa Xaa Xaa
65                  70                  75                  80

Xaa Xaa Xaa Xaa Xaa Ser Pro Ser Ser Ile Asn Tyr Arg Thr
                85                  90
```

<210> SEQ ID NO 87
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 87

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser His Tyr
            20                  25                  30

His Ile Thr Tyr Gly Glu Thr Gly Gly Asn Ser Pro Val Gln Glu Phe
            35                  40                  45

Thr Val Pro Gly Ser Ser Thr Ala Thr Ile Ser Gly Leu Ser Pro
        50                  55                  60

Gly Val Asp Tyr Thr Ile Thr Val Tyr Ala Phe Tyr Ser Asp Asp
65                  70                  75                  80

Leu Tyr Phe Ala Phe Ser Pro Ser Ser Ile Asn Tyr Arg Thr
                85                  90

<210> SEQ ID NO 88
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 88

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser His Tyr
            20                  25                  30

Gly Ile Thr Tyr Gly Glu Thr Gly Gly Asn Ser Pro Val Gln Glu Phe
            35                  40                  45

Thr Val Pro Gly Ser Ser Thr Ala Thr Ile Ser Gly Leu Ser Pro
        50                  55                  60

Gly Val Asp Tyr Thr Ile Thr Val Tyr Ala Tyr His Ser Tyr Asp Asp
65                  70                  75                  80

Ile Tyr Tyr Ala Leu Ser Pro Ser Ser Ile Asn Tyr Arg Thr
                85                  90

<210> SEQ ID NO 89
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 89

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser His Tyr
            20                  25                  30

Ala Ile Thr Tyr Gly Glu Thr Gly Gly Asn Ser Pro Val Gln Glu Phe
            35                  40                  45

```
Thr Val Pro Gly Ser Ser Thr Ala Thr Ile Ser Gly Leu Ser Pro
        50                  55                  60

Gly Val Asp Tyr Thr Ile Thr Val Tyr Ala Tyr His Ser Tyr Asp Asp
 65                  70                  75                  80

Ile Phe Leu Ala Asp Ser Pro Ser Ser Ile Asn Tyr Arg Thr
                 85                  90
```

<210> SEQ ID NO 90
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 90

```
Val Ser Ser Val Pro Thr Lys Leu Glu Val Val Ala Ala Thr Pro Thr
 1               5                  10                  15

Ser Leu Leu Ile Ser Trp Asp Ala Ser Ser Ser Val Ser His Tyr
                 20                  25                  30

Glu Ile Thr Tyr Gly Glu Thr Gly Gly Asn Ser Pro Val Gln Glu Phe
             35                  40                  45

Thr Val Pro Gly Ser Ser Ser Thr Ala Thr Ile Ser Gly Leu Ser Pro
        50                  55                  60

Gly Val Asp Tyr Thr Ile Thr Val Tyr Ala Tyr Tyr Ser His Glu Asp
 65                  70                  75                  80

Ile Phe Tyr Ala Val Ser Pro Ser Ser Ile Asn Tyr Arg Thr
                 85                  90
```

<210> SEQ ID NO 91
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 91

```
Val Ser Ser Val Pro Thr Lys Leu Glu Val Val Ala Ala Thr Pro Thr
 1               5                  10                  15

Ser Leu Leu Ile Ser Trp Asp Ala Ser Ser Ser Val Ser His Tyr
                 20                  25                  30

Glu Ile Thr Tyr Gly Glu Thr Gly Gly Asn Ser Pro Val Gln Glu Phe
             35                  40                  45

Thr Val Pro Gly Ser Ser Ser Thr Ala Thr Ile Ser Gly Leu Ser Pro
        50                  55                  60

Gly Val Asp Tyr Thr Ile Thr Val Ala Ala Tyr His Ser Tyr His Asp
 65                  70                  75                  80

Ile Phe Tyr Ala Val Ser Pro Ser Ser Ile Asn Tyr Arg Thr
                 85                  90
```

<210> SEQ ID NO 92
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 92

```
Val Ser Ser Val Pro Thr Lys Leu Glu Val Val Ala Ala Thr Pro Thr
```

```
                  1               5                  10                  15
Ser Leu Leu Ile Ser Trp Asp Ala Ser Ser Ser Val Ser His Tyr
                20                  25                  30

Glu Ile Thr Tyr Gly Glu Thr Gly Gly Asn Ser Pro Val Gln Glu Phe
                35                  40                  45

Thr Val Pro Gly Ser Ser Thr Ala Thr Ile Ser Gly Leu Ser Pro
            50                  55                  60

Gly Val Asp Tyr Thr Ile Thr Val Thr Ala Tyr Asp Ser Tyr Tyr Asp
 65                  70                  75                  80

Ile Tyr Ile Ala Tyr Ser Pro Ser Ser Ile Asn Tyr Arg Thr
                85                  90
```

<210> SEQ ID NO 93
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 93

```
Val Ser Ser Val Pro Thr Lys Leu Glu Val Val Ala Ala Thr Pro Thr
 1               5                  10                  15

Ser Leu Leu Ile Ser Trp Asp Ala Ser Ser Ser Val Ser Tyr Tyr
                20                  25                  30

Glu Ile Thr Tyr Gly Glu Thr Gly Gly Asn Ser Pro Val Gln Glu Phe
                35                  40                  45

Thr Val Pro Gly Ser Ser Thr Ala Thr Ile Ser Gly Leu Ser Pro
            50                  55                  60

Gly Val Asp Tyr Thr Ile Thr Val Ile Ala Phe Tyr Ser His Asp Asp
 65                  70                  75                  80

Ile Tyr Ile Ser Asp Ser Pro Ser Ser Ile Asn Tyr Arg Thr
                85                  90
```

<210> SEQ ID NO 94
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 94

```
Val Ser Ser Val Pro Thr Lys Leu Glu Val Val Ala Ala Thr Pro Thr
 1               5                  10                  15

Ser Leu Leu Ile Ser Trp Asp Ala Ser Ser Ser Val Ser His Tyr
                20                  25                  30

Ala Ile Thr Tyr Gly Glu Thr Gly Gly Asn Ser Pro Val Gln Glu Phe
                35                  40                  45

Thr Val Pro Gly Ser Ser Thr Ala Thr Ile Ser Gly Leu Ser Pro
            50                  55                  60

Gly Val Asp Tyr Thr Ile Thr Val Tyr Ala Tyr Tyr Ser Tyr Asp
 65                  70                  75                  80

Leu Tyr Val Ser Asp Ser Pro Ser Ser Ile Asn Tyr Arg Thr
                85                  90
```

<210> SEQ ID NO 95
<211> LENGTH: 94
<212> TYPE: PRT

<213> ORGANISM: Artificial Sequence
<220> FEATURE:
<223> OTHER INFORMATION: synthetically constructed Fibronectin Type III
      domain polypeptide

<400> SEQUENCE: 95

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser His Tyr
            20                  25                  30

Ala Ile Thr Tyr Gly Glu Thr Gly Gly Asn Ser Pro Val Gln Glu Phe
        35                  40                  45

Thr Val Pro Gly Ser Ser Ser Thr Ala Thr Ile Ser Gly Leu Ser Pro
    50                  55                  60

Gly Val Asp Tyr Thr Ile Thr Val Phe Ala Tyr Tyr Ser Tyr Asp Asp
65                  70                  75                  80

Ile Tyr Tyr Ala Tyr Ser Pro Ser Ser Ile Asn Tyr Arg Thr
                85                  90

<210> SEQ ID NO 96
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 96

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser His Tyr
            20                  25                  30

Asp Ile Thr Tyr Gly Glu Thr Gly Gly Asn Ser Pro Val Gln Glu Phe
        35                  40                  45

Thr Val Pro Gly Ser Ser Ser Thr Ala Thr Ile Ser Gly Leu Ser Pro
    50                  55                  60

Gly Val Asp Tyr Thr Ile Thr Val His Ala Tyr Tyr Ser Tyr Asp Asp
65                  70                  75                  80

Ile Tyr Val Ala Ile Ser Pro Ser Ser Ile Asn Tyr Arg Thr
                85                  90

<210> SEQ ID NO 97
<211> LENGTH: 93
<212> TYPE: PRT
<213> ORGANISM: Homo sapiens
<220> FEATURE:
<223> OTHER INFORMATION: Fibronectin Type III repeat 07 domain
      polypeptide

<400> SEQUENCE: 97

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
    50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro
                85                  90

<210> SEQ ID NO 98
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 98

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Ala Tyr Tyr Ile Tyr Thr Tyr Lys Ser Asp Lys Thr Arg Tyr Leu Glu
        35                  40                  45

Glu Val Val His Ala Asp Gln Ser Ser Cys Thr Phe Asp Asn Leu Ser
    50                  55                  60

Pro Gly Leu Tyr Tyr Gly Val Gly Ala Val Thr Val Arg Pro His
65                  70                  75                  80

Pro Thr Ala Gly Pro Ile Ser Asp Thr Ile Ile Pro
                85                  90

<210> SEQ ID NO 99
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 99

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

His Tyr Leu Ile Tyr Thr Tyr Gly His His Ser Ala Gly Leu Glu Glu
        35                  40                  45

Val Val His Ala Asp Gln Ser Ser Cys Thr Phe Asp Asn Leu Ser Pro
    50                  55                  60

Gly Leu Gly Tyr Ser Val Tyr Val Asn Thr Val Ala Tyr Lys Thr Met
65                  70                  75                  80

Gly Pro Ile Ser Asp Thr Ile Ile Pro
                85

<210> SEQ ID NO 100
<211> LENGTH: 94
<212> TYPE: PRT
<213> ORGANISM: Homo sapiens
<220> FEATURE:
<223> OTHER INFORMATION: Fibronectin Type III repeat 10 domain
      polypeptide

<400> SEQUENCE: 100

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

```
Arg Ile Thr Tyr Gly Glu Gly Gly Asn Ser Pro Val Gln Glu Phe
         35                  40                  45

Thr Val Pro Gly Ser Lys Ser Thr Ala Thr Ile Ser Gly Leu Lys Pro
 50                  55                  60

Gly Val Asp Tyr Thr Ile Thr Val Tyr Ala Val Thr Gly Arg Gly Asp
 65                  70                  75                  80

Ser Pro Ala Ser Ser Lys Pro Ile Ser Ile Asn Tyr Arg Thr
                 85                  90

<210> SEQ ID NO 101
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 101

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Thr Tyr
             20                  25                  30

Tyr Ile Met Tyr Ser Leu Trp Gln His Tyr Val Thr Asn Ala Leu Gln
         35                  40                  45

Glu Phe Thr Val Pro Gly Ser Lys Ser Thr Ala Thr Ile Ser Gly Leu
 50                  55                  60

Lys Pro Gly Val Phe Tyr Gly Ile Leu Val Tyr Ala Val Ser Trp Trp
 65                  70                  75                  80

Ser Arg Trp Pro Ile Ser Ile Asn Tyr Arg Thr
                 85                  90

<210> SEQ ID NO 102
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 102

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Ser Tyr
             20                  25                  30

Tyr Ile Lys Tyr Ser Thr Cys Ser His Tyr Val Arg Ser Gly Val Gly
         35                  40                  45

Gln Glu Phe Thr Val Pro Gly Ser Lys Ser Thr Ala Thr Ile Ser Gly
 50                  55                  60

Leu Lys Pro Gly Val Asp Tyr Met Ile Asp Val Asn Ala Val Leu Ser
 65                  70                  75                  80

Glu Gly Arg Gly Asp Pro Ile Ser Ile Asn Tyr Arg Thr
                 85                  90

<210> SEQ ID NO 103
<211> LENGTH: 84
<212> TYPE: PRT
<213> ORGANISM: Artificial Sequence
<220> FEATURE:
<223> OTHER INFORMATION: synthetically constructed Fibronectin Type III
      domain polypeptide
```

<400> SEQUENCE: 103

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Gly Tyr
            20                  25                  30

Thr Thr Tyr Ser Tyr Arg Asp Ser Gln Glu Phe Thr Val Pro Gly Ser
        35                  40                  45

Lys Ser Thr Ala Thr Ile Ser Gly Leu Lys Pro Gly Val Ile Tyr Asn
50                  55                  60

Ile Leu Val Ser Ala Val Ser Glu Trp Trp Lys Tyr Pro Ile Ser Ile
65                  70                  75                  80

Asn Tyr Arg Thr

<210> SEQ ID NO 104
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 104

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Glu Ile Trp Tyr Glu Ser Tyr Phe Tyr Val Leu Trp Gln Glu Phe Thr
        35                  40                  45

Val Pro Gly Ser Lys Ser Thr Ala Thr Ile Ser Gly Leu Lys Pro Gly
50                  55                  60

Val Ser Tyr Glu Ile Thr Val Ser Ala Val Tyr Trp His Tyr Ala Tyr
65                  70                  75                  80

Pro Ile Ser Ile Asn Tyr Arg Thr
                85

<210> SEQ ID NO 105
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 105

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Leu Tyr
            20                  25                  30

Ala Ile Met Tyr Thr Ala Tyr Glu Tyr Arg Val Met Asp Ala Lys Leu
        35                  40                  45

Tyr Gln Glu Phe Thr Val Pro Gly Ser Lys Ser Thr Ala Thr Ile Ser
50                  55                  60

Gly Leu Lys Pro Gly Val Ser Tyr Tyr Ile Asn Val Ala Ala Val Tyr
65                  70                  75                  80

Leu His Arg Tyr Phe Tyr Pro Ile Ser Ile Asn Tyr Arg Thr
                85                  90

<210> SEQ ID NO 106

```
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 106

Val Ser Asp Val Pro Arg Asp Leu Glu Val Val Ala Ala Thr Pro Thr
1               5                   10                  15

Ser Leu Leu Ile Pro Trp Asp Ala Pro Ala Val Thr Val Arg Gly Tyr
            20                  25                  30

Lys Ile Asp Tyr Val Val Gln Thr Trp Ala Tyr Tyr Gln Glu Phe Thr
        35                  40                  45

Val Pro Gly Ser Lys Ser Thr Ala Thr Ile Ser Gly Leu Lys Pro Gly
    50                  55                  60

Val Ser Tyr Ala Ile Thr Val Leu Ala Val Tyr Arg Trp Tyr Tyr Ser
65                  70                  75                  80

Pro Ile Ser Ile Asn Tyr Arg Thr
                85

<210> SEQ ID NO 107
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 107

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Gly Tyr
            20                  25                  30

Gly Ile Asp Tyr Gly Gln Arg Asp Tyr Gln Gln Gly Ser Gln Gln Glu
        35                  40                  45

Phe Thr Val Pro Gly Ser Lys Ser Thr Ala Thr Ile Ser Gly Leu Lys
    50                  55                  60

Pro Gly Val Gln Tyr Asp Ile Tyr Val Gly Ala Val Glu Thr Tyr Val
65                  70                  75                  80

Tyr Ala Arg Pro Ile Ser Ile Asn Tyr Arg Thr
                85                  90

<210> SEQ ID NO 108
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 108

Val Ser Asp Val Pro Arg Asp Leu Glu Val Val Ala Ala Thr Pro Thr
1               5                   10                  15

Ser Leu Leu Ile Ser Asp Ala Pro Ala Val Thr Val Arg Ser Tyr Tyr
            20                  25                  30

Ile Tyr Tyr Tyr Asp Tyr Asp Gly Gly Ser Val Gln Glu Phe Thr Val
        35                  40                  45

Pro Gly Ser Lys Ser Thr Ala Thr Ile Ser Gly Leu Lys Pro Gly Val
    50                  55                  60
```

```
Ser Tyr Val Ile Ser Val Ala Ala Val Trp Tyr Ala Ala Tyr Arg Tyr
 65                  70                  75                  80

Pro Ile Ser Ile Asn Tyr Arg Thr
                 85
```

<210> SEQ ID NO 109
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 109

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Asn Tyr
                 20                  25                  30

Leu Ile Asp Tyr Gly Tyr Lys Asn Tyr Ser Ile Ala Gly Gln Glu Phe
             35                  40                  45

Thr Val Pro Gly Ser Lys Ser Ile Ala Thr Ile Ser Gly Leu Lys Pro
         50                  55                  60

Gly Val Phe Tyr Ala Ile Leu Val Ala Ala Val Arg Tyr Phe Trp Tyr
 65                  70                  75                  80

Phe Pro Ile Ser Ile Asn Tyr Arg Thr
                 85
```

<210> SEQ ID NO 110
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 110

```
Ile Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Gly Tyr
                 20                  25                  30

Ser Ile His Tyr Tyr Tyr Ser Phe Thr Gly Gln Glu Phe Thr Val
             35                  40                  45

Pro Gly Ser Lys Ser Thr Ala Thr Ile Ser Gly Leu Lys Pro Gly Val
         50                  55                  60

Ser Tyr Trp Ile Arg Val Trp Ala Val Arg Phe Trp Glu Tyr Leu Pro
 65                  70                  75                  80

Pro Ile Ser Ile Asn Tyr Arg Thr
                 85
```

<210> SEQ ID NO 111
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 111

```
Val Ser Asp Val Pro Arg Asp Leu Glu Val Val Ala Ala Thr Pro Thr
  1               5                  10                  15

Ser Leu Leu Ile Ser Trp Asp Ala Pro Ala Val Thr Val Arg Gly Tyr
```

```
                  20                  25                  30

Asp Ile Ala Tyr Gly Val Asn Tyr Tyr Tyr Ser Tyr Gln Glu Phe
            35                  40                  45

Thr Val Pro Gly Ser Lys Ser Thr Ala Thr Ile Ser Gly Leu Lys Pro
    50                  55                  60

Gly Val Val Tyr Gly Ile Tyr Val Ala Ala Val Arg Tyr Trp His Tyr
65                  70                  75                  80

Leu Phe Pro Ile Ser Ile Asn Tyr Arg Thr
                85                  90

<210> SEQ ID NO 112
<211> LENGTH: 81
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 112

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ile Tyr
            20                  25                  30

Ser Ile Gly Ser Gln Glu Phe Thr Val Pro Gly Ser Lys Ser Thr Ala
        35                  40                  45

Thr Ile Ser Gly Leu Lys Pro Gly Val Trp Tyr Trp Ile Tyr Val Ala
    50                  55                  60

Ala Val Arg Ala Trp Ser Tyr Trp His Pro Ile Ser Ile Asn Tyr Arg
65                  70                  75                  80

Thr

<210> SEQ ID NO 113
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 113

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Glu Tyr
            20                  25                  30

Tyr Ile Tyr Tyr Gly Ser Ser Gln Glu Thr Glu Gly Gln Glu Phe Thr
        35                  40                  45

Val Pro Gly Ser Lys Ser Thr Ala Thr Ile Ser Gly Leu Lys Pro Gly
    50                  55                  60

Val Asn Tyr Ser Ile Gly Val Ala Ala Val Gln Asn Ile Tyr Thr Tyr
65                  70                  75                  80

Tyr Pro Ile Ser Ile Asn Tyr Arg Thr
                85

<210> SEQ ID NO 114
<211> LENGTH: 89
<212> TYPE: PRT
<213> ORGANISM: Homo sapiens
<220> FEATURE:
<223> OTHER INFORMATION: Fibronectin Type III repeat 14 domain
      polypeptide
```

<400> SEQUENCE: 114

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ser Tyr
            20                  25                  30

Glu Ile Gly Tyr Glu Tyr Ile Tyr Leu Gln Tyr Ser Gln Glu Phe Thr
        35                  40                  45

Val Pro Gly Ser Lys Ser Thr Ala Thr Ile Ser Gly Leu Lys Pro Gly
    50                  55                  60

Val Met Tyr Ser Ile Val Val Tyr Ala Val Asn Lys Val Tyr Ser Tyr
65                  70                  75                  80

Phe Pro Ile Ser Ile Asn Tyr Arg Thr
                85
```

<210> SEQ ID NO 115
<211> LENGTH: 88
<212> TYPE: PRT
<213> ORGANISM: Artificial Sequence
<220> FEATURE:
<223> OTHER INFORMATION: synthetically constructed Fibronectin Type III domain polypeptide

<400> SEQUENCE: 115

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Thr Tyr
            20                  25                  30

Ser Ile Ser Tyr Phe Asp Tyr Leu His Leu Tyr Ser Gln Glu Phe Thr
        35                  40                  45

Val Gln Gly Ser Lys Ser Thr Ala Thr Ile Ser Gly Leu Lys Pro Gly
    50                  55                  60

Val Tyr Tyr Ala Ile Tyr Val Trp Ala Val Gly Trp Trp Leu Ala Asp
65                  70                  75                  80

Pro Ile Ser Ile Asn Tyr Arg Thr
                85
```

<210> SEQ ID NO 116
<211> LENGTH: 93
<212> TYPE: PRT
<213> ORGANISM: Artificial Sequence
<220> FEATURE:
<223> OTHER INFORMATION: synthetically constructed Fibronectin Type III domain polypeptide

<400> SEQUENCE: 116

```
Val Ser Asp Val Pro Arg Asp Leu Gly Val Val Ala Ala Thr Pro Thr
1               5                   10                  15

Ser Leu Leu Ile Ser Trp Asp Ala Pro Ala Val Thr Val Arg Lys Tyr
            20                  25                  30

Met Ile Ser Tyr Thr Leu Met Gly His Leu His Tyr Gly Ala Ser Gln
        35                  40                  45

Glu Phe Thr Val Pro Gly Ser Lys Ser Thr Ala Thr Ile Ser Gly Leu
    50                  55                  60

Lys Pro Gly Val Val Tyr Tyr Gly Ile Tyr Val Leu Ala Val Ser Glu
65                  70                  75                  80

Tyr Gln Val Ala Ser Pro Ile Ser Ile Asn Tyr Arg Thr
                85                  90
```

<210> SEQ ID NO 117
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 117

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ser Tyr
            20                  25                  30

Asn Ile Ser Tyr Ser Lys Tyr His Tyr Ser Pro Ala Tyr Gln Glu Phe
        35                  40                  45

Thr Val Pro Gly Ser Lys Ser Thr Ala Thr Ile Ser Gly Leu Lys Pro
    50                  55                  60

Gly Val Gln Tyr Tyr Ile Ser Val Ser Ala Val His Ala His Asn Val
65                  70                  75                  80

Ala Gly Pro Ile Ser Ile Asn Tyr Arg Thr
            85                  90

<210> SEQ ID NO 118
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide
<220> FEATURE:
<221> NAME/KEY: VARIANT
<222> LOCATION: 68
<223> OTHER INFORMATION: Xaa = any amino acid

<400> SEQUENCE: 118

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Gly Gly
            20                  25                  30

Tyr Gly Ile Gly Tyr Ala Lys Ala Gly Ser Val Asp Ala Tyr Gln Glu
        35                  40                  45

Phe Thr Val Pro Gly Ser Lys Ser Thr Thr Ile Ser Gly Leu Lys
    50                  55                  60

Pro Gly Val Xaa Tyr Tyr Ile Tyr Val Arg Ala Val Phe Ala His Pro
65                  70                  75                  80

Ala Tyr Pro Ile Ser Ile Asn Tyr Arg Thr
            85                  90

<210> SEQ ID NO 119
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 119

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Lys Tyr
            20                  25                  30

-continued

Gln Ile Ser Tyr Gly Tyr Ser Asn Thr Asp Gln Glu Phe Thr Val
         35                  40                  45

Pro Gly Ser Lys Ser Thr Ala Thr Ile Ser Gly Leu Lys Pro Gly Val
 50                  55                  60

Asp Tyr Trp Ile Tyr Val Ser Ala Val Ala Trp Gln Ala Asp Gln Gly
 65                  70                  75                  80

Pro Ile Ser Ile Asn Tyr Arg Thr
                 85

<210> SEQ ID NO 120
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 120

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Thr Tyr
             20                  25                  30

Ser Ile Ser Tyr Arg Tyr Gly Lys Trp Ser Gly Gln Glu Phe Thr Val
         35                  40                  45

Pro Gly Ser Lys Ser Thr Ala Thr Ile Ser Gly Leu Lys Pro Gly Val
 50                  55                  60

Tyr Tyr Asp Ile Gly Val Thr Ala Val Thr Ser Val Val Ser Gly Pro
 65                  70                  75                  80

Ile Ser Ile Asn Tyr Arg Thr
                 85

<210> SEQ ID NO 121
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 121

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Gln Val
             20                  25                  30

Tyr Val Ile Ala Tyr Arg Tyr Val Arg Ser Trp Gly Gln Glu Phe
         35                  40                  45

Thr Val Pro Gly Ser Lys Ser Thr Ala Thr Ile Ser Gly Leu Lys Pro
 50                  55                  60

Gly Val Tyr Tyr Ser Ile Asn Val Leu Ala Val Tyr Tyr Arg Thr Trp
 65                  70                  75                  80

Arg Pro Ile Ser Ile Asn Tyr Arg Thr
                 85

<210> SEQ ID NO 122
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide -continued

<400> SEQUENCE: 122

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ser Tyr
            20                  25                  30

Asp Ile Ser Tyr Asn Gly Met Ala Tyr Thr Lys Thr Leu Val Gln Glu
        35                  40                  45

Phe Thr Val Pro Gly Ser Lys Ser Thr Ala Thr Ile Ser Gly Leu Lys
    50                  55                  60

Pro Gly Val Asn Tyr Leu Ile Asp Val Ile Ala Val Ser Phe Arg Arg
65                  70                  75                  80

Trp Trp Ser Pro Ile Ser Ile Asn Tyr Arg Thr
                85                  90

<210> SEQ ID NO 123
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 123

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Asn Tyr
            20                  25                  30

Ala Ile Ser Tyr Gln Asp Asp Ser Pro Tyr Val Gln Glu Phe Thr Val
        35                  40                  45

Pro Gly Ser Lys Ser Thr Ala Thr Ile Ser Gly Leu Lys Pro Gly Val
    50                  55                  60

Asn Tyr Asp Ile Ser Val Thr Ala Val Gly Trp Trp Arg Ser Gly Met
65                  70                  75                  80

Pro Ile Ser Ile Asn Tyr Arg Thr
                85

<210> SEQ ID NO 124
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 124

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Thr Tyr
            20                  25                  30

Asp Ile Gly Tyr Ser Ser Phe Asn Ser Ser Thr Leu Tyr Val Gln Glu
        35                  40                  45

Phe Thr Val Pro Gly Ser Lys Ser Thr Ala Thr Ile Ser Gly Leu Lys
    50                  55                  60

Pro Gly Val Asn Tyr Asp Ile Ser Val Thr Ala Val Arg Leu Gln Glu
65                  70                  75                  80

Ser Gln Arg Pro Ile Ser Ile Asn Tyr Arg Thr
                85                  90

-continued

```
<210> SEQ ID NO 125
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 125
```

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Glu Tyr
            20                  25                  30

Asp Ile Tyr Tyr Val Asp Ser Tyr Tyr Phe Glu Gly Gln Tyr Pro
        35                  40                  45

His Gln Glu Phe Thr Val Pro Gly Ser Lys Ser Thr Ala Thr Ile Ser
50                  55                  60

Asp Leu Lys Pro Gly Val Thr Tyr Asp Ile Gly Val Lys Ala Val Tyr
65                  70                  75                  80

Asn Gly Ser Arg Ile Val Glu Pro Ile Ser Ile Asn Tyr Arg Thr
            85                  90                  95

```
<210> SEQ ID NO 126
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 126
```

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Val Tyr
            20                  25                  30

Glu Ile Ser Tyr Tyr Ser Ser Glu Ser Tyr Leu Pro Gly Gln Glu Phe
        35                  40                  45

Thr Val Pro Gly Ser Lys Ser Thr Ala Thr Ile Ser Gly Leu Lys Pro
50                  55                  60

Gly Val Thr Tyr Asp Ile His Val Ser Val Ala Tyr Arg Gly Ala
65                  70                  75                  80

Ser Pro Ile Ser Ile Asn Tyr Arg Thr
            85

```
<210> SEQ ID NO 127
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 127
```

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Glu Tyr
            20                  25                  30

Leu Ile Gly Tyr Ala Val Thr Glu Tyr Gly Asp Arg Gln Glu Phe Thr
        35                  40                  45

Val Pro Gly Ser Lys Ser Thr Ala Thr Ile Ser Gly Leu Lys Pro Gly
50                  55                  60

```
Val Leu Tyr Asp Ile Arg Val Leu Ala Val Tyr Ala Arg Trp Pro Lys
 65                  70                  75                  80

Pro Ile Ser Ile Asn Tyr Arg Thr
                85

<210> SEQ ID NO 128
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 128

Val Ser Asp Val Pro Arg Asp Leu Glu Val Ala Ala Thr Pro Thr
  1               5                  10                  15

Ser Leu Pro Ile Ser Trp Asp Ala Pro Ala Val Thr Val Arg Tyr Tyr
                 20                  25                  30

Ser Ile Trp Tyr Tyr His Tyr Tyr Pro Tyr Ala Gln Glu Phe Thr Val
                 35                  40                  45

Pro Gly Ser Lys Ser Thr Ala Thr Ile Ser Ser Leu Lys Gln Gly Val
 50                  55                  60

Arg Tyr Phe Ile Asp Val Leu Ala Val Ala Trp Val Arg Trp Ala Tyr
 65                  70                  75                  80

Pro Ile Ser Ile Asn Tyr Arg Thr
                85

<210> SEQ ID NO 129
<211> LENGTH: 89
<212> TYPE: PRT
<213> ORGANISM: Homo sapiens
<220> FEATURE:
<223> OTHER INFORMATION: Fibronectin Type III repeat 14 domain
      polypeptide

<400> SEQUENCE: 129

Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Gly Phe
                 20                  25                  30

Gln Val Asp Ala Val Pro Ala Asn Gly Gln Thr Pro Ile Gln Arg Thr
                 35                  40                  45

Ile Lys Pro Asp Val Arg Ser Tyr Thr Ile Thr Gly Leu Gln Pro Gly
 50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
                85

<210> SEQ ID NO 130
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 130

Asn Val Ser Pro Pro Arg Arg Ala Arg Val Thr Asp Ala Thr Glu Thr
  1               5                  10                  15
```

```
Thr Ile Thr Ile Ser Trp Arg Thr Lys Thr Glu Ile Thr Ser Phe
                20                  25                  30

Trp Val Trp Ala Lys Pro Tyr Ser Tyr Trp Gly Ser Ile Gln Arg
        35                  40                  45

Thr Ile Lys Pro Asp Val Arg Ser Tyr Thr Ile Thr Gly Leu Gln Pro
    50                  55                  60

Gly Thr Trp Tyr Ala Ile Asn Leu Tyr Thr Leu Thr Tyr Arg Phe Trp
65                  70                  75                  80

Gly Asp Pro Val Val Ile Asp Ala Ser Thr
                85                  90

<210> SEQ ID NO 131
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 131

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Tyr Phe
                20                  25                  30

Gly Asp Val Ser Ala Gly Pro Ser Ser Thr Tyr Ile Glu Ser Ile Gln
        35                  40                  45

Arg Thr Ile Lys Pro Asp Val Arg Ser Tyr Thr Ile Thr Gly Leu Gln
    50                  55                  60

Pro Gly Thr Trp Tyr Asn Ile Val Leu Gln Thr Leu Tyr Ser Trp Ser
65                  70                  75                  80

Tyr Trp Pro Val Val Ile Asp Ala Ser Thr
                85                  90

<210> SEQ ID NO 132
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 132

Asn Val Ser Pro Pro Arg Arg Ala Arg Val Thr Asp Ala Thr Glu Thr
1               5                   10                  15

Thr Ile Thr Ile Ser Trp Ser Thr Lys Thr Glu Thr Ile Thr Ser Phe
                20                  25                  30

Val Val Gly Ala Arg Pro Tyr Tyr Tyr Pro Tyr Ile Gln Arg Thr Ile
        35                  40                  45

Lys Pro Asp Val Arg Ser Tyr Thr Ile Thr Gly Leu Gln Pro Gly Thr
    50                  55                  60

Val Tyr Gly Ile Trp Leu Gln Thr Leu Arg Tyr Tyr Gly Tyr Thr
65                  70                  75                  80

Pro Val Val Ile Asp Ala Ser Thr
                85

<210> SEQ ID NO 133
<211> LENGTH: 87
<212> TYPE: PRT
<213> ORGANISM: Artificial Sequence
<220> FEATURE:
```

<223> OTHER INFORMATION: synthetically constructed Fibronectin Type III
      domain polypeptide

<400> SEQUENCE: 133

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ala Phe
            20                  25                  30

Glu Val Val Ala His Pro Asn Tyr Asp Tyr Tyr Ile Gln Arg Thr Ile
        35                  40                  45

Lys Pro Asp Val Arg Ser Tyr Thr Ile Thr Gly Leu Gln Pro Gly Thr
    50                  55                  60

Ser Tyr Trp Ile Tyr Leu Tyr Thr Leu Tyr Ser Arg Arg Tyr Leu Pro
65                  70                  75                  80

Val Val Ile Asp Ala Ser Thr
                85

<210> SEQ ID NO 134
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 134

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ser Phe
            20                  25                  30

Ser Val Ile Ala Phe Pro Leu Arg Glu Arg Ala Ala Thr Ile Gln Arg
        35                  40                  45

Thr Ile Lys Pro Asp Val Arg Ser Tyr Thr Ile Thr Gly Leu Gln Pro
    50                  55                  60

Gly Thr Leu Tyr Ser Ile Ile Leu Asn Thr Leu Trp Arg Tyr Tyr Pro
65                  70                  75                  80

Ile Pro Val Val Ile Asp Ala Ser Thr
                85

<210> SEQ ID NO 135
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 135

Asn Val Ser Pro Pro His Arg Ala Arg Val Thr Asp Ala Thr Glu Thr
1               5                   10                  15

Thr Ile Thr Ile Ser Trp Arg Thr Lys Thr Glu Thr Ile Thr Asn Phe
            20                  25                  30

Leu Val Tyr Ala Tyr Pro Thr Glu His Val Arg Ile Gln Arg Thr Ile
        35                  40                  45

Lys Pro Asp Val Arg Ser Tyr Thr Ile Thr Gly Leu Gln Pro Gly Thr
    50                  55                  60

Lys Tyr Trp Ile Tyr Leu Tyr Thr Leu Ile Tyr Asn Met Tyr Tyr Pro
65                  70                  75                  80

Val Val Ile Asp Ala Ser Thr

```
<210> SEQ ID NO 136
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 136

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Ser Val Trp Ala Gln Pro Gly Tyr Leu Glu Glu Ile Gln Arg Thr Ile
        35                  40                  45

Lys Pro Asp Val Arg Ser Tyr Thr Ile Thr Gly Leu Gln Pro Gly Thr
    50                  55                  60

Ser Tyr Asp Ser Ile Ala Leu Ser Thr Leu Gly Arg Tyr Arg Trp Ser
65                  70                  75                  80

Asp Pro Val Val Ile Asp Ala Ser Thr
                85

<210> SEQ ID NO 137
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 137

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gln Phe
            20                  25                  30

His Val Thr Ala Gly Pro His Trp Val Gly Arg Ile Gln Arg Thr Ile
        35                  40                  45

Lys Pro Asp Val Arg Ser Tyr Thr Ile Thr Gly Leu Gln Pro Gly Thr
    50                  55                  60

Ala Tyr Leu Ile Tyr Ala Leu Ser Thr Leu Arg Ser Tyr Arg Tyr Gln
65                  70                  75                  80

Trp Pro Val Val Ile Asp Ala Ser Thr
                85

<210> SEQ ID NO 138
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 138

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Tyr Phe
            20                  25                  30

His Val Ser Ala Leu Pro Leu Val Tyr Gly Ser Tyr Ile Gln Arg Thr
        35                  40                  45
```

Ile Lys Pro Asp Val Arg Ser Tyr Thr Ile Thr Gly Leu Gln Pro Gly
 50                  55                  60

Thr Thr Tyr Asp Ile Tyr Leu Ser Thr Leu Asn Ser His Trp Leu Thr
 65                  70                  75                  80

Ala Pro Val Val Ile Asp Ala Ser Thr
                 85

<210> SEQ ID NO 139
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 139

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Arg Phe
                 20                  25                  30

Tyr Val Glu Ala Thr Pro Ser Ala Ala Ala Asn Thr Ser Ile Gln Arg
             35                  40                  45

Thr Ile Lys Pro Asp Val Arg Ser Tyr Thr Ile Thr Gly Leu Gln Pro
 50                  55                  60

Gly Thr Met Tyr Gln Ile Trp Leu Ala Thr Leu Ser Tyr Tyr Ala Ser
 65                  70                  75                  80

His Tyr Pro Val Val Ile Asp Ala Ser Thr
                 85                  90

<210> SEQ ID NO 140
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 140

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Ser Phe
                 20                  25                  30

Gly Val Thr Ala Lys Pro Val Trp Ser Trp Gly Ser Ile Gln Arg Thr
             35                  40                  45

Ile Lys Pro Asp Val Arg Ser Tyr Thr Ile Thr Gly Leu Gln Pro Gly
 50                  55                  60

Thr Gly Tyr Ala Ile Ser Leu Tyr Thr Leu Leu Arg Tyr Trp Tyr Arg
 65                  70                  75                  80

Tyr Tyr Pro Val Val Ile Asp Ala Ser Thr
                 85                  90

<210> SEQ ID NO 141
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 141

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Thr Ala Phe
            20                  25                  30

Tyr Val Gln Ala Tyr Pro Tyr Ser Asp His Ser Ile Gln Arg Thr Ile
            35                  40                  45

Lys Pro Asp Val Arg Ser Tyr Thr Ile Thr Gly Leu Gln Pro Gly Thr
        50                  55                  60

Tyr Tyr Asp Ile Thr Leu Ser Thr Leu Arg Ser Tyr Tyr Tyr Arg Pro
65                  70                  75                  80

Val Val Ile Asp Ala Ser Thr
                85

<210> SEQ ID NO 142
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 142

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
            35                  40                  45

Leu Glu Glu Val Val His Ala Asp Gln Ser Ser Cys Thr Phe Asp Asn
        50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro
                85                  90

<210> SEQ ID NO 143
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 143

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Gly Tyr Thr Ile Val Ala Val Ser Tyr Ser Phe Tyr Tyr Tyr Leu Glu
            35                  40                  45

Glu Val Val His Ala Asp Gln Ser Ser Cys Thr Phe Asp Asn Leu Ser
        50                  55                  60

Pro Gly Leu Ser Tyr Asp Glu Val Tyr Val Thr Val Ala Tyr Lys
65                  70                  75                  80

Ser His Gly Val Pro Ile Ser Asp Thr Ala Pro Ser
                85                  90

<210> SEQ ID NO 144
<211> LENGTH: 94

```
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 144

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 145
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 145

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Thr Tyr
            20                  25                  30

Gln Ile Gly Tyr Gly Tyr Asn Arg Gly Thr Ser Gln Glu Phe Thr Val
        35                  40                  45

Pro Gly Ser Lys Ser Thr Ala Thr Ile Ser Gly Leu Lys Pro Gly Val
    50                  55                  60

Ser Tyr Gly Ile Tyr Val Tyr Ala Val Tyr Glu Trp Ser Tyr Ser Pro
65                  70                  75                  80

Ile Ser Ile Asn Tyr Arg Thr
                85

<210> SEQ ID NO 146
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 146

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Ser Ile Thr Tyr Thr Tyr Tyr Gln Ala Phe Gly Thr Gln Glu Phe Thr
        35                  40                  45

Val Pro Gly Ser Lys Ser Thr Ala Thr Ile Ser Gly Leu Lys Pro Gly
    50                  55                  60

Val Gly Tyr Tyr Ile Gln Val Tyr Ala Val Gly Asp Arg Val Ser Asn
```

```
                65                  70                  75                  80
Gly Gly Pro Ile Ser Ile Asn Tyr Arg Thr
                    85                  90

<210> SEQ ID NO 147
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 147

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Gly Ile Tyr Tyr Ser Met Ser Ser Tyr Gly Arg Gln Glu Phe Thr Val
                35                  40                  45

Pro Gly Ser Lys Ser Thr Ala Thr Ile Ser Gly Leu Lys Pro Gly Val
        50                  55                  60

Thr Tyr Gln Ile Tyr Met Ser Ala Val Asp Asn Trp Gly Val Gly Tyr
65                  70                  75                  80

Pro Ile Ser Ile Asn Tyr Arg Thr
                85

<210> SEQ ID NO 148
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 148

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
                35                  40                  45

Ile Lys Pro Asp Val Arg Ser Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 149
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 149

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Ser Phe
                20                  25                  30
```

```
Thr Val Trp Ala Ser Pro Arg Ser Tyr Thr His Ile Gln Arg Thr Ile
            35                  40                  45

Lys Pro Asp Val Arg Ser Tyr Thr Ile Thr Gly Leu Gln Pro Gly Thr
 50                  55                  60

Tyr Tyr Arg Ile Tyr Leu Tyr Thr Leu Tyr Asn Thr Tyr Phe Ser Pro
 65                  70                  75                  80

Val Val Ile Asp Ala Ser Thr
                85
```

<210> SEQ ID NO 150
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 150

```
Asn Val Ser Pro Pro Arg His Ala Arg Val Thr Asp Ala Thr Glu Thr
 1               5                  10                  15

Thr Ile Thr Ile Ser Trp Arg Thr Lys Thr Glu Thr Ile Thr Ser Phe
            20                  25                  30

Arg Val Trp Ala Ala Pro Thr Met Tyr Gln Tyr Leu Tyr Ile Gln Arg
            35                  40                  45

Thr Ile Lys Pro Asp Val Arg Ser Tyr Thr Ile Thr Gly Leu Gln Pro
 50                  55                  60

Gly Thr Tyr Tyr Gln Ala Ile Ile Leu Gly Thr Leu Ser Thr Ser Asn
 65                  70                  75                  80

Thr Pro Ser Pro Val Val Ile Asp Ala Ser Thr
                85                  90
```

<210> SEQ ID NO 151
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 151

```
Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Ser Phe
            20                  25                  30

Phe Val Gln Ala Tyr Pro Tyr Gly Glu Leu Tyr Ile Gln Arg Thr Ile
            35                  40                  45

Lys Pro Asp Val Arg Ser Tyr Thr Ile Thr Gly Leu Gln Pro Gly Thr
 50                  55                  60

Ser Tyr Gly Ile Arg Leu Ser Thr Leu Ile Asp Ser Asp Ser Tyr Gly
 65                  70                  75                  80

Pro Val Val Ile Asp Ala Ser Thr
                85
```

<210> SEQ ID NO 152
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 152

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Arg Phe
            20                  25                  30

Thr Val Ala His Pro Gly Tyr Pro Gly Tyr Ile Gln Arg Thr Ile
        35                  40                  45

Lys Pro Asp Val Arg Ser Tyr Thr Ile Thr Gly Leu Gln Pro Gly Thr
    50                  55                  60

Tyr Tyr Ser Ile Asp Leu Arg Thr Leu Ala Tyr Ala Gln Gly Tyr Ser
65                  70                  75                  80

Pro Val Val Ile Asp Ala Ser Thr
                85

<210> SEQ ID NO 153
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 153

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Arg Phe
            20                  25                  30

Thr Val Thr Ala Asp Pro Trp Tyr Trp Tyr Gly Ile Gln Arg Thr Ile
        35                  40                  45

Lys Pro Asp Val Arg Ser Tyr Thr Ile Thr Gly Leu Gln Pro Gly Thr
    50                  55                  60

Tyr Tyr Ser Gly Ile Val Leu Asp Thr Leu Ser Trp Val Ser Gly Gly
65                  70                  75                  80

Tyr Pro Val Val Ile Asp Ala Ser Thr
                85

<210> SEQ ID NO 154
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 154

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Asn Phe
            20                  25                  30

Ser Val Gln Ala Gly Pro Ser Ile Tyr Tyr Gly Tyr Tyr Ile Gln Arg
        35                  40                  45

Thr Ile Lys Pro Asp Val Arg Ser Tyr Thr Ile Thr Gly Leu Gln Pro
    50                  55                  60

Gly Thr Gln Tyr Ser Ile Ser Leu Arg Thr Leu Trp Arg Trp Tyr Gly
65                  70                  75                  80

Thr Tyr Trp Pro Val Val Ile Asp Ala Ser Thr
                85                  90

<210> SEQ ID NO 155
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 155

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
            20                  25                  30

Leu Val Asn Ala Trp Pro His Trp Ala Asn Val Ile Gln Arg Thr Ile
        35                  40                  45

Lys Pro Asp Val Arg Ser Tyr Thr Ile Thr Gly Leu Gln Pro Gly Thr
    50                  55                  60

Phe Tyr Val Ile Tyr Leu Ala Thr Leu Gln Tyr Ser Ser Val Tyr Ser
65                  70                  75                  80

Pro Val Val Ile Asp Ala Ser Thr
                85

<210> SEQ ID NO 156
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 156

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ser Phe
            20                  25                  30

Ala Val His Ala Gln Pro Val Tyr Ala Asn Trp Ile Gln Arg Thr Ile
        35                  40                  45

Lys Pro Asp Val Arg Ser Tyr Thr Ile Thr Gly Leu Gln Pro Gly Thr
    50                  55                  60

Tyr Tyr Gly Ile Asn Leu Ala Thr Leu Tyr Gly Pro Asn Tyr Trp Pro
65                  70                  75                  80

Val Val Ile Asp Ala Ser Thr
                85

<210> SEQ ID NO 157
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 157

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Tyr Phe
            20                  25                  30

Ser Val Phe Ala Tyr Pro Glu Ser Gly Ala Tyr Asn Ile Gln Arg Thr
        35                  40                  45

Ile Lys Pro Asp Val Arg Ser Tyr Thr Ile Thr Gly Leu Gln Pro Gly

```
                50              55              60

Thr Ala Tyr Asp Ile Lys Leu Asp Thr Leu Leu Ser Ser Tyr Trp Tyr
65                  70                  75                  80

His Pro Val Val Ile Asp Ala Ser Thr
                85
```

<210> SEQ ID NO 158
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 158

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Thr Phe
                20                  25                  30

Gly Val Tyr Ala Met His Pro Glu Glu Gly Tyr Tyr Tyr Ile Gln
            35                  40                  45

Arg Thr Ile Lys Pro Asp Val Arg Ser Tyr Thr Ile Thr Gly Leu Gln
        50                  55                  60

Pro Gly Thr Trp Tyr Gly Ile Gly Leu Asp Thr Leu Tyr Ser Val His
65                  70                  75                  80

Asp Glu Arg Pro Val Val Ile Asp Ala Ser Thr
                85                  90
```

<210> SEQ ID NO 159
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 159

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Arg Phe
                20                  25                  30

Tyr Val Thr Asp Ala Leu Pro Gly Asp Ala Tyr Arg Tyr His Arg Ile
            35                  40                  45

Gln Arg Thr Ile Lys Pro Asp Val Arg Ser Tyr Thr Ile Thr Gly Leu
        50                  55                  60

Gln Pro Gly Thr Leu Tyr Gly Ile Ser Leu Thr Thr Leu Tyr Tyr Ala
65                  70                  75                  80

Ser Ala Ile Pro Val Val Ile Asp Ala Ser Thr
                85                  90
```

<210> SEQ ID NO 160
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 160

```
Pro Leu Ser Pro Pro Thr Asn Leu His Leu Glu Ala Asn Pro Asp Thr
1               5                   10                  15
```

```
Gly Val Leu Thr Val Ser Trp Glu Arg Ser Thr Thr Pro Asp Ile Thr
            20                  25                  30

Gly Tyr Arg Ile Thr Thr Thr Pro Thr Asn Gly Gln Gln Gly Asn Ser
        35                  40                  45

Leu Glu Glu Val Val His Ala Asp Gln Ser Ser Cys Thr Phe Asp Asn
50                  55                  60

Leu Ser Pro Gly Leu Glu Tyr Asn Val Ser Val Tyr Thr Val Lys Asp
65                  70                  75                  80

Asp Lys Glu Ser Val Pro Ile Ser Asp Thr Ile Ile Pro
                85                  90
```

<210> SEQ ID NO 161
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 161

```
Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Arg Asp Ile Thr
            20                  25                  30

Thr Tyr Gly Ile Glu Thr Glu Tyr Asp His Ser Val Gly Leu Glu Glu
        35                  40                  45

Val Val His Ala Asp Gln Ser Ser Cys Thr Phe Asp Asn Leu Ser Pro
50                  55                  60

Gly Leu Asn Tyr Asp Val Glu Val Val Thr Val Gly Trp Gly Val Tyr
65                  70                  75                  80

Gln Arg Pro Ile Ser Asp Thr Ile Ile Pro
                85                  90
```

<210> SEQ ID NO 162
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide
<220> FEATURE:
<221> NAME/KEY: VARIANT
<222> LOCATION: 65
<223> OTHER INFORMATION: Xaa = any amino acid

<400> SEQUENCE: 162

```
Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Thr Tyr Val Ile Ser Thr Val Thr Ser His Thr Gly Pro Arg Leu Glu
        35                  40                  45

Glu Val Val His Ala Asp Gln Ser Ser Cys Thr Phe Asp Asn Leu Ser
50                  55                  60

Xaa Gly Leu Cys Tyr Asp Val Tyr Val Tyr Val Thr Val Asp Thr Ala
65                  70                  75                  80

Tyr Thr Thr Pro Ile Ser Asp Thr Ile Ile Pro
                85                  90
```

```
<210> SEQ ID NO 163
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 163

Ser Leu Ser Pro Pro Thr Asn Leu His Leu Glu Ala Asn Pro Asp Thr
1               5                   10                  15

Gly Val Leu Thr Val Gly Trp Glu Arg Ser Thr Thr Pro Gly Ile Thr
                20                  25                  30

Ser Tyr Ser Ile Asp Thr Ala Lys Asp Val Pro Tyr Leu Glu Glu
            35                  40                  45

Val Val His Ala Asp Gln Ser Ser Cys Thr Phe Asp Asn Leu Ser Pro
50                  55                  60

Gly Leu Asn Tyr Thr Val Val Ala Thr Val Gly Trp Ser Val Asp
65                  70                  75                  80

Gly Pro Ile Ser Asp Thr Ile Ile Pro
                85

<210> SEQ ID NO 164
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 164

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
                20                  25                  30

Tyr Tyr Glu Ile Asn Thr Thr Gly Tyr Tyr Gly Phe Tyr Pro Gly Gly
            35                  40                  45

Leu Glu Glu Val Val His Ala Asp Gln Ser Ser Cys Thr Phe Asp Asn
50                  55                  60

Leu Ser Pro Gly Leu Tyr Tyr Gln Val Thr Gln Thr Val Val Tyr
65                  70                  75                  80

Ser Met Trp Tyr His Pro Ile Ser Asp Thr Ile Ile Pro
                85                  90

<210> SEQ ID NO 165
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 165

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
                20                  25                  30

Tyr Tyr Gly Ile Trp Thr Leu Thr Trp Leu Gln Tyr Tyr Ser Tyr Arg
            35                  40                  45

Trp Gly Leu Glu Glu Ala Val His Ala Asp Gln Ser Ser Cys Thr Phe
50                  55                  60
```

```
Asp Asn Leu Ser Pro Gly Leu Val Tyr Leu Val Tyr Val Gly Thr Val
 65                  70                  75                  80

Arg Ser Pro Met Ala Arg Pro Ile Ser Asp Thr Ile Ile Pro
                 85                  90
```

<210> SEQ ID NO 166
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 166

```
Pro Leu Ser Pro Pro Thr Asn Leu His Leu Glu Ala Asn Pro Asp Thr
  1               5                  10                  15

Gly Val Leu Thr Val Ser Trp Glu Arg Ser Thr Thr Pro Asp Ile Thr
                 20                  25                  30

Trp Tyr Trp Ile Gly Thr Trp Tyr Ser Gly Tyr Met Val Gly Leu Glu
             35                  40                  45

Glu Val Val His Ala Asp Gln Ser Ser Cys Thr Phe Asp Asn Leu Ser
 50                  55                  60

Pro Gly Leu Thr Tyr Trp Val Leu Val Gly Thr Val Val Arg Ser Pro
 65                  70                  75                  80

Ser Arg Arg Pro Ile Ser Asp Thr Ile Ile Pro
                 85                  90
```

<210> SEQ ID NO 167
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 167

```
Pro Leu Ser Pro Pro Thr Asn Leu His Leu Glu Ala Asn Pro Asp Thr
  1               5                  10                  15

Gly Val Leu Thr Val Ser Trp Glu Arg Ser Thr Thr Pro Asp Val Thr
                 20                  25                  30

Thr Tyr Ser Ile Tyr Thr Tyr Gly Tyr Trp Asp Ser His Tyr Met Ser
             35                  40                  45

Leu Glu Glu Val Val His Ala Asp Gln Ser Arg Cys Thr Phe Asp Asn
 50                  55                  60

Leu Ser Pro Gly Leu Tyr Tyr Ser Val Glu Val Tyr Thr Val Tyr Tyr
 65                  70                  75                  80

Gly Leu Tyr Val Val Pro Ile Ser Asp Thr Ile Ile Pro
                 85                  90
```

<210> SEQ ID NO 168
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 168

```
Pro Leu Ser Pro Pro Thr Asn Leu His Leu Glu Ala Asn Pro Asp Thr
  1               5                  10                  15
```

```
Gly Val Leu Thr Val Ser Trp Glu Arg Ser Thr Thr Pro Asp Ile Thr
            20                  25                  30

Thr Tyr Gly Ile Glu Thr Gln Thr Val Glu Trp Val Tyr Tyr Leu Glu
        35                  40                  45

Glu Val Val His Ala Asp Gln Ser Ser Cys Thr Phe Asp Asn Leu Ser
50                  55                  60

Pro Gly Leu Tyr Tyr Asn Val Thr Val Gly Thr Val Met Leu Asp Ala
65                  70                  75                  80

Ala Tyr Pro Ile Ser Asp Thr Ile Ile Pro
                85                  90
```

<210> SEQ ID NO 169
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 169

```
Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Asp Tyr Tyr Ile Ile Thr Arg Ser Arg Trp Gly Tyr Leu Glu Glu Val
        35                  40                  45

Val His Ala Asp Gln Ser Ser Cys Thr Phe Asp Asn Leu Ser Pro Gly
50                  55                  60

Leu Arg Tyr His Val Tyr Val Trp Thr Val Gly His Tyr Arg Asp Pro
65                  70                  75                  80

Ile Ser Asp Thr Ile Ile Pro
                85
```

<210> SEQ ID NO 170
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 170

```
Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Asn Tyr Leu Ile Gln Thr Asp Tyr Phe Ala Phe Ile Lys Gly Val Leu
        35                  40                  45

Glu Glu Val Val His Ala Asp Gln Ser Ser Cys Thr Phe Asp Asn Leu
50                  55                  60

Ser Pro Gly Leu Tyr Tyr Val Gly Val Asp Thr Val Ser Val Pro
65                  70                  75                  80

Ser His Gly Pro Ile Ser Asp Thr Ile Ile Pro
                85                  90
```

<210> SEQ ID NO 171
<211> LENGTH: 92
<212> TYPE: PRT
<213> ORGANISM: Artificial Sequence
<220> FEATURE:

<223> OTHER INFORMATION: synthetically constructed Fibronectin Type III
      domain polypeptide

<400> SEQUENCE: 171

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Tyr Tyr Thr Ile Ala Thr Ala Asp Tyr Thr Tyr Ser Tyr Ala His Leu
        35                  40                  45

Glu Glu Val Val His Ala Asp Gln Ser Ser Cys Thr Phe Asp Asn Leu
50                  55                  60

Ser Pro Gly Leu Asn Tyr Glu Val Gly Val Gly Thr Val Ser Val Tyr
65                  70                  75                  80

Ser Tyr Ile Gly Pro Ile Ser Asp Thr Ile Ile Pro
                85                  90

<210> SEQ ID NO 172
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 172

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Tyr Tyr Ser Ile Asp Thr Trp Thr Phe Gly Gln Trp Gly Leu Glu Glu
        35                  40                  45

Val Val His Ala Asp Gln Ser Ser Cys Thr Phe Asp Asn Leu Ser Pro
50                  55                  60

Gly Leu Tyr Tyr Tyr Val Glu Val Val Thr Val Tyr Glu Trp Ala Tyr
65                  70                  75                  80

Ser Tyr Pro Ile Ser Asp Thr Ile Ile Pro
                85                  90

<210> SEQ ID NO 173
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 173

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Met Tyr Ala Ile Thr Thr Tyr Glu Tyr Ser Arg Ala Trp Gln Tyr Leu
        35                  40                  45

Glu Glu Val Val His Ala Asp Gln Ser Ser Cys Thr Phe Asp Asn Leu
50                  55                  60

Ser Pro Gly Leu Thr Tyr Tyr Val Glu Val Tyr Thr Val Arg Tyr Thr
65                  70                  75                  80

Trp Ser Asp Pro Ile Ser Asp Thr Ile Ile Pro

<210> SEQ ID NO 174
<211> LENGTH: 95
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 174

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Asp Tyr Asn Ile Ser Thr Trp Leu Tyr Thr Ser Val Ser Val Tyr Thr
        35                  40                  45

Glu Leu Glu Glu Val Val His Ala Gly Gln Ser Ser Cys Thr Phe Asp
    50                  55                  60

Asn Leu Ser Pro Gly Leu Ala Tyr Val Val Tyr Val Trp Ser Thr Val
65                  70                  75                  80

Trp Glu His Phe Tyr Pro Ser Pro Ile Ser Asp Thr Ile Ile Pro
                85                  90                  95

<210> SEQ ID NO 175
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 175

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Trp Tyr Trp Ile Asn Thr Ser Leu Ala Asn Val Arg Met Ser Leu Glu
        35                  40                  45

Glu Val Val His Ala Asp Gln Ser Gly Cys Thr Phe Asp Asn Leu Ser
    50                  55                  60

Pro Gly Leu Tyr Tyr Asp Val Gln Val Arg Thr Val Ser Ala Ala Glu
65                  70                  75                  80

Gly Tyr Pro Ile Ser Asp Thr Ile Ile Pro
                85                  90

<210> SEQ ID NO 176
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 176

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Lys Tyr Ile Ile Tyr Thr Gly Tyr Gly Ala Ser Tyr Asp Leu Glu Glu
        35                  40                  45

Val Val His Ala Asp Gln Ser Ser Cys Thr Phe Asp Asn Leu Ser Pro
 50                  55                  60

Gly Leu Lys Tyr Thr Val Thr Val Trp Thr Val Ser Tyr Ala Ser Gln
 65                  70                  75                  80

Val Pro Ile Ser Asp Thr Ile Ile Pro
                 85

<210> SEQ ID NO 177
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 177

Pro Leu Ser Pro Pro Thr Asn Leu His Leu Glu Ala Asn Pro Asp Thr
 1               5                  10                  15

Gly Val Leu Thr Val Ser Trp Glu Arg Ser Thr Thr Pro Asp Ile Thr
                 20                  25                  30

Met Tyr Ser Ile Tyr Thr Tyr Asp Tyr Thr Arg Asn Tyr Val Leu Glu
                 35                  40                  45

Glu Ala Val His Ala Asp Gln Ser Ser Cys Thr Phe Asp Asn Leu Ser
 50                  55                  60

Pro Gly Leu Tyr Gly Tyr Val Gly Val Gly Thr Val Thr Gly Ala
 65                  70                  75                  80

Gly Trp His Pro Ile Ser Asp Thr Ile Ile Pro
                 85                  90

<210> SEQ ID NO 178
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 178

Pro Leu Ser Pro Pro Thr Asn Leu His Leu Glu Val Asn Pro Asp Thr
 1               5                  10                  15

Gly Val Leu Thr Val Ser Trp Glu Arg Ser Thr Thr Pro Gly Ile Thr
                 20                  25                  30

Gln Tyr Asp Ile Ala Thr Leu Ser Tyr Gly Gly Arg Ser Gly Gly Leu
                 35                  40                  45

Glu Glu Val Val His Ala Asp Gln Ser Ser Cys Thr Phe Asp Asn Leu
 50                  55                  60

Ser Pro Gly Leu Ser Tyr Val Val Ser Val Ser Thr Val Thr Ser Asn
 65                  70                  75                  80

Glu Tyr Ser Ala Pro Ile Ser Asp Thr Ile Ile Pro
                 85                  90

<210> SEQ ID NO 179
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 179

Pro Leu Ser Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Met Tyr Asp Ile Lys Thr Ile Tyr Tyr Lys Ala Tyr Tyr Gly Leu
        35                  40                  45

Glu Glu Val Val His Ala Asp Gln Ser Ser Cys Thr Phe Asp Asn Leu
50                  55                  60

Ser Pro Gly Leu Tyr Tyr Phe Val Gly Val Thr Val Glu Arg Pro
65                  70                  75                  80

Arg Tyr Tyr Pro Ile Ser Asp Thr Ile Ile Pro
                85                  90

<210> SEQ ID NO 180
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 180

Pro Leu Ser Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Tyr Tyr Tyr Ile Asp Thr Asn Gly Tyr Trp Ser Tyr Leu Glu Glu
        35                  40                  45

Val Val His Ala Asp Gln Ser Ser Cys Thr Phe Asp Asn Leu Ser Pro
50                  55                  60

Gly Leu Gly Tyr Pro Val Gly Tyr Val Arg Thr Val Tyr Ala Gly Trp
65                  70                  75                  80

Leu Lys Gly Pro Ile Ser Asp Thr Ile Ile Pro
                85                  90

<210> SEQ ID NO 181
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 181

Pro Leu Ser Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Tyr Tyr Tyr Ile Gly Thr Tyr Gln Gly Thr Thr Tyr Glu His Leu Glu
        35                  40                  45

Glu Val Val His Ala Asp Gln Ser Ser Cys Thr Phe Asp Asn Leu Ser
50                  55                  60

Pro Gly Leu Ile Tyr Leu Val Tyr Val Ser Thr Val Tyr Trp Asp Ser
65                  70                  75                  80

Met Ser Ser Pro Ile Ser Asp Thr Ile Ile Pro
                85                  90

<210> SEQ ID NO 182
<211> LENGTH: 91

-continued

```
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 182

Pro Leu Ser Pro Pro Ala Asn Leu Arg Leu Glu Ala Asn Pro Asp Thr
1               5                   10                  15

Gly Val Leu Thr Val Ser Trp Glu Arg Ser Thr Thr Pro Asp Ile Thr
            20                  25                  30

Arg Tyr Val Ile Ala Thr Gly Tyr Gly Gly Ser Trp Tyr His Leu Glu
        35                  40                  45

Glu Val Val His Ala Asp Gln Ser Arg Cys Thr Phe Asp Asn Leu Ser
    50                  55                  60

Pro Gly Leu Ala Tyr Tyr Val Asp Val Tyr Thr Val Thr Pro Gly Glu
65                  70                  75                  80

Lys His Ser Pro Ile Ser Asp Thr Ile Ile Pro
                85                  90

<210> SEQ ID NO 183
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 183

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Lys Tyr Ile Ile Ser Thr Tyr Val Asp Tyr Gly Gly Tyr Leu Glu Glu
        35                  40                  45

Val Val His Ala Asp Gln Ser Ser Cys Thr Phe Asp Asn Leu Ser Pro
    50                  55                  60

Gly Leu Gly Tyr Ser Val Thr Val Ser Thr Val Ser Ala Gly Trp Asp
65                  70                  75                  80

Ser Pro Ile Ser Asp Thr Ile Ile Pro
                85

<210> SEQ ID NO 184
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 184

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Ser Tyr Arg Ile Ser Thr Glu Trp Arg Trp Arg Tyr Thr Gly Leu Glu
        35                  40                  45

Glu Val Val His Ala Asp Gln Ser Ser Cys Thr Phe Asp Asn Leu Ser
    50                  55                  60

Pro Gly Leu Ile Tyr Gly Val Gly Val Ser Thr Val Trp Lys His Asn
```

```
                65                  70                  75                  80
Ser Gln Ala Pro Ile Ser Asp Thr Ile Ile Pro
                85                  90

<210> SEQ ID NO 185
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 185

Pro Leu Ser Pro Pro Thr Asn Leu His Leu Glu Ala Asn Pro Asp Thr
  1               5                  10                  15

Gly Val Leu Thr Val Ser Trp Glu Arg Ser Thr Thr Pro Asp Ile Thr
                20                  25                  30

Met Tyr Tyr Ile Ser Thr Gly Gly Ser Ser Tyr Lys Pro Asp Arg Leu
                35                  40                  45

Glu Glu Val Val His Ala Asp Gln Ser Ser Cys Thr Phe Asp Asn Leu
            50                  55                  60

Ser Pro Gly Leu Asp Tyr Met Val Tyr Val Arg Thr Val Met Tyr Tyr
 65                  70                  75                  80

Asn Arg Ser Pro Ile Ser Asp Thr Ile Ile Pro
                85                  90

<210> SEQ ID NO 186
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 186

Pro Leu Ser Pro Pro Thr Asn Leu His Leu Glu Ala Asn Pro Asp Thr
  1               5                  10                  15

Gly Val Leu Thr Val Ser Trp Glu Arg Ser Thr Thr Pro Asp Ile Thr
                20                  25                  30

Gly Tyr Ser Ile Ala Thr Tyr Leu Thr Tyr Ser Asn Leu Val Gly Leu
                35                  40                  45

Glu Glu Val Val His Ala Asp Gln Ser Ser Cys Thr Phe Asp Asn Leu
            50                  55                  60

Ser Pro Gly Leu Ser Tyr Lys Val Ser Val Tyr Thr Val Tyr Gly Tyr
 65                  70                  75                  80

Ser Tyr Gly Pro Ile Ser Asp Thr Ile Ile Pro
                85                  90

<210> SEQ ID NO 187
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 187

Pro Leu Ser Pro Pro Thr Asn Leu His Leu Glu Ala Asn Pro Asp Thr
  1               5                  10                  15

Gly Val Leu Thr Val Ser Trp Glu Arg Ser Thr Thr Ser Asp Ile Thr
                20                  25                  30
```

```
Lys Tyr Tyr Ile Ala Thr Trp Phe Gly Asp Tyr Gly Tyr Ser Leu Glu
        35                  40                  45

Glu Val Val His Ala Asp Gln Ser Ser Cys Thr Phe Asp Asn Leu Ser
 50                  55                  60

Pro Gly Leu Gln Tyr Gly Val Ser Val Ala Thr Val Lys Gly Gly Gln
 65                  70                  75                  80

Ala His Tyr Pro Ile Ser Asp Thr Ile Ile Pro
                85                  90

<210> SEQ ID NO 188
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 188

Pro Leu Ser Pro Pro Thr Asn Leu His Leu Glu Ala Asn Pro Asp Thr
 1               5                  10                  15

Gly Val Leu Thr Val Ser Trp Glu Arg Ser Thr Thr Pro Asp Ile Thr
             20                  25                  30

Lys Tyr Tyr Ile Leu Thr Ser Gly Tyr Trp Gly Gly Leu Glu Glu
        35                  40                  45

Val Val His Ala Asp Gln Ser Ser Cys Thr Phe Asp Asn Leu Ser Pro
 50                  55                  60

Gly Leu Thr Tyr Leu Val Ser Val Trp Thr Val Thr His Tyr Ala Gly
 65                  70                  75                  80

Tyr Pro Ile Ser Asp Thr Ile Ile Pro
                85

<210> SEQ ID NO 189
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 189

Pro Leu Ser Pro Pro Thr Asn Leu His Leu Glu Ala Asn Pro Asp Thr
 1               5                  10                  15

Gly Val Leu Thr Val Ser Trp Glu Arg Ser Thr Thr Pro Asp Ile Thr
             20                  25                  30

Tyr Tyr Ser Ile Thr Thr Ser Phe Tyr Tyr Ser Glu Leu Glu Glu Val
        35                  40                  45

Val His Ala Asp Gln Ser Ser Cys Thr Phe Asp Asn Leu Ser Pro Gly
     50                  55                  60

Leu Lys Tyr Met Val Ser Val Ser Thr Val Ser Tyr Ser Val Gly Ser
 65                  70                  75                  80

Pro Ile Ser Asp Thr Ile Ile Pro
                85

<210> SEQ ID NO 190
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide
```

```
<220> FEATURE:
<221> NAME/KEY: VARIANT
<222> LOCATION: 71
<223> OTHER INFORMATION: Xaa = any amino acid

<400> SEQUENCE: 190

Pro Leu Ser Pro Pro Thr Asn Leu His Leu Glu Ala Asn Pro Asp Thr
 1               5                  10                  15

Gly Val Leu Thr Val Ser Trp Glu Arg Ser Thr Thr Pro Asp Ile Thr
            20                  25                  30

Thr Tyr Tyr Ile Ser Thr Gln Gly Gln Asp Glu Arg Gly Tyr Val Leu
        35                  40                  45

Glu Glu Val Val His Ala Asp Gln Ser Ser Cys Thr Phe Asp Lys Leu
 50                  55                  60

Ser Pro Gly Leu Ile Tyr Xaa Val Ile Val Trp Thr Val Asp Asp Asn
65                  70                  75                  80

Arg Tyr Asp Pro Ile Ser Asp Thr Ile Ile Pro
                85                  90

<210> SEQ ID NO 191
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 191

Pro Leu Ser Pro Pro Thr Asn Leu His Leu Glu Ala Asn Pro Asp Thr
 1               5                  10                  15

Gly Val Leu Thr Val Ser Trp Glu Arg Ser Thr Thr Pro Asp Ile Thr
            20                  25                  30

Arg Tyr Tyr Ile Arg Thr Ser Tyr Val Arg His Gly Arg Leu Glu Glu
        35                  40                  45

Val Val His Ala Asp Gln Ser Ser Cys Thr Phe Asp Asn Leu Ser Pro
 50                  55                  60

Gly Leu Tyr Tyr Asn Val Ser Val Ser Thr Val Gly Tyr Tyr Tyr Met
65                  70                  75                  80

Leu Pro Ile Ser Asp Thr Ile Ile Pro
                85

<210> SEQ ID NO 192
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 192

Pro Leu Ser Pro Pro Thr Asn Leu His Leu Glu Ala Asn Pro Asp Thr
 1               5                  10                  15

Gly Val Leu Thr Val Ser Arg Glu Arg Ser Thr Thr Pro Asp Ile Thr
            20                  25                  30

Thr Tyr Ser Ile Tyr Thr His Ser Gly Ala Leu Tyr Val Leu Glu Glu
        35                  40                  45

Val Val His Ala Asp Gln Ser Ser Cys Thr Phe Asp Asn Pro Ser Pro
 50                  55                  60

Gly Leu Asn Tyr Asn Val Ser Val Ser Thr Val His Ser Arg Trp Arg
65                  70                  75                  80
```

```
Tyr Gly Pro Ile Ser Asp Thr Ile Ile Pro
                85                  90

<210> SEQ ID NO 193
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 193

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Met Tyr Gly Ile Val Thr Ile Tyr Thr Arg Tyr Tyr Ser Leu Glu Glu
        35                  40                  45

Val Val His Ala Asp Gln Ser Ser Cys Thr Phe Asp Asn Leu Ser Pro
    50                  55                  60

Gly Leu Ile Tyr Trp Val Tyr Val Leu Thr Val Tyr Tyr Ser Trp Tyr
65                  70                  75                  80

Arg Pro Ile Ser Asp Thr Ile Ile Pro
                85

<210> SEQ ID NO 194
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 194

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Thr Tyr Val Ile Asp Thr Gly Ala Ala Val Asn Tyr Val Leu Glu Glu
        35                  40                  45

Val Val His Ala Asp Gln Ser Ser Cys Thr Phe Asp Asn Leu Ser Pro
    50                  55                  60

Gly Leu Gln Tyr Ser Val Asp Val Val Thr Val Trp Tyr Ser Trp
65                  70                  75                  80

Tyr Met Pro Ile Ser Asp Thr Ile Ile Pro
                85                  90

<210> SEQ ID NO 195
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 195

Pro Leu Ser Pro Pro Thr Asn Pro His Leu Glu Ala Asn Pro Asp Thr
1               5                   10                  15

Gly Val Leu Thr Val Ser Trp Glu Arg Ser Thr Thr Pro Asp Ile Thr
            20                  25                  30
```

Thr Tyr Trp Ile Gly Thr Tyr Ser Ala Asp Glu Arg Leu Glu Glu
                35                  40                  45

Val Val His Ala Asp Gln Ser Ser Cys Thr Phe Asp Asn Leu Ser Pro
 50                  55                  60

Gly Leu Tyr Tyr Ala Val Val Gly Thr Val Gly Val Trp Tyr Arg
65                  70                  75                  80

Val Ala Pro Ile Ser Asp Thr Ile Ile Pro
                85                  90

<210> SEQ ID NO 196
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 196

Pro Leu Ser Pro Pro Thr Asn Leu His Leu Glu Ala Asn Pro Asp Thr
 1               5                  10                  15

Gly Val Leu Thr Val Ser Trp Glu Arg Ser Thr Thr Pro Asp Ile Thr
                20                  25                  30

Tyr Tyr Tyr Ile His Thr Tyr Tyr Trp Lys His Trp Gln Ser Leu Glu
                35                  40                  45

Glu Val His Ala Asp Gln Ser Ser Cys Thr Phe Asp Asn Leu Ser
 50                  55                  60

Pro Gly Leu Lys Tyr Gly Val Trp Val Ser Thr Val Tyr Arg Val Val
65                  70                  75                  80

Tyr Tyr Pro Ile Ser Asp Thr Ile Ile Pro
                85                  90

<210> SEQ ID NO 197
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 197

Pro Leu Ser Pro Pro Thr Asn Leu His Leu Glu Ala Ser Pro Asp Thr
 1               5                  10                  15

Gly Val Leu Thr Val Ser Trp Glu Arg Ser Thr Thr Pro Asp Ile Thr
                20                  25                  30

Thr Tyr Leu Ile Leu Thr Tyr Leu Gly Tyr Ser Arg Val Leu Glu Glu
                35                  40                  45

Val Val His Ala Asp Gln Ser Ser Cys Thr Phe Asp Asn Leu Ser Pro
 50                  55                  60

Gly Leu Trp Tyr Met Val Tyr Val Asp Thr Val Gly Arg Val Pro Tyr
65                  70                  75                  80

Ile Gly Pro Ile Ser Asp Thr Ile Ile Pro
                85                  90

<210> SEQ ID NO 198
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 198

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Val Tyr Tyr Ile Tyr Thr Tyr Thr Tyr Asn Ala Asp Leu Ile Leu Glu
        35                  40                  45

Glu Val Val His Ala Asp Gln Ser Ser Cys Thr Phe Asp Asn Leu Ser
    50                  55                  60

Pro Gly Leu Ile Tyr Ser Val Tyr Val Gly Thr Val Ala Ser Asp Asp
65                  70                  75                  80

Gly Arg Pro Ile Ser Asp Thr Ile Ile Pro
                85                  90

<210> SEQ ID NO 199
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 199

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Ala Tyr Val Ile Tyr Thr Tyr Ser Glu Ser Asp Gly Arg Val Leu Glu
        35                  40                  45

Glu Val Val His Ala Asp Gln Ser Ser Cys Thr Phe Asp Asn Leu Ser
    50                  55                  60

Pro Gly Leu Arg Tyr Ser Val Lys Val Ser Thr Val Tyr Tyr Ser Tyr
65                  70                  75                  80

Ala Tyr Pro Ile Ser Asp Thr Ile Ile Pro
                85                  90

<210> SEQ ID NO 200
<211> LENGTH: 94
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 200

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

-continued

```
<210> SEQ ID NO 201
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 201

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Gly Tyr
                20                  25                  30

Tyr Ile Ser Tyr Tyr His Ser Thr Arg Asp Ser Gln Glu Phe Thr
            35                  40                  45

Val Pro Gly Ser Lys Ser Thr Ala Thr Ile Ser Gly Leu Lys Pro Gly
50                  55                  60

Val Ser Tyr Tyr Val Gly Val Gly Ala Val Trp Lys Lys Asp Tyr Tyr
65                  70                  75                  80

Phe Pro Ile Ser Ile Asn Tyr Arg Thr
                85

<210> SEQ ID NO 202
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 202

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Tyr Ile Leu Tyr Gly Asp Tyr Asn Ala Tyr Met Asp Tyr Ala Gly Gln
            35                  40                  45

Glu Phe Thr Val Pro Gly Ser Lys Ser Thr Ala Thr Ile Ser Gly Leu
50                  55                  60

Lys Pro Gly Val Gly Tyr Val Glu Ile Asp Val Tyr Ala Val Arg Thr
65                  70                  75                  80

Ser Glu Glu Gln Pro Ile Ser Ile Asn Tyr Arg Thr
                85                  90

<210> SEQ ID NO 203
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 203

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ala Tyr
                20                  25                  30

Gln Ile Arg Tyr Ala Tyr Tyr Ser Val Gly Arg Gln Glu Phe Thr Val
            35                  40                  45

Pro Gly Ser Lys Ser Thr Ala Thr Ile Ser Gly Leu Arg Pro Gly Val
50                  55                  60
```

```
Lys Tyr His Ile Ser Val Tyr Ala Val Asn Gly Gly Met Val Thr Asp
 65                  70                  75                  80

Pro Ile Ser Ile Asn Tyr Arg Thr
                85
```

<210> SEQ ID NO 204
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 204

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Trp Ile Ile Tyr Trp Glu Ala Trp Glu Tyr Val Gln Ala Gln Glu Phe
            35                  40                  45

Thr Val Pro Gly Ser Lys Ser Thr Ala Thr Ile Ser Gly Leu Lys Pro
 50                  55                  60

Gly Val His Tyr Gly Ile Met Val Ser Ala Val Ser Gly Glu Gln Pro
 65                  70                  75                  80

Trp Tyr Pro Ile Ser Ile Asn Tyr Arg Thr
                85                  90
```

<210> SEQ ID NO 205
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 205

```
Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Ile Tyr
                20                  25                  30

Ser Ile Tyr Tyr Tyr Ser Tyr Val Met Arg Gly Tyr Tyr Phe Gln Glu
            35                  40                  45

Phe Thr Val Leu Gly Ser Lys Ser Thr Ala Thr Ile Ser Gly Leu Lys
 50                  55                  60

Pro Gly Val Asn Tyr Asp Ile Asn Val Gln Ala Val Tyr His Arg Gly
 65                  70                  75                  80

Trp Arg Tyr Pro Ile Ser Ile Asn Tyr Arg Thr
                85                  90
```

<210> SEQ ID NO 206
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 206

```
Val Ser Asp Val Pro Arg Asp Leu Glu Val Val Ala Ala Thr Pro Thr
 1               5                  10                  15
```

-continued

```
Ser Leu Leu Ile Ser Trp Asp Ala Pro Ala Val Ala Val Arg Ala Tyr
            20                  25                  30

Ser Ile Asp Tyr Tyr His Asp Asn Gly Asp Gly Thr Gln Glu Phe Thr
        35                  40                  45

Val Pro Gly Ser Lys Ser Thr Ala Thr Ile Ser Gly Leu Lys Pro Gly
 50                  55                  60

Val Thr Tyr Gly Ile Leu Val Tyr Ala Val Val Ser Asn Met Gly Ile
 65                  70                  75                  80

Pro Ile Ser Ile Asn Tyr Arg Thr
                85

<210> SEQ ID NO 207
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 207

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Ser Tyr
            20                  25                  30

Tyr Ile Gly Tyr Ser Ala Tyr Asp Glu Tyr Gly Gly Arg Gln Glu Phe
        35                  40                  45

Thr Val Pro Gly Ser Lys Ser Thr Ala Thr Ile Ser Gly Leu Lys Pro
 50                  55                  60

Gly Val Ser Tyr Ser Ile Asn Val Phe Ala Val Tyr Thr Met Thr Gly
 65                  70                  75                  80

Arg Ala Pro Ile Ser Ile Asn Tyr Arg Thr
                85                  90

<210> SEQ ID NO 208
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 208

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Lys Tyr
            20                  25                  30

Ser Ile Tyr Tyr Phe Ser Ser Tyr Ser Gly Ile Ala Gln Glu Phe Thr
        35                  40                  45

Val Pro Gly Ser Lys Ser Thr Ala Thr Ile Ser Gly Leu Lys Pro Gly
 50                  55                  60

Val Tyr Tyr Gly Ile Tyr Val Glu Ala Val Tyr His His Tyr Ser Pro
 65                  70                  75                  80

Pro Ile Ser Ile Asn Tyr Arg Thr
                85

<210> SEQ ID NO 209
<211> LENGTH: 87
<212> TYPE: PRT
<213> ORGANISM: Artificial Sequence
<220> FEATURE:
```

<223> OTHER INFORMATION: synthetically constructed Fibronectin Type III
domain polypeptide

<400> SEQUENCE: 209

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Asn Tyr
            20                  25                  30

Tyr Ile Gln Tyr Met Val Asn Tyr Asn Asp Thr Gln Glu Phe Thr Val
        35                  40                  45

Pro Gly Ser Lys Ser Thr Ala Thr Ile Ser Gly Leu Lys Pro Gly Val
    50                  55                  60

Tyr Tyr Asp Ile Lys Val Ala Ala Val Tyr Val Ala Glu Asp Arg Pro
65                  70                  75                  80

Ile Ser Ile Asn Tyr Arg Thr
                85

<210> SEQ ID NO 210
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 210

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Lys Tyr
            20                  25                  30

Tyr Ile Thr Tyr Tyr Arg Gly Arg Ser Gly Asn Gln Glu Phe Thr Val
        35                  40                  45

Pro Gly Ser Lys Ser Thr Ala Thr Ile Ser Gly Leu Lys Pro Gly Val
    50                  55                  60

Lys Tyr His Ile Leu Val Ser Ala Val Lys Tyr Pro Phe Arg Arg Leu
65                  70                  75                  80

Pro Ile Ser Ile Asn Tyr Arg Thr
                85

<210> SEQ ID NO 211
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 211

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Thr Tyr
            20                  25                  30

Trp Ile Val Tyr Tyr Arg Ser Val Tyr Ser Asn Gly Gln Glu Phe Thr
        35                  40                  45

Val Pro Gly Ser Lys Ser Thr Ala Thr Ile Ser Gly Leu Lys Pro Gly
    50                  55                  60

Val Ile Tyr Ser Ile Arg Val Ile Ala Val Ser Tyr Tyr Tyr Tyr Gly
65                  70                  75                  80

Pro Ile Ser Ile Asn Tyr Arg Thr

<210> SEQ ID NO 212
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 212

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Thr Tyr
            20                  25                  30

Ser Ile Ser Tyr Ser Phe Gly Leu Asp Tyr Glu Tyr Asp Gln Glu Phe
        35                  40                  45

Thr Val Pro Gly Ser Lys Ser Thr Ala Thr Ile Ser Gly Leu Lys Pro
    50                  55                  60

Gly Val Gln Tyr Tyr Ile Val Val Asp Ala Val Ala Gly Trp Gln Tyr
65                  70                  75                  80

Tyr Pro Ile Ser Ile Asn Tyr Arg Thr
                85

<210> SEQ ID NO 213
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 213

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Gly Tyr
            20                  25                  30

Ser Ile Lys Tyr Gly Ser Thr Ile Ser Ala Asp Gln Glu Phe Thr Val
        35                  40                  45

Pro Gly Ser Lys Ser Thr Ala Thr Ile Ser Gly Leu Lys Pro Gly Val
    50                  55                  60

Phe Tyr Val Ile Met Val Trp Ala Val Tyr Tyr Ala Tyr Ala Asn Tyr
65                  70                  75                  80

Pro Ile Ser Ile Asn Tyr Arg Thr
                85

<210> SEQ ID NO 214
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 214

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ser Tyr
            20                  25                  30

His Ile Tyr Asp Tyr Tyr Asn Val His Ser Tyr Tyr Gly Gln Glu Phe
        35                  40                  45

```
Thr Val Pro Gly Ser Lys Ser Thr Ala Thr Ile Ser Gly Leu Lys Pro
            50                  55                  60

Gly Val Ser Tyr Ala Ile Tyr Val Gly Ala Val Asn Glu Lys Gln Leu
65                  70                  75                  80

Gly Pro Ile Ser Ile Asn Tyr Arg Thr
                85
```

<210> SEQ ID NO 215
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 215

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Thr Tyr
            20                  25                  30

Val Ile Ser Tyr Met Ser Tyr Asp Ala Gln Gly Gly Gln Asn Gln Glu
        35                  40                  45

Phe Thr Val Pro Gly Ser Lys Ser Thr Ala Thr Ile Ser Gly Leu Lys
50                  55                  60

Pro Gly Val Ala Tyr Asn Ile Ile Val Ser Ala Val Gly Gly Gly Gln
65                  70                  75                  80

Gln Ala Val Pro Ile Ser Ile Asn Tyr Arg Thr
                85                  90
```

<210> SEQ ID NO 216
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 216

```
Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Glu Tyr
            20                  25                  30

Ser Ile Tyr His Ser Trp Thr Leu Val Tyr Arg Arg Gln Glu Phe Thr
        35                  40                  45

Val Pro Gly Ser Lys Ser Thr Ala Thr Ile Ser Gly Leu Lys Pro Gly
50                  55                  60

Val Asn Tyr Tyr Ile Tyr Val Gly Ala Val Asp Asn Gly Tyr Gly Pro
65                  70                  75                  80

Asp Pro Ile Ser Ile Asn Tyr Arg Thr
                85
```

<210> SEQ ID NO 217
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide
<220> FEATURE:
<221> NAME/KEY: VARIANT
<222> LOCATION: 45, 58, 72

<223> OTHER INFORMATION: Xaa = any amino acid

<400> SEQUENCE: 217

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Leu Arg Tyr Tyr
            20                  25                  30

Glu Ile Lys Tyr Ser Gly Ser Ser Leu Tyr Val Gln Xaa Phe Thr Val
        35                  40                  45

Pro Gly Ser Lys Ser Thr Ala Thr Ile Xaa Gly Leu Lys Pro Gly Val
    50                  55                  60

Ser Tyr Asn Ile Gly Val Ser Xaa Val Trp Gln Ala Phe Trp Pro Val
65                  70                  75                  80

Pro Ile Ser Ile Asn Tyr Arg Thr
                85

<210> SEQ ID NO 218
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 218

Val Ser Asp Val Pro Arg Asp Leu Gly Val Val Ala Ala Thr Pro Thr
1               5                   10                  15

Ser Leu Arg Ile Ser Trp Asp Ala Pro Ala Val Thr Val Arg Ser Tyr
            20                  25                  30

Asp Ile Tyr Tyr Trp Tyr Thr Thr Gly Gly Ser Gln Glu Phe Thr Val
        35                  40                  45

Pro Gly Ser Lys Ser Thr Ala Thr Ile Ser Gly Leu Lys Pro Gly Val
    50                  55                  60

Met Tyr Asn Ile Tyr Val Thr Ala Val Asp Ala Asp Val Gly Gly Pro
65                  70                  75                  80

Ile Ser Ile Asn Tyr Arg Thr
                85

<210> SEQ ID NO 219
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 219

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Arg Tyr
            20                  25                  30

Tyr Ile Gly Tyr Asn Trp Gln Ser Pro Ala Trp Asn Gln Glu Phe Thr
        35                  40                  45

Val Pro Gly Ser Lys Ser Thr Ala Thr Ile Ser Gly Leu Lys Pro Gly
    50                  55                  60

Val Tyr Tyr Gln Ile Tyr Val Ala Ala Val Leu Arg Tyr Gly Asp Tyr
65                  70                  75                  80

Ala Pro Ile Ser Ile Asn Tyr Arg Thr
                85

<210> SEQ ID NO 220
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 220

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ser Tyr
            20                  25                  30

Ser Ile Gly Tyr Phe Gly Ala Tyr Arg Asn Trp Val Gln Glu Phe Thr
        35                  40                  45

Val Pro Gly Ser Lys Ser Thr Ala Thr Ile Ser Gly Leu Lys Pro Gly
    50                  55                  60

Val Thr Tyr Tyr Ile Glu Val Tyr Ala Val Tyr Ser Asn Pro Val Tyr
65                  70                  75                  80

Pro Ile Ser Ile Asn Tyr Arg Thr
                85

<210> SEQ ID NO 221
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 221

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Lys Tyr
            20                  25                  30

Gln Ile Tyr Tyr Tyr Tyr Ser Ala Tyr Val Lys Glu Ser Gln Glu Phe
        35                  40                  45

Thr Val Pro Gly Ser Lys Ser Thr Ala Thr Ile Ser Gly Leu Lys Pro
    50                  55                  60

Gly Val Ser Tyr Asn Ile Ala Val Tyr Ala Val Ser Lys Ser Arg Tyr
65                  70                  75                  80

Gln Pro Pro Ile Ser Ile Asn Tyr Arg Thr
                85                  90

<210> SEQ ID NO 222
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 222

Val Ser Asp Val Pro Arg Asp Leu Glu Val Val Ala Ala Thr Pro Thr
1               5                   10                  15

Ser Leu Leu Thr Ser Trp Asp Ala Pro Ala Val Thr Val Arg Asn Tyr
            20                  25                  30

Ala Ile Tyr Tyr Tyr Asp Asp Thr Gly Arg Gln Glu Phe Thr Val
        35                  40                  45

Pro Gly Ser Lys Ser Thr Ala Thr Ile Ser Gly Leu Lys Pro Gly Val
            50                  55                  60

Asp Tyr Tyr Ile Gly Val Glu Ala Val Trp Tyr Trp Val Ser Ser Pro
 65                  70                  75                  80

Ile Ser Ile Asn Tyr Arg Thr
                85

<210> SEQ ID NO 223
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 223

Val Ser Asp Val Pro Arg Asp Leu Glu Val Val Ala Ala Thr Pro Thr
 1                5                  10                  15

Ser Leu Leu Ile Ser Trp Asp Ala Pro Ala Val Thr Val Arg Thr Tyr
                20                  25                  30

Thr Ile Trp Tyr Val Gln Arg Tyr Ala Tyr Ser Gln Glu Phe Thr Val
            35                  40                  45

Pro Gly Ser Lys Ser Thr Ala Thr Ile Ser Gly Leu Lys Pro Gly Val
        50                  55                  60

Ser Tyr Ser Ile Ser Val Arg Ala Val Ser Thr Asp Arg Tyr Tyr Pro
 65                  70                  75                  80

Ile Ser Ile Asn Tyr Arg Thr
                85

<210> SEQ ID NO 224
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 224

Val Ser Asp Val Pro Arg Asp Leu Glu Val Val Ala Ala Thr Pro Thr
 1               5                  10                  15

Ser Leu Leu Ile Ser Trp Asp Ala Pro Ala Val Thr Val Arg Tyr Tyr
                20                  25                  30

Ser Ile Ala Tyr Trp Gln Leu Tyr Leu Pro Val Gln Glu Phe Thr Val
            35                  40                  45

Pro Gly Ser Lys Ser Thr Ala Thr Ile Ser Gly Leu Lys Pro Gly Val
        50                  55                  60

Ser Tyr Gly Ile Thr Val Glu Ala Val Met Ser Gly Tyr Ser Ile Tyr
 65                  70                  75                  80

Pro Ile Ser Ile Asn Tyr Arg Thr
                85

<210> SEQ ID NO 225
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 225

Val Ser Asp Val Pro Arg Asp Leu Glu Val Val Ala Ala Ala Pro Thr

```
                1               5                  10                 15
Ser Leu Leu Ile Ser Trp Asp Ala Pro Ala Val Thr Val Arg Lys Tyr
                20                 25                 30

Tyr Ile Trp Tyr Gly Tyr Ser Tyr Phe Val Ala Tyr Ser Ser Tyr Gln
        35                 40                 45

Glu Phe Thr Val Pro Gly Ser Lys Ser Thr Ala Thr Ile Ser Gly Leu
        50                 55                 60

Lys Pro Gly Val Arg Tyr Tyr Ile Gly Val Leu Ala Val Lys Tyr Pro
 65                 70                 75                 80

Gly Asp Tyr Tyr Pro Ile Ser Ile Asn Tyr Arg Thr
                    85                 90

<210> SEQ ID NO 226
<211> LENGTH: 86
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 226

Val Ser Asp Val Pro Arg Asp Leu Glu Val Val Ala Ala Thr Pro Thr
 1               5                  10                 15

Ser Leu Leu Ile Ser Trp Asp Ala Pro Ala Val Thr Val Arg Tyr His
                20                 25                 30

Ser Ile Gly Tyr Asn Tyr Tyr Gly Met Tyr Gln Glu Phe Thr Val Pro
        35                 40                 45

Gly Ser Lys Ser Thr Ala Thr Ile Ser Gly Leu Lys Pro Gly Val Tyr
 50                 55                 60

Tyr Tyr Ile Tyr Val Arg Ala Val Thr Gly Arg Glu Ala Ala Pro Ile
 65                 70                 75                 80

Ser Ile Asn Tyr Arg Thr
                85

<210> SEQ ID NO 227
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 227

Val Ser Asp Val Pro Arg Asp Leu Glu Val Val Ala Ala Thr Pro Thr
 1               5                  10                 15

Ser Leu Leu Ile Ser Trp Asp Ala Pro Ala Val Thr Val Arg Thr Tyr
                20                 25                 30

Gln Ile Glu Tyr Val Ser Ser Tyr Tyr Arg Trp Thr Gln Glu Phe Thr
        35                 40                 45

Val Pro Gly Ser Lys Ser Thr Ala Thr Ile Ser Gly Leu Lys Pro Gly
 50                 55                 60

Val Val Tyr Phe Ile Tyr Val Ala Ala Val Arg Asp Gly Pro Asn Asp
 65                 70                 75                 80

Pro Ile Ser Ile Asn Tyr Arg Thr
                85

<210> SEQ ID NO 228
<211> LENGTH: 87
<212> TYPE: PRT
```

<213> ORGANISM: Artificial Sequence
<220> FEATURE:
<223> OTHER INFORMATION: synthetically constructed Fibronectin Type III
      domain polypeptide

<400> SEQUENCE: 228

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ser Tyr
            20                  25                  30

Lys Ile Ser Tyr Tyr Gly Tyr His Trp Val Tyr Gln Glu Phe Thr Val
        35                  40                  45

Pro Gly Ser Lys Ser Thr Ala Thr Ile Ser Gly Leu Lys Pro Gly Val
    50                  55                  60

Ser Tyr Leu Ile Ser Val Ser Ala Val Asp Tyr Tyr Gly Val Leu Pro
65                  70                  75                  80

Ile Ser Ile Asn Tyr Arg Thr
                85

<210> SEQ ID NO 229
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 229

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Thr Tyr
            20                  25                  30

Tyr Ile Gly Tyr Gly Met Tyr Thr Tyr Gly Gln Glu Phe Thr Val Pro
        35                  40                  45

Gly Ser Lys Ser Thr Thr Thr Ile Ser Gly Leu Lys Pro Gly Val Val
    50                  55                  60

Tyr Asp Ile Tyr Val Trp Ala Val Gly Phe Gly Arg Tyr Val Asp Pro
65                  70                  75                  80

Ile Ser Ile Asn Tyr Arg Thr
                85

<210> SEQ ID NO 230
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 230

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Asn Tyr
            20                  25                  30

Tyr Ile Gly Tyr Arg Tyr Val Ala Asn Trp Cys Tyr Gln Glu Phe
        35                  40                  45

Thr Val Pro Gly Ser Lys Ser Thr Ala Thr Ile Ser Gly Leu Lys Pro
    50                  55                  60

Gly Val Ser Tyr Trp Ile Thr Ala Lys Ala Val Val Phe Glu Gly Asp
65                  70                  75                  80

His Pro Ile Ser Ile Asn Tyr Arg Thr
                85

<210> SEQ ID NO 231
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 231

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Lys Tyr
            20                  25                  30

Tyr Ile Gly Tyr Lys Leu Gln Val Met Glu Pro Asp Gln Glu Phe Thr
        35                  40                  45

Val Pro Gly Ser Lys Ser Thr Ala Thr Ile Ser Gly Leu Lys Pro Gly
    50                  55                  60

Val Glu Tyr Trp Ile Gly Val Asp Ala Val Ser Tyr Tyr Trp Gly Phe
65                  70                  75                  80

Asp Pro Ile Ser Ile Asn Tyr Arg Thr
                85

<210> SEQ ID NO 232
<211> LENGTH: 86
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 232

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Gly Tyr
            20                  25                  30

Gly Ile Tyr Tyr Gly Asp Thr Gly Asp Thr Gln Glu Phe Thr Val Pro
        35                  40                  45

Gly Ser Lys Ser Thr Ala Thr Ile Ser Gly Leu Lys Pro Gly Val Met
    50                  55                  60

Tyr Ser Ile Val Val Phe Ala Val Glu Trp Tyr Met Trp Gln Pro Ile
65                  70                  75                  80

Ser Ile Asn Tyr Arg Thr
                85

<210> SEQ ID NO 233
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 233

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

```
Trp Ile Gln Tyr Tyr Ile Tyr Ser Arg Gly Thr Gln Glu Phe Thr
             35                  40                  45

Val Pro Gly Ser Lys Ser Thr Ala Thr Ile Ser Gly Leu Lys Pro Gly
 50                  55                  60

Val Asn Tyr Ser Ile Gly Val Gln Ala Val Gln Ala Tyr Phe Gly Glu
 65                  70                  75                  80

Pro Ile Ser Ile Asn Tyr Arg Thr
                 85
```

<210> SEQ ID NO 234
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 234

```
Val Ser Asp Val Pro Arg Asp Leu Glu Val Val Ala Ala Thr Pro Thr
 1                5                  10                  15

Ser Leu Leu Ile Ser Trp Asp Ala Pro Ala Val Thr Val Arg Ser Tyr
             20                  25                  30

Arg Ile Met Tyr Ser Gly Tyr Tyr Ala Trp Glu Tyr Ser Arg Gln Glu
             35                  40                  45

Phe Thr Val Pro Gly Ser Lys Ser Thr Ala Thr Ile Ser Gly Leu Lys
 50                  55                  60

Pro Gly Val Ile Tyr Ala Ile His Val Ser Ala Val Val Thr Asn Trp
 65                  70                  75                  80

Glu Gly Pro Ile Ser Ile Asn Tyr Arg Thr
                 85                  90
```

<210> SEQ ID NO 235
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 235

```
Val Ser Asp Val Pro Arg Asp Leu Glu Val Val Ala Ala Thr Pro Thr
 1                5                  10                  15

Ser Leu Leu Ile Ser Trp Asp Ala Pro Ala Val Thr Val Arg Asp Tyr
             20                  25                  30

Trp Ile Tyr Tyr Arg Tyr Ser Trp Pro Tyr Gly Ser Gln Glu Phe Thr
             35                  40                  45

Val Pro Gly Ser Lys Ser Thr Ala Thr Ile Ser Gly Leu Lys Pro Gly
 50                  55                  60

Val Thr Tyr Asp Ile Gln Val Glu Ala Val Tyr Gly Ser Glu Ser Gly
 65                  70                  75                  80

Pro Ile Ser Ile Asn Tyr Arg Thr
                 85
```

<210> SEQ ID NO 236
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide -continued

<400> SEQUENCE: 236

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Tyr Gly Ile Tyr Tyr Ala Gly Lys Ala Gly Gly Asp Tyr Phe Ile Thr
        35                  40                  45

Gln Glu Phe Thr Val Pro Gly Ser Lys Ser Thr Ala Thr Ile Ser Gly
    50                  55                  60

Leu Lys Pro Gly Val Glu Tyr Arg Ile Tyr Val Ala Ala Val Gly Tyr
65                  70                  75                  80

His Tyr Thr Pro Pro Ile Ser Ile Asn Tyr Arg Thr
                85                  90

<210> SEQ ID NO 237
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 237

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Asn Tyr
            20                  25                  30

Ser Ile Lys Tyr Lys Tyr Ile Pro Tyr Val Ser His Gln Glu Phe Thr
        35                  40                  45

Val Pro Gly Ser Lys Ser Thr Ala Thr Ile Ser Gly Leu Lys Pro Gly
    50                  55                  60

Val Thr Tyr Ser Ile Arg Val Gln Ala Val Tyr Tyr Leu Ile Glu Arg
65                  70                  75                  80

Tyr Pro Ile Ser Ile Asn Tyr Arg Thr
                85

<210> SEQ ID NO 238
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 238

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Ile Tyr
            20                  25                  30

Tyr Ile Ala Tyr Gly Tyr Pro Gly Trp Arg Ala Gly Ser Gln
        35                  40                  45

Glu Phe Thr Val Pro Gly Ser Lys Ser Thr Ala Thr Ile Ser Gly Leu
    50                  55                  60

Lys Pro Gly Val Thr Tyr Gly Ile Ser Val Ser Ala Val Glu Glu Arg
65                  70                  75                  80

Arg Lys Val Pro Ile Ser Ile Asn Tyr Arg Thr
                85                  90

```
<210> SEQ ID NO 239
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 239

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
                20                  25                  30

Gln Val Asp Ala Val Pro Ala Asn Gly Gln Thr Pro Ile Gln Arg Thr
            35                  40                  45

Ile Lys Pro Asp Val Arg Ser Tyr Thr Ile Thr Gly Leu Gln Pro Gly
        50                  55                  60

Thr Asp Tyr Lys Ile Tyr Leu Tyr Thr Leu Asn Asp Asn Ala Arg Ser
65                  70                  75                  80

Ser Pro Val Val Ile Asp Ala Ser Thr
                85

<210> SEQ ID NO 240
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 240

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Asp Phe
                20                  25                  30

Glu Val Ala Ala Leu Pro Met Val Ser Thr Gly Ile Gln Arg Thr Ile
            35                  40                  45

Lys Pro Asp Val Arg Ser Tyr Thr Ile Thr Gly Leu Gln Pro Gly Thr
        50                  55                  60

Thr Tyr Tyr Ile Ser Leu Tyr Thr Leu Asp Asp Asp Gly Pro Gly Thr
65                  70                  75                  80

Pro Val Val Ile Asp Ala Ser Thr
                85

<210> SEQ ID NO 241
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 241

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ser Phe
                20                  25                  30

Asn Val Val Ala Tyr Pro Ser Ser Gln Asp Gly Ile Gln Arg Thr Ile
            35                  40                  45

Lys Pro Asp Val Arg Ser Tyr Thr Ile Thr Gly Leu Gln Pro Gly Thr
        50                  55                  60
```

```
Gly Tyr Gln Ile His Leu Thr Thr Leu Gly His Leu Ser Phe Ser Pro
 65                  70                  75                  80

Val Val Ile Asp Ala Ser Thr
                85
```

<210> SEQ ID NO 242
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 242

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Tyr Phe
                 20                  25                  30

Thr Val Asp Ala Ala Pro Ser Leu Val Val Asp Asn Ile Gln Arg Thr
             35                  40                  45

Ile Lys Pro Asp Val Arg Ser Tyr Thr Ile Thr Gly Leu Gln Pro Gly
 50                  55                  60

Thr Tyr Tyr Ile Ile Leu Leu Tyr Thr Leu Tyr Asn Tyr Asp Ala Leu
 65                  70                  75                  80

Pro Val Val Ile Asp Ala Ser Thr
                85
```

<210> SEQ ID NO 243
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 243

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Leu Phe
                 20                  25                  30

Glu Val Tyr Ala Asp Pro Gln Val Ser Asn Gly Thr Tyr Ile Gln Arg
             35                  40                  45

Thr Ile Lys Pro Asp Val Arg Ser Tyr Thr Ile Thr Gly Leu Gln Pro
 50                  55                  60

Gly Thr Tyr Tyr Arg Ile Gly Leu Tyr Thr Leu Ser Asp Tyr Glu Lys
 65                  70                  75                  80

Ser Thr Pro Val Val Ile Asp Ala Ser Thr
                85                  90
```

<210> SEQ ID NO 244
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 244

```
Asn Val Ser Pro Pro Arg Arg Ala Arg Val Thr Asp Ala Thr Glu Thr
  1               5                  10                  15
```

Thr Ile Thr Ile Ser Trp Arg Thr Lys Thr Glu Ile Thr Arg Phe
            20                  25                  30

Phe Val Ser Ala Val Pro Phe Glu Thr Gly Thr Ile Gln Arg Thr Ile
        35                  40                  45

Lys Pro Asp Val Arg Ser Tyr Thr Ile Thr Gly Leu Gln Pro Gly Thr
 50                      55                  60

Ala Tyr Asp Ile Ala Leu Tyr Thr Leu Phe Gly Tyr Tyr Tyr Pro
 65                  70                  75                  80

Val Val Ile Asp Ala Ser Thr
                85

<210> SEQ ID NO 245
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 245

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Ile Thr Asp Phe
            20                  25                  30

Gly Val Val Ala Ser Pro Tyr Leu Gly Gln Gly Ile Gln Arg Thr Ile
        35                  40                  45

Lys Pro Asp Val Arg Ser Tyr Thr Ile Thr Gly Leu Gln Pro Gly Thr
 50                      55                  60

Ala Tyr Ser Ile Lys Leu His Thr Leu His Val His Asp Tyr Tyr Pro
 65                  70                  75                  80

Val Val Ile Asp Ala Ser Thr
                85

<210> SEQ ID NO 246
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 246

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Ile Thr Tyr Phe
            20                  25                  30

Tyr Val Ala Ala Asp Pro Thr Glu Asp Gly Lys Ile Gln Arg Thr Ile
        35                  40                  45

Lys Pro Asp Val Arg Ser Tyr Thr Ile Thr Gly Leu Gln Pro Gly Thr
 50                      55                  60

Tyr Tyr Thr Ile His Leu Arg Thr Leu Tyr Tyr Leu Val Ala Val Pro
 65                  70                  75                  80

Val Val Ile Asp Ala Ser Thr
                85

<210> SEQ ID NO 247
<211> LENGTH: 87
<212> TYPE: PRT
<213> ORGANISM: Artificial Sequence
<220> FEATURE:

<223> OTHER INFORMATION: synthetically constructed Fibronectin Type III
domain polypeptide
<220> FEATURE:
<221> NAME/KEY: VARIANT
<222> LOCATION: 75
<223> OTHER INFORMATION: Xaa = any amino acid

<400> SEQUENCE: 247

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Tyr Phe
             20                  25                  30

Asp Val Ala Ala Asn Pro Ser Tyr Leu Gly Ala Ile Gln Arg Thr Ile
         35                  40                  45

Lys Pro Asp Val Arg Ser Tyr Thr Ile Thr Gly Leu Gln Pro Gly Thr
 50                  55                  60

Ala Tyr Asp Ile Ala Leu Gly Thr Leu Glu Xaa Tyr Val Ser Gly Pro
 65                  70                  75                  80

Val Val Ile Asp Ala Ser Thr
                 85
```

<210> SEQ ID NO 248
<211> LENGTH: 90
<212> TYPE: PRT
<213> ORGANISM: Artificial Sequence
<220> FEATURE:
<223> OTHER INFORMATION: synthetically constructed Fibronectin Type III
    domain polypeptide

<400> SEQUENCE: 248

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Tyr Phe
             20                  25                  30

Gly Val Gly Ala Asp Pro Ala Met Tyr Ile Glu Tyr Pro Tyr Ile Gln
         35                  40                  45

Arg Thr Ile Lys Pro Asp Val Arg Ser Tyr Thr Ile Thr Gly Leu Gln
 50                  55                  60

Pro Gly Thr Gln Tyr Gly Ile Tyr Leu Thr Thr Leu Ser Gln Ala Ser
 65                  70                  75                  80

Asp Tyr Pro Val Val Ile Asp Ala Ser Thr
                 85                  90
```

<210> SEQ ID NO 249
<211> LENGTH: 87
<212> TYPE: PRT
<213> ORGANISM: Artificial Sequence
<220> FEATURE:
<223> OTHER INFORMATION: synthetically constructed Fibronectin Type III
    domain polypeptide

<400> SEQUENCE: 249

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Tyr Phe
             20                  25                  30

Gly Val Arg Ala Tyr Pro Thr Tyr Arg Ser Ser Ile Gln Arg Thr Ile
         35                  40                  45

Lys Pro Asp Val Arg Ser Tyr Thr Ile Thr Gly Leu Gln Pro Gly Thr
 50                  55                  60
```

```
Leu Tyr Arg Ile Ser Leu Tyr Thr Leu Asp Ser Ala Gly Tyr Asn Pro
 65                  70                  75                  80

Val Val Ile Asp Ala Ser Thr
                85
```

<210> SEQ ID NO 250
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 250

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Gln Phe
                20                  25                  30

Ser Val Tyr Ala Tyr Pro Ala Arg Ser Lys Tyr His Ile Gln Arg Thr
            35                  40                  45

Ile Lys Pro Asp Val Arg Ser Tyr Thr Ile Thr Gly Leu Gln Pro Gly
 50                  55                  60

Thr Gly Tyr Arg Ile Tyr Leu Gln Thr Leu Gly Tyr Ser Asp Glu
 65                  70                  75                  80

Pro Val Val Ile Asp Ala Ser Thr
                85
```

<210> SEQ ID NO 251
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 251

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Glu Phe
                20                  25                  30

Asp Val Gly Ala Asp Pro Gly Lys Gly His Ala Ile Gln Arg Thr Ile
            35                  40                  45

Lys Pro Asp Val Arg Ser Tyr Thr Ile Thr Gly Leu Gln Pro Gly Thr
 50                  55                  60

Ser Tyr Leu Ile Gly Leu Arg Thr Leu Asn Arg Val Leu His Tyr Pro
 65                  70                  75                  80

Val Val Ile Asp Ala Ser Thr
                85
```

<210> SEQ ID NO 252
<211> LENGTH: 86
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 252

```
Asn Val Ser Pro Pro Arg Arg Ala Arg Val Thr Asp Ala Thr Glu Thr
  1               5                  10                  15

Thr Ile Thr Ile Ser Trp Arg Thr Lys Thr Glu Thr Ile Thr Ser Phe
```

```
                        20                  25                  30

Arg Val Asp Ala Gly Pro Gly Val Ala Gly Ser Ile Gln Arg Thr Ile
                35                  40                  45

Lys Pro Asp Val Arg Ser Tyr Thr Ile Thr Gly Leu Gln Pro Gly Thr
         50                  55                  60

Tyr Tyr Gln Ile Gln Leu Ala Ala Leu Ala Tyr Gly Tyr Tyr Pro Val
 65                  70                  75                  80

Val Ile Asp Ala Ser Thr
                85

<210> SEQ ID NO 253
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 253

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Arg Phe
                20                  25                  30

Tyr Val Ser Ala Gln Pro Arg Phe Tyr Tyr Asn Ile Gln Arg Thr
                35                  40                  45

Ile Lys Pro Asp Val Arg Ser Tyr Thr Ile Thr Gly Leu Gln Pro Gly
         50                  55                  60

Thr Asp Tyr Thr Ile Gly Leu Tyr Thr Leu Gly Val Tyr Met His Tyr
 65                  70                  75                  80

Pro Val Val Ile Asp Ala Ser Thr
                85

<210> SEQ ID NO 254
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 254

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Tyr Phe
                20                  25                  30

Ser Val Glu Ala Tyr Pro Arg Trp Tyr Ala Leu Ile Gln Arg Thr Ile
                35                  40                  45

Lys Pro Asp Val Arg Ser Tyr Thr Ile Thr Gly Leu Gln Pro Gly Thr
         50                  55                  60

Ser Tyr Tyr Ile Tyr Leu Trp Thr Leu Met Met Asp Thr Ser Ser Pro
 65                  70                  75                  80

Val Val Ile Asp Ala Ser Thr
                85

<210> SEQ ID NO 255
<211> LENGTH: 89
<212> TYPE: PRT
<213> ORGANISM: Artificial Sequence
<220> FEATURE:
<223> OTHER INFORMATION: synthetically constructed Fibronectin Type III
``` domain polypeptide

<400> SEQUENCE: 255

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Glu Phe
            20                  25                  30

Phe Val Met Ala Glu Pro Tyr Tyr Gly Glu Gly Tyr Tyr Ile Gln Arg
        35                  40                  45

Thr Ile Lys Pro Asp Val Arg Ser Tyr Thr Ile Thr Gly Leu Gln Pro
    50                  55                  60

Gly Thr Ser Tyr Ser Ile Asn Leu Tyr Thr Leu Lys Arg Pro Tyr Leu
65                  70                  75                  80

Tyr Pro Val Val Ile Asp Ala Ser Thr
                85

<210> SEQ ID NO 256
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 256

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ser Phe
            20                  25                  30

Tyr Val Met Ala Gln Pro Thr Asn Tyr Tyr Gly Gln Ser Thr Tyr Ile
        35                  40                  45

Gln Arg Thr Ile Lys Pro Asp Val Arg Ser Tyr Thr Ile Thr Gly Leu
    50                  55                  60

Gln Pro Gly Thr Tyr Tyr Gly Ile Gln Leu Tyr Thr Leu Met Tyr Arg
65                  70                  75                  80

Ala Ser Ala Pro Val Val Ile Asp Ala Ser Thr
                85                  90

<210> SEQ ID NO 257
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 257

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Thr Phe
            20                  25                  30

Asp Val Tyr Ala Tyr Pro Gly Tyr Gly Gly Ser Tyr Trp Ser Ile Gln
        35                  40                  45

Arg Thr Ile Lys Pro Asp Val Arg Ser Tyr Thr Ile Thr Gly Leu Gln
    50                  55                  60

Pro Gly Thr Ser Tyr Glu Ile Glu Leu Glu Thr Leu His Tyr Ser His
65                  70                  75                  80

Ala Tyr Pro Val Val Ile Asp Ala Ser Thr
                85                  90

<210> SEQ ID NO 258
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 258

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Tyr Phe
            20                  25                  30

Ser Val Leu Ala His Pro Leu Glu Val Ser Ser Tyr Ser Ile Gln Arg
        35                  40                  45

Thr Ile Lys Pro Asp Val Arg Ser Tyr Thr Ile Thr Gly Leu Gln Pro
    50                  55                  60

Gly Thr Gly Tyr Arg Ile Phe Leu Ser Thr Leu Arg Trp Tyr Tyr Gly
65                  70                  75                  80

Met Pro Val Val Ile Asp Ala Ser Thr
                85

<210> SEQ ID NO 259
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 259

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Tyr Phe
            20                  25                  30

Ser Val Tyr Ala Asn Pro Met Tyr Pro Phe Tyr Ile Gln Arg Thr Ile
        35                  40                  45

Lys Pro Asp Val Arg Ser Tyr Thr Ile Thr Gly Leu Gln Pro Gly Thr
    50                  55                  60

Tyr Tyr Glu Ile Tyr Leu Gly Thr Leu Tyr Tyr Phe Ala Thr Tyr Pro
65                  70                  75                  80

Val Val Ile Asp Ala Ser Thr
                85

<210> SEQ ID NO 260
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 260

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Tyr Phe
            20                  25                  30

Tyr Val Ser Ala Tyr Pro Tyr Tyr Val Ala Tyr Asp Ile Gln Arg Thr
            35                  40                  45

```
Ile Lys Pro Asp Val Arg Ser Tyr Thr Ile Thr Gly Leu Gln Pro Gly
 50                  55                  60

Thr Tyr Tyr Asp Ile Asn Leu Ser Thr Leu Ser Tyr Ser Asp Asn Ser
 65                  70                  75                  80

Pro Val Val Ile Asp Ala Ser Thr
                 85
```

<210> SEQ ID NO 261
<211> LENGTH: 91
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 261

```
Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Tyr Phe
                 20                  25                  30

Lys Val Arg Ala Tyr Pro Ala Tyr Asn Tyr Gly Gly Trp Ser Ile Gln
             35                  40                  45

Arg Thr Ile Lys Pro Asp Val Arg Ser Tyr Thr Ile Thr Gly Leu Gln
 50                  55                  60

Pro Gly Thr Tyr Tyr Ser Ile Tyr Leu Asp Leu Tyr Leu Gly Ala
 65                  70                  75                  80

Tyr Trp Tyr Pro Val Val Ile Asp Ala Ser Thr
                 85                  90
```

<210> SEQ ID NO 262
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 262

```
Asn Val Ser Pro Pro Arg Ser Ala Arg Val Thr Asp Ala Thr Glu Thr
 1               5                  10                  15

Thr Ile Thr Ile Ser Trp Arg Thr Lys Thr Glu Thr Ile Thr Tyr Phe
                 20                  25                  30

Val Val Gly Ala Phe Pro Ala Tyr Ser Ala His Val Asp Ile Gln Arg
             35                  40                  45

Thr Ile Lys Pro Asp Val Arg Ser Tyr Thr Ile Thr Gly Leu Gln Pro
 50                  55                  60

Gly Thr Gly Tyr Ile Ile Asn Leu Glu Thr Leu Ile Asn Ala Thr Gly
 65                  70                  75                  80

Tyr Pro Val Val Ile Asp Ala Ser Thr
                 85
```

<210> SEQ ID NO 263
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 263

```
Asn Val Ser Pro Pro Arg Arg Ala Arg Val Thr Asp Ala Thr Glu Thr
```

```
               1               5                  10                 15
          Thr Ile Thr Ile Ser Trp Arg Thr Lys Thr Glu Thr Ile Thr Gln Phe
                          20                  25                 30
          Trp Val Leu Ala Gly Pro Ser Val Trp Thr Gly Arg Met Ser Ile Gln
                      35                  40                  45
          Arg Thr Ile Lys Pro Asp Val Arg Ser Tyr Thr Ile Thr Gly Leu Gln
                      50                  55                  60
          Pro Gly Thr Thr Tyr Tyr Ile Gly Leu Tyr Thr Leu Gln Tyr Tyr Glu
           65                  70                  75                  80
          Tyr Ser Pro Val Val Ile Asp Ala Ser Thr
                          85                  90
```

<210> SEQ ID NO 264
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 264

```
          Asn Val Ser Pro Pro Arg Arg Ala Arg Val Thr Asp Ala Thr Glu Thr
           1               5                  10                 15
          Thr Ile Thr Ile Ser Trp Arg Thr Lys Thr Glu Thr Ile Thr Thr Phe
                          20                  25                 30
          Arg Val Trp Ala Arg Pro Tyr Leu Tyr Tyr Trp Ile Gln Arg Thr Ile
                      35                  40                  45
          Lys Pro Asp Val Arg Ser Tyr Thr Ile Thr Gly Leu Gln Pro Gly Thr
                      50                  55                  60
          His Tyr Asp Ile Gly Leu Ser Thr Leu Ser Ser Thr Trp Tyr Tyr Pro
           65                  70                  75                  80
          Val Val Ile Asp Ala Ser Thr
                          85
```

<210> SEQ ID NO 265
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 265

```
          Asn Val Ser Pro Pro Arg Arg Ala Arg Val Thr Asp Ala Thr Glu Thr
          1               5                   10                 15
          Thr Ile Thr Ile Ser Trp Arg Thr Lys Thr Glu Thr Ile Thr Tyr Phe
                          20                  25                 30
          His Val Asn Ala Gln Pro Ser Ser Pro Pro Trp Ile Gln Arg Thr Ile
                      35                  40                  45
          Lys Pro Asp Val Arg Ser Tyr Thr Ile Thr Gly Leu Gln Pro Gly Thr
               50                  55                  60
          Tyr Tyr Gly Ile Ser Leu Tyr Thr Leu Ser Trp Arg Gly Glu Tyr His
           65                  70                  75                  80
          Pro Val Val Ile Asp Ala Ser Thr
                          85
```

<210> SEQ ID NO 266
<211> LENGTH: 91
<212> TYPE: PRT

```
<213> ORGANISM: Artificial Sequence
<220> FEATURE:
<223> OTHER INFORMATION: synthetically constructed Fibronectin Type III
      domain polypeptide

<400> SEQUENCE: 266

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Arg Phe
            20                  25                  30

Ser Val Leu Ala Tyr Pro Ser Lys Arg Thr Thr Tyr Thr Pro Ile Gln
        35                  40                  45

Arg Thr Ile Lys Pro Asp Val Arg Ser Tyr Thr Ile Thr Gly Leu Gln
    50                  55                  60

Pro Gly Thr Gly Tyr Thr Ile Arg Leu Tyr Thr Leu Ser Pro Tyr Tyr
65                  70                  75                  80

Trp Val Tyr Pro Val Val Ile Asp Ala Ser Thr
                85                  90

<210> SEQ ID NO 267
<211> LENGTH: 84
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 267

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Trp Phe
            20                  25                  30

Tyr Val Ser Ala Phe Pro Leu Leu Val Asp Gly Ile Gln Arg Thr Ile
        35                  40                  45

Lys Pro Asp Val Arg Ser Tyr Thr Ile Thr Gly Leu Gln Pro Gly Thr
    50                  55                  60

Tyr Tyr Gly Ile Asn Leu Tyr Thr Leu Ser Ser Tyr Pro Val Val Ile
65                  70                  75                  80

Asp Ala Ser Thr

<210> SEQ ID NO 268
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 268

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Tyr Phe
            20                  25                  30

Tyr Val Tyr Ala Lys Pro Arg Tyr Ile Asn Ser Ile Gln Arg Thr Ile
        35                  40                  45

Lys Pro Asp Val Arg Ser Tyr Thr Ile Thr Gly Leu Gln Pro Gly Thr
    50                  55                  60

Asp Tyr Ser Ile Tyr Leu Asp Thr Leu Tyr Trp Gly Gly Glu Tyr Gly
65                  70                  75                  80
```

```
Pro Val Val Ile Asp Ala Ser Thr
                85
```

<210> SEQ ID NO 269
<211> LENGTH: 93
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 269

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ala Phe
            20                  25                  30

Asn Val Tyr Ala Ser Pro Glu Tyr Trp Arg Tyr Gly Tyr Phe Arg Phe
        35                  40                  45

Ile Gln Arg Thr Ile Lys Pro Asp Val Arg Ser Tyr Thr Ile Thr Gly
    50                  55                  60

Leu Gln Pro Gly Thr Gly Tyr Tyr Ile Tyr Leu Tyr Thr Leu Tyr His
65                  70                  75                  80

Lys Tyr Gly Tyr Tyr Pro Val Val Ile Asp Ala Ser Thr
                85                  90
```

<210> SEQ ID NO 270
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 270

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ala Phe
            20                  25                  30

Tyr Val His Ala Val Pro Met Leu Trp Val Val Asn Gly Ile Gln Arg
        35                  40                  45

Thr Ile Lys Pro Asp Val Arg Ser Tyr Thr Ile Thr Gly Leu Gln Pro
    50                  55                  60

Gly Thr Ser Tyr Thr Ile Asn Leu Glu Thr Leu Arg Met Ser Ser His
65                  70                  75                  80

Tyr Tyr Pro Val Val Ile Asp Ala Ser Thr
                85                  90
```

<210> SEQ ID NO 271
<211> LENGTH: 88
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 271

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ser Phe
            20                  25                  30

Tyr Val Arg Ala Leu Pro Val Ser Ala Trp Pro Ile Gln Arg Thr Ile
```

```
            35                  40                  45

Lys Pro Asp Val Arg Ser Tyr Thr Ile Thr Gly Leu Gln Pro Gly Thr
 50                  55                  60

Gly Tyr Asn Ile Gly Leu Val Thr Leu Tyr Tyr Gly Ala Ser Tyr Val
 65                  70                  75                  80

Pro Val Val Ile Asp Ala Ser Thr
                 85

<210> SEQ ID NO 272
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 272

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Ala Phe
                 20                  25                  30

Tyr Val Gly Ala His Pro Trp Tyr Asn Leu Glu Ile Gln Arg Thr Ile
            35                  40                  45

Lys Pro Asp Val Arg Ser Tyr Thr Ile Thr Gly Leu Gln Pro Gly Thr
 50                  55                  60

Gly Tyr Val Ile Ser Leu Tyr Thr Leu Trp His His Asn Glu Ala Pro
 65                  70                  75                  80

Val Val Ile Asp Ala Ser Thr
                 85

<210> SEQ ID NO 273
<211> LENGTH: 89
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 273

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Ser Phe
                 20                  25                  30

Trp Val His Ala Tyr Pro Ser Gly Ala Ser Gly Gly Ile Gln Arg Thr
            35                  40                  45

Ile Lys Pro Asp Val Arg Ser Tyr Thr Ile Thr Gly Leu Gln Pro Gly
 50                  55                  60

Thr Asn Tyr Gly Ile Ala Leu Ala Thr Leu Thr His Tyr Tyr Thr Tyr
 65                  70                  75                  80

Ser Pro Val Val Ile Asp Ala Ser Thr
                 85

<210> SEQ ID NO 274
<211> LENGTH: 90
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 274
```

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Gly Phe
                20                  25                  30

His Val Phe Ala Ser Pro Trp Tyr Ser Gly Ser Gln Ser Ile Gln Arg
            35                  40                  45

Thr Ile Lys Pro Asp Val Arg Ser Tyr Thr Ile Thr Gly Leu Gln Pro
        50                  55                  60

Gly Thr Thr Tyr Tyr Ile Gly Leu Asn Thr Leu Tyr Ile Pro Gly His
65                  70                  75                  80

Glu Pro Pro Val Val Ile Asp Ala Ser Thr
                85                  90
```

<210> SEQ ID NO 275
<211> LENGTH: 92
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 275

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Ser Phe
                20                  25                  30

Tyr Val Asp Ala Gly Pro Trp Tyr Arg Pro Asp Ala Tyr Glu Tyr Ile
            35                  40                  45

Gln Arg Thr Ile Lys Pro Asp Val Arg Ser Tyr Thr Ile Thr Gly Leu
        50                  55                  60

Gln Pro Gly Thr Gly Tyr Ser Ile Gln Leu Tyr Thr Leu Tyr Ala Tyr
65                  70                  75                  80

Ala Tyr Leu Tyr Pro Val Val Ile Asp Ala Ser Thr
                85                  90
```

<210> SEQ ID NO 276
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 276

```
Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Leu Phe
                20                  25                  30

Tyr Val Tyr Ala Tyr Pro Arg Tyr Tyr Pro Gly Ile Gln Arg Thr Ile
            35                  40                  45

Lys Pro Asp Val Arg Ser Tyr Thr Ile Thr Gly Leu Gln Pro Gly Thr
        50                  55                  60

Ser Tyr Ser Ile Tyr Leu Ser Thr Leu Trp Asp Thr Lys Gly Tyr Pro
65                  70                  75                  80

Val Val Ile Asp Ala Ser Thr
                85
```

<210> SEQ ID NO 277

```
<211> LENGTH: 87
<212> TYPE: PRT
<213> ORGANISM: Artificial Sequence
<220> FEATURE:
<223> OTHER INFORMATION: synthetically constructed Fibronectin Type III
      domain polypeptide

<400> SEQUENCE: 277

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Thr Phe
            20                  25                  30

Met Val Val Ala Tyr Pro Met Phe Gln Tyr Arg Ile Gln Arg Thr Ile
        35                  40                  45

Lys Pro Asp Val Arg Ser Tyr Thr Ile Thr Gly Leu Gln Pro Gly Thr
50                  55                  60

Ser Tyr Thr Ile Tyr Leu Gln Thr Leu Gly Tyr Ala Ser Trp Tyr Pro
65                  70                  75                  80

Val Val Ile Asp Ala Ser Thr
                85

<210> SEQ ID NO 278
<211> LENGTH: 5
<212> TYPE: PRT
<213> ORGANISM: Artificial Sequence
<220> FEATURE:
<223> OTHER INFORMATION: synthetically constructed consensus sequence

<400> SEQUENCE: 278

Ser Gly Gly Glu Trp
1               5

<210> SEQ ID NO 279
<211> LENGTH: 9
<212> TYPE: PRT
<213> ORGANISM: Artificial Sequence
<220> FEATURE:
<223> OTHER INFORMATION: synthetically constructed consensus sequence

<400> SEQUENCE: 279

Gly Tyr Ile Val Glu Tyr Arg Glu Lys
1               5

<210> SEQ ID NO 280
<211> LENGTH: 96
<212> TYPE: PRT
<213> ORGANISM: Homo sapiens
<220> FEATURE:
<223> OTHER INFORMATION: Fibronectin Type III repeat 10 domain
      polypeptide

<400> SEQUENCE: 280

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
50                  55                  60

Gly Val Asp Tyr Thr Ile Thr Val Tyr Ala Val Thr Gly Arg Gly Asp
65                  70                  75                  80
```

Ser Pro Ala Ser Ser Lys Pro Ile Ser Ile Asn Tyr Arg Thr Glu Ile
                85                  90                  95

<210> SEQ ID NO 281
<211> LENGTH: 91
<212> TYPE: PRT
<213> ORGANISM: Homo sapiens
<220> FEATURE:
<223> OTHER INFORMATION: Fibronectin Type III repeat 08 domain
      polypeptide

<400> SEQUENCE: 281

Ala Val Pro Pro Thr Asp Leu Arg Phe Thr Asn Ile Gly Pro Asp
1               5                   10                  15

Thr Met Arg Val Thr Trp Ala Pro Pro Ser Ile Asp Leu Thr Asn
                20                  25                  30

Phe Leu Val Arg Tyr Ser Pro Val Lys Asn Glu Glu Asp Val Ala Glu
                35                  40                  45

Leu Ser Ile Ser Pro Ser Asp Asn Ala Val Val Leu Thr Asn Leu Leu
    50                  55                  60

Pro Gly Thr Glu Tyr Val Val Ser Val Ser Val Tyr Glu Gln His
65                  70                  75                  80

Glu Ser Thr Pro Leu Arg Gly Arg Gln Lys Thr
                85                  90

<210> SEQ ID NO 282
<211> LENGTH: 88
<212> TYPE: PRT
<213> ORGANISM: Homo sapiens
<220> FEATURE:
<223> OTHER INFORMATION: Fibronectin Type III repeat 13 domain
      polypeptide

<400> SEQUENCE: 282

Pro Ala Pro Thr Asp Leu Lys Phe Thr Gln Val Thr Pro Thr Ser Leu
1               5                   10                  15

Ser Ala Gln Trp Thr Pro Pro Asn Val Gln Leu Thr Gly Tyr Arg Val
                20                  25                  30

Arg Val Thr Pro Lys Glu Lys Thr Gly Pro Met Lys Glu Ile Asn Leu
                35                  40                  45

Ala Pro Asp Ser Ser Ser Val Val Val Ser Gly Leu Met Val Ala Thr
    50                  55                  60

Lys Tyr Glu Val Ser Val Tyr Ala Leu Lys Asp Thr Leu Thr Ser Arg
65                  70                  75                  80

Pro Ala Gln Gly Val Val Thr Thr
                85

<210> SEQ ID NO 283
<211> LENGTH: 88
<212> TYPE: PRT
<213> ORGANISM: Homo sapiens
<220> FEATURE:
<223> OTHER INFORMATION: Fibronectin Type III repeat 04 domain
      polypeptide

<400> SEQUENCE: 283

Pro Ser Pro Arg Asp Leu Gln Phe Val Glu Val Thr Asp Val Lys Val
1               5                   10                  15

Thr Ile Met Trp Thr Pro Pro Glu Ser Ala Val Thr Gly Tyr Arg Val
                20                  25                  30

Asp Val Ile Pro Val Asn Leu Pro Gly Glu His Gly Gln Arg Leu Pro

```
                35                  40                  45

Ile Ser Arg Asn Thr Phe Ala Glu Val Thr Gly Leu Ser Pro Gly Val
 50                  55                  60

Thr Tyr Tyr Phe Lys Val Phe Ala Val Ser His Gly Arg Glu Ser Lys
 65                  70                  75                  80

Pro Leu Thr Ala Gln Gln Thr Thr
                85

<210> SEQ ID NO 284
<211> LENGTH: 88
<212> TYPE: PRT
<213> ORGANISM: Homo sapiens
<220> FEATURE:
<223> OTHER INFORMATION: Fibronectin Type III repeat 05 domain
      polypeptide

<400> SEQUENCE: 284

Lys Leu Asp Ala Pro Thr Asn Leu Gln Phe Val Asn Glu Thr Asp Ser
  1               5                  10                  15

Thr Val Leu Val Arg Trp Thr Pro Pro Arg Ala Gln Ile Thr Gly Tyr
                 20                  25                  30

Arg Leu Thr Val Gly Leu Thr Arg Arg Gly Gln Pro Arg Gln Tyr Asn
                 35                  40                  45

Val Gly Pro Ser Val Ser Lys Tyr Pro Leu Arg Asn Leu Gln Pro Ala
 50                  55                  60

Ser Glu Tyr Thr Val Ser Leu Val Ala Ile Lys Gly Asn Gln Glu Ser
 65                  70                  75                  80

Pro Lys Ala Thr Gly Val Phe Thr
                85

<210> SEQ ID NO 285
<211> LENGTH: 89
<212> TYPE: PRT
<213> ORGANISM: Homo sapiens
<220> FEATURE:
<223> OTHER INFORMATION: Fibronectin Type III repeat 09 domain
      polypeptide

<400> SEQUENCE: 285

Gly Leu Asp Ser Pro Thr Gly Ile Asp Phe Ser Asp Ile Thr Ala Asn
  1               5                  10                  15

Ser Phe Thr Val His Trp Ile Ala Pro Arg Ala Thr Ile Thr Gly Tyr
                 20                  25                  30

Arg Ile Arg His His Pro Glu His Phe Ser Gly Arg Pro Arg Glu Asp
                 35                  40                  45

Arg Val Pro His Ser Arg Asn Ser Ile Thr Leu Thr Asn Leu Thr Pro
 50                  55                  60

Gly Thr Glu Tyr Val Val Ser Ile Val Ala Leu Asn Gly Arg Glu Glu
 65                  70                  75                  80

Ser Pro Leu Leu Ile Gly Gln Gln Ser
                85

<210> SEQ ID NO 286
<211> LENGTH: 90
<212> TYPE: PRT
<213> ORGANISM: Homo sapiens
<220> FEATURE:
<223> OTHER INFORMATION: Fibronectin Type III repeat 15 domain
      polypeptide

<400> SEQUENCE: 286
```

```
Ala Ile Asp Ala Pro Ser Asn Leu Arg Phe Leu Ala Thr Thr Pro Asn
  1               5                  10                  15

Ser Leu Leu Val Ser Trp Gln Pro Arg Ala Arg Ile Thr Gly Tyr
             20                  25                  30

Ile Ile Lys Tyr Glu Lys Pro Gly Ser Pro Arg Glu Val Val Pro
             35                  40                  45

Arg Pro Arg Pro Gly Val Thr Glu Ala Thr Ile Thr Gly Leu Glu Pro
 50                  55                  60

Gly Thr Glu Tyr Thr Ile Tyr Val Ile Ala Leu Lys Asn Asn Gln Lys
 65                  70                  75                  80

Ser Glu Pro Leu Ile Gly Arg Lys Lys Thr
             85                  90

<210> SEQ ID NO 287
<211> LENGTH: 90
<212> TYPE: PRT
<213> ORGANISM: Homo sapiens
<220> FEATURE:
<223> OTHER INFORMATION: Fibronectin Type III repeat 12 domain
      polypeptide

<400> SEQUENCE: 287

Asn Ile Asp Arg Pro Lys Gly Leu Ala Phe Thr Asp Val Asp Val Asp
  1               5                  10                  15

Ser Ile Lys Ile Ala Trp Glu Ser Pro Gln Gly Gln Val Ser Arg Tyr
             20                  25                  30

Arg Val Thr Tyr Ser Ser Pro Glu Asp Gly Ile His Glu Leu Phe Pro
             35                  40                  45

Ala Pro Asp Gly Glu Glu Asp Thr Ala Glu Leu Gln Gly Leu Arg Pro
 50                  55                  60

Gly Ser Glu Tyr Thr Val Ser Val Val Ala Leu His Asp Asp Met Glu
 65                  70                  75                  80

Ser Gln Pro Leu Ile Gly Thr Gln Ser Thr
             85                  90

<210> SEQ ID NO 288
<211> LENGTH: 89
<212> TYPE: PRT
<213> ORGANISM: Homo sapiens
<220> FEATURE:
<223> OTHER INFORMATION: Fibronectin Type III repeat 02 domain
      polypeptide

<400> SEQUENCE: 288

Pro Leu Val Ala Thr Ser Glu Ser Val Thr Glu Ile Thr Ala Ser Ser
  1               5                  10                  15

Phe Val Val Ser Trp Val Ser Ala Ser Asp Thr Val Ser Gly Phe Arg
             20                  25                  30

Val Glu Tyr Glu Leu Ser Glu Glu Gly Asp Glu Pro Gln Tyr Leu Asp
             35                  40                  45

Leu Pro Ser Thr Ala Thr Ser Val Asn Ile Pro Asp Leu Leu Pro Gly
 50                  55                  60

Arg Lys Tyr Ile Val Asn Val Tyr Gln Ile Ser Glu Asp Gly Glu Gln
 65                  70                  75                  80

Ser Leu Ile Leu Ser Thr Ser Gln Thr
             85

<210> SEQ ID NO 289
```

<211> LENGTH: 88
<212> TYPE: PRT
<213> ORGANISM: Homo sapiens
<220> FEATURE:
<223> OTHER INFORMATION: Fibronectin Type III repeat 03 domain
      polypeptide

<400> SEQUENCE: 289

Pro Asp Ala Pro Pro Asp Pro Thr Val Asp Gln Val Asp Asp Thr Ser
1               5                   10                  15

Ile Val Val Arg Trp Ser Arg Pro Gln Ala Pro Ile Thr Gly Tyr Arg
            20                  25                  30

Ile Val Tyr Ser Pro Ser Val Glu Gly Ser Ser Thr Glu Leu Asn Leu
        35                  40                  45

Pro Glu Thr Ala Asn Ser Val Thr Leu Ser Asp Leu Gln Pro Gly Val
    50                  55                  60

Gln Tyr Asn Ile Thr Ile Tyr Ala Val Glu Glu Asn Gln Glu Ser Thr
65                  70                  75                  80

Pro Val Val Ile Gln Gln Glu Thr
                85

<210> SEQ ID NO 290
<211> LENGTH: 90
<212> TYPE: PRT
<213> ORGANISM: Homo sapiens
<220> FEATURE:
<223> OTHER INFORMATION: Fibronectin Type III repeat 11 domain
      polypeptide

<400> SEQUENCE: 290

Glu Ile Asp Lys Pro Ser Gln Met Gln Val Thr Asp Val Gln Asp Asn
1               5                   10                  15

Ser Ile Ser Val Lys Trp Leu Pro Ser Ser Ser Pro Val Thr Gly Tyr
            20                  25                  30

Arg Val Thr Thr Thr Pro Lys Asn Gly Pro Gly Pro Thr Lys Thr Lys
        35                  40                  45

Thr Ala Gly Pro Asp Gln Thr Glu Met Thr Ile Glu Gly Leu Gln Pro
    50                  55                  60

Thr Val Glu Tyr Val Val Ser Val Tyr Ala Gln Asn Pro Ser Gly Glu
65                  70                  75                  80

Ser Gln Pro Leu Val Gln Thr Ala Val Thr
                85                  90

<210> SEQ ID NO 291
<211> LENGTH: 86
<212> TYPE: PRT
<213> ORGANISM: Homo sapiens
<220> FEATURE:
<223> OTHER INFORMATION: Fibronectin Type III repeat 06 domain
      polypeptide

<400> SEQUENCE: 291

Pro Gly Ser Ser Ile Pro Pro Tyr Asn Thr Glu Val Thr Glu Thr Thr
1               5                   10                  15

Ile Val Ile Thr Trp Thr Pro Ala Pro Arg Ile Gly Phe Lys Leu Gly
            20                  25                  30

Val Arg Pro Ser Gln Gly Gly Glu Ala Pro Arg Glu Val Thr Ser Asp
        35                  40                  45

Ser Gly Ser Ile Val Val Ser Gly Leu Thr Pro Gly Val Glu Tyr Val
    50                  55                  60

```
Tyr Thr Ile Gln Val Leu Arg Asp Gly Gln Glu Arg Asp Ala Pro Ile
 65                  70                  75                  80

Val Asn Lys Val Val Thr
                 85

<210> SEQ ID NO 292
<211> LENGTH: 93
<212> TYPE: PRT
<213> ORGANISM: Homo sapiens
<220> FEATURE:
<223> OTHER INFORMATION: Fibronectin Type III repeat 01 domain
      polypeptide

<400> SEQUENCE: 292

Ser Ser Ser Gly Pro Val Glu Val Phe Ile Thr Glu Thr Pro Ser Gln
  1               5                  10                  15

Pro Asn Ser His Pro Ile Gln Trp Asn Ala Pro Gln Pro Ser His Ile
                 20                  25                  30

Ser Lys Tyr Ile Leu Arg Trp Arg Pro Lys Asn Ser Val Gly Arg Trp
             35                  40                  45

Lys Glu Ala Thr Ile Pro Gly His Leu Asn Ser Tyr Thr Ile Lys Gly
 50                  55                  60

Leu Lys Pro Gly Val Val Tyr Glu Gly Gln Leu Ile Ser Ile Gln Gln
 65                  70                  75                  80

Tyr Gly His Gln Glu Val Thr Arg Phe Asp Phe Thr Thr
                 85                  90

<210> SEQ ID NO 293
<211> LENGTH: 538
<212> TYPE: PRT
<213> ORGANISM: Mus musculus

<400> SEQUENCE: 293

Met Arg Gly Ser Gly Pro Arg Gly Ala Gly His Arg Arg Thr Gln Gly
  1               5                  10                  15

Arg Gly Gly Gly Asp Asp Thr Pro Arg Val Pro Ala Ser Leu Ala Gly
                 20                  25                  30

Cys Tyr Ser Ala Pro Leu Lys Gly Pro Leu Trp Thr Cys Leu Leu
             35                  40                  45

Cys Ala Ala Leu Arg Thr Leu Leu Ala Ser Pro Ser Asn Glu Val Asn
 50                  55                  60

Leu Leu Asp Ser Arg Thr Val Met Gly Asp Leu Gly Trp Ile Ala Phe
 65                  70                  75                  80

Pro Lys Asn Gly Trp Glu Glu Ile Gly Glu Val Asp Glu Asn Tyr Ala
                 85                  90                  95

Pro Ile His Thr Tyr Gln Val Cys Lys Val Met Glu Gln Asn Gln Asn
                100                 105                 110

Asn Trp Leu Leu Thr Ser Trp Ile Ser Asn Glu Gly Ala Ser Arg Ile
            115                 120                 125

Phe Ile Glu Leu Lys Phe Thr Leu Arg Asp Trp Gln Gln Pro Phe Leu
130                 135                 140

Glu Asp Trp Gly Thr Cys Lys Glu Thr Phe Asn Met Tyr Tyr Phe Glu
145                 150                 155                 160

Ser Asp Asp Glu Asn Gly Arg Ser Ile Lys Glu Asn Gln Tyr Ile Lys
                165                 170                 175

Ile Asp Thr Ile Ala Ala Asp Glu Ser Phe Thr Glu Leu Asp Leu Gly
                180                 185                 190
```

Asp Arg Val Met Lys Leu Asn Thr Glu Val Arg Asp Val Gly Pro Leu
            195                 200                 205

Ser Lys Lys Gly Phe Tyr Leu Ala Phe Gln Asp Val Gly Ala Cys Ile
 210                 215                 220

Ala Leu Val Ser Val Arg Val Tyr Tyr Lys Lys Cys Pro Ser Val Val
225                 230                 235                 240

Arg His Leu Ala Ile Phe Pro Asp Thr Ile Thr Gly Ala Asp Ser Ser
            245                 250                 255

Gln Leu Leu Glu Val Ser Gly Ser Cys Val Asn His Ser Val Thr Asp
            260                 265                 270

Asp Pro Pro Lys Met His Cys Ser Ala Glu Gly Glu Trp Leu Val Pro
            275                 280                 285

Ile Gly Lys Cys Met Cys Lys Ala Gly Tyr Glu Glu Lys Asn Gly Thr
290                 295                 300

Cys Gln Val Cys Arg Pro Gly Phe Phe Lys Ala Ser Pro His Ser Gln
305                 310                 315                 320

Thr Cys Ser Lys Cys Pro Pro His Ser Tyr Ser His Glu Glu Ala Ser
            325                 330                 335

Thr Ser Cys Val Cys Glu Lys Asp Tyr Phe Arg Lys Asp Ser Asp Pro
            340                 345                 350

Pro Thr Met Ala Cys Thr Thr Pro Ser Pro Val Thr Asn Val Lys Lys
            355                 360                 365

Gly Lys Ile Ala Lys Asn Ser Ile Ser Leu Ser Trp Gln Glu Pro Asp
            370                 375                 380

Arg Pro Asn Gly Ile Ile Leu Glu Tyr Glu Ile Lys Tyr Phe Glu Lys
385                 390                 395                 400

Asp Gln Glu Thr Ser Tyr Thr Ile Ile Lys Ser Lys Glu Thr Ser Ile
            405                 410                 415

Thr Ala Glu Gly Leu Lys Pro Ala Ser Val Tyr Val Phe Gln Ile Arg
            420                 425                 430

Ala Arg Thr Ala Ala Gly Tyr Gly Val Phe Ser Arg Arg Phe Glu Phe
            435                 440                 445

Glu Thr Thr Pro Val Ser Val Ala Ala Ser Asn Asp Gln Ser Gln Ile
            450                 455                 460

Pro Ile Ile Ala Val Ser Val Thr Val Gly Val Ile Leu Leu Ala Val
465                 470                 475                 480

Met Ile Gly Phe Leu Leu Ser Gly Arg Arg Cys Gly Tyr Ser Lys Ala
            485                 490                 495

Lys Gln Asp Pro Glu Glu Glu Lys Met His Phe His Asn Gly His Ser
            500                 505                 510

Lys Gln Ile Val Gln Asn Lys Ser Lys Arg Leu Tyr Tyr Asp Asp Asp
            515                 520                 525

Cys Cys Ser Gly Gln Ala Ile Cys Ser Asn
530                 535

<210> SEQ ID NO 294
<211> LENGTH: 6
<212> TYPE: PRT
<213> ORGANISM: Artificial Sequence
<220> FEATURE:
<223> OTHER INFORMATION: synthetic construct

<400> SEQUENCE: 294

Thr Leu Asp Ile Val Asp
 1               5

<210> SEQ ID NO 295
<211> LENGTH: 6
<212> TYPE: PRT
<213> ORGANISM: Artificial Sequence
<220> FEATURE:
<223> OTHER INFORMATION: synthetic construct

<400> SEQUENCE: 295

Asp Leu Tyr Tyr Ser Tyr
1               5

<210> SEQ ID NO 296
<211> LENGTH: 6
<212> TYPE: PRT
<213> ORGANISM: Artificial Sequence
<220> FEATURE:
<223> OTHER INFORMATION: synthetic construct

<400> SEQUENCE: 296

Asp Val Leu Ile Val Tyr
1               5

<210> SEQ ID NO 297
<211> LENGTH: 16
<212> TYPE: PRT
<213> ORGANISM: Artificial Sequence
<220> FEATURE:
<223> OTHER INFORMATION: synthetic construct

<400> SEQUENCE: 297

His Asn Glu Ile Phe Phe Lys Ile Lys Thr Arg Leu Glu Ala Lys Arg
1               5                   10                  15

<210> SEQ ID NO 298
<211> LENGTH: 16
<212> TYPE: PRT
<213> ORGANISM: Artificial Sequence
<220> FEATURE:
<223> OTHER INFORMATION: synthetic construct

<400> SEQUENCE: 298

Tyr Lys Glu Ile His Phe Lys Val Lys Thr Lys Leu Glu Ser Gln Arg
1               5                   10                  15

<210> SEQ ID NO 299
<211> LENGTH: 16
<212> TYPE: PRT
<213> ORGANISM: Artificial Sequence
<220> FEATURE:
<223> OTHER INFORMATION: synthetic construct

<400> SEQUENCE: 299

His Asn Val Val Gln Phe Lys Ile Lys Thr Lys Leu Lys Ala Glu Arg
1               5                   10                  15

<210> SEQ ID NO 300
<211> LENGTH: 96
<212> TYPE: PRT
<213> ORGANISM: Artificial Sequence
<220> FEATURE:
<223> OTHER INFORMATION: synthetic construct

<400> SEQUENCE: 300

Asp Ser Glu Val Asn Gln Glu Ala Lys Pro Glu Val Lys Pro Glu Val
1               5                   10                  15

Lys Pro Glu Thr His Ile Asn Leu Lys Val Ser Asp Gly Ser Ser Glu

```
                    20                  25                  30

Ile Phe Phe Lys Ile Lys Lys Thr Thr Pro Leu Arg Arg Leu Met Glu
            35                  40                  45

Ala Phe Ala Lys Arg Gln Gly Lys Glu Met Asp Ser Leu Arg Phe Leu
        50                  55                  60

Tyr Asp Gly Ile Arg Ile Gln Ala Asp Gln Thr Pro Glu Asp Leu Asp
65                  70                  75                  80

Met Glu Asp Asn Asp Ile Ile Glu Ala His Arg Glu Gln Ile Gly Gly
                85                  90                  95

<210> SEQ ID NO 301
<211> LENGTH: 97
<212> TYPE: PRT
<213> ORGANISM: Artificial Sequence
<220> FEATURE:
<223> OTHER INFORMATION: synthetic construct

<400> SEQUENCE: 301

Met Ser Asp Gln Glu Ala Lys Pro Ser Thr Glu Asp Leu Gly Asp Lys
1               5                   10                  15

Lys Glu Gly Glu Tyr Ile Lys Leu Lys Val Ile Gly Gln Asp Ser Ser
            20                  25                  30

Glu Ile His Phe Lys Val Lys Met Thr Thr His Leu Lys Lys Leu Met
        35                  40                  45

Glu Ser Tyr Ala Gln Arg Gln Gly Val Pro Met Asn Ser Leu Arg Phe
    50                  55                  60

Leu Phe Glu Gly Gln Arg Ile Ala Asp Asn His Thr Pro Lys Glu Leu
65                  70                  75                  80

Gly Met Glu Glu Glu Asp Val Ile Glu Val Tyr Gln Glu Gln Thr Gly
                85                  90                  95

Gly

<210> SEQ ID NO 302
<211> LENGTH: 93
<212> TYPE: PRT
<213> ORGANISM: Artificial Sequence
<220> FEATURE:
<223> OTHER INFORMATION: synthetic construct

<400> SEQUENCE: 302

Met Ala Asp Glu Lys Pro Lys Glu Gly Val Lys Thr Glu Asn Asn Asp
1               5                   10                  15

His Ile Asn Leu Lys Val Ala Gly Gln Asp Gly Ser Val Val Gln Phe
            20                  25                  30

Lys Ile Lys Arg His Thr Pro Leu Ser Lys Leu Met Glu Ala Tyr Ser
        35                  40                  45

Glu Arg Gln Gly Leu Ser Met Arg Gln Ile Arg Phe Arg Phe Asp Gly
    50                  55                  60

Gln Pro Ile Asn Glu Thr Asp Thr Pro Ala Gln Leu Glu Met Glu Asp
65                  70                  75                  80

Glu Asp Thr Ile Asp Val Phe Gln Gln Gln Thr Gly Gly
                85                  90

<210> SEQ ID NO 303
<211> LENGTH: 13
<212> TYPE: PRT
<213> ORGANISM: Artificial Sequence
<220> FEATURE:
<223> OTHER INFORMATION: synthetic construct
```

<400> SEQUENCE: 303

Tyr Arg Tyr Tyr Tyr Tyr Asp Leu Tyr Tyr Ser Tyr
1               5                   10

<210> SEQ ID NO 304
<211> LENGTH: 13
<212> TYPE: PRT
<213> ORGANISM: Artificial Sequence
<220> FEATURE:
<223> OTHER INFORMATION: synthetic construct

<400> SEQUENCE: 304

Tyr Arg Tyr Tyr Tyr Tyr Asp Ile Tyr Tyr Ala Val
1               5                   10

<210> SEQ ID NO 305
<211> LENGTH: 13
<212> TYPE: PRT
<213> ORGANISM: Artificial Sequence
<220> FEATURE:
<223> OTHER INFORMATION: synthetic construct

<400> SEQUENCE: 305

Tyr Arg Tyr Tyr Tyr Glu Glu Phe Phe Asp Tyr Ala Val
1               5                   10

<210> SEQ ID NO 306
<211> LENGTH: 13
<212> TYPE: PRT
<213> ORGANISM: Artificial Sequence
<220> FEATURE:
<223> OTHER INFORMATION: synthetic construct

<400> SEQUENCE: 306

Tyr Arg Phe Tyr Tyr Glu Glu Phe Phe Asp Tyr Ala Tyr
1               5                   10

<210> SEQ ID NO 307
<211> LENGTH: 13
<212> TYPE: PRT
<213> ORGANISM: Artificial Sequence
<220> FEATURE:
<223> OTHER INFORMATION: synthetic construct

<400> SEQUENCE: 307

Tyr Arg Tyr Tyr Tyr Asp Asp Phe Leu Asp Phe Ala Phe
1               5                   10

<210> SEQ ID NO 308
<211> LENGTH: 13
<212> TYPE: PRT
<213> ORGANISM: Artificial Sequence
<220> FEATURE:
<223> OTHER INFORMATION: synthetic construct

<400> SEQUENCE: 308

Tyr Arg Tyr Tyr Tyr Tyr Tyr Asn Ile Phe Phe Ala Asp
1               5                   10

<210> SEQ ID NO 309
<211> LENGTH: 13
<212> TYPE: PRT
<213> ORGANISM: Artificial Sequence
<220> FEATURE:
<223> OTHER INFORMATION: synthetic construct

```
<400> SEQUENCE: 309

His His Tyr Phe Tyr Asp Asp Asp Leu Tyr Phe Ala Phe
1               5                   10

<210> SEQ ID NO 310
<211> LENGTH: 13
<212> TYPE: PRT
<213> ORGANISM: Artificial Sequence
<220> FEATURE:
<223> OTHER INFORMATION: synthetic construct

<400> SEQUENCE: 310

His Gly Tyr Tyr His Tyr Asp Asp Ile Tyr Tyr Ala Leu
1               5                   10

<210> SEQ ID NO 311
<211> LENGTH: 13
<212> TYPE: PRT
<213> ORGANISM: Artificial Sequence
<220> FEATURE:
<223> OTHER INFORMATION: synthetic construct

<400> SEQUENCE: 311

His Ala Tyr Tyr His Tyr Asp Asp Ile Phe Leu Ala Asp
1               5                   10

<210> SEQ ID NO 312
<211> LENGTH: 13
<212> TYPE: PRT
<213> ORGANISM: Artificial Sequence
<220> FEATURE:
<223> OTHER INFORMATION: synthetic construct

<400> SEQUENCE: 312

His Glu Tyr Tyr Tyr His Glu Asp Ile Phe Tyr Ala Val
1               5                   10

<210> SEQ ID NO 313
<211> LENGTH: 13
<212> TYPE: PRT
<213> ORGANISM: Artificial Sequence
<220> FEATURE:
<223> OTHER INFORMATION: synthetic construct

<400> SEQUENCE: 313

His Glu Ala Tyr His Tyr His Asp Ile Phe Tyr Ala Val
1               5                   10

<210> SEQ ID NO 314
<211> LENGTH: 13
<212> TYPE: PRT
<213> ORGANISM: Artificial Sequence
<220> FEATURE:
<223> OTHER INFORMATION: synthetic construct

<400> SEQUENCE: 314

His Glu Thr Tyr Asp Tyr Tyr Asp Ile Tyr Ile Ala Tyr
1               5                   10

<210> SEQ ID NO 315
<211> LENGTH: 13
<212> TYPE: PRT
<213> ORGANISM: Artificial Sequence
<220> FEATURE:
<223> OTHER INFORMATION: synthetic construct

<400> SEQUENCE: 315
```

```
Tyr Glu Ile Phe Tyr His Asp Asp Ile Tyr Ile Ser Asp
1               5                   10

<210> SEQ ID NO 316
<211> LENGTH: 13
<212> TYPE: PRT
<213> ORGANISM: Artificial Sequence
<220> FEATURE:
<223> OTHER INFORMATION: synthetic construct

<400> SEQUENCE: 316

His Ala Tyr Tyr Tyr Asp Asp Leu Tyr Val Ser Asp
1               5                   10

<210> SEQ ID NO 317
<211> LENGTH: 13
<212> TYPE: PRT
<213> ORGANISM: Artificial Sequence
<220> FEATURE:
<223> OTHER INFORMATION: synthetic construct

<400> SEQUENCE: 317

His Ala Phe Tyr Tyr Tyr Asp Asp Ile Tyr Tyr Ala Tyr
1               5                   10

<210> SEQ ID NO 318
<211> LENGTH: 13
<212> TYPE: PRT
<213> ORGANISM: Artificial Sequence
<220> FEATURE:
<223> OTHER INFORMATION: synthetic construct

<400> SEQUENCE: 318

His Asp His Tyr Tyr Asp Asp Ile Tyr Val Ala Ile
1               5                   10

<210> SEQ ID NO 319
<211> LENGTH: 14
<212> TYPE: PRT
<213> ORGANISM: Artificial Sequence
<220> FEATURE:
<223> OTHER INFORMATION: synthetic construct

<400> SEQUENCE: 319

His Ala Tyr Phe Tyr Ser Tyr Tyr Asp Ile Phe Tyr Ser Asp
1               5                   10

<210> SEQ ID NO 320
<211> LENGTH: 14
<212> TYPE: PRT
<213> ORGANISM: Artificial Sequence
<220> FEATURE:
<223> OTHER INFORMATION: synthetic construct

<400> SEQUENCE: 320

Tyr Arg Tyr Phe Tyr Ser Tyr Tyr Asp Ile Phe Tyr Ala Asp
1               5                   10

<210> SEQ ID NO 321
<211> LENGTH: 20
<212> TYPE: PRT
<213> ORGANISM: Artificial Sequence
<220> FEATURE:
<223> OTHER INFORMATION: synthetic construct

<400> SEQUENCE: 321
```

Ser Ser Ser Ser Val Ser Gly Ser Ser Tyr Tyr Ser Tyr Tyr Asp
1               5                   10                  15

Leu Tyr Tyr Ser
            20

<210> SEQ ID NO 322
<211> LENGTH: 21
<212> TYPE: PRT
<213> ORGANISM: Artificial Sequence
<220> FEATURE:
<223> OTHER INFORMATION: synthetic construct

<400> SEQUENCE: 322

Ser Ser Ser Ser Val Ser Gly Ser Ser Tyr Trp Thr Tyr Glu Trp
1               5                   10                  15

Gly Tyr Met Tyr Asp
            20

<210> SEQ ID NO 323
<211> LENGTH: 22
<212> TYPE: PRT
<213> ORGANISM: Artificial Sequence
<220> FEATURE:
<223> OTHER INFORMATION: synthetic construct

<400> SEQUENCE: 323

Tyr Ser Val Trp Asp Val Ala Gly Tyr Ser Tyr Tyr Pro Tyr Tyr
1               5                   10                  15

Gly Leu Tyr Tyr Ser Gln
            20

<210> SEQ ID NO 324
<211> LENGTH: 26
<212> TYPE: PRT
<213> ORGANISM: Artificial Sequence
<220> FEATURE:
<223> OTHER INFORMATION: synthetic construct

<400> SEQUENCE: 324

Pro Trp Ala Tyr Ser Gln Ser Val Ala Gly Ser Ser Tyr Tyr Gly
1               5                   10                  15

Thr Pro Trp Gly Glu Gly Trp Tyr Ser Trp
            20                  25

<210> SEQ ID NO 325
<211> LENGTH: 20
<212> TYPE: PRT
<213> ORGANISM: Artificial Sequence
<220> FEATURE:
<223> OTHER INFORMATION: synthetic construct

<400> SEQUENCE: 325

Pro Ala Asn Ser Val Ser Gly Ser Ser Ser Tyr Glu Trp Tyr Gly Trp
1               5                   10                  15

Gly Trp Thr Tyr
            20

<210> SEQ ID NO 326
<211> LENGTH: 21
<212> TYPE: PRT
<213> ORGANISM: Artificial Sequence
<220> FEATURE:
<223> OTHER INFORMATION: synthetic construct

<400> SEQUENCE: 326

```
Ser Ser Ser Ser Val Ser Ser Tyr Ser Tyr Trp Glu Phe Glu Tyr
1               5                   10                  15

Gly Tyr Trp Ser Tyr
            20
```

<210> SEQ ID NO 327
<211> LENGTH: 21
<212> TYPE: PRT
<213> ORGANISM: Artificial Sequence
<220> FEATURE:
<223> OTHER INFORMATION: synthetic construct

<400> SEQUENCE: 327

```
Ser Ser Ser Ser Val Ser Gly Ser Ser Tyr Gln Glu Trp Ser Tyr
1               5                   10                  15

Gly Trp Ser Ser Glu
            20
```

<210> SEQ ID NO 328
<211> LENGTH: 25
<212> TYPE: PRT
<213> ORGANISM: Artificial Sequence
<220> FEATURE:
<223> OTHER INFORMATION: synthetic construct

<400> SEQUENCE: 328

```
Tyr Val Gly Tyr Gly Ser Ser Val Ala Gly Ser Ser Tyr Tyr Tyr
1               5                   10                  15

Glu Gly Asp Asp Leu Tyr Ser Ser Met
            20                  25
```

<210> SEQ ID NO 329
<211> LENGTH: 17
<212> TYPE: PRT
<213> ORGANISM: Artificial Sequence
<220> FEATURE:
<223> OTHER INFORMATION: synthetic construct

<400> SEQUENCE: 329

```
Gly Tyr Trp Phe Ile Asp Gly Tyr Ser Ser Tyr Tyr Asp Asn Tyr Gly
1               5                   10                  15

Trp
```

<210> SEQ ID NO 330
<211> LENGTH: 23
<212> TYPE: PRT
<213> ORGANISM: Artificial Sequence
<220> FEATURE:
<223> OTHER INFORMATION: synthetic construct

<400> SEQUENCE: 330

```
Ser Ser Ser Ser Val Ser Gly Ser Ser Ser Tyr Tyr Asp Tyr Tyr
1               5                   10                  15

Tyr Gly Met Tyr Trp Ser Gln
            20
```

<210> SEQ ID NO 331
<211> LENGTH: 25
<212> TYPE: PRT
<213> ORGANISM: Artificial Sequence
<220> FEATURE:
<223> OTHER INFORMATION: synthetic construct

<400> SEQUENCE: 331

-continued

```
Tyr Gln Asn Ser Ser Trp Ser Gly Val Ser Gly Ser Ser Ser Leu Tyr
  1               5                  10                  15

Ser Glu Tyr Trp Gly Glu Tyr Tyr Ser
             20                  25

<210> SEQ ID NO 332
<211> LENGTH: 23
<212> TYPE: PRT
<213> ORGANISM: Artificial Sequence
<220> FEATURE:
<223> OTHER INFORMATION: synthetic construct

<400> SEQUENCE: 332

Ser Ser Ser Ser Val Ser Gly Tyr Ser Tyr Thr Gly Phe Tyr Asp
  1               5                  10                  15

Tyr Gly Phe Trp Ser Tyr Trp
             20

<210> SEQ ID NO 333
<211> LENGTH: 21
<212> TYPE: PRT
<213> ORGANISM: Artificial Sequence
<220> FEATURE:
<223> OTHER INFORMATION: synthetic construct

<400> SEQUENCE: 333

Ser Ser Ser Ser Val Ser Gly Ser Ser Tyr Tyr Met Glu Trp Asp
  1               5                  10                  15

Tyr Tyr Tyr Ser Glu
             20

<210> SEQ ID NO 334
<211> LENGTH: 21
<212> TYPE: PRT
<213> ORGANISM: Artificial Sequence
<220> FEATURE:
<223> OTHER INFORMATION: synthetic construct

<400> SEQUENCE: 334

Ser Ser Ser Ser Val Ser Gly Ser Ser Thr Trp Leu Tyr Asp Trp
  1               5                  10                  15

Gly Tyr Met Trp Tyr
             20

<210> SEQ ID NO 335
<211> LENGTH: 26
<212> TYPE: PRT
<213> ORGANISM: Artificial Sequence
<220> FEATURE:
<223> OTHER INFORMATION: synthetic construct

<400> SEQUENCE: 335

Gly Tyr Gly Tyr Gln Pro Trp Tyr Val Asp Gly Ser Ser Tyr Tyr Thr
  1               5                  10                  15

Phe Ile Ser Ala Ser Glu Tyr Tyr Tyr Met
             20                  25

<210> SEQ ID NO 336
<211> LENGTH: 25
<212> TYPE: PRT
<213> ORGANISM: Artificial Sequence
<220> FEATURE:
<223> OTHER INFORMATION: synthetic construct
```

-continued

<400> SEQUENCE: 336

Tyr Gly Arg Asn Tyr Thr Met Asp Val Ser Ser Tyr Ser Val Val
1               5                   10                  15

Tyr Glu Asp Trp Gly Ser Tyr Trp Ser
            20                  25

<210> SEQ ID NO 337
<211> LENGTH: 20
<212> TYPE: PRT
<213> ORGANISM: Artificial Sequence
<220> FEATURE:
<223> OTHER INFORMATION: synthetic construct

<400> SEQUENCE: 337

Ser Ser Ser Ser Val Ser Gly Ser Ser Ser Tyr Ile Gln Tyr Tyr Asp
1               5                   10                  15

Leu Tyr Tyr Ala
            20

<210> SEQ ID NO 338
<211> LENGTH: 21
<212> TYPE: PRT
<213> ORGANISM: Artificial Sequence
<220> FEATURE:
<223> OTHER INFORMATION: synthetic construct

<400> SEQUENCE: 338

Ser Ser Ser Ser Val Ser Gly Ser Ser Ser Tyr Leu Pro Tyr Tyr Asp
1               5                   10                  15

Ile Tyr Tyr Ser Tyr
            20

<210> SEQ ID NO 339
<211> LENGTH: 21
<212> TYPE: PRT
<213> ORGANISM: Artificial Sequence
<220> FEATURE:
<223> OTHER INFORMATION: synthetic construct

<400> SEQUENCE: 339

Ser Ser Ser Ser Val Ser Gly Ser Ser Ser Phe Tyr Asp Val Gly Trp
1               5                   10                  15

Gly Tyr Tyr Ser Ile
            20

<210> SEQ ID NO 340
<211> LENGTH: 27
<212> TYPE: PRT
<213> ORGANISM: Artificial Sequence
<220> FEATURE:
<223> OTHER INFORMATION: synthetic construct

<400> SEQUENCE: 340

Gly Tyr Tyr Met Asn Tyr Met Val Asp Gly Ser Ser Tyr Trp
1               5                   10                  15

Tyr Asp Glu Tyr Gly Gln Tyr Trp Trp Ser Glu
            20                  25

<210> SEQ ID NO 341
<211> LENGTH: 22
<212> TYPE: PRT
<213> ORGANISM: Artificial Sequence
<220> FEATURE:
<223> OTHER INFORMATION: synthetic construct

<400> SEQUENCE: 341

Ser Ser Ser Ser Val Ser Gly Ser Ser Thr Met Tyr Ser Tyr Gly
1               5                   10                  15

Trp Gly Glu Tyr Tyr Tyr
            20

<210> SEQ ID NO 342
<211> LENGTH: 21
<212> TYPE: PRT
<213> ORGANISM: Artificial Sequence
<220> FEATURE:
<223> OTHER INFORMATION: synthetic construct

<400> SEQUENCE: 342

Ser Ser Ser Ser Val Ser Gly Ser Ser Tyr Tyr Ser Glu Tyr Tyr
1               5                   10                  15

Tyr Trp Trp Ser Glu
            20

<210> SEQ ID NO 343
<211> LENGTH: 24
<212> TYPE: PRT
<213> ORGANISM: Artificial Sequence
<220> FEATURE:
<223> OTHER INFORMATION: synthetic construct

<400> SEQUENCE: 343

Ala Tyr Ala Ser Ser Gln Ser Thr Val His Gly Ser Tyr Ser Tyr Trp
1               5                   10                  15

Glu Tyr Gln Trp Gly His Met Tyr
            20

<210> SEQ ID NO 344
<211> LENGTH: 25
<212> TYPE: PRT
<213> ORGANISM: Artificial Sequence
<220> FEATURE:
<223> OTHER INFORMATION: synthetic construct

<400> SEQUENCE: 344

Gly Tyr Ala Tyr Tyr Gly Glu Ser Val Trp Gly Ser Ser Ser Asn Tyr
1               5                   10                  15

Gly Asp Asn Gln Ile Glu Tyr Tyr Phe
            20                  25

<210> SEQ ID NO 345
<211> LENGTH: 21
<212> TYPE: PRT
<213> ORGANISM: Artificial Sequence
<220> FEATURE:
<223> OTHER INFORMATION: synthetic construct

<400> SEQUENCE: 345

Ser Ser Ser Ser Val Ser Gly Ser Ser Ser Tyr Gln Glu Trp Leu Tyr
1               5                   10                  15

Gly Trp Tyr Ser Thr
            20

<210> SEQ ID NO 346
<211> LENGTH: 25
<212> TYPE: PRT
<213> ORGANISM: Artificial Sequence
<220> FEATURE:

<223> OTHER INFORMATION: synthetic construct

<400> SEQUENCE: 346

Ser Trp Gly Glu Tyr Gly Tyr Ser Val Asp Gly Ser Ser Ser Tyr Tyr
1               5                   10                  15
Ser Trp Tyr Tyr Gly Trp Tyr Ser Glu
            20                  25

<210> SEQ ID NO 347
<211> LENGTH: 25
<212> TYPE: PRT
<213> ORGANISM: Artificial Sequence
<220> FEATURE:
<223> OTHER INFORMATION: synthetic construct

<400> SEQUENCE: 347

Ala Arg Gln Gly His Tyr Glu Asp Val Gln Ser Ser Ser Ser Tyr Arg
1               5                   10                  15
His Trp Glu Phe Gly Tyr Trp Ser Gln
            20                  25

<210> SEQ ID NO 348
<211> LENGTH: 21
<212> TYPE: PRT
<213> ORGANISM: Artificial Sequence
<220> FEATURE:
<223> OTHER INFORMATION: synthetic construct

<400> SEQUENCE: 348

Tyr Glu Ser Glu Val Ser Gly Ser Ser Ser Tyr Trp Val Tyr Ser Trp
1               5                   10                  15
Gly Ser Tyr Trp Lys
            20

<210> SEQ ID NO 349
<211> LENGTH: 23
<212> TYPE: PRT
<213> ORGANISM: Artificial Sequence
<220> FEATURE:
<223> OTHER INFORMATION: synthetic construct

<400> SEQUENCE: 349

Ser Ser Ser Ser Val Ser Gly Ser Ser Ser Tyr Tyr Tyr Asp Glu Ala
1               5                   10                  15
Tyr Glu Trp Tyr Tyr Ser Trp
            20

<210> SEQ ID NO 350
<211> LENGTH: 23
<212> TYPE: PRT
<213> ORGANISM: Artificial Sequence
<220> FEATURE:
<223> OTHER INFORMATION: synthetic construct

<400> SEQUENCE: 350

Ser Ser Ser Ser Val Ser Gly Ser Ser Ser Tyr Trp Tyr Met Trp Asp
1               5                   10                  15
Gly Tyr Val Ser Ser Trp Tyr
            20

<210> SEQ ID NO 351
<211> LENGTH: 23
<212> TYPE: PRT
<213> ORGANISM: Artificial Sequence

```
<220> FEATURE:
<223> OTHER INFORMATION: synthetic construct

<400> SEQUENCE: 351

Ser Ser Ser Ser Val Ser Gly Ser Ser Tyr Glu Gly Phe Glu Glu
1               5                   10                  15

Tyr Gly Trp Tyr Ser Tyr Tyr
            20

<210> SEQ ID NO 352
<211> LENGTH: 22
<212> TYPE: PRT
<213> ORGANISM: Artificial Sequence
<220> FEATURE:
<223> OTHER INFORMATION: synthetic construct

<400> SEQUENCE: 352

Ser Ser Ser Ser Val Ser Gly Ser Ser Tyr Trp Glu Trp Val Pro
1               5                   10                  15

Trp Gly Tyr Tyr Ser Tyr
            20

<210> SEQ ID NO 353
<211> LENGTH: 21
<212> TYPE: PRT
<213> ORGANISM: Artificial Sequence
<220> FEATURE:
<223> OTHER INFORMATION: synthetic construct

<400> SEQUENCE: 353

Ser Ser Ser Ser Val Ser Gly Ser Ser Tyr Tyr Ser Glu Glu Trp
1               5                   10                  15

Gly Tyr Tyr Ser Tyr
            20

<210> SEQ ID NO 354
<211> LENGTH: 21
<212> TYPE: PRT
<213> ORGANISM: Artificial Sequence
<220> FEATURE:
<223> OTHER INFORMATION: synthetic construct

<400> SEQUENCE: 354

Ser Ser Ser Ser Val Ser Gly Ser Ser Tyr Tyr Trp Ala Asp Trp
1               5                   10                  15

Tyr Tyr Trp Ser Val
            20

<210> SEQ ID NO 355
<211> LENGTH: 19
<212> TYPE: PRT
<213> ORGANISM: Artificial Sequence
<220> FEATURE:
<223> OTHER INFORMATION: synthetic construct

<400> SEQUENCE: 355

Tyr Glu Ser Tyr Gln Tyr Val Trp Gly Ser Ser Ser Glu His Gly Tyr
1               5                   10                  15

Trp Tyr Trp

<210> SEQ ID NO 356
<211> LENGTH: 20
<212> TYPE: PRT
<213> ORGANISM: Artificial Sequence
```

```
<220> FEATURE:
<223> OTHER INFORMATION: synthetic construct

<400> SEQUENCE: 356

Asp Arg Tyr Tyr Val Ser Gly Ser Ser Glu Tyr Glu Ser Asn Tyr
1               5                   10                  15

Tyr Tyr Lys Trp
            20

<210> SEQ ID NO 357
<211> LENGTH: 21
<212> TYPE: PRT
<213> ORGANISM: Artificial Sequence
<220> FEATURE:
<223> OTHER INFORMATION: synthetic construct

<400> SEQUENCE: 357

Ser Ser Ser Ser Val Ser Gly Ser Ser Leu Thr Asp Tyr Gly Tyr
1               5                   10                  15

Ala Tyr Tyr Ser Tyr
            20

<210> SEQ ID NO 358
<211> LENGTH: 23
<212> TYPE: PRT
<213> ORGANISM: Artificial Sequence
<220> FEATURE:
<223> OTHER INFORMATION: synthetic construct

<400> SEQUENCE: 358

Trp Ser Arg Tyr Trp Gly Trp Val Ser Gly Ser Ser Ser Ser Trp
1               5                   10                  15

His Pro Gln Ser Pro Tyr Tyr
            20

<210> SEQ ID NO 359
<211> LENGTH: 23
<212> TYPE: PRT
<213> ORGANISM: Artificial Sequence
<220> FEATURE:
<223> OTHER INFORMATION: synthetic construct

<400> SEQUENCE: 359

Ser Ser Ser Ser Val Ser Gly Ser Ser Tyr Thr Trp Tyr Pro Gln Trp
1               5                   10                  15

Asp Gly Tyr Ser Val Tyr Ala
            20

<210> SEQ ID NO 360
<211> LENGTH: 25
<212> TYPE: PRT
<213> ORGANISM: Artificial Sequence
<220> FEATURE:
<223> OTHER INFORMATION: synthetic construct

<400> SEQUENCE: 360

Tyr Gln Thr Arg Leu Tyr Pro Tyr Val Ser Ser Ser Ser Val Glu
1               5                   10                  15

Glu Phe Asp Trp Gly Tyr Ser Trp Ser
            20                  25

<210> SEQ ID NO 361
<211> LENGTH: 21
<212> TYPE: PRT
```

<213> ORGANISM: Artificial Sequence
<220> FEATURE:
<223> OTHER INFORMATION: synthetic construct

<400> SEQUENCE: 361

Ser Ser Ser Ser Val Ser Gly Ser Ser Trp Phe Gln Tyr His Trp
1               5                   10                  15

Gly Ser Tyr Tyr Tyr
            20

<210> SEQ ID NO 362
<211> LENGTH: 25
<212> TYPE: PRT
<213> ORGANISM: Artificial Sequence
<220> FEATURE:
<223> OTHER INFORMATION: synthetic construct

<400> SEQUENCE: 362

Trp Lys Gln Gly Trp Thr Met Gly Val Asp Gly Tyr Ser Ser Trp Gly
1               5                   10                  15

Thr Val Met Asp Leu Tyr Tyr Tyr Tyr
            20                  25

<210> SEQ ID NO 363
<211> LENGTH: 25
<212> TYPE: PRT
<213> ORGANISM: Artificial Sequence
<220> FEATURE:
<223> OTHER INFORMATION: synthetic construct

<400> SEQUENCE: 363

Glu Gly Asp Tyr Tyr Ser Val Tyr Gly Ser Ser Ser Trp Met Ile Ser
1               5                   10                  15

Glu Tyr Trp Gly Tyr His Trp Ser Asn
            20                  25

<210> SEQ ID NO 364
<211> LENGTH: 22
<212> TYPE: PRT
<213> ORGANISM: Artificial Sequence
<220> FEATURE:
<223> OTHER INFORMATION: synthetic construct

<400> SEQUENCE: 364

Ser Ser Ser Ser Val Ser Gly Ser Ser Ser Trp Tyr Pro Phe Ser Glu
1               5                   10                  15

Tyr Gly Trp Ala Ser Leu
            20

<210> SEQ ID NO 365
<211> LENGTH: 21
<212> TYPE: PRT
<213> ORGANISM: Artificial Sequence
<220> FEATURE:
<223> OTHER INFORMATION: synthetic construct

<400> SEQUENCE: 365

Ser Ser Ser Ser Val Ser Gly Tyr Tyr Ser Tyr Phe Ala Tyr Tyr Asp
1               5                   10                  15

Tyr Tyr Tyr Ser Tyr
            20

<210> SEQ ID NO 366
<211> LENGTH: 21

```
<212> TYPE: PRT
<213> ORGANISM: Artificial Sequence
<220> FEATURE:
<223> OTHER INFORMATION: synthetic construct

<400> SEQUENCE: 366

Ser Ser Ser Ser Val Ser Gly Ser Ser Ser Tyr Phe Lys Glu Asp Trp
1               5                   10                  15

Tyr Tyr Tyr Ser Tyr
            20

<210> SEQ ID NO 367
<211> LENGTH: 21
<212> TYPE: PRT
<213> ORGANISM: Artificial Sequence
<220> FEATURE:
<223> OTHER INFORMATION: synthetic construct

<400> SEQUENCE: 367

Tyr Phe Gly Trp Gly Val Ser Gly Ser Ser Tyr Gly Ser Tyr Tyr
1               5                   10                  15

Gly Val Pro Phe Tyr
            20

<210> SEQ ID NO 368
<211> LENGTH: 22
<212> TYPE: PRT
<213> ORGANISM: Artificial Sequence
<220> FEATURE:
<223> OTHER INFORMATION: synthetic construct

<400> SEQUENCE: 368

Ile Met Glu Ser Gly Val Ser Gly Ser Ser Tyr His Leu Phe Asp
1               5                   10                  15

Pro Val Tyr Tyr Ser Asp
            20

<210> SEQ ID NO 369
<211> LENGTH: 23
<212> TYPE: PRT
<213> ORGANISM: Artificial Sequence
<220> FEATURE:
<223> OTHER INFORMATION: synthetic construct

<400> SEQUENCE: 369

Ser Ser Ser Ser Val Ser Gly Ser Tyr Tyr His Ser Tyr Glu Tyr
1               5                   10                  15

Ser Ser Leu Tyr Tyr Ser Trp
            20

<210> SEQ ID NO 370
<211> LENGTH: 21
<212> TYPE: PRT
<213> ORGANISM: Artificial Sequence
<220> FEATURE:
<223> OTHER INFORMATION: synthetic construct

<400> SEQUENCE: 370

Ser Ser Ser Ser Val Ser Gly Ser Ser Tyr His Trp Ser Pro Phe
1               5                   10                  15

Tyr Tyr Trp Ser Tyr
            20

<210> SEQ ID NO 371
```

<211> LENGTH: 19
<212> TYPE: PRT
<213> ORGANISM: Artificial Sequence
<220> FEATURE:
<223> OTHER INFORMATION: synthetic construct

<400> SEQUENCE: 371

Gly Tyr Trp Tyr Val Ser Tyr Gly Tyr Ser Tyr Pro Trp Tyr Asp Asp
1               5                   10                  15

Thr Tyr Tyr

<210> SEQ ID NO 372
<211> LENGTH: 24
<212> TYPE: PRT
<213> ORGANISM: Artificial Sequence
<220> FEATURE:
<223> OTHER INFORMATION: synthetic construct

<400> SEQUENCE: 372

Tyr Gln Gly Gly Ser Tyr Trp Val Ser Gly Ser Ser Tyr Gln His
1               5                   10                  15

Pro Gln Met Gly Ser Thr Tyr Tyr
            20

<210> SEQ ID NO 373
<211> LENGTH: 23
<212> TYPE: PRT
<213> ORGANISM: Artificial Sequence
<220> FEATURE:
<223> OTHER INFORMATION: synthetic construct

<400> SEQUENCE: 373

Ser Ser Ser Ser Val Ser Gly Ser Ser Tyr Gln Ser Phe Gly Tyr
1               5                   10                  15

Asn Glu Tyr Trp Ser Ser Gly
            20

<210> SEQ ID NO 374
<211> LENGTH: 22
<212> TYPE: PRT
<213> ORGANISM: Artificial Sequence
<220> FEATURE:
<223> OTHER INFORMATION: synthetic construct

<400> SEQUENCE: 374

Gly Tyr Asp Glu Ser Val Met Gly Ser Ser Tyr Arg Glu Tyr Asp
1               5                   10                  15

Gly Leu Tyr Tyr Ser Tyr
            20

<210> SEQ ID NO 375
<211> LENGTH: 25
<212> TYPE: PRT
<213> ORGANISM: Artificial Sequence
<220> FEATURE:
<223> OTHER INFORMATION: synthetic construct

<400> SEQUENCE: 375

Val Trp Gln Glu Trp Ala Tyr Tyr Val His Gly Ser Tyr Ser Tyr Ser
1               5                   10                  15

Asp Trp Gly Tyr Ala Tyr Tyr Glu Trp
            20                  25

<210> SEQ ID NO 376

```
<211> LENGTH: 22
<212> TYPE: PRT
<213> ORGANISM: Artificial Sequence
<220> FEATURE:
<223> OTHER INFORMATION: synthetic construct

<400> SEQUENCE: 376

Ser Ser Ser Ser Val Ser Gly Ser Ser Ser Tyr Thr Asp Trp Gly Ser
1               5                   10                  15

Glu Met Leu Ser Trp Tyr
            20

<210> SEQ ID NO 377
<211> LENGTH: 25
<212> TYPE: PRT
<213> ORGANISM: Artificial Sequence
<220> FEATURE:
<223> OTHER INFORMATION: synthetic construct

<400> SEQUENCE: 377

Gln Tyr His Tyr Asp Ser Asp Ser Val Ser Gly Tyr Ser Tyr Val
1               5                   10                  15

Tyr His Asp Trp Gly Ile Glu Tyr Tyr
            20                  25

<210> SEQ ID NO 378
<211> LENGTH: 22
<212> TYPE: PRT
<213> ORGANISM: Artificial Sequence
<220> FEATURE:
<223> OTHER INFORMATION: synthetic construct

<400> SEQUENCE: 378

Ser Ser Ser Gly Tyr Val Gln Gly Ser Ser Tyr Trp Ala Gly Tyr
1               5                   10                  15

Gly Tyr Tyr Tyr Ser Tyr
            20

<210> SEQ ID NO 379
<211> LENGTH: 21
<212> TYPE: PRT
<213> ORGANISM: Artificial Sequence
<220> FEATURE:
<223> OTHER INFORMATION: synthetic construct

<400> SEQUENCE: 379

Ser Ser Ser Ser Val Ser Gly Ser Tyr Ser Tyr Trp Tyr Gly Tyr Gly
1               5                   10                  15

Tyr Tyr Tyr Ser His
            20

<210> SEQ ID NO 380
<211> LENGTH: 24
<212> TYPE: PRT
<213> ORGANISM: Artificial Sequence
<220> FEATURE:
<223> OTHER INFORMATION: synthetic construct

<400> SEQUENCE: 380

Tyr Gly Ser Ser Phe Tyr His Val Ser Gly Ser Ser Tyr Tyr Ala
1               5                   10                  15

Phe Thr Tyr Gly Tyr Tyr Ser Tyr
            20
```

```
<210> SEQ ID NO 381
<211> LENGTH: 21
<212> TYPE: PRT
<213> ORGANISM: Artificial Sequence
<220> FEATURE:
<223> OTHER INFORMATION: synthetic construct

<400> SEQUENCE: 381

Ser Ser Ser Ser Val Ser Gly Ser Ser Tyr Tyr Asp Ser Met Tyr
 1               5                  10                  15

Tyr Trp Trp Ala Asp
            20

<210> SEQ ID NO 382
<211> LENGTH: 25
<212> TYPE: PRT
<213> ORGANISM: Artificial Sequence
<220> FEATURE:
<223> OTHER INFORMATION: synthetic construct

<400> SEQUENCE: 382

Gly Glu Gly Tyr Ser Met Val Asp Gly Ser Tyr Ser Tyr Tyr Glu Met
 1               5                  10                  15

Phe Ser Asp Glu Gly Trp Trp Ser Trp
            20                  25

<210> SEQ ID NO 383
<211> LENGTH: 23
<212> TYPE: PRT
<213> ORGANISM: Artificial Sequence
<220> FEATURE:
<223> OTHER INFORMATION: synthetic construct

<400> SEQUENCE: 383

Ser Ser Ser Ser Val Ser Gly Ser Tyr Ser Tyr Tyr Gly Trp Glu Trp
 1               5                  10                  15

Asp Gly Trp Trp Ser Trp Gln
            20

<210> SEQ ID NO 384
<211> LENGTH: 22
<212> TYPE: PRT
<213> ORGANISM: Artificial Sequence
<220> FEATURE:
<223> OTHER INFORMATION: synthetic construct

<400> SEQUENCE: 384

Ser Gln Phe Ser Gly Val Ser Gly Ser Tyr Ser Tyr Tyr His Glu His
 1               5                  10                  15

Trp Gly Tyr Tyr Ser Tyr
            20

<210> SEQ ID NO 385
<211> LENGTH: 21
<212> TYPE: PRT
<213> ORGANISM: Artificial Sequence
<220> FEATURE:
<223> OTHER INFORMATION: synthetic construct

<400> SEQUENCE: 385

Ser Ser Ser Ser Val Ser Gly Ser Ser Tyr Tyr Gln Glu Tyr Trp
 1               5                  10                  15

Gly Tyr Trp Ser Tyr
            20
```

-continued

<210> SEQ ID NO 386
<211> LENGTH: 23
<212> TYPE: PRT
<213> ORGANISM: Artificial Sequence
<220> FEATURE:
<223> OTHER INFORMATION: synthetic construct

<400> SEQUENCE: 386

Ser Ser Ser Ser Val Ser Gly Ser Ser Tyr Tyr Gln Tyr Ala Pro
1               5                   10                  15

Tyr Gln Trp Tyr Ser Trp Gln
            20

<210> SEQ ID NO 387
<211> LENGTH: 25
<212> TYPE: PRT
<213> ORGANISM: Artificial Sequence
<220> FEATURE:
<223> OTHER INFORMATION: synthetic construct

<400> SEQUENCE: 387

Gly Ser Phe Gly Phe His Asp Pro Val Tyr Gly Ser Ser Tyr Tyr
1               5                   10                  15

Gln Tyr Met Asp Tyr Tyr Tyr Ser Tyr
            20                  25

<210> SEQ ID NO 388
<211> LENGTH: 21
<212> TYPE: PRT
<213> ORGANISM: Artificial Sequence
<220> FEATURE:
<223> OTHER INFORMATION: synthetic construct

<400> SEQUENCE: 388

Ser Ser Ser Ser Val Ser Gly Ser Tyr Ser Tyr Tyr Ser Glu Tyr Trp
1               5                   10                  15

Tyr Asp Phe Ser Trp
            20

<210> SEQ ID NO 389
<211> LENGTH: 21
<212> TYPE: PRT
<213> ORGANISM: Artificial Sequence
<220> FEATURE:
<223> OTHER INFORMATION: synthetic construct

<400> SEQUENCE: 389

Ser Ser Ser Ser Val Ser Gly Ser Ser Ser Tyr Tyr Ser Thr Tyr Trp
1               5                   10                  15

Tyr Asp Trp Ser Gly
            20

<210> SEQ ID NO 390
<211> LENGTH: 24
<212> TYPE: PRT
<213> ORGANISM: Artificial Sequence
<220> FEATURE:
<223> OTHER INFORMATION: synthetic construct

<400> SEQUENCE: 390

Asp His Gly Asp Gly Leu Tyr Asp Val His Gly Ser Ser Ser Tyr Tyr
1               5                   10                  15

Ser Tyr Tyr Trp Gly Ser Tyr Tyr
            20

```
<210> SEQ ID NO 391
<211> LENGTH: 21
<212> TYPE: PRT
<213> ORGANISM: Artificial Sequence
<220> FEATURE:
<223> OTHER INFORMATION: synthetic construct

<400> SEQUENCE: 391

Ser Ser Ser Ser Val Ser Gly Ser Ser Ser Tyr Tyr Val Gly Asp Gly
1               5                   10                  15
Tyr Tyr Trp Ser Glu
            20

<210> SEQ ID NO 392
<211> LENGTH: 21
<212> TYPE: PRT
<213> ORGANISM: Artificial Sequence
<220> FEATURE:
<223> OTHER INFORMATION: synthetic construct

<400> SEQUENCE: 392

Ser Ser Ser Ser Val Ser Gly Ser Ser Ser Tyr Tyr Trp Asp Glu Gly
1               5                   10                  15
Tyr Tyr Trp Ser Ile
            20

<210> SEQ ID NO 393
<211> LENGTH: 21
<212> TYPE: PRT
<213> ORGANISM: Artificial Sequence
<220> FEATURE:
<223> OTHER INFORMATION: synthetic construct

<400> SEQUENCE: 393

Ser Ser Ser Ser Val Ser Gly Ser Ser Tyr Tyr Tyr Trp His Asp Ser
1               5                   10                  15
Tyr Trp Trp Ser Val
            20

<210> SEQ ID NO 394
<211> LENGTH: 21
<212> TYPE: PRT
<213> ORGANISM: Artificial Sequence
<220> FEATURE:
<223> OTHER INFORMATION: synthetic construct

<400> SEQUENCE: 394

Ser Ser Ser Ser Val Ser Gly Ser Ser Ser Tyr Tyr Tyr Phe Tyr Asp
1               5                   10                  15
Tyr Trp Met Ala Tyr
            20

<210> SEQ ID NO 395
<211> LENGTH: 22
<212> TYPE: PRT
<213> ORGANISM: Artificial Sequence
<220> FEATURE:
<223> OTHER INFORMATION: synthetic construct

<400> SEQUENCE: 395

Ser Ser Ser Ser Val Ser Gly Ser Ser Ser Tyr Tyr Tyr Ile Tyr Arg
1               5                   10                  15
Asp Leu Ser Tyr Ala Glu
```

```
                  20

<210> SEQ ID NO 396
<211> LENGTH: 21
<212> TYPE: PRT
<213> ORGANISM: Artificial Sequence
<220> FEATURE:
<223> OTHER INFORMATION: synthetic construct

<400> SEQUENCE: 396

Ser Ser Ser Ser Val Ser Gly Ser Ser Tyr Tyr Ser Tyr Tyr
1               5                   10                  15

Tyr Tyr Trp Ala Thr
            20

<210> SEQ ID NO 397
<211> LENGTH: 23
<212> TYPE: PRT
<213> ORGANISM: Artificial Sequence
<220> FEATURE:
<223> OTHER INFORMATION: synthetic construct

<400> SEQUENCE: 397

Ser Ser Ser Ser Val Ser Tyr Tyr Ser Ser Tyr Tyr Tyr Asp Tyr Tyr
1               5                   10                  15

Tyr Asp Leu Tyr Tyr Ser Asn
            20

<210> SEQ ID NO 398
<211> LENGTH: 23
<212> TYPE: PRT
<213> ORGANISM: Artificial Sequence
<220> FEATURE:
<223> OTHER INFORMATION: synthetic construct

<400> SEQUENCE: 398

Ser Ser Ser Ser Val Ser Tyr Tyr Ser Thr Tyr Tyr Tyr Asp Tyr Tyr
1               5                   10                  15

Tyr Asp Leu Tyr Tyr Ser Asn
            20

<210> SEQ ID NO 399
<211> LENGTH: 27
<212> TYPE: PRT
<213> ORGANISM: Artificial Sequence
<220> FEATURE:
<223> OTHER INFORMATION: synthetic construct

<400> SEQUENCE: 399

Tyr Tyr Ser Tyr Tyr Ser Tyr Ser Val Ser Tyr Tyr Ser Tyr Tyr
1               5                   10                  15

Tyr Asp Tyr Tyr Tyr Asp Leu Tyr Tyr Ser Asn
            20                  25

<210> SEQ ID NO 400
<211> LENGTH: 23
<212> TYPE: PRT
<213> ORGANISM: Artificial Sequence
<220> FEATURE:
<223> OTHER INFORMATION: synthetic construct

<400> SEQUENCE: 400

Ser Ser Ser Ser Val Ser Tyr Tyr Ser Ser Tyr Tyr Tyr Asp Tyr Tyr
1               5                   10                  15
```

Tyr Asp Leu Tyr Tyr Ser Tyr
            20

<210> SEQ ID NO 401
<211> LENGTH: 21
<212> TYPE: PRT
<213> ORGANISM: Artificial Sequence
<220> FEATURE:
<223> OTHER INFORMATION: synthetic construct

<400> SEQUENCE: 401

Ser Ser Ser Ser Val Ser Ser Tyr Tyr Ser Tyr Tyr Tyr Ser His Tyr
1               5                   10                  15

Tyr Tyr Tyr Ser Tyr
            20

<210> SEQ ID NO 402
<211> LENGTH: 21
<212> TYPE: PRT
<213> ORGANISM: Artificial Sequence
<220> FEATURE:
<223> OTHER INFORMATION: synthetic construct

<400> SEQUENCE: 402

Ser Ser Ser Ser Val Ser Gly Ser Lys Ser Tyr Tyr Ser Tyr Tyr
1               5                   10                  15

Tyr Tyr Tyr Ser Phe
            20

<210> SEQ ID NO 403
<211> LENGTH: 21
<212> TYPE: PRT
<213> ORGANISM: Artificial Sequence
<220> FEATURE:
<223> OTHER INFORMATION: synthetic construct

<400> SEQUENCE: 403

Ser Ser Pro Ser Val Ser Gly Ser Lys Ser Tyr Tyr Ser Tyr Tyr
1               5                   10                  15

Tyr Tyr Tyr Ser Tyr
            20

<210> SEQ ID NO 404
<211> LENGTH: 21
<212> TYPE: PRT
<213> ORGANISM: Artificial Sequence
<220> FEATURE:
<223> OTHER INFORMATION: synthetic construct

<400> SEQUENCE: 404

Ser Ser Ser Ser Val Ser Ser Tyr Tyr Ser Tyr Tyr Tyr Ser Tyr Tyr
1               5                   10                  15

Tyr Tyr Tyr Ser Tyr
            20

<210> SEQ ID NO 405
<211> LENGTH: 21
<212> TYPE: PRT
<213> ORGANISM: Artificial Sequence
<220> FEATURE:
<223> OTHER INFORMATION: synthetic construct

<400> SEQUENCE: 405

Ser Ser Ser Ser Val Ser Gly Ser Lys Ser Tyr Tyr Ser Tyr Tyr
1               5                   10                  15

Tyr Tyr Tyr Ser Tyr
         20

<210> SEQ ID NO 406
<211> LENGTH: 21
<212> TYPE: PRT
<213> ORGANISM: Artificial Sequence
<220> FEATURE:
<223> OTHER INFORMATION: synthetic construct

<400> SEQUENCE: 406

Ser Ser Ser Ser Val Ser Ser Ser Tyr Ser Tyr Tyr Tyr Ser Tyr Tyr
1               5                   10                  15

Tyr Tyr Tyr Ser Tyr
         20

<210> SEQ ID NO 407
<211> LENGTH: 21
<212> TYPE: PRT
<213> ORGANISM: Artificial Sequence
<220> FEATURE:
<223> OTHER INFORMATION: synthetic construct

<400> SEQUENCE: 407

Ser Ser Ser Ser Val Ser Pro Tyr Tyr Ser Tyr Tyr Tyr Ser Tyr Tyr
1               5                   10                  15

Tyr Tyr Tyr Ser Tyr
         20

<210> SEQ ID NO 408
<211> LENGTH: 21
<212> TYPE: PRT
<213> ORGANISM: Artificial Sequence
<220> FEATURE:
<223> OTHER INFORMATION: synthetic construct

<400> SEQUENCE: 408

Ser Ser Ser Ser Val Tyr Gly Ser Lys Ser Tyr Tyr Tyr Ser Tyr Tyr
1               5                   10                  15

Tyr Tyr Tyr Ser Tyr
         20

<210> SEQ ID NO 409
<211> LENGTH: 22
<212> TYPE: PRT
<213> ORGANISM: Artificial Sequence
<220> FEATURE:
<223> OTHER INFORMATION: synthetic construct

<400> SEQUENCE: 409

Ser Ser Ser Tyr Ser Val Ser Ser Ser Tyr Ser Tyr Tyr Tyr Ser Tyr
1               5                   10                  15

Tyr Tyr Tyr Tyr Ser Tyr
         20

<210> SEQ ID NO 410
<211> LENGTH: 21
<212> TYPE: PRT
<213> ORGANISM: Artificial Sequence
<220> FEATURE:
<223> OTHER INFORMATION: synthetic construct

<400> SEQUENCE: 410

Ser Ser Ser Ser Val Ser Gly Ser Ser Ser Tyr Tyr Tyr Ser Tyr Tyr

Tyr Ser Tyr Ser Tyr
            20

<210> SEQ ID NO 411
<211> LENGTH: 23
<212> TYPE: PRT
<213> ORGANISM: Artificial Sequence
<220> FEATURE:
<223> OTHER INFORMATION: synthetic construct

<400> SEQUENCE: 411

Ser Tyr Ser Ser Ser Val Ser Gly Ser Ser Ser Tyr Tyr Tyr Ser
1               5                   10                  15

Tyr Tyr Tyr Tyr Tyr Ser Tyr
            20

<210> SEQ ID NO 412
<211> LENGTH: 23
<212> TYPE: PRT
<213> ORGANISM: Artificial Sequence
<220> FEATURE:
<223> OTHER INFORMATION: synthetic construct

<400> SEQUENCE: 412

Tyr Tyr Ser Tyr Tyr Ser Tyr Ser Val Ser Tyr Tyr Tyr Ser Tyr Ser
1               5                   10                  15

Ser Tyr Ser Ser Ser Ser Tyr
            20

<210> SEQ ID NO 413
<211> LENGTH: 21
<212> TYPE: PRT
<213> ORGANISM: Artificial Sequence
<220> FEATURE:
<223> OTHER INFORMATION: synthetic construct

<400> SEQUENCE: 413

Ser Ser Ser Tyr Val Ser Gly Ser Lys Ser Tyr Tyr Ser Ser Ser Tyr
1               5                   10                  15

Tyr Ser Tyr Ser Tyr
            20

<210> SEQ ID NO 414
<211> LENGTH: 21
<212> TYPE: PRT
<213> ORGANISM: Artificial Sequence
<220> FEATURE:
<223> OTHER INFORMATION: synthetic construct

<400> SEQUENCE: 414

Ser Ser Ser Ser Val Ser Gly Ser Tyr Ser Tyr Tyr Ser Ser Tyr Tyr
1               5                   10                  15

Tyr Ser Tyr Ser Tyr
            20

<210> SEQ ID NO 415
<211> LENGTH: 23
<212> TYPE: PRT
<213> ORGANISM: Artificial Sequence
<220> FEATURE:
<223> OTHER INFORMATION: synthetic construct

<400> SEQUENCE: 415

```
Ser Ser Ser Ser Ser Tyr Val Ser Ser Tyr Tyr Ser Tyr Tyr Ser Tyr
1               5                   10                  15

Tyr Tyr Tyr Tyr Tyr Ser Tyr
            20
```

<210> SEQ ID NO 416
<211> LENGTH: 13
<212> TYPE: PRT
<213> ORGANISM: Artificial Sequence
<220> FEATURE:
<223> OTHER INFORMATION: synthetic construct

<400> SEQUENCE: 416

```
His His Tyr Phe Tyr Asp Asp Asp Leu Tyr Phe Ala Phe
1               5                   10
```

<210> SEQ ID NO 417
<211> LENGTH: 13
<212> TYPE: PRT
<213> ORGANISM: Artificial Sequence
<220> FEATURE:
<223> OTHER INFORMATION: synthetic construct

<400> SEQUENCE: 417

```
His Gly Tyr Tyr His Tyr Asp Asp Ile Tyr Tyr Ala Leu
1               5                   10
```

<210> SEQ ID NO 418
<211> LENGTH: 13
<212> TYPE: PRT
<213> ORGANISM: Artificial Sequence
<220> FEATURE:
<223> OTHER INFORMATION: synthetic construct

<400> SEQUENCE: 418

```
His Ala Tyr Tyr His Tyr Asp Asp Ile Phe Leu Ala Asp
1               5                   10
```

<210> SEQ ID NO 419
<211> LENGTH: 13
<212> TYPE: PRT
<213> ORGANISM: Artificial Sequence
<220> FEATURE:
<223> OTHER INFORMATION: synthetic construct

<400> SEQUENCE: 419

```
His Glu Tyr Tyr Tyr His Glu Asp Ile Phe Tyr Ala Val
1               5                   10
```

<210> SEQ ID NO 420
<211> LENGTH: 13
<212> TYPE: PRT
<213> ORGANISM: Artificial Sequence
<220> FEATURE:
<223> OTHER INFORMATION: synthetic construct

<400> SEQUENCE: 420

```
His Glu Ala Tyr His Tyr His Asp Ile Phe Tyr Ala Val
1               5                   10
```

<210> SEQ ID NO 421
<211> LENGTH: 13
<212> TYPE: PRT
<213> ORGANISM: Artificial Sequence
<220> FEATURE:
<223> OTHER INFORMATION: synthetic construct

<400> SEQUENCE: 421

His Glu Thr Tyr Asp Tyr Tyr Asp Ile Tyr Ile Ala Tyr
1               5                   10

<210> SEQ ID NO 422
<211> LENGTH: 13
<212> TYPE: PRT
<213> ORGANISM: Artificial Sequence
<220> FEATURE:
<223> OTHER INFORMATION: synthetic construct

<400> SEQUENCE: 422

Tyr Glu Ile Phe Tyr His Asp Asp Ile Tyr Ile Ser Asp
1               5                   10

<210> SEQ ID NO 423
<211> LENGTH: 13
<212> TYPE: PRT
<213> ORGANISM: Artificial Sequence
<220> FEATURE:
<223> OTHER INFORMATION: synthetic construct

<400> SEQUENCE: 423

His Ala Tyr Tyr Tyr Tyr Asp Asp Leu Tyr Val Ser Asp
1               5                   10

<210> SEQ ID NO 424
<211> LENGTH: 13
<212> TYPE: PRT
<213> ORGANISM: Artificial Sequence
<220> FEATURE:
<223> OTHER INFORMATION: synthetic construct

<400> SEQUENCE: 424

His Ala Phe Tyr Tyr Tyr Asp Asp Ile Tyr Tyr Ala Tyr
1               5                   10

<210> SEQ ID NO 425
<211> LENGTH: 13
<212> TYPE: PRT
<213> ORGANISM: Artificial Sequence
<220> FEATURE:
<223> OTHER INFORMATION: synthetic construct

<400> SEQUENCE: 425

His Asp His Tyr Tyr Tyr Asp Asp Ile Tyr Val Ala Ile
1               5                   10

<210> SEQ ID NO 426
<211> LENGTH: 13
<212> TYPE: PRT
<213> ORGANISM: Artificial Sequence
<220> FEATURE:
<223> OTHER INFORMATION: synthetic construct

<400> SEQUENCE: 426

His Ala Tyr Phe Tyr Tyr Tyr Asp Ile Phe Tyr Ser Asp
1               5                   10

<210> SEQ ID NO 427
<211> LENGTH: 13
<212> TYPE: PRT
<213> ORGANISM: Artificial Sequence
<220> FEATURE:
<223> OTHER INFORMATION: synthetic construct

<400> SEQUENCE: 427

```
Tyr Arg Tyr Phe Tyr Tyr Asp Ile Phe Tyr Ala Asp
1               5                   10

<210> SEQ ID NO 428
<211> LENGTH: 13
<212> TYPE: PRT
<213> ORGANISM: Artificial Sequence
<220> FEATURE:
<223> OTHER INFORMATION: synthetic construct

<400> SEQUENCE: 428

Tyr Arg Tyr Tyr Tyr Tyr Asp Ile Tyr Tyr Ala Val
1               5                   10

<210> SEQ ID NO 429
<211> LENGTH: 13
<212> TYPE: PRT
<213> ORGANISM: Artificial Sequence
<220> FEATURE:
<223> OTHER INFORMATION: synthetic construct

<400> SEQUENCE: 429

Tyr Arg Tyr Tyr Tyr Glu Glu Phe Phe Asp Tyr Ala Val
1               5                   10

<210> SEQ ID NO 430
<211> LENGTH: 13
<212> TYPE: PRT
<213> ORGANISM: Artificial Sequence
<220> FEATURE:
<223> OTHER INFORMATION: synthetic construct

<400> SEQUENCE: 430

Tyr Arg Phe Tyr Tyr Glu Glu Phe Phe Asp Tyr Ala Tyr
1               5                   10

<210> SEQ ID NO 431
<211> LENGTH: 13
<212> TYPE: PRT
<213> ORGANISM: Artificial Sequence
<220> FEATURE:
<223> OTHER INFORMATION: synthetic construct

<400> SEQUENCE: 431

Tyr Arg Tyr Tyr Tyr Asp Asp Phe Leu Asp Phe Ala Phe
1               5                   10

<210> SEQ ID NO 432
<211> LENGTH: 13
<212> TYPE: PRT
<213> ORGANISM: Artificial Sequence
<220> FEATURE:
<223> OTHER INFORMATION: synthetic construct

<400> SEQUENCE: 432

Tyr Arg Tyr Tyr Tyr Tyr Asn Ile Phe Phe Ala Asp
1               5                   10

<210> SEQ ID NO 433
<211> LENGTH: 13
<212> TYPE: PRT
<213> ORGANISM: Artificial Sequence
<220> FEATURE:
<223> OTHER INFORMATION: synthetic construct

<400> SEQUENCE: 433
```

His Ala Tyr Phe Tyr Tyr Asp Ile Phe Tyr Ser Asp
1               5                   10

<210> SEQ ID NO 434
<211> LENGTH: 13
<212> TYPE: PRT
<213> ORGANISM: Artificial Sequence
<220> FEATURE:
<223> OTHER INFORMATION: synthetic construct

<400> SEQUENCE: 434

His Gly Tyr Tyr Tyr Tyr His Asp Ile Phe Tyr Ala Leu
1               5                   10

<210> SEQ ID NO 435
<211> LENGTH: 13
<212> TYPE: PRT
<213> ORGANISM: Artificial Sequence
<220> FEATURE:
<223> OTHER INFORMATION: synthetic construct

<400> SEQUENCE: 435

Tyr Ala Tyr Tyr His Tyr Asp Asp Ile Tyr Phe Ala Phe
1               5                   10

<210> SEQ ID NO 436
<211> LENGTH: 13
<212> TYPE: PRT
<213> ORGANISM: Artificial Sequence
<220> FEATURE:
<223> OTHER INFORMATION: synthetic construct

<400> SEQUENCE: 436

His His Tyr Tyr Tyr Tyr Asn Asp Ile Phe Phe Ala Asp
1               5                   10

<210> SEQ ID NO 437
<211> LENGTH: 13
<212> TYPE: PRT
<213> ORGANISM: Artificial Sequence
<220> FEATURE:
<223> OTHER INFORMATION: synthetic construct

<400> SEQUENCE: 437

Tyr Asp Tyr Tyr Tyr Tyr Asp Asp Ile Tyr Phe Ala Asp
1               5                   10

<210> SEQ ID NO 438
<211> LENGTH: 13
<212> TYPE: PRT
<213> ORGANISM: Artificial Sequence
<220> FEATURE:
<223> OTHER INFORMATION: synthetic construct

<400> SEQUENCE: 438

Tyr Glu Phe Tyr His Asp Asp Asp Leu Tyr Tyr Ala Phe
1               5                   10

<210> SEQ ID NO 439
<211> LENGTH: 13
<212> TYPE: PRT
<213> ORGANISM: Artificial Sequence
<220> FEATURE:
<223> OTHER INFORMATION: synthetic construct

<400> SEQUENCE: 439

His Gly Tyr Tyr Tyr Tyr Asp Asp Ile Phe Val Ala Val

```
1               5                   10
```

<210> SEQ ID NO 440
<211> LENGTH: 13
<212> TYPE: PRT
<213> ORGANISM: Artificial Sequence
<220> FEATURE:
<223> OTHER INFORMATION: synthetic construct

<400> SEQUENCE: 440

```
His Glu Tyr Tyr Tyr His Glu Asp Ile Phe Tyr Ala Val
1               5                   10
```

<210> SEQ ID NO 441
<211> LENGTH: 13
<212> TYPE: PRT
<213> ORGANISM: Artificial Sequence
<220> FEATURE:
<223> OTHER INFORMATION: synthetic construct

<400> SEQUENCE: 441

```
His Ala Tyr Tyr His Tyr Asp Asp Ile Phe Leu Ala Asp
1               5                   10
```

<210> SEQ ID NO 442
<211> LENGTH: 13
<212> TYPE: PRT
<213> ORGANISM: Artificial Sequence
<220> FEATURE:
<223> OTHER INFORMATION: synthetic construct

<400> SEQUENCE: 442

```
Asn Ala Tyr Tyr Tyr Tyr Asp Asp Ile Phe Val Ala Asp
1               5                   10
```

<210> SEQ ID NO 443
<211> LENGTH: 13
<212> TYPE: PRT
<213> ORGANISM: Artificial Sequence
<220> FEATURE:
<223> OTHER INFORMATION: synthetic construct

<400> SEQUENCE: 443

```
His Glu Tyr Tyr Tyr His Asp Asp Ile Phe Tyr Ala Phe
1               5                   10
```

<210> SEQ ID NO 444
<211> LENGTH: 13
<212> TYPE: PRT
<213> ORGANISM: Artificial Sequence
<220> FEATURE:
<223> OTHER INFORMATION: synthetic construct

<400> SEQUENCE: 444

```
Tyr Glu Ile Phe Tyr His Asp Asp Ile Tyr Ile Ser Asp
1               5                   10
```

<210> SEQ ID NO 445
<211> LENGTH: 13
<212> TYPE: PRT
<213> ORGANISM: Artificial Sequence
<220> FEATURE:
<223> OTHER INFORMATION: synthetic construct

<400> SEQUENCE: 445

```
His Asp Tyr Tyr Asn His Asp Asp Ile Phe Ile Ala Tyr
1               5                   10
```

<210> SEQ ID NO 446
<211> LENGTH: 13
<212> TYPE: PRT
<213> ORGANISM: Artificial Sequence
<220> FEATURE:
<223> OTHER INFORMATION: synthetic construct

<400> SEQUENCE: 446

Tyr Glu Ser Tyr Asn Tyr Asp Asp Ile Tyr Tyr Ala Val
 1               5                  10

<210> SEQ ID NO 447
<211> LENGTH: 13
<212> TYPE: PRT
<213> ORGANISM: Artificial Sequence
<220> FEATURE:
<223> OTHER INFORMATION: synthetic construct

<400> SEQUENCE: 447

Tyr Glu Phe Tyr Asp Val Glu Asp Ile Tyr Val Ser Tyr
 1               5                  10

<210> SEQ ID NO 448
<211> LENGTH: 13
<212> TYPE: PRT
<213> ORGANISM: Artificial Sequence
<220> FEATURE:
<223> OTHER INFORMATION: synthetic construct

<400> SEQUENCE: 448

His Ser Tyr Tyr Asp Ile Glu Asp Ile Tyr Ile Ala Asp
 1               5                  10

<210> SEQ ID NO 449
<211> LENGTH: 97
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (30),(33)
<223> OTHER INFORMATION: Xaa = Asn, Asp, His, Ile, Leu, Phe, Tyr, or Val
<220> FEATURE:
<221> NAME/KEY: VARIANT
<222> LOCATION: (31)...(31)
<223> OTHER INFORMATION: Xaa = His, Leu, Phe, or Tyr
<220> FEATURE:
<221> NAME/KEY: VARIANT
<222> LOCATION: (41)...(46)
<223> OTHER INFORMATION: Xaa = any amino acid except Cys and can be
     shown 5-6 times
<220> FEATURE:
<221> NAME/KEY: VARIANT
<222> LOCATION: (48),(50)
<223> OTHER INFORMATION: Xaa = any amino acid except Cys
<220> FEATURE:
<221> NAME/KEY: VARIANT
<222> LOCATION: (76)...(88)
<223> OTHER INFORMATION: Xaa = any amino acid except Cys and can be
     shown 7-13 times

<400> SEQUENCE: 449

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Xaa Xaa Tyr
             20                  25                  30

Xaa Ile Thr Tyr Gly Glu Thr Gly Xaa Xaa Xaa Xaa Xaa Xaa Gln Xaa

```
                35                  40                  45

Phe Xaa Val Pro Gly Ser Lys Ser Thr Ala Thr Ile Ser Gly Leu Ser
 50                  55                  60

Pro Gly Val Asp Tyr Thr Ile Thr Val Tyr Ala Xaa Xaa Xaa Xaa
65                  70                  75                  80

Xaa Xaa Xaa Xaa Xaa Xaa Xaa Ser Pro Ile Ser Ile Asn Tyr Arg
                85                  90                  95

Thr

<210> SEQ ID NO 450
<211> LENGTH: 96
<212> TYPE: PRT
<213> ORGANISM: Artificial Sequence
<220> FEATURE:
<223> OTHER INFORMATION: synthetic construct

<400> SEQUENCE: 450

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp His Tyr
                20                  25                  30

Val Ile Thr Tyr Gly Glu Thr Gly Gly Asn Ser Pro Val Gln Glu Phe
                35                  40                  45

Thr Val Pro Gly Ser Lys Ser Thr Ala Thr Ile Ser Gly Leu Ser Pro
 50                  55                  60

Gly Val Asp Tyr Thr Ile Thr Val Tyr Ala Trp Val Ser Asp Glu Tyr
65                  70                  75                  80

Thr His Gly Tyr Tyr Ser Tyr Ser Pro Ile Ser Ile Asn Tyr Arg Thr
                85                  90                  95

<210> SEQ ID NO 451
<211> LENGTH: 95
<212> TYPE: PRT
<213> ORGANISM: Artificial Sequence
<220> FEATURE:
<223> OTHER INFORMATION: synthetic construct

<400> SEQUENCE: 451

Val Ser Ser Val Pro Thr Lys Leu Glu Val Val Ala Ala Thr Pro Thr
 1               5                  10                  15

Ser Leu Leu Ile Ser Trp Asp Ala Pro Ala Val Thr Val Asp His Tyr
                20                  25                  30

Val Ile Thr Tyr Gly Glu Thr Gly Gly Tyr Ala Gly Val Gln Glu Phe
                35                  40                  45

Thr Val Pro Gly Ser Lys Ser Thr Ala Thr Ile Ser Gly Leu Ser Pro
 50                  55                  60

Gly Val Asp Tyr Thr Ile Thr Val Tyr Ala Tyr Thr Gln Tyr Glu Asn
65                  70                  75                  80

Ile Phe Val Gly Tyr Gln Ser Pro Ile Ser Ile Asn Tyr Arg Thr
                85                  90                  95

<210> SEQ ID NO 452
<211> LENGTH: 96
<212> TYPE: PRT
<213> ORGANISM: Artificial Sequence
<220> FEATURE:
<223> OTHER INFORMATION: synthetic construct

<400> SEQUENCE: 452
```

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

His Ile Thr Tyr Gly Glu Thr Gly Gly Ser Ser Gly Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Trp Met Tyr Asp Gly Tyr
65                  70                  75                  80

Glu Tyr Thr Tyr Gln Gly Thr Ser Pro Ile Ser Ile Asn Tyr Arg Thr
                85                  90                  95

<210> SEQ ID NO 453
<211> LENGTH: 93
<212> TYPE: PRT
<213> ORGANISM: Artificial Sequence
<220> FEATURE:
<223> OTHER INFORMATION: synthetic construct

<400> SEQUENCE: 453

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Gly Trp Ser Gly Tyr Gln Glu Phe
        35                  40                  45

Glu Val Pro Gly Ser Lys Ser Thr Ala Thr Ile Ser Gly Leu Ser Pro
    50                  55                  60

Gly Val Asp Tyr Thr Ile Thr Val Tyr Ala Tyr Gly Tyr Pro Tyr Val
65                  70                  75                  80

Lys Tyr Asn Lys Ser Pro Ile Ser Ile Asn Tyr Arg Thr
                85                  90

<210> SEQ ID NO 454
<211> LENGTH: 93
<212> TYPE: PRT
<213> ORGANISM: Artificial Sequence
<220> FEATURE:
<223> OTHER INFORMATION: synthetic construct

<400> SEQUENCE: 454

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Tyr Ile Thr Tyr Gly Glu Thr Gly Ala Ala Phe Gly Tyr Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Tyr Gly Tyr Pro Tyr Val
65                  70                  75                  80

Lys Tyr Asn Lys Ser Pro Ile Ser Ile Asn Tyr Arg Thr
                85                  90

<210> SEQ ID NO 455
<211> LENGTH: 93
<212> TYPE: PRT
<213> ORGANISM: Artificial Sequence
<220> FEATURE:
<223> OTHER INFORMATION: synthetic construct

<400> SEQUENCE: 455

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Asn Ser Pro Val Gln Glu Phe
        35                  40                  45

Thr Val Pro Gly Ser Lys Ser Thr Ala Thr Ile Ser Gly Leu Ser Pro
    50                  55                  60

Gly Val Asp Tyr Thr Ile Thr Val Tyr Ala Gly Tyr Ser Asp Ser Trp
65                  70                  75                  80

Asn Trp Pro Tyr Ser Pro Ile Ser Ile Asn Tyr Arg Thr
                85                  90

<210> SEQ ID NO 456
<211> LENGTH: 90
<212> TYPE: PRT
<213> ORGANISM: Artificial Sequence
<220> FEATURE:
<223> OTHER INFORMATION: synthetic construct

<400> SEQUENCE: 456

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

Tyr Ile Thr Tyr Gly Glu Thr Gly His Tyr Trp Tyr Tyr Gln Ala Phe
        35                  40                  45

Ala Val Pro Gly Ser Lys Ser Thr Ala Thr Ile Ser Gly Leu Ser Pro
    50                  55                  60

Gly Val Asp Tyr Thr Ile Thr Val Tyr Ala Pro Phe Ser Val Pro Val
65                  70                  75                  80

Met Ser Pro Ile Ser Ile Asn Tyr Arg Thr
                85                  90

<210> SEQ ID NO 457
<211> LENGTH: 92
<212> TYPE: PRT
<213> ORGANISM: Artificial Sequence
<220> FEATURE:
<223> OTHER INFORMATION: synthetic construct

<400> SEQUENCE: 457

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
            20                  25                  30

Tyr Ile Thr Tyr Gly Glu Thr Gly His Tyr Trp Tyr Tyr Gln Ala Phe
        35                  40                  45

Ala Val Pro Gly Ser Lys Ser Thr Ala Thr Ile Ser Gly Leu Ser Pro
    50                  55                  60

Gly Val Asp Tyr Thr Ile Thr Val Tyr Ala Ser Val Leu Tyr Gly Ser
65                  70                  75                  80

Arg Tyr Tyr Ser Pro Ile Ser Ile Asn Tyr Arg Thr
                85                  90

```
<210> SEQ ID NO 458
<211> LENGTH: 100
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (25)...(32)
<223> OTHER INFORMATION: Xaa = any amino acid except Cys and can be
      shown 4-8 times
<220> FEATURE:
<221> NAME/KEY: VARIANT
<222> LOCATION: (34)...(34)
<223> OTHER INFORMATION: Xaa = any amino acid except Cys
<220> FEATURE:
<221> NAME/KEY: VARIANT
<222> LOCATION: (56)...(59)
<223> OTHER INFORMATION: Xaa = Ser or Tyr
<220> FEATURE:
<221> NAME/KEY: VARIANT
<222> LOCATION: (79)...(91)
<223> OTHER INFORMATION: Xaa = any amino acid except Cys and can be
      shown 7-13 times

<400> SEQUENCE: 458

Val Ser Ser Val Pro Thr Lys Leu Glu Val Val Ala Ala Thr Pro Thr
 1               5                  10                  15

Ser Leu Leu Ile Ser Trp Asp Ala Xaa Xaa Xaa Xaa Xaa Xaa Xaa Xaa
            20                  25                  30

Val Xaa Tyr Tyr Arg Ile Thr Tyr Gly Glu Thr Gly Gly Asn Ser Pro
        35                  40                  45

Val Gln Glu Phe Thr Val Pro Xaa Xaa Xaa Xaa Thr Ala Thr Ile Ser
 50                  55                  60

Gly Leu Ser Pro Gly Val Asp Tyr Thr Ile Thr Val Tyr Ala Xaa Xaa
 65                  70                  75                  80

Xaa Xaa Xaa Xaa Xaa Xaa Xaa Xaa Xaa Xaa Ser Pro Ile Ser Ile
                85                  90                  95

Asn Tyr Arg Thr
            100

<210> SEQ ID NO 459
<211> LENGTH: 90
<212> TYPE: PRT
<213> ORGANISM: Artificial Sequence
<220> FEATURE:
<223> OTHER INFORMATION: synthetic construct

<400> SEQUENCE: 459

Val Ser Ser Val Pro Thr Lys Leu Glu Val Val Ala Ala Thr Pro Thr
 1               5                  10                  15

Ser Leu Leu Ile Ser Trp Asp Ala Gly Arg Trp Phe Val Glu Tyr Tyr
            20                  25                  30

Arg Ile Thr Tyr Gly Glu Thr Gly Gly Asn Ser Pro Val Gln Glu Phe
            35                  40                  45

Thr Val Pro Tyr Ser Ser Thr Ala Thr Ile Ser Gly Leu Ser Pro
 50                  55                  60

Gly Val Asp Tyr Thr Ile Thr Val Tyr Ala His Tyr Trp Ser Thr Trp
 65                  70                  75                  80

Tyr Ser Pro Ile Ser Ile Asn Tyr Arg Thr
            85                  90

<210> SEQ ID NO 460
```

```
<211> LENGTH: 90
<212> TYPE: PRT
<213> ORGANISM: Artificial Sequence
<220> FEATURE:
<223> OTHER INFORMATION: synthetic construct

<400> SEQUENCE: 460

Val Ser Ser Val Pro Thr Lys Leu Glu Val Val Ala Ala Thr Pro Thr
1               5                   10                  15

Ser Leu Leu Ile Ser Trp Asp Ala Asn Ser Trp Tyr Val Thr Tyr Tyr
            20                  25                  30

Arg Ile Thr Tyr Gly Glu Thr Gly Gly Asn Ser Pro Val Gln Glu Phe
        35                  40                  45

Thr Val Pro Tyr Ser Ser Thr Ala Thr Ile Ser Gly Leu Ser Pro
    50                  55                  60

Gly Val Asp Tyr Thr Ile Thr Val Tyr Ala His Tyr Trp Ser Thr Trp
65                  70                  75                  80

Tyr Ser Pro Ile Ser Ile Asn Tyr Arg Thr
                85                  90

<210> SEQ ID NO 461
<211> LENGTH: 90
<212> TYPE: PRT
<213> ORGANISM: Artificial Sequence
<220> FEATURE:
<223> OTHER INFORMATION: synthetic construct

<400> SEQUENCE: 461

Val Ser Ser Val Pro Thr Lys Leu Glu Val Val Ala Ala Thr Pro Thr
1               5                   10                  15

Ser Leu Leu Ile Ser Trp Asp Ala Gly Tyr Trp Tyr Val Gln Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Ser Thr Ala Thr Ile Ser Gly Leu Ser Pro
    50                  55                  60

Gly Val Asp Tyr Thr Ile Thr Val Tyr Ala Tyr Tyr Asp Asp Trp Glu
65                  70                  75                  80

Trp Ser Pro Ile Ser Ile Asn Tyr Arg Thr
                85                  90

<210> SEQ ID NO 462
<211> LENGTH: 90
<212> TYPE: PRT
<213> ORGANISM: Artificial Sequence
<220> FEATURE:
<223> OTHER INFORMATION: synthetic construct

<400> SEQUENCE: 462

Val Ser Ser Val Pro Thr Lys Leu Glu Val Val Ala Ala Thr Pro Thr
1               5                   10                  15

Ser Leu Leu Ile Ser Trp Asp Ala Gly Tyr Trp Phe Ile Asp Tyr Tyr
            20                  25                  30

Arg Ile Thr Tyr Gly Glu Thr Gly Gly Asn Ser Pro Val Gln Glu Phe
        35                  40                  45

Thr Val Pro Gly Tyr Ser Thr Ala Thr Ile Ser Gly Leu Ser Pro
    50                  55                  60

Gly Val Asp Tyr Thr Ile Thr Val Tyr Ala Tyr Tyr Asp Asn Tyr Gly
65                  70                  75                  80
```

Trp Ser Pro Ile Ser Ile Asn Tyr Arg Thr
             85                  90

<210> SEQ ID NO 463
<211> LENGTH: 98
<212> TYPE: PRT
<213> ORGANISM: Artificial Sequence
<220> FEATURE:
<223> OTHER INFORMATION: synthetic construct

<400> SEQUENCE: 463

Val Ser Ser Val Pro Thr Lys Leu Glu Val Val Ala Ala Thr Pro Thr
1               5                   10                  15

Ser Leu Leu Ile Ser Trp Asp Ala Leu His Tyr Ser Gly Arg Gly Lys
            20                  25                  30

Val His Tyr Tyr Arg Ile Thr Tyr Gly Glu Thr Gly Gly Asn Ser Pro
        35                  40                  45

Val Gln Glu Phe Thr Val Pro Gly Ser Ser Thr Ala Thr Ile Ser
    50                  55                  60

Gly Leu Ser Pro Gly Val Asp Tyr Thr Ile Thr Val Tyr Ala Tyr Tyr
65                  70                  75                  80

Gln Ser Tyr Gly Tyr Trp Tyr Tyr Met Ser Pro Ile Ser Ile Asn Tyr
                85                  90                  95

Arg Thr

<210> SEQ ID NO 464
<211> LENGTH: 98
<212> TYPE: PRT
<213> ORGANISM: Artificial Sequence
<220> FEATURE:
<223> OTHER INFORMATION: synthetic construct
<220> FEATURE:
<221> NAME/KEY: VARIANT
<222> LOCATION: (5)...(5)
<223> OTHER INFORMATION: Xaa = any amino acid except Cys

<400> SEQUENCE: 464

Val Ser Ser Val Xaa Thr Lys Leu Glu Val Val Ala Ala Thr Pro Thr
1               5                   10                  15

Ser Leu Leu Ile Ser Trp Asp Ala Trp Ser Ser Trp Tyr Tyr Tyr Ile
            20                  25                  30

Ser Tyr Tyr Arg Ile Thr Tyr Gly Glu Thr Gly Gly Asn Ser Pro Val
        35                  40                  45

Gln Glu Phe Thr Val Pro Gly Ser Ser Tyr Thr Ala Thr Ile Ser Gly
    50                  55                  60

Leu Ser Pro Gly Val Asp Tyr Thr Ile Thr Val Tyr Ala Trp Tyr Tyr
65                  70                  75                  80

Asp Gln Tyr Tyr Tyr Leu Val Glu Ser Ser Pro Ile Ser Ile Asn Tyr
                85                  90                  95

Arg Thr

<210> SEQ ID NO 465
<211> LENGTH: 94
<212> TYPE: PRT
<213> ORGANISM: Artificial Sequence
<220> FEATURE:
<223> OTHER INFORMATION: synthetic construct

<400> SEQUENCE: 465

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

Arg Ile Thr Tyr Gly Glu Thr Gly Asn Ser Pro Val Gln Glu Phe
        35                  40                  45

Thr Val Pro Gly Ser Ser Thr Ala Thr Ile Ser Gly Leu Ser Pro
    50                  55                  60

Gly Val Asp Tyr Thr Ile Thr Val Tyr Ala Tyr Trp Trp Tyr Arg Tyr
65                  70                  75                  80

Tyr Tyr Tyr Ser Tyr Ser Pro Ile Ser Ile Asn Tyr Arg Thr
                85                  90

<210> SEQ ID NO 466
<211> LENGTH: 92
<212> TYPE: PRT
<213> ORGANISM: Artificial Sequence
<220> FEATURE:
<223> OTHER INFORMATION: synthetic construct

<400> SEQUENCE: 466

Val Ser Ser Val Pro Thr Lys Leu Glu Val Val Ala Ala Thr Pro Thr
1               5                   10                  15

Ser Leu Leu Ile Ser Trp Asp Ala Glu Tyr Phe Tyr Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Tyr Ser Thr Ala Thr Ile Ser Gly Leu Ser Pro
    50                  55                  60

Gly Val Asp Tyr Thr Ile Thr Val Tyr Ala Tyr Asp Gln Tyr Tyr Ser
65                  70                  75                  80

Ser Tyr Gly Ser Pro Ile Ser Ile Asn Tyr Arg Thr
                85                  90

<210> SEQ ID NO 467
<211> LENGTH: 94
<212> TYPE: PRT
<213> ORGANISM: Artificial Sequence
<220> FEATURE:
<223> OTHER INFORMATION: synthetic construct

<400> SEQUENCE: 467

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Ser Thr Ala Thr Ile Ser Gly Leu Ser Pro
    50                  55                  60

Gly Val Asp Tyr Thr Ile Thr Val Tyr Ala Tyr Tyr Trp Tyr Gln Tyr
65                  70                  75                  80

Ser Tyr Tyr Gln Tyr Ser Pro Ile Ser Ile Asn Tyr Arg Thr
                85                  90

<210> SEQ ID NO 468
<211> LENGTH: 95
<212> TYPE: PRT
<213> ORGANISM: Artificial Sequence
<220> FEATURE:
<223> OTHER INFORMATION: synthetically constructed Fibronectin Type III

```
        repeat 07 domain polypeptide
<220> FEATURE:
<221> NAME/KEY: VARIANT
<222> LOCATION: (1)...(95)
<223> OTHER INFORMATION: Xaa = any amino acid
<220> FEATURE:
<221> NAME/KEY: VARIANT
<222> LOCATION: (42)...(50)
<223> OTHER INFORMATION: Xaa = any amino acid and can be shown 4-9 times
<220> FEATURE:
<221> NAME/KEY: VARIANT
<222> LOCATION: (82)...(87)
<223> OTHER INFORMATION: Xaa = any amino acid and can be shown 5-6 times

<400> SEQUENCE: 468

Pro Leu Ser Pro Pro Thr Asn Leu His Leu Glu Ala Asn Pro Asp Thr
1               5                   10                  15

Gly Val Leu Thr Val Ser Trp Glu Arg Ser Thr Thr Pro Asp Ile Thr
            20                  25                  30

Xaa Tyr Xaa Ile Xaa Thr Xaa Xaa Xaa Xaa Xaa Xaa Xaa Xaa Xaa Xaa
        35                  40                  45

Xaa Xaa Leu Glu Glu Val Val His Ala Asp Gln Ser Ser Cys Thr Phe
    50                  55                  60

Asp Asn Leu Ser Pro Gly Leu Xaa Tyr Xaa Val Xaa Val Xaa Thr Val
65                  70                  75                  80

Xaa Xaa Xaa Xaa Xaa Xaa Xaa Pro Ile Ser Asp Thr Ile Ile Pro
                85                  90                  95

<210> SEQ ID NO 469
<211> LENGTH: 93
<212> TYPE: PRT
<213> ORGANISM: Artificial Sequence
<220> FEATURE:
<223> OTHER INFORMATION: synthetically constructed Fibronectin Type III
        repeat 10 domain polypeptide
<220> FEATURE:
<221> NAME/KEY: VARIANT
<222> LOCATION: (1)...(93)
<223> OTHER INFORMATION: Xaa = any amino acid
<220> FEATURE:
<221> NAME/KEY: VARIANT
<222> LOCATION: (40)...(48)
<223> OTHER INFORMATION: Xaa = any amino acid and can be shown 4-9 times
<220> FEATURE:
<221> NAME/KEY: VARIANT
<222> LOCATION: (80)...(85)
<223> OTHER INFORMATION: Xaa = any amino acid and can be shown 5-6 times

<400> SEQUENCE: 469

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Xaa Tyr
            20                  25                  30

Xaa Ile Xaa Tyr Xaa Xaa Xaa Xaa Xaa Xaa Xaa Xaa Xaa Xaa Xaa Xaa
        35                  40                  45

Gln Glu Phe Thr Val Pro Gly Ser Lys Ser Thr Ala Thr Ile Ser Gly
    50                  55                  60

Leu Lys Pro Gly Val Xaa Tyr Xaa Ile Xaa Val Xaa Ala Val Xaa Xaa
65                  70                  75                  80

Xaa Xaa Xaa Xaa Xaa Pro Ile Ser Ile Asn Tyr Arg Thr
                85                  90

<210> SEQ ID NO 470
<211> LENGTH: 93
<212> TYPE: PRT
```

```
<213> ORGANISM: Artificial Sequence
<220> FEATURE:
<223> OTHER INFORMATION: synthetically constructed Fibronectin Type III
      repeat 14 domain polypeptide
<220> FEATURE:
<221> NAME/KEY: VARIANT
<222> LOCATION: (1)...(93)
<223> OTHER INFORMATION: Xaa = any amino acid
<220> FEATURE:
<221> NAME/KEY: VARIANT
<222> LOCATION: (40)...(48)
<223> OTHER INFORMATION: Xaa = any amino acid and can be shown 4-9 times
<220> FEATURE:
<221> NAME/KEY: VARIANT
<222> LOCATION: (80)...(85)
<223> OTHER INFORMATION: Xaa = any amino acid and can be shown 5-6 times

<400> SEQUENCE: 470

Asn Val Ser Pro Pro Arg Arg Ala Arg Val Thr Asp Ala Thr Glu Thr
1               5                   10                  15

Thr Ile Thr Ile Ser Trp Arg Thr Lys Thr Glu Thr Ile Thr Xaa Phe
            20                  25                  30

Xaa Val Xaa Ala Xaa Pro Xaa Xaa Xaa Xaa Xaa Xaa Xaa Xaa Xaa Xaa
        35                  40                  45

Ile Gln Arg Thr Ile Lys Pro Asp Val Arg Ser Tyr Thr Ile Thr Gly
    50                  55                  60

Leu Gln Pro Gly Thr Xaa Tyr Xaa Ile Xaa Leu Xaa Thr Leu Xaa Xaa
65                  70                  75                  80

Xaa Xaa Xaa Xaa Xaa Pro Val Val Ile Asp Ala Ser Thr
                85                  90

<210> SEQ ID NO 471
<211> LENGTH: 10
<212> TYPE: PRT
<213> ORGANISM: Artificial Sequence
<220> FEATURE:
<223> OTHER INFORMATION: synthetically constructed linker

<400> SEQUENCE: 471

Gly Gly Gly Gly Ser Gly Gly Gly Gly Ser
1               5                   10

<210> SEQ ID NO 472
<211> LENGTH: 10
<212> TYPE: PRT
<213> ORGANISM: Artificial Sequence
<220> FEATURE:
<223> OTHER INFORMATION: synthetically constructed linker

<400> SEQUENCE: 472

Gly Ser Gly Ser Gly Ser Gly Ser Gly Ser
1               5                   10

<210> SEQ ID NO 473
<211> LENGTH: 7
<212> TYPE: PRT
<213> ORGANISM: Artificial Sequence
<220> FEATURE:
<223> OTHER INFORMATION: synthetically constructed linker

<400> SEQUENCE: 473

Pro Ser Thr Ser Thr Ser Thr
1               5

<210> SEQ ID NO 474
<211> LENGTH: 7
```

-continued

```
<212> TYPE: PRT
<213> ORGANISM: Artificial Sequence
<220> FEATURE:
<223> OTHER INFORMATION: synthetically constructed linker

<400> SEQUENCE: 474

Glu Ile Asp Lys Pro Ser Gln
 1               5
```